US012564583B2

(12) United States Patent
Burnette et al.

(10) Patent No.: US 12,564,583 B2
(45) Date of Patent: Mar. 3, 2026

(54) SMALL MOLECULES AGAINST CEREBLON TO ENHANCE EFFECTOR T CELL FUNCTION

(71) Applicant: H. LEE MOFFITT CANCER CENTER AND RESEARCH INSTITUTE, INC., Tampa, FL (US)

(72) Inventors: Pearlie Burnette, Tampa, FL (US); Harshani Lawrence, Tampa, FL (US); Nicholas J. Lawrence, Tampa, FL (US)

(73) Assignee: Lee Moffitt Cancer Center and Research Institute, Inc., Tampa, FL (US)

( * ) Notice: Subject to any disclaimer, the term of this patent is extended or adjusted under 35 U.S.C. 154(b) by 676 days.

(21) Appl. No.: 17/834,380

(22) Filed: Jun. 7, 2022

(65) Prior Publication Data

US 2023/0226035 A1 Jul. 20, 2023

Related U.S. Application Data

(63) Continuation of application No. 16/084,068, filed as application No. PCT/US2017/022711 on Mar. 16, 2017, now Pat. No. 11,395,820.
(Continued)

(51) Int. Cl.
*A61K 31/4545* (2006.01)
*A61K 31/4015* (2006.01)
(Continued)

(52) U.S. Cl.
CPC ...... *A61K 31/4545* (2013.01); *A61K 31/4015* (2013.01); *A61K 31/404* (2013.01);
(Continued)

(58) Field of Classification Search
CPC .. A61K 31/4015; A61K 31/404; A61K 31/45; A61K 31/4523; A61K 31/4525; A61K 31/454; A61K 31/4545; A61K 31/4725; A61K 31/50; A61K 31/513; A61K 31/517; A61K 31/5377; A61P 1/04; A61P 11/06; A61P 25/00; A61P 25/16;
(Continued)

(56) References Cited

U.S. PATENT DOCUMENTS 3,126,395 A 3/1964 Kitahonoki
3,185,708 A 5/1965 Mims
(Continued)

FOREIGN PATENT DOCUMENTS

CL 2021000046 6/2021
CL 2021000073 7/2021
(Continued)

OTHER PUBLICATIONS

Alvarez-Gutierrez, et al., Solid phase synthesis of 1-substituted pyroglutamates, Tetrahedron Lett. 2000, 41(6), 851-4.
(Continued)

*Primary Examiner* — Savitha M Rao
(74) *Attorney, Agent, or Firm* — Meunier Carlin & Curfman LLC

(57) ABSTRACT

Disclosed are small molecules against cereblon to enhance effector T cell function. Methods of making these molecules and methods of using them to treat various disease states are also disclosed.

7 Claims, 24 Drawing Sheets

Specification includes a Sequence Listing.

Related U.S. Application Data

(60) Provisional application No. 62/454,028, filed on Feb. 2, 2017, provisional application No. 62/395,757, filed on Sep. 16, 2016, provisional application No. 62/309,246, filed on Mar. 16, 2016.

(51) Int. Cl.

| | |
|---|---|
| ***A61K 31/404*** | (2006.01) |
| ***A61K 31/45*** | (2006.01) |
| ***A61K 31/4523*** | (2006.01) |
| ***A61K 31/4525*** | (2006.01) |
| ***A61K 31/454*** | (2006.01) |
| ***A61K 31/4725*** | (2006.01) |
| ***A61K 31/50*** | (2006.01) |
| ***A61K 31/513*** | (2006.01) |
| ***A61K 31/517*** | (2006.01) |
| ***A61K 31/5377*** | (2006.01) |

(52) U.S. Cl.

CPC .......... *A61K 31/45* (2013.01); *A61K 31/4523* (2013.01); *A61K 31/4525* (2013.01); *A61K 31/454* (2013.01); *A61K 31/4725* (2013.01); *A61K 31/50* (2013.01); *A61K 31/513* (2013.01); *A61K 31/517* (2013.01); *A61K 31/5377* (2013.01)

(58) Field of Classification Search

CPC .. A61P 25/28; A61P 29/00; A61P 3/10; A61P 35/00; A61P 37/02; A61P 43/00; A61P 9/04; A61P 9/12; C07D 207/416; C07D 211/88; C07D 237/04; C07D 239/22; C07D 239/54; C07D 401/04; C07D 401/12; C07D 403/04; C07D 405/04; C07D 405/12; C07D 417/12; C07D 473/04

See application file for complete search history.

(56) References Cited

U.S. PATENT DOCUMENTS

| | | | |
|---|---|---|---|
| 3,232,295 | A | 2/1966 | Mims |
| 3,314,953 | A | 4/1967 | Vazakas et al. |
| 3,565,794 | A | 2/1971 | Pigache |
| 3,705,162 | A | 12/1972 | Ivars et al. |
| 3,975,388 | A | 8/1976 | Hakim et al. |
| 4,217,130 | A | 8/1980 | Kawai et al. |
| 4,397,854 | A | 8/1983 | Sircar |
| 4,404,203 | A | 9/1983 | Sircar |
| 4,559,157 | A | 12/1985 | Smith et al. |
| 4,608,392 | A | 8/1986 | Jacquet et al. |
| 4,619,916 | A | 10/1986 | Di Stazio et al. |
| 4,748,155 | A | 5/1988 | Sisto et al. |
| 4,816,454 | A | 3/1989 | Zoller et al. |
| 4,820,508 | A | 4/1989 | Wortzman |
| 4,938,949 | A | 7/1990 | Borch et al. |
| 4,992,478 | A | 2/1991 | Geria |
| 5,167,649 | A | 12/1992 | Zook |
| 5,741,793 | A | 4/1998 | Young et al. |
| 5,859,008 | A | 1/1999 | Jonas et al. |
| 6,054,579 | A | 4/2000 | Harriman |
| 6,399,611 | B1 | 6/2002 | Jonas et al. |
| 6,455,472 | B1 | 9/2002 | Fischer et al. |
| 6,531,473 | B2 | 3/2003 | Jonas et al. |
| 6,656,937 | B2 | 12/2003 | Germann |
| 6,960,648 | B2 | 11/2005 | Bonny |
| 7,238,711 | B1 | 7/2007 | Grainger |
| 7,541,474 | B2 | 6/2009 | Bunel et al. |
| 7,790,723 | B2 | 9/2010 | Eggenweiler et al. |
| 7,850,955 | B2 | 12/2010 | Saito et al. |
| 7,989,466 | B2 | 8/2011 | Grainger et al. |
| 8,012,997 | B2 | 9/2011 | Robarge et al. |
| 8,481,558 | B2 | 7/2013 | Grainger et al. |
| 8,629,157 | B2 | 1/2014 | Berry et al. |
| 8,785,357 | B2 | 7/2014 | Mosier et al. |
| 2002/0035243 | A1 | 3/2002 | Imfeld et al. |
| 2002/0072601 | A1 | 6/2002 | Mathias et al. |
| 2002/0111356 | A1 | 8/2002 | Jonas et al. |
| 2002/0120100 | A1 | 8/2002 | Bonny |
| 2003/0032594 | A1 | 2/2003 | Bonny |
| 2003/0064987 | A1 | 4/2003 | Germann |
| 2004/0048859 | A1 | 3/2004 | Germann |
| 2005/0222160 | A1 | 10/2005 | Eggenweiler et al. |
| 2008/0045557 | A1 | 2/2008 | Grainger et al. |
| 2008/0311164 | A1 | 12/2008 | Saito et al. |
| 2012/0065401 | A1 | 3/2012 | Grainger et al. |
| 2014/0073801 | A1 | 3/2014 | Storer et al. |
| 2015/0291562 | A1 | 10/2015 | Crew et al. |
| 2016/0016913 | A1 | 1/2016 | Lewis et al. |
| 2016/0039788 | A1 | 2/2016 | Ladner et al. |
| 2016/0058872 | A1 | 3/2016 | Crew et al. |
| 2017/0121321 | A1 | 5/2017 | Crew et al. |

FOREIGN PATENT DOCUMENTS

| | | |
|---|---|---|
| CN | 103497175 | 1/2014 |
| CN | 105037721 | 11/2015 |
| DE | 3434680 | 4/1986 |
| DE | 19604388 | 8/1997 |
| EP | 0498268 | 8/1992 |
| EP | 0738715 | 10/1996 |
| EP | 2386565 | 11/2011 |
| EP | 3932922 | 1/2022 |
| GB | 962857 | 7/1964 |
| GB | 1002856 | 9/1965 |
| JP | 36014610 | 5/1957 |
| JP | 36016624 | 9/1961 |
| JP | 38002520 | 3/1963 |
| JP | 38024889 | 11/1963 |
| JP | 38026678 | 12/1963 |
| JP | 54079269 | 6/1979 |
| JP | 09315946 | 12/1997 |
| JP | 11049755 | 2/1999 |
| JP | 2003145933 | 5/2003 |
| JP | 2012123292 | 6/2012 |
| WO | 95/01348 | 1/1995 |
| WO | 9901103 | 1/1999 |
| WO | 2000035871 | 6/2000 |
| WO | 0042071 A3 | 7/2000 |
| WO | 01/53261 | 7/2001 |
| WO | 2005016326 | 2/2005 |
| WO | 2005/028436 | 3/2005 |
| WO | 2007062817 | 6/2007 |
| WO | 2007078013 | 7/2007 |
| WO | 1964842 | 9/2008 |
| WO | 2009092764 | 7/2009 |
| WO | 2013021363 | 2/2013 |
| WO | 2014164704 | 10/2014 |
| WO | 2015137846 | 9/2015 |
| WO | 2016105518 | 6/2016 |
| WO | 2016197032 | 12/2016 |
| WO | 2016210141 | 12/2016 |
| WO | 2017007612 | 1/2017 |
| WO | 2017197051 | 11/2017 |
| WO | 2018071606 | 4/2018 |
| WO | 2018098275 | 5/2018 |
| WO | 2018189554 | 10/2018 |
| WO | 2019078522 | 4/2019 |
| WO | 2019078588 | 4/2019 |
| WO | 2020014440 | 1/2020 |
| WO | 2020014460 | 1/2020 |

OTHER PUBLICATIONS

Arora, et al., A comprehensive review of lenalidomide in B-cell non-Hodgkin lymphoma. Ther Adv Hematol. 2016, 7, 209-21.

Balaev, et al., Alternative synthesis of lenalidomide, Pharm. Chem. J. 2013, 46, 676-8.

Barta, et al., Synthesis of Novel Chiral Phosphorous Triamides Based on (S)-N-(Pyrrolidin-2-ylmethyl)aniline and Their Application in Asymmetric Catalysis, Eur. J. Org. Chem. 2009, 24, 4102-16.

(56) References Cited

OTHER PUBLICATIONS

Basavaiah, et al., Chiral diamides as efficient catalytic precursors for the borane-mediated asymmetric reduction of prochiral ketones, Tetrahedron: Asymmetry 2007, 18(8), 968-74.
Battersby, et al., Specific chemical fission of peptide links. III. Fission of peptides containing one glutamic acid residue, J. Chem. Soc. 1961, 524-30.
Behr, et al., Chiral N-dienyl-L-pyroglutamic esters in asymmetric hetero-Diels-Alder reactions with acylnitroso dienophiles, Tetrahedron 1996, 52(9), 3283-302.
Belzile, et al., HIV-1 Vpr-mediated G2 arrest involves the DDB1-CUL4AVPRBP E3 ubiquitin ligase. PLoS Pathog. 2007, 3, e85.
Benoiton, et al., N-9-fluorenylmethoxycarbonylpyroglutamate: preparation of the acid, chloride and succinimidyl ester, Intl. J. Peptide & Protein Res. 1994, 43(4), 321-4.
Bjorklund, et al., Rate of CRL4(CRBN) substrate Ikaros and Aiolos degradation underlies differential activity of lenalidomide and pomalidomide in multiple myeloma cells by regulation of c-Myc and IRF4. Blood Cancer J. 2015, 5, e354.
Bjorkman, et al., Peptides related to melanostatin (Pro-Leu-Gly-amide) as inhibitors of oxotremorine-induced tremor, Acta Pharmaceutica Suecica 1976, 13(4), 289-98.
Briere, et al., Regioselective reductions of various 3-aminosuccinimides; application to the synthesis of two heterocyclic systems, Tetrahedron 1997, 53(6), 2075-86.
Brunel, et al., A Practical Method for the Large-Scale Synthesis of Diastereomerically Pure (2R,5S)-3-Phenyl-2-(8-quinolinoxy)-1,3-diaza-2-phosphabicyclo-[3.3.0]-octane Ligand (Quiphos). Synthesis and X-ray Structure of Its Corresponding Chiral π-Allyl Palladium Complex, J. Org. Chem. 1999, 64(24), 8940-2.
Chamberlain, et al., Structure of the human Cereblon-DDB1-lenalidomide complex reveals basis for responsiveness to thalidomide analogs. Nat. Struct. Mol Biol. 2014, 21, 803-9.
Chen, et al., The modified resolution process of 1,1'-binaphthol by kinetic control crystallization, Huaxue Yu Nianhe 2007, 29(3), 157-60. English Abstract included in text.
Clayden, et al., Conformational arm-wrestling: battles for stereochemical control in benzamides bearing matched and mismatched chiral 2- and 6-substituents, Org. Biomol. Chem. 2006, 4(3), 444-54.
Davis, et al., Peptide synthesis from heterocyclic intermediates. I. 2-Thioxo-5-thiazolidone derivatives of valine, leucine, norleucine, methionine, L-tyrosine, glutamine, α-amino-isobutyric acid, and aminomalonamide, J. Chem. Soc. 1951 2419-25.
Diggle. Thalidomide: 40 years on. Int J Clin Pract. 2001, 55, 627-31.
Du, et al., A new method for optical resolution of Binol by molecular complexation with (S)-5-oxopyrrolidine-2-carboxanilide, Tetrahedron Lett. 2002, 43(30), 5273-6.
Dubinskaya, et al., Bactericidal ability of a number of mixed nitrogen containing inhibitors of hydrosulfide corrosion, Praktika Protivokorrozionnoi Zashchity 2013, 3, 23-8. English Abstract—Machine Translation.
Edwards, et al., Synthesis and application to asymmetric allylic amination of substituted monodonor diazaphospholidine ligands, Tetrahedron 2003, 59(34), 6473-80.
Ellis, et al., Michael addition reactions between various nucleophilic glycine equivalents and (S,E)-1-enoyl-5-oxo-N-phenylpyrrolidine-2-carboxamide, an optimal type of chiral Michael acceptor in the asymmetric synthesis of β-phenyl pyroglutamic acid and related compounds, Tetrahedron: Asymmetry 2009, 20(22), 2629-34.
Eriksson, et al., Synthesis and alkaline hydrolysis of some N-substituted phthalimides, Acta Pharmaceutica Suecica 1973, 10(1), 63-74.
Fabro, et al., Teratogenic activity of thalidomide and related compounds, Life Sciences 1964, 3(9), 987-92.
Fang et al., A calcium- and calpain-dependent pathway determines the response to lenalidomide in myelodysplastic syndromes. Nat. Med. 2016, 22, 727-34.
Farid et al., New insights about HERG blockade obtained from protein modeling, potential energy mapping, and docking studies. Bioorg. Med. Chem. 2006, 14, 3160-73.
Fionda et al., The IMiDs targets IKZF-1/3 and IRF4 as novel negative regulators of NK cell-activating ligands expression in multiple myeloma. Oncotarget. 2015, 6, 23609-30.
Fischer et al., Structure of the DDB1-CRBN E3 ubiquitin ligase in complex with thalidomide. Nature. 2014, 512, 49-53.
Fox, et al., Design, Synthesis, and Preliminary Pharmacological Evaluation of N-Acyl-3-aminoglutarimides as Broad-Spectrum Chemokine Inhibitors in Vitro and Anti-inflammatory Agents in Vivo. J. Med. Chem. 2002, 45(2), 360-70.
Fox, et al., Identification of 3-(Acylamino)azepan-2-ones as Stable Broad-Spectrum Chemokine Inhibitors Resistant to Metabolism in Vivo. J. Med. Chem. 2005, 48(3), 867-74.
Frank, et al., Toxicity to protozoa of thalidomide breakdown products and counteraction by nicotinic acid and glutamine, Proc. Soc. Exp. Biol. Med. 1963, 114, 326-8.
Friesner, et al., Extra precision glide: docking and scoring incorporating a model of hydrophobic enclosure for protein-ligand complexes. J. Med. Chem. 2006, 49, 6177-96.
Gandhi, et al., Immunomodulatory agents lenalidomide and pomalidomide co-stimulate T cells by inducing degradation of T cell repressors Ikaros and Aiolos via modulation of the E3 ubiquitin ligase complex CRL4(CRBN.). Br. J. Haematol. 2014, 164, 811-21.
Gandhi, et al. Measuring cereblon as a biomarker of response or resistance to lenalidomide and pomalidomide requires use of standardized reagents and understanding of gene complexity. Br. J. Haematol. 2014, 164, 233-44.
Gawron, et al., pH Effects on the kinetics of the cystine-cyanide reaction, J. Am. Chem. Soc. 1964, 86(11), 2283-6.
Gopalakrishnan, et al., Immunomodulatory drugs target IKZF1-IRF4-MYC axis in primary effusion lymphoma in a cereblon-dependent manner and display synergistic cytotoxicity with BRD4 inhibitors. Oncogene. 2016, 35, 1797-810.
Guo, et al., Probing the alpha-helical structural stability of stapled p53 peptides: molecular dynamics simulations and analysis. Chem. Biol. Drug. Des. 2010, 75, 348-59.
Hagner, et al., CC-122, a pleiotropic pathway modifier, mimics an interferon response and has antitumor activity in DLBCL. Blood. 2015, 126, 779-89.
Hartmann, et al., Thalidomide mimics uridine binding to an aromatic cage in cereblon. J. Struct. Biol. 2014, 188, 225-32.
Hashem, et al., Novel pyrazolo, isoxazolo, and thiazolo steroidal systems and model analogs containing dimethoxylaryl (or dihydroxylaryl) groups and derivatives. Synthesis, spectral properties, and biological activity, J. Med. Chem. 1976, 19, 229-39.
Haslett, et al., Thalidomide costimulates primary human T lymphocytes, preferentially inducing proliferation, cytokine production, and cytotoxic responses in the CD8+ subset. J. Exp. Med. 1998, 187, 1885-92.
Huang, et al., The synthesized for chiral agent (S)-2-(anilinomethyl)pyrrolidine, Jiangxi Shifan Daxue Xuebao, Ziran Kexueban 2011, 35(4), 347-349. English Abstract included in text.
Humne, et al., Iodine-mediated facile dehydrogenation of dihydropyridazin-3(2H)one, Chinese Chem. Lett. 2011, 22(12), 1435-8.
Iriuchijima, et al., A convenient synthesis of (R)- and (S)-2-anilinomethylpyrrolidines, Synthesis 1978, (9), 684-5.
Ito, et al., Identification of a Primary Target of Thalidomide Teratogenicity. Science 2010, 327(5971), 1345-50.
Jonasova, et al., High level of full-length cereblon mRNA in lower risk myelodysplastic syndrome with isolated 5q deletion is implicated in the efficacy of lenalidomide. Eur. J. Haematol. 2015, 95, 27-34.
Jones, et al., Outcomes and Resource Use of Sepsis-associated Stays by Presence on Admission, Severity, and Hospital Type. Med. Care 2016, 54, 303-10.
Jorgensen, et al., Development and testing of the OPLS all-atom force field on conformational energetics and properties of organic liquids. J. Am. Chem. Soc. 1996, 118, 11225-36.

(56) References Cited

OTHER PUBLICATIONS

Kagayama, et al., Synthesis and biological evaluation of novel phthalazinone derivatives as topically active phosphodiesterase 4 inhibitors, Bioorg. Med. Chem. 2009, 17, 6959-70.
Kaldrikyan, et al., Pyrimidines LIX. Synthesis and biological properties of N-substituted dihydrouracils and dihydrothiouracils. Pharm. Chem. J. 1983, 17, 727-30.
Kameyama, et al., Effect of N-phthalylaspartic imide on motor activity and hypnotic activity in mice, Tohoku Yakka Daigaku Kiyo 1962, 9, 51-5.
Kaminski et al., Evaluation and reparametrization of the OPLS-AA force field for proteins via comparison with accurate quantum chemical calculations on peptides. J. Phys. Chem. B. 2001, 105, 6474-87.
Khan, et al., Syntheses and antiinflammatory activity of some 6-aryl-2,3,4,5-tetrahydro-3-pyridazinones, Indian J. Chem., B: Org. Chem. Med. Chem. 2000, 39B(8), 614-9.
Kim W, Lee S, Son Y, Ko C, Ryu WS. DDB1 Stimulates Viral Transcription of Hepatitis B Virus via HBx-Independent Mechanisms. J. Virol. 2016, 90, 9644-53.
Kimura, et al., Development of New P-Chiral Phosphorodiamidite Ligands Having a Pyrrolo[1,2-c]diazaphosphol-1-one Unit and Their Application to Regio- and Enantioselective Iridium-Catalyzed Allylic Etherification, J. Org. Chem. 2007, 72(3), 707-14.
Kiso, Efficient solid phase peptide synthesis. Use of methanesulfonic acid α-amino deprotecting procedure and new coupling reagent, 2-(benzotriazol-1-yl)oxy-1,3-dimethylimidazolidinium hexafluorophosphate (BOI),International Journal of Peptide & Protein Research 1992, 40(3-4), 308-14.
Kohn, et al., Synthesis and characterization of chiral 1,2-diamines from 5-oxo-pyrrolidine-(S)-2-carboxylic acid, Tetrahedron: Asymmetry 2007, 18(14), 1735-41.
Kronke, et al., Lenalidomide induces ubiquitination and degradation of CK1alpha in del(5q) MDS. Nature. 2015, 523, 183-8.
Kronke, et al., Lenalidomide causes selective degradation of IKZF1 and IKZF3 in multiple myeloma cells. Science. 2014, 343, 301-5.
Kupfer, et al., Stimulation by o,p'-DDD of cortisol metabolism in the guinea pig, Life Sci. 1964, 3(9), 959-64.
LeBlanc, et al., Immunomodulatory drug costimulates T cells via the B7-CD28 pathway. Blood. 2004, 103, 1787-90.
Lebraud, et al., Protein Degradation by In-Cell Self-Assembly of Proteolysis Targeting Chimeras. ACS Cent Sci. 2016, 2, 927-34.
Lee, et al., Syntheses of anilide derivatives from amino acids and their biological activities. I. Preparation of (R)-2-pyrrolidone-5-carbox-anilide derivatives and their effects on the germination of plant seeds, Taehan Hwahakhoe Chi 1981, 25(1), 38-43. English Abstract included in text.
Lepper, et al., Comparative Molecular Field Analysis and Comparative Molecular Similarity Indices Analysis of Thalidomide Analogues as Angiogenesis Inhibitors, J. Med. Chem. 2004, 47(9), 2219-27.
Li, et al., Very fast empirical prediction and rationalization of protein pKa values. Proteins. 2005, 61, 704-21.
Lindner et al. The molecular mechanism of thalidomide analogs in hematologic malignancies. J. Mol. Med. (Berl) 94:1327-1334, 2016.
List, et al., Efficacy of lenalidomide in myelodysplastic syndromes. N. Engl. J. Med. 2005, 352, 549-57.
Lu, et al., Thalidomide metabolites in mice and patients with multiple myeloma. Clin. Cancer. Res. 2003, 9, 1680-8.
Lu, et al., Hijacking the E3 Ubiquitin Ligase Cereblon to Efficiently Target BRD4. Chem. Biol. 2015, 22, 755-63.
Mahon, et al., E3 ligases and their rewiring by viral factors. Biomolecules. 2014, 4, 897-930.
Martin, et al., A novel approach to the discovery of small-molecule ligands of CDK2. Chembiochem. 2012, 13, 2128-36.
Martyna, et al., Explicit reversible integrators for extended systems dynamics. Mol. Physics. 1996, 87, 1117-57.
McDaniel, et al., Molecular action of lenalidomide in lymphocytes and hematologic malignancies. Adv. Hematol. 2012, 2012, 513702.
McDaniel, et al., Reversal of T-cell tolerance in myelodysplastic syndrome through lenalidomide immune modulation. Leukemia. 2012, 26, 1425-9.
Luptakova, et al., Lenalidomide enhances anti-myeloma cellular immunity, Cancer immunology, immunotherapy: 2013, 62:39-49.
Misiti, et al., Effects of 3-phthalimidoglutarimide and N-phthaloyl-DL-as-partimide on rat pregnancy, J. Med. Chem. 1963, 6, 464-5.
Mizukami, et al., Sulfonamide derivatives as analytical reagents. I. 2'-Mercaptosulfonanilide derivatives, Chem. Pharm. Bull. 1965, 13(1), 33-9.
Nunes, et al., Signalling through CD28 T-cell activation pathway involves an inositol phospholipid-specific phospholipase C activity. Biochem. J. 1993, 293 (Pt 3), 835-42.
O'Brien, et al., Ikaros imposes a barrier to CD8+ T cell differentiation by restricting autocrine IL-2 production. J Immunol. 2014, 192, 5118-29.
Onat, et al., Stimulation of gap junctional intercellular communication by thalidomide and thalidomide analogs in human fetal skin fibroblasts (HFFF2) and in rat liver epithelial cells (WB-F344), Biochem. Pharmacol. 2001, 62(8), 1081-6.
Otahal, et al., Lenalidomide enhances antitumor functions of chimeric antigen receptor modified T cells. Oncoimmunology. 2016, 5, e1115940.
Ott, et al., Tetrahydroisoquino [2,1-d][1,4]benzodiazepines. Synthesis and Neuropharmacological Activity, J. Med. Chem. 1968, 11(4), 777-7.
Papaioannou, et al., Facile preparation of the 1-hydroxybenzotriazolyl ester of N-tritylpyroglutamic acid and its application to the synthesis of TRH, [D-His2]TRH and analogs incorporating cis- and trans-4-hydroxy-L-proline,Acta Chemica Scandinavica 1995, 49(2), 103-14.
Paul, et al., Zinc binding to the HCCH motif of HIV-1 virion infectivity factor induces a conformational change that mediates protein-protein interactions. Proc Natl. Acad. Sci. USA. 2006, 103, 18475-80.
Petzold et al. Structural basis of lenalidomide-induced CK1alpha degradation by the CRL4 CRBN ubiquitin ligase, Nature 532: 127-130, 2016.
Pitarch, et al., Chemical and pharmacological study of a series of substituted pyridazones, Eur. J. Med. Chem. 1974, 9(6), 644-50.
Ponder, et al., An efficient newton-like method for molecular mechanics energy minimization of large molecules. J. Comp. Chem. 1987, 8, 1016-24.
Qin, et al., (S)-5-Oxo-N-phenylpyrrolidine-2-carboxamide, Acta Crystallographica, Section E: Structure Reports Online 2011, 67(10), 02763.
Raina, et al., Protac-induced BET protein degradation as a therapy for castration-resistant prostate cancer. Proc. Natl. Acad. Sci. USA. 2016, 113, 7124-9.
Rajadhyaksha, et al., Behavioral characterization of cereblon forebrain-specific conditional null mice: a model for human non-syndromic intellectual disability. Behavioural Brain Res. 2012, 226, 428-34.
Rhodes, et al., Synthesis of 2,6-dioxo-3-phthalimidopiperidine-3,4,4,5,5,-d5 and 2,5-dioxo-3-phthalimidopyrrolidine-3,4,4-d3 from L-deuterioglutamic acid and L-deuterioaspartic acid, J. Pharm. Sci. 1965, 54(10), 1440-3.
Rigo, et al., Studies on pyrrolidinones. Synthesis and reactivity of some N-protected pyroglutamic derivatives, J. Heterocyclic Chem. 1995, 32(5), 1599-604.
Robak, et al., Antibody therapy alone and in combination with targeted drugs in chronic lymphocytic leukemia. Semin. Oncol. 2016, 43, 280-90.
Rosnati, et al., Substances structurally related to 2-phthalimidoglutarimide (thalidomide), Farmaco, Edizione Scientifica 1965, 20(1), 3-24. English Summary included in text.
Ryckaert, et al., Numerical integration of the cartesian equations of motion of a system with constraints: molecular dynamics of n-alkanes. J. Comp. Physics. 1977, 23, 327-41.
Saenz, et al., Novel BET protein proteolysis targeting chimera (BET-Protac) exerts superior lethal activity than bromodomain inhibitor (BETi) against post-myeloproliferative neoplasm (MPN) secondary (s) AML cells. Leukemia. 2017, 31(9), 1951-61.

(56) References Cited

OTHER PUBLICATIONS

Saigo, et al., Optical resolution of 2-(anilinomethyl)pyrrolidine, Bull. Chem. Soc. Japan 1982, 55(7), 2299-300.
Sakamoto, et al., Protacs: chimeric molecules that target proteins to the Skp1-Cullin-F box complex for ubiquitination and degradation. Proc. Natl. Acad. Sci. USA. 2001, 98, 8554-9.
Sakamoto, et al., Development of Protacs to target cancer-promoting proteins for ubiquitination and degradation. Mol. Cell Proteomics. 2003, 2, 1350-8.
Sakamoto. Protacs for treatment of cancer. Pediatr. Res. 2010, 67, 505-8.
Sastry, et al., Protein and ligand preparation: parameters, protocols, and influence on virtual screening enrichments. J. Comp. Aided Mol. Des. 2013, 27, 221-34.
Shannon, et al., Thalidomide increases the synthesis of IL-2 in cultures of human mononuclear cells stimulated with Concanavalin-A, Staphylococcal enterotoxin A, and purified protein derivative. Immunopharmacology. 1995, 31, 109-16.
Sherman, et al., Use of an induced fit receptor structure in virtual screening. Chem. Biol. Drug Des. 2006, 67, 83-4.
Sherman, Novel procedure for modeling ligand/receptor induced fit effects. J. Med. Chem. 2006, 49, 534-53.
Siddiqui, et al., Synthesis and antiinflammatory activity of 6-(substituted-aryl)-2,3,4,5-tetrahydro-3-thiopyridazinones, Indian J. Heterocyclic Chem. 2004, 13(3), 257-60.
Signorini, et al., Energetic fitness of histidine protonation states in PDB structures. J. Phys. Chem. B. 2004, 108, 12252-7.
Singhal, et al., Antitumor activity of thalidomide in refractory multiple myeloma. N. Engl. J. Med. 1999, 341, 1565-71.
Smith, et al., Relation between the chemical structure and embryotoxic activity of thalidomide and related compounds, Symp. Embryopathic Act. Drugs 1965, 194-209.
Toyama, et al., Synthesis of optically active N2-phthaloylaspartimide, Yakugaku Zasshi 1964, 84(4), 372-3.
Toyoizumi, et al., Combined therapy with chemotherapeutic agents and herpes simplex virus type IICP34.5 mutant (HSV-1716) in human non-small cell lung cancer, Human Gene Therapy, 1999, 10(18), 3013-29.
Veerman, et al., Synthesis and evaluation of analogs of the phenylpyridazinone NPD-001 as potent trypanosomal TbrPDEB1 phosphodiesterase inhibitors and in vitro trypanocidal, Bioorg. Med. Chem. 2016, 24(7), 1573-81.
Wiget, et al., Sulfur incorporation generally improves Ricin inhibition in pterin-appended glycine-phenylalanine dipeptide mimics, BOMCL, 2013, 6799-6804.
Winter, et al., Selective Target Protein Degradation via Phthalimide Conjugation. Science. 2015, 348, 1376-81.
Wuest, et al., Teratological studies in the thalidomide field, Life Sci. 1966, 5(5), 393-6.
Yuan, et al., Facile and efficient asymmetric synthesis of α-aminoalkylphosphonic acids, Chinese J. Chem. 2005, 23(12), 1671-6.
Yuan, et al., A new and efficient asymmetric synthesis of 1-amino-1-alkylphosphonic acids, Heteroatom Chem. 2000, 11(7), 528-35.
Yuan, et al., Organophosphorus compounds. 79. A convenient asymmetric synthesis of 1-aminoalkylphosphonic acids, Chinese Chem. Lett. 1993, 4(9), 753-6.
Yuan, et al., Efficient synthesis of aryl hydroxylactams by reducing imides with activated zinc dust, Synthetic Communications 2006, 36(4), 435-44.
Zengerle, et al., Selective Small Molecule Induced Degradation of the BET Bromodomain Protein BRD4. ACS Chem. Biol. 2015, 10, 1770-7.
Zhang, et al., Lenalidomide efficacy in activated B-cell-like subtype diffuse large B-cell lymphoma is dependent upon IRF4 and cereblon expression. Br. J. Haematol. 2013, 160, 487-502.
Zhou, et al., Immunotherapy in mantle cell lymphoma: Anti-CD20-based therapy and beyond, Am. J. Hematol. 2008, 83 (2), 144-9.
Zhu, et al., Cereblon expression is required for the antimyeloma activity of lenalidomide and pomalidomide. Blood. 2011, 118, 4771-9.
Boichenko, I. et al., "A FRET-based assay for the identification and characterization of cereblon ligands", Journal of Medicinal Chemistry, Jan. 5, 2016, vol. 59, No. 2, pp. 770-774, See abstract; p. 771; and figure 1.
Karaluka, V. et al., "B(OCH2CF3)3-mediated direct amidation of pharmaceutically relevant building blocks in cyclopentyl methyl ether", Organic & Biomolecular Chemistry, 2015, vol. 13, No. 44, pp. 10888-10894 See abstract; p. 10889; scheme 2; and compound 3n.
Pourvali, A. et al., "A new method for peptide synthesis in the N->C direction: amide assembly through silver-promoted reaction of thioamides", Chemical Communications, 2014, vol. 50, No. 100, pp. 15963-15966 See abstract; table 1; and entry 5.
El-Zahabi, M. A. et al., Synthesis of new cyclic imides derivatives with potential hypolipidemic activity, Medicinal Chemistry Research, 2012, vol. 21, No. 1, pp. 75-84, See abstract; p. 75; and scheme 2.
The International Search Report and Written Opinion issued for Application No. PCT/US2017/022711, dated Jun. 29, 2017, 16 pages.
International Search Report and Written Opinion issued for Application No. PCT/US2019/041413, dated Oct. 1, 2019, 8 pages.
Partial Supplementary European Search Report issued for Application No. 17767524.6, dated Sep. 25, 2019.
De, et al., "Possible antineoplastic agents II", Journal of Pharmaceuticals Sci., 66:2, 1977, 232-235.
Fink, et al., "The novel mechanism of lenalidomide activity", Blood 126:21, 2015, 2366-2369.
Extended European Search Report issued for Application No. EP17767524.6, dated Jan. 14, 2020, 13 pages.
Examination Report No. 1 issued for Australian Application No. 2017232906, dated Mar. 29, 2021.
Kodi Philip, "In Vitro Antifungal Activity Screening of Some New Glutamoyl derivatives", Research Journal of Chemical Sciences (2014), vol. 4, No. 8, pp. 17-24.
Office Action issued for Japanese Application No. 2018-548365, dated Apr. 27, 2021.
Office Action issued for Mexican Patent Application No. MX/a/2018/011216, dated Jun. 17, 2021.
Office Action and Search report issued for Chinese Application No. 201780030049.3, dated Jul. 19, 2021.
Office Action and Search report issued for Chinese Application No. 201780030049.3, dated Dec. 29, 2021.
Examination Report No. 2 issued for Australian Application No. 2017232906, dated Jan. 13, 2022.
Office Action issued for Mexican Application No. MX/a/2018/011216, dated Oct. 14, 2021.
Office Action issued for Korean Application No. 10-2018-7029689, dated Sep. 17, 2021.
Official Action issued for Korean Patent Application No. 10-2018-7029689, dated Mar. 11, 2022.
Choi, Bo-Gil, et al. "Synthesis of antineoplaston A10 analogs as potential antitumor agents." Archives of pharmacal research 21.2 (1998): 157-163.
Search report and written opinion for Singapore Application 11202012464W from IPOS, dated Oct. 5, 2022.
Braña, M. F., et al., "Discovering a new analogue of thalidomide which may be used as a potent modulator of TNF-α production," European Journal of Medicinal Chemistry, vol. 44, No. 9, 2009, pp. 3533-3542.
CAS Database Registry, Accession No. 1494653-61-0 for 2-cyano-N-(2,6-dioxo-3-piperidinyl)-3fluoro-benzenesulfonamide, Dec. 13, 2013, 3 pages.
Choi, B. G., et al., "Synthesis of Antineoplaston A10 Analogs as Potential Antitumor Agents," Archives of Pharmacal Research, vol. 21, No. 2, 1998, pp. 157-163.
Iwakura, Y., et al., "Syntheses and Properties of New Aromatic-Aliphatic Copolyimides," vol. 175, No. 1, Die Makromolekulare Chemie, vol. 175, 1974, pp. 137-159.

(56) References Cited

OTHER PUBLICATIONS

Lindner, S., et al., "Chemical Inactivation of the E3 Ubiquitin Ligase Cereblon by Pomalidomide-based *Homo*-PROTACs," Journal of Visualized Experiments, Issue 147, 2019, 9 pages.
Maniaci, C., et al., "*Homo*-PROTACs: bivalent small-molecule dimerizers of the VHL E3 ubiquitin ligase to induce self-degradation," Nature Communications, vol. 8, No. 1, 2017, 14 pages.
Steinebach, C., et al., "A MedChem toolbox for cereblon-directed PROTACs," Medical Chemical Communication, vol. 10, No. 6, 2019, pp. 1037-1041.
Steinebach, C., et al., "*Homo*-PROTACs for the Chemical Knockdown of Cereblon," ACS Chemical Biology, vol. 13, No. 9, 2018, pp. 2771-2782.
First Examination Report, dated Jul. 15, 2022, received in corresponding IN Application No. 202117005720 (and English translation).
Office Action, dated Jun. 29, 2022, received in corresponding EA Application No. 202190248 (and English translation).
Examination Report, dated Jul. 25, 2023, received in related AU Application No. 2022203645.
Office Action, dated Mar. 29, 2023, received in related CA Application No. 3,017,740.
Office Action, dated Jan. 18, 2024, received in related CA Application No. 3,017,740.
Office Action, dated Mar. 28, 2022, received in related CN Application No. 201780030049.3 (English translation).
Office Action, dated Oct. 20, 2023, received in related CN Application No. 2019800507962 (English translation).
Office Action, dated May 5, 2023, received in related CN Application No. 2019800507962 (English translation).
Search Report, dated May 5, 2023, received in related CN Application No. 2019800507962 (English translation).
Office Action, dated Mar. 16, 2022, received in related EP Application No. 17767524.6.
Office Action, dated Mar. 11, 2022, received in related KR Application No. 1020187029689 (and English translation).
Notice of Allowance, dated Jan. 10, 2023, received in related KR Application No. 1020187029689 (English translation).
Extended European Search Report, dated Mar. 10, 2022, received in corresponding EP Application No. 19833126.6.
Office Action and Search Report, dated Feb. 11, 2022, received in corresponding CL Application No. 202100061 (and English translation).
Office Action, dated Feb. 1, 2022, received in corresponding JP Application No. 2018548365 (and English translation).
Office Action, dated Sep. 20, 2022, received in corresponding JP Application No. 2018548365 (English translation).
Decision to Grant, dated Apr. 4, 2023, received in corresponding JP Application No. 2018548365 (English translation).
Office Action, dated Jul. 11, 2023, received in corresponding JP Application No. 2022075760 (English translation).
Office Action, dated Aug. 1, 2023, received in corresponding JP Application No. 2021500551 (English translation).
Office Action issued for U.S. Appl. No. 17/259,005, dated Sep. 7, 2022.
Notice of Allowance, issued for U.S. Appl. No. 17/259,005, dated Mar. 24, 2023.

LEN = Lenalidomide POM = Pomolidomide Thal = Thalidomide

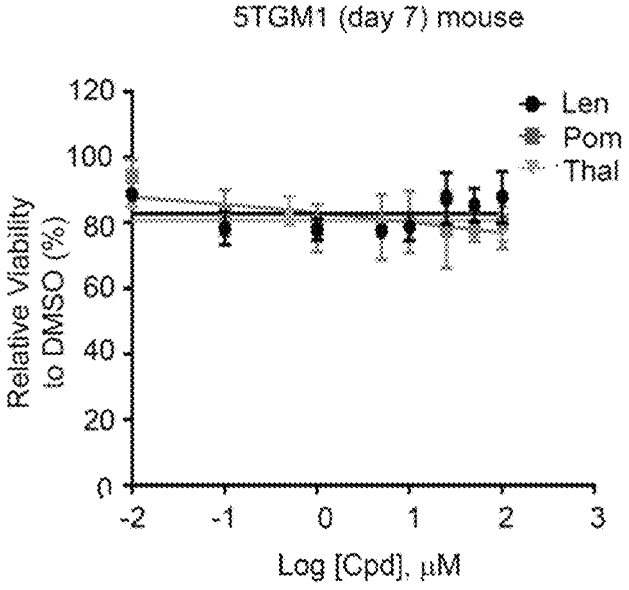
FIG. 5F
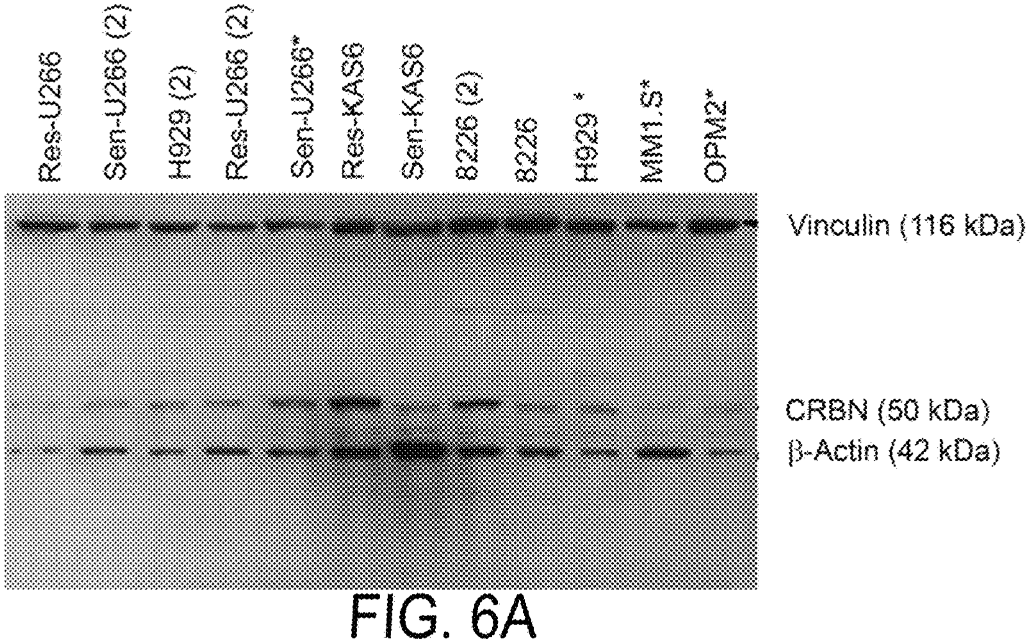
FIG. 6A
| Drug | $IC_{50}$ (μM) | | | |
|---|---|---|---|---|
| | H929 (day 4) | H929 (day 7) | U266 | MM1.S |
| Lenalidomide | >100 | 7.00 +/- 1.80 | 16.04 +/- 1.52 | 13.06 +/- 2.01 |
| Pomalidomide | 0.52 +/- 3.34 | 0.05 +/- 1.35 | 0.614 +/- 1.52 | 0.41 +/- 1.23 |
| Thalidomide | N/A | N/A | N/A | >100 |
FIG. 6B hCRBN
mCRBN
gCRBN
hmCRBN
RMSD
Rg Profile
RMSD (Angstrom)
Residue Number

```
human-WT 319 TSLCCKQCQETEITTKNEIFSLSLGPMAAYVNPHGYVHETLTVYKACNLNLIGRPSTEHS
hE377V       TSLCCKQCQETEITTKNEIFSLSLGPMAAYVNPHGYVHETLTVYKACNLNLIGRPSTVHS
hV388I       TSLCCKQCQETEITTKNEIFSLSLGPMAAYVNPHGYVHETLTVYKACNLNLIGRPSTEHS
hm           TSLCCKQCQETEITTKNEIFSLSLGPMAAYVNPHGYVHETLTVYKACNLNLIGRPSTVHS

human-WT     WFPGYAWTVAQCKICASHIGWKFTATKKDMSPQKFWGLTRSALLPT 425
hE377V       WFPGYAWTVAQCKICASHIGWKFTATKKDMSPQKFWGLTRSALLPT
hV388I       WFPGYAWTIAQCKICASHIGWKFTATKKDMSPQKFWGLTRSALLPT
hm           WFPGYAWTIAQCKICASHIGWKFTATKKDMSPQKFWGLTRSALLPT
```

FIG. 9A

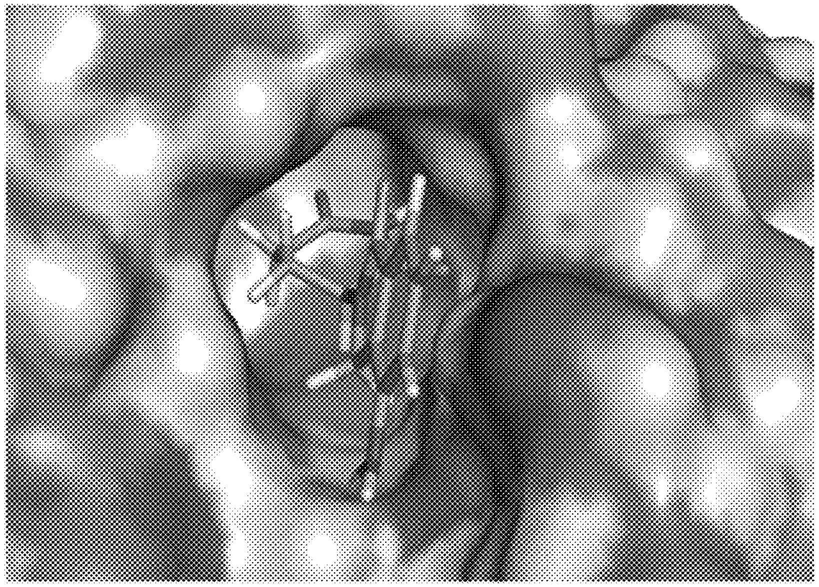

FIG. 9B

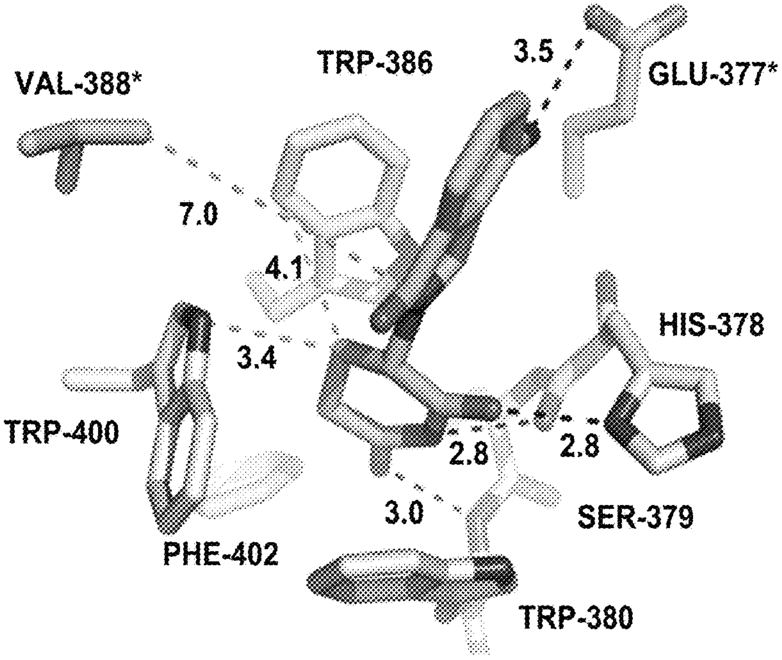

FIG. 9C

Cereblon targeting group (R=H)

BET targeting group dBET1 (R=H)
Me-dBET1 (R=Me)

SEQUENCE LISTING

```
<160> NUMBER OF SEQ ID NOS: 8

<210> SEQ ID NO 1
<211> LENGTH: 32
<212> TYPE: DNA
<213> ORGANISM: Artificial Sequence
<220> FEATURE:
<223> OTHER INFORMATION: SYNTHETIC CONSTRUCT

<400> SEQUENCE: 1

ccagtctgtg ttgtaaacag agccaagaaa cc                                32


<210> SEQ ID NO 2
<211> LENGTH: 32
<212> TYPE: DNA
<213> ORGANISM: Artificial Sequence
<220> FEATURE:
<223> OTHER INFORMATION: SYNTHETIC CONSTRUCT

<400> SEQUENCE: 2

ggtttcttgg ctctgtttac aacacagact gg                                32


<210> SEQ ID NO 3
<211> LENGTH: 38
<212> TYPE: DNA
<213> ORGANISM: Artificial Sequence
<220> FEATURE:
<223> OTHER INFORMATION: SYNTHETIC CONSTRUCT

<400> SEQUENCE: 3

ggttatgcat ggaccatcgc acagtgtaaa atttgtgc                          38
```

<210> SEQ ID NO 4
<211> LENGTH: 37
<212> TYPE: DNA
<213> ORGANISM: Artificial Sequence
<220> FEATURE:
<223> OTHER INFORMATION: SYNTHETIC CONSTRUCT

<400> SEQUENCE: 4
gcacaaattt tacactgtgc gatggtccat gcataac 37

<210> SEQ ID NO 5
<211> LENGTH: 38
<212> TYPE: DNA
<213> ORGANISM: Artificial Sequence
<220> FEATURE:
<223> OTHER INFORMATION: SYNTHETIC CONSTRUCT

<400> SEQUENCE: 5
cgtccgagca ccgaagcaag ctggtttccg ggttatgc 38

<210> SEQ ID NO 6
<211> LENGTH: 38
<212> TYPE: DNA
<213> ORGANISM: Artificial Sequence
<220> FEATURE:
<223> OTHER INFORMATION: SYNTHETIC CONSTRUCT

<400> SEQUENCE: 6
gcataacccg gaaaccagct tgcttcggtg ctcggacg 38

<210> SEQ ID NO 7
<211> LENGTH: 38
<212> TYPE: DNA
<213> ORGANISM: Artificial Sequence
<220> FEATURE:
<223> OTHER INFORMATION: SYNTHETIC CONSTRUCT

<400> SEQUENCE: 7
cgagcaccga acatagcgcg tttccgggtt atgcatgg 38

<210> SEQ ID NO 8
<211> LENGTH: 38
<212> TYPE: DNA
<213> ORGANISM: Artificial Sequence
<220> FEATURE:
<223> OTHER INFORMATION: SYNTHETIC CONSTRUCT

<400> SEQUENCE: 8
ccatgcataa cccggaaacg cgctatgttc ggtgctcg 38

SMALL MOLECULES AGAINST CEREBLON TO ENHANCE EFFECTOR T CELL FUNCTION

CROSS REFERENCE TO RELATED APPLICATIONS

This application is a continuation application of U.S. application Ser. No. 16/084,068, filed Sep. 11, 2018, which is a national stage application filed under 35 U.S.C. § of PCT/US2017/022711, filed Mar. 16, 2017, which claims the benefit of U.S. Provisional Patent Application No. 62/309,246, filed Mar. 16, 2016; U.S. Provisional Patent Application No. 62/395,757 filed Sep. 16, 2016; and U.S. Provisional Patent Application No. 62/454,028 filed Feb. 2, 2017, the disclosures of which are expressly incorporated herein by reference.

DESCRIPTION OF THE TEXT FILE SUBMITTED ELECTRONICALLY

The contents of the text file submitted electronically herewith are incorporated herein by reference in their entirety: A computer readable format copy of the Sequence 15 Listing (filename: 10645-005US2_SequenceListing, created on Jun. 7, 2022, file size 1.8 kilobyte).

BACKGROUND

Emerging from its beginnings as a catastrophic teratogen, analogs derived from thalidomide, known as immunomodulatory drugs (IMiDs), are now rapidly emerging for the treatment of cancer. One of the hallmarks of IMiD therapy is its association with T-lymphocytes activation (McDaniel, J. M. et al., *Advances in hematology* 2012:513702 (2012). One of the anti-cancer mechanisms posited for this drug class is an emergent immunological response against endogenous tumor-associated antigens that restores functional immunosurveillance against developing tumor cells. Numerous barriers impede anti-tumor immunity with complexity that has largely evolved to keep autoimmune recognition in check. Using a zebrafish model, thalidomide was shown to suppress an E3-ubiquitin ligase substrate receptor known as cereblon, which subsequently results in abnormal limb development (Ito, T. et al., *Science* 327(5971):1345 (2010)). Cereblon is conserved across all vertebrate species. It has been stated that "structural differences among IMiD drug analogs will influence the potency and selectivity of substrate recognition and degradation (Chamberlain et al). As yet, the physiological role of cereblon, with regard to involvement in immune regulation, has not yet been determined. Cereblon physiological role in T-cell signaling and homeostasis was demonstrated using homozygous crbn germline knockouts achieved by flp-mediated excision of exon 3 and 4 after mating with ovum promoter-Cre recombinase-expressing transgenic mice (Rajadhyaksha, A. M., et al. *Behavioural brain research* 226(2):428 (2012)). The knockout ablates crbn expression in tissues of hematopoietic origin. Peripheral blood and splenic lymphocytes with a naïve phenotype are increased in number in deficient mice compared to wild-type C57BL6 littermates with age. To explore the intrinsic threshold for activation of crbn−/− T-cells, in vitro studies and adoptive cell transfers were conducted into fully mismatched allogeneic host and sublethally-irradiated congenic mice. These studies show cereblon's role in regulating IL-2, IFNg and T-cell receptor activation. Using B16 melanoma, we demonstrate that the genetic ablation of cereblon leads to a significant delay in tumor growth. Our study sets the stage for future development of cereblon-specific targeted therapy for potentiation of immunotherapy in malignant diseases and establishes a novel mode of signaling regulation in T-cells. Many of the features associated with crbn deficiency are notable with IMiD therapy (McDaniel, J. M., et al. Id.; Luptakova, K. J., et al., *Cancer immunology, immunotherapy*: CII 62(1):39 (2013); Zhou, Y., et al., *American journal of hematology* 83 (2), 144 (2008)). Lenaliomide, one of the most immunologically active IMiDs was confirmed to bind to the CRBN-DDB1 complex using beads and quantitative mass spectrometry (MS) (Kronke, J., et al., *Science* 343(6168):301 (2014)).

SUMMARY

In accordance with the purposes of the disclosed materials and methods, as embodied and broadly described herein, the disclosed subject matter, in one aspect, relates to compounds, compositions and methods of making and using compounds and compositions.

The disclosed compounds can have a structure represented by Formula I:

Formula I

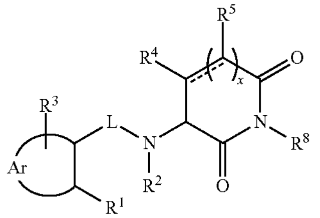

wherein,

Ar is cycloalkyl, aryl, heterocycloalkyl, or heteroaryl;

L is absent or a linker selected from the group consisting of —$SO_2$, —$SO_2$R'; $SO_2$R'R", —$SO_2$NR'R"; —$SO_2$NR'R"C(═O); —NR'$SO_2$R"; —R'$SO_2$NR'R'; —C(═O); —C(═O)R'; —OC(═O)R'; —C(═O)NR'R"; —NR'C(═O)R"; —NR'C(═O)R"C(═O); —OR'; —NR'R"; —SR'; —$N_3$—C(═O)OR'; —O(CR'R")$_r$C(═O)R'; —O(CR'R")$_r$NR"C(═O)R'; —O(CR'R")$_r$NR"$SO_2$R'; —OC(═O)NR'R"; —NR'C(═O)OR"; and substituted or unsubstituted $C_1$-$C_6$ aliphatic alkyl;

wherein R', R", and R'" are individually selected from hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6;

$R^1$, $R^2$, and $R^3$ are individually selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, substituted or unsubstituted alkenyl, substituted or unsubstituted alkynyl, substituted or unsubstituted cycloalkyl, substituted or unsubstituted heterocyclyl, and combinations thereof or wherein $R^1$ and $R^2$ combine to form a 5-7 membered heterocyclic ring; and wherein when $R^1$ and $R^2$ combine to form a 5-7 membered heterocyclic ring, Ar is optionally not fused to the 5-7 membered heterocyclic ring but is a substituent of the 5-7 membered heterocyclic ring;

$R^4$ and $R^5$ are individually selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof;

$R^8$ is selected from the group consisting of hydrogen, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, substituted or unsubstituted aryl, substituted or unsubstituted alkylaryl, and combinations thereof; and X is 0, 1, or 2.

The disclosed compounds can have a structure represented by Formula II:

Formula II

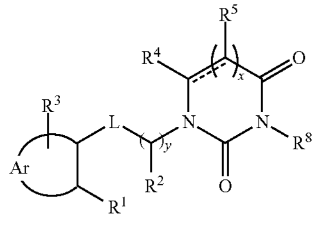

wherein,

Ar is aryl, cycloalkyl, heterocycloalkyl, or heteroaryl group;

L is absent or a linker selected from the group consisting of $—SO_2$, $—SO_2R'$; $SO_2R'R''$, $—SO_2NR'R''$; $—SO_2NR'R''C(═O)$; $—NR'SO_2R''$; $—R'SO_2NR'R'''$; $—C(═O)$; $—C(═O)R'$; $—OC(═O)R'$; $—C(═O)NR'R''$; $—NR'C(═O)R''$; $—NR'C(═O)R''C(═O)$; $—OR'$; $—NR'R''$; $—SR'$; $—N_3—C(═O)OR'$; $—O(CR'R'')_rC(═O)R'$; $—O(CR'R'')_rNR''C(═O)R'$; $—O(CR'R'')_rNR''SO_2R'$; $—OC(═O)NR'R''$; $—NR'C(═O)OR''$; and substituted or unsubstituted $C_1$-$C_6$ aliphatic alkyl;

wherein R', R'', and R''' are individually selected from hydrogen; substituted or unsubstituted alkyl; substituted or unsubstituted alkenyl; substituted or unsubstituted ether; substituted or unsubstituted cycloalkyl;

substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6;

$R^1$, $R^2$, and $R^3$ are individually selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, substituted or unsubstituted alkenyl, substituted or unsubstituted alkynyl, substituted or unsubstituted cycloalkyl, heterocyclyl, and combinations thereof or wherein $R^1$ and $R^2$ combine to form a 5-7 membered heterocyclic ring; and wherein when $R^1$ and $R^2$ combine to form a 5-7 membered heterocyclic ring, Ar is optionally not fused to the 5-7 membered heterocyclic ring but is a substituent of the 5-7 membered heterocyclic ring;

$R^4$ and $R^5$ are individually selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof;

$R^8$ is selected from the group consisting of hydrogen, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, substituted or unsubstituted aryl, substituted or unsubstituted alkylaryl, and combinations thereof; and x is 0, 1, or 2, y is from 1 to 6; and wherein the bond --- is present or absent.

The disclosed compounds can have a structure represented by Formula III:

Formula III

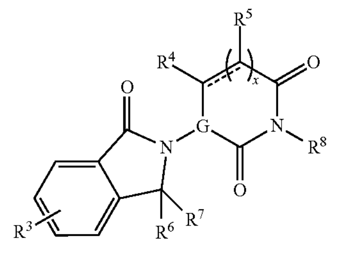

wherein,

G comprises C, S, N, substituted of unsubstituted $C_1$-$C_8$ alkyl, or combinations thereof;

$R^3$ is selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, substituted or unsubstituted cycloalkyl, and combinations thereof;

$R^4$, $R^5$, and $R^8$ are individually selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted aryl, substituted or unsubstituted alkylaryl, substituted or unsubstituted alkenyl, substituted or unsubstituted alkynyl, substituted or unsubstituted cycloalkyl, heterocyclyl, and combinations thereof; and $R^6$ and $R^7$ are individually =O, hydrogen, $C_1$-$C_8$ alkyl, or $R^6$ and $R^7$ combine to form =O;

x is 0, 1, or 2; and wherein the bond --- is present or absent.

The disclosed compounds can have a structure represented by Formula IV:

Formula IV

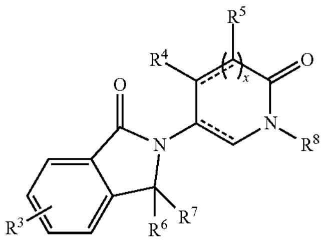

wherein, $R^3$ is selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, and combinations thereof;

$R^4$, $R^5$, and $R^8$ are individually selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted aryl, substituted or unsubstituted alkylaryl, substituted or unsubstituted alkenyl, substituted or unsubstituted alkynyl, substituted or unsubstituted cycloalkyl, heterocyclyl, and combinations thereof; and $R^6$ and $R^7$ are individually =O, hydrogen, $C_1$-$C_8$ alkyl, or $R^6$ and $R^7$ combine to form =O;

x is 0, 1, or 2; and wherein the bond --- is present or absent.

The disclosed compounds can have a structure represented by Formula V:

Formula V

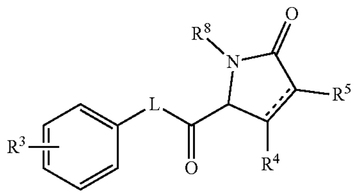

wherein,

L is absent or a linker selected from the group consisting of —$SO_2$, —$SO_2$R'; $SO_2$R'R", —$SO_2$NR'R"; —$SO_2$NR'R"C(=O); —NR'$SO_2$R"; —R'$SO_2$NR'R'; —C(=O); —C(=O)R'; —OC(=O)R'; —C(=O)NR'R"; —NR'C(=O)R"; —NR'C(=O)R"C(=O); —OR'; —NR'R"; —SR'; —$N_3$—C(=O)OR'; —O(CR'R")$_r$C(=O)R'; —O(CR'R")$_r$NR"C(=O)R'; —O(CR'R")$_r$NR"$SO_2$R'; —OC(=O)NR'R"; —NR'C(=O)OR"; and substituted or unsubstituted $C_1$-$C_6$ aliphatic alkyl;

wherein R', R", and R"' are individually selected from hydrogen; substituted or unsubstituted alkyl; substituted or unsubstituted alkenyl; substituted or unsubstituted ether; or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6;

$R^3$, $R^4$, and $R^5$ are individually selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, substituted or unsubstituted alkenyl, substituted or unsubstituted alkynyl, substituted or unsubstituted cycloalkyl, and combinations thereof; and $R^8$ is selected from the group consisting of hydrogen, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, substituted or unsubstituted aryl, substituted or unsubstituted alkylaryl, and combinations thereof.

The disclosed compounds can have a structure represented by Formula VI:

Formula VI

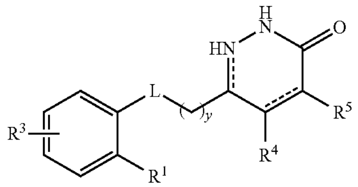

wherein,

L is absent or a linker selected from the group consisting of —$SO_2$, —$SO_2$R'; $SO_2$R'R", —$SO_2$NR'R"; —$SO_2$NR'R"C(═O); —NR'$SO_2$R"; —R'$SO_2$NR'R'"; —C(═O); —C(═O)R'; —OC(═O)R'; —C(═O)NR'R"; —NR'C(═O)R"; —NR'C(═O)R"C(═O); —OR'; —NR'R"; —SR'; —$N_3$—C(═O)OR'; —O(CR'R")$_r$C(═O)R'; —O(CR'R")$_r$NR"C(═O)R'; —O(CR'R")$_r$NR"$SO_2$R'; —OC(═O)NR'R"; —NR'C(═O)OR"; and substituted or unsubstituted $C_1$-$C_6$ aliphatic alkyl;

wherein R', R", and R'" are individually selected from hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6; and $R^1$, $R^3$, $R^4$, and $R^5$ are individually selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, and combinations thereof;

y is 0, 1, or 2; and wherein the bond --- is present or absent.

In specific aspects, the disclosed subject matter relates to methods for reducing the risk of, preventing, or treating a subject having an autoimmune disease or disorder. In other specific aspects, the disclosed subject matter relates to methods for inducing degradation of a target protein in a cell. In other specific aspects, the disclosed subject matter relates to methods for reducing the risk of, preventing, or treating a disease state or condition in a patient wherein dysregulated protein activity is responsible for said disease state or condition. In other specific aspects, the disclosed subject matter relates to methods for inhibiting a cereblon E3 Ubiquitin Ligase binding moiety (CLM), the method comprising administering an effective amount of a compound according to any one of the preceding claims. In other specific aspects, the disclosed subject matter relates to methods for reducing the risk of, preventing, or treating cancer in a subject. In other specific aspects, the disclosed subject matter relates to methods for treating a genetic disease or disorder in a subject.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

FIG. 4A shows the relative IL-2 mRNA production with increasing concentrations anti-CD3 (0.01-10 μg/mL) stimulation. FIG. 4B shows IL-2 secretion by ELISA in unstimulated cells and after treatment with anti-CD3 (5 μg/mL) with increasing concentrations of lenalidomide. FIG. 4C shows proliferation in human T cells and FIG. 4**D shows mouse T cells treated with DMSO (vehicle) or lenalidomide (10 μM) measured by S-phase transition as indicated by incorporation of Bromodeoxyuridine (BrdU) with detection by flow-cytometry in cells stained for CD8+ surface expression.

FIGS. 5A-5F show IMiDs inhibit growth of human but not mouse multiple myeloma cells. FIG. 5A shows relative expression of CRBN/vinculin in human multiple myeloma cell lines U266, H929, MM1.S and OPM2. Human multiple myeloma cell lines (FIGS. 5B-5F) were cultured for 4 days (FIG. 5B) or 7 days (FIGS. 5C-5F) with increasing concentrations of lenalidomide (Len), pomalidomide (Pom) and vehicle (DMSO). 5TGM1 is a mouse multiple myeloma cell line treated simultaneously with MM1.S. Percentage relative cell viability is shown.

FIGS. 6A-6B are western blot analysis and IMiD compound sensitivity of multiple myeloma cells. FIG. 6B shows a raw western blot for vinculin (116 kDa), CRBN (50 kDa) and β-actin (42 kDa) protein in several sensitive and resistant human multiple myeloma cell lines. Resistant but not sensitive U266 cells were subsequently found to contain mycoplasma contamination and were not used further. FIG. 6B shows $IC_{50}$ (μM) for lenalidomide, pomalidomide, and thalidomide ±S.D. in H929, U266, and MM1.S multiple myeloma cells. N/A=not available.

FIG. 7A shows ribbon overlays of human (purple, PDB 4TZ4), chicken (blue, PDB 4CI2) X-ray crystal structures and post-MD structure of mouse (PDB 4TZ4) cereblon with residues His378, Trp380, Trp400, Tyr402 and ligands thalidomide, lenalidomide and pomalidomide shown for reference. FIG. 7B shows superposition of ligand poses of lenalidomide for the post-MD equilibrated systems of the CRBN thalidomide binding site after induced fit docking (IFD) for hCRBN, hmCRBN, gCRBN, shown with the post-MD equilibrated protein structure of hCRBN (red) shown for reference. FIG. 7C are overlays of human and mouse cereblon (Val380 and Ile391 for mCRBN; Glu377 and Val388 for hCRBN), are demarcated as thin tubes.

FIG. 8A shows RMSD profiles of hCRBN. Profiles were created using backbone atoms and were calculated with hCRBN-DDB1 complex (Bottom Graph), hCRBN alone (Middle Graph), and binding site residues N335 to A421 (Top Graph). All measurement units are in Angstroms. FIG. 8Q shows distance between various moieties and ligand as a function of time.

FIGS. 9A-9K shows human and mouse CRBN binds IMiDs with similar affinities. FIG. 9A shows sequence alignment of human CRBN and human to mouse mutations. Mutations introduced to convert human to mouse are highlighted in red. FIG. 9B shows IMiD interaction in the hydrophobic binding pocket. FIG. 9C shows lenalidomide (green) interacts with the TBD site (gray) through hydrogen bonds (dashed black lines) with backbone residues His378, Ser379 and Trp380 VDW interactions (dashed green lines) occur with the side-chains of Trp380, Trp386, Trp400, and Tyr402 (mouse: Trp383, Trp389, Trp403, and Phe405). The two residues differing between the human and the mouse proteins are highlighted in cyan. Titration of human TBD (FIG. 9D) wild type, (FIG. 9E) E377V, (FIG. 9F) V388I, and (FIG. 9G) E377V/V388I (hm-CRBN-TBD) to lenalidomide (red), pomalidomide (green), thalidomide (blue) and phthalimide (black) by intrinsic tryptophan fluorescence assay. $K_D$ values were calculated based on the magnitude of fluorescence differences ($1-F/F_0$). FIGS. 9H-9K shows isothermal titration calorimetry saturation curve using lenalidomide (LEN) for human TBD and mutants.

FIG. 10A shows SDS-PAGE gel showing purification steps: L: ladder, A: total lysate, B: soluble lysate, C: after $1^{st}$ GST purification, D: GST-cleavage mixture, E: $2^{nd}$ GST purification, F: $1^{st}$ size exclusion chromatography (SEC), G: $3^{rd}$ GST, and H: final SEC. FIG. 10B shows expression of recombinant TBD with Cys to Ser mutations.

T is the total lysate and S is the soluble protein extract. FIG. 10C shows structure of human TBD (PDB 4CI2) in green, showing coordination of the zinc ion (red sphere) to the four cysteine residues. FIG. 10D shows schematic of the zincon assay: zincon dye absorbs at 480 nm and upon chelation with zinc absorbs at 620-630 nm). FIG. 10E shows wavelength scans showing a decrease at 480 nm and concomitant increase at 630 nm upon incremental addition of zinc. FIG. 10F shows linear regression curve obtained from FIG. 10E.

FIGS. 13E and 13F show schematic view of lenalidomide interaction in the binding pocket of full-length human cereblon; human full-length CRBN (salmon) and DDB1 (blue) with bound lenalidomide (magenta) (PDB 5FQD), superimposed with mouse TBD-CRBN (cyan) (PDB 4TZU). Hydrogen bonds and hydrophobic interactions are shown in red and black dashed lines, respectively.

FIG. 14A shows structure of dBET1 and N-methyl-dBET1. FIG. 14B shows saturation binding curves of human TBD wild type titrated with JQ1, dBET1, m-dBET1 and lenalidomide (LEN) by fluorescence assay. FIG. 14C shows human T cells purified from PBMCs activated by anti-CD3ε/CD28 treated with JQ1, dBET and DMSO for 72 h and cell viability determined by flow cytometry (calculated using Zombie NIR™ staining). FIG. 14D shows purified Crbn$^{+/+}$ and Crbn$^{-/-}$ mouse T cells activated by anti-CD3ε/CD28- and treated with JQ1 (at indicated doses) for 72 h. C-Myc mRNA levels were determine by qRT-PCR and normalized to 02M expression (control gene). FIG. 14E shows percentage of T cells expressing CD98 on the cell surface, FIG. 14F cell viability (indicated by 7-AAD negative cells) and FIG. 14G percentage of cells divided (calculated using CellTrace Violet staining) as determined by flow cytometry.

FIG. 15A shows purified Crbn$^{+/+}$ mouse CD8+ T cells activated by anti-CD3ε/CD28- and treated with JQ1 (at indicated doses) for 72 h. C-Myc mRNA levels were determine by qRT-PCR and normalized to β2M expression (control gene). FIG. 15B shows percentage of T cells expressing CD98 on the cell surface, FIG. 15C cell viability (indicated by 7-AAD negative cells) and FIG. 15D percentage of cells divided (calculated using CellTrace Violet staining) as determined by flow cytometry. FIG. 15E shows human and mouse T cells were activated with α-CD3ε/CD28, 12 h after activation cells were treated with increasing concentrations of dBET1 for 12 h. Protein expression levels of BRD4, c-Myc, CRBN, β-actin were determined by western blot FIG. 15F MM1.S and 5TGM cells were treated with increasing concentrations of dBET1 for 24 hours. Protein expression levels of BRD4, c-Myc, CRBN, β-actin were determined by western blot.

DETAILED DESCRIPTION

Figure 1:
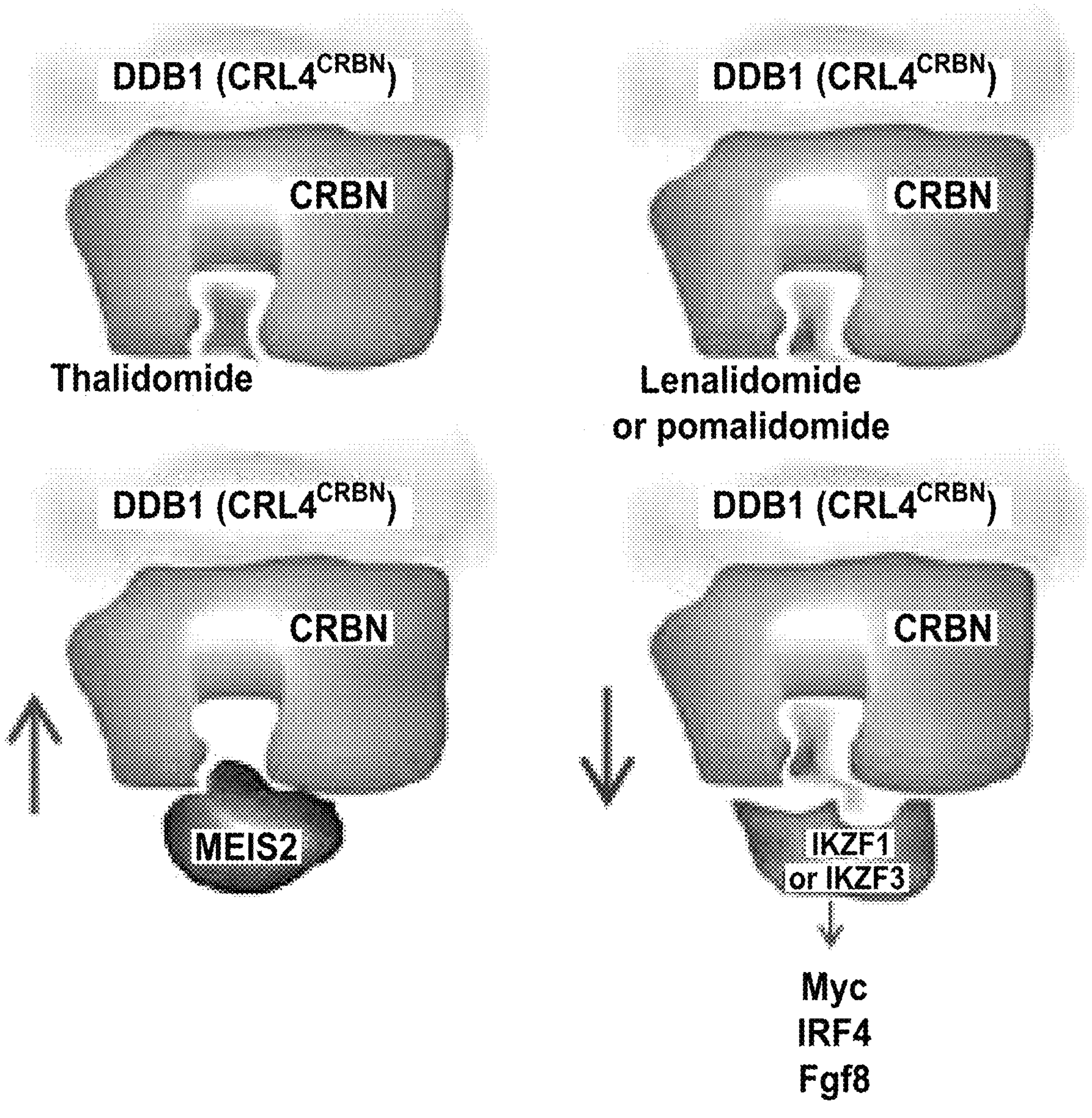
FIG. 1 is a schematic diagram showing a current model of IMiD Mode of Action.

The materials, compounds, compositions, and methods described herein may be understood more readily by reference to the following detailed description of specific aspects of the disclosed subject matter, the Figures, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A^n$ is used herein as merely a generic substitutent in the definitions below.

The term "alkoxy" as used herein is an alkyl group bound through a single, terminal ether linkage; that is, an "alkoxy" group can be defined as $-OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This may be presumed in structural formulae herein wherein an asymmetric alkene is present, or it may be explicitly indicated by the bond symbol C═C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

"Aryl", as used herein, refers to 5-, 6- and 7-membered aromatic rings. The ring can be a carbocyclic, heterocyclic, fused carbocyclic, fused heterocyclic, bicarbocyclic, or biheterocyclic ring system, optionally substituted as described above for alkyl. Broadly defined, "Ar", as used herein, includes 5-, 6- and 7-membered single-ring aromatic groups that can include from zero to four heteroatoms. Examples include, but are not limited to, benzene, pyrrole, furan, thiophene, imidazole, oxazole, thiazole, triazole, pyrazole, pyridine, pyrazine, pyridazine and pyrimidine. Those aryl groups having heteroatoms in the ring structure can also be referred to as "heteroaryl", "aryl heterocycles", or "heteroaromatics".

The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, and —CN. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles, or both rings are aromatic.

"Alkylaryl" or "aryl-alkyl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, containing carbon and one to four heteroatoms each selected from non-peroxide oxygen, sulfur, and N(Y) wherein Y is absent or is H, O, ($C_{1-4}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms containing carbon and 1, 2, 3, or 4 heteroatoms each selected from non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl include, but are not limited to, furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C═O.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O— alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The terms "amine" and "amino" are art-recognized and refer to both unsubstituted and substituted amines, e.g., a moiety that can be represented by the general formula: $—NR_9R_{10}$ or $NR_9R_{10}R'_{10}$, wherein $R_9$, $R_{10}$, and $R'_{10}$ each independently represent a hydrogen, an alkyl, an alkenyl, $—(CH_2)_m—R's$ or $R_9$ and $R_{10}$ taken together with the N atom to which they are attached complete a heterocycle having from 4 to 8 atoms in the ring structure; R's represents an aryl, a cycloalkyl, a cycloalkenyl, a heterocycle or a polycycle; and m is zero or an integer in the range of 1 to 8. In some embodiments, only one of $R_9$ or $R_{10}$ can be a carbonyl, e.g., $R_9$, $R_{10}$ and the nitrogen together do not form an imide. In some embodiments, the term "amine" does not encompass amides, e.g., wherein one of $R_9$ and $R_{10}$ represents a carbonyl. In some embodiments, $R_9$ and $R_{10}$ (and optionally $R'_{10}$) each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula $—CONR_9R_{10}$ wherein $R_9$ and $R_{10}$ are as defined above.

"Halogen", as used herein, refers to fluorine, chlorine, bromine, or iodine.

The term "carboxylic acid" as used herein is represented by the formula —C(O)OH. A "carboxylate" as used herein is represented by the formula —C(O)O—.

The term "ester" as used herein is represented by the formula $—OC(O)A^1$ or $—C(O)OA^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula $—NO_2$.

The term "cyano" as used herein is represented by the formula —CN

The term "azido" as used herein is represted by the formula $—N_3$.

The term "sulfonyl" is used herein to refer to the sulfo-oxo group represented by the formula $—S(O)_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula $—S(O)_2NH_2$.

The term "thiol" as used herein is represented by the formula —SH.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aryloxy, substituted aryloxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

It is to be understood that the compounds provided herein may contain chiral centers. Such chiral centers may be of either the (R—) or (S—) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R—) form is equivalent, for compounds that undergo epimerization in vivo, to administration of the compound in its (S—) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples and Figures.

Compounds

Disclosed herein are compounds comprising an E3 Ubiquitin Ligase binding moiety ("ULM") that is a cereblon E3 Ubiquitin Ligase binding moiety ("CLM"). The compounds disclosed herein can be grouped into various classes. For example, the compounds can include the classes:

Class 2A
Glutarimide-amide
Glutarimide-sulfonamide

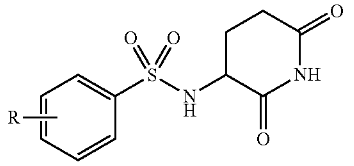

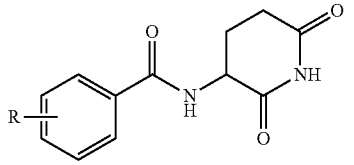

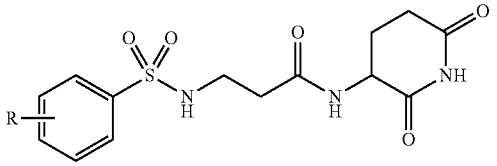

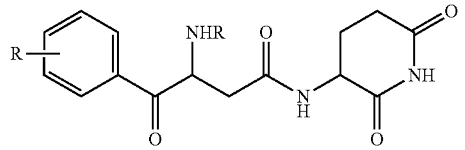

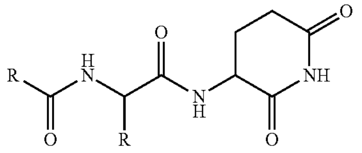

Class 2B
Glutarimide-amine

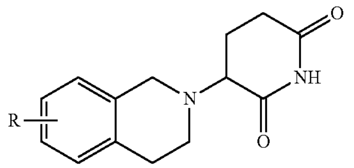

-continued
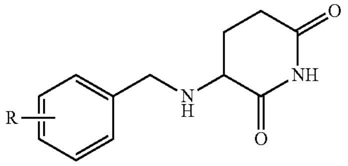
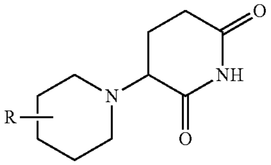
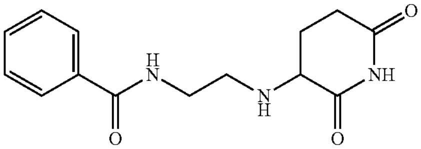
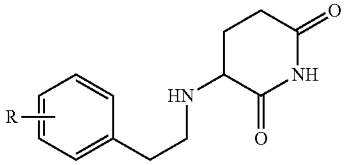
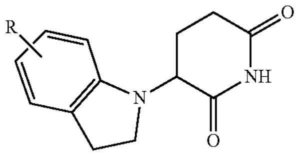
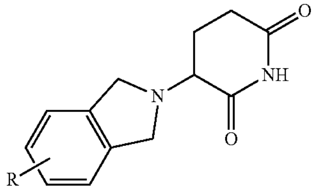
Class 3
Uracil
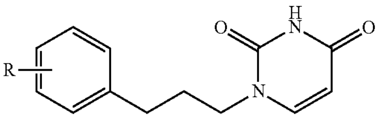
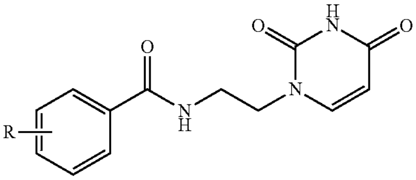
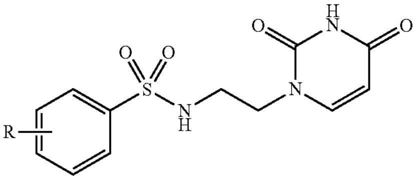
Class 4
Dihydrouracil
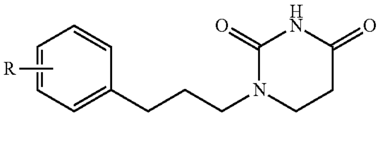
-continued
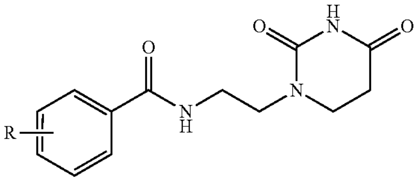
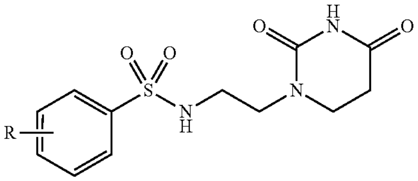
Class 5 Other
Pyroglutaramide
Pyridinone
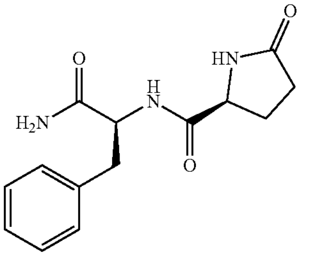
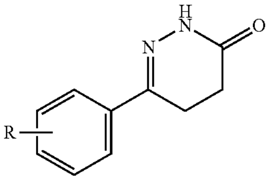
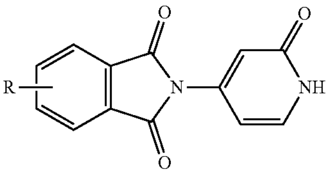
Class 6
Succinimides
Hydantoins
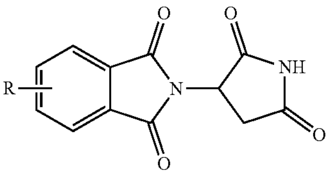
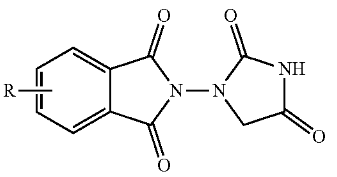
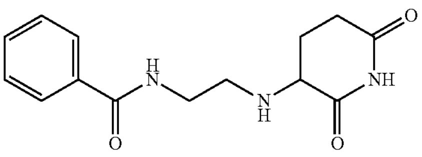

-continued
Class 7
N-alkyl imides
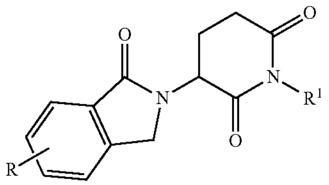
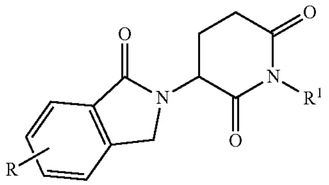
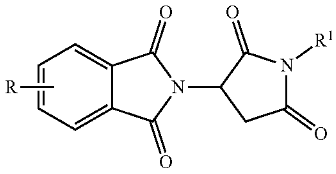
$R^1$ = alkyl, alkylaryl
Acyclic imides/amides
SY1-184
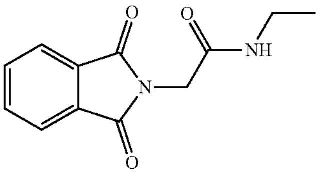
SY2-002
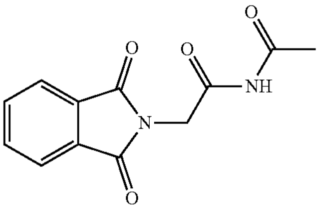
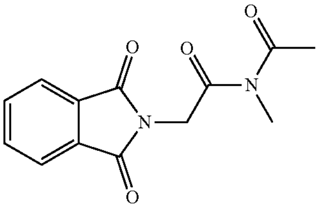
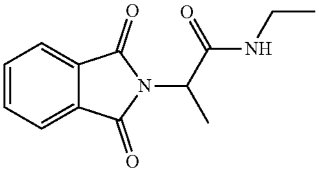
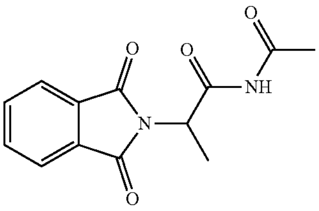
-continued
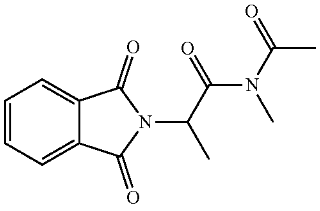
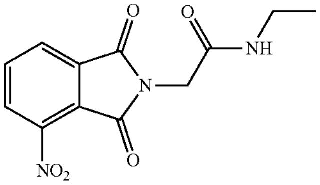
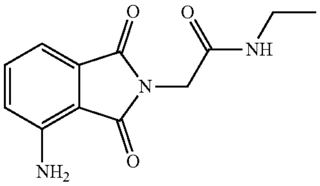
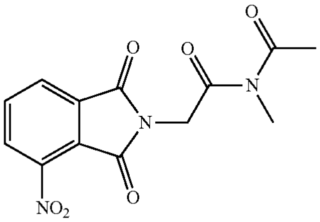
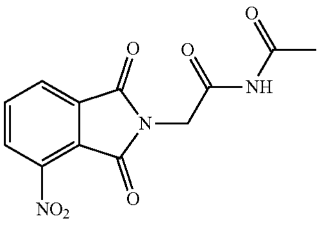
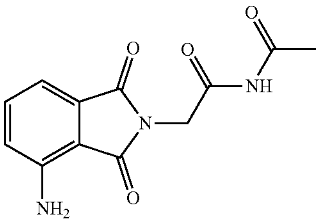
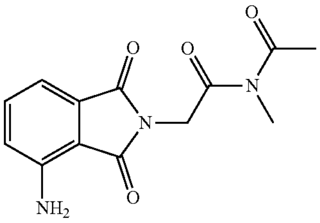
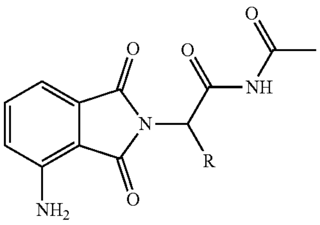

-continued

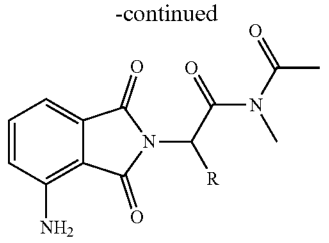

R = Me, Et, Pr, i-Pr, etc.

In some aspects, the compounds disclosed herein can be represented by Formula I: wherein, Formula I

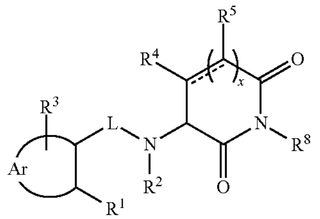

Ar is aryl, cycloalkyl, heterocycloalkyl, or heteroaryl group;

L is absent or a linker selected from the group consisting of —$SO_2$, —$SO_2$R'; $SO_2$R'R", —$SO_2$NR'R"; —$SO_2$NR'R"C(═O); —NR'$SO_2$R"; —R'$SO_2$NR'R'"; —C(═O); —C(═O)R'; —OC(═O)R'; —C(═O)NR'R"; —NR'C(═O)R"; —NR'C(═O)R"C(═O); —OR'; —NR'R"; —SR'; —$N_3$—C(═O)OR'; —O(CR'R")$_r$C(═O)R'; —O(CR'R")$_r$NR"C(═O)R'; —O(CR'R")$_r$NR"$SO_2$R'; —OC(═O)NR'R"; —NR'C(═O)OR"; and substituted or unsubstituted $C_1$-$C_6$ aliphatic alkyl;

wherein R', R", and R'" are individually selected from hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6;

$R^1$, $R^2$, and $R^3$ are individually selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, and combinations thereof or wherein $R^1$ and $R^2$ combine to form a 5-7 membered heterocyclic ring; and wherein when $R^1$ and $R^2$ combine to form a 5-7 membered heterocyclic ring, Ar is optionally not fused to the 5-7 membered heterocyclic ring but is a substituent of the 5-7 membered heterocyclic ring;

$R^4$ and $R^5$ are individually selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof;

$R^8$ is selected from the group consisting of hydrogen, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, substituted or unsubstituted aryl, substituted or unsubstituted alkylaryl, and combinations thereof; and x is 0, 1, or 2.

In some examples of Formula I, Ar can include an aromatic group such phenyl, pyrrolyl, furanyl, thiophenyl, imidazolyl, oxazolyl, thiazolyl, triazolyl, pyrazolyl, pyridinyl, pyrazinyl, pyridazinyl, pyrazolyl, oxazoyl, isoxazoyl, or pyrimidinyl, furyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide), isoquinolinyl, quinolinyl, piperidine, piperazine, pyrimidine, thiane, thiopyran, morpholine, oxazine, tetrahydropyran, pyrolidine, pyroline, imidazoline, pyrazoline, indoline, benzofuran, indoline, indole In certain specific examples, Ar includes phenyl.

In certain specific examples, Ar includes isoquinolinyl or quinolinyl.

In certain specific examples, Ar piperidine.

The Ar group can be substituted or unsubstituted. For example, the substituent on Ar can be selected from hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof. In certain embodiments, the substituent on Ar can be selected from H, Cl, F, Br, I, CN, $NO_2$, $NH_2$, $CF_3$, $CO_2H$, $CO_2NH_2$, $CO_2NHR^5$, $CO_2R^5$, C(O)$R^5$, C(O)$NH_2$, C(O)$NHR^5$, and $C_1$-$C_6$ alkyl optionally substituted with alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol.

In certain specific examples, Ar is substituted with $NO_2$, $NH_2$, OH, alkyl, aryl, halogen, amide, ether, or a combination thereof.

In the disclosed compounds of Formula I, there can be from 1 to 5 different substituents $R^3$, e.g., 1, 2, 3, 4, or 5 $R^3$ substituents. The substituents can be the same or different. In specific examples, $R^3$ is $SO_2NH_2$, $SO_2NHR'$, or $NHSO_2R'$, wherein R' is $C_1$-$C_6$ alkyl or $C_1$-$C_6$ cycloalkyl optionally substituted with $C_1$-$C_6$ alkyl, $C_1$-$C_6$ alkoxyl, hydroxyl, or halide. In other examples, $R^3$ is NHC(O)R', wherein R' is $C_1$-$C_6$ alkyl or $C_1$-$C_6$ cycloalkyl optionally substituted with $C_1$-$C_6$ alkyl, $C_1$-$C_6$ alkoxyl, cycloalky, cycloheteroalkyl, hydroxyl, or halide. In other examples, $R^3$ is $C_1$-$C_6$ alkyl or $C_1$-$C_6$ cycloalkyl. In other examples, $R^3$ is $C_1$-$C_6$ alkoxyl. In other examples, $R^3$ is halide. In other examples, n is 2 and each $R^3$ is selected from the group consisting of $C_1$-$C_6$ alkyl, $C_1$-$C_6$ alkoxyl, halide, $SO_2NH_2$, $SO_2NHR'$, and $NHSO_2R'$, wherein R' is $C_1$-$C_6$ alkyl or $C_1$-$C_6$ cycloalkyl optionally substituted with $C_1$-$C_6$ alkyl, $C_1$-$C_6$ alkoxyl, hydroxyl, or halide. In other examples, $R^3$ is hydrogen, halogen, hydroxyl, substituted or unsubstituted amine, substituted or unsubstituted amide, nitro, ester, morpholino, dioxolane, substituted or unsubstituted $C_1$-$C_6$ alkyl, or combinations thereof.

In some examples of Formula I, L is absent. In other examples of Formula I, L is a linker. When L is present, L can be $SO_2$, —$SO_2R'$; —$SO_2R'R''$, —$SO_2NR'R''$; —$SO_2NR'R''C(=O)$; —$NR'SO_2R''$; $R'SO_2NR'R'$; C(=O); C(=O)R'; —OC(=O)R'; —C(=O)NR'R''; —NR'C(=O)R''; —NR'C(=O)R''C(=O); substituted or unsubstituted $C_1$-$C_6$ aliphatic alkyl, wherein R', R'', and R' are individually selected from hydrogen; substituted or unsubstituted alkyl; substituted or unsubstituted alkenyl; substituted or unsubstituted ether substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6.

In some specific examples of Formula I, R', R'', and R''' can be individually selected from hydrogen; substituted or unsubstituted $C_1$-$C_8$ alkyl; substituted or unsubstituted $C_1$-$C_8$ ether; or substituted or unsubstituted amine.

In some embodiments of Formula I, $R^1$ can be hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, and combinations thereof. For example, $R^1$ can be selected from H, Cl, F, Br, I, CN, $NO_2$, $NH_2$, $CF_3$, $CO_2H$, $CO_2NH_2$, $CO_2NHR^5$, $CO_2R^5$, $C(O)R^5$, $C(O)NH_2$, $C(O)NHR^5$, and $C_1$-$C_6$ alkyl optionally substituted with alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol.

In certain specific examples, $R^1$ can be hydrogen, halogen, hydroxyl, substituted or unsubstituted amine, substituted or unsubstituted amide, nitro, ester, morpholino, dioxolane, substituted or unsubstituted $C_1$-$C_6$ alkyl, and combinations thereof.

In other specific examples, $R^1$ can be selected from the group consisting of hydrogen, substituted or unsubstituted amine, substituted or unsubstituted $C_1$-$C_6$ alkyl, and combinations thereof.

In some embodiments of Formula I, $R^2$ can be hydrogen, halogen, hydroxyl, azide, alkoxyl, sulfhydryl, carbonyl, carboxyl, cyano, silyl, ether, alkylthio, sulfonyl, sulfonamido, ketone, aldehyde, substituted or unsubstituted amine, substituted or unsubstituted amide, nitro, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, and combinations thereof. For example, $R^2$ can be selected from H and $C_1$-$C_6$ alkyl optionally substituted with alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol.

In some embodiments of Formula I, $R^1$ and $R^2$ can combine to form a 5-7 membered heterocyclic ring. When $R^1$ and $R^2$ combine to form a 5-7 membered heterocyclic ring, L can be absent or present.

In some embodiments of Formula I, $R^4$ is selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof.

In some embodiments of Formula I, $R^5$ is selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof.

In specific embodiments of Formula I, $R^4$ and $R^5$ are both hydrogen. In some embodiments of Formula I, one of $R^4$ and $R^5$ are hydrogen.

In certain specific examples, x is 0.

In certain specific examples, x is 1.

In some embodiments of Formula I, the compound can have a structure as represented by Formula I-A:

Formula I-A

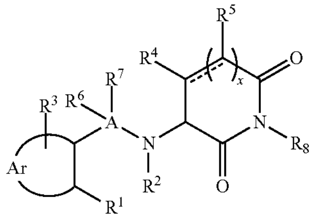

wherein,

A comprises C, S; substituted of unsubstituted $C_1$-$C_8$ alkyl, or combinations thereof; and $R^6$ and $R^7$ are individually =O, hydrogen, $C_1$-$C_8$ alkyl, or $R^6$ and $R^7$ combine to form =O.

In some embodiments of Formula I-A, the compound can have a structure as represented by Formula I-A-1:

Formula I-A-1

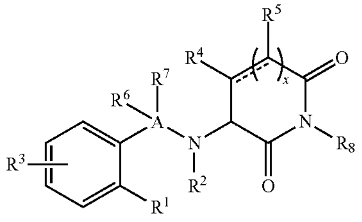

wherein,

A comprises C, S; substituted of unsubstituted $C_1$-$C_8$ alkyl, or combinations thereof;

$R^1$, $R^2$, and $R^3$ are individually selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, and combinations thereof; and $R^6$ and $R^7$ are individually =O, hydrogen, $C_1$-$C_8$ alkyl, or $R^6$ and $R^7$ combine to form =O.

In some examples of Formula I-A, the compound can have a structure as represented below:

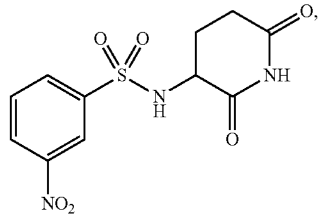

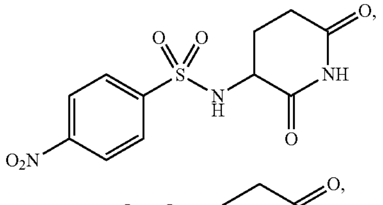

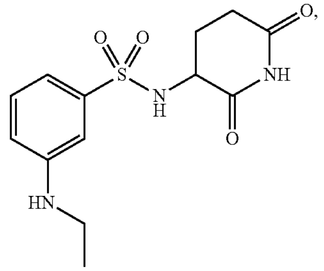

-continued

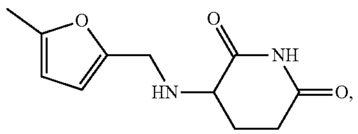

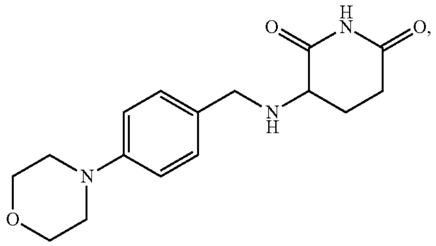

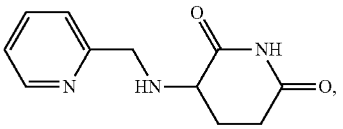

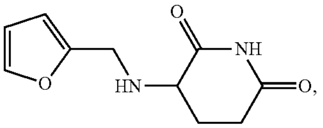

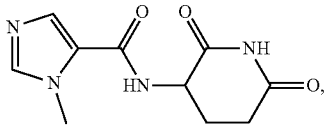

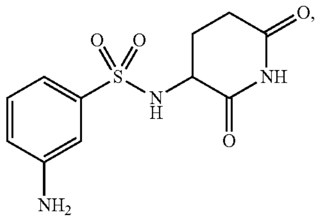

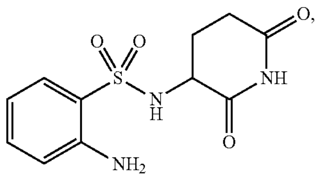

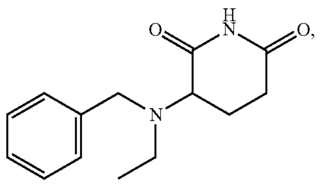

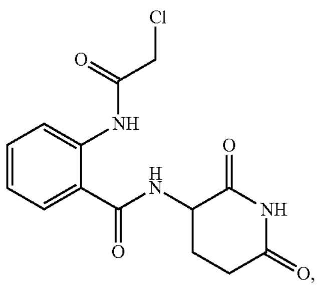

-continued

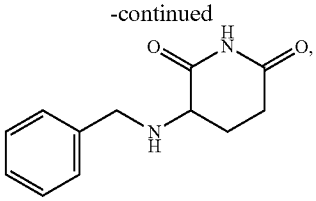

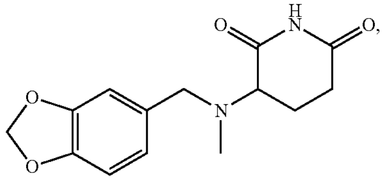

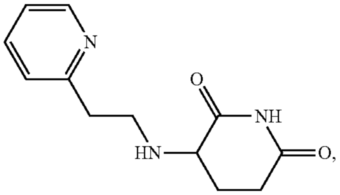

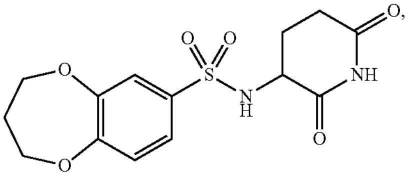

or

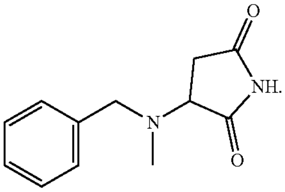

In some embodiments of Formula I, the compound can have a structure as represented by Formula I-B:

Formula I-B

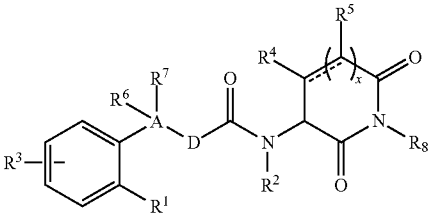

wherein,

A comprises C, S, N, substituted of unsubstituted $C_1$-$C_8$ alkyl, or combinations thereof;

D is —NR', carbonyl, substituted of unsubstituted $C_1$-$C_8$ alkyl, or substituted of unsubstituted $C_1$-$C_8$ ether; and $R^6$ and $R^7$ are individually =O, hydrogen, $C_1$-$C_8$ alkyl, or $R^6$ and $R^7$ combine to form =O.

In some examples of Formula I-B, $R^1$ is selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof.

In some examples of Formula I-B, $R^1$ is hydrogen, imino, amido, carbonyl, carboxyl, cyano, substituted or unsubstituted alkyl, or substituted or unsubstituted alkylhalide.

In some examples of Formula I-B, $R^2$ is selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof.

In some examples of Formula I-B, $R^2$ is hydrogen, substituted or unsubstituted alkyl, or substituted or unsubstituted alkylhalide.

In some examples of Formula I-B, $R^3$ is selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, and combinations thereof.

In some embodiments of Formula I-B, the compound can have a structure as represented below:

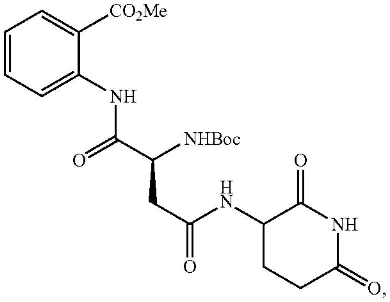

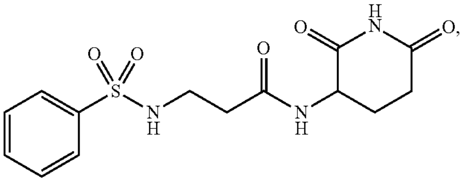

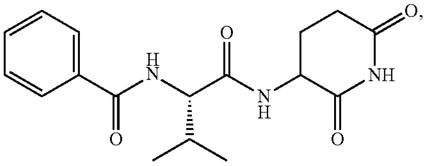

or

-continued

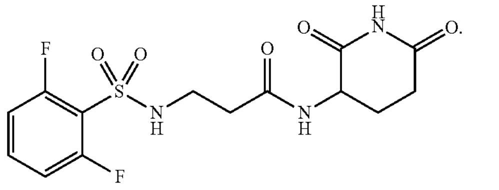

In some embodiments of Formula I, the compound can have a structure as represented by Formula I-C:

Formula I-C

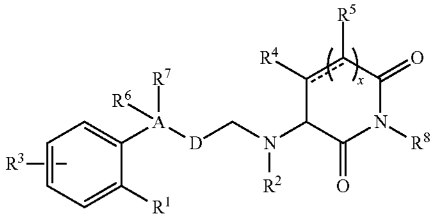

wherein,

A comprises C, S, N, substituted of unsubstituted $C_1$-$C_8$ alkyl, or combinations thereof;

D is —NR', carbonyl, or substituted of unsubstituted $C_1$-$C_8$ alkyl;

$R^6$ and $R^7$ are individually =O, hydrogen, $C_1$-$C_8$ alkyl, or $R^6$ and $R^7$ combine to form =O.

In some embodiments of Formula I-C, the compound can have a structure as represented below:

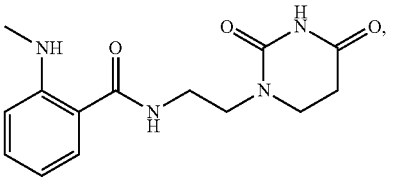

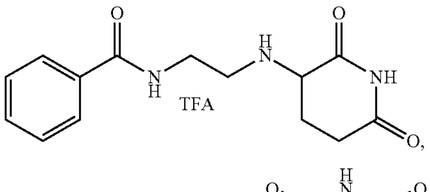

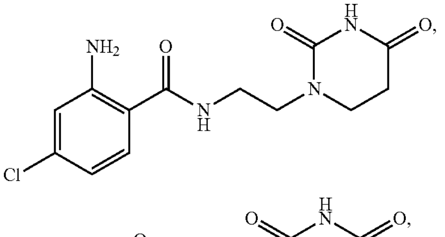

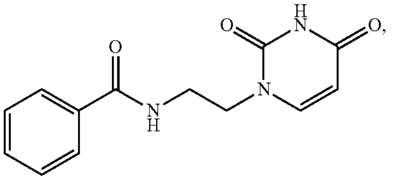

-continued

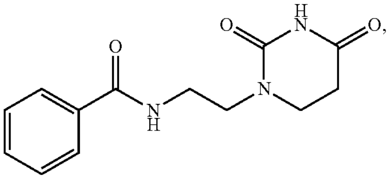

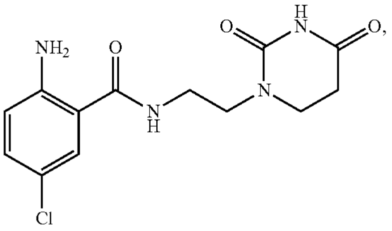

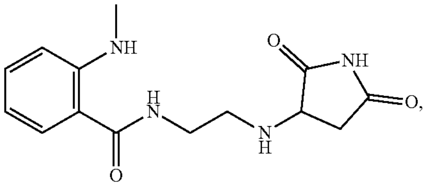

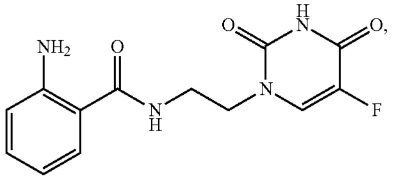

or

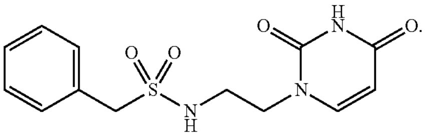 [SMILES: O=c1ccn(CCNS(=O)(=O)Cc2ccccc2)c(=O)[nH]1]

In some embodiments of Formula I, the compound can have a structure as represented by Formula I-D:

Formula I-D

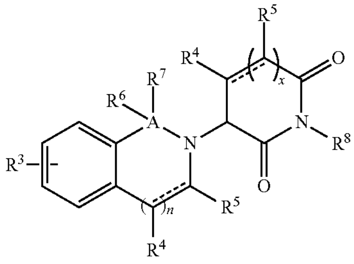

wherein,

A is absent or comprises C, S, N, substituted of unsubstituted $C_1$-$C_8$ alkyl, or combinations thereof;

$R^6$ and $R^7$ are individually =O, hydrogen, $C_1$-$C_8$ alkyl, or $R^6$ and $R^7$ combine to form =O; and n and y are independently 0, 1, or 2.

In some embodiments of Formula I, the compound can have a structure as represented by Formula I-E:

Formula I-E

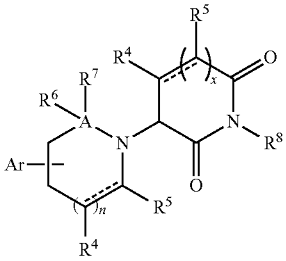

wherein,

A is absent or comprises C, S, N, substituted of unsubstituted $C_1$-$C_8$ alkyl, or combinations thereof;

$R^6$ and $R^7$ are individually =O, hydrogen, $C_1$-$C_8$ alkyl, or $R^6$ and $R^7$ combine to form =O; and n is from 0 to 2.

For example, the compound of Formula I-D and I-E can have a structure as represented below:

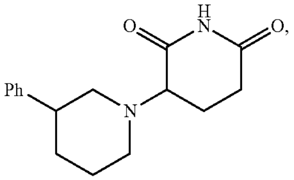

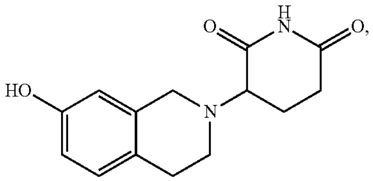

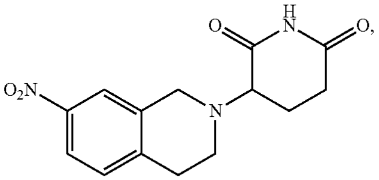

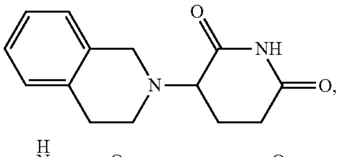

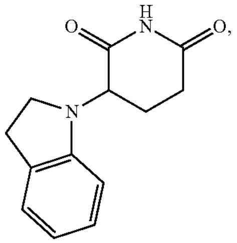

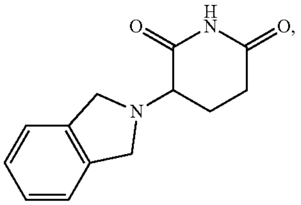

-continued

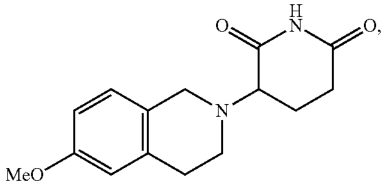

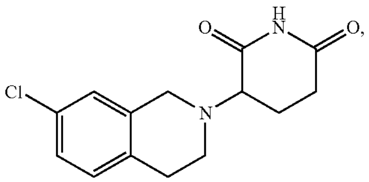

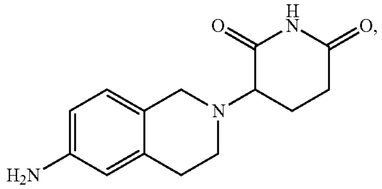

or

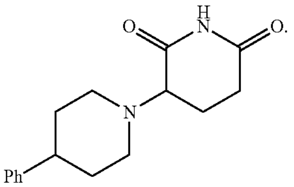

In some embodiments of Formula I, the compound has a structure as represented below

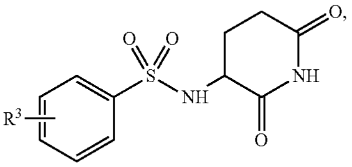

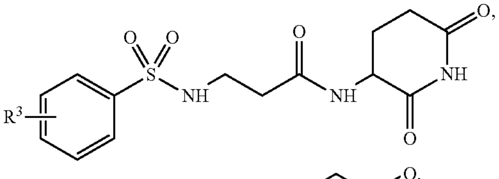

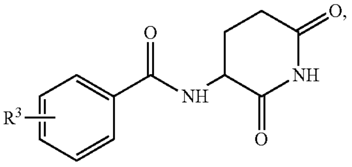

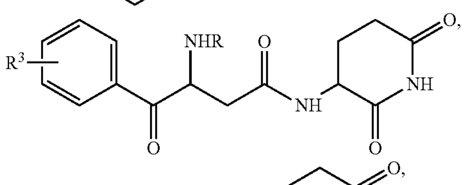

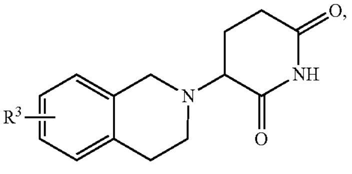

-continued

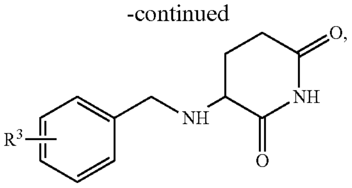

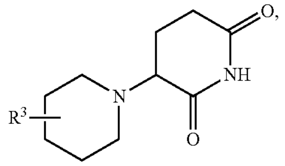

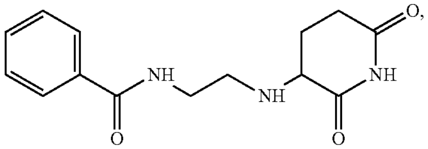

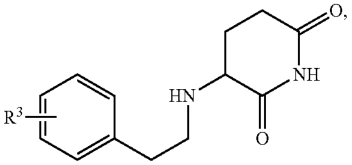

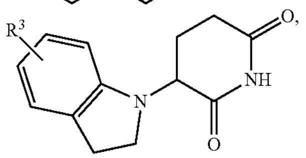

or

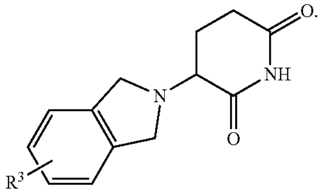

In some aspects, the compounds disclosed herein can be represented by Formula II:

Formula II

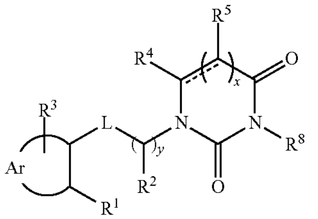

wherein,

Ar is aryl, cycloalkyl, heterocycloalkyl, or heteroaryl group;

L is absent or a linker selected from the group consisting of —$SO_2$, —$SO_2$R'; $SO_2$R'R", —$SO_2$NR'R"; —$SO_2$NR'R"C(═O); —NR'$SO_2$R"; —R'$SO_2$NR'R'"; —C(═O); —C(═O)R'; —OC(═O)R'; —C(═O)NR'R"; —NR'C(═O)R"; —NR'C(═O)R"C(═O); —OR'; —NR'R"; —SR'; —$N_3$—C(═O)OR'; —O(CR'R")$_r$C(═O)R'; —O(CR'R")$_r$NR"C(═O)R'; —O(CR'R")$_r$NR"$SO_2$R'; —OC(═O)NR'R"; —NR'C(═O)OR"; and substituted or unsubstituted $C_1$-$C_6$ aliphatic alkyl;

wherein R', R", and R'" are individually selected from hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6;

$R^1$, $R^2$, and $R^3$ are individually selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof or wherein $R^1$ and $R^2$ combine to form a 5-7 membered heterocyclic ring; and wherein when $R^1$ and $R^2$ combine to form a 5-7 membered heterocyclic ring, Ar is optionally not fused to the 5-7 membered heterocyclic ring but is a substituent of the 5-7 membered heterocyclic ring;

$R^4$ and $R^5$ are individually selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof;

$R^8$ is selected from the group consisting of hydrogen, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, substituted or unsubstituted aryl, substituted or unsubstituted alkylaryl, and combinations thereof; and x is 0, 1, or 2, y is from 1 to 6; and wherein the bond --- is present or absent.

In some examples of Formula II, Ar is as described herein. For example, Ar can include an aryl or heteroaryl group.

In certain specific examples of Formula II, Ar includes phenyl.

In certain specific examples of Formula II, Ar includes isoquinolinyl or quinolinyl.

The Ar group can be substituted or unsubstituted as described herein. For example, the Ar group can be selected from H, Cl, F, Br, I, CN, $NO_2$, $NH_2$, $CF_3$, $CO_2H$, $CO_2NH_2$, $CO_2NHR^5$, $CO_2R^5$, C(O)$R^5$, C(O)$NH_2$, C(O)$NHR^5$, and $C_1$-$C_6$ alkyl optionally substituted with alkyl, alkoxy, alkenyl, alkynyl, aryl, heteroaryl, aldehyde, amino, carboxylic acid, ester, ether, halide, hydroxy, ketone, nitro, silyl, sulfooxo, sulfonyl, sulfone, sulfoxide, or thiol. In the disclosed compounds of Formula II, there can be from 1 to 5 different substituents $R^3$, e.g., 1, 2, 3, 4, or 5 $R^3$ substituents.

In some examples of Formula II, L is absent. In other examples of Formula II, L is a linker. When L is present, L can be $SO_2$, $—SO_2R'$; $—SO_2R'R''$, $—SO_2NR'R''$; $—SO_2NR'R''C(═O)$; $—NR'SO_2R''$; $R'SO_2NR'R'$; C(═O); C(═O)R'; —OC(═O)R'; —C(═O)NR'R''; —NR'C(═O)R''; —NR'C(═O)R''C(═O); substituted or unsubstituted $C_1$-$C_6$ aliphatic alkyl, wherein R', R'', and R' are individually selected from hydrogen; substituted or unsubstituted alkyl; substituted or unsubstituted alkenyl; substituted or unsubstituted ether substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6.

In some specific examples of Formula II, R', R'', and R''' can be individually selected from hydrogen; substituted or unsubstituted $C_1$-$C_8$ alkyl; substituted or unsubstituted $C_1$-$C_8$ ether; or substituted or unsubstituted amine.

In some embodiments of Formula II, $R^1$ can be as described herein. For example, $R^1$ can be hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, and combinations thereof. For example, $R^1$ can be selected from H, Cl, F, Br, I, CN, $NO_2$, $NH_2$, $CF_3$, $CO_2H$, $CO_2NH_2$, $CO_2NHR^5$, $CO_2R^5$, $C(O)R^5$, $C(O)NH_2$, $C(O)NHR^5$, and $C_1$-$C_6$ alkyl optionally substituted with alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol.

In some embodiments of Formula II, $R^2$ can be hydrogen, halogen, hydroxyl, azide, alkoxyl, sulfhydryl, carbonyl, carboxyl, cyano, silyl, ether, alkylthio, sulfonyl, sulfonamido, ketone, aldehyde, substituted or unsubstituted amine, substituted or unsubstituted amide, nitro, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, and combinations thereof. For example, $R^2$ can be selected from H and $C_1$-$C_6$ alkyl optionally substituted with alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol.

In some embodiments of Formula II, $R^1$ and $R^2$ can combine to form a 5-7 membered heterocyclic ring. When $R^1$ and $R^2$ combine to form a 5-7 membered heterocyclic ring, L can be absent or present.

In some embodiments of Formula II, $R^4$ is selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof.

In some embodiments of Formula II, $R^5$ is selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof.

In specific embodiments of Formula II, $R^4$ and $R^5$ are both hydrogen. In some embodiments of Formula II, one of $R^4$ and $R^5$ are hydrogen.

In certain specific examples of Formula II, x is 0.

In certain specific examples of Formula II, x is 1.

In some embodiments of Formula II, the compound can have a structure as represented by Formula II-A:

Formula II-A

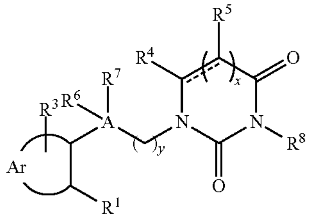

wherein,

A comprises C, S, N, substituted of unsubstituted $C_1$-$C_8$ alkyl, or combinations thereof;

$R^6$ and $R^7$ are individually ═O, hydrogen, $C_1$-$C_8$ alkyl, or $R^6$ and $R^7$ combine to form ═O.

In some embodiments of Formula II-A, the compound can have a structure as represented by Formula II-A-1:

Formula II-A-1

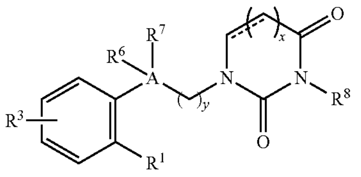

wherein,

A comprises C, S, N, substituted of unsubstituted $C_1$-$C_8$ alkyl, or combinations thereof;

$R^6$ and $R^7$ are individually ═O, hydrogen, $C_1$-$C_8$ alkyl, or $R^6$ and $R^7$ combine to form ═O.

In some embodiments of Formula II-A, the compound can have a structure as represented below:

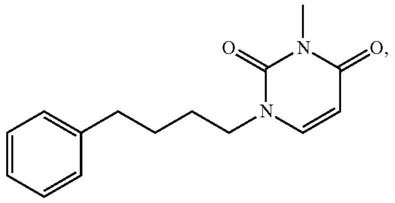

-continued

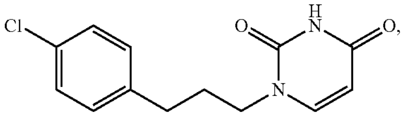

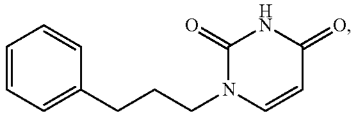

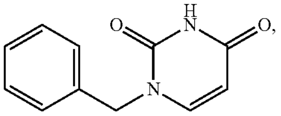

or

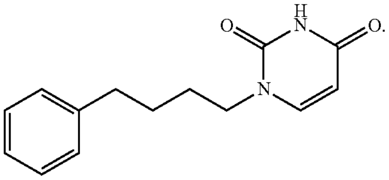

In some embodiments of Formula II, the compound can have a structure as represented by Formula II-B:

Formula II-B

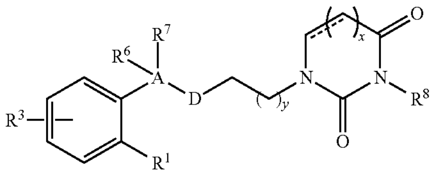

wherein,

A comprises C, S, N, substituted of unsubstituted $C_1$-$C_8$ alkyl, or combinations thereof;

D is —NR', carbonyl, or substituted of unsubstituted $C_1$-$C_8$ alkyl;

$R^6$ and $R^7$ are individually ═O, hydrogen, $C_1$-$C_8$ alkyl, or $R^6$ and $R^7$ combine to form ═O.

In some embodiments of Formula II-B, the compound can have a structure as represented below:

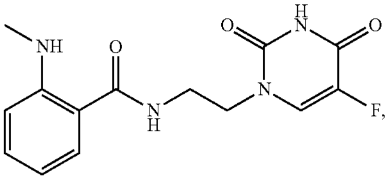

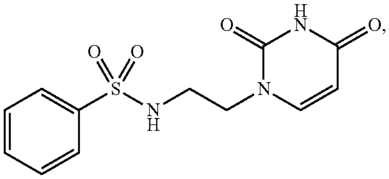

-continued

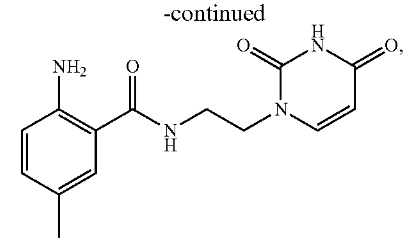

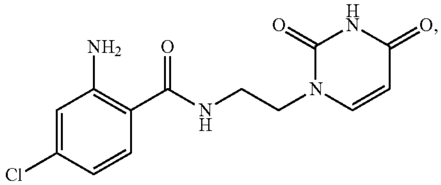

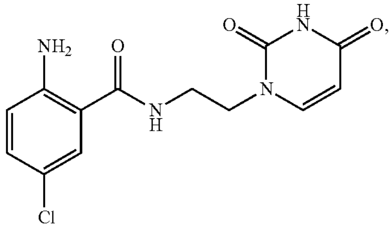

or

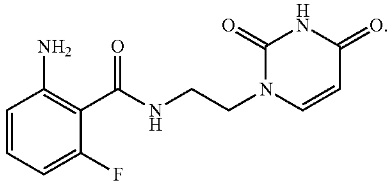

In some embodiments of Formula II, the compound can have a structure as represented below:

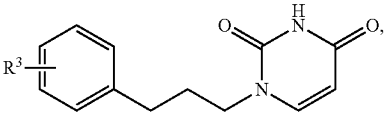

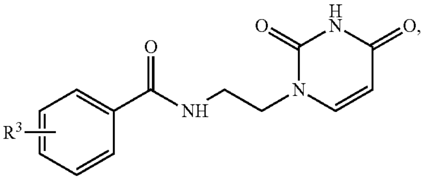

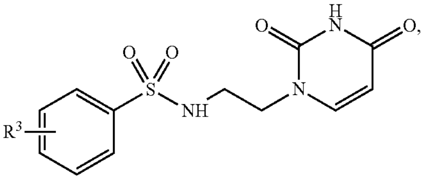

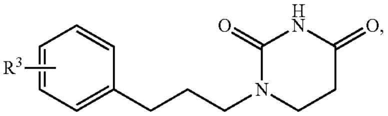

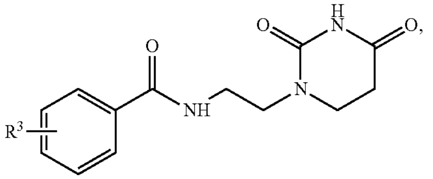

or

-continued

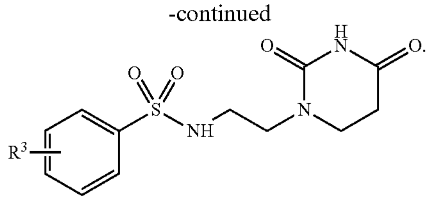

In some aspects, the compounds disclosed herein can be represented by Formula III:

Formula III

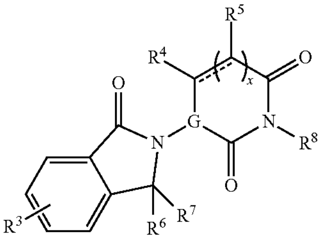

wherein,

G comprises C, S, N, substituted of unsubstituted $C_1$-$C_8$ alkyl, or combinations thereof;

$R^3$ is selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, and combinations thereof;

$R^4$, $R^5$, and $R^8$ are individually selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted aryl, substituted or unsubstituted alkylaryl, substituted or unsubstituted alkenyl, substituted or unsubstituted alkynyl, substituted or unsubstituted cycloalkyl, heterocyclyl, and combinations thereof; and $R^6$ and $R^7$ are individually =O, hydrogen, $C_1$-$C_8$ alkyl, or $R^6$ and $R^7$ combine to form =O;

x is 0, 1, or 2; and wherein the bond --- is present or absent.

In some examples of Formula III, $R^3$, $R^4$, and $R^5$, are as described herein.

In some examples of Formula III, $R^8$ is selected from the group consisting of hydrogen, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, substituted or unsubstituted aryl, substituted or unsubstituted alkylaryl, and combinations thereof.

In some embodiments of Formula III, T the compound has a structure as represented by Formula III-A:

Formula III-A

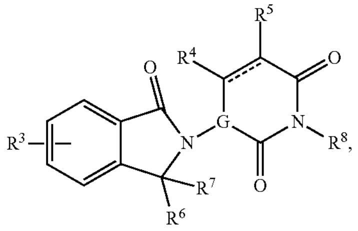

wherein $R^3$, $R^4$, $R^5$, $R^6$, $R^7$, and $R^8$ are as described herein.

In some embodiments of Formula III, T the compound has a structure as represented by Formula III-B:

Formula III-B

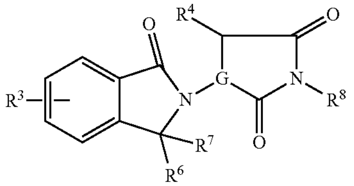

wherein $R^3$, $R^4$, $R^6$, $R^7$, and $R^8$ are as described herein.

In some embodiments of Formula III, the compound can have a structure as represented below

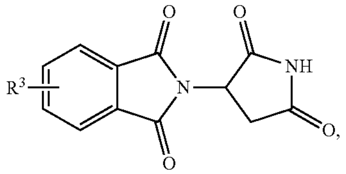

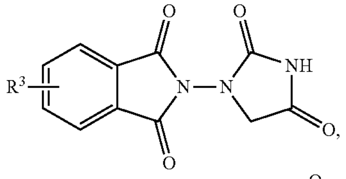

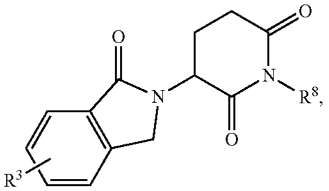

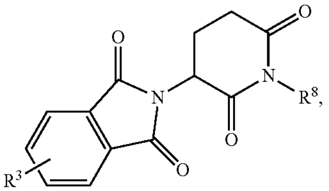

or

-continued

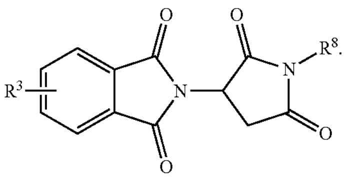

In specific examples of Formula III, the compound can have a structure as represented below:

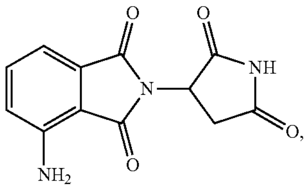

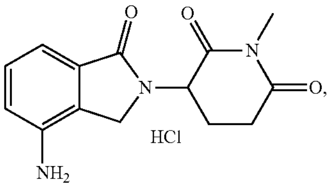

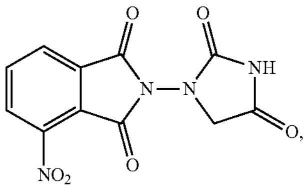

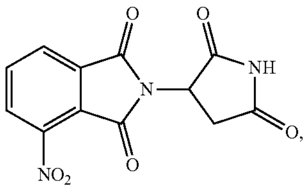

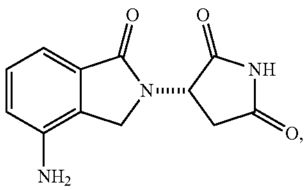

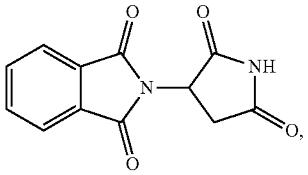

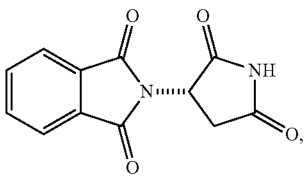

-continued

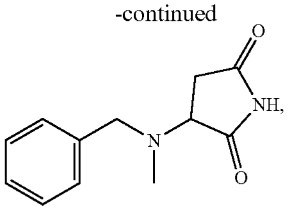

or

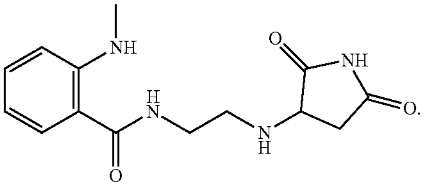 [SMILES: CNc1ccccc1C(=O)NCCNC1CC(=O)NC1=O]

In some aspects, the compounds disclosed herein can have a structure represented by Formula IV:

Formula IV

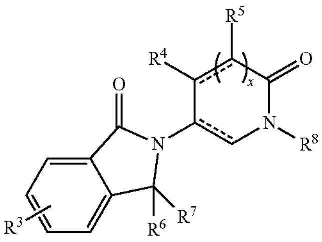

wherein, $R_3$ is selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, and combinations thereof;

$R^4$, $R^5$, and $R^8$ are individually selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted aryl, substituted or unsubstituted alkylaryl, substituted or unsubstituted alkenyl, substituted or unsubstituted alkynyl, substituted or unsubstituted cycloalkyl, heterocyclyl, and combinations thereof; and $R^6$ and $R^7$ are individually ═O, hydrogen, $C_1$-$C_8$ alkyl, or $R^6$ and $R^7$ combine to form ═O;

x is 0, 1, or 2; and wherein the bond --- is present or absent.

In some aspects, the compounds disclosed herein can have a structure represented by Formula V:

Formula V

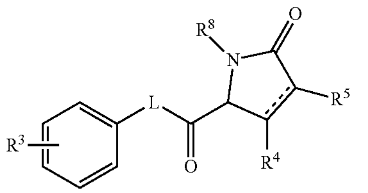

wherein,

L is absent or a linker selected from the group consisting of $—SO_2$, $—SO_2R'$; $SO_2R'R''$, $—SO_2NR'R''$; $—SO_2NR'R''C(═O)$; $—NR'SO_2R''$; $—R'SO_2NR'R'$; —C(═O); —C(═O)R'; —OC(═O)R'; —C(═O)NR'R''; —NR'C(═O)R''; —NR'C(═O)R''C(═O); —OR'; —NR'R''; —SR'; $—N_3—C(═O)OR'$; $—O(CR'R'')_rC(═O)R'$; $—O(CR'R'')_rNR''C(═O)R'$; $—O(CR'R'')_rNR''SO_2R'$; —OC(═O)NR'R''; —NR'C(═O)OR''; and substituted or unsubstituted $C_1$-$C_6$ aliphatic alkyl;

wherein R', R'', and R''' are individually selected from hydrogen; substituted or unsubstituted alkyl; substituted or unsubstituted alkenyl; substituted or unsubstituted ether; or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6; and $R^3$, $R^4$, and $R^5$ are individually selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, and combinations thereof. In some examples, $R^8$ is H.

In some aspects, the compounds disclosed herein can have a structure represented by Formula VI:

Formula VI

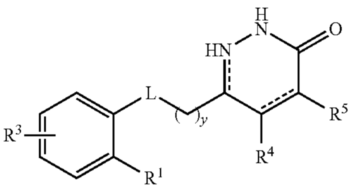

wherein,

L is absent or a linker selected from the group consisting of $—SO_2$, $—SO_2R'$; $SO_2R'R''$, $—SO_2NR'R''$; $—SO_2NR'R''C(═O)$; $—NR'SO_2R''$; $—R'SO_2NR'R'''$; —C(═O); —C(═O)R'; —OC(═O)R'; —C(═O)NR'R''; —NR'C(═O)R''; —NR'C(═O)R''C(═O); —OR'; —NR'R''; —SR'; $—N_3—C(═O)OR'$; $—O(CR'R'')_rC(═O)R'$; $—O(CR'R'')_rNR''C(═O)R'$; $—O(CR'R'')_rNR''SO_2R'$; —OC(═O)NR'R''; —NR'C(═O)OR''; and substituted or unsubstituted $C_1$-$C_6$ aliphatic alkyl;

wherein R', R'', and R''' are individually selected from hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6; and $R^1$, $R^3$, $R^4$, and $R^5$ are individually selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, and combinations thereof;

y is 0, 1, or 2; and wherein the bond --- is present or absent.

In some aspects, the compounds disclosed herein can have a structure represented by Formula VII:

Formula VII

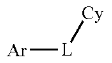

wherein,

Ar is selected from substituted or unsubstituted phenyl, substituted or unsubstituted pyrrolyl, substituted or unsubstituted furanyl, substituted or unsubstituted thiophenyl, substituted or unsubstituted imidazolyl, substituted or unsubstituted oxazolyl, substituted or unsubstituted thiazolyl, substituted or unsubstituted triazolyl, pyrazolyl, substituted or unsubstituted pyridinyl, substituted or unsubstituted pyrazinyl, substituted or unsubstituted pyridazinyl, substituted or unsubstituted pyrazolyl, substituted or unsubstituted oxazoyl, substituted or unsubstituted isoxazoyl, substituted or unsubstituted pyrimidinyl, substituted or unsubstituted furyl, substituted or unsubstituted triazinyl, substituted or unsubstituted oxazoyl, substituted or unsubstituted isoxazoyl, substituted or unsubstituted thiazolyl, substituted or unsubstituted isothiazoyl, substituted or unsubstituted pyrazolyl, substituted or unsubstituted pyrrolyl, pyrazinyl, tetrazolyl, pyridyl, (or its N-oxide), thienyl, substituted or unsubstituted pyrimidinyl, substituted or unsubstituted indolyl, substituted or unsubstituted isoquinolyl, substituted or unsubstituted quinolyl, substituted or unsubstituted isoquinolinyl, substituted or unsubstituted quinolinyl, substituted or unsubstituted piperidine, substituted or unsubstituted piperazine, substituted or unsubstituted pyrimidine, substituted or unsubstituted thiane, substituted or unsubstituted thiopyran, substituted or unsubstituted morpholine, substituted or unsubstituted oxazine, substituted or unsubstituted tetrahydropyran, substituted or unsubstituted pyrolidine, substituted or unsubstituted pyroline, substituted or unsubstituted imidazoline, substituted or unsubstituted pyrazoline, substituted or unsubstituted indoline, substituted or unsubstituted benzofuran, substituted or unsubstituted indoline, substituted or unsubstituted indole.

L is absent or a linker selected from the group consisting of $—SO_2$, $—SO_2R'$; $SO_2R'R''$, $—SO_2NR'R''$; $—SO_2NR'R''C(═O)$; $—NR'SO_2R''$; $—R'SO_2NR'R'''$; —C(═O); —C(═O)R'; —OC(═O)R'; —C(═O)NR'R''; —NR'C(═O)R''; —NR'C(═O)R''C(═O); —OR'; —NR'R''; —SR'; $—N_3—C(═O)OR'$; $—O(CR'R'')_rC(═O)R'$; $—O(CR'R'')_rNR''C(═O)R'$; $—O(CR'R'')_rNR''SO_2R'$; —OC(═O)NR'R''; —NR'C(═O)OR''; and substituted or unsubstituted $C_1$-$C_6$ aliphatic alkyl;

wherein R', R'', and R''' are individually selected from hydrogen; substituted or unsubstituted alkyl; substituted or unsubstituted ether; substituted or unsubstituted alkenyl; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6; and Cy is selected from substituted or unsubstituted glutarimide, substituted or unsubstituted succinimide, substituted or unsubstituted succinamide, substituted or unsubstituted hydantoin, substituted or unsubstituted uracil, substituted or unsubstituted dihydrouracil.

As described herein, Ar can include phenyl, pyrrolyl, furanyl, thiophenyl, imidazolyl, oxazolyl, thiazolyl, triazolyl, pyrazolyl, pyridinyl, pyrazinyl, pyridazinyl, pyrazolyl, oxazoyl, isoxazoyl, piperidine, piperazine, isoquinoline, quinolone, or pyrimidinyl. The Ar group can be substituted with H, Cl, F, Br, I, CN, $NO_2$, $NH_2$, $CF_3$, $CO_2H$, $CO_2NH_2$, $CO_2NHR^5$, $CO_2R^5$, $C(O)R^5$, $C(O)NH_2$, $C(O)NHR^5$, and $C_1$-$C_6$ alkyl optionally substituted with alkyl, alkoxy, alkenyl, alkynyl, aryl, heteroaryl, aldehyde, amino, carboxylic acid, ester, ether, halide, hydroxy, ketone, nitro, silyl, sulfooxo, sulfonyl, sulfone, sulfoxide, or thiol.

In some specific embodiments, the compounds disclosed herein can include glutarimide analogs with aromatic/heterocyclic tails:

In some specific embodiments, the compounds disclosed herein can include uracil or dihydrouracil analogs.

In some specific embodiments, the compounds disclosed herein can include succinimide and hydantoin analogs.

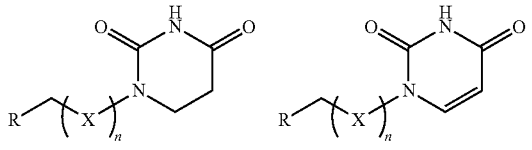

n = 1, 2, 3 or 4
X = C, N, O

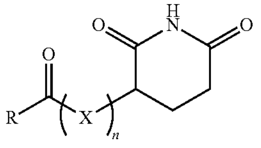

n = 1, 2, 3 or 4
X = C, O, N

In some specific embodiments, the compounds disclosed herein can include

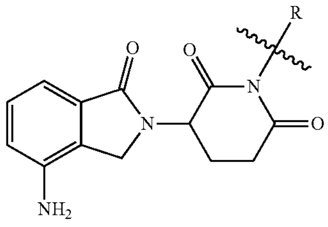

LEN (R = H)

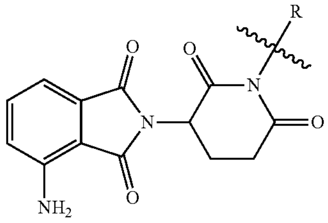

POM (R = H)

= Point of attachment

R=Me, Et, propyl, butyl, pentyl, hexyl, heptyl

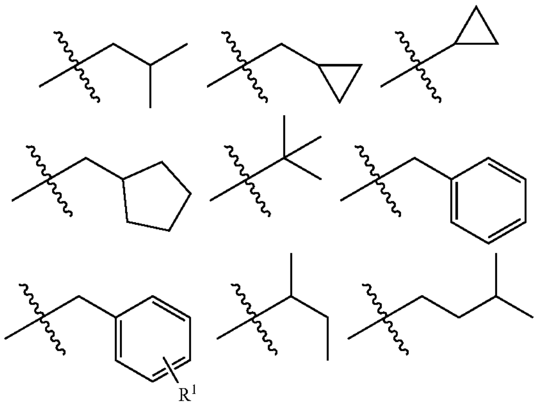

$R^1$ = Me, OMe, OH, Cl, Br, F, $NH_2$

-continued

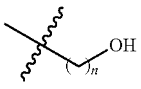 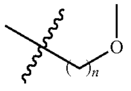 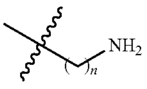

n = 1-4 n = 1-4 n = 1-4

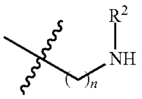 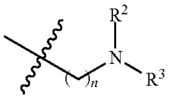 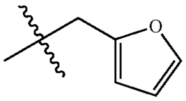

n = 1-4 n = 1-4

$R^3$ = Me, Et, $R^2$ = Me, Et, or COR (amides)

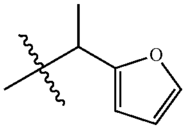 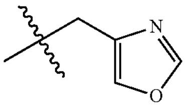

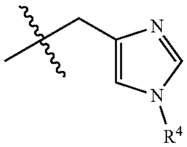 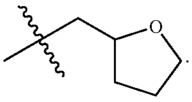.

$R^4$ = H, Me

In some specific embodiments, the compounds disclosed herein can be represented by the formulas below:

Also reverse amide and sulfonamide/reverse sulfonamide in ALL series

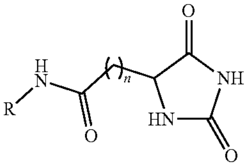 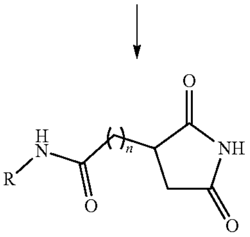

n = 1, 2, 3 and 4

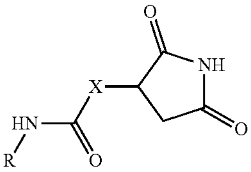 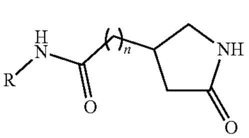

X = C, NH, NR′ (R′ = alkyl and aryl)

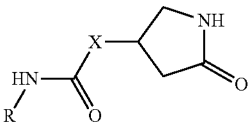 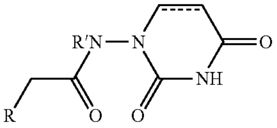

X = C, NH

X = C, NH, NR′ (R′ = alkyl and aryl) both $CH_2CH_2$ and CH═CH

-continued

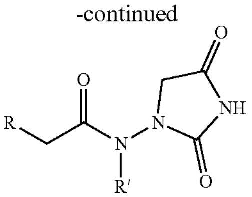

wherein R is aromatic, heterocyclic, alicyclic, bicyclic ring systems and aliphatic groups.

Specific examples of compounds disclosed herein can include

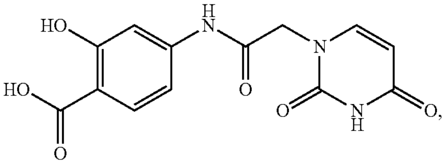,

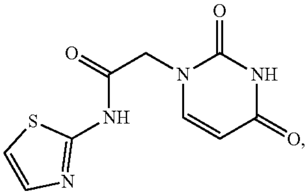,

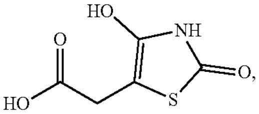,

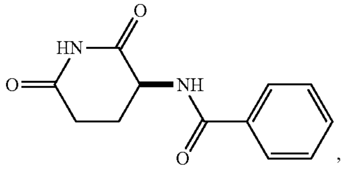,

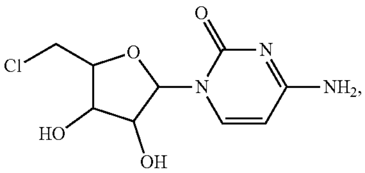,

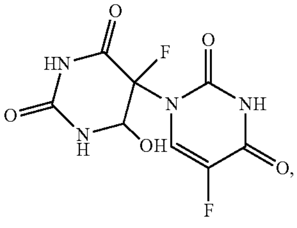,

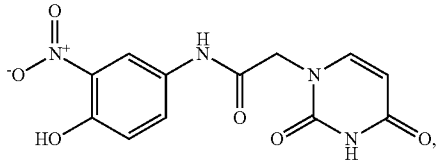,

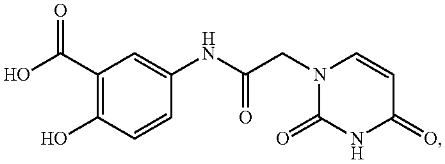,

-continued
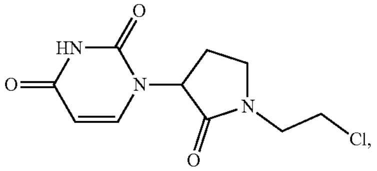
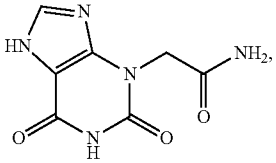
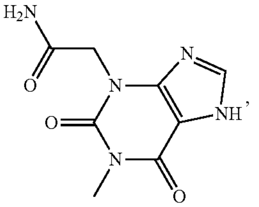
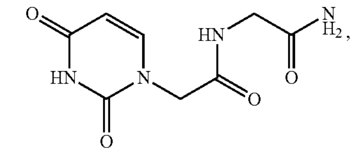
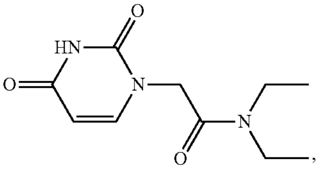
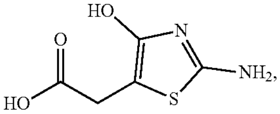
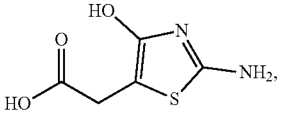
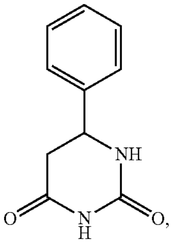
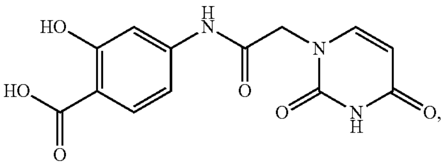
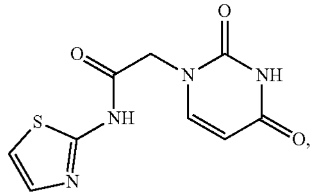
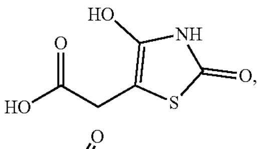
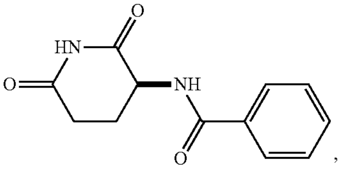
-continued
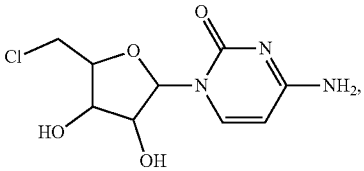
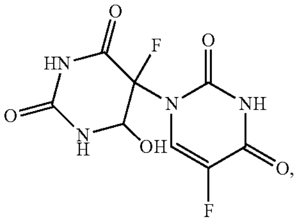
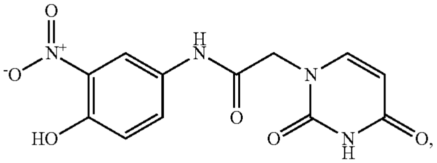
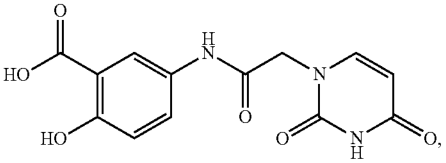
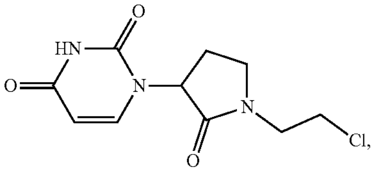
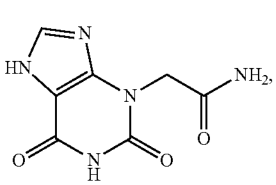
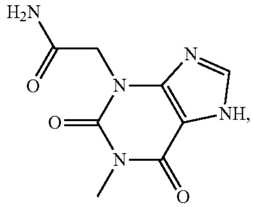
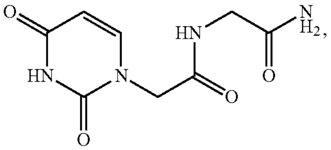
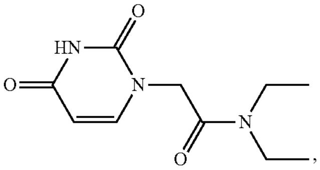
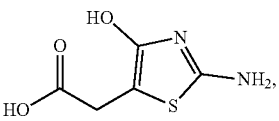
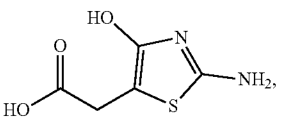

-continued
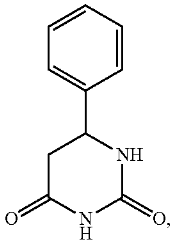
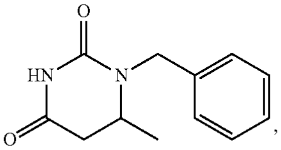
,
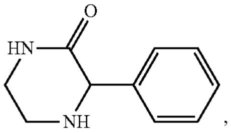
,
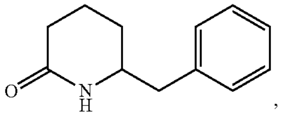
,
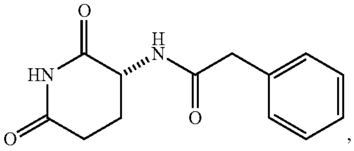
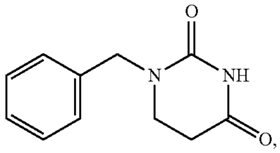
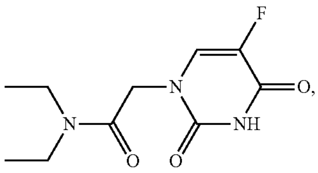
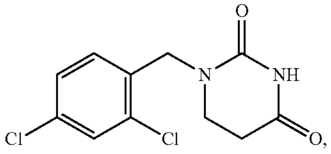
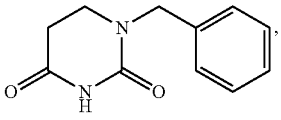
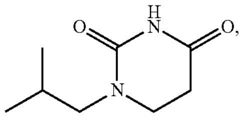
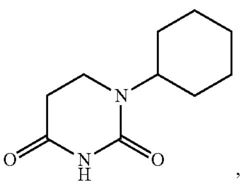
,
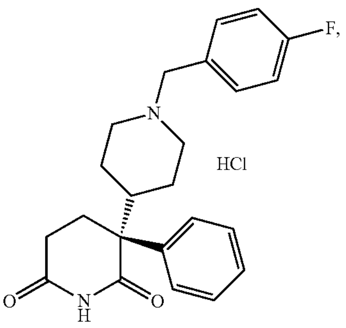
-continued
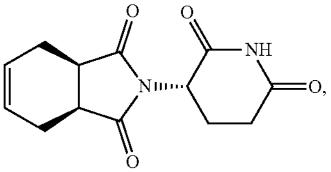
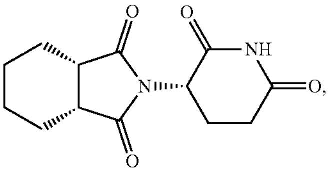
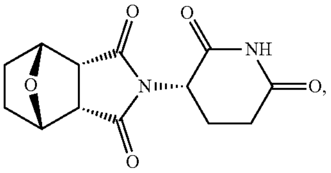
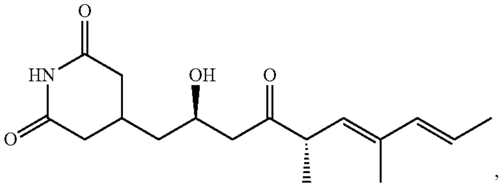
,
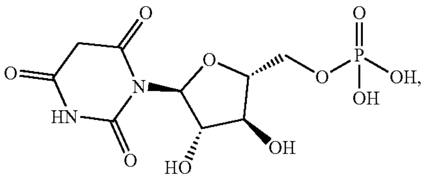
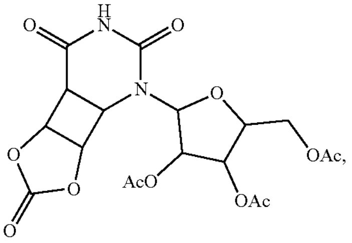
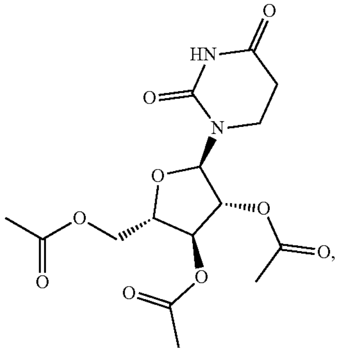
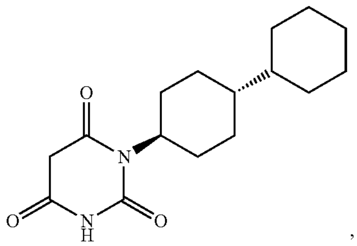
, -continued
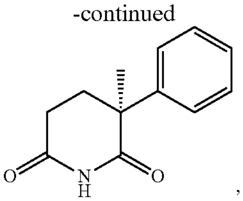
,
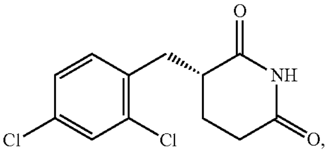
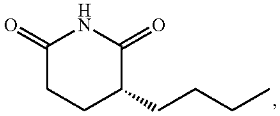
,
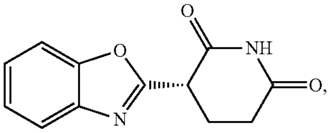
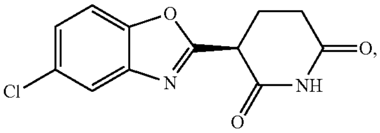
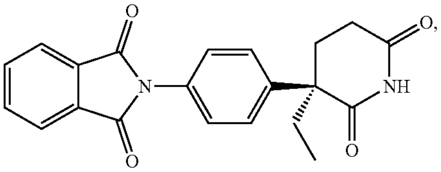
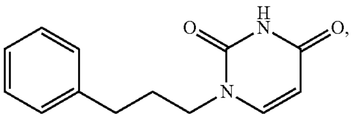
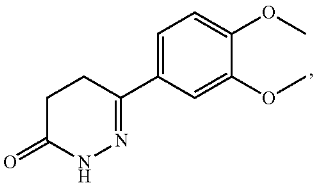
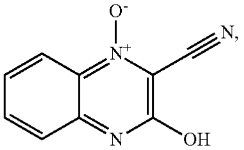
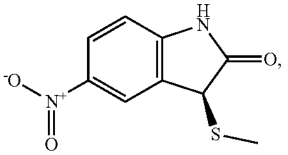
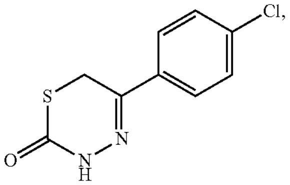
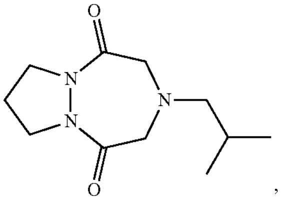
,
-continued
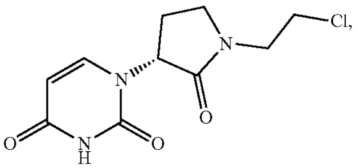
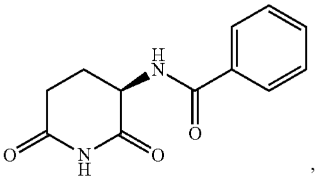
,
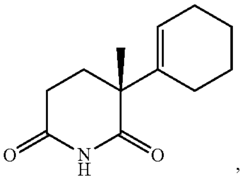
,
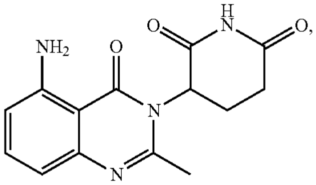
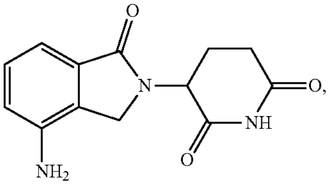
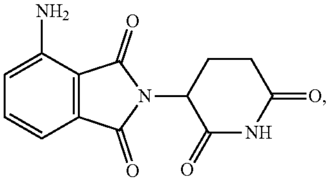
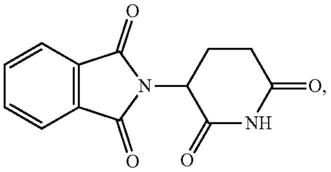
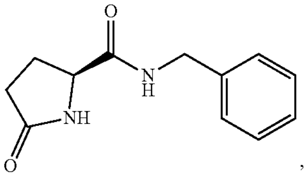
,
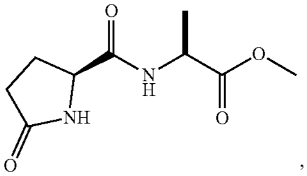
,
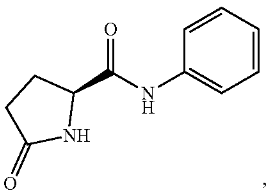
, -continued
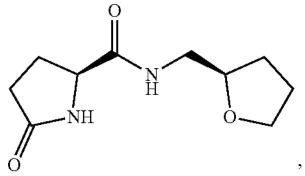
,
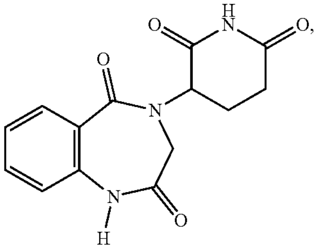
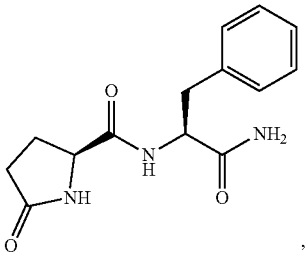
,
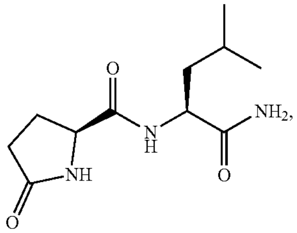
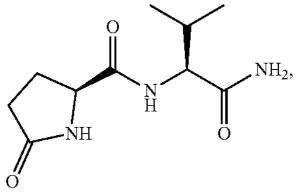
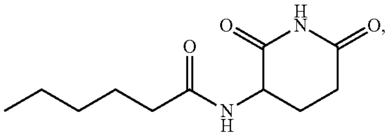
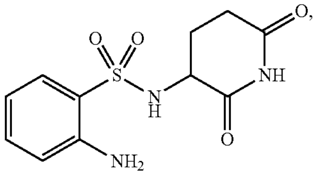
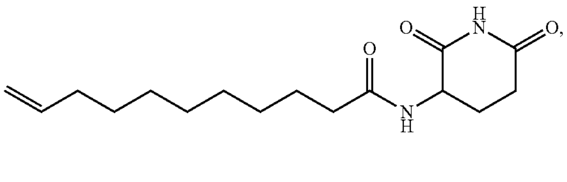
-continued
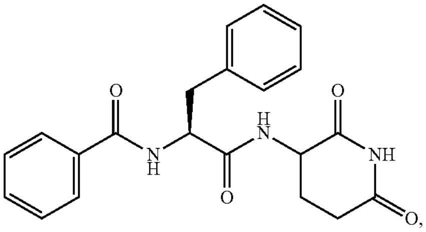
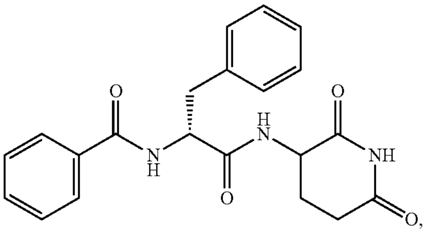
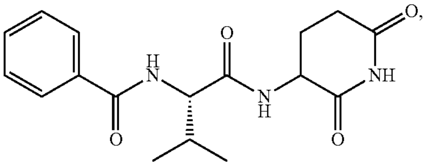
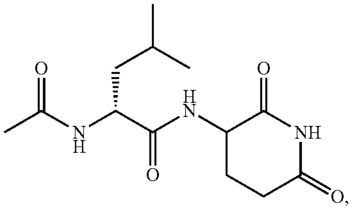
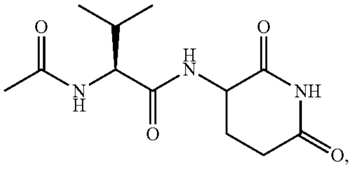
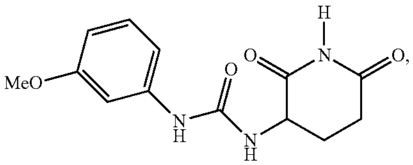
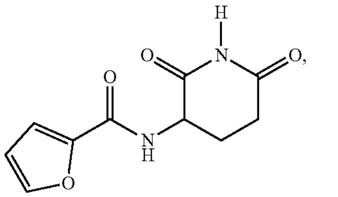
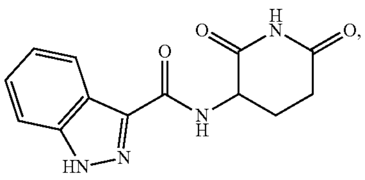
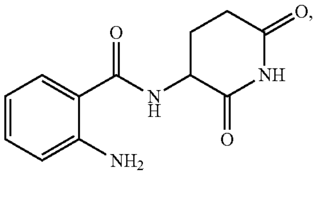

-continued
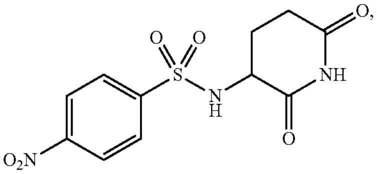
,
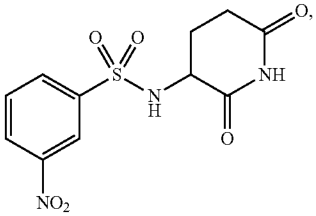
,
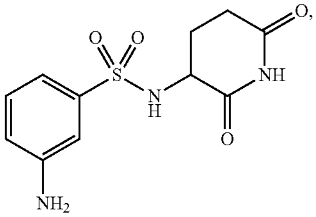
,
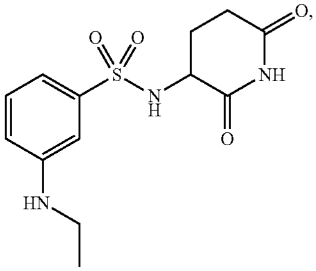
,
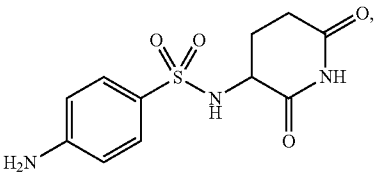
,
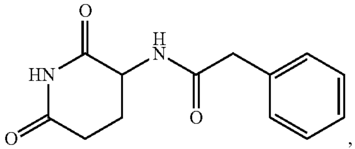
,
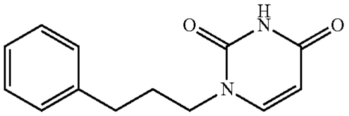
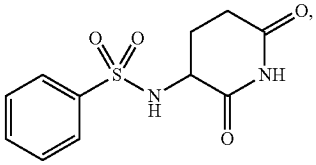
,
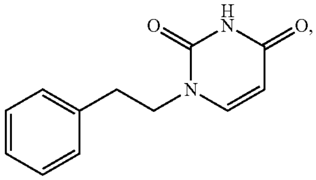
,
-continued
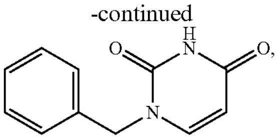
,
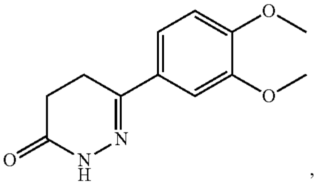
,
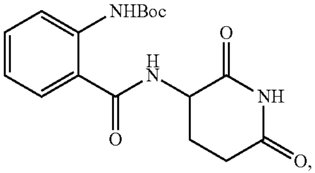
,
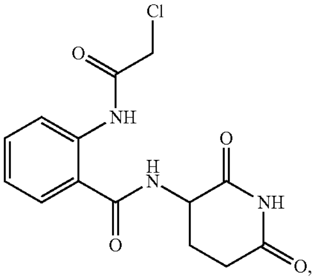
,
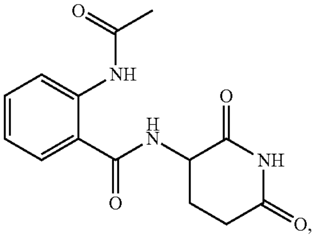
,
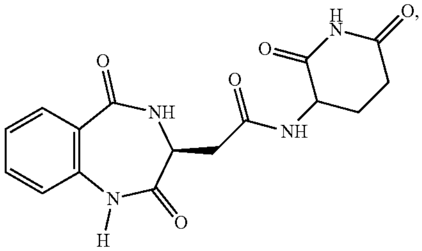
,
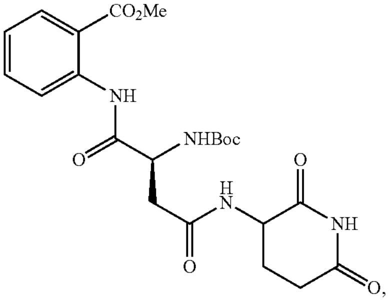
,
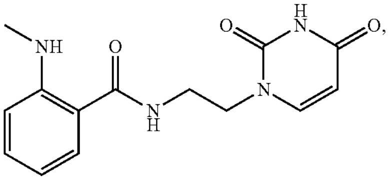
, -continued
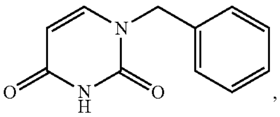,
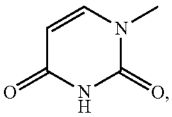
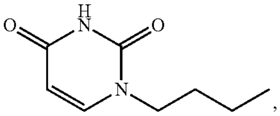,
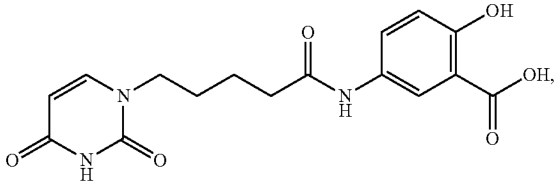
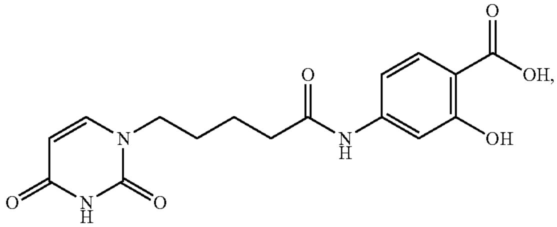
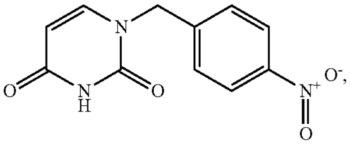
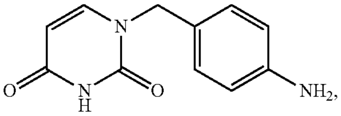
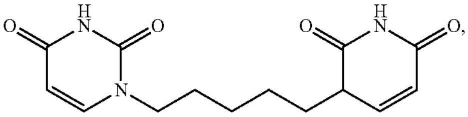
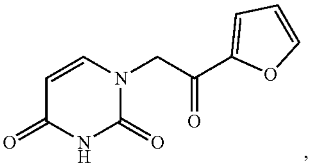,
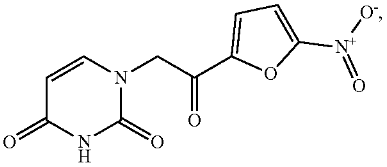
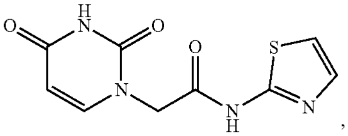,
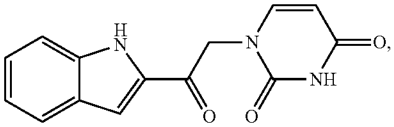
-continued
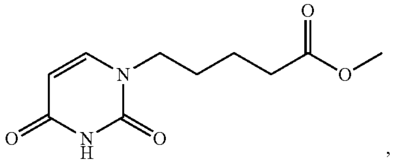,
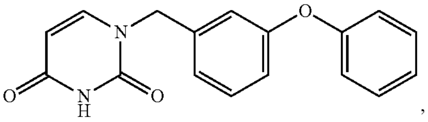,
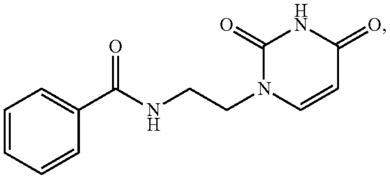
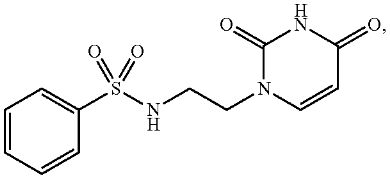
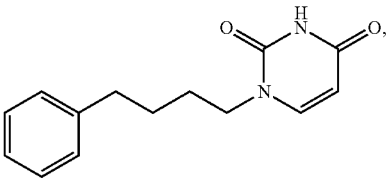
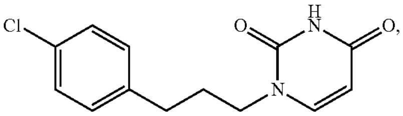
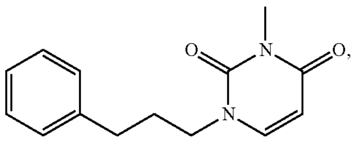
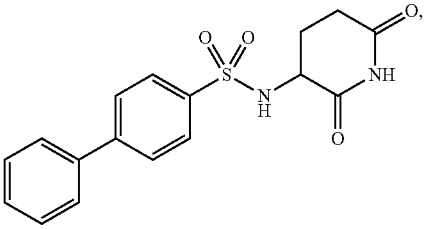
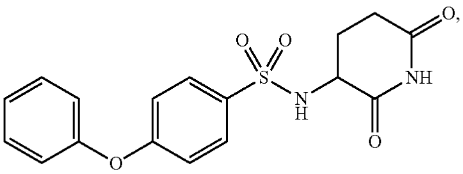
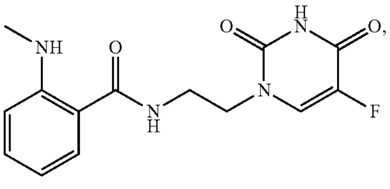

-continued
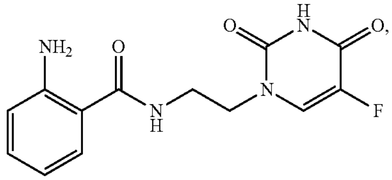
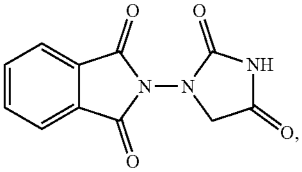
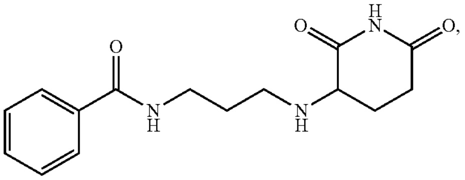
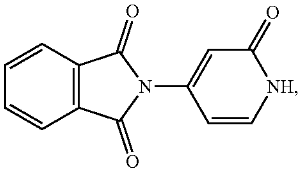
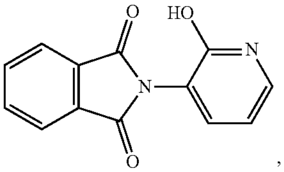
,
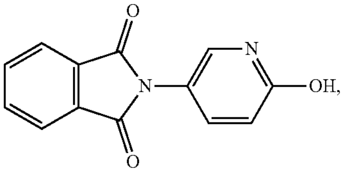
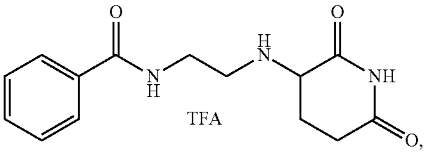
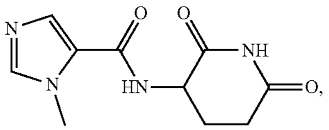
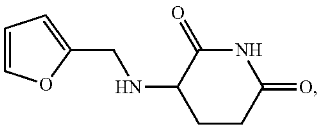
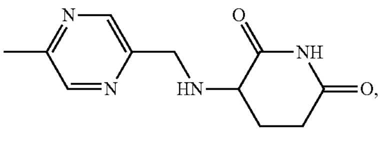
-continued
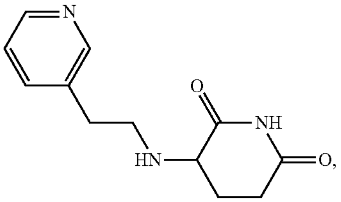
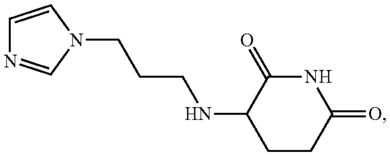
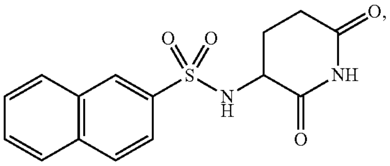
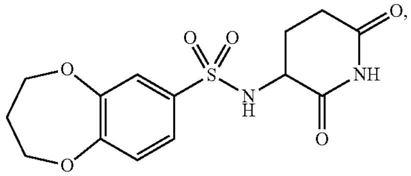
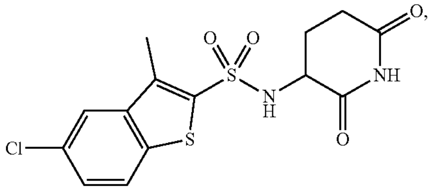
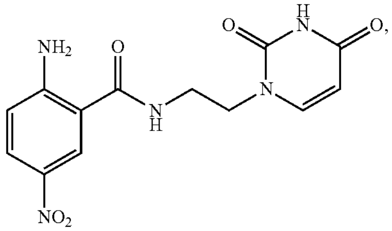
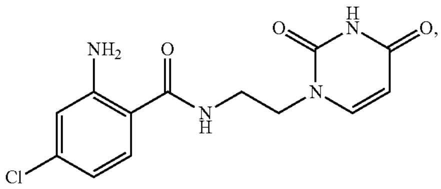
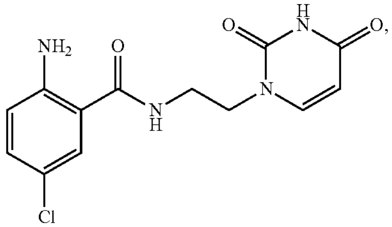

-continued

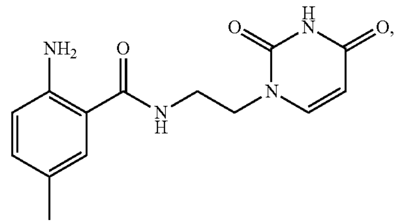

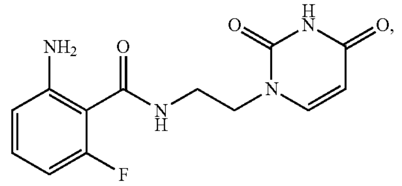

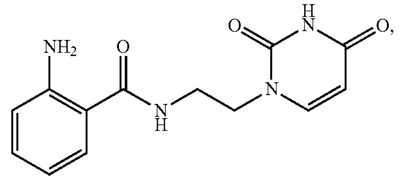

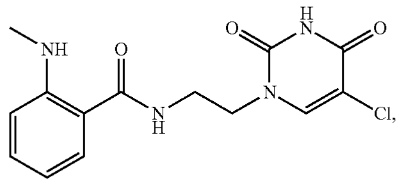

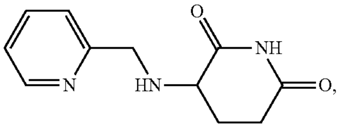

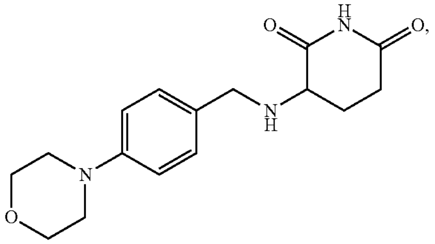

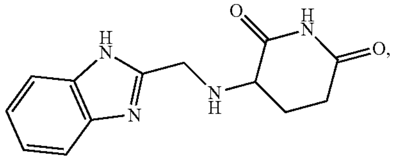

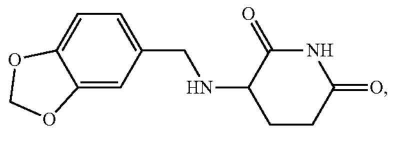

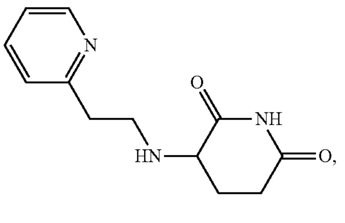

-continued

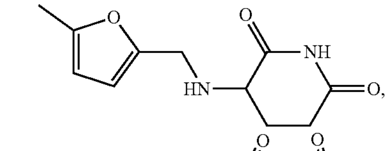

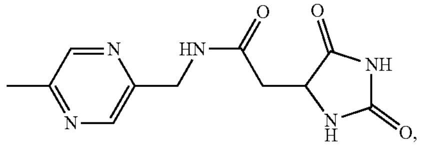

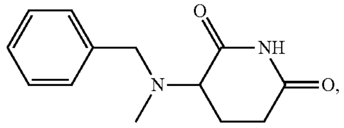

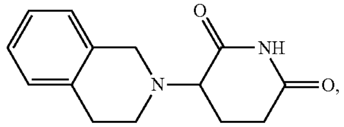

In some aspects, the compounds disclosed herein can be represented by Formula VIII:

Formula VIII

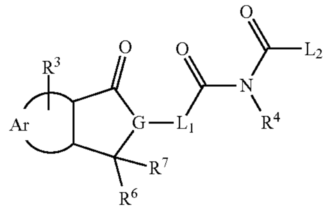

wherein,

G comprises C, S, N, substituted of unsubstituted $C_1$-$C_8$ alkyl, or combinations thereof;

Ar is aryl, cycloalkyl, heterocycloalkyl, or heteroaryl group;

$L_1$ and $L_2$ are individually absent or a linker selected from the group consisting of —$SO_2$, —$SO_2R'$; $SO_2R'R''$, —$SO_2NR'R''$; —$SO_2NR'R''C(=O)$; —$NR'SO_2R''$; —$R'SO_2NR'R'''$; —C(=O); —C(=O)R'; —OC(=O)R'; —C(=O)NR'R''; —NR'C(=O)R''; —NR'C(=O)R''C(=O); —OR'; —NR'R''; —SR'; —$N_3$—C(=O)OR'; —$O(CR'R'')_rC(=O)R'$; —$O(CR'R'')_rNR''C(=O)R'$; —$O(CR'R'')_rNR''SO_2R'$; —OC(=O)NR'R''; —NR'C(=O)OR''; substituted or unsubstituted $C_1$-$C_8$ aliphatic alkyl; substituted or unsubstituted $C_1$-$C_8$ alkylhalide, substituted or unsubstituted $C_1$-$C_8$ alkenyl, substituted or unsubstituted $C_1$-$C_8$ alkynyl, substituted or unsubstituted ether;

wherein R', R'', and R''' are individually selected from hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6;

$R^6$ and $R^7$ are individually hydrogen, $C_1$-$C_8$ alkyl, ether, or $R^6$ and $R^7$ combine to form =O;

$R^4$ is selected from hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine.

In some examples of Formula VIII, Ar can include an aromatic group as disclosed herein such as phenyl, pyrrolyl, furanyl, thiophenyl, imidazolyl, oxazolyl, thiazolyl, triazolyl, pyrazolyl, pyridinyl, pyrazinyl, pyridazinyl, pyrazolyl, oxazoyl, isoxazoyl, or pyrimidinyl, furyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide), isoquinolinyl, quinolinyl.

In certain specific examples, Ar includes phenyl.

The Ar group can be substituted or unsubstituted. For example, the substituent on Ar can be selected from hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof. In certain embodiments, the substituent on Ar can be selected from H, Cl, F, Br, I, CN, $NO_2$, $NH_2$, $CF_3$, $CO_2H$, $CO_2NH_2$, $CO_2NHR^5$, $CO_2R^5$, $C(O)R^5$, $C(O)NH_2$, $C(O)NHR^5$, and $C_1$-$C_6$ alkyl optionally substituted with alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol.

In certain specific examples, Ar is substituted with $NO_2$, $NH_2$, OH, alkyl, aryl, halogen, amide, ether, or a combination thereof.

In the disclosed compounds of Formula VIII, there can be from 1 to 5 different substituents $R^3$, e.g., 1, 2, 3, 4, or 5 $R^3$ substituents. The substituents can be the same or different. In specific examples, $R^3$ is $SO_2NH_2$, $SO_2NHR'$, or $NHSO_2R'$, wherein R' is $C_1$-$C_6$ alkyl or $C_1$-$C_6$ cycloalkyl optionally substituted with $C_1$-$C_6$ alkyl, $C_1$-$C_6$ alkoxyl, hydroxyl, or halide. In other examples, $R^3$ is NHC(O)R', wherein R' is $C_1$-$C_6$ alkyl or $C_1$-$C_6$ cycloalkyl optionally substituted with $C_1$-$C_6$ alkyl, $C_1$-$C_6$ alkoxyl, cycloalky, cycloheteroalkyl, hydroxyl, or halide. In other examples, $R^3$ is $C_1$-$C_6$ alkyl or $C_1$-$C_6$ cycloalkyl. In other examples, $R^3$ is $C_1$-$C_6$ alkoxyl. In other examples, $R^3$ is halide. In other examples, n is 2 and each $R^3$ is selected from the group consisting of $C_1$-$C_6$ alkyl, $C_1$-$C_6$ alkoxyl, halide, $SO_2NH_2$, $SO_2NHR'$, and $NHSO_2R'$, wherein R' is $C_1$-$C_6$ alkyl or $C_1$-$C_6$ cycloalkyl optionally substituted with $C_1$-$C_6$ alkyl, $C_1$-$C_6$ alkoxyl, hydroxyl, or halide. In other examples, $R^3$ is hydrogen, halogen, hydroxyl, substituted or unsubstituted amine, substituted or unsubstituted amide, nitro, ester, morpholino, dioxolane, substituted or unsubstituted $C_1$-$C_6$ alkyl, or combinations thereof.

In some examples of Formula VIII, $L_1$ and $L_2$ comprises substituted or unsubstituted $C_1$-$C_8$ aliphatic alkyl, substituted or unsubstituted $C_1$-$C_8$ alkenyl; substituted or unsubstituted $C_1$-$C_8$ ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine.

In some specific examples of Formula VIII, G comprises N.

In some embodiments of Formula VIII, $R^4$ is selected from the group consisting of hydrogen, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted heterocyclyl, and combinations thereof.

In some embodiments of Formula VIII, the compounds can be represented by Formula VIII-A:

Formula VIII-A

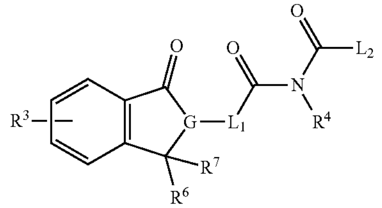

wherein,

G comprises C, S, N, substituted of unsubstituted $C_1$-$C_8$ alkyl, or combinations thereof;

$L_1$ and $L_2$ are individually absent or a linker selected from the group consisting of —$SO_2$, —$SO_2R'$; $SO_2R'R''$, —$SO_2NR'R''$; —$SO_2NR'R''C(=O)$; —$NR'SO_2R''$; —$R'SO_2NR'R'''$; —C(=O); —C(=O)R'; —OC(=O)R'; —C(=O)NR'R''; —NR'C(=O)R''; —NR'C(=O)R''C(=O); —OR'; —NR'R''; —SR'; —$N_3$—C(=O)OR'; —$O(CR'R'')_rC(=O)R'$; —$O(CR'R'')_rNR''C(=O)R'$; —$O(CR'R'')_rNR''SO_2R'$; —OC(=O)NR'R''; —NR'C(=O)OR''; substituted or unsubstituted $C_1$-$C_8$ aliphatic alkyl; substituted or unsubstituted $C_1$-$C_8$ alkylhalide, substituted or unsubstituted $C_1$-$C_8$ alkenyl, substituted or unsubstituted $C_1$-$C_8$ alkynyl, substituted or unsubstituted ether;

wherein R', R'', and R''' are individually selected from hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6;

$R^6$ and $R^7$ are individually hydrogen, $C_1$-$C_8$ alkyl, ether, or $R^6$ and $R^7$ combine to form =O;

$R^4$ is selected from hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine.

In some aspects, the compounds disclosed herein can be represented by Formula IX:

Formula IX

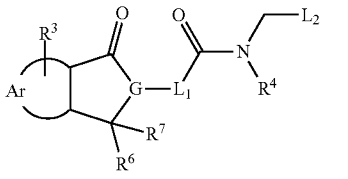

wherein,

G comprises C, S, N, substituted of unsubstituted $C_1$-$C_8$ alkyl, or combinations thereof;

Ar is aryl, cycloalkyl, heterocycloalkyl, or heteroaryl group;

$L_1$ and $L_2$ are individually absent or a linker selected from the group consisting of —$SO_2$, —$SO_2$R'; $SO_2$R'R", —$SO_2$NR'R"; —$SO_2$NR'R"C(═O); —NR'$SO_2$R"; —R'$SO_2$NR'R'"; —C(═O); —C(═O)R'; —OC(═O)R'; —C(═O)NR'R"; —NR'C(═O)R"; —NR'C(═O)R"C(═O); —OR'; —NR'R"; —SR'; —$N_3$—C(═O)OR'; —O(CR'R")$_r$C(═O)R'; —O(CR'R")$_r$NR"C(═O)R'; —O(CR'R")$_r$NR"$SO_2$R'; —OC(═O)NR'R"; —NR'C(═O)OR"; substituted or unsubstituted $C_1$-$C_8$ aliphatic alkyl; substituted or unsubstituted $C_1$-$C_8$ alkylhalide, substituted or unsubstituted $C_1$-$C_8$ alkenyl, substituted or unsubstituted $C_1$-$C_8$ alkynyl, substituted or unsubstituted ether;

wherein R', R", and R'" are individually selected from hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6;

$R^6$ and $R^7$ are individually hydrogen, $C_1$-$C_8$ alkyl, ether, or $R^6$ and $R^7$ combine to form ═O;

$R^4$ is selected from hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine.

In some examples of Formula IX, Ar can include an aromatic group as disclosed herein such as phenyl, pyrrolyl, furanyl, thiophenyl, imidazolyl, oxazolyl, thiazolyl, triazolyl, pyrazolyl, pyridinyl, pyrazinyl, pyridazinyl, pyrazolyl, oxazoyl, isoxazoyl, or pyrimidinyl, furyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide), isoquinolinyl, quinolinyl.

In certain specific examples, Ar includes phenyl.

The Ar group can be substituted or unsubstituted. For example, the substituent on Ar can be selected from hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof. In certain embodiments, the substituent on Ar can be selected from H, Cl, F, Br, I, CN, $NO_2$, $NH_2$, $CF_3$, $CO_2H$, $CO_2NH_2$, $CO_2NHR^5$, $CO_2R^5$, C(O)$R^5$, C(O)$NH_2$, C(O)$NHR^5$, and $C_1$-$C_6$ alkyl optionally substituted with alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol.

In certain specific examples, Ar is substituted with $NO_2$, $NH_2$, OH, alkyl, aryl, halogen, amide, ether, or a combination thereof.

In the disclosed compounds of Formula IX, there can be from 1 to 5 different substituents $R^3$, e.g., 1, 2, 3, 4, or 5 $R^3$ substituents. The substituents can be the same or different. In specific examples, $R^3$ is $SO_2NH_2$, $SO_2$NHR', or $NHSO_2$R', wherein R' is $C_1$-$C_6$ alkyl or $C_1$-$C_6$ cycloalkyl optionally substituted with $C_1$-$C_6$ alkyl, $C_1$-$C_6$ alkoxyl, hydroxyl, or halide. In other examples, $R^3$ is NHC(O)R', wherein R' is $C_1$-$C_6$ alkyl or $C_1$-$C_6$ cycloalkyl optionally substituted with $C_1$-$C_6$ alkyl, $C_1$-$C_6$ alkoxyl, cycloalky, cycloheteroalkyl, hydroxyl, or halide. In other examples, $R^3$ is $C_1$-$C_6$ alkyl or $C_1$-$C_6$ cycloalkyl. In other examples, $R^3$ is $C_1$-$C_6$ alkoxyl. In other examples, $R^3$ is halide. In other examples, n is 2 and each $R^3$ is selected from the group consisting of $C_1$-$C_6$ alkyl, $C_1$-$C_6$ alkoxyl, halide, $SO_2NH_2$, $SO_2$NHR', and $NHSO_2$R', wherein R' is $C_1$-$C_6$ alkyl or $C_1$-$C_6$ cycloalkyl optionally substituted with $C_1$-$C_6$ alkyl, $C_1$-$C_6$ alkoxyl, hydroxyl, or halide. In other examples, $R^3$ is hydrogen, halogen, hydroxyl, substituted or unsubstituted amine, substituted or unsubstituted amide, nitro, ester, morpholino, dioxolane, substituted or unsubstituted $C_1$-$C_6$ alkyl, or combinations thereof.

In some examples of Formula IX, $L_1$ and $L_2$ comprises substituted or unsubstituted $C_1$-$C_8$ aliphatic alkyl, substituted or unsubstituted $C_1$-$C_8$ alkenyl; substituted or unsubstituted $C_1$-$C_8$ ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine.

In some specific examples of Formula IX, G comprises N.

In some embodiments of Formula IX, $R^4$ is selected from the group consisting of hydrogen, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted heterocyclyl, and combinations thereof.

In some embodiments of Formula IX, the compounds can be represented by Formula IX-A:

Formula IX-A

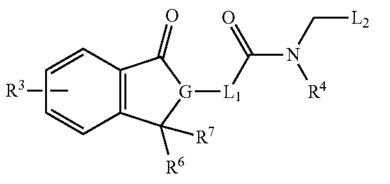

wherein,

G comprises C, S, N, substituted of unsubstituted $C_1$-$C_8$ alkyl, or combinations thereof;

$L_1$ and $L_2$ are individually absent or a linker selected from the group consisting of —$SO_2$, —$SO_2R'$; $SO_2R'R''$, —$SO_2NR'R''$; —$SO_2NR'R''C(=O)$; —$NR'SO_2R''$; —$R'SO_2NR'R'''$; —C(=O); —C(=O)R'; —OC(=O)R'; —C(=O)NR'R"; —NR'C(=O)R"; —NR'C(=O)R"C(=O); —OR'; —NR'R"; —SR'; —$N_3$—C(=O)OR'; —$O(CR'R'')_rC(=O)R'$; —$O(CR'R'')_rNR''C(=O)R'$; —$O(CR'R'')_rNR''SO_2R'$; —OC(=O)NR'R"; —NR'C(=O)OR"; substituted or unsubstituted $C_1$-$C_8$ aliphatic alkyl; substituted or unsubstituted $C_1$-$C_8$ alkylhalide, substituted or unsubstituted $C_1$-$C_8$ alkenyl, substituted or unsubstituted $C_1$-$C_8$ alkynyl, substituted or unsubstituted ether;

wherein R', R", and R'" are individually selected from hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6;

$R^6$ and $R^7$ are individually hydrogen, $C_1$-$C_8$ alkyl, ether, or $R^6$ and $R^7$ combine to form =O;

$R^4$ is selected from hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine.

In some embodiments, the compositions disclosed herein do not include

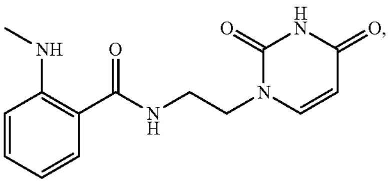

-continued

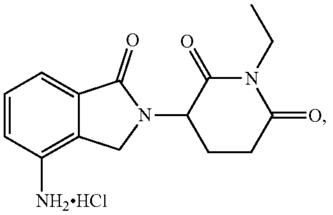

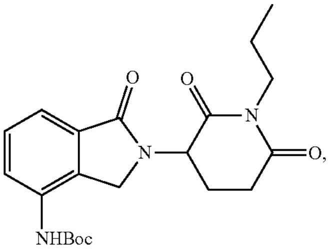

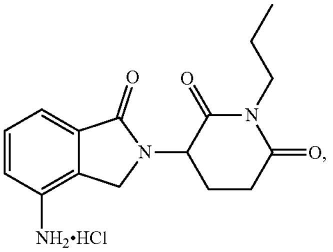

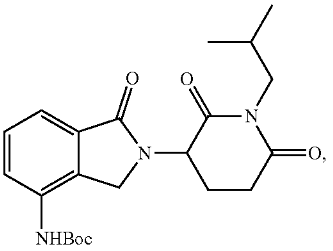

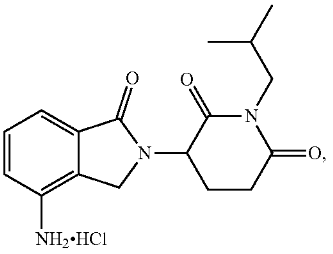

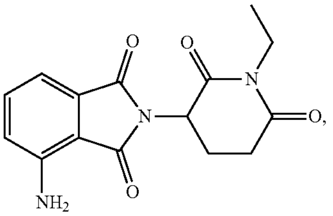

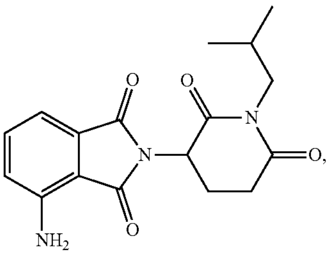

-continued

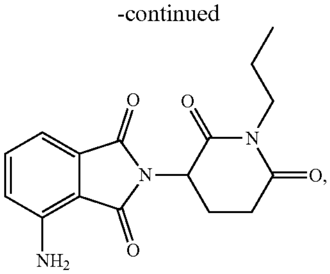
,

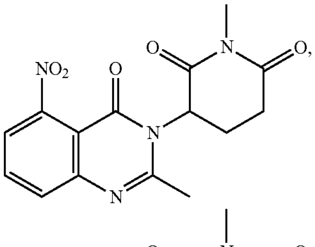
,

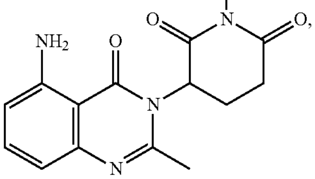
,

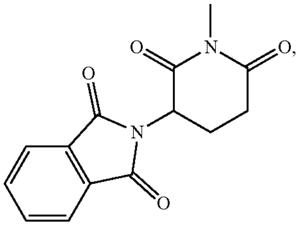
, or

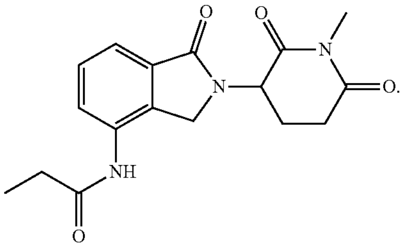
.

Method

Disclosed herein are methods for treating a disease state or condition in a patient wherein dysregulated protein activity is responsible for said disease state or condition. As described herein, the compounds disclosed comprises an E3 Ubiquitin Ligase binding moiety ("ULM") that is a cereblon E3 Ubiquitin Ligase binding moiety ("CLM"). Cereblon suppressed the expression of lower molecular weight isoforms of IKZF1 and IKZF3 in a temporally-regulated manner during T-cell activation. This regulation of IKZF in crbn−/− T-cells after activation indicates that cereblon may be involved in its regulation and that it is a native substrate of the CRBN/Cul4A/Rbx1 E3-ubiquitin ligase complex. This data suggests that cereblon substrates may have a non-canonical outcome. The compounds disclosed herein has significant therapeutic potential in cancers, such as solid tumors and blood-borne tumors; heart disease, such as congestive heart failure; and viral, genetic, inflammatory, allergic, and autoimmune diseases.

Methods of reducing the risk of, preventing, or treating a subject having an autoimmune disease or disorder are provided herein. In specific examples, methods of reducing the risk of developing, preventing, or treating graft versus host disease (GVHD) in a subject are provided. GVHD may be due to a transplantation procedure involving the implantation of immunogenic tissue including but are not limited to, solid organ transplants (such as heart, kidney, and liver), tissue grafts (such as skin, intestine, pancreas, cornea, gonad, bone, and cartilage), and cellular transplants (such as cells from pancreas, brain and nervous tissue, muscle, skin, bone, cartilage, and liver). In such procedures, organ rejection is an obstacle to complete recovery. The individual's immune system recognizes antigens (HLA or minor H antigens) on the implanted tissue as foreign and mounts an immune response against it, which injures and destroys the implanted tissue. The method can include administering to the subject an effective amount of a compound or composition as disclosed herein. The methods can further include administering a second compound or composition, such as, for example, an immunosuppressant.

The autoimmune diseases can include, for example, rheumatoid arthritis, multiple sclerosis, juvenile-onset diabetes, systemic lupus erythematosus, autoimmune uveoretinitis, autoimmune vasculitis, bullous pemphigus, myasthenia gravis, autoimmune thyroiditis or Hashimoto's disease, Sjogren's syndrome, granulomatous orchitis, autoimmune oophoritis, Crohn's disease, sarcoidosis, rheumatic carditis, ankylosing spondylitis, Grave's disease, and autoimmune thrombocytopenic purpura.

In one embodiment, an effective amount of one or more compounds or compositions disclosed herein is administered to a patient at risk of developing or have an autoimmune disease or disorder and who is in need of treatment thereof. The patient can be a human or other mammal, such as a primate (monkey, chimpanzee, ape, etc.), dog, cat, cow, pig, or horse, or other animals at risk of developing or have an autoimmune disease or disorder.

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Further provided herein are methods of treating a genetic disease or disorder in a subject, comprising administering to the subject an effective amount of a compound or composition as disclosed herein. The methods can further comprise administering a second compound or composition.

"Genetic disorder" can be caused by and/or based on changes in one or more genes that are inherited from at least one of the parents. Examples include urea cycle disorders, thalassemia, but also the embodiments of diseases or symptoms such as varicosis, vaginitis, depression or Sudden Infant Death Syndrome etc., that are based on or caused by these changes. The genetic disorder can be epigenetic which is defined as an inherited change in phenotype or gene expression which is not caused by changes to the gene sequence but is caused other mechanism/non-genetic factors.

The genetic disorder treating using the compounds disclosed herein can include disorders that manifests itself in symptoms or diseases selected from urea cycle disorders, thalassemia, cystic fibrosis, rheumatoid arthritis, Siogren's syndrome, uveitis, varicosis, polymyositis, and dermatomyositis, arteriosclerosis, amyotrophic lateral sclerosis, asociality, affective disorders, systemic lupus erythematosus. It rest also in cardiovascular and neurological diseases, type II diabetes, neurodegenerative diseases, Rubinstein-Taybi-Syndrome, Rett syndrome, Friedreich's ataxia, Huntingdon's disease, multiple sclerosis, depression. It might also include mucositis, skin/mucosal itching, degenerative diseases of the eye, eating disorders and obesity, drug induced weight gain, pruritus, alcoholism, grey hair, hair loss, cardiac injury, lack of neuronal growth, osteoporosis, bone and joint diseases, epithelial damage, desmosis, Parkinson's disease, myelodysplastic syndrome, fibrotic lung diseases, hepatic encephalopathies, infections by human papilloma virus (HPV) or autoimmune diseases or also vaginitis or Sudden Infant Death Syndrome. In general, as already stated in the definition of "genetic disorder" the use refers only to diseases/symptoms listed in this paragraph as far as their cause rests in a genetic disorder, especially in an epigenetic disorder.

Genetic disorders in general include the 22q11.2 deletion syndrome, Angelman Syndrome, Canavan disease, celiac disease, Charcot-Marie-Tooth disease, Color blindness, Cri du chat, Down syndrome, Cystic fibrosis, Duchenne muscular dystrophy, Haemophilia, Klinefelter's syndrome, neurofibromatosis, phenylketonuria, Prader-Willi syndrome, sickle cell disease, Tay-Sachs disease, Turner syndrome etc.

In some embodiments, the composition can be used to treat a genetic disorder being selected from or manifests itself in symptoms or diseases selected from urea cycle disorders, thalassemia, cystic fibrosis, rheumatoid arthritis, Siogren's syndrome, uveitis, polymyositis, and dermatomyositis, arteriosclerosis, amyotrophic lateral sclerosis, asociality, affective disorders, systemic lupus erythematosus, immune response, varicosis, vaginitis, including chronic recurrent yeast vaginitis, depression or Sudden Infant Death Syndrome, preferably selected from depression, varicosis, or Sudden Infant Death Syndrome.

Methods of inducing degradation of a target protein in a cell are also provided. The methods comprise contacting the cell with an effective amount of a compound or composition as disclosed herein.

Methods of inhibiting a cereblon E3 Ubiquitin Ligase binding moiety (CLM) are also provided. The methods comprise contacting the cell with an effective amount of a compound or composition as disclosed herein.

Methods of reducing the risk of, preventing, or treating other disease state or condition in a patient are also provided. In some embodiments of the methods described herein, the disease state or condition can include asthma, multiple sclerosis, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome, Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barré syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

The activity of the compounds to reduce the risk of, treat, prevent, or inhibit a disease condition can be determined using molecular dynamic simulation. In particular, molecular dynamic simulations can be performed using the known crystal structures of CRBN in various species. Several libraries are available for screening inhibitors.

The compounds can be assayed using known techniques in the art. For example, the biological assay can include overexpress human CRBN into CRBN−/− T-cells to determine the ability for each unique aminoacid to contribute to protein interactions with Myc, Ikaros and to identify new substrates involved in metabolite regulation. The CRBN-Cul4 in vitro Ub assay can be development using recombinant. Cell based analysis can be used to assess the expression of Myc and Ikaros will be used for screening purposes in treated cells. Expression of Myc and Ikaros will be visualized using luciferase-based expression assays as described previously. Development of substrate-targeted reduction in luciferase expression using IMiD compounds and constructs. The results show the ability of test chemical "HITS" to block CRBN-Cul4 mediated ubiquitination of target substrates using in vitro ubiquitination assays and luciferase constructs.

Administration

The disclosed compounds can be administered either sequentially or simultaneously in separate or combined pharmaceutical formulations. When one or more of the disclosed compounds is used in combination with a second therapeutic agent the dose of each compound can be either the same as or differ from that when the compound is used alone. Appropriate doses will be readily appreciated by those skilled in the art.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly(D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy,* 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

Kits for practicing the methods of the invention are further provided. By "kit" is intended any manufacture (e.g., a package or a container) comprising at least one reagent, e.g., anyone of the compounds described in Table 1. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

EXAMPLES

Example 1: Molecular Dynamic Simulation

Figure 2:
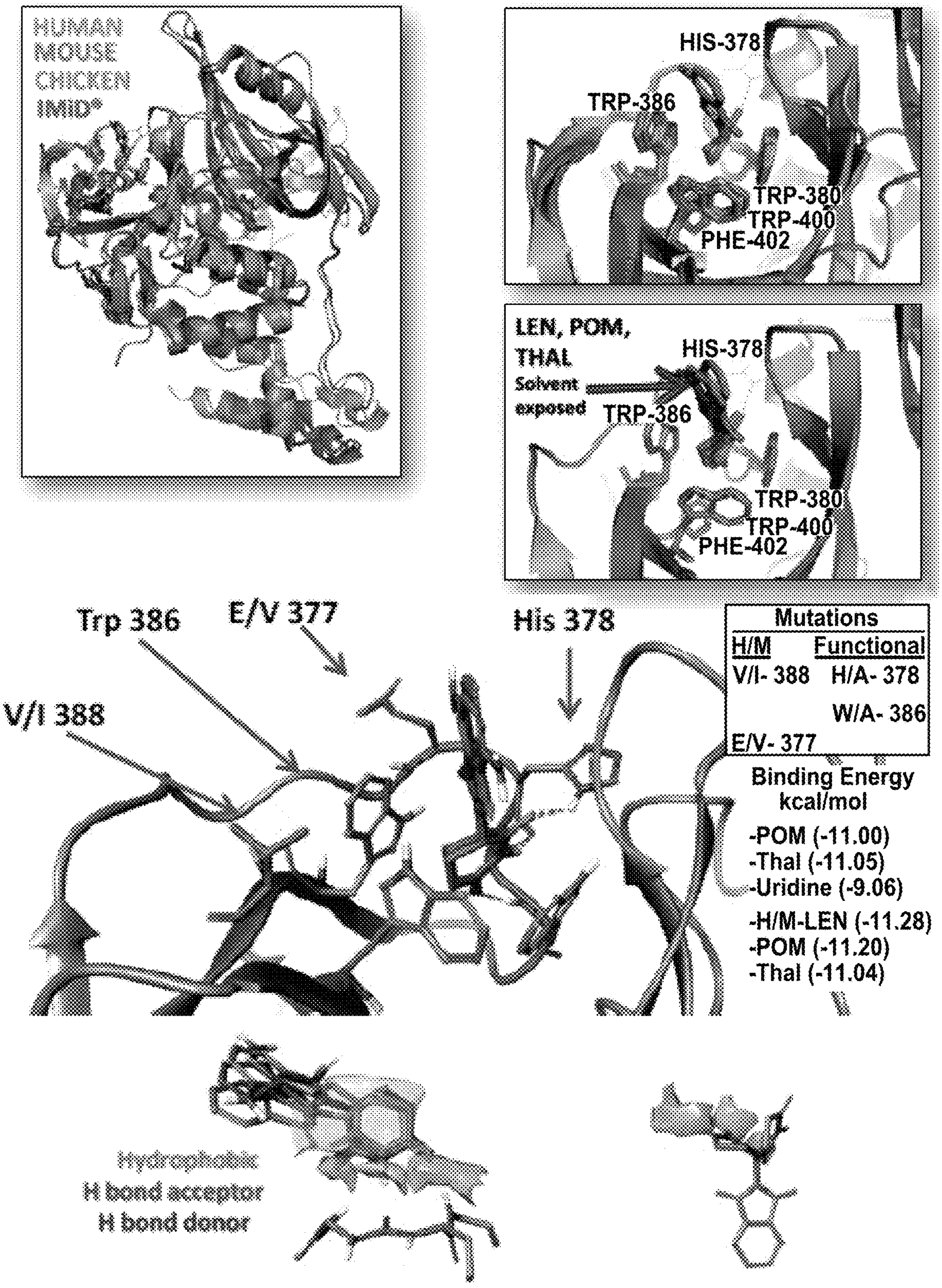
FIG. 2 are images showing structural analysis of CRBN and binding site confirmation using molecular dynamic simulations.

Using the molecular dynamic modeling approach, five compounds from the Diversity Set V structures that mimic IMiD's interaction with CRBN as shown in FIG. 2 were identified. The features of these compounds are preserved through TBD interactions, and may therefore represent novel compounds with potential to serve as leads for the synthesis of new chemical structures. This also provides proof-of-principle for conducting virtual screens to identify new molecular structures to build chemical libraries (TEST KITS) for physical and biological screening. Experiments determine the ability for these new drugs to interact with recombinant murine and human CRBN, and the potential of these compounds to modulate protein-protein interactions between CRBN/DDB1 complex proteins and substrates and to modulate the function of CRBN during immune activation.

Several libraries are available for screening inhibitors. Virtual analysis was formulated and then theoretical design of chemical test kit and virtual screen of test kit were carried out. Physical binding studies were also completed for the initial compounds using DSF and FP assays after they are fully tested. TEST KITs that represent the compounds identified from each of the available chemical libraries based on virtual chemical structures were also made.

| | |
|---|---|
| Lawrence ChemDisv library<br>Chemical Biology Core libraries | 32,000 compounds |
| LifeChemicals | 6,000 compounds |
| NCl fucused collections | 4,000 compounds |
| ChemDiv | 30,000 compounds |
| ChemBridge | 60,000 compounds |
| Kinase libraries.<br>For virtual screening | 2,000 compounds |
| NCl collection<br>Experimental screening | 140,000 compounds |
| Florida Translational Research Program | 340,000 compounds |

High throughput screen using FP allow testing for direct physical interaction from the chemical libraries defined in Step 2 above. The activity of the compounds identified can be confirmed through DSF and Biacore studies or crystallography. This will establish a new group of compounds to be called (NON-IMiD Mimics). If binding properties can be confirmed, then additional studies will be required to fully understand these molecules.

Biological Assays:

Step 1: Overexpress human CRBN into CRBN−/− T-cells to determine the ability for each unique aminoacid to contribute to protein interactions with Myc, Ikaros and to identify new substrates involved in metabolite regulation.

Step 2: Develop CRBN-Cul4 in vitro Ub assay using recombinant.

Step 3: Cell based analysis to assess the expression of Myc and Ikaros for screening purposes in treated cells. Expression of Myc and Ikaros is visualized using luciferase-based expression assays as described previously. Development of substrate-targeted reduction in luciferase expression using partent IMiD compounds and constructs.

Step 4: Determine the ability of test chemical "HITS" to block CRBN-Cul4 mediated ubiquitination of target substrates using in vitro ubiquitination assays, luciferase constructs as defined in Steps 1-3.

Metabolomic studies can be conducted using mass spectrometry in WT and KO T-cells and in IMiD-treated human T-cells after TCR stimulation.

Results:

Specific examples of compounds shown to bind to the thalidomide binding domain (TBD) of cereblon are described in Table 1. The data on differentially-regulated transcripts present after activation of CRBN−/− T-cells relative to WT-T-cells has revealed a novel target and potential mechanism of immune modulation mediated by Ikaros and Myc-induced changes in metabolic function. Normal T-cell metabolism involves the flexible utilization of metabolites to suite the energy demands of the cell during homeostasis and activation. Glucose use is low in naïve cells, but is increased dramatically after activation to meet the cells high energy demands. CD28 stimulation is critical for the induction of glycolysis and stimulation of glucose transporters. Suppression of CRBN may modulate this pathway allowing for greater utilization of glucose/glutamine during activation.

TABLE 1

Biological activity of compounds.

| Compound Name<br>Structure and Molecular Weight | Compound Class | IL-2 (%) (Relative to DMSO) | Viability (%) (Relative to DMSO) | Cereblon Binding (≥50% inhibition at 200 μM) |
|---|---|---|---|---|
| 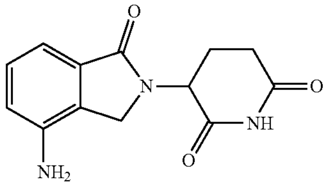<br>Lenalidomide<br>M.W. = 259.27 | 1 | 216 | 99.9 | Yes |
| 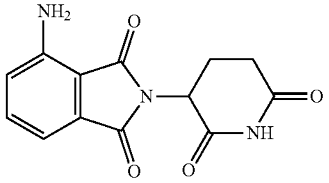<br>Pomalidomide<br>M.W. = 273.25 | 1 | 208.6 | 96.3 | Yes |

TABLE 1-continued
| | | | | |
|---|---|---|---|---|
| 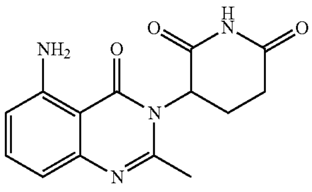<br>MA5-169B2<br>M.W. = 286.29<br>(CC-122)<br>(1) | 1 | 283.4 | 84.4 | Yes |
| 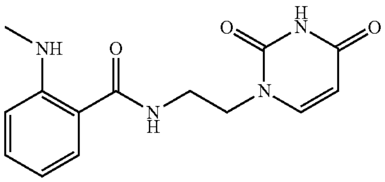<br>SG4-181<br>M.W. = 288.31<br>(MANT-uracil in-house)<br>(171) | 1 | 158.7 | 97.0 | Yes |
| 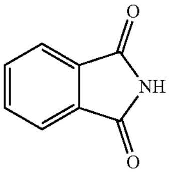<br>Phthlimide<br>M.W. = 147.13 | 1 | 110.8 | 92.4 | No |
| 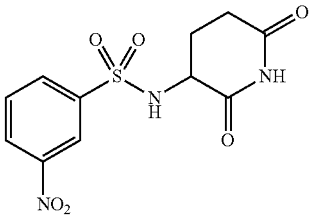<br>SG4-159<br>M.W. = 313.28<br>(27)<br>*Anti-tumor activity | 2A | 143.7 | 80.0 | Yes* |
| 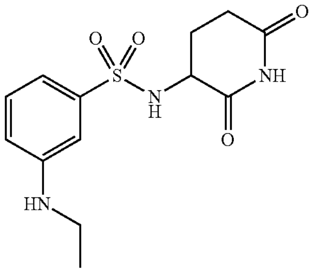<br>SG4-163-02<br>M.W. = 311.36<br>(29) | 2A | 124.4 | 100 | Yes* |

TABLE 1-continued
| | | | | |
|---|---|---|---|---|
| 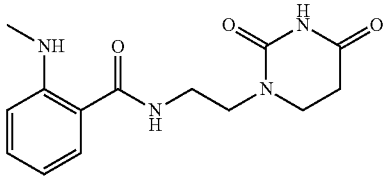<br>SG5-091<br>M.W. = 290.32<br>(170) | 4 | 167.5 | 101.2 | Yes* |
| 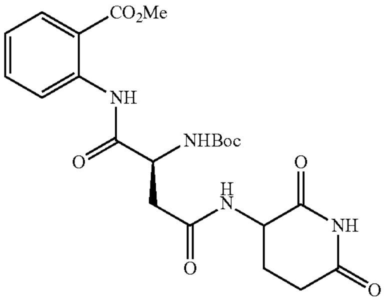<br>SR1-080<br>M.W. = 476.49<br>(141) | 2A | 25.0 | 85.6 | Yes* |
| 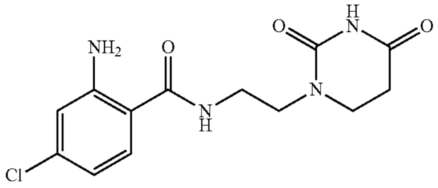<br>SG5-125<br>M.W. = 310.74<br>(190) | 4 | 14.1 | 78.7 | Yes* |
| 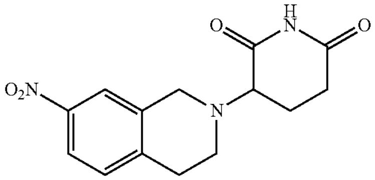<br>MA7-075<br>M.W. = 289.29<br>(182) | 2B | 23.0 | 84.2 | Yes* |
| 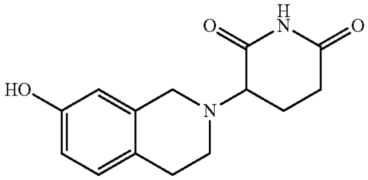<br>MA7-098<br>M.W. = 260.29<br>(188) | 2B | 32.2 | 102.0 | Yes* |

TABLE 1-continued
| | | | | |
|---|---|---|---|---|
| 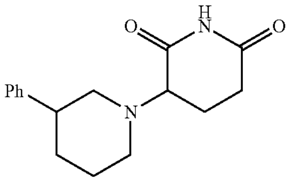<br>MA7-081<br>M.W. = 272.35<br>(184) | 2B | 45.3 | 92.1 | Yes* |
| 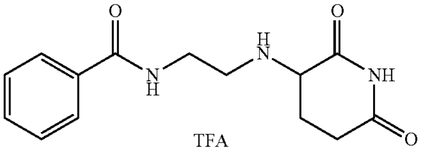<br>TFA<br>MA6-105<br>M.W. = 372.32<br>(157) | 2B | 46.7 | 68.2 | Yes* |
| 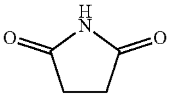<br>Succinimide<br>M.W. = 99.09<br>(172) | 6 | 199.7 | 75.3 | Yes |
| 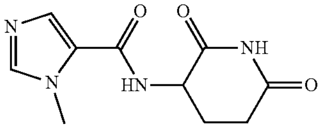<br>MA6-116<br>M.W. = 236.23<br>(7) | 2A | 148.0 | 95.3 | Yes |
| 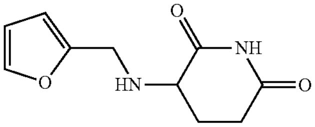<br>MA6-122-1<br>M.W. = 208.22<br>(8) | 2B | 136.9 | 95.9 | Yes |
| 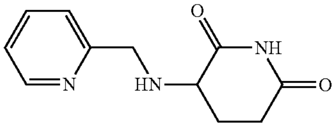<br>MA6-122-2<br>M.W. = 219.24<br>(9) | 2B | 7.8 | 84.9 | Yes |

TABLE 1-continued
| | | | | |
|---|---|---|---|---|
| 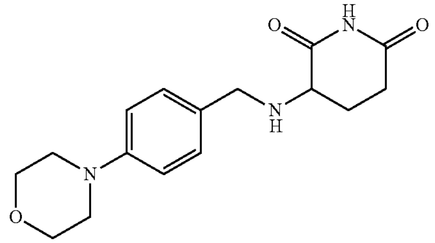<br>MA6-122-3<br>M.W. = 303.36<br>(10) | 2B | 14.9 | 94.5 | Yes |
| 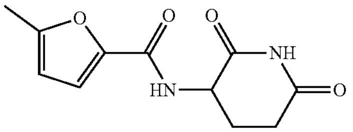<br>MA6-122-10<br>M.W. = 222.24<br>(14) | 2B | 48.0 | 84.7 | Yes |
| 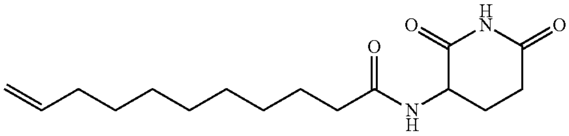<br>SG4-136<br>M.W. = 294.40<br>(18)<br>*Anti-tumor activity | 2A | 15.6 | 82.3 | Yes |
| 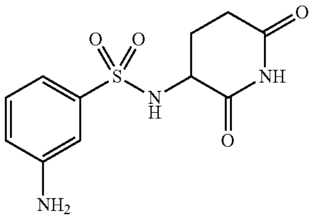<br>SG4-163-01<br>M.W. = 283.30<br>(28) | 2A | 127.0 | 99.7 | Yes |
| 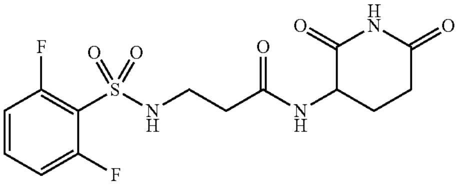<br>MA6-174-4<br>M.W. = 375.35<br>(36) | 2A | 120.1 | 99.4 | Yes |

TABLE 1-continued
| | | | | |
|---|---|---|---|---|
| 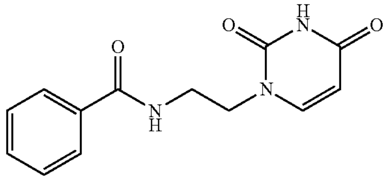<br>SG5-0001<br>M.W. = 259.27<br>(52) | 3 | 124.5 | 84.2 | Yes |
| 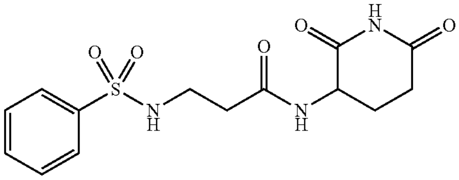<br>MA6-168<br>M.W. = 339.37<br>(63) | 2A | 32.7 | 77.2 | Yes |
| 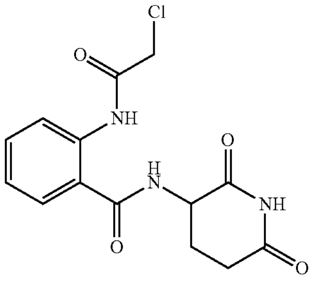<br>SR1-067-2<br>M.W. = 323.73<br>(69)<br>*Anti-tumor activity | 2A | 40.3 | 69.9 | Yes |
| 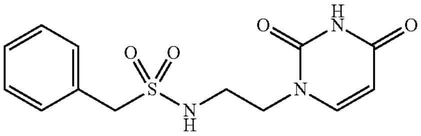<br>SG5-068<br>M.W. = 309.34<br>(164) | 3 | 138.2 | 76.7 | Yes |
| 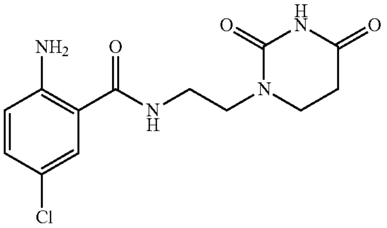<br>SG5-127<br>M.W. = 310.74<br>(191) | 4 | 20.6 | 78.8 | Yes |

TABLE 1-continued
| | | | | |
|---|---|---|---|---|
| 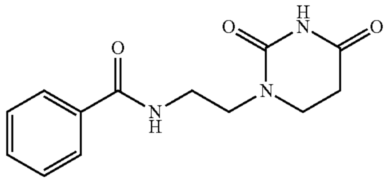<br>SG5-129<br>M.W. = 261.28<br>(192) | 4 | 47.1 | 84.9 | Yes |
| 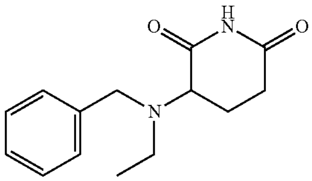<br>MA7-004<br>M.W. = 246.31<br>(189) | 2B | 32.1 | 99.1 | Yes |
| 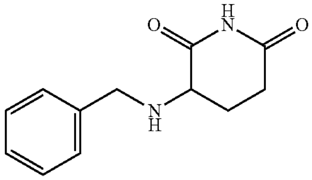<br>MA7-090<br>M.W. = 218.26<br>(186)<br>*Anti-tumor activity | 2B | 40.4 | 98.0 | Yes |
| 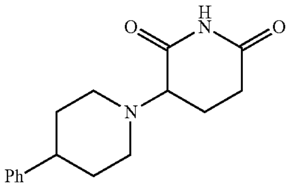<br>MA7-080<br>M.W. = 272.35<br>(183) | 2B | 41.5 | 100.3 | Yes |
| 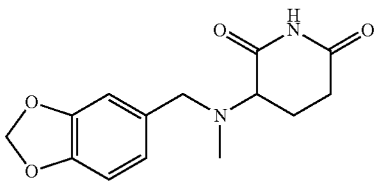<br>MA7-088<br>M.W. = 276.29<br>(185) | 2B | 43 | 106.2 | Yes |

TABLE 1-continued
| | | | | |
|---|---|---|---|---|
| 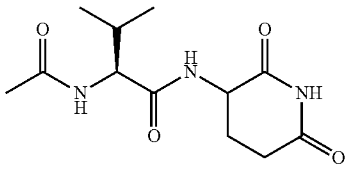<br>SG4-143<br>M.W. = 269.30<br>(23) | 2A | 126.4 | 79.4 | DSF (check)<br>FI (borderline) |
| 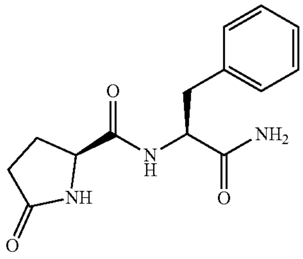<br>SR1-060<br>M.W. = 275.31<br>(74) | 5 | 39.8 | 74.7 | No |
| 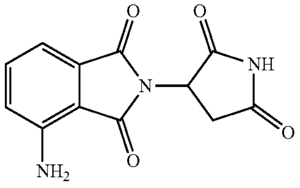<br>SG5-081<br>M.W. = 259.22<br>(168) | 6 | 193.8 | 97.0 | No |
| 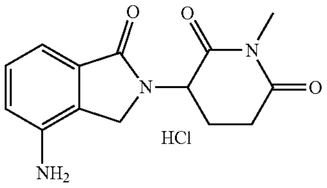<br>SG5-046<br>M.W. = 309.75<br>(89) | 7 | 199.2 | 106.5 | No |
| 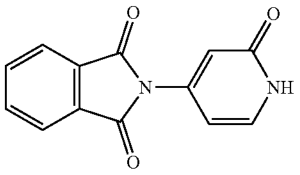<br>MA6-090<br>M.W. = 240.22<br>(5) | 5 | 123.3 | 95.3 | No |

TABLE 1-continued
| | | | | |
|---|---|---|---|---|
| 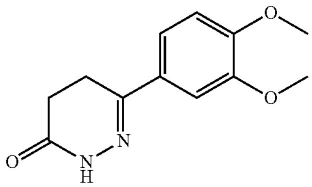 MA6-064 M.W. = 234.26 (4) | 5 | 12.4 | 100.1 | No |
| 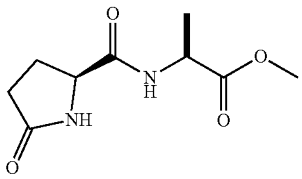 SR1-045 M.W. = 214.22 (112) | 5 | 11.7 | 100.8 | No |
| 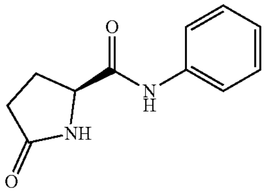 SR1-046 M.W. = 204.23 (113) | 5 | 0.5 | 106.5 | No |
| 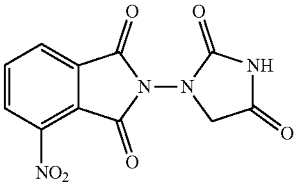 SG5-058 M.W. = 290.19 (90) | 6 | 50.0 | 96.4 | No |
| 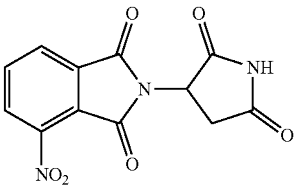 SG5-078 M.W. = 289.20 (167) | 6 | 133.4 | 81.9 | No |

TABLE 1-continued
| | | | | |
|---|---|---|---|---|
| 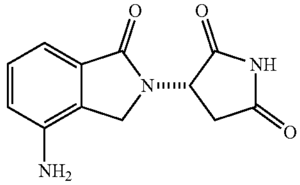<br>SG5-102<br>M.W. = 245.24<br>(176) | 6 | 124.9 | | No |
| 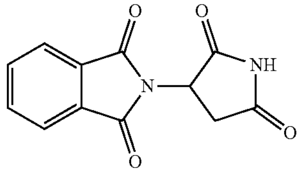<br>SG5-086<br>M.W. = 244.21<br>(169) | 6 | 10.9 | 75.3 | No |
| 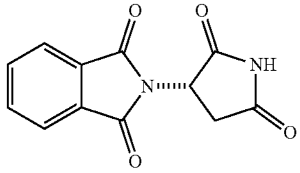<br>SG5-092<br>M.W. = 244.21<br>(174) | 6 | 44.4 | 85.6 | No |
| 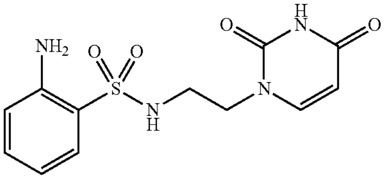<br>SG5-072<br>M.W. = 310.33<br>(166) | 3 | 31.8 | 74.6 | No |
| 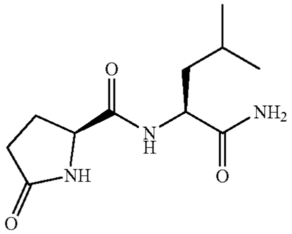<br>SR1-061<br>M.W. = 241.29<br>(114) | 5 | 24.6 | 110.5 | No |

TABLE 1-continued

| Compound Name<br>Structure and Molecular Weight | Compound Class | Sensitive cell line | Viability (%) (Relative to DMSO) | Cereblon Binding (≥50% inhibition at 200 μM) |
|---|---|---|---|---|
| 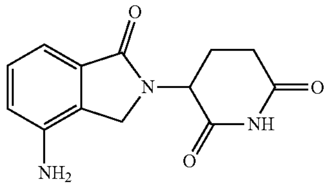<br>Lenalidomide<br>M.W. = 259.27 | 1 | U266<br>MM1.S<br>THP-1<br>U-937<br>K562<br>HL-60<br>Lymphocytes | 47.9<br>47.4<br>76.9<br>99.4<br>100.8<br>82.7<br>99.9 | Yes |
| 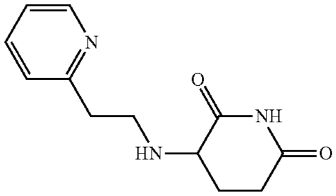<br>MA6-122-9<br>M.W. = 233.27<br>(13) | 2B | U266<br>MM1.S<br>THP-1<br>U-937<br>K562<br>HL-60<br>Lymphocytes | 27.0<br>29.9<br>98.8<br>58.4<br>80.0<br>81.8<br>91.1 | Yes |
| 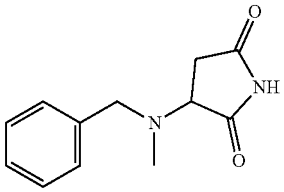<br>MA7-038<br>M.W. = 218.26<br>(64) | 6 | U266<br>MM1.S<br>THP-1<br>U-937<br>K562<br>HL-60<br>Lymphocytes | 0<br>1.1<br>32.6<br>98.5<br>116.7<br>10.15<br>96.8 | No |
| 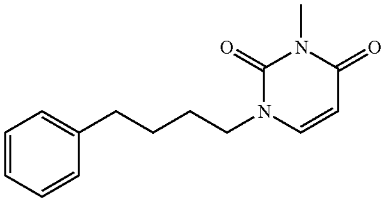<br>SG5-042<br>M.W. = 258.32<br>(87) | 5 | U266<br>MM1.S<br>THP-1<br>U-937<br>K562<br>HL-60<br>Lymphocytes | 32.7<br>43.0<br>32.8<br>50.5<br>17.7<br>39.3<br>94.2 | No |
| 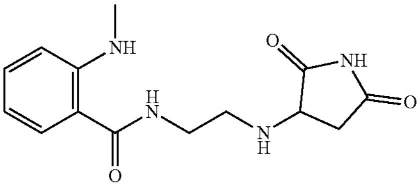<br>•2 TFA<br>MA7-046.2TFA<br>M.W. = 518.37<br>(177) | 6 | U266<br>MMI.S<br>THP-1<br>U-937<br>K562<br>HL-60<br>Lymphocytes | 0.1<br>53.6<br>41.1<br>6.3<br>21.1<br>12.0<br>92.6 | No |

TABLE 1-continued
| Compound Name Structure and Molecular Weight | Compound Class | IL-2 (%) (Relative to DMSO) | Viability (%) (Relative to DMSO) | Cereblon Binding (≥50% inhibition at 200 μM) |
|---|---|---|---|---|
| 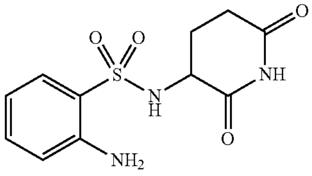 SG4-135-01 M.W. = 283.30 (17) | 2A | 54.7 | 99.1 | Yes* |
| 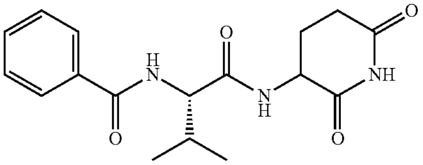 SG4-141 M.W. = 331.37 (21) | 2A | 84.5 | 99.1 | Yes* |
| 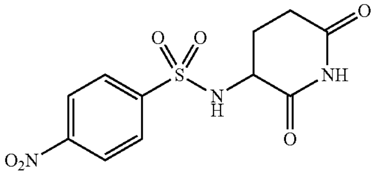 SG4-154B2 M.W. = 313.28 (26) | 2A | 56.3 | 93.4 | Yes* |
| 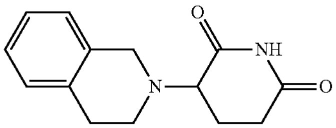 MA6-136 M.W. = 244.29 (32) | 2B | 105.4 | 99.5 | Yes* |
| 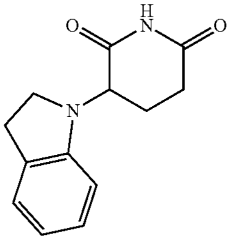 MA6-180-3 M.W. = 230.27 (40) | 2B | 85.0 | 98.7 | Yes* |

TABLE 1-continued
| | | | | |
|---|---|---|---|---|
| 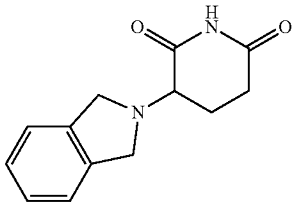<br>MA7-002<br>M.W. = 230.27<br>(41) | 2B | 69.0 | 84.8 | Yes* |
| 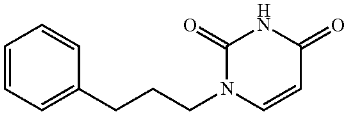<br>SG4-170<br>(NSC211769 in-house)<br>M.W. = 230.27<br>(47) | 3 | 99.7 | 93.1 | Yes* |
| 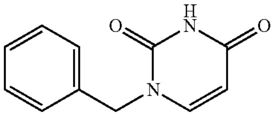<br>SG4-174<br>M.W. = 202.21<br>(50) | 3 | 88.2 | 79.5 | Yes* |
| 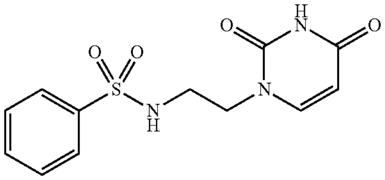<br>SG5-002<br>M.W. = 295.31<br>(53) | 3 | 90.8 | 77.8 | Yes* |
| 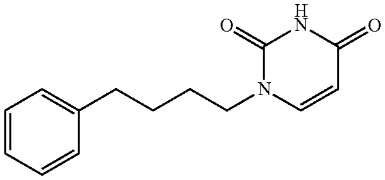<br>SG5-003<br>M.W. = 244.29<br>(54) | 3 | 101.8 | 86.4 | Yes* |
| 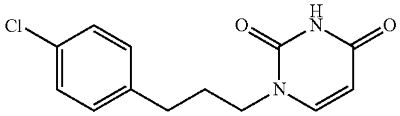<br>SG5-004<br>M.W. = 264.71<br>(55) | 3 | 93.9 | 90.7 | Yes* |

TABLE 1-continued
| | | | | |
|---|---|---|---|---|
| 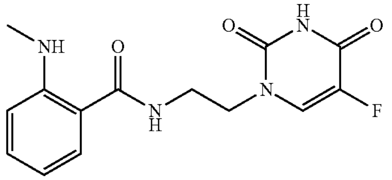 SG5-016 M.W. = 306.30 (59) | 3 | 75.1 | 79.2 | Yes* |
| 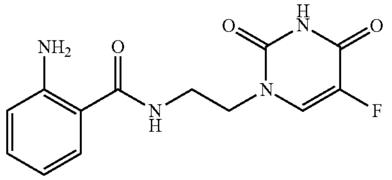 SG5-017 M.W. = 292.27 (60) | 3 | 109.0 | 89.7 | Yes* |
| 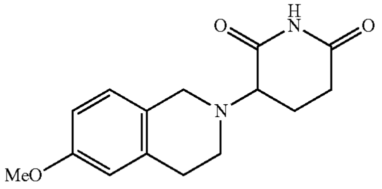 MA7-050 M.W. = 274.32 (66) | 2B | 79.0 | 74.4 | Yes* |
| 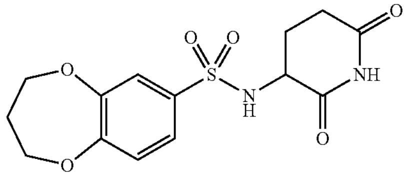 SG5-030 M.W. = 340.35 (78) | 2A | 61.6 | 73.6 | Yes* |
| 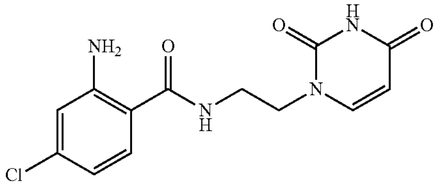 SG5-034 M.W. = 308.72 (81) | 3 | 67.3 | 70.4 | Yes* |

TABLE 1-continued

| | | | | |
|---|---|---|---|---|
| 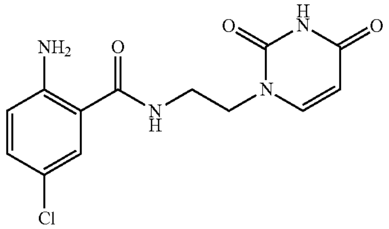 SG5-035 M.W. = 308.72 (82) | 3 | 51.2 | 74.8 | Yes* |
| 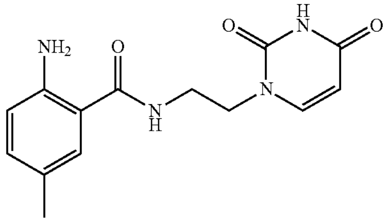 SG5-036 M.W. = 288.31 (83) | 3 | 83.7 | 75.2 | Yes* |
| 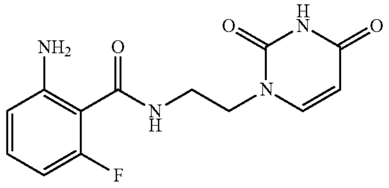 SG5-037 M.W. = 292.27 (84) | 3 | 107.0 | 95.0 | Yes* |
| 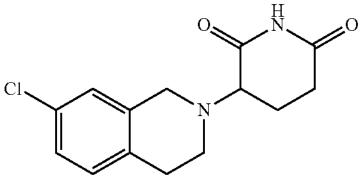 MA7-074 M.W. = 278.74 (181) | 2B | 69.9 | 93.2 | Yes* |
| 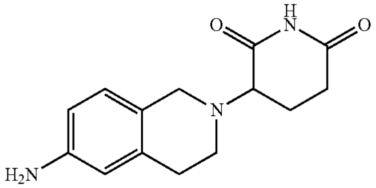 MA7-096 M.W. = 259.31 (187) | 2B | 54.6 | 95.8 | Yes* |

Discussion: It has been shown that cereblon suppresses the expression of lower molecular weight isoforms of IKZF1 and IKZF3 in a temporally-regulated manner during T-cell activation. This regulation of IKZF in crbn−/− T-cells after activation indicates that cereblon may be involved in its regulation and that it is a native substrate of the CRBN/Cul4A/Rbx1 E3-ubiquitin ligase complex. This data suggests that cereblon substrates may have a non-canonical outcome. This data, using a genetic approach, is consistent with the idea that crbn inhibition leads to the functional potentiation of T-cells that has long been associated with IMiDs. The current model adapted from Fischer et al is shown in FIG. 1. The data brings into question the role of the solvent exposed portion of the compounds in the recruitment of IKZF1 and 3. This supports that hypothesis that new inhibitors based on the binding motif may produce a new class that could have differential selectivity and or potency with regard to CRBN suppression. To address this idea, molecular dynamic simulations using the known crystal structures were performed. Sequence similarity was observed for all three species of CRBN tested in this model with regard to the Thalidomide Binding Domain (TBD). Using these structures, molecular dynamics and induced fit docking that shows similar binding modes by three IMiDs in human and murine TBD of cereblon. (FIG. 2) were performed and sets the stage for high throughput virtual screens to test for novel chemicals that will fit into the highly stable, fixed binding pocket of CRBN.

Example 2: Conserved Ligand Binding and Ubiquitin Conjugating Activity of Mouse and Human Cereblon In this example, small molecules, such as dBET1, are designed to degrade bromodomain containing 4 (BRD4) based on Proteolysis Targeting Chimera (PROTAC) technology. These molecules contain bifunctional head groups that engage specific proteins and target them for degradation by the proteosome. dBET1 exploits the interaction between thalidomide and cereblon (CRBN), an E3-ubiquitin ligase receptor for the DDB1/Cul4/Rbx1 complex. However, there are known human-versus mouse-specific differences in the ability of thalidomide and other immunomodulatory drugs, including lenalidomide and pomalidomide, to degrade CRBN substrates. To further assess species-related structural differences of CRBN, complementary theoretical, biophysical and biological assays were conducted using a series of recombinant thalidomide binding domain (TBD) proteins, recombinant CRBN-DDB1 complex and chemical probes. Here, a lower binding affinity for lenalidomide was identified, and likely other immunomodulatory drugs, to the TBD compared to the CRBN-DDB1 complex which appears to be mediated by a disordered loop (351-353) that is stabilized by N-terminal residues. However, binding of CRBN to immunomodulatory drugs and PROTAC small molecules is not impaired by amino acid differences in mouse CRBN suggesting that there are no conformational changes that would be predicted to impact function. Using dBET1, a structurally-related inactive control compound, and CRBN genetically deficient ($Crbn^{-/-}$) T cells, it was shown that mouse CRBN successfully directs the protein destruction of BRD4. From these cross-species structure-function analyses, the substrate binding function and ligand-induced ubiquitin-proteasome targeting by mouse CRBN was confirmed which paves the way for preclinical development of PROTAC therapeutics in cancer.

Materials and Methods

Animals and cell lines: Germline Crbn deficient mice ($Crbn^{-/-}$) were a gift from Dr. Anjali Rajadhyaksha (12). Gene deletion was confirmed using wild-type and Crbn-KO-specific primers as described previously. C57BL/6 ($Crbn^{+/+}$) mice were purchased from Jackson Laboratory (Farmington, CT) and were then bred to $Crbn^{-/-}$ mice. $Crbn^{+/+}$ and $Crbn^{-/-}$ littermates from $Crbn^{+/-}$ intercrosses were used for these studies. Mice were maintained and bred at the H. Lee Moffitt Cancer Center and Research Institute under a protocol approved by the Institutional Animal Care and Use Committee (IACUC). The human multiple myeloma cells including U266, H929, MM1.S, and the mouse multiple myeloma cell line 5TGM1, were gifts of Drs. Ken Shain and Connor Lynch (Moffitt Cancer Center, Tampa, FL). All cell lines were mycoplasma free and sequence verified.

T cell isolation, activation and drug treatments: Human polyclonal CD3+ T cells or CD8+ T cells were isolated from peripheral blood donations to the Southwest Florida Blood Services. Since personal identifying information is unavailable, the research was deemed non-human research. Human and mouse T cells were isolated from $Crbn^{+/+}$ and $Crbn^{-/-}$ splenocytes by immunomagnetic negative selection (Miltenyi Biotec, San Diego, CA) and >95% purity was confirmed by flow cytometry. For drug treatment experiments, 12-well flat bottom plates were coated with 5 μg/ml anti-CD3ε(clone #HIT3a, eBioscience or clone #145-2C11) in 1 L PBS at 37° C. for 60 min. Cells were plated at 2-4×10$^6$ cells per well with anti-CD28 (clone #CD28.2, eBioscience or clone #37.51, eBioscience). Following 12 h of activation, the cells were treated with DMSO (0.1%, Sigma-Aldrich, MO), lenalidomide (10 μM) (Celgene, N.J.), pomalidomide (Sigma-Aldrich), and JQ1 (doses indicated) (Cat #SML0974, Sigma-Aldrich). N-methyl-lenalidomide, dBET1, and N-methyl-dBET1 were all synthesized at Moffitt Cancer Center (described in supplementary material) and used at the doses indicated. After 12 h of drug treatment, cells were harvested and protein levels were examined by western blot analysis. For proliferation experiments using mouse T cells, 0.1-10 μg/mL anti-CD3ε(clone #145-2C11, eBioscience) was used with cells plated with and without anti-CD28 for 72 h. For cytokine expression, supernatants were harvested at 24 or 48 h for IL-2 determination. Cytokines were quantified from standard curves by enzyme-linked immunosorbent assay (ELISA) according to the manufacturer's protocol. Kits were purchased from eBioscience (IL-2) and R&D Systems for other cytokines. For functional analysis of T cells treated with JQ1, murine CD8+ T cells from $Crbn^{+/+}$ splenocytes were labeled with 5-10 μM CellTrace Violet (C34557, ThermoFisher) and activated with 5 μg/mL anti-CD3ε and 1 μg/mL anti-CD28 for 72 h in round-bottom 96-well plates. Cells were stained with CD98-PE (clone #RL388, Biolegend) and 7-AAD (BD Pharmingen) and analyzed on a BD LSRII.

qRT-PCR: Isolated T cells from $Crbn^{+/+}$ and $Crbn^{-/-}$ mice were lysed, homogenized (Qiashredder, Qiagen), and total RNA extracted (RNeasy, Qiagen) according to manufacturer protocol. Complementary DNA was generated from isolated RNA (iScript cDNA synthesis Kit, Bio-Rad). RNA expression was analyzed by quantitative real time-polymerase chain reaction (qRT-PCR) using Taqman Universal PCR Master Mix for Taqman probes (Thermo Fischer Scientific) against (cDNA) c-Myc (Mm00487804_m1) and (cDNA) β2M (Mm00437762_m1). Samples were run on an Applied Biosystems 7900 HT and Sequence Detection Systems software.

Treatment of multiple myeloma cells: Mouse and human multiple myeloma cell lines were plated at 2-4×10$^6$ cells per well in a 12-well plate with various concentrations of lenalidomide, pomalidomide, and thalidomide. To confirm target degradation, the cells were treated with varying concentrations of dBET1 (0, 0.01, 0.1, 1, and 10 μM) for 12-24 h. Following drug treatment, protein levels were examined by western blot analysis relative to vinculin or β-actin to normalize for protein expression. For proliferation studies, 1-2×$10^4$ cells per well were seeded in a 96-well plate and were treated with using cell-counting-8 kit (CCK8) (Dojindo, Rockville, MD) according to manufacturer's protocol.

General chemistry information: All reagents were purchased from commercial suppliers and used without further purification (except where mentioned otherwise). $^1$H NMR spectra were recorded on an Agilent-Varian Mercury 400 MHz spectrometer with DMSO-$d_6$ as the solvent. All coupling constants are measured in Hertz, and the chemical shifts (δH) are quoted in parts per million relative to TMS (δ 0), which was used as the internal standard. High-resolution mass spectroscopy was carried out on an Agilent 6210 LC-MS (ESI-TOF) system. HPLC analysis was performed using a JASCO HPLC system equipped with a PU-2089 Plus quaternary gradient pump and a UV-2075 Plus UV-Vis detector, using an Alltech Kromasil C-18 column (150×4.6 mm, 5 μm) and an Agilent Eclipse XDB-$C_{18}$ column (150×4.6 mm, 5 μm). The purities of the final compounds used for the biochemical and functional studies were >95% as measured by HPLC. Melting points were recorded on an Optimelt automated melting point system (Stanford Research Systems). Thin-layer chromatography was performed using silica gel 60 F254 plates (Fisher Scientific), with observation under UV when necessary. Anhydrous dimethylformamide was used as purchased from Sigma Aldrich. Burdick and Jackson HPLC-grade solvents were purchased from VWR for HPLC, HPLC-MS and high-resolution mass analysis. dBET1 (HPLC purity 98%) was prepared from JQ1 as described (5). Detailed theoretical calculations and synthesis of N-methyl-lenalidomide and N-methyl-dBET1 are provided below.

Cloning, protein expression and purification: The full-length hCRBN protein in complex with the DNA-damage binding protein (DDB1) was a generous gift from Celgene Corporation (San Diego, CA). Details of protein expression of the human TBD is provided below.

Zincon assay: All chemicals used in this assay were purchased from Sigma-Aldrich. The assay was adapted from previously published methods (13). A zinc concentration standard curve was prepared in 50 mM borate buffer, pH 9.0 containing 4 M NaCl, and 8 M urea and 40 μM zincon (2-carboxy-2'-hydroxy-5'-sulfoformazylbenzene) dye. Purified proteins were acidified with 300 mM HCl to facilitate the release of the zinc ions bound to the protein. The protein polypeptide was separated from the water soluble layer by centrifugation. The solution was then spiked with 10-20 μM zinc sulfate. Absorption spectra between 400-750 nm were recorded. $\lambda_{max}$ of free zincon and zincon-Zn complex were measured at 480 nm and 620-630 nm, respectively. Absorbance at 630 nm of different zinc concentrations were used to generate the linear regression curve. Concentration of zinc containing protein was extrapolated based on the linear regression curve.

Isothermal titration calorimetry (ITC): The binding of CRBN-DDB1 complex and CRBN-TBD wild-type and mutant variants to lenalidomide, pomalidomide, and thalidomide were analyzed with MicroCal iTC200 titration calorimeter (Malvern, Westborough, MA). The compound phthalimide was used as the negative control. The proteins were re-buffered into binding buffer [50 mM HEPES (pH 7.5, Sigma-Aldrich), 200 mM NaCl, 0.1 mM TCEP and 0.6% DMSO]. For the titrations of the protein constructs, a total of 19 (aliquots (2.05 μl each) of the respective compounds (~600 μM) were injected into 200 μl of the protein solutions (40 μM) at 25° C. The ITC cell mixture was constantly stirred at 1000 rpm and recorded for 160 s between injections at low feedback. The corrected heat values were fitted using a nonlinear least square curve-fitting algorithm (Microcal Origin 7.0, OriginLab, Northampton, MA) to obtain binding constants ($K_D$).

Intrinsic tryptophan fluorescence assay: Binding of compounds to wild-type and mutant TBD was monitored by fluorescence spectroscopy, using an adapted previously published method (14). All chemicals used in this assay were purchased from Sigma-Aldrich unless otherwise stated. In this assay, changes in emission spectra are induced by interactions of these compounds with the three Trp residues (Trp380, Trp386 and Trp400) in the binding site (15, 16). TBD proteins (final concentration, 10 μM) were incubated with varying final concentrations (0-750 μM) of compounds in assay buffer (50 mM Tris, pH 7.5, 200 mM NaCl, 0.1% Pluronic-F127, and 1 mM TCEP) to a final volume of 40 μl in a black 96-well half area plate (Corning, Corning, NY). A 0.5% final DMSO concentration was used in each well. Samples were excited at 280 nm and fluorescence emission intensities were measured at 340 nm using Wallac Envision 2102 multilabel plate reader (Perkin Elmer, Waltham, MA). All measurements were done in triplicate and corrected for inner filter effect to subtract for ligand-associated fluorescence, as described (17). The magnitude of fluorescence difference (1-F/$F_0$) was measured where F is the fluorescence emission at a given concentration of ligand; $F_0$ is the intrinsic fluorescence intensity of 10 μM of TBD protein alone. Graph plotting and curve fitting to obtain apparent dissociation constant ($K_D$) values were calculated by fitting the relative change in intrinsic fluorescence at 340 nm (1-F/$F_0$) versus ligand concentration to a nonlinear regression with one-site binding hyperbola with GraphPad Prism Sofware (GraphPad Software, La Jolla, CA).

Molecular Dynamics

Protein Preparation for Theoretical Modeling: The preparation of the protein systems for human cereblon (hCRBN, PDB 4TZ4(1), murine cereblon (mCRBN, PDB 4TZC and 4TZU)(1) and galline cereblon (gCRBN, PDB 4CI1, 4CI2, and 4CI3)(2) were done using the Schrödinger software suite (Maestro, version 9.7, Schrödinger, LLC, New York, NY, 2014). Protein structure coordinates were downloaded from the Protein Data Bank (PDB) (3, 4) and prepared with the Protein Preparation Wizard (PrepWizard) in Maestro [Schrödinger Suite 2014-1 Protein Preparation Wizard; Epik version 2.7, Schrödinger, LLC, New York, NY, 2013; Impact version 6.2, Schrödinger, LLC, New York, NY, 2014; Prime version 3.5, Schrödinger, LLC, New York, NY, 2014)(5). Bond orders were assigned, including disulfide bridges, and original hydrogens were deleted and later replaced to reduce bad contacts and other crystal artifacts before protonation and hydrogen bond optimization. Missing side-chains were added and optimized using Prime (version 3.5)(6, 7). Cofactors used in crystallization (such as sulfate or phosphate ions), ligands, and additional protein dimers were then deleted. All waters were retained for assisting in the determination of side chain protonation states and initial hydrogen bond optimization. Hydrogen atoms were then added to the protein, remaining cofactors, and to any added structural waters. The program PROPKA(8) was used for the prediction of protein ionization states at 7.4 pH and ProtAssign was used for hydrogen bond optimization. After automatic hydrogen assignment, visual inspection was used to flip residues and change protonation states at protein-protein interfaces when appropriate. Specific attention was given to the tautomeric states for His residues, which were assumed to be neutral, and potential metal-ligation and hydrogen-bonding interactions were considered. The N6 nitrogen for H378 was kept protonated for each system. Four of the six crystallographic structures of CRBN used in this study appear to show the H378 δ-nitrogen coordinated with the carbonyl oxygen of the ligand. This posits the assumption of a hydrogen bond and that the H378 δ-nitrogen must therefore be protonated (9, 10). PROPKA analysis before and after simulations also confirm this assumption. As such, all MD systems were generated with the neutral H378 δ-nitrogen as being protonated. All waters more than 3 Å from heterogen (HET) groups were then removed.

Molecular Dynamics: hCRBN and gCRBN were co-crystallized with DNA damage-binding protein 1 (DDB1), whereas mCRBN was truncated (108 defined residues for mCRBN compared to 380 defined residues for hCRBN and gCRBN) and monomeric (i.e. not complexed with DDB1). DDB1 was included in the simulations for hCRBN and gCRBN. The thalidomide binding domain for hCRBN and mCRBN differs by only three residues. Therefore, to further increase sampling and determine any structural dependence on these residues, the original hCRBN sequence of the equilibrated representative structure was mutated to the mCRBN sequence with the following mutations, C366S, E377V, and V388I to form a hCRBN to mCRBN mutant (hmCRBN). Another system was also constructed from the hCRBN representative structure with the NF nitrogen on the H378 residue protonated (hCRBN-pNε) to compare and provide insight into the protonation states of H378. After protein refinement, a total of five protein systems (hCRBN, hCRBN-pNε, mCRBN, gCRBN, and hmCRBN) were constructed for MD simulation.

MD simulations were performed with the Desmond MD program (Desmond Molecular Dynamics System, version 3)(11, 12). Periodic boundary conditions were imposed on a cubic simulation box extending at least 10 Å from the protein. The simulation box was then solvated with TIP3P waters (13) electrically neutralized by introducing sodium ions, and the OPLS-2005 all-atom force field (14, 15) was applied to all atoms (16) was used to constrain all bonds in the system and the REference System Propagator Algorithm (RESPA)(17) with an integration time step of 2 fs was employed. Long-range electrostatics were calculated using the Particle Mesh Ewald (PME) algorithm (18) with a real-space cutoff of 13 Å. A cutoff of 16 Å was employed for van der Waals interactions. The systems were simulated in an NPT ensemble using the Martyna-Tuckerman-Tobias-Klein (MTTK) barostat (19, 20) at a constant pressure of 1 atm and a temperature of 310 K using the Nose-Hoover temperature coupling scheme (21).

All systems were energy minimized with a truncated newtonian conjugate gradient (TNCG) method (22) followed by multiple restrained minimizations to randomize systems before equilibration and final simulation. Heavy atoms of the protein were held fixed during heating for an initial 12 ps NVT ensemble simulation at 10 K with the Berendsen thermostat(23). This was followed by simulations at 1 atm in the NPT ensemble for 12 ps at 10 K and 24 ps at 310 K. Unrestrained equilibration MD was then performed for 24 ps at 310 K and 1 atm. Finally, unconstrained production MD was performed on the hCRBN and mCRBN systems for 100 ns. Due to the stability observed in hCRBN, its close similarity to gCRBN, and since the hCRBN-pNε system was derived from the equilibrated hCRBN system, the gCRBN and hCRBN-pNε systems were only run for 50 ns. Energies were recorded every 2 ps and trajectory frames were recorded every 5 ps.

Final system equilibration was determined by the observation of asymptotic behavior of the potential energy, Root Mean Square Deviation (RMSD), and Radius of Gyration (Rg) profiles and visual inspection of trajectories guided by Root Mean Square Fluctuation (RMSF) profiles.

Induced Fit Docking: After equilibration was determined, a hierarchical average linkage clustering method based on RMSD was utilized to determine an average representative structure for each equilibrated system. The program PROPKA was then implemented again on the equilibrated structures to test consistency of side chain protontion states at 7.4 pH. These representative structures were then used for docking with the induced-fit docking (IFD) method in the Schrödinger software suite (24, 25). The IFD methodology incorporates both the docking program Glide (26, 27) to account for ligand flexibility and the Refinement module in the Prime program to account for receptor flexibility. The Schrödinger IFD protocol attempts to model induced-fit effects from alterations in binding site conformation due to ligand binding in order to increase accuracy of binding affinity estimates and prediction of possible binding modes.

As a check for the placement of the grid used in the docking studies and for further analysis of the binding cavity, Schrödinger's SiteMap program (28, 29) (SiteMap, version 3.0, Schrödinger, LLC, New York, NY, 2014) was employed. SiteMap searches the protein structure for likely binding sites and highlights regions within the binding site suitable for occupancy by hydrophobic groups, hydrogen-bond donors, acceptors, or metal-binding functionality of the ligand.

The ligands thalidomide, pomalidomide, and lenalidomide were prepared using the program LigPrep (LigPrep, version 2.9, Schrödinger, LLC, New York, NY, 2014) and the OPLS-2005 all-atom force field was applied to all ligand atoms. The position of the cubic docking grid was centered on the original co-crystallized ligand centroids and was given a size of 29 Å. A constrained minimization of the receptor was performed with an RMSD cutoff of 0.18 Å. An initial softened potential Glide docking of the ligand set was then implemented with the standard precision (SP) mode and a van der Waals scaling factor of 0.5 was applied to the non-polar atoms of the receptor and ligands. The resulting top 20 poses of the ligands were used to sample protein plasticity by conformational searches and minimizations of binding pocket residues within 6 Å of any ligand pose for all complexes obtained. The new receptor conformations were then redocked using complexes within 30 kcal/mol from the best scoring structure. Glide docking parameters for this step were reset to the default hard potential function with a van der Waals scaling of 1.0 and SP mode.

The estimated binding affinity of each complex was reported in the GlideScore and used to compare differences between each ligand while the Emodel score is used to inter-compare poses of the ligands. Emodel places more significance on weighting force field components (electrostatic and van der Waals energies), making it better for comparing conformers as opposed to comparing chemically-distinct species.

Theoretical Calculations

Determination of Equilibration for MD systems: Final system equilibration was determined by the observation of asymptotic behavior of the potential energy, RMSD, and Rg profiles and visual inspection of trajectories guided by RMSF profiles.

Figures 8A, 8B, 8C, 8D, 8E, 8F, 8G, 8H, 8I, 8J, 8K, 8L:
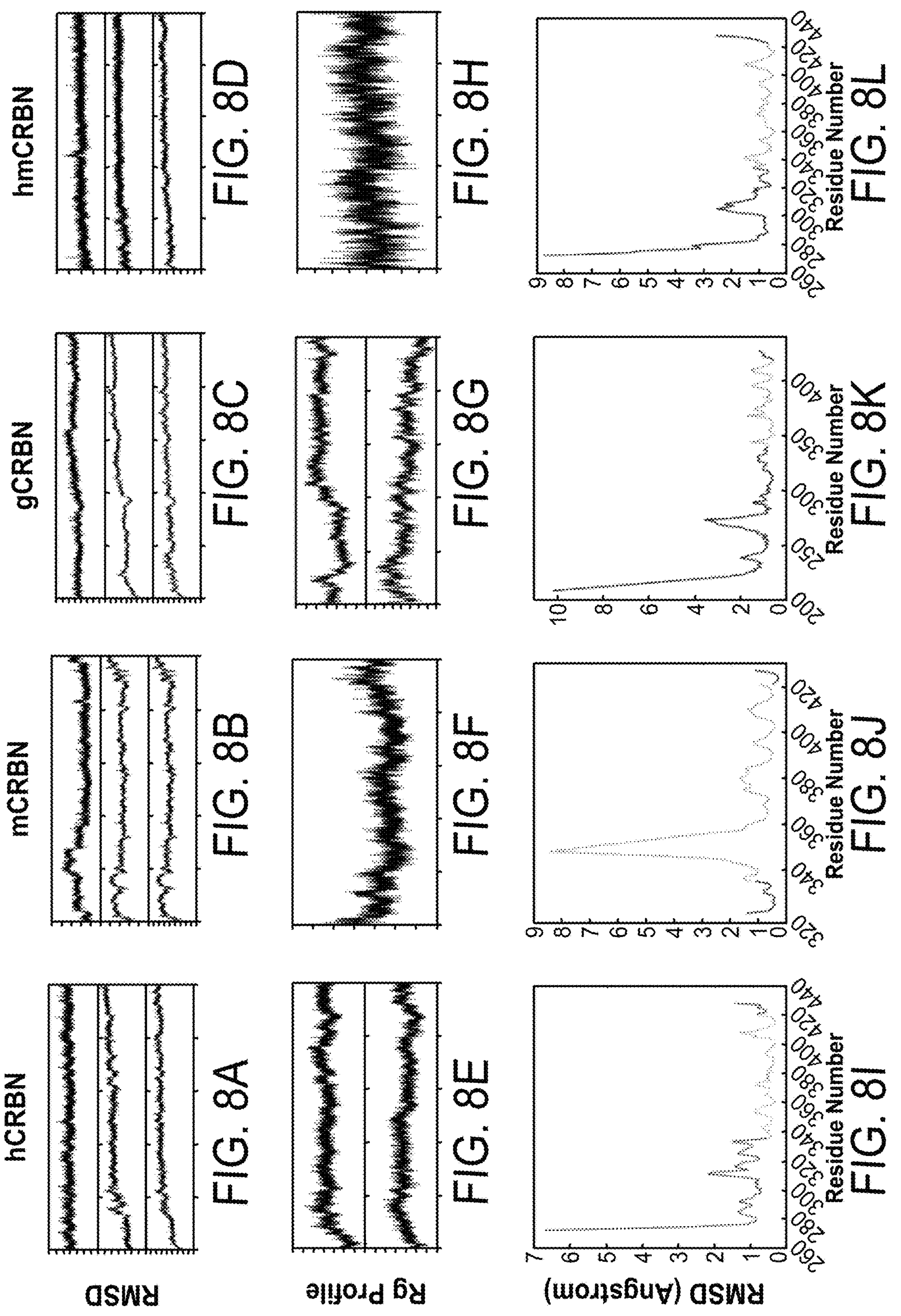
FIGS. 8A-8Q.
FIG. 8B shows RMSD profiles of mCRBN. Profiles were created using backbone atoms and were calculated with all hCRBN residues (Bottom Graph), binding site residues N335 to A421 (Middle Graph), and residues (357, 377, 379-383, 388-390, 401, 402, 404) located 6 Å away from the ligand (Top Graph). All measurement units are in Angstroms.
FIG. 8C shows RMSD profiles of gCRBN. Profiles were created using backbone atoms and were calculated with hCRBN-DDB1 complex (Bottom Graph), gCRBN alone (Middle Graph), and binding site residues N337 to A423 (Top Graph). All measurement units are in Angstroms.
FIG. 8D shows RMSD profiles of hmCRBN. Profiles were created using backbone atoms and were calculated with hmCRBN-DDB1 complex (Bottom Graph), hmCRBN alone (Middle Graph), and binding site residues N335 to A421 (Top Graph). All measurement units are in Angstroms.
FIG. 8E shows Rg profiles of hCRBN. Profiles were created from all atoms and were calculated with hCRBN/DDB1 complex (Bottom Graph) and hCRBN alone (Top Graph). All measurement units are in Angstroms.
FIG. 8F shows Rg profiles of mCRBN. Profiles were created from all atoms. All measurement units are in Angstroms.
FIG. 8G shows Rg profiles of gCRBN. Profiles were created from all atoms and were calculated with gCRBN-DDB1 complex (Bottom Graph) and hCRBN alone (Top Graph). All measurement units are in Angstroms.
FIG. 8H shows Rg profiles of hmCRBN. Profiles were created from all atoms and were calculated with hmCRBN-DDB1 complex (Bottom Graph) and hmCRBN alone (Top Graph). All measurement units are in Angstroms.
FIG. 8I shows RMSF profile of hCRBN. Profiles were created using backbone atoms and were calculated with hCRBN alone (DDB1 RMSF available upon request). Binding site residues N335 to A421 displayed as dashed line. All measurement units are in Angstroms.
FIG. 8J shows RMSF profile of mCRBN. Profiles were created using backbone atoms of mCRBN. Binding site residues N335 to A421 displayed as dashed line. All measurement units are in Angstroms.
FIG. 8K shows RMSF profile of gCRBN. Profiles were created using backbone atoms and were calculated with gCRBN alone (DDB1 RMSF available upon request). Binding site residues N337 to A423 displayed as dashed line. All measurement units are in Angstroms.
FIG. 8L shows RMSF profile of hmCRBN. Profiles were created using backbone atoms and were calculated with hmCRBN alone (DDB1 RMSF available upon request). Binding site residues N335 to A421 displayed as dashed line. All measurement units are in Angstroms.
Figure 8M:
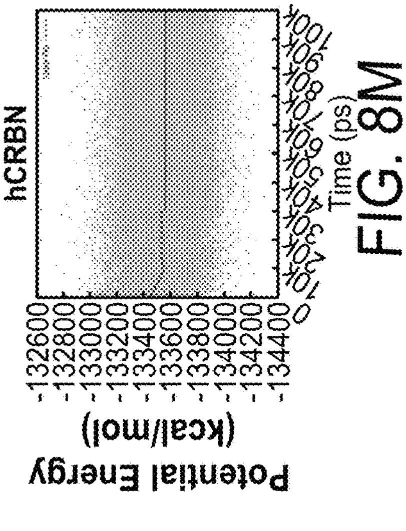
FIG. 8M shows potential energy profile of hCRBN simulation. Multiple linear fits were characterized to determine asymptotic behavior by minimizing slope.

Equilibration of hCRBN model system: RMSD profiles of hCRBN in complex with DDB1 appear to show equilibration after approximately 25 ns with an average RMSD (FIG. 8A) of 3.21 Å for the equilibrated region. Compared to the crystallographic structure resolution of 3.01 Å, the system RMSD is slightly outside the error of the reported PDB X-ray diffraction resolution. However, the RMSD profile of hCRBN residues associated with the known binding site (i.e. residues N335 to A421 and excluding DDB1) displays significant rigidity despite minimal asymptotic behavior portrayed by the RMSD graphs of the whole hCRBN chain. Further investigation using RMSF profiles (FIG. 8I) finds that much of the displacement can be attributed to the solvent exposed N terminus tail region and from the DDB1 chain. RMSD profiles without the tail regions do show asymptotic behavior and the binding site structure is believed to be valid for the length of simulation. In a similar trend, Rg profiles (FIG. 8E) do not appear to show equilibrated behavior for the hCRBN/DDB1 complex but do display clear asymptotic behavior after approximately 17 ns for hCRBN alone. The potential energy graphs (FIG. 8M) also show asymptotic behavior after approximately 30 ns. From this data, all structures, analyses, and statistics for hCRBN are performed using the last 70 ns of the simulation and the stability and accuracy of the protein model of hCRBN are considered comparative to the original crystal structure (PDB 4TZ4) for the purposes of this study.

Figure 8N:
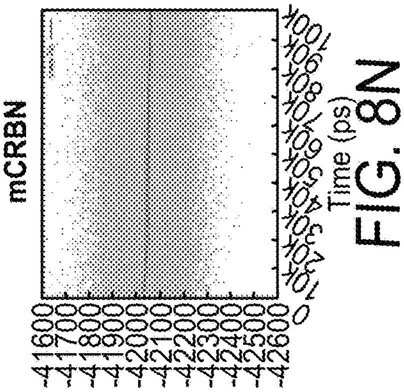
FIG. 8N shows potential energy profile of mCRBN simulation. Multiple linear fits were characterized to determine asymptotic behavior by minimizing slope.

Equilibration of mCRBN model system: The mCRBN system does not appear to be able to reach equilibrium. The average RMSD (FIG. 8B) of approximately 3.27 Å is well outside the reported crystallographic structure resolution of 1.88 Å. The Rg profile (FIG. 8F) and potential energy graph (FIG. 8N) of the mCRBN simulation do no display asymptotic behavior. The RMSF profile (FIG. 8J) and visual inspection reveals unfolding events of residues near the truncated regions of the protein which are the primary contributions to the average RMSD. However, the proximal residues 6 Å away from the ligand appear stable after 38 ns and may be able to be used for limited qualitative analysis. However, given the evidence provided, this model is not adequate for further modeling and analyses should be viewed ephectically. All structures, analyses, and statistics for mCRBN are performed using the last 62 ns of the simulation.

Figure 8O:
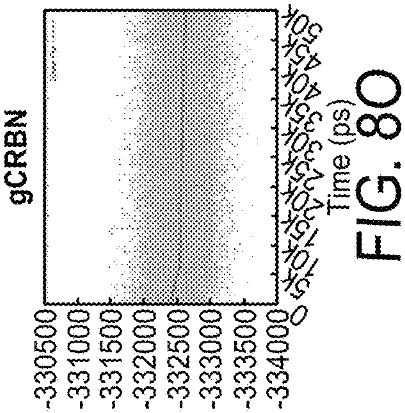
FIG. 8O shows potential energy profile of gCRBN simulation. Multiple linear fits were characterized to determine asymptotic behavior by minimizing slope.

Equilibration of gCRBN model system: RMSD profiles of gCRBN in complex with DDB1 appear to show equilibration after approximately 32 ns with an average RMSD (FIG. 8C) of 3.82 Å for the equilibrated region. Compared to the crystallographic structure resolution of 2.98 Å, the system RMSD is outside the error of the reported PDB X-ray diffraction resolution. However, in a similar trend to hCRBN, the RMSD profile of gCRBN residues associated with the known binding site (i.e. residues N335 to A421 and excluding DDB1) displays significant rigidity despite minimal asymptotic behavior portrayed by the RMSD graphs of the whole gCRBN chain. Further investigation using RMSF profiles (FIG. 8K) finds that, again comparable to hCRBN, much of the displacement can be attributed to the solvent exposed N terminus tail region and from the DDB1 chain. RMSD profiles without the tail regions do show asymptotic behavior and the binding site structure is believed to be valid for the length of simulation. Rg profiles (FIG. 8G) do not appear to show equilibrated behavior for the gCRBN/DDB1 complex but do display clear asymptotic behavior after approximately 22 ns for gCRBN alone. Despite potential energy graphs (FIG. 8O) showing some continued declination, the error of the minimized fitted slope does encompass zero gradient after 7 ns. From this data, all structures, analyses, and statistics for gCRBN are performed using the last 27 ns of the simulation and the stability and accuracy of the protein model for the residues associated with the known binding site of gCRBN are considered comparative to the original crystal structure (PDB 4CI2) for the purposes of this study.

Figure 8P:
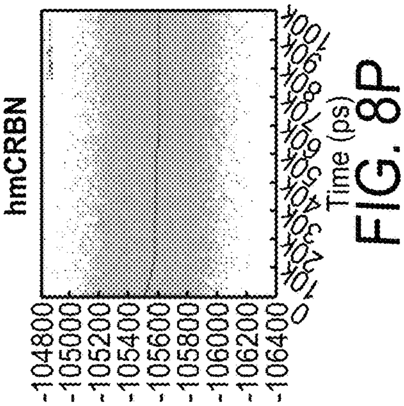
FIG. 8P shows potential energy profile of hmCRBN simulation. Multiple linear fits were characterized to determine asymptotic behavior by minimizing slope.
Figure 8Q:
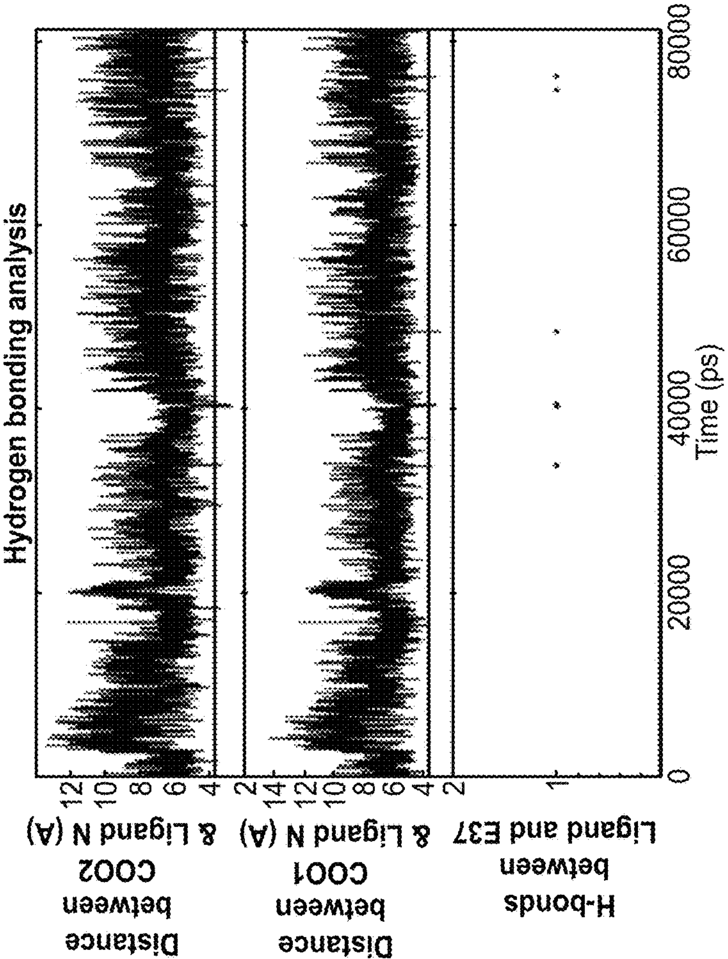

Equilibration of hmCRBN model system: Equilibration can be safely assumed after 40 ns from the RMSD profiles of hmCRBN in complex with DDB1 with an average RMSD (FIG. 8D) of 2.82 Å for the equilibrated region. Compared to the crystallographic structure resolution of 3.01 Å and the average RMSD calculated for the progenitor hCRBN system of 3.21 Å, the hmCRBN average system RMSD is well within error. Moreover, the RMSD profile of hmCRBN residues associated with the known binding site (i.e. residues N335 to A421 and excluding DDB1) also displays significant rigidity in confluence with the original hCRBN system. Further investigation of RMSF profiles (FIG. 8L) finds, once again similar to the hCRBN system, that much of the displacement can be attributed to the solvent exposed N terminus tail region and from the DDB1 chain. Rg profiles (FIG. 8H) do not appear to advance any evidence against equilibration and purport fluctuations directly analogous to the hCRBN system. The potential energy graphs (FIG. 8P) also show asymptotic behavior after approximately 30 ns. From this data, all structures, analyses, and statistics for hCRBN are performed using the last 60 ns of the simulation and the stability and accuracy of the protein model of hCRBN are considered comparative to the original crystal structure (PDB 4CI2) for the purposes of this study.

Determination of H378 protonation states: Determination of protonation states for protein side chains is an inherently difficult process. Crystallographic resolutions are rarely sufficient to resolve individual hydrogen atoms and current methods for determining NMR coupling constants are not applicable to large proteins (9). This results in the need for indirect evidence to statistically characterize the ionization states for certain side chains. Hydrogen bonding analysis is a common practice of inferring protonation states (30). The determination of a hydrogen bond, however, is not a well-defined parameter that largely succumbs to best practices. For this study, we use the metrics of a donor-acceptor distance of less than 3.5 Å and three point angle of greater than 90 degrees to quantify a hydrogen bond (31). For this study, careful attention must be made the residue H378 due to its involvement in the suspected IMiD binding motif. Four of the six crystallographic structures of CRBN used in this study appear to show the H378 δ-nitrogen coordinated with the carbonyl oxygen of the ligand. This posits the assumption of a hydrogen bond and that the H378 δ-nitrogen must therefore be protonated. Unfortunately, studies have shown that reported structures do not necessarily portray the most stable isomer or statistically weight tautomeric states (30, 32). For further insight into this issue, a separate system using a representative structure from the equilibrated hCRBN system was run to query alternate protonation states of this particular residue. PROPKA analysis before and after simulations also confirm the assumption of a protonated H378 δ-nitrogen. As such, all MD systems were generated with the neutral H378 δ-nitrogen as being protonated.

Detailed Chemical Methods

Synthesis of tert-Butyl (2-(2,6-dioxopiperidin-3-yl)-1-oxoisoindolin-4-yl)carbamate (1)

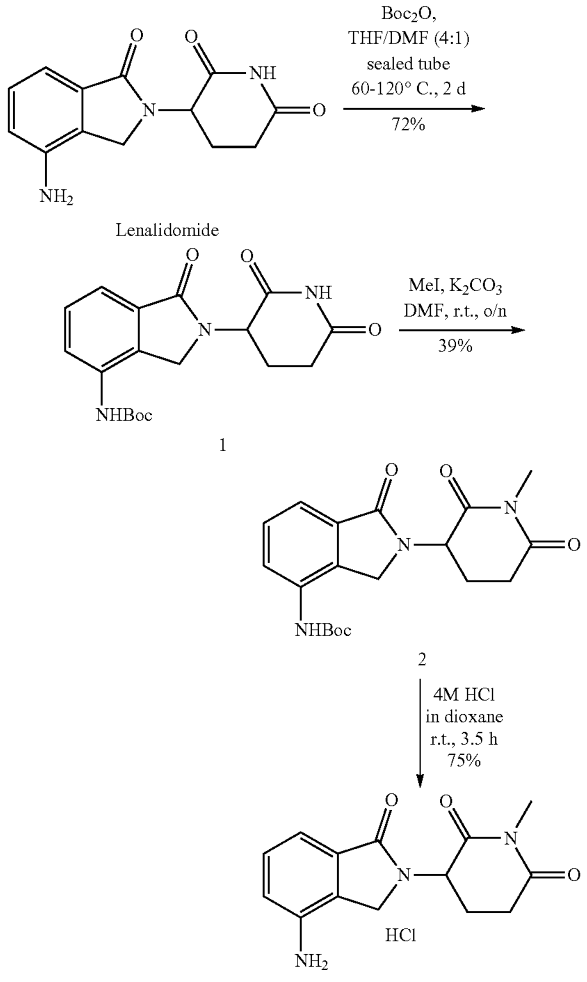

Lenalidomide

1

2

3

Lenalidomide (259 mg, 1 mmol) and $Boc_2O$ (218 mg, 1.1 mmol) were mixed in THF (1 mL) in a sealed tube and stirred at 60° C. overnight. The next day, $Boc_2O$ (110 mg, 0.5 equiv.), THF (1 mL), and DMF (0.5 mL) were added and the solution was further stirred at 120° C. overnight. Water (20 mL) was added and the mixture was sonicated. The precipitate was filtered, washed with water (10 mL), and dried. The resulting solid was triturated using EtOH/EtOAc/hexanes and filtered to give the desired product as an off-white solid (258 mg, 72%). Mp: 196-198° C. HPLC-MS (ESI+): m/z 741.3 [(100%, 2M+Na)$^+$], 719.4 [(40%, 2M+H)$^+$], 360.2 [(90%, M+H)$^+$]. $^1$H NMR (400 MHz, DMSO-$d_6$): δ 11.00 (s, 1H), 9.21 (s, 1H), 7.74 (dd, J=6.8, 1.7 Hz, 1H), 7.49-7.39 (m, 2H), 5.10 (dd, J=13.3, 4.7 Hz, 1H), 4.41 (d, J=17.6 Hz, 1H), 4.32 (d, J=17.6 Hz, 1H), 2.95-2.83 (m, 1H), 2.64-2.54 (m, 1H), 2.40-2.26 (m, 1H), 2.05-1.95 (m, 1H), 1.46 (s, 9H). Compound 1 was reported previously [1].

tert-Butyl (2-(1-methyl-2,6-dioxopiperidin-3-yl)-1-oxoisoindolin-4-yl)carbamate (2): To a mixture of 1 (100 mg, 0.278 mmol) and $K_2CO_3$ (38 mg, 0.278 mmol) in DMF (0.8 mL) was added methyl iodide (0.017 mL, 0.278 mmol) dropwise at room temperature under Argon. The mixture was stirred overnight. Water (10 mL) was added and extracted with EtOAc (2×20 mL). The combined organic layers were dried ($Na_2SO_4$), filtered, and concentrated under reduced pressure. The resulting yellow oil was purified by flash chromatography ($SiO_2$) eluting with hexanes in EtOAc (80% to 100%) to provide the title compound as a white solid (40.37 mg, 39%). Mp: 192° C. (dec). HPLC-MS (ESI+): m/z 741.3 [(100%, 2M+Na)$^+$], 719.4 [(40%, 2M+H)$^+$], 360.2 [(90%, M+H)$^+$]. $^1$H NMR (400 MHz, DMSO-$d_6$): δ 9.20 (s, 1H), 7.73 (dd, J=6.5, 2.3 Hz, 1H), 7.49-7.41 (m, 2H), 5.16 (dd, J=13.4, 5.1 Hz, 1H), 4.42 (d, J=17.6 Hz, 1H), 4.30 (d, J=17.6 Hz, 1H), 3.02-2.90 (m, 1H), 2.99 (s, 3H), 2.80-2.71 (m, 1H), 2.40-2.27 (m, 1H), 2.07-1.97 (m, 1H), 1.46 (s, 9H).

3-(4-Amino-1-oxoisoindolin-2-yl)-1-methylpiperidine-2,6-dione (3 or N$^1$-methyl-lenalidomide): 2 (35 mg, 0.093 mmol) was stirred in 4 M HCl in dioxane (0.5 mL) for 3.5 h at room temperature. The white suspension was concentrated under reduced pressure and the resulting solid was triturated in DCM/hexanes, washed with EtOAc and hexanes (10 mL each), and dried to provide the title compound as light yellow flakes (21.81 mg, 75%). Mp: 207° C. (dec). HPLC: 99% [$t_R$=11.6 min, 10% MeOH, 90% water (with 0.1% TFA), 20 min]. $^1$H NMR (400 MHz, DMSO-$d_6$): δ 7.29 (t, J=7.5 Hz, 1H), 7.11 (d, J=7.5 Hz, 1H), 6.99 (d, J=7.5 Hz, 1H), 5.17 (dd, J=13.4, 4.7 Hz, 1H), 5.20-4.80 (br s, 2H, disappeared on $D_2O$ shake), 4.28 (d, J=17.0 Hz, 1H), 4.17 (d, J=17.0 Hz, 1H), 3.05-2.91 (m, 1H), 2.99 (s, 3H), 2.80-2.70 (m, 1H), 2.39-2.25 (m, 1H), 2.08-1.97 (m, 1H). HPLC-MS (ESI+): m/z 569.2 [(30%, 2M+Na)$^+$], 274.2 [(100%, M+H)$^+$]. LC-MS (ESI+): 569.2 [40%, (2M+Na)$^+$], 296.1 [100%, (M+Na)$^+$]. HRMS (ESI+): m/z calcd for $C_{14}H_{15}N_3O_3$ (M+H)$^+$274.1186, found 274.1176.

Detailed protein production of WT and mutant CRBN: The gene coding for the human TBD (aa 317-425) was synthesized and subcloned into the BamHI-NotI restriction sites of the pGEX-6P-1 vector by GeneArt® Gene Synthesis. The gene was engineered with silent mutations that utilize the favored *E. coli* codons. TBD E377V, V388I, H378A and W380A mutations were performed using polymerase chain reaction. The primers used were 5'-CCAGTCTGTGTTGTAAACAGAGCCAAGAAACC-3' (SEQ ID NO.:1) and 5'-GGTTTCTTGGCTCTGTTTACAACACAGACTGG-3' (SEQ ID NO.:2); 5'-GGTTATGCATGGACCATCGCACAGTGTAAAATTTGTGC-3' (SEQ ID NO.:3) and 5'-GCACAAATTTTACACTGTGCGATGGTCCATGCATAAC-3' (SEQ ID NO.:4), 5'-CGTCCGAGCACCGAAGCAAGCTGGTTTCCGGGTTATGC-3' (SEQ ID NO.:5) and 5'-GCATAACCCGGAAACCAGCTTGCTTCGGTGCTCGGACG-3' (SEQ ID NO.:6); and 5'-CGAGCACCGAACATAGCGCGTTTCCGGGTTATGCATGG-3' (SEQ ID NO.:7) and 5'-CCATGCATAACCCGGAAACGCGCTATGTTCGGTGCTCG-3' (SEQ ID NO.:8), respectively. Mutations were confirmed by sequencing. The recombinant DNA plasmids were transformed into *E. coli* Rosetta™ 2(DE3)pLysS competent cells (EMD Millipore, Billerica, MA) for subsequent protein expression. The GST-tagged TBD proteins linked with PreScission protease proteolytic site were expressed and purified as follows: A single colony of freshly transformed cells was cultured at 37° C. for 16 h in 5 mL of Luria-Bertani (LB; Thermo Fisher Scientific) medium containing 100 μg/mL of ampicillin (Sigma-Aldrich). 1 mL of the culture was then used to inoculate 25 mL of Terrific Broth-phosphate medium (TB; Thermo Fisher Scientific) with 100 μg/mL ampicillin at 37° C. for 16 h. The culture was then transferred to 1.5 L of TB medium supplemented with 50 μM $ZnCl_2$ (Sigma-Aldrich). The resultant culture was incubated with continuous shaking at 250 rpm to an $OD_{600}$ of 0.70 and then induced with isopropyl-β-D-thiogalactopyranoside (IPTG; 0.5 mM final concentration; Thermo Fisher Scientific). The cells were cultured at 16° C. for 20 h and harvested by centrifugation at 6000 rpm for 30 min. The cells were lysed by sonication in 50 mM Tris (pH 8.0; Sigma-Aldrich), 500 mM NaCl (Thermo Fisher Scientific), 1 mM TCEP (Sigma-Aldrich), 0.1% Triton X-100 (Sigma-Aldrich), 10 μM $ZnCl_2$ (Acros Organics, Thermo Fisher Scientific) and protease inhibitor cocktail (Roche). The protein was then purified by affinity chromatography on an AKTA Explorer or AKTA Purifier (GE Healthcare Life Sciences) using a glutathione-Sepharose matrix (GE Healthcare Life Sciences, Pittsburgh, PA) pre-equilibrated with 50 mM Tris (pH 8.0), 500 mM NaCl, 1 mM TCEP, and 10 μM $ZnCl_2$, and eluted with the same buffer with the addition of 10 mM reduced glutathione (Sigma-Aldrich). Purity of the protein in the different fractions was determined by SDS-PAGE and the best fractions were pooled. GST was cleaved from the pooled GST-TBD fractions by digestion with PreScission protease at 4° C. for 4 h. GST was removed from the resultant digest by a second round of GST affinity chromatography. Proteins were further purified by size-exclusion chromatography in a Superdex 75 column (GE Healthcare Life Sciences). Fractions with >90% purity were pooled, concentrated by ultrafiltration (10K Amicon tubes, EMD Millipore) and stored at −80° C.

Results

Figure 3A:
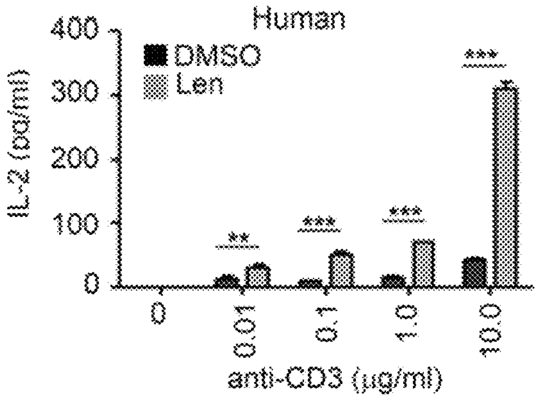
FIGS. 3A-3E show lenalidomide augments IL-2 production in the absence of CD28 co-stimulation in human but not mouse T cells. T cells purified from healthy donor peripheral blood mononuclear cells (PBMCs) were stimulated in the presence of increasing concentrations of anti-CD3ε antibody in the presence of 10 μM lenalidomide (Len) or vehicle control (DMSO). IL-2 production was measured in culture supernatant of cells stimulated with increasing concentrations of anti-CD3α alone (FIGS. 3A, 3C) or with 1 μg/ml anti-CD28 antibody to provide co-stimulation in the presence of DMSO (vehicle control) or 10 μM lenalidomide (Len). Cytokine levels were determined by ELISA in human T cells (FIGS. 3A, 3B) and mouse T cells (FIGS. 3C, 3D) isolated from the spleen of C57BL6 mice. Western blot analysis of human and mouse T cells stimulated with anti-CD3ε 5 μg/ml+1 μg/ml anti-CD28 antibody treated for 24 h with DMSO, 10 and 20 μM lenalidomide (FIG. 3E). Results are representative of three independent experiments. WB shows expression of IKZF1, CRBN and β-actin. Statistical analysis was conducted ANOVA, followed by Dunnett's multiple comparison test. *=$p<0.05$, *=$p<0.001$
Figure 3B:
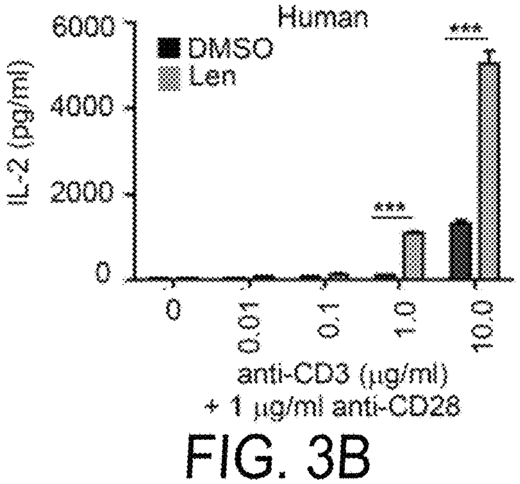
Figure 3C:
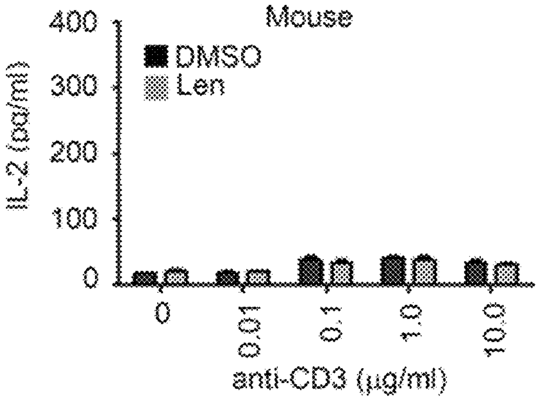
Figure 3D:
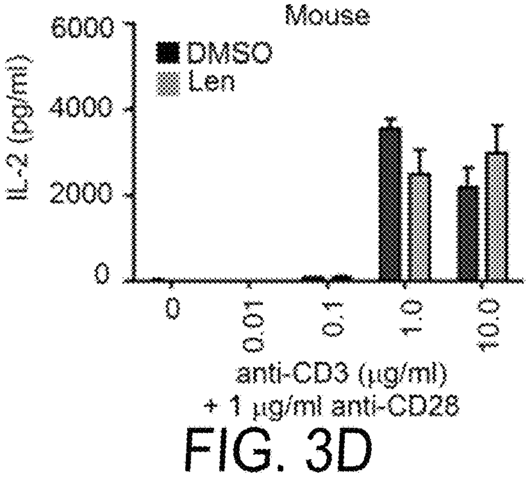
Figure 3E:
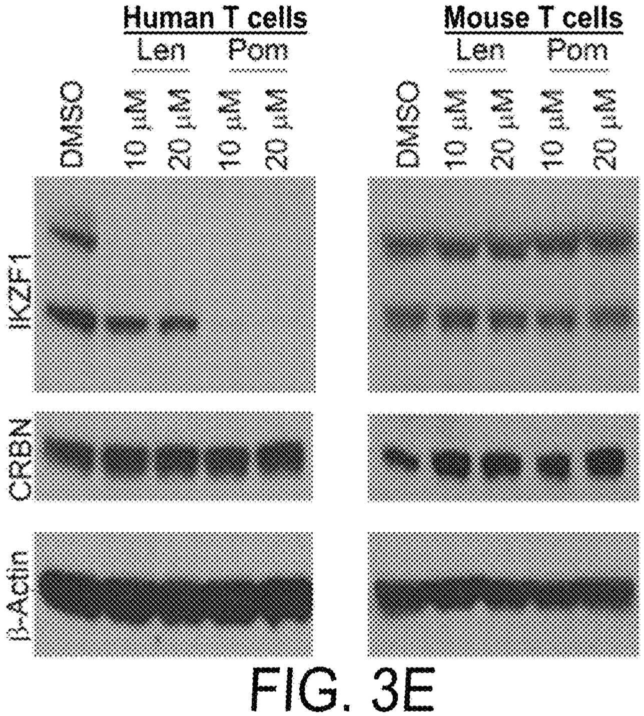
Figure 4A:
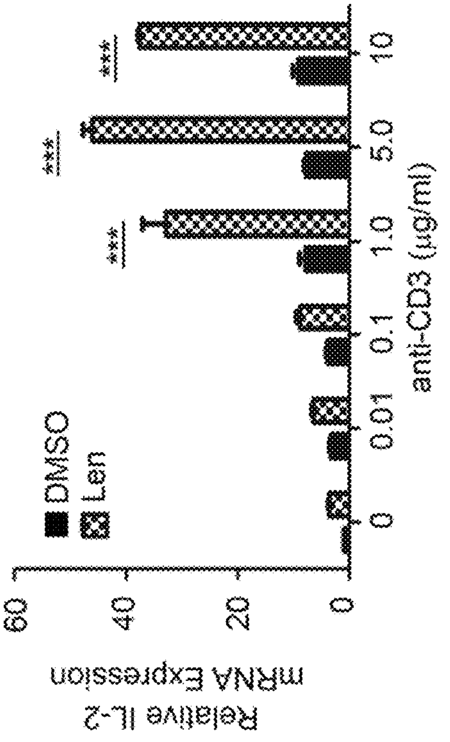
FIGS. 4A-4D show dose of anti-CD3 and lenalidomide to induce IL-2 and proliferation by T cells.
Figure 4B:
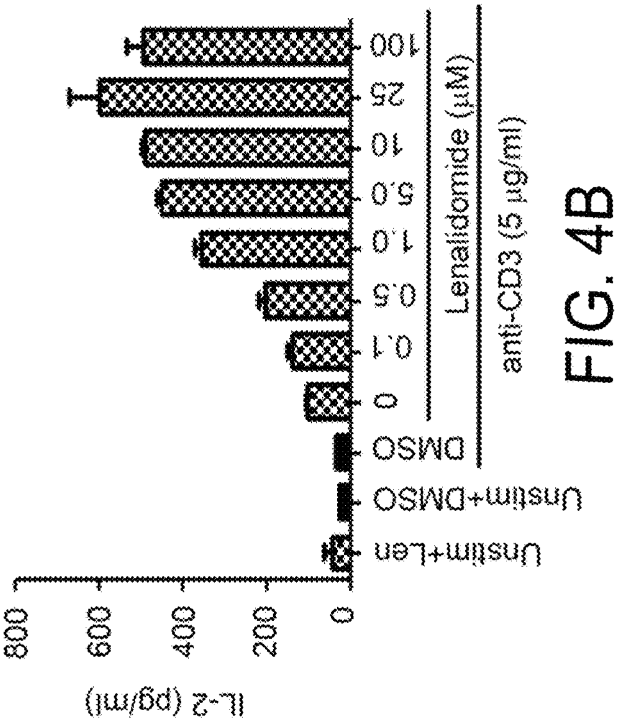
Figure 4C:
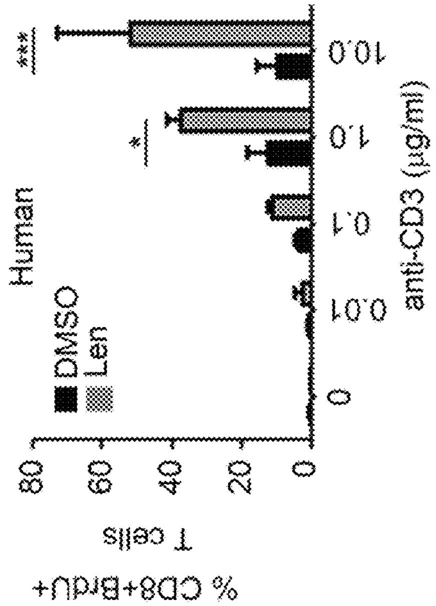
Figure 4D:
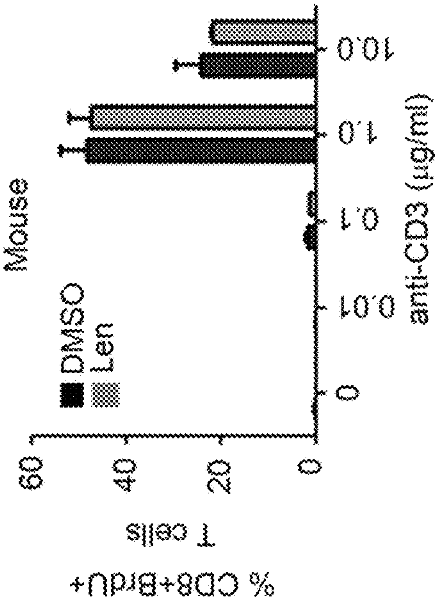

Functional Resistance of Mouse Cells to Immunomodulatory Compounds. Immunomodulatory drug-induced ubiquitin-mediated degradation of IKZF1 and IKZF3 (11) appears sufficient to augment T cell activity to increase IL-2 production (18) in the absence of anti-CD28 costimulation (19-24). In lenalidomide-treated human T cells stimulated with anti-CD36 antibody to cross-link the T cell receptor (TCR) and induce intracellular signal transduction, the levels of IL2 mRNA (FIG. 4A) and protein (FIG. 4B) (24, 25) were significantly increased relative to DMSO-(vehicle) treated cells. Comparing purified human (FIGS. 3A, 3B) and mouse T cells (FIGS. 3C, 3D) pretreated with vehicle or 10 μM lenalidomide, only human T cells displayed the expected lenalidomide-induced increase in IL-2 (FIGS. 3C-3D and FIGS. 4C-4D) when stimulated ±anti-CD28 antibody using doses of anti-CD3ε that ranged from 0.01-10 μM. Further, as predicted from previous structural and functional studies in multiple myeloma cell lines, IKZF1 was unaffected after treatment with lenalidomide in mouse T cells compared to almost completely depleted in human cells (FIG. 3E) (10, 11).

Figure 5A:
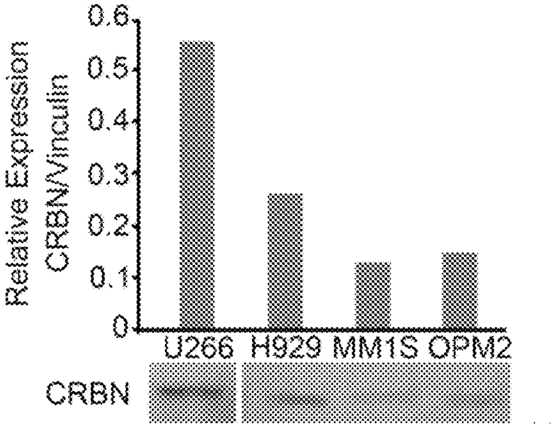
Figure 5B:
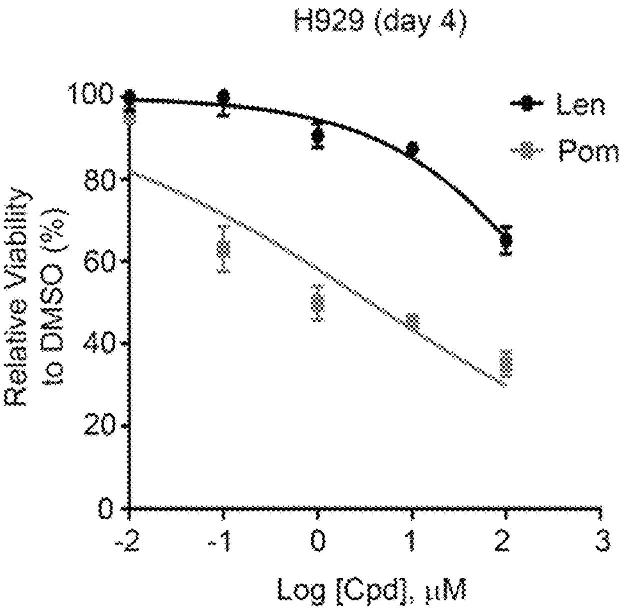
Figure 5C:
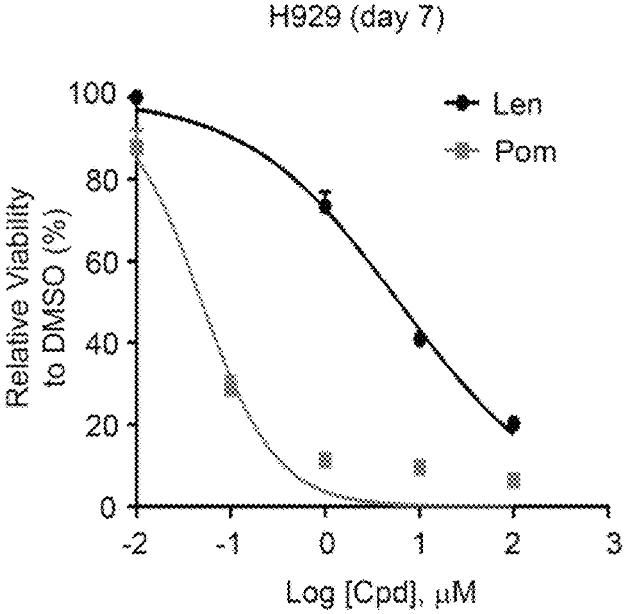
Figure 5D:
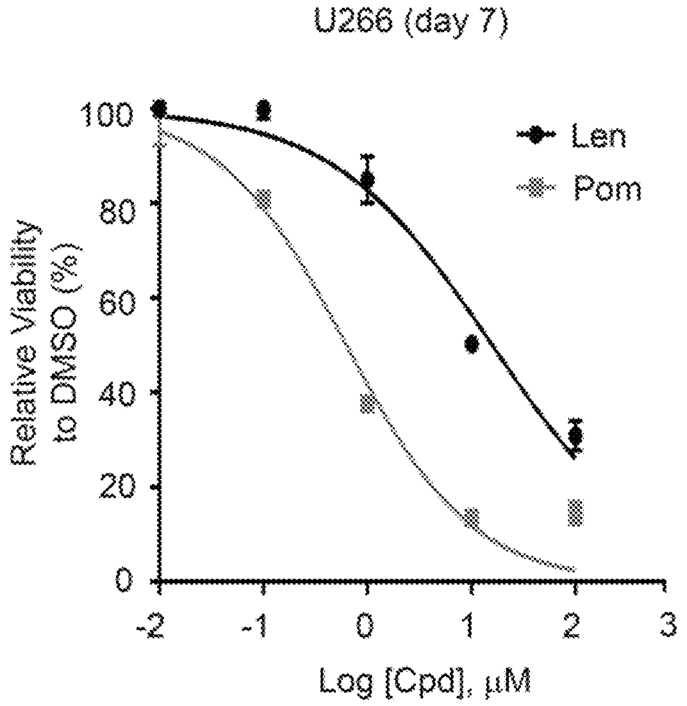
Figure 5E:
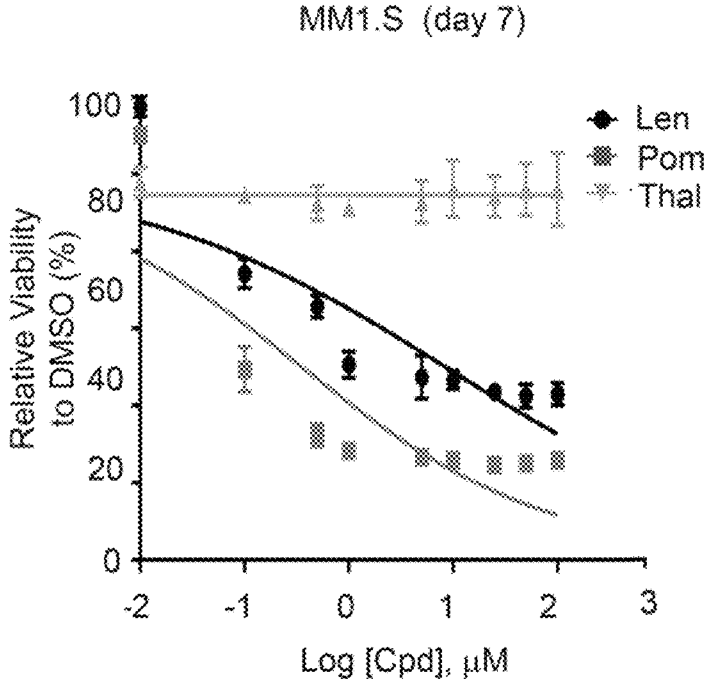

The antiproliferative effects of thalidomide, lenalidomide and pomalidomide reportedly differ based on CRBN expression levels (26-28). Human multiple myeloma cell lines U266, H929, MM1.S, and OPM2 differ in their levels of CRBN (FIG. 5A), but all show a time-dependent sensitivity to immunomodulatory compounds, with $IC_{50}$ doses of pomalidomide and lenalidomide of 0.05 to 0.61 μM and 7.00 to 16.04 μM, respectively (FIGS. 5B-5E, FIG. 6). In contrast, the mouse multiple myeloma cell line 5TGM1 was highly resistant to the suppressive effects of immunomodulatory compounds (FIG. 5F) although CRBN was expressed at levels similar to human MM1.S myeloma (see also FIG. 14). In growth suppression assays with these four cell lines, thalidomide had no suppressive function, even at doses up to 200 μM (FIGS. 5E, 5F and data not shown).

Figure 7A:
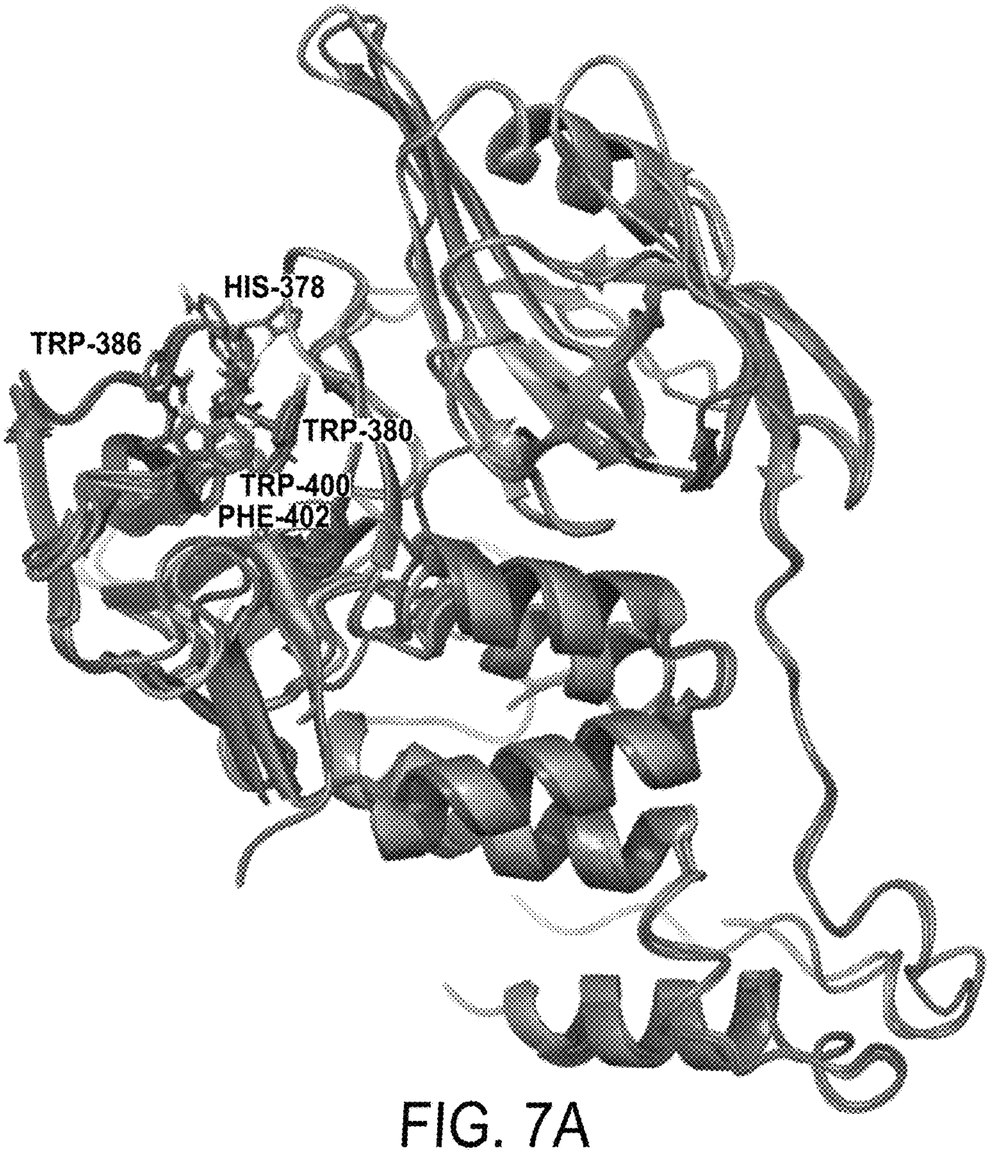
FIGS. 7A-7C show structure of cereblon is conserved across different species.

Thalidomide binding domain of CRBN has a conserved immunomodulatory compound binding motif. Based on crystal structures, immunomodulatory compounds bind to a conserved pocket within the thalidomide binding domain (TBD) located in the C-terminus of CRBN (FIG. 7A)(15, 16). These interactions are governed by hydrogen bonding, aromatic quadrupole, and Van der Waals (VDW) interactions. Analysis of the X-ray crystal structures of CRBN [human (hCRBN), mouse (mCRBN) and chicken (gCRBN)] in complex with thalidomide, lenalidomide, and pomalidomide, respectively (FIG. 7A) shows negligible variations of root mean square deviation (RMSD) between the inhibitor poses. Thus, an in-depth theoretical investigation of the molecular binding mechanics of immunomodulatory compounds in complex with CRBN was conducted to explore possible differences in drug interactions between mouse and human CRBN caused by induced fit, protein flexibility, or crystal artifacts.

Figure 7B:
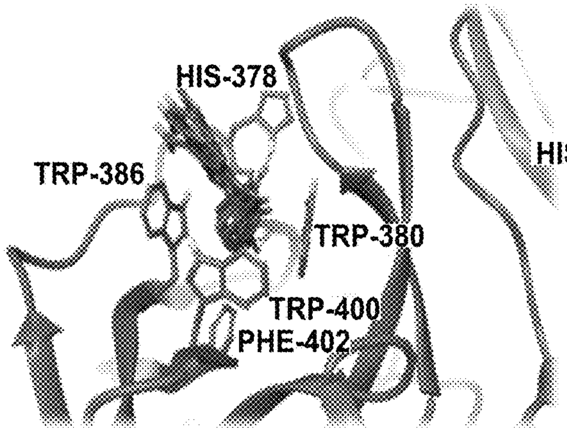
Figure 7C:
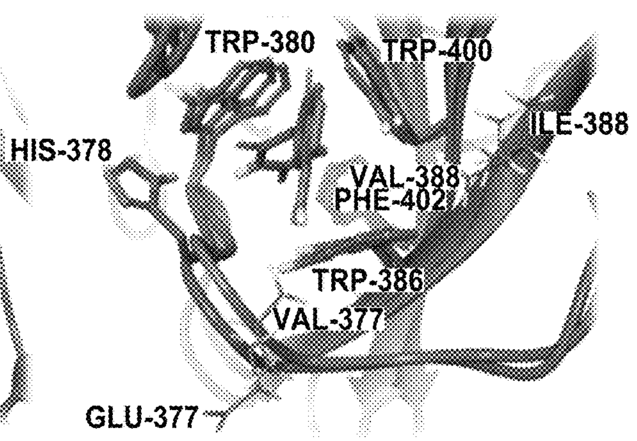

For molecular dynamics (MD), simulations of the crystal structures of hCRBN (PDB 4TZ4)(15) and gCRBN (PDB 4TZC and 4TZU)(15) in complex with DNA damage-binding protein 1 (DDB1) were used. The crystal structure of mCRBN (PDB 4CI1, 4CI2, and 4CI3)(16) is monomeric and truncated to contain only the TBD (108 defined residues compared to 380 defined residues for hCRBN and gCRBN) and is not suitable for computational modeling. The species-specific amino acid differences in mouse CRBN include C366S, E377V and V388I. Therefore, to further increase sampling and determine any structural dependence on these residues, the original hCRBN sequence of the equilibrated representative structure was mutated to the mouse sequence. The mCRBN analog and hmCRBN hybrid developed from the hCRBN system is capable of reproducing the crystal ligand poses of mCRBN (PDB 4TZC and 4TZU) with minimal conformational deviation (FIG. 7C) and was used for modeling purposes. Binding modes do not appear to differ between models and compounds as there are no significant differences in RMSD calculations between X-ray crystal binding poses (Table 2) and post-MD equilibrated models (FIGS. 7B and 7C). Induced fit docking (IFD) also predicts no observable difference in binding affinity between models and compounds (Table 2). All poses are within 1.8 Å RMSD, which is the expected threshold for the IFD protocol (29).

Val388 of hCRBN recruits CK1α upon immunomodulatory compound binding (10). However, the side chain of Val388 is >6 Å away from the immunomodulatory drug, and it is thus unlikely to alter binding affinity to the drugs. The second distinct amino acid is Glu377, which in the mouse is Val379, and could establish a weak hydrogen bond with lenalidomide's amino group. However, hydrogen bond analysis (FIG. 8) of MD simulations suggests minimal interaction occurs between this residue and bound immunomodulatory drugs, mainly due to backbone dihedral strain tending to force the charged carboxyl moiety away from the binding site.

TABLE 2

| | | hmCRBN Post MD | hCRBN Post MD | hCRBN Crystal | gCRBN Post MD | gCRBN Crystal | mCRBN Post MD | mCRBN Crystal |
|---|---|---|---|---|---|---|---|---|
| Thalidomide | Glide Score | −11.040 | −11.049 | −10.789 | −11.408 | −10.724 | −10.082 | −9.344 |
| | Emodel | −81.796 | −83.437 | −78.630 | −77.239 | −79.853 | −63.197 | −63.881 |
| | Pose RMSD | — | — | — | 1.6615[a] | 1.1036[a] | 7.1958[b] | 7.0379[b] |
| Lenalidomide | Glide Score | −11.279 | −11.574 | −10.965 | −10.976 | −10.494 | −8.0373 | −9.544 |
| | Emodel | −85.454 | −87.014 | −79.857 | −78.197 | −77.976 | −52.240 | −57.118 |
| | Pose RMSD | 0.5944[c] | 0.7384[c] | 1.7233[c] | 1.5859[d] | 1.0053[d] | — | — |
| Pomalidomide | Glide Score | −11.200 | −10.996 | −10.800 | −10.256 | −11.634 | −7.760 | −8.339 |
| | Emodel | −89.915 | −86.330 | −81.008 | −80.357 | −84.483 | −51.789 | −58.872 |
| | Pose RMSD | — | — | — | 1.7592[e] | 0.9482[e] | 4.6167[f] | 2.8715[f] |

[a]Pose RMSD calculated using PDB 4CI1 for comparison.
[b]Pose RMSD calculated using PDB 4TZC for comparison.
[c]Pose RMSD calculated using PDB 4TZ4 for comparison.
[d]Pose RMSD calculated using PDB 4CI2 for comparison.
[e]Pose RMSD calculated using PDB 4CI3 for comparison.
[f]Pose RMSD calculated using PDB 4TZU for comparison.

Figure 9D:
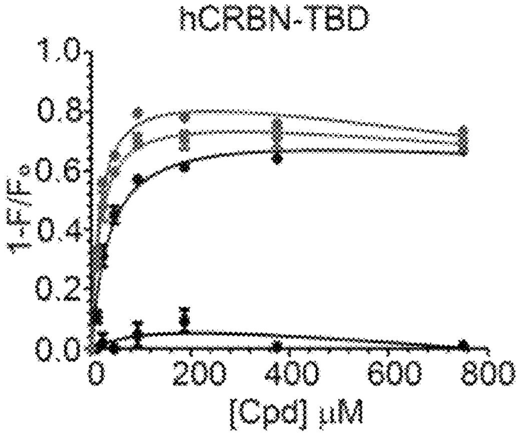
Figure 9E:
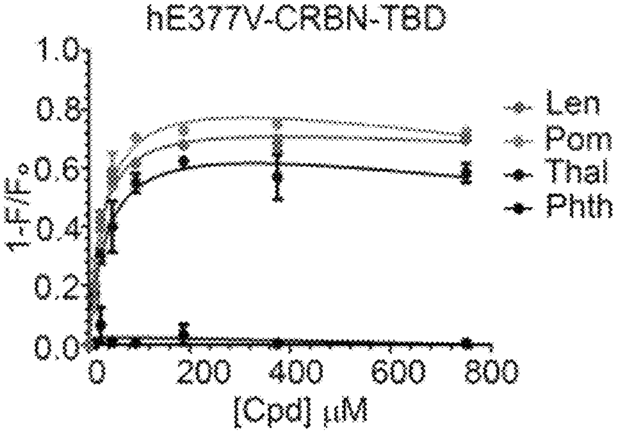
Figure 9F:
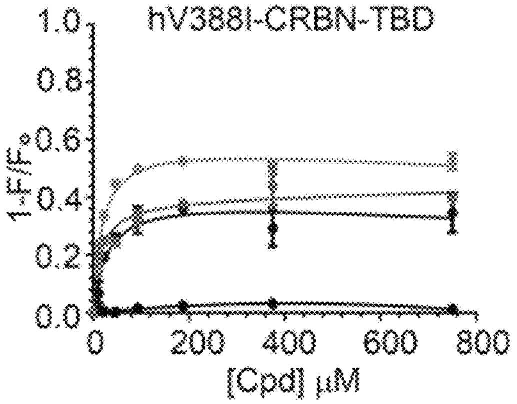
Figure 9G:
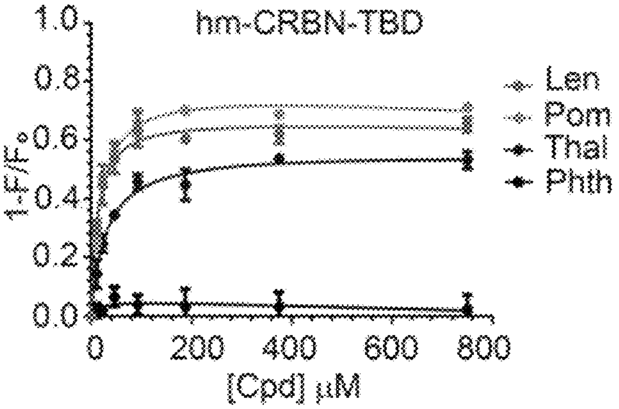
Figure 9H:
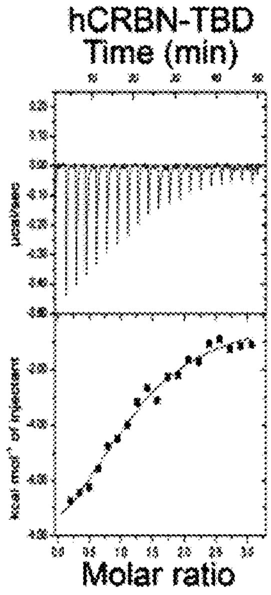
Figure 9I:
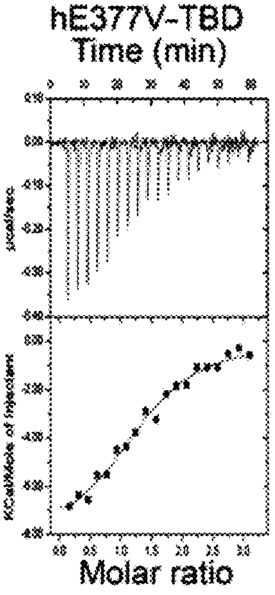
Figure 9J:
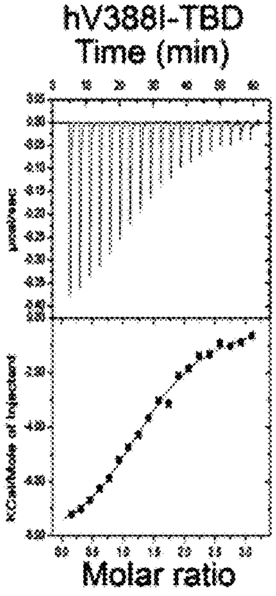
Figure 9K:
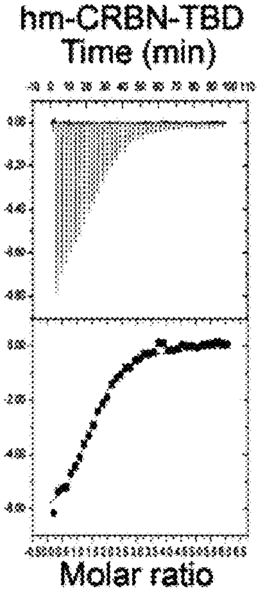
Figure 10A:
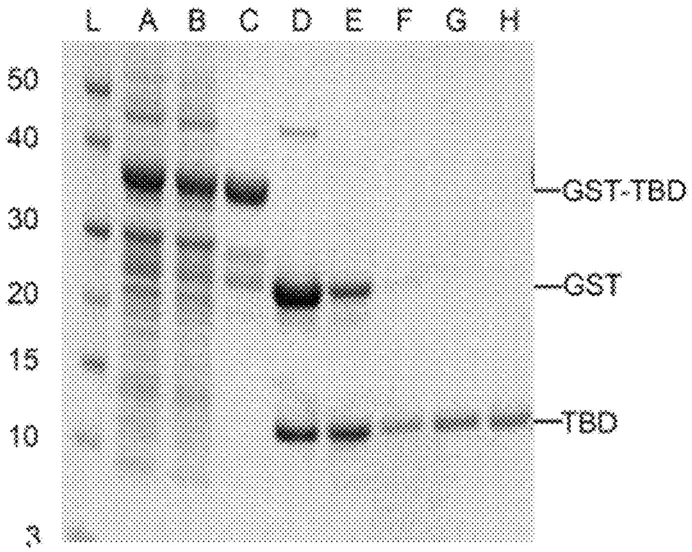
FIGS. 10A-10F show recombinant TBD protein expression and purification and zinc binding domain analysis using the zincon assay.
Figure 10B:
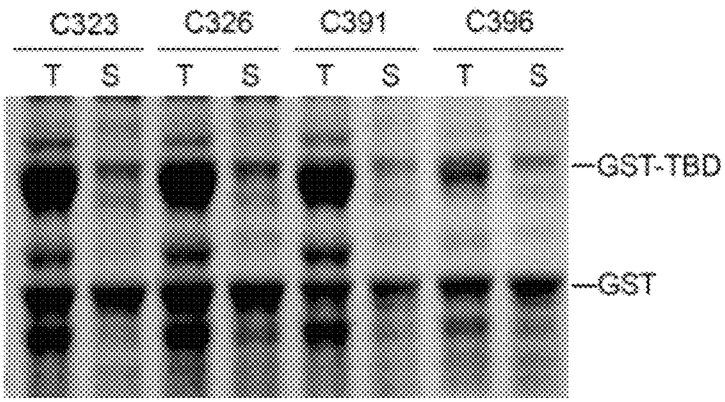
Figure 10C:
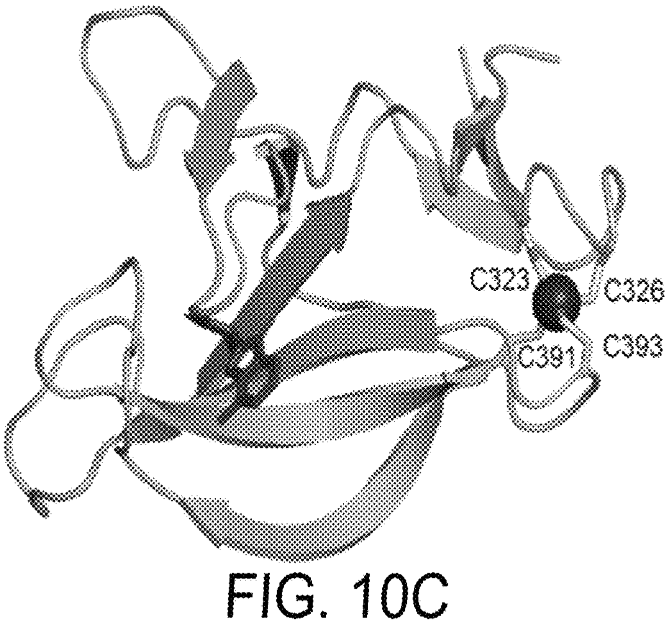
Figure 10D:
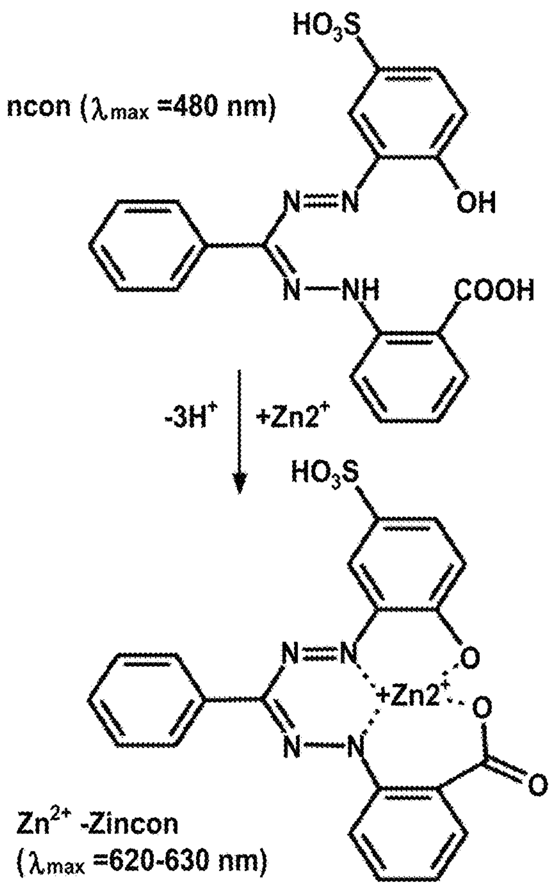
Figure 10E:
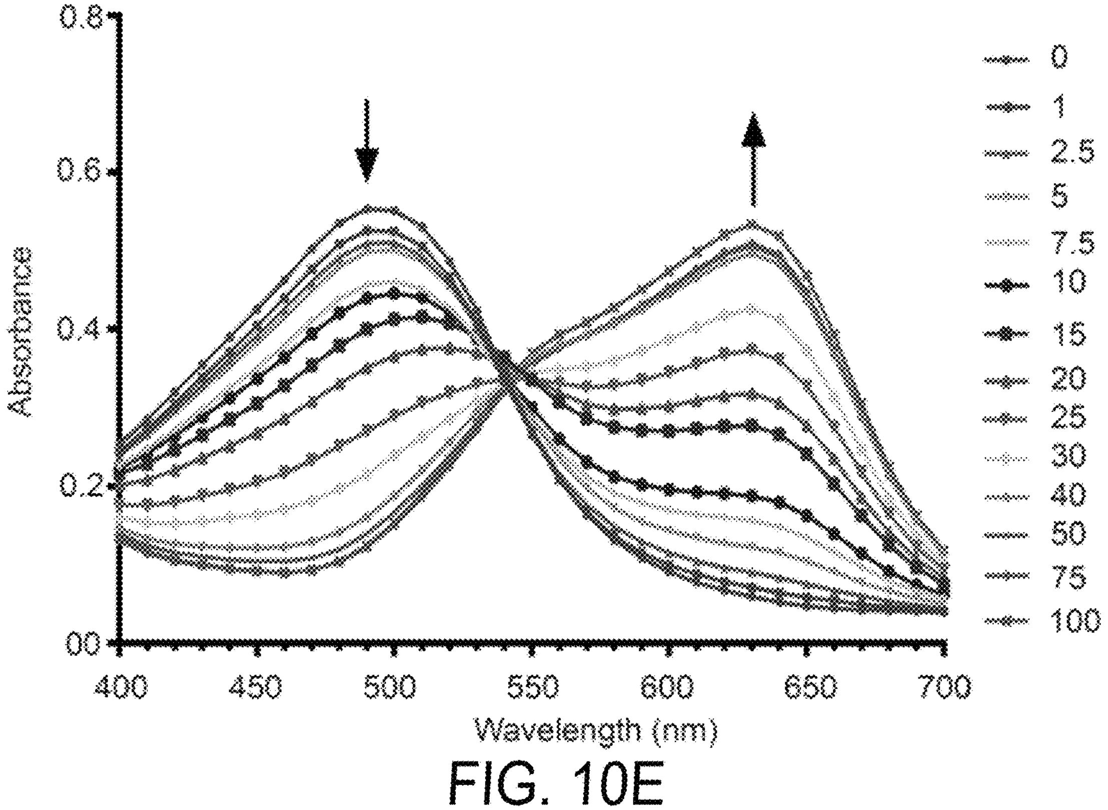
Figure 10F:
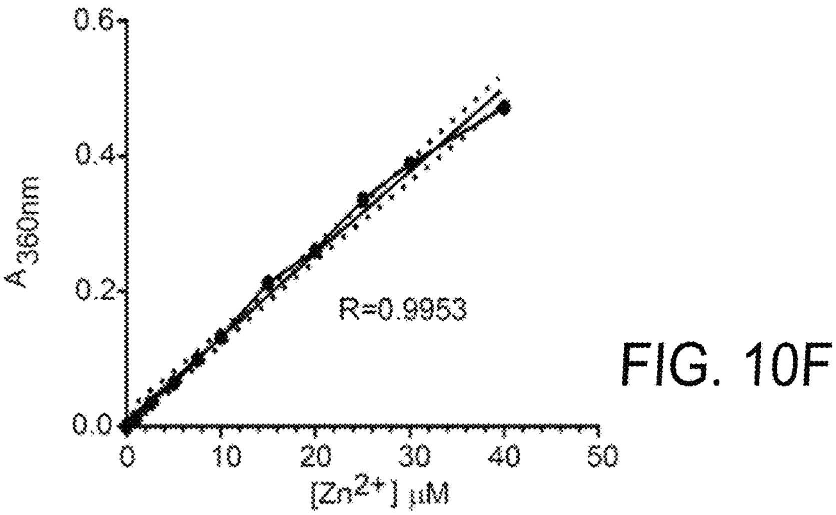
Figure 11A:
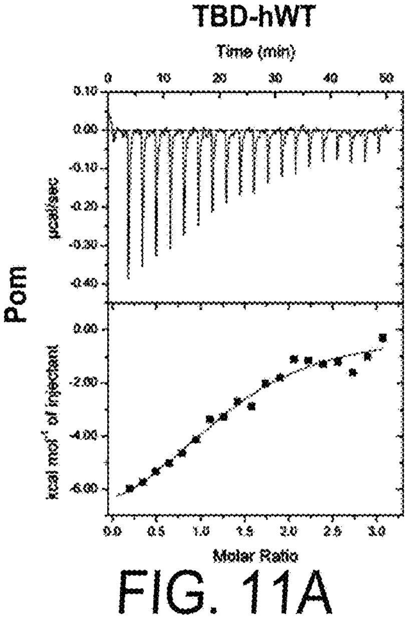
FIGS. 11A-11L shows binding affinity of IMiDs to TBD variants by ITC. ITC binding curves of pomalidomide (FIGS. 11A-11D), thalidomide (FIGS. 11E-11H), phthalimide (FIGS. 11I-11L) with wild type and mutant TBD constructs.
Figure 11B:
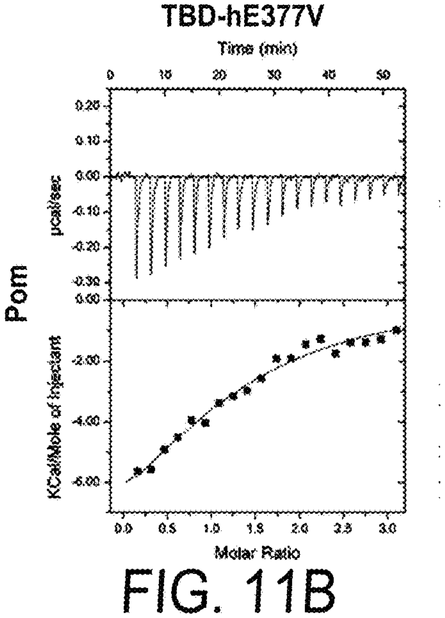
Figure 11C:
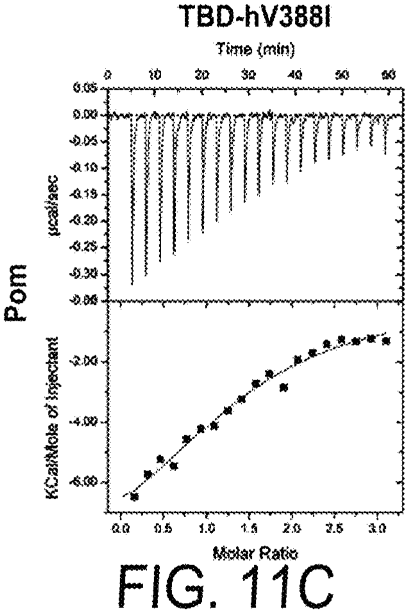
Figure 11D:
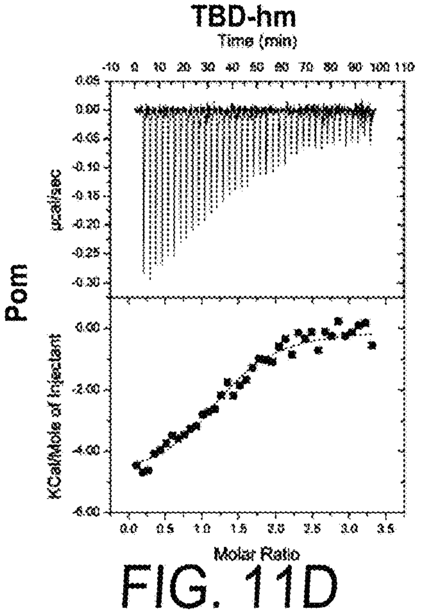
Figure 11E:
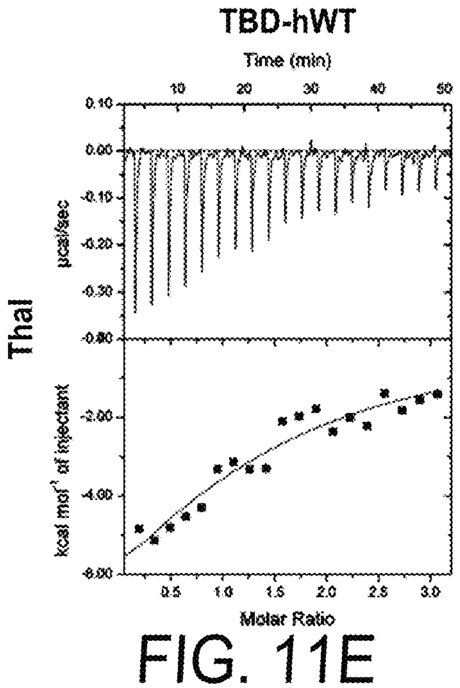
Figure 11F:
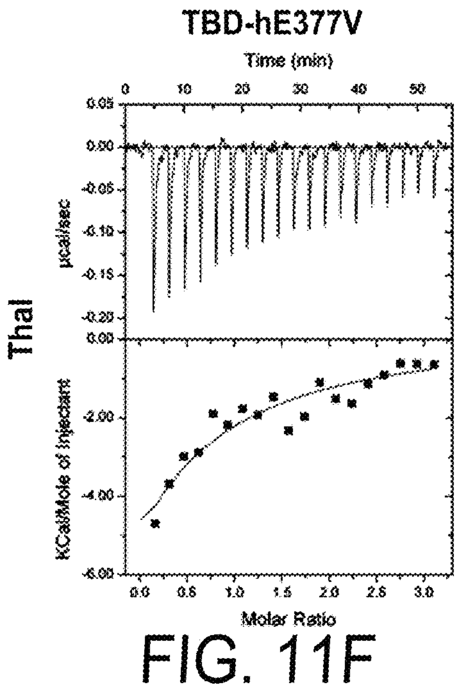
Figure 11G:
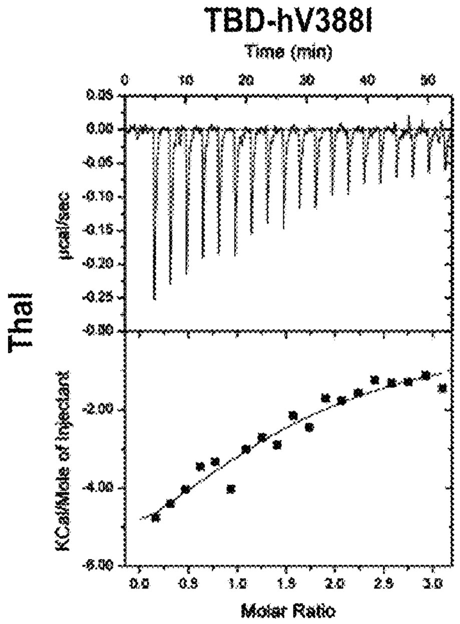
Figure 11H:
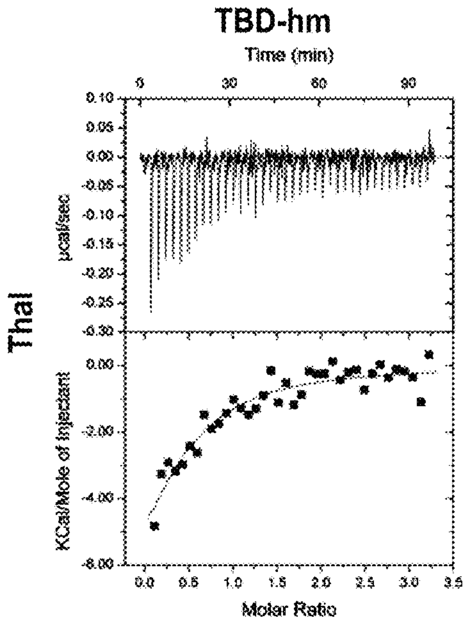
Figure 11I:
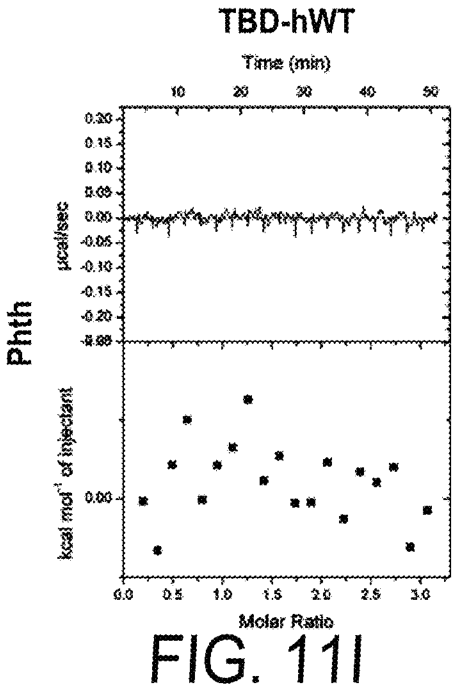
Figure 11J:
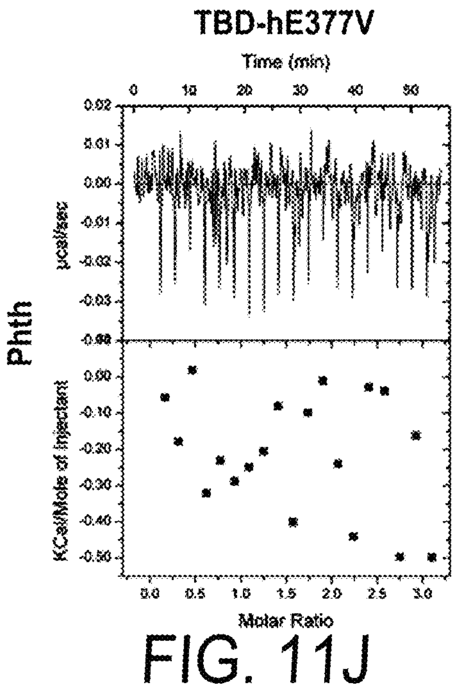
Figure 11K:
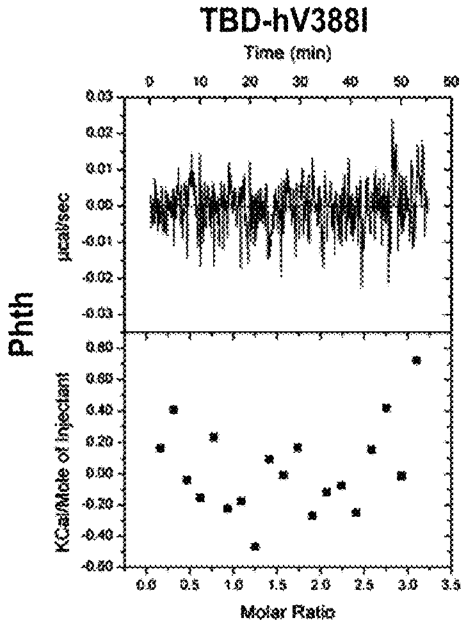
Figure 11L:
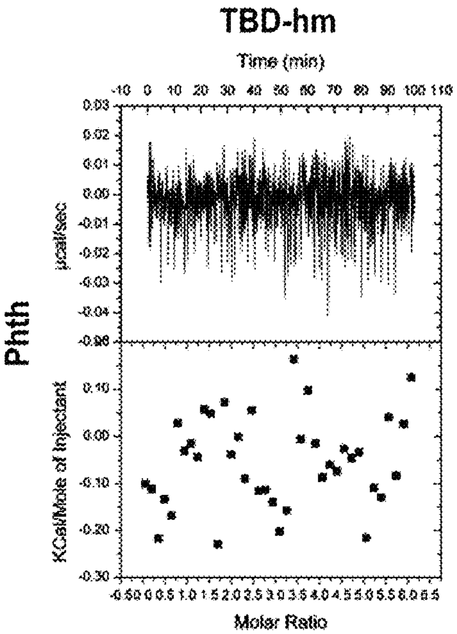

Immunomodulatory compound binding is functionally conserved in mouse and human CRBN. The species-specific amino acid differences in mouse CRBN-TBD at Val380 (equivalent to Glu377) and Ile391 (equivalent to Val388) (FIG. 9A) appear to have no relevance in the structure or corresponding immunomodulatory drug binding interaction (FIGS. 9B, 9C). To test the effects of these two non-conserved amino acids on binding affinity, recombinant human TBD was expressed and mutated to the mouse variant, and analyzed for immunomodulatory drug binding by two distinct assays, intrinsic tryptophan fluorescence assay (IF) and isothermal titration calorimetry (ITC). The C366S amino acid mutation was not studied in binding assays as it more than 20 Å away from the immunomodulatory drug binding pocket. The TBD motif (residues 319-425) was expressed in *E. coli* (FIG. 9A, FIG. 10A). The TBD is structurally stabilized by four cysteine residues (Cys323, Cys326, Cys391 and Cys394) that coordinate a single zinc ion (15, 16), located ~18 Å from the drug interacting site. To gain insights on the role of zinc, mutations in the CXXC domain of the TBD were also generated. Mutating any of the cysteine residues resulted in insoluble protein that aggregated in inclusion bodies (FIG. 10). This is indicative of misfolding due to loss of $Zn^{2+}$ ion coordination. To rule out improper folding or destabilization, a zincon assay (13) was performed on purified protein of all expressed recombinant CRBN-TBD proteins. These analyses revealed a 1:1 stoichiometric ratio of $Zn^{2+}$ bound to the TBD recombinant protein (FIGS. 10C-10F). Moreover, protein secondary structure consistent with proper folding was also evident using circular dichroism (data not shown). Notably, both IF (FIGS. 9D-9G) and ITC (FIGS. 9H-9K, FIG. 13) analyses demonstrated similar $K_D$ values at equilibrium for each compound tested in binding to wild type, E377V, V388I, and E377V/V388I (hm)-CRBN-TBD (Table 1).

Figure 12:
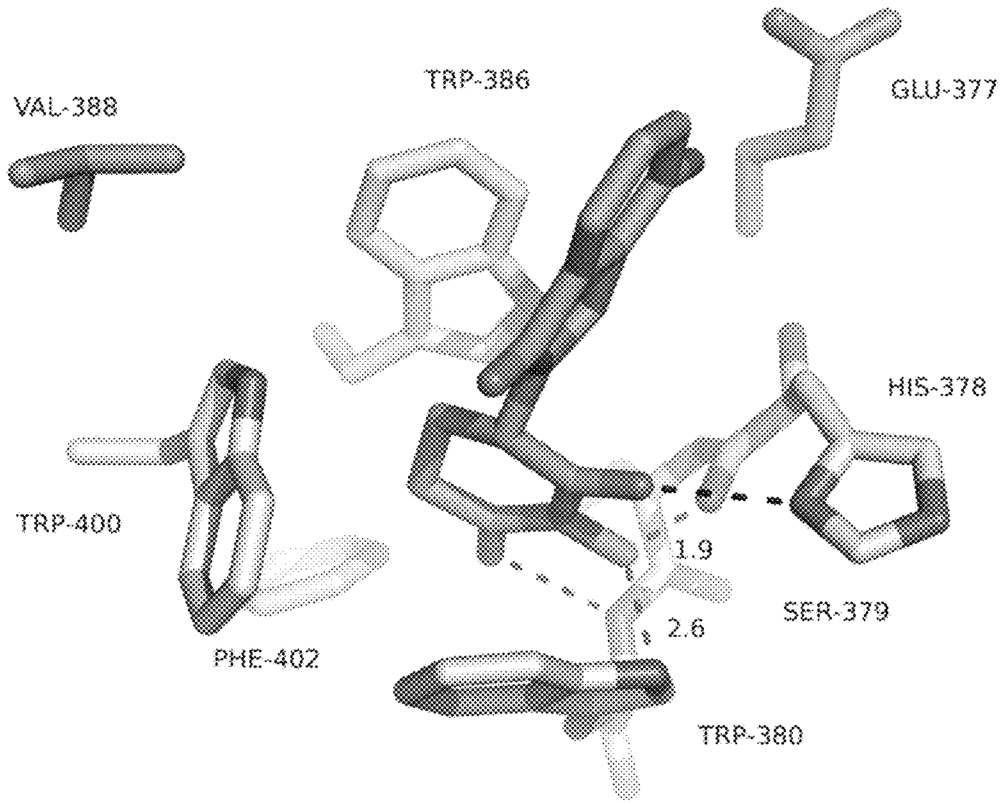
FIG. 12 shows the binding pocket with N-methyl-lenalidomide.

To assess the impact of binding pocket residues, Ala mutations of two residues were generated (FIGS. 9B, 9C) (7, 26, 27). Trp380A mutation completely abolished ligand interaction. H-bond formation and hydrophobic interaction with Trp380 are critical for immunomodulatory drug binding. In contrast, the binding affinity of H378A to immunomodulatory compounds was similar to the wild-type protein (Table 1) demonstrating that this mutation alone does not impact protein-ligand interactions. Though His378 forms two H-bonds to the glutarimide ring (FIG. 9C), mutating this residue to Ala did not impact binding. This may suggest that the backbone carbonyl of Ala is able to form H-bond to the —NH group of the glutarimide ring. To further probe the role of His378 side-chain in immunomodulatory drug binding, we conducted a pH-dependence study to measure the binding affinity of lenalidomide to CRBN-TBD by ITC. The $K_D$ values measured at pH 4.5, 5.5, 6.5 and 7.5 are 21.4±3, 23.7±8, 23.8±7 and 11.3±2 μM, respectively. Thus, protonation and deprotonation of the His378 imidazole group has no impact on immunomodulatory drug binding to the TBD. To gain more insight on immunomodulatory compound binding to CRBN-TBD, we synthesized N-methyl-lenalidomide as a negative control, where the methyl group in the glutarimide ring is predicted to cause steric hindrance in the binding pocket (FIG. 12). As expected, N-methyl-lenalidomide shows no binding to CRBN-TBD using both methods.

Figure 13A:
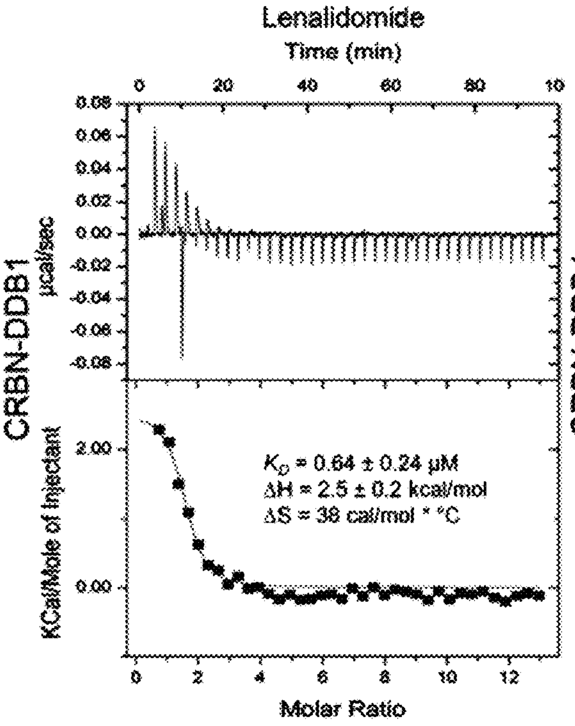
FIGS. 13A-13F shows lenalidomide binds to the TBD and CRBN-DDB1 protein complex. ITC binding curves of lenalidomide (FIGS. 13A, 13C) and N-methyl-lenalidomide (FIGS. 13B, 13D) titrated with (FIGS. 13A, 13B) CRBN-DDB1 complex and (FIGS. 13C, 13D) CRBN-TBD.
Figure 13B:
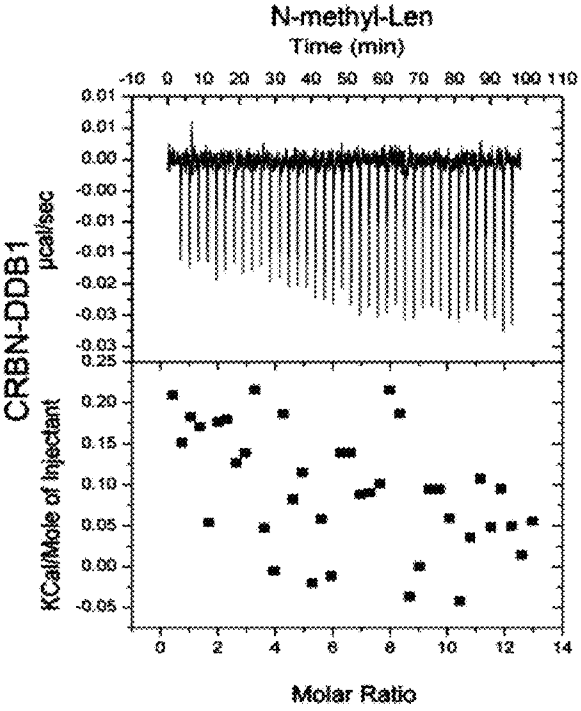
Figure 13A:
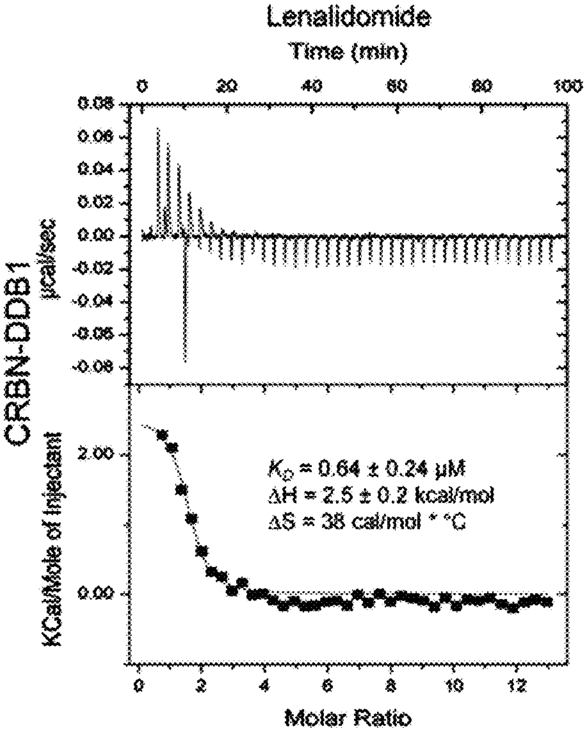
Figure 13B:
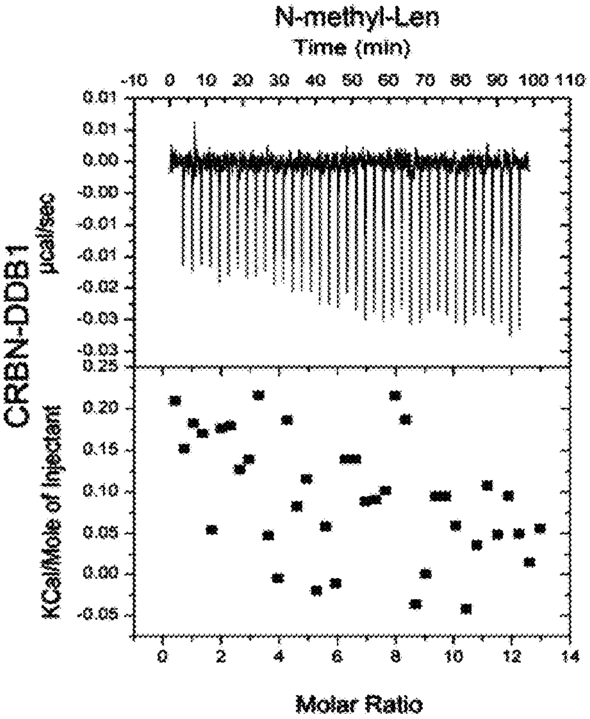
Figure 13C:
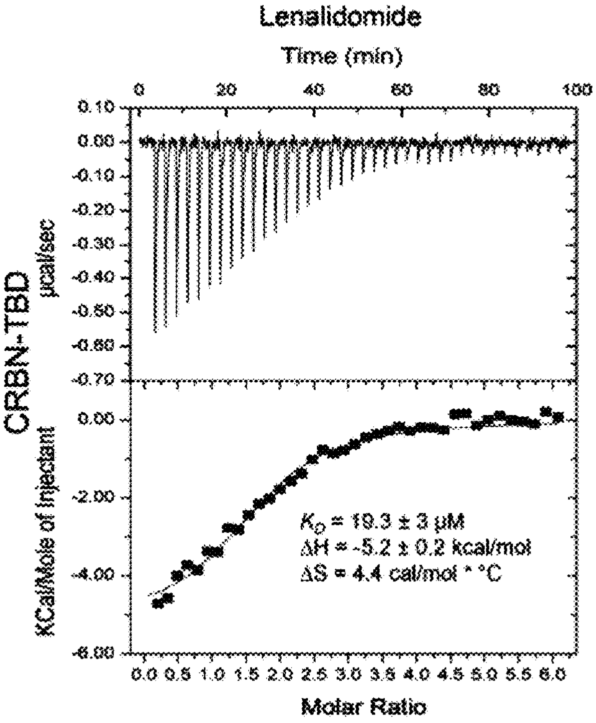
Figure 13D:
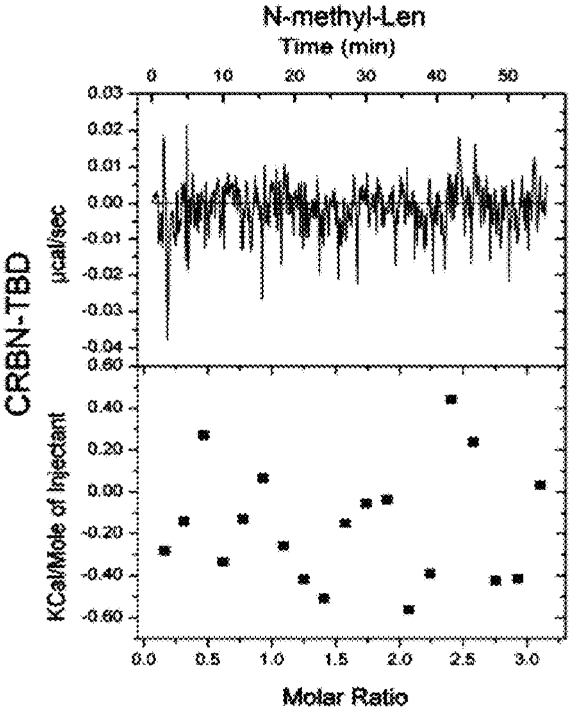

Finally, binding affinities of CRBN-TBD and full-length CRBN in complex with DDB1 was compared to lenalidomide using ITC to assess the impact of residues outside of the TBD. The full-length CRBN-DDB1 complex displayed a $K_D$ value of 0.64 μM±0.24 μM (pH 7.0) (FIG. 13A). This affinity is similar to published data using a fluorescence polarization (FP)-based assay (32). Moreover, these results are consistent with a single binding site within the protein complex. In support of this notion, N-methyl-lenalidomide disrupted the CRBN-DDB1 complex interaction (FIG. 13B) indicating that the complex-drug interaction is mediated solely by the hydrophobic binding pocket of the TBD. Interestingly, the binding affinity of lenalidomide to the CRBN-TBD is about 30-fold lower than the full-length CRBN-DDB1 complex. Moreover, full-length CRBN and CRBN-TBD have exothermic and endothermic reactions, respectively. Therefore, residues in the full-length protein appear to augment protein-ligand interactions in the binding pocket.

Figure 14A:
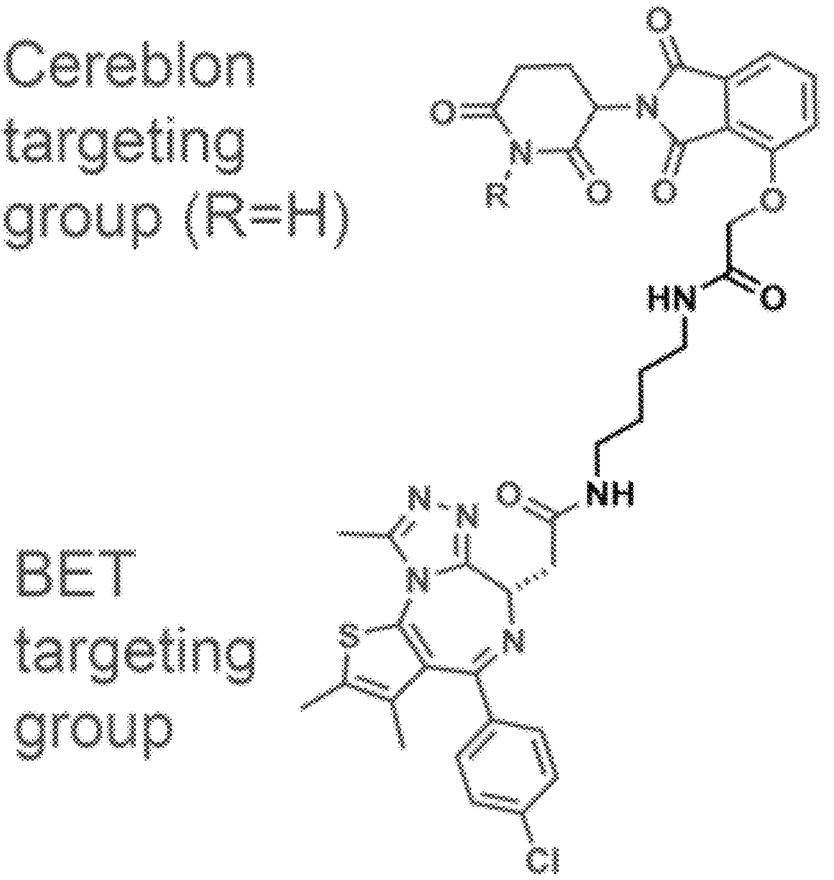
FIGS. 14A-14G shows functional activity of lenalidomide, JQ1 and dBET1 in human and mouse T cells and binding affinities of JQ1, dBET1 and Len to human CRBN.
Figure 14B:
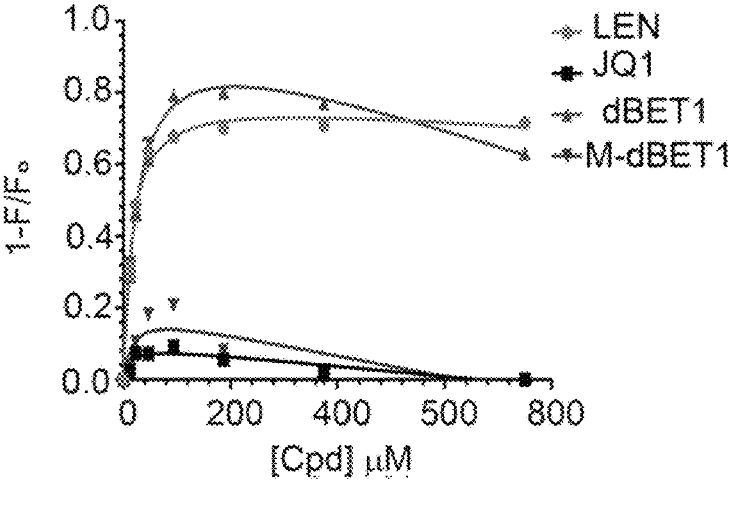
Figure 14C:
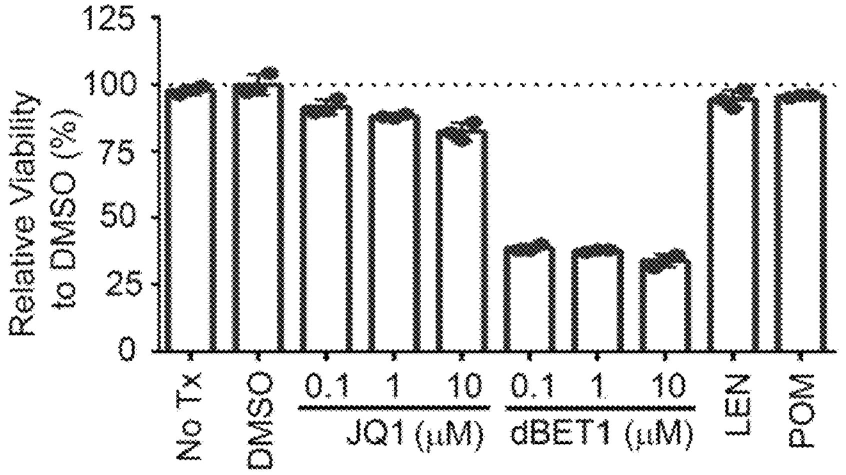
Figure 14D:
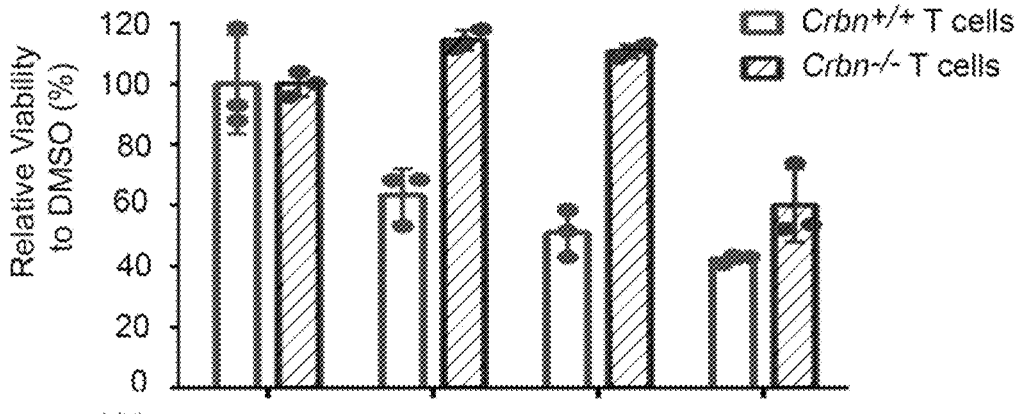
Figure 14E:
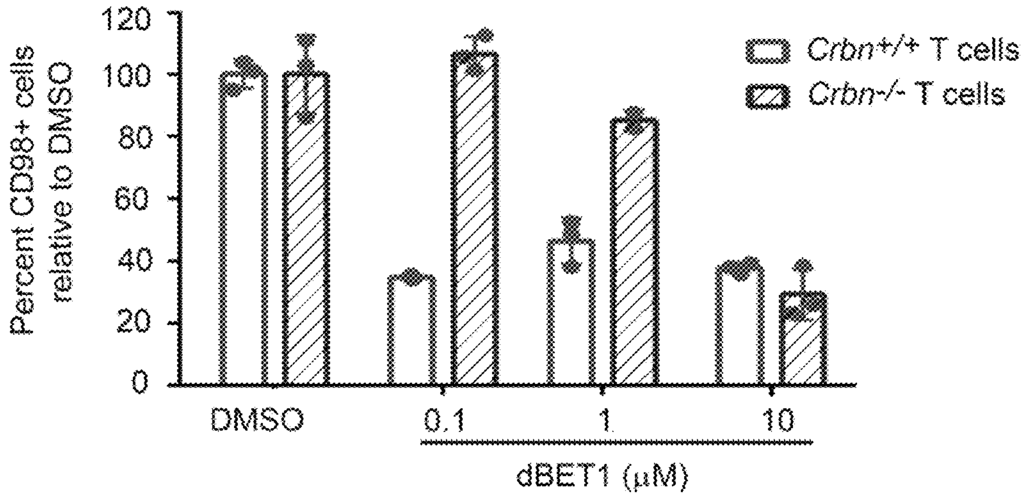
Figure 14F:
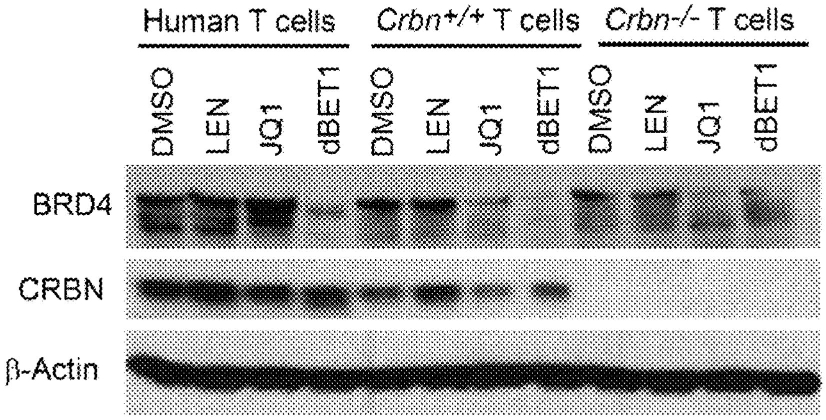
Figure 14G:
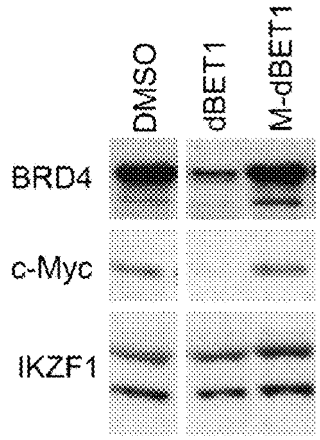
Figure 15A:
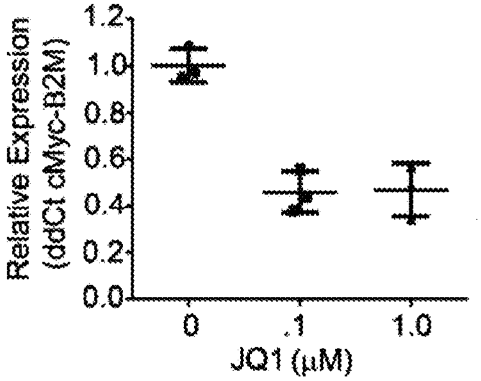
FIGS. 15A-15F shows drug treatment of human and mouse T cells and multiple myeloma cell lines.
Figure 15B:
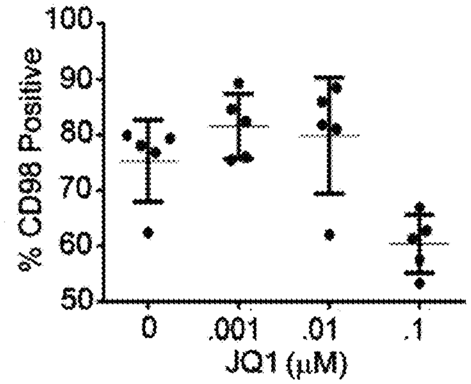
Figure 15C:
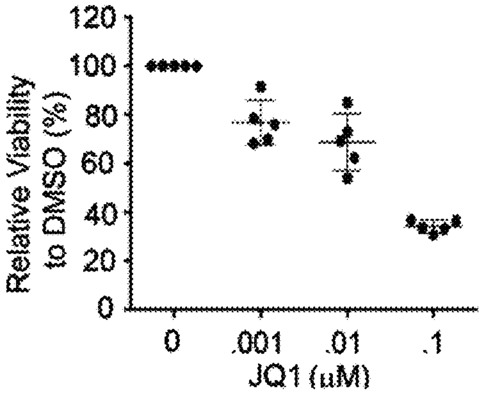
Figure 15D:
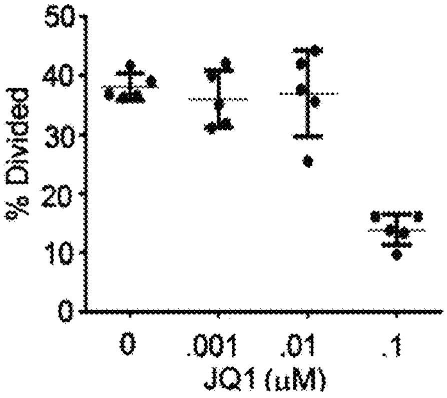
Figure 15E:
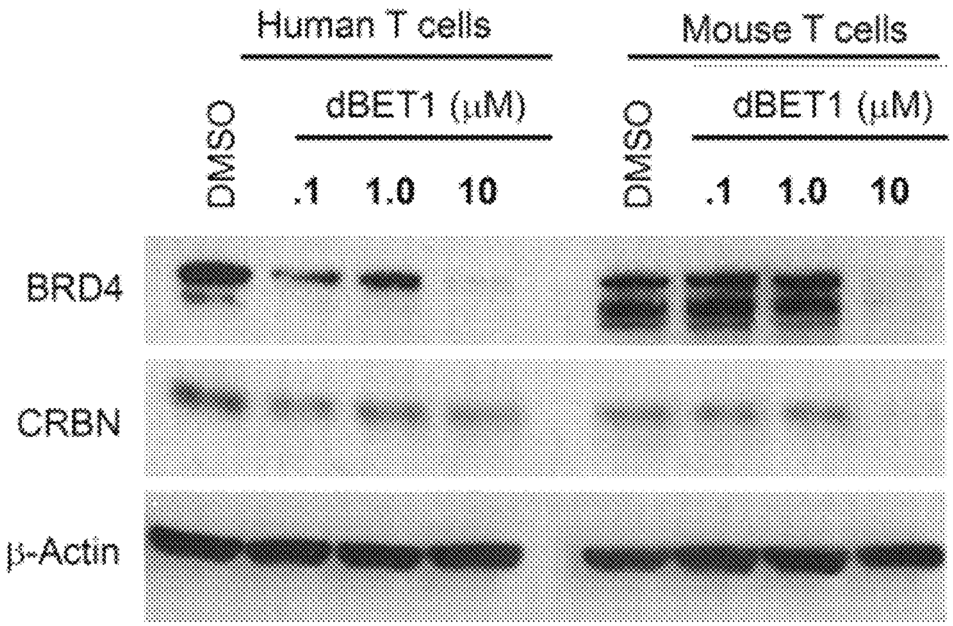
Figure 15F:
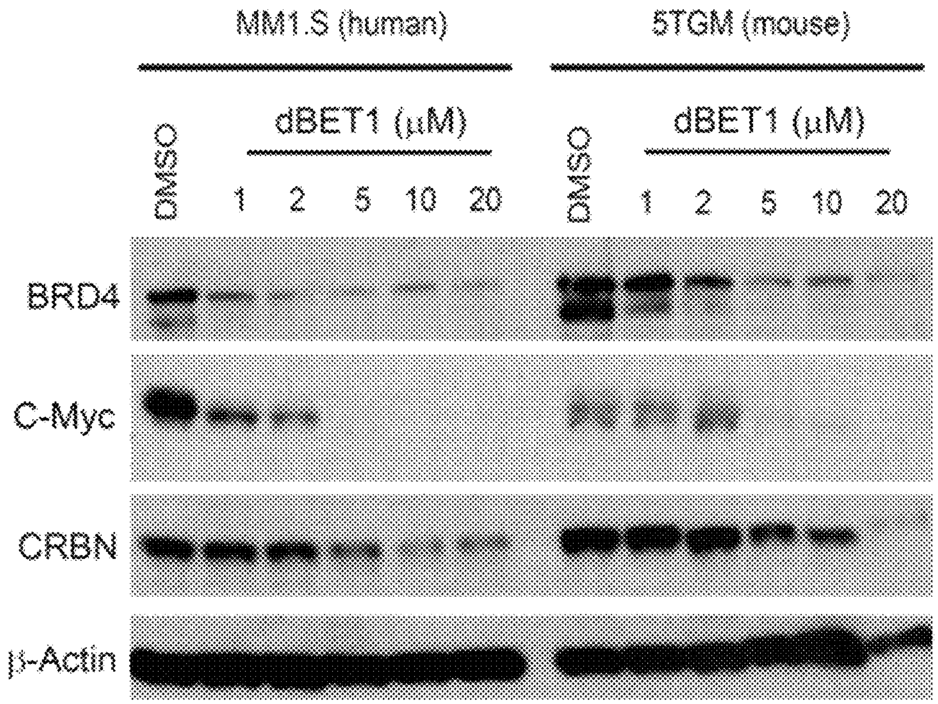

Acquired ubiquitin-proximity ligation in mouse cells establishes conserved functions of mouse and human CRBN. The structures of dBET1 and N-methyl-dBET1 (used as a negative control based on the results of N-methyl-Len) are provided in FIG. 14A and show the cereblon and BET targeting groups. Using IF (FIG. 14B), the binding affinity of dBET1 for CRBN-TBD is shown to be similar to that of lenalidomide, whereas, as expected, JQ1 alone does not bind to CRBN-TBD. Methylation of dBET1 in the glutarimide ring confirms that the binding of this analog is mediated by the TBD hydrophobic binding interaction which is similar for classical immunomodulatory compounds. JQ1 treatment of primary mouse T cells was then tested and verified to have function (FIGS. 15A-15D). Suppression of c-Myc mRNA (FIG. 15A), reduction in the surface expression of the important c-Myc target molecule CD98 (FIG. 15B), compromised viability (FIG. 15C) and proliferation (FIG. 15D) confirms that BRD4 is a suitable target in these cells. To establish the function of dBET1 in activated human T cells, results are shown in FIG. 14C. The relative viability is reduced after treatment with dBET1 compared to both DMSO and JQ1. Therefore, the growth suppressive effect is enhanced by the heterobifunctional conjugate. As expected, lenalidomide and pomalidomide have no effect on viability although they increase proliferation (FIG. 14C, FIG. 4 and data not shown). Using purified $Crbn^{+/+}$ and $Crbn^{-/-}$ mouse T cells activated with anti-CD3+ anti-CD28, we show that dBET1 suppresses viability and reduces the percentage of cells expressing the c-Myc target CD98 (FIGS. 14D and 14E, respectively). A differential response to dBET1 treatment is clearly observed between $Crbn^{+/+}$ and $Crbn^{-/-}$ T cells indicating that the response at lower doses is CRBN-dependent. Proximity-associated ubiquitin conjugating functions of mouse and human CRBN were then confirmed in human T cells, $Crbn^{+/+}$ and $Crbn^{-/-}$ T cells (FIGS. 14F, 14G) and in human MM1.S and mouse 5TGM1 multiple myeloma cells (FIG. 15E) treated with dBET1. BRD4 protein and c-Myc expression were dramatically suppressed by dBET1 treatment in all cell types (FIG. 15). Further, in activated mouse T cells, the decrease in BRD4 protein level is CRBN-dependent in response to dBET1 although there is a slight reduction in protein expression after JQ1 that is not dependent on CRBN (FIG. 14F). Notably, the functional response to dBET1 is reversed by incubation with M-dBET1 showing that human T cells also respond through interactions mediated by the hydrophobic pocket of the CRBN-TBD. Thus, mouse and human BRD4 is successfully targeted for degradation through a CRBN-dependent process.

Discussion

Divergent drug metabolism (30) and minor primary sequence-related differences in the thalidomide-binding domain (TBD) of CRBN (10) have been proposed to explain the species-specific pharmacological activity of the immunomodulatory compounds. Using molecular dynamics (MD), minimal conformational deviation or fluctuation was observed in mouse vs. human CRBN crystal structures and equilibrated MD structures, thus, rigid, induced fit, and quantum polarized virtual docking on both crystal and MD equilibrated structures showed no quantitative difference in theoretical binding energy or in the pose position of thalidomide, pomalidomide, or lenalidomide.

Using ITC and fluorescence-based empirical binding assays, we establish that the dissociation constants of thalidomide and other immunomodulatory compounds to mouse CRBN are similar to human CRBN, which is consistent with analysis of the crystal structure of human CRBN-DDB1 in complex with lenalidomide (pdb codes: 4CI2, 4TZ4)(15, 16). The $K_D$ values of immunomodulatory compounds in complex with the human TBD (aa 317-425) are in the μM range, which is similar to those of *C. elegans* and *Magnetospirillum gryphiswaldense* (14). The W380A hydrophobic binding pocket mutant completely abolished binding, confirming that, as suggested previously (15), this is one of the key residues of the binding pocket. This result also suggests that Trp380 is essential in the hydrophobic cage to work synergistically with other residues (Trp386, Trp400 and Phe402) for ligand interaction.

Figure 13E:
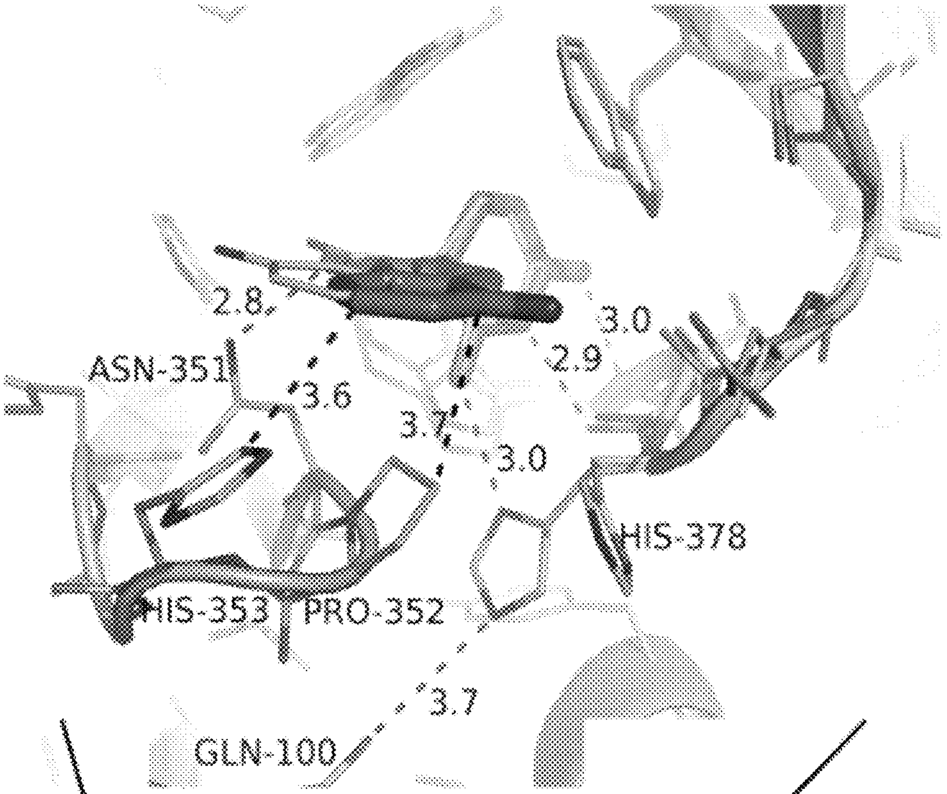
Figure 13F:
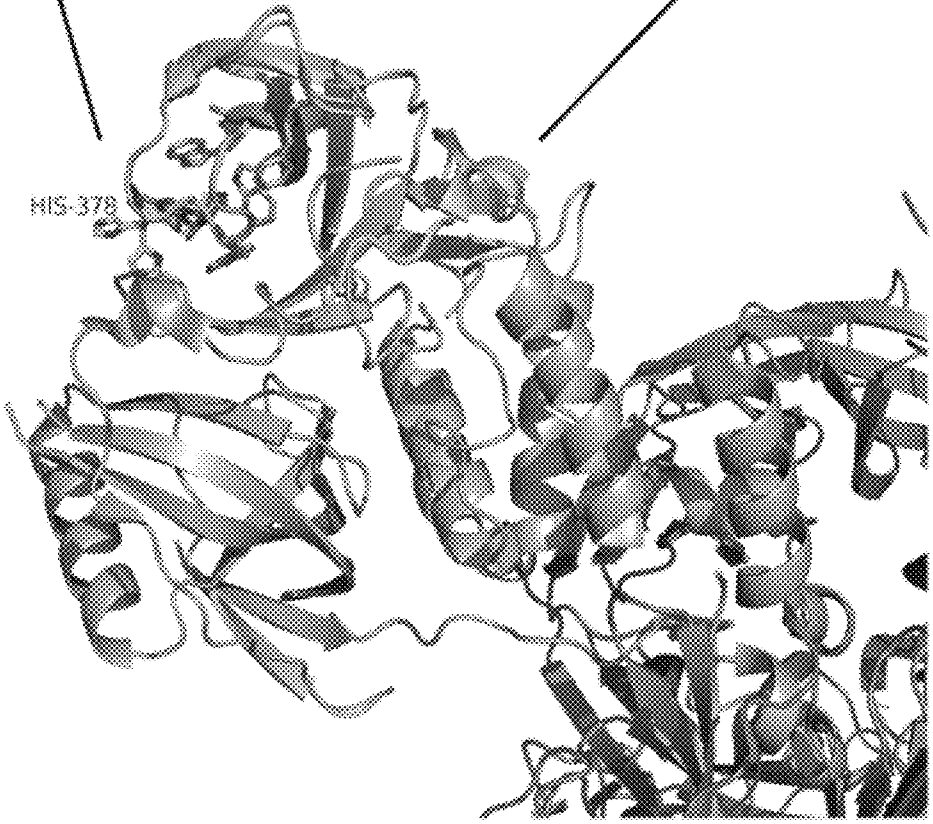

Notably, there is a marked difference in binding affinity between the CRBN-DDB1 complex and the CRBN-TBD protein to lenalidomide by ITC. A conformational change in full-length CRBN-DDB1 may occur upon lenalidomide binding as shown by the difference in their ΔH and ΔS values (FIG. 13). Despite the rigidity of the TBD binding pocket, it appears the N-terminal domain of CRBN that is missing in the TBD construct plays an important role in ligand binding. In fact, the X-ray crystal structure reveals that there are residues outside the TBD which affect CRBN affinity for immunomodulatory drugs (FIG. 13F). A closer inspection of the crystal structure of full-length CRBN in complex with lenalidomide illustrates that a disordered loop in the TBD consisting of residues Asn351, Pro352, and His353 further stabilize the interaction of lenalidomide. Asn351 forms a hydrogen bond to lenalidomide and both Pro352 and His353 form hydrophobic interactions with the aromatic system of the immunomodulatory drugs (FIG. 13E). Importantly, the residues in this loop are identical in human and mouse CRBN (FIG. 9A) although it is absent in the crystal structures of mouse TBD. It is likely that the loop is in a highly unstructured and dynamic region consequently leading to poor electron density in the mouse structure. Collectively, the results suggest that the N-terminal residues stabilize this region and strengthen the binding affinity to lenalidomide and other immunomodulatory drugs. Alternatively, other residues outside the TBD could have stabilized this loop. In addition, the side-chain of Gln100, which is located in the LON domain of CRBN, forms a weak hydrogen bond interaction to the $\varepsilon^2$NH group of His378. This in turn positions the $\delta^1$NH of His378 as a hydrogen donor to lenalidomide. This could account for the higher binding affinity of immunomodulatory drugs to the full-length CRBN protein and explain the H378A mutation results using the TBD construct. Based on the importance of these structural domains in binding to the conserved glutarimide ring present in dBET1 and all immunomodulatory drugs, we synthesized N-methyl derivatives which are useful in assessing the functional contribution of this ligand interaction in vivo.

Despite their teratogenic properties (31), thalidomide and immunomodulatory compounds are approved treatments for multiple myeloma (32), myelodysplastic syndrome (MDS) associated with a somatically acquired deletion in chromosome 5 (del5q MDS)(33) and B cell malignancies (9, 34, 35). As anti-cancer agents, immunomodulatory compounds appear to act through intrinsic effects on tumor cell survival (36, 37) and via extrinsic effects on the anti-tumor immune potentiation of T cells and natural killer (NK) cells (34, 38) that involves the degradation of select protein substrates (7, 8, 39-41). The mechanism by which these drugs induce limb deformities in human, chickens and zebrafish, and anti-neoplastic activity in humans, but not in mice, appears dependent on CRBN.

When bound to immunomodulatory drugs, CRBN induces the destruction of several substrates including the transcription factors IKZF1 and IKZF3 (7), and/or casein kinase 1α (CK1α)(11). In T cells, IKZF-family transcription factors repress IL2 transcription so that ubiquitin-mediated destruction of IKZF proteins induces activation of T cells consistent with data shown in FIG. 3 (11, 42). Based on X-ray crystallography and biochemical analysis, a single non-conserved amino acid in mouse CRBN, Ile391 (equivalent to Val388 in human CRBN), blocks the interface between residues 317-442 of CRBN, lenalidomide's solvent exposed surface, and CK1α (10, 11). Further, using the BaF3 mouse lymphoma cell line that is inherently resistant to immunomodulatory compounds, forced expression of human CRBN was sufficient to restore both IKZF1 and CK1α degradation and to induce drug-induced myelosuppression (10). It is important to note, however, that CRBN from chicken has the identical amino acid residue, Ile391, as mouse, but shows drug sensitivity to thalidomide (43). CRBN, which was first identified in mild autosomal recessive non-syndromic intellectual disability (ID) (12), has poorly defined physiological substrates. It is still possible that the classical immunomodulatory drugs may displace an endogenous substrate that cooperates with CRBN and contributes to the biological effects.

In this study, our data indicate that human and mouse CRBN likely share the same binding affinities and mechanisms. We conclude that dBET1 enters and is stable in mouse cells, binds mouse CRBN, and provokes the degradation of specified protein targets in a CRBN-dependent manner. Further, the TBD of human and mouse CRBN have similar affinities and binding modes for immunomodulatory compounds. Based on our data with $Crbn^{-/-}$ T cells, dBET1-associated degradation of BRD4 is totally reliant on CRBN. Thus, the endogenous E3-ubiquitin ligase activity and assembly of the DDB1-CUL4A ubiquitin ligase complex containing CRBN is fundamentally conserved across the vertebrate lineage, including the mouse suggesting that Ile391 only impacts some targets and possibly only in relationship to classical immunomodulatory molecules (10, 11). This observation, along with the high degree conservation of CRBN, indicates that selective pressure has maintained the overall structure and function in CRBN for over 400 million years. Moreover, it is likely that other substrates targeted by PROTAC molecules may adopt an active conformation that is susceptible to CRBN-directed, cullin-RING E3 ligase-mediated polyubiquitination. Substrate restrictions or conformational restraints for PROTAC sensitivity are unexplored. However, the redirection of cullin-E3 ligases to aberrantly degrade host proteins has been well studied in viral infection (44) including a role for DDB1 in the regulation of hepatitis B virus DNA replication (45) and human immunodeficiency virus-1 (HIV-1) infectivity (46). Interestingly, BRD4 controls the papillomavirus E2 ubiquitin regulation suggesting that it has the ability to regulate proteins by engaging the proteosome (45). Many substrates require post-translational modifications to trigger sensitivity, and both cytoplasmic and nuclear proteins can be targeted for degradation (44). In the case of human immunodeficiency virus-1 (HIV-1) Vif protein, a zinc-binding region governs selectivity for the cullin-family member (47). Therefore, the zinc ion coordination complex in CRBN may play a structural role in CRBN and participate in substrate recruitment of some proteins. Importantly, our studies establish that mouse platforms can indeed be used for preclinical development of derivatives of PROTAC-based chemical degraders and other drug classes designed to re-direct CRBN's ligase activity toward specified endogenous proteins (1, 2, 5, 48-50). Toxicology and functional testing of such agents in rodents and mouse tumor models may yield important preclinical information.

Example 3: Synthesis of Compounds

MA6-019

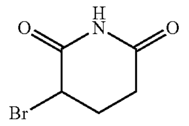

3-Bromopiperidine-2,6-dione (MA6-019): This compound was prepared using a literature procedure[1]. In a sealed reaction vessel, glutarimide (2 g, 17.68 mmol) was dissolved in dry chloroform under argon atmosphere and $Br_2$ (908.54 uL, 1 equiv.) was added via a syringe at room temperature. The reaction mixture heated at 110° C. (oil bath) for 1 h, cap was removed and further stirred at r.t. for 30 minutes. The crude product was evaporated and brown solid was purified using $SiO_2$ column chromatography (EtOAc-hexane, 0%-100% gradient elution). The product was obtained as a white crystalline solid (0.93 g, 55%). HPLC-MS (ESI): m/z 192.0 [100%, $(M+H)^+$]. $^1H$ NMR (400 MHz, Chloroform-d) δ 7.92 (s, 1H), 4.63 (app t, J=3.5 Hz, 1H), 3.00-2.91 (m, 1H), 2.72-2.70 (m, 1H), 2.68-2.66 (m, 1H), 2.36-2.28 (m, 1H).

Scheme 1

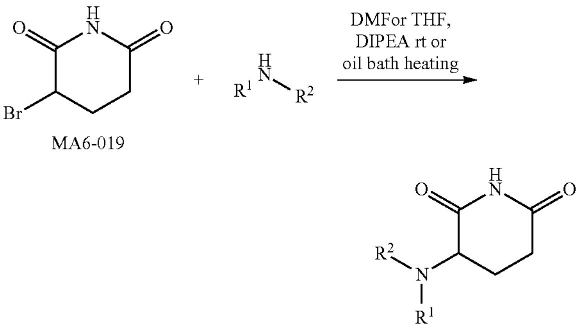

$R^1$ = H, alkyl, aryl, heteroaryl
$R^2$ = alkyl, aryl, heteroaryl

Method 1: A mixture of MA6-019 (1 equiv.) and corresponding amine or amine hydrochloride (1 equiv.) was dissolved in dry DMF or THF followed by the addition of diisopropylethtylamine (DIPEA) or trimethylamine (TEA) (2.1 equiv., unless mentioned otherwise). The reaction mixture was stirred at the indicated temperature until completion as shown by TLC and/or HPLCMS. The crude mixture was diluted with aq.$NaHCO_3$ (~5 mL) and extracted with EtOAc (~10 mL×2). The organic layer was dried ($Na_2SO_4$) and concentrated under reduced pressure. The title products were purified by trituration, $SiO_2$ chromatography or reverse phase HPLC.

MA6-136

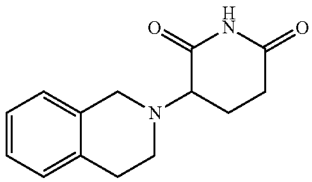

3-(3,4-Dihydroisoquinolin-2(1H)-yl)piperidine-2,6-dione (MA6-136): This compound was obtained as a beige solid (126 mg, 66%) from MA6-019 (150 mg, 1 equiv.) and 1,2,3,4-tetrahydroisoquinoline (99.1 uL, 1 equiv.) using the general procedure method 1 (Scheme 1) (reaction temperature 72° C., solvent THF (0.5 mL), DIPEA (272 μL) reaction time 1.5 h). Purification was carried out using $SiO_2$ column chromatography (eluent: MeOH-DCM, up to 10% MeOH). Mp: 178° C. (dec). HPLC: 98% [$t_R$=8.3 min, Gradient 5-95% MeOH-water (with 0.1% TFA), 20 min]. $^1$H NMR (400 MHz, DMSO-$d_6$): δ 10.68 (s, 1H, disappeared on $D_2O$ shake), 7.11-7.08 (m, 3H), 7.05-7.00 (m, 1H), 3.92 (d, J=14.9 Hz, 1H), 3.79 (d, J=14.9 Hz, 1H), 3.63 (dd, J=11.2, 4.4 Hz, 1H), 2.99 (dt, J=11.5, 5.8 Hz, 1H), 2.88 (dt, J=11.4, 5.4 Hz, 1H), 2.77 (q, J=5.8 Hz, 2H), 2.65-2.53 (m, 2H), 2.21-2.09 (m, 1H), 1.97-1.87 (m, 1H). HPLC-MS (ESI): m/z 245.2 [100%, $(M+H)^+$]. LC-MS (ESI+): 245.1 [100%, $(M+Na)^+$], 267.1 [40%, $(M+Na)^+$]. HRMS (ESI+): m/z calcd for $C_{14}H_{16}N_2O_2$ $(M+H)^+$245.1284, found 245.1285.

Scheme 2

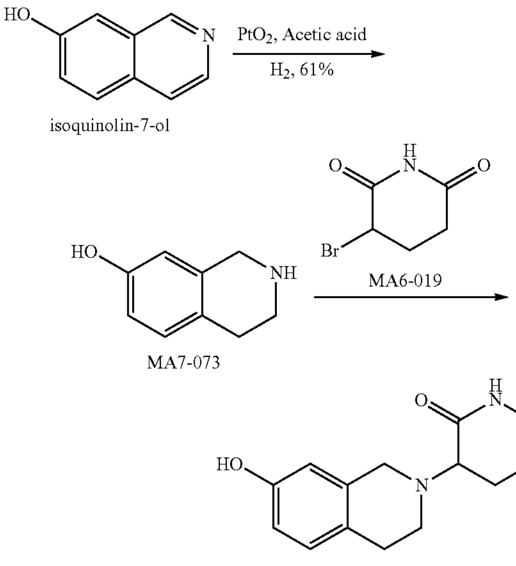

isoquinolin-7-ol

MA6-019

MA7-073

MA7-098

3-(7-Hydroxy-3,4-dihydroisoquinolin-2(1H)-yl)piperidine-2,6-dione, (MA7-098). First, MA7-073 was synthesized via hydrogenation of starting material isoquinolinol (100 mg, 0.68 mmol) in acetic acid (5.0 mL), with $PtO_2$ (28.27 mg, 0.01 mmol) for 48 h (Scheme 2). The solvent was evaporated, and the black gummy product was partitioned with EtOAc and aqueous $NaHCO_3$. The organic layer was dried ($Na_2SO_4$), evaporated, and the crude product was triturated with EtOAc/hexane to obtain MA7-073 (63 mg, 61%) as a beige solid. $^1$H NMR (400 MHz, DMSO-$d_6$): δ 9.02 (s, 1H), 6.82 (d, J=8.4 Hz, 1H), 6.50 (dd, J=8.4, 2.8 Hz, 1H), 6.38 (d, J=2.4 Hz, 1H), 4.10 (brs, 1H), 3.72 (s, 2H), 2.88 (t, J=6.0 Hz, 2H), 2.54 (t, J=5.6 Hz, 2H). The MA7-098 was obtained as a white solid (16 mg, 18%) from MA6-019 (64.3 mg, 1 equiv.) and MA7-073 (50 mg, 1 equiv.) using the general method 1 (Scheme 1) (reaction was carried out at room temperature, solvent DMF (1.5 mL), DIPEA (116 μL), reaction time 15 h). Purification was carried out using $SiO_2$ column chromatography (eluent: MeOH:DCM, up to 12% MeOH). HPLC: 93% [$t_R$=7.34 min, Gradient 5-95% MeOH-water (with 0.1% TFA), 20 min]. $^1$H NMR (400 MHz, DMSO-$d_6$): δ 10.6 (brs, 1H), 9.12 (brs, 1H), 6.86 (d, J=8.0 Hz, 1H), 6.52 (dd, J=8.4, 2.8 Hz, 1H), 6.40 (d, J=2.8 Hz, 1H), 3.80 (d, J=14.8 Hz, 1H), 3.68 (d, J=14.8 Hz, 1H), 3.58 (dd, J=10.8, 4.4 Hz, 1H), 2.96-2.90 (m, 1H), 2.85-2.79 (m, 1H), 2.65-2.52 (m, 4H), 2.18-2.08 (m, 1H), 1.92-1.88 (m, 1H); HPLC-MS (ESI): m/z 261 $(M+H)^+$.

MA7-081-2

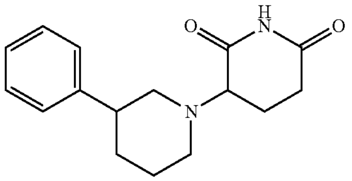

4-Phenyl-[1,3'-bipiperidine]-2',6'-dione (MA7-081-2). This compound was obtained from MA6-019 (100 mg, 0.52 mmol.) and 3-phenylpiperidine (83.9 mg, 0.52 mmol.) using the general method 1 (Scheme 1) (reaction was carried out at room temperature, solvent DMF (0.5 mL), DIPEA (181.4 μL) reaction time ~16 h). The pure MA7-081 (59 mg, 39%) was obtained as a beige solid after $SiO_2$ chromatography with DCM: MeOH (gradient elution, up to 15% MeOH). The HPLC-MS showed 2 diastereoisomers (peak retention time, $t_R$=6.86 and 7.04 min.). Both peaks showed HPLC-MS (ESI): m/z 273 $(M+H)^+$. $^1$H NMR (400 MHz, DMSO-$d_6$): δ 11.44 (brs, 1H), 10.14 (brs, 1H), 7.37-7.28 (m, 5H), 4.57 (4.57, 1H), 3.25-3.16 (br m, 2H), 3.09-3.02 (brm, 2H), 2.71-2.65 (br m, 2H), 2.38-2.14 (m, 3H), 0.92-1.83 (m, 2H), 1.77-1.65 (m, 1H).

MA7-080

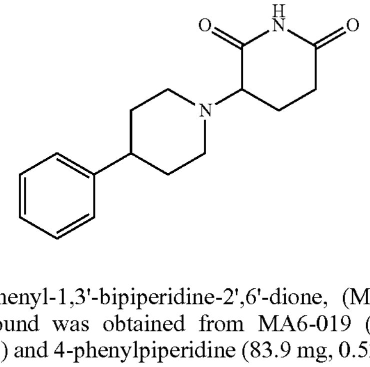

4-Phenyl-1,3'-bipiperidine-2',6'-dione, (MA7-080). This compound was obtained from MA6-019 (100 mg, 0.52 mmol.) and 4-phenylpiperidine (83.9 mg, 0.52 mmol.) using the general method 1 (Scheme 1) (reaction was carried out at room temperature, solvent DMF (0.5 mL), DIPEA (181.4 μL) reaction time ~16 h). The pure MA7-080 (65 mg, 46%) was obtained as a beige solid after triturating the crude product using EtOAc/hexane. HPLC: 98% [$t_R$=9.8 min, MeOH:water 20:80 (with 0.1% TFA), 20 min]. $^1$H NMR (400 MHz, DMSO-$d_6$) δ 10.62 (s, 1H), 7.30-7.15 (m, 5H), 3.45 (dd, J=11.2, 4.4 Hz, 1H), 2.90-2.72 (m, 3H), 2.60-2.56

(m, 3H), 2.52 (m, overlapped with DMSO peak, 1H) 2.10-2.00 (m, 1H), 1.91-1.85 (m, 1H), 1.75-1.65 (m, 2H), 1.62-1.56 (m, 2H); HPLC-MS (ESI): m/z 273 [100%, $(M+H)^+$].

MA7-090

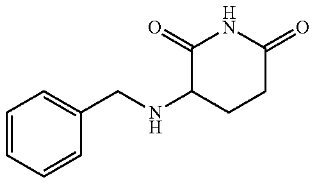

3-(Benzylamino)piperidine-2,6-dione (MA7-090). This compound was obtained from MA6-019 (100 mg, 0.52 mmol.) and benzylamine (56.89 μL, 0.52 mmol.) using the general method 1 (Scheme 1) (reaction was carried out at room temperature, solvent DMF (0.5 mL), DIPEA (181 μL), reaction time ~18 h). The pure MA7-090 (31 mg, 30%) was obtained as an oil after $SiO_2$ chromatography using MeOH/DCM gradient elution (product was eluted with 7% MeOH). HPLC: 97% [$t_R$=9.8 min, MeOH:water 10:80 (with 0.1% TFA), 20 min]. $^1$H NMR (400 MHz, DMSO-$d_6$) δ 10.73 (brs, 1H), 7.35-7.21 (m, 5H), 3.80 (s, 2H), 3.30-3.29 (m, overlapped with $H_2O$ peak, 2H), 2.74 (brs, 1H), 2.07-2.01 (m, 2H), 1.78-1.68 (m, 1H); HPLC-MS (ESI): m/z 219 $(M+H)^+$.

MA7-144-2

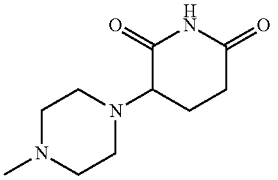

3-(4-Methylpiperazin-1-yl)piperidine-2,6-dione, (MA7-144-2). This compound was obtained from MA6-019 (50 mg, 0.26 mmol.) and N-methylpiperazine (434.7 μL, 3.91 mmol.) using the general method 1 (Scheme 1) (reaction was carried out at room temperature, reaction time ~2 h). Aqueous $NaHCO_3$ (5 mL) was added to the reaction mixture, and the solid obtained was filtered. The pure MA7-144-2 (45 mg, 82%) was obtained as a grey solid after trituration with EtOAc/Hexane. $^1$H NMR (400 MHz, DMSO-$d_6$) δ 10.62 (brs, 1H), 3.31 (dd, overlapped with the water peak, 1H), 2.66-2.53 (m, 5H), 2.4-2.45 (m, 1H, overlapped with DMSO), 2.27 (br s, 4H), 2.13 (s, 3H), 2.06-1.96 (m, 1H), 1.87-1.79 (m, 1H); HPLC-MS (ESI): m/z 212 $(M+H)^+$.

MA6-132

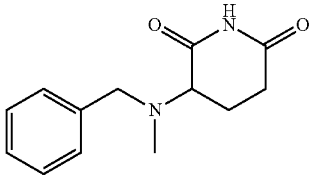

3-[Benzyl(methyl)amino]piperidine-2,6-dione (MA6-132): This was obtained as a beige solid (126 mg, 66%) from MA6-019 (150 mg, 1 equiv.) and N-methyl-1-phenylmethanamine (94.7 mg, 1 equiv.) using the general method 1 (Scheme 1) (reaction temperature 72° C., solvent THF, reaction time ~16 h). The title compound was purified by triturating the crude product using EtOAc/hexane. HPLC: 89% [$t_R$=8.0 min, Gradient 5-95% MeOH-water (with 0.1% TFA), 20 min]. $^1$H NMR (400 MHz, DMSO-$d_6$) δ 10.64 (s, 1H), 7.38-7.29 (m, 4H), 7.27-7.18 (m, 1H), 3.76 (s, 2H), 3.60 (dd, J=12.1, 4.7 Hz, 1H), 2.61 (ddd, J=17.5, 12.4, 5.4 Hz, 1H), 2.57-2.53 (m, 1H), 2.24 (s, 3H), 2.09 (qd, J=12.5, 4.7 Hz, 1H), 1.97-1.88 (m, 1H). HPLC-MS (ESI): m/z 233.2 [100%, $(M+H)^+$]. LC-MS (ESI+): 255.1 [100%, $(M+Na)^+$], 267.1 [40%, $(M+Na)^+$]. HRMS (ESI+): m/z calcd for $C_{13}H_{16}N_2O_2$ $(M+H)^+$233.12845, found 233.12835.

MA6-122-1

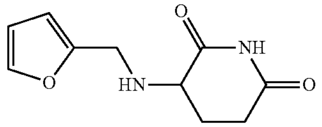

3-[(Furan-2-ylmethyl)amino]piperidine-2,6-dione (MA6-122-1): Using general method 1 (Scheme 1), MA6-122-1 was obtained as a green oil (71 mg, 44%) by heating MA6-019 (150 mg, 0.78 mmol) and furfurylamine (104.4 uL, 1 equiv.) at 62° C. using DMF (1.0 mL) and DIPEA (1 equiv.) (reaction time, 18 h). Purification was carried out using $SiO_2$ chromatography (eluent: MeOH-DCM, 0 to 12% MeOH). HPLC: 99% [$t_R$=11.0 min, MeOH:water 80:20, with 0.1% TFA, 20 min]. $^1$H NMR (400 MHz, DMSO-$d_6$) δ 10.72 (s, 1H), 7.55 (dd, J=1.8, 0.8 Hz, 1H), 6.37 (dd, J=3.1, 1.8 Hz, 1H), 6.31-6.17 (m, 1H), 3.78 (d, J=5.9 Hz, 2H), 3.29 (s, 1H), 2.66 (brs, 1H), 2.53-2.49 (m, 2H), 2.03 (dq, J=13.2, 4.9 Hz, 1H), 1.80-1.56 (m, 1H). HPLC-MS (ESI): m/z 209.2 [100%, $(M+H)^+$]. LC-MS (ESI+): 231.0 [100%, $(M+Na)^+$]. HRMS (ESI+): m/z calcd for $C_{10}H_{12}N_2O_3$ $(M+H)^+$ 209.09207, found 209.09190.

MA6-122-2

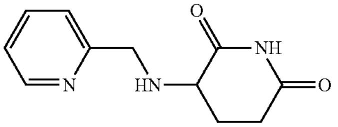

3-[(pyridin-2-ylmethyl)amino]piperidine-2,6-dione (MA6-122-2): Using general method 1 (Scheme 1), MA6-122-1 was obtained as a green oil (35 mg, 20%) by heating MA6-019 (150 mg, 0.78 mmol) and pyridin-2-ylmethanamine (79.56 uL, 1 equiv.) at 62° C. using DMF (1.0 mL) and DIPEA (1 equiv.) (reaction time, 18 h). Purification was carried out using $SiO_2$ chromatography (eluent: MeOH-DCM, 0 to 12% MeOH). HPLC: 98% [$t_R$=12.7 min, water 0.1% TFA, 20 min]. $^1$H NMR (400 MHz, DMSO-$d_6$) δ 10.76 (s, 1H), 8.51 (d, J=4.1 Hz, 1H), 7.75 (t, J=6.9 Hz, 1H), 7.42 (d, J=7.8 Hz, 1H), 7.25 (t, J=5.4, 1H), 3.91 (brs, 2H), 3.39 (dd, J=10.7, 4.9 Hz, 1H), 2.58-2.53 (m, 1H), 2.44 (t, J=8.8, 1H), 2.10 (dd, J=12.8, 4.9 Hz, 1H), 1.87-1.68 (m, 1H). HPLC-MS (ESI): m/z 220.2 [100%, $(M+H)^+$]. LC-MS (ESI+): m/z 242.1 [100%, $(M+Na)^+$], 220.1 [55%, $(M+H)^+$]. HRMS (ESI+): m/z calcd for $C_{11}H_{13}N_3O_2$ $(M+H)^+$ 220.1080, found 220.1082.

MA7-077

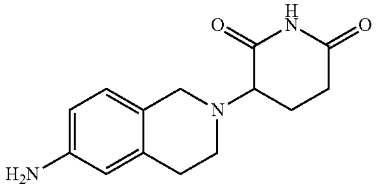

3-(6-Amino-3,4-dihydroisoquinolin-2(1H)-yl)piperidine-2,6-dione (MA7-096): First 1,2,3,4-tetrahydroisoquinolin-6-amine bis hydrochloride was prepared from tert-butyl 6-amino-3,4-dihydroisoquinoline-2(1H)-carboxylate. A suspension of tert-butyl 6-amino-3,4-dihydroisoquinoline-2(1H)-carboxylate (200 mg, 0.81 mmol) in HCl (2 mL, 4 M, in dioxane, 8 mmol) was stirred at room temperature for 15 h. The mixture was concentrated and residual HCl removed by co-evaporation ethyl acetate (2×4 mL) to provide 1,2,3,4-tetrahydroisoquinolin-6-amine bis-hydrochloride as a pale yellow solid (176 mg, 99%) and used without further purification. Using general method 1 (Scheme 1), MA7-096 was obtained as a yellow solid (21 mg, 22%). First 1,2,3,4-tetrahydroisoquinolin-6-amine bis-hydrochloride (79.9 mg, 0.36 mmol) was heated with DIPEA (123.2 μL, 0.72 mmol) in DMF (0.5 ml) at 70° C. for 10 min. The mixture was cooled and MA6-019 (70 mg, 0.36 mmol) added and stirred and at room temperature for 18 h. Purification by SiO2 column chromtorgaphy and trituration with DCM/hexanes gave MA7-096. $^1H$ NMR (400 MHz, DMSO-$d_6$) δ 10.66 (s, 1H), 6.64 (d, J=8.1 Hz, 1H), 6.31 (dd, J=8.1, 2.4 Hz, 1H), 6.25 (d, J=2.4 Hz, 1H), 4.76 (s, 2H), 3.68 (d, J=13.8 Hz, 1H), 3.58 (d, J=13.8 Hz, 1H), 3.51 (dd, J=10.7, 4.3 Hz, 1H), 2.90-2.71 (m, 2H), 2.73-2.54 (m, 3H), 2.15-2.04 (m, 1H), 1.89 (dq, J=13.8, 4.9 Hz, 1H). HPLC-MS (ESI+): m/z 260.2 [100%, $(M+H)^+$]. m/z calcd for $C_{14}H_{17}N_3O_2$ $(M+H)^+$ 260.1394, found 260.1397.

MA7-144-1

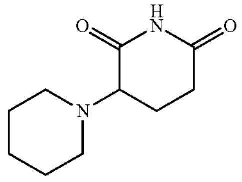

[1,3'-Bipiperidine]-2',6'-dione (MA7-144-1). This compound was obtained from MA6-019 (50 mg, 0.26 mmol.) and piperidine (485.8 μL, 3.91 mmol.) using the general method 1 (Scheme 1) (reaction was carried out at room temperature, reaction time ~2 h). Aqueous $NaHCO_3$ (5 mL) was added to the reaction mixture, and the solid obtained was filtered. The pure MA7-144-1 (41 mg, 80%) was obtained as a grey solid after trituration with EtOAc/hexane. HPLC: 99% [$t_R$=3.2 min, MeCN (5%) and water (95%, with 0.1% TFA, 20 min]. $^1H$ NMR (400 MHz, DMSO-$d_6$) δ 10.56 (s, 1H), 3.37-3.28 (m, 1H), 2.66-2.39 (m, 5H), 2.03-1.92 (m, 1H), 1.83-1.77 (m, 1H), 1.50-1.32 (m, 6H). HPLC-MS (ESI+): m/z 197.2 [100%, $(M+H)^+$]. m/z calcd for $C_{10}H_{16}N_2O_2$ $(M+H)^+$260.1285, found 197.1288.

MA7-050

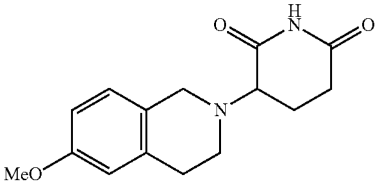

N-(2,6-Dioxopiperidin-3-yl)-3-[(3-nitrophenyl)sulfonamido]propanamide (MA7-050): This was obtained from MA6-019 (50 mg, 0.26 mmol.) and 6-methoxy-1,2,3,4-tetrahydroisoquinoline hydrochloride (102.9 mg) using the general method 1 (Scheme 1) (reaction was carried out at room temperature, reaction time ~2 h). Aqueous $NaHCO_3$ (5 mL) was added to the reaction mixture, and the solid obtained was filtered. Purification by washing with water and trituration from ethyl acetate/hexanes gave MA7-050 as a greenish biege solid (79 mg, 55%). HPLC: >98% [$t_R$=7.7 min, 5-95% gradient MeOH, water (with 0.1% TFA), 20 min]. $^1H$ NMR (400 MHz, DMSO) δ 10.64 (s, 1H), 6.93 (d, J=8.0, 1H), 6.68 (dd, J=8.0, J=4.0, 1H), 6.66 (m, 1H), 3.78 (m, 2H), 3.70 (s, 3H), 3.59 (dd J=8.0, J=4.0, 1H), 2.90-2.98 (m, 1H), 2.81-2.88 (m, 1H), 2.70-2.79 (m, 2H), 2.65-2.50 (m, 2H), 2.20-2.08 (m, 1H), 1.95-1.85 (m, 1H). HRMS (ESI+): m/z calcd for $C_{15}H_{18}N_2O_3$ $(M+H)^+$275.13902, found 275.1389, m/z calcd for $C_{15}H_{18}N_2O_3Na$ $(M+Na)^+$ 297.1209, found 297.1204. HPLC-MS: HPLC-MS (ESI+): m/z 275.2 [100%, $(M+H)^+$], 571.3 [10%, $(2M+Na)^+$].

MA7-051

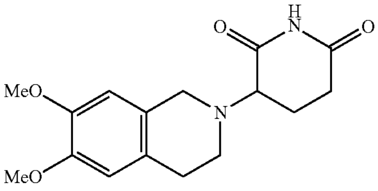

3-(6,7-Dimethoxy-3,4-dihydroisoquinolin-2(1H)-yl)piperidine-2,6-dione (MA7-051). This was obtained from 6,7-dimethoxy-1,2,3,4-tetrahydroisoquinoline (100.6 mg) and MA6-019 (100 mg) using the general method 1 (Scheme 1) (reaction was carried out at room temperature, reaction time ~18 h). Aqueous $NaHCO_3$ (5 mL) was added to the reaction mixture, and extracted with EtOAc (2×5 mL), dried ($Na_2SO_4$), evaporated to obtain the crude product, which was triturated with EtOAc/hexanes to provide the pure compound MA7-051 as an off white solid (107 mg, 75%).

HPLC: >96% [$t_R$=7.7 min, 5-95% gradient MeOH, water (with 0.1% TFA), 20 min]. $^1H$ NMR (400 MHz, DMSO) δ 10.64 (s, 1H), 6.65 (s, 1H), 6.60 (s, 1H), 3.83-3.72 (m, 2H), 3.69 (s, 3H), 3.68 (s, 3H), 3.58 (d, J=8.0, 1H), 2.95-2.89 (m, 1H), 2.86-2.80 (m, 1H), 2.65-2.75 (m, 2H), 2.65-2.52 (m, 2H), 2.20-2.08 (m, 1H), 1.95-1.85 (m, 1H). HRMS (ESI+): m/z calcd for $C_{16}H_{21}N_2O_4$ $(M+H)^+$305.1495, found 305.1489, m/z calcd for $C_{16}H_{20}N_2O_4Na$ $(M+Na)^+$327.1315, found 327.1315. HPLC-MS: HPLC-MS (ESI+): m/z 305.2 [100%, $(M+H)^+$], 631.3 [10%, $(2M+Na)^+$].

MA7-052

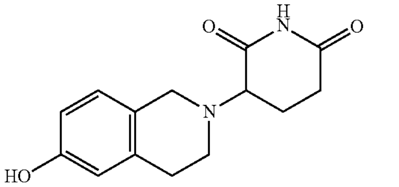

3-(6-Hydroxy-3,4-dihydroisoquinolin-2(1H)-yl)piperidine-2,6-dione (MA7-052): MA7-050 (45 mg. 0.16 mmol) was dissolved in DCM (1 mL) and placed in an ice bath. Boron tribromide (656.4 μL) was added slowly. The mixture was stirred overnight and queched with water. Purification by washing with water (3 mL), 10% aq. $NH_3$ (3 mL), and trituration from ethyl acetate gave MA7-052 as a cream color solid (32 mg, 82%). HPLC: ~92% [$t_R$=2.5 min, 2% MeOH, 98% water (with 0.1% TFA), 20 min]. $^1$H NMR (400 MHz, DMSO) δ 10.66 (s, 1H), 9.07 (s, 1H), 6.79 (d, J=8.0, 1H), 6.51 (dd, J=8.0, 4.0, 1H), 6.46 (m, 1H), 3.76 (dd, J=12.0, 4.0, 2H), 3.56 (dd, J=8.0, 4.0, 1H), 2.95-2.85 (m, 1H), 2.83-2.77 (m, 1H), 2.65-2.75 (m, 2H), 2.65-2.52 (m, 2H), 2.20-2.08 (m, 1H), 1.95-1.85 (m, 1H). HRMS (ESI+): m/z calcd for $C_{14}H_{17}N_2O_3$ $(M+H)^+$261.1233, found 261.1240, m/z calcd for $C_{14}H_{16}N_2O_3Na$ $(M+Na)^+$283.1053, found 283.1048. HPLC-MS: HPLC-MS (ESI+): m/z 261.2 [60%, $(M+H)^+$], 259.1 [50%, $(M-H)^-$].

MA7-074

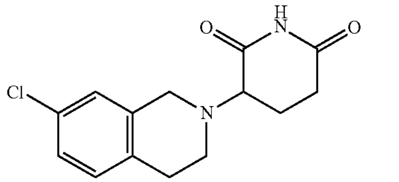

3-(7-Chloro-3,4-dihydroisoquinolin-2(1H)-yl)piperidine-2,6-dione (MA7-074): 7-Chloro-1,2,3,4-tetrahydroisoquinoline (75.0 mg) was dissolved in DMF (0.7 mL). MA6-019 (86.0 mg) and DIPEA (a56.8 μL) were added into the mixture and stirred for 16 h. Purification by washing with aq. $NaHCO_3$ (5 mL) and trituration from ethyl acetate/hexanes gave MA7-074 as a biege solid (77 mg, 62%). HPLC: >99% [$t_R$=11.6 min, 15% MeOH, 85 water (with 0.1% TFA), 20 min]. $^1$H NMR (400 MHz, DMSO) δ 10.71 (s, 1H), 7.17-7.11 (m, 3H), 3.94 (d, J=16 Hz, 1H), 3.79 (d, J=16 Hz, 1H), 3.65 (dd J=8.0, J=4.0, 1H), 2.90-2.95 (m, 1H), 2.90-2.81 (m, 1H), 2.70-2.80 (m, 2H), 2.65-2.50 (m, 2H), 2.20-2.08 (m, 1H), 1.95-1.85 (m, 1H). HRMS (ESI+): m/z calcd for $C_{14}H_{16}ClN_2O_2$$(M+H)^+$279.0894, found 279.0894, m/z calcd for $C_{14}H_{15}ClN_2O_2Na$ $(M+Na)^+$301.0714, found 301.0711. HPLC-MS: HPLC-MS (ESI+): m/z 279.2 [40%, $(M+H)^+$], 277.1 [100%, $(M-H)^-$].

MA7-075

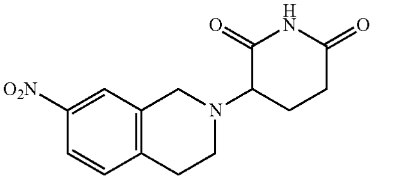

3-(7-Nitro-3,4-dihydroisoquinolin-2(1H)-yl)piperidine-2,6-dione (MA7-075): This was prepared in the same way as (MA7-074) using 7-nitro-1,2,3,4-tetrahydroisoquinoline (200 mg) and MA6-019 (215 mg). Purification by washing with water and trituration from acetone/hexanes gave MA7-075 as a biege solid (189 mg, 58%). HPLC: >99% [$t_R$=3.9 min, 15% MeOH, 85% water (with 0.1% TFA), 20 min]. $^1$H NMR (400 MHz, DMSO) δ 10.71 (s, 1H), 7.98-7.95 (m, 2H), 7.36-7.39 (m, 1H), 4.07 (d, J=16.0 Hz, 1H), 3.91 (d, J=16.0 Hz, 1H) 3.69 (dd, J=8.0 Hz, 4.0 Hz, 1H), 2.99-3.08 (m, 1H), 2.87-2.93 (m, 3H), 2.53-2.66 (m, 2H), 2.19-2.09 (m, 1H), 1.93-1.87 (m, 1H). HRMS (ESI+): m/z calcd for $C_{14}H_{16}N_3O_4$ $(M+H)^+$290.1135, found 290.1134, m/z calcd for $C_{14}H_{15}N_3O_4Na$ $(M+Na)^+$312.0954, found 312.0959. HPLC-MS: HPLC-MS (ESI+): m/z 290.2 [100%, $(M+H)^+$], 288.2 [100%, $(M-H)^-$].

MA6-122-3

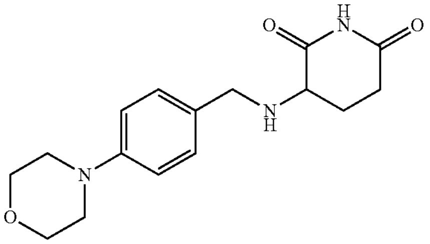

3-[(4-Morpholinobenzyl)amino]piperidine-2,6-dione (MA6-122-3): Using general method 1 (Scheme 1), this was obtained as a gray solid (121 mg, 50%) by heating MA6-019 (150 mg, 0.78 mmol) and (4-morpholinophenyl)methanamine (150.2 mg, 1 equiv.) at 62° C. using DMF as solvent and DIPEA as base (reaction time, 18 h). Purification was carried out using $SiO_2$ column chromatography (eluent: MeOH-DCM, 0 to 12% MeOH). HPLC: 83% [$t_R$=9.52 min, Gradient 5-95% MeOH-water (with 0.1% TFA), 20 min]. $^1$H NMR (400 MHz, DMSO-$d_6$) δ 11.32 (s, 1H), 9.25 (s, 1H), 7.37 (d, J=8.4 Hz, 2H), 7.00 (d, J=8.5 Hz, 2H), 4.17 (s, 1H), 4.13 (brd, J=4.0 Hz, 2H), 3.74 (t, J=5.0 Hz, 4H), 3.14 (d, J=5.07 Hz, 4H), 2.68-2.64 (m, 2H), 2.41-2.25 (m, 1H), 2.11-2.00 (m, 1H). LC-MS (ESI+): 326.2 [100%, $(M+Na)^+$]. HRMS (ESI+): m/z calcd for $C_{16}H_{21}N_3O_3$ $(M+H)^+$ 304.16557, found 305.16475.

MA6-122-5

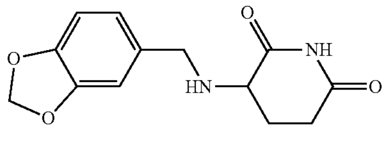

3-{(Benzo[d][1,3]dioxol-5-ylmethyl)amino}piperidine-2,6-dione (MA6-122-5): Using general method 1 (Scheme 1), this was obtained as a green oil (19 mg, 9%) by heating MA6-019 (150 mg, 0.78 mmol) and benzo[d][1,3]dioxol-5-ylmethanamine (118.1 mg, 1 equiv.) at 62° C. using DMF as solvent and DIPEA as base (reaction time, 18 h). Purification was carried out using $SiO_2$ column chromatography (eluent: MeOH-DCM, 0 to 12% MeOH). HPLC: 91% [$t_R$=9.8 min, Gradient 5-95% MeOH-water (with 0.1% TFA), 20 min]. $^1$H NMR (400 MHz, DMSO-$d_6$) δ 10.70 (s, 1H), 6.92 (s, 1H), 6.83 (d, J=7.9 Hz, 1H), 6.78 (d, J=7.9 Hz, 1H), 5.97 (brs, 2H), 3.70 (brs, 2H), 3.27 (dd, J=10.1, 4.8 Hz, 1H), 2.75-2.65

(m, 1H), 2.55-2.51 (m, 1H), 2.03 (dd, J=13.2, 4.9 Hz, 1H), 1.76-1.61 (m, 1H). HPLC-MS (ESI): n/z 263.2 [100%, $(M+H)^+$]. HRMS (ESI+): m/z calcd for $C_{13}H_{14}N_2O_4$ $(M+H)^+$263.10263, found 263.1027.

MA6-122-6

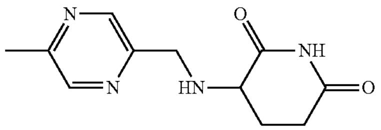

3-{[(5-Methylpyrazin-2-yl)methyl]amino}piperidine-2,6-dione (MA6-122-6): Using general method 1 (Scheme 1), this was obtained as a dark green solid (91 mg, 50%) by heating MA6-019 (150 mg, 0.78 mmol) and (5-methylpyrazin-2-yl)methanamine (96.2 mg, 1 equiv.) at 62° C. using DMF as solvent and DIPEA as base (reaction time, 18 h). Purification was carried out using $SiO_2$ column chromatography (eluent: MeOH-DCM, 0 to 12% MeOH). HPLC: 99% [$t_R$=5.7 min, Gradient 5-95% MeOH-water (with 0.1% TFA), 20 min]. $^1$H NMR (400 MHz, DMSO-$d_6$) δ 10.75 (s, 1H), 8.55 (d, J=1.4 Hz, 1H), 8.47 (d, J=1.4 Hz, 1H), 3.93 (s, 2H), 3.39 (dd, J=10.7, 4.9 Hz, 1H), 3.09 (brs, 1H), 2.56-2.51 (m, 2H), 2.47 (s, 3H), 2.08 (dq, J=14.5, 4.9 Hz, 1H), 1.74 (dq, J=14.2, 6.8 Hz, 1H). HPLC-MS (ESI): m/z 235.2 [100%, $(M+H)^+$]. HRMS (ESI+): m/z calcd for $C_{13}H_{14}N_2O_4$ $(M+H)^+$263.10263, found 263.1027. LC-MS (ESI+): 257.0 [100%, $(M+Na)^+$], 235.1 [40%, $(M+H)^+$]. HRMS (ESI+): m/z calcd for $C_{11}H_{14}N_4O_2$ $(M+H)^+$235.11895, found 235.11955.

MA6-122-7

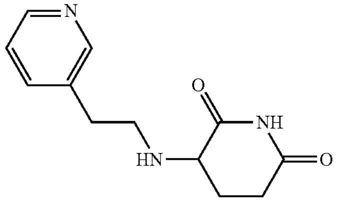

3-{[2-(Pyridin-3-yl)ethyl]amino}piperidine-2,6-dione (MA6-122-7): Using general method 1 (Scheme 1), this was obtained as a thick green oil (19 mg, 10%) by heating MA6-019 (150 mg, 0.78 mmol) and 2-(pyridin-3-yl)ethan-1-amine (95.4 mg, 1 equiv.) at 62° C. using DMF as solvent and DIPEA as base (reaction time, 18 h). HPLC: 97% [$t_R$=2.4 min, Isocratic 1% MeOH, 99% water (with 0.1% TFA), 20 min]. Purification was carried out using $SiO_2$ column chromatography (eluent: MeOH-DCM, 0 to 12% MeOH). $^1$H NMR (400 MHz, DMSO-$d_6$) δ 10.70 (s, 1H), 8.45 (d, J=2.1 Hz, 1H), 8.40 (dd, J=4.8, 1.6 Hz, 1H), 7.65 (dt, J=7.8, 2.0 Hz, 1H), 7.30 (dd, J=7.7, 4.8 Hz, 1H), 3.38 (dd, J=10.8, 4.6 Hz, 1H), 2.91-2.79 (m, 3H), 2.74 (t, J=7.0 Hz, 2H), 2.04 (dq, J=13.2, 5.0 Hz, 1H), 1.76-1.61 (m, 1H). HPLC-MS (ESI): m/z 234.2 [100%, $(M+H)^+$]. LC-MS (ESI+): 234.1 [100%, $(M+H)^+$]. HRMS (ESI+): m/z calcd for $C_{12}H_{15}N_3O_2$ $(M+H)^+$234.12370, found 234.12299.

MA6-122-8

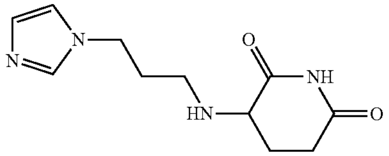

3-{[3-(1H-imidazol-1-yl)propyl)amino]}iperidine-2,6-dione (MA6-122-8): Using general method 1 (Scheme 1), this was obtained as a bluish oil (20 mg, 11%) by heating MA6-019 (150 mg, 0.78 mmol) and 3-(1H-imidazol-1-yl)propan-1-amine (97.8 mg, 1 equiv.) at 62° C. using DMF as solvent and DIPEA as base (reaction time, 18 h). Purification was carried out using $SiO_2$ column chromatography (eluent: MeOH-DCM, 0 to 12% MeOH). $^1$H NMR (400 MHz, DMSO-$d_6$) δ 10.71 (s, 1H), 7.61 (s, 1H), 7.16 (s, 1H), 6.88 (s, 1H), 4.01 (t, J=7.0 Hz, 2H), 2.59 (dt, J=12.6, 6.6 Hz, 1H), 2.54 (dd, J=5.7, 2.9 Hz, 2H), 2.48-2.44 (m, 1H), 1.99 (dd, J=13.1, 5.1 Hz, 1H), 1.84 (p, J=6.5, 6.0 Hz, 2H), 1.77-1.65 (m, 1H). ). HPLC-MS (ESI): m/z 237.2 [100%, $(M+H)^+$]. LC-MS (ESI+): 237.1 [100%, $(M+H)^+$]. HRMS (ESI+): m/z calcd for $C_{11}H_{16}N_4O_2$ $(M+H)^+$237.13460, found 237.13501.

MA6-122-9

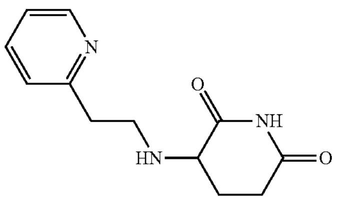

3-((2-(Pyridin-2-yl)ethyl)amino)piperidine-2,6-dione (MA6-122-9): Using general method 1 (Scheme 1), this was obtained as an oil (20 mg, 11%) by heating MA6-019 (150 mg, 0.78 mmol) and 2-(pyridin-2-yl)ethan-1-amine (95.4 mg, 1 equiv.) at 62° C. using DMF as solvent and DIPEA as base (reaction time, 18 h). Purification was carried out using $SiO_2$ column chromatography (eluent: MeOH-DCM, 0 to 12% MeOH). HPLC: 99% [$t_R$=2.1 min, Isocratic 30% MeOH, 70% water (with 0.1% TFA), 20 min]. $^1$H NMR (400 MHz, DMSO-$d_6$) δ 10.73 (s, 1H), 8.55-8.45 (m, 1H), 7.69 (dd, J=7.7, 1.9 Hz, 1H), 7.28 (d, J=7.8 Hz, 1H), 7.20 (ddd, J=7.5, 4.9, 0.9 Hz, 1H), 3.47-3.40 (m, 1H), 2.98 (dd, J=10.7, 4.9 Hz, 2H), 2.90 (s, 1H), 2.89 (s, 2H), 2.57-2.51 (m, 2H), 2.07 (ddd, J=13.0, 9.3, 4.4 Hz, 1H), 1.78-1.63 (m, 1H). HPLC-MS (ESI): m/z 234.2 [100%, $(M+H)^+$]. LC-MS (ESI+): 234.1 [100%, $(M+H)^+$], 256.1 [50%, $M+Na)^+$]. HRMS (ESI+): m/z calcd for $C_{12}H_{15}N_3O_2$ $(M+H)^+$ 234.12370, found 234.12396.

MA6-122-10

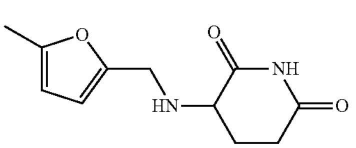

3-{[(5-Methylfuran-2-yl)methyl]amino}piperidine-2,6-dione (MA6-122-10): Using general method 1 (Scheme 1), this was obtained as a dark green solid (126 mg, 73%) by heating MA6-019 (150 mg, 0.78 mmol) and (5-methylfuran- 2-yl)methanamine (86.8 mg, 1 equiv.) at 62° C. using DMF as solvent and DIPEA as base (reaction time, 18 h). Purification was carried out using $SiO_2$ column chromatography (eluent: MeOH-DCM, 0 to 12% MeOH). HPLC: 87% [$t_R$=7.9 min, Gradient 5-95% MeOH-water (with 0.1% TFA), 20 min]. $^1$H NMR (400 MHz, DMSO-$d_6$) δ 10.75 (s, 1H), 6.12 (d, J=2.7 Hz, 1H), 5.97 (d, J=2.9 Hz, 1H), 3.74 (s, 2H), 3.37 (d, J=7.9 Hz, 2H), 2.52 (d, J=6.9 Hz, 2H), 2.22 (s, 3H), 2.05 (dq, J=13.9, 4.6 Hz, 1H), 1.78-1.62 (m, 1H). HPLC-MS (ESI): ): m/z 245.2 [100%, $(M+Na)^+$], 467.3 [20%, $(2M+N\ Na)^+$]. LC-MS (ESI+): 245.1 [100%, $(M+H)^+$]. HRMS (ESI+): m/z calcd for $C_{11}H_{14}N_2O_3$ $(M+Na)^+$245.08966, found 245.08942.

Scheme 3

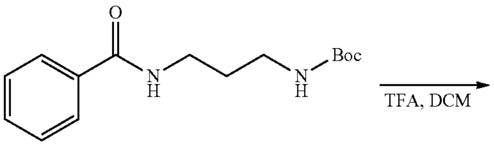

Boc-amine precursor

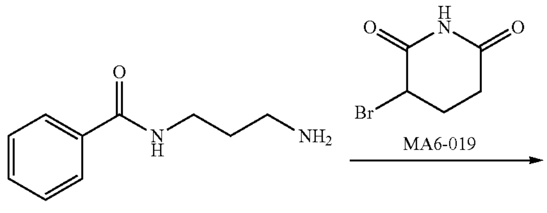

MA6-019

MA6-094

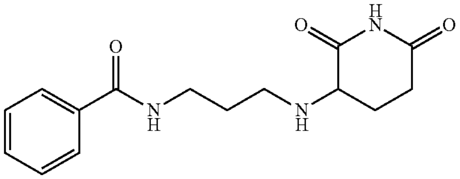

MA6-098

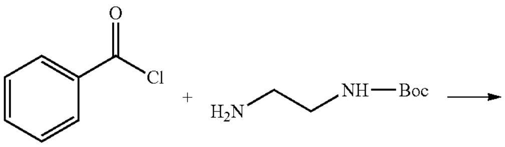

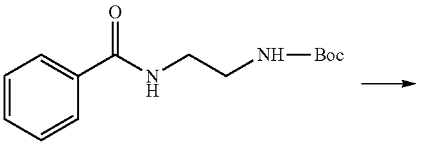

MA6-093

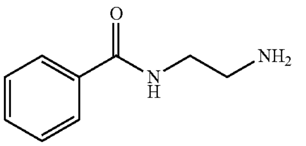

MA6-095

N-(3-aminopropyl)benzamide (MA6-094). This compound was prepared according to a procedure reported in (BOMCL, 2013, 6799-6804) (Scheme 3). The MA6-094 was prepared by deprotecting the Boc-protected amine precursor using DCM (2.0 mL) and TFA (200 μL). The mixture was evaporated to obtain a brown oil (179 mg, 100%) and used in the next step without further purification. HPLC-MS (ESI) m/z 165 $(M+H)^+$.

N-(2-aminoethyl)benzamide (MA6-095). First benzoyl chloride (140 mg, 1 mmol), and tert-butyl 2-aminoethylcarbamate (160 mg, 1 mmol) in dry DCM was stirredunder argon. After 2h, the TLC showed completion of the reaction. The reaction mixture was diluted with DCM (20 mL), and washed with $NaHCO_3$ (20 mL). The organic layer was evaporated, and the product obtained was triturated with EtOH (0.5 mL) and hexane (3 mL) to give tert-butyl 2-benzamidoethylcarbamate MA6-093 as a off-white solid (205 mg, 78%). $^1$H NMR (400 MHz, DMSO-$d_6$) δ 8.44 (t, J=5.2 Hz, 1H), 7.83-7.82 (m, 2H), 7.53-7.42 (m, 3H), 6.91 (t, J=5.6 Hz, 1H), 3.27 (q, J=6.4 Hz, 2H), 3.092 (q, J=6.0 Hz, 2H), 1.36 (s, 9H). The MA6-093 (195 mg, 0.74 mmol) in DCM: TFA (20:80, 2 mL) was stirred for 2 h at r.t., and monitored by TLC. The TFA/DCM mixture was evaporated at r.t., and washed with MeOH (1 mL), and water (3 mL). The product obtained was dried in the lyophilizer to obtain a light brown solid as MA5-095. $^1$H NMR (400 MHz, DMSO-$d_6$) δ 8.64 (t, J=5.6 Hz, 1H), 7.87 (m 4H), 7.56-7.46 (m, 3H), 3.514 (q, J=6.0 Hz, 2H), 3.00 (q, J=65.6 Hz, 2H).

N-{3-[(2,6-Dioxopiperidin-3-yl)amino]propyl}benzamide (MA6-098): Using general method 1 (Scheme 1), this was obtained as a purple solid (11 mg, 14%) by heating MA6-019 (53.9 mg, 0.78 mmol) and MA6-094 (50 mg, 1 equiv.) at 60° C. using DMF (1.0 mL) and DIPEA (1 equiv.) (reaction time, 6 h). Purification was carried out using $SiO_2$ column chromatography (eluent: MeOH-DCM, 0 to 20% MeOH). HPLC: 87% [$t_R$=10.7 min, Gradient 5-95% MeOH-water (with 0.1% TFA), 20 min]. $^1$H NMR (400 MHz, DMSO-$d_6$) δ 10.72 (s, 1H), 8.49 (t, J=5.5 Hz, 1H), 7.88-7.79 (m, 2H), 7.55-7.48 (m, 1H), 7.48-7.39 (m, 2H), 3.41-3.36 (m, 1H), 3.32-3.28 (m, 1H), 2.74-2.58 (m, 2H), 2.56-2.52 (m, 2H), 2.05 (dt, J=13.2, 4.9 Hz, 1H), 1.75-1.68 (m, 3H). HPLC-MS (ESI): ): m/z 290.2 [100%, $(M+H)^+$]. LC-MS (ESI+): 312.1 [100%, $(M+Na)^+$]. HRMS (ESI+): m/z calcd for $C_{19}H_{15}N_3O_3$ $(MH)^+$289.14426, found 289.14431.

MA6-105

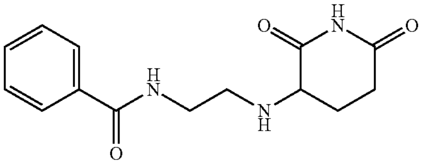

N-(2-(2,6-Dioxopiperidin-3-ylamino)ethyl)benzamide (MA6-105). Using general method 1 (Scheme 1), this was obtained as an off white solid (20 mg) by heating MA6-019 (58.5 mg, 0.30 mmol) and MA6-095 (50 mg, 0.3 mmol, see Scheme 3) at 60° C. using DMF (0.5 mL) and DIPEA (159 μL, 0.9 mmol.) (reaction time, 16 h). The crude mixture was purified by preperative HPLC using gradient elution of MeOH-water, 5-95% with 0.1 TFA to obtain pure MA6-105.TFA salt. $^1$H NMR (400 MHz, DMSO-$d_6$) δ 11.39 (s, 1H), 9.22 (brs, 1H), 9.11 (brs, 1H), 8.70 (t, J=5.6 Hz, 1H), 7.89-7.85 (m, 2H), 7.58-7.54 (m, 1H), 7.52-7.47 (m, 2H), 4.35 (broad d, 1H), 3.68-3.56 (m, 2H), 3.21 (brs, 2H), 2.69-2.65 (s, 2H), 2.33-2.26 (m, 1H), 2.08-1.97 (m, 1H); HPLC-MS (ESI):): m/z 276 [100%, $(M+H)^+$].

MA6-180-3

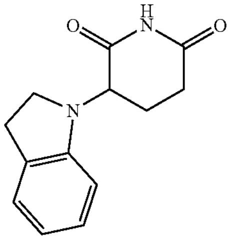

3-(Indolin-1-yl)piperidine-2,6-dione (MA6-180-3): This was obtained as a beige solid (62 mg, 53%) from MA6-019 (150 mg, 1 equiv.) and indoline (62.0 mg, 1 equiv.) using the general method 1 (Scheme 1) (reaction temperature 70° C., solvent THF, reaction time 16 h). Purification was carried out using $SiO_2$ column chromatography (eluent: MeOH-DCM, up to 15% MeOH). HPLC: 99% [$t_R$=13.6 min, Gradient 5-95% MeOH-water (with 0.1% TFA), 20 min]. $^1$H NMR (400 MHz, DMSO-$d_6$) δ 10.81 (s, 1H), 7.01 (J=7.2, 0.8 Hz, 1H), 6.93 (td, J=7.8, 0.8 Hz, 1H), 6.53 (td, J=7.4, 0.9 Hz, 1H), 6.48 (d, J=7.8 Hz, 1H), 4.63 (dd, J=13.1, 4.9 Hz, 1H), 3.41 (ddd, J=9.6, 8.4, 5.9 Hz, 1H), 3.27 (q, J=9.3 Hz, 1H), 2.99-2.87 (m, 2H), 2.79 (ddd, J=17.4, 13.5, 5.4 Hz, 1H), 2.62-2.58 (m, 1H), 2.20 (qd, J=13.1, 4.4 Hz, 1H), 2.01-1.92 (m, 1H). HPLC-MS (ESI): ): m/z 231.2 [100%, $(M+H)^+$]. LC-MS (ESI+): 231.1 [100%, (M+H]. HRMS (ESI+): m/z calcd for $C_{13}H_{14}N_2O_2$ $(M)^+$230.1055, found 230.1056.

Scheme 4

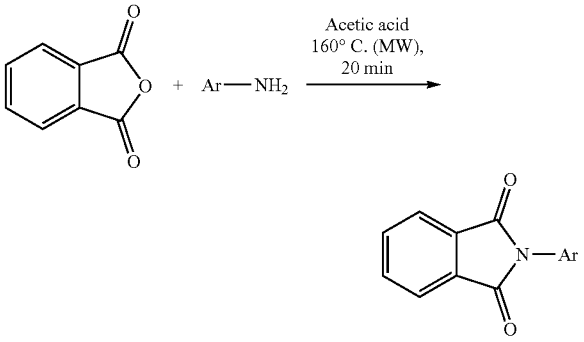

Method 2: Using a microwave vial, a mixture of phthalic anhydride (110.1 mg, 1 equiv.) and appropriate amine (1 equiv.) was dissolved in acetic acid (1 mL) and the reaction was heated in microwave at 120° C. for 20 min. After the reaction completion (monitored by HPLC-MS), the volatiles were removed under reduced pressure and the crude product was partitioned with EtOAc and water. The organic layer was dried ($Na_2SO_4$) and evaporated to get the pure product.

MA6-090

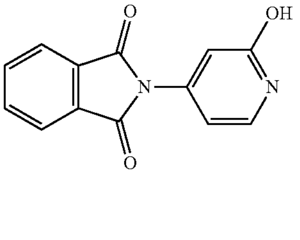

2-(2-Hydroxypyridin-4-yl)isoindoline-1,3-dione (MA6-090): This compound was obtained as a white solid (143 mg, 59%) from phthalic anhydride (110.12 mg) and 4-amino-pyridin-2-ol (148.12 mg) using the general method 2 (Scheme 4). Mp: 288° C. (dec). HPLC: 97% [$t_R$=13.3 min, Gradient 5-95% MeOH-water (with 0.1% TFA), 20 min]. $^1$H NMR (400 MHz, DMSO-$d_6$): δ 11.76 (s, 1H, disappeared on $D_2O$ shake), 7.99-7.96 (m, 2H), 7.94-7.91 (m, 2H), 7.51 (d, J=7.0 Hz, 1H), 6.48 (d, J=2.0 Hz, 1H), 6.40 (dd, J=7.0, 2.0 Hz, 1H). HPLC-MS (ESI): m/z 241.1 [100%, $(M+H)^+$], 503.1.6 [30%, $(2M+Na)^+$], 481.2 [25%, $(2M+H)^+$]. LC-MS (ESI+): 241.1 [100%, $(M+H)^+$], 263.0 [15%, $(M+Na)^+$]. HRMS (ESI+): m/z calcd for $C_{13}H8N_2O_3(M)^+$240.0535, found 240.0538.

MA6-100

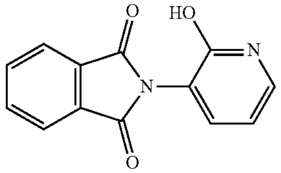

2-(2-Hydroxypyridin-3-yl)isoindoline-1,3-dione (MA6-100): This compound was obtained as a beige solid (173 mg, 72%) from phthalic anhydride (110.12 mg) and 3-amino-pyridin-2-ol (148.12 mg) using the general method 2 (Scheme 4). Mp: 295° C. (dec). HPLC: 97% [$t_R$=12.1 min, Gradient 5-95% MeOH-water (with 0.1% TFA), 20 min]. $^1$H NMR (400 MHz, DMSO-$d_6$): δ 12.20 (s, 1H, disappeared on $D_2O$ shake), 7.98-7.95 (m, 2H), 7.94-7.91 (m, 2H), 7.68 (dd, J=6.8, 2.1 Hz, 1H), 7.56 (d, J=6.0 Hz, 1H), 6.35 (t, J=6.8 Hz, 1H). HPLC-MS (ESI): m/z 241.1 [100%, $(M+H)^+$], 503.1 [50%, $(2M+Na)^+$], 481.2 [45%, $(2M+H)^+$]. LC-MS (ESI+): 241.1 [100%, $(M+H)^+$]. HRMS (ESI+): m/z calcd for $C_{13}H_8N_2O_3(M+H)^+$241.0608, found 241.0617.

MA6-104

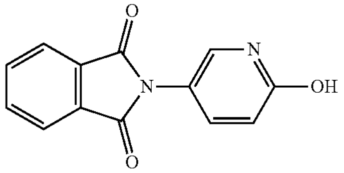

2-(6-Hydroxypyridin-3-yl)isoindoline-1,3-dione (MA6-104): This compound was obtained as a yellow solid (121 mg, 50%) from phthalic anhydride (110.12 mg) and 5-ami-nopyridin-2-ol (148.12 mg) using the general method 2 (Scheme 4). Mp: 284° C. (dec). HPLC: 95% [$t_R$=12.8 min, Gradient 5-95% MeOH-water (with 0.1% TFA), 20 min]. $^1$H NMR (400 MHz, DMSO-$d_6$): 11.85 (s, 1H, disappeared on $D_2O$ shake), 7.95-7.92 (m, 2H), 7.90-7.87 (m, 2H), 7.58 (d, J=2.7 Hz, 1H), 7.49 (dd, J=9.7, 2.8 Hz, 1H), 6.42 (d, J=9.6 Hz, 1H). HPLC-MS (ESI): m/z 241.1 [100%, $(M+H)^+$], 503.1 [60%, $(2M+Na)^+$], 481.2 [40%, $(2M+H)^+$]. LC-MS (ESI+): 273.1 [100%, $(M+Na)^+$], 241.1 [95%, $(M+H)^+$]. HRMS (ESI+): m/z calcd for $C_{13}H_8N_2O_3(M+H)^+$241.0608, found 241.0615.

Scheme 5

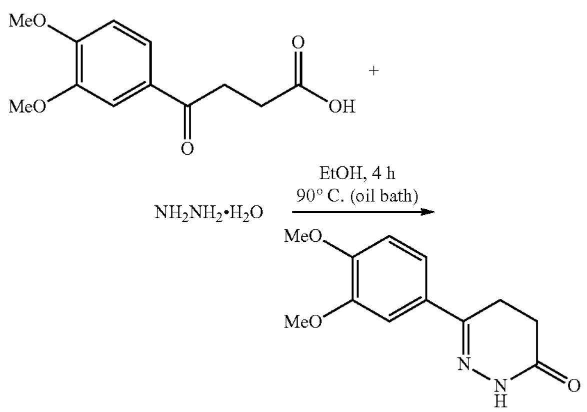

MA6-064
(NSC251211)

6-(3,4-Dimethoxyphenyl)-4,5-dihydropyridazin-3(2H)-one (MA6-064): Commercially available 4-(3,4-dimethoxyphenyl)-4-oxobutanoic acid (119.1 mg, 1 equiv.) was dissolved in dry EtOH (0.5 mL) and hydrazine monohydrate (48.7 μL, 2 equiv.) was added (scheme 5). The reaction vessel was immersed into a pre-heated oil (external temperature 90° C.) and stirred for 4 h. After the completion of the reaction (monitored by TLC), the volatiles were evaporated under reduced pressure and the crude was purified using $SiO_2$ column chromatography (eluent EtOAc-Hexane, 0-100%). The title compound was obtained as a light yellow solid (103 mg, 87%). Mp: 164-166° C. (reported: 165-167° C., 170-173).[2,3] HPLC: 97% [$t_R$=13.3 min, Gradient 5-95% MeOH-water (with 0.1% TFA), 30 min]. $^1$H NMR (400 MHz, Chloroform-d) δ 8.55 (s, 1H, 85% reduction on $D_2O$ shake), 7.41 (d, J=2.0 Hz, 1H), 7.18 (dd, J=8.4, 2.0 Hz, 1H), 6.87 (d, J=8.4 Hz, 1H), 3.93 (s, 3H), 3.92 (s, 3H), 3.02-2.94 (m, 2H), 2.64-2.57 (m, 2H). HPLC-MS (ESI): m/z 235.2 [100%, $(M+H)^+$], 491.2 [80%, $(2M+Na)^+$], 257.2 [20%, $(M+Na)^+$]. LC-MS (ESI+): m/z 257.1 [$(M+Na)^+$]. HRMS (ESI+): m/z calcd for $C_{12}H_{14}N_2O_3(M)^+$234.1004, found 234.1004.

MA7-002

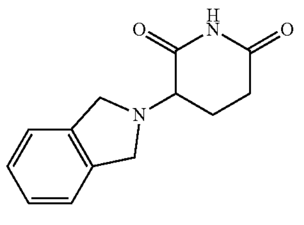

3-(Isoindolin-2-yl)piperidine-2,6-dione (MA7-002). This compound was obtained as a dark grey solid (79 mg, 66%) from MA6-019 (100 mg, 1 equiv.) and 1,2,3,4-tetrahydroisoquinoline (62.0 mg, 1 equiv.) using the general method 1 (Scheme 1) (reaction temperature 72° C., solvent THF (1.0 mL), reaction time 14 h). Purification was carried out using $SiO_2$ column chromatography (eluent: MeOH-DCM, up to 12% MeOH). HPLC: 95% [$t_R$=9.4 min, Gradient 5-95% IPA-water, 20 min]. $^1$H NMR (400 MHz, DMSO-$d_6$): δ 10.72 (s, 1H), 7.25-7.18 (m, 4H), 4.10 (d, J=10.8, 2H), 4.04 (d, J=10.8, 2H), 3.61 (dd, J=8.8, 4.8 Hz, 1H), 2.57 (t, J=6.4 Hz, 2H), 2.107-2.011 (m, 2H); HPLC-MS (ESI): m/z 231 $(M+H)^+$.

MA7-004

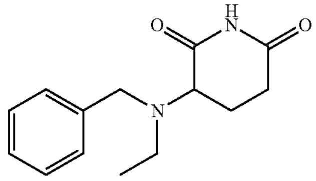

3-(Benzyl(ethyl)amino)piperidine-2,6-dione (MA7-004). This compound was obtained as a dark grey solid (29 mg, 22%) from MA6-019 (100 mg, 1 equiv.) and N-benzylethylamine (70.4 mg) using the general method 1 (Scheme 1) (reaction temperature 85'C, solvent THF (1.0 mL), reaction time 16 h). Purification was carried out using $SiO_2$ column chromatography (eluent: MeOH-DCM, up to 15% MeOH). HPLC: 98% [$t_R$=9.4 min, 20:80 MeOH-water, 0.1% TFA, 20 min]. HPLC-MS (ESI): m/z 247 $(M+H)^+$; HRMS (ESI+): m/z calcd for $C_{14}H_{18}N_2O_2(M+H)^+$247.1445, found 247.1372.

Scheme 6

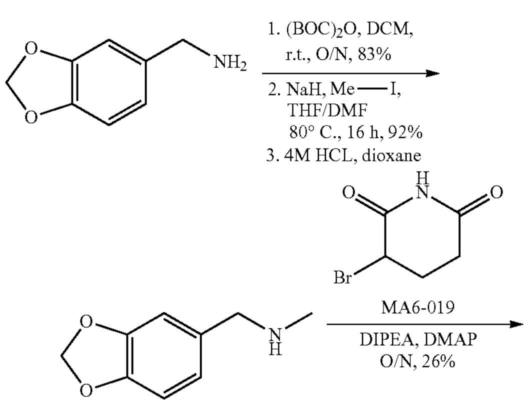

MA7-086

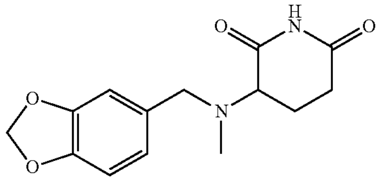

MA7-088

3-((Benzo[d][1,3]dioxol-5-ylmethyl)(methyl)amino)piperidine-2,6-dione (MA7-088). The starting material benzo[d][1,3]dioxol-5-ylmethanamine (2.0 g, 13.23 mmol) (Scheme 6) in a r.b. flask, was added anhydrous DCM and Boc-anhydride (3.18 g, 14.55 mmol). The reaction was stirred overnight and monitored using HPLC-MS. The solvent was evaporated to obtain a yellow oil, the product crystalized upon standing at r.t. The crude mixture was dissolved in EtOAc (150 mL), and washed with $NaHCO_3$ (50 mL), and brine (100 mL). The organic layer was dried ($Na_2SO_4$) and evaporated to obtain the Boc-intermediate as a oily yellow solid (2.77 g, 83%); $^1$H NMR (400 MHz, DMSO-$d_6$): δ7.32 (t, J=6.0 Hz, 1H), 6.83 (d, J=8.0 Hz, 1H), 6.77 (d, J=1.6 Hz, 1H), 6.69 (dd, J=8.0, 1.6 Hz, 1H), 5.97 (s, 2H), 4.01 (d, J=6.0 Hz, 2H), 1.38 (s, 9H). In a microwave vial, NaH (79.6 mg, 1.99 mmol) was added to dry THF (1 mL) and DMF (1 mL) under inert conditions. The mixture was cooled to 0° C. and the Boc-intermediate (250 mg, 0.99 mmol), from the previous step was added followed by methyliodide (68.13 μL, 1.09 mmol) and stirred for 16 h. The reaction was monitored by tlc. The product was extracted with EtOAc (2×30 mL) and evaporated. The crude product was triturated with EtOAc/Hexane to obtain the methylated-Boc intermediate (243 mg, 92%) and used in the next step without further purification; $^1$H NMR (400 MHz, DMSO-$d_6$): δ 6.87 (d, J=8.0 Hz, 1H), 6.79 (s, 1H), 6.70 (d, J=8.0 Hz, 1H), 5.98 (s, 2H), 4.25 (s, 2H), 2.71 (s, 3H), 1.4 (s, 9H). The methylated-Boc-intermediate (200 mg, 0.75 mmol) from the previous reaction was dissolved in THF (2.0 mL), added HCl (4M, 940 μL) and stirred overnight. The mixture was extracted with EtOAc (2×20 mL), dried ($Na_2SO_4$), evaporated and the product was triturated with EtOAc/Hexanes to obtain MA7-086 as a yellow oil (118 mg, 78%) and used without further purification in the next step; $^1$H NMR (400 MHz, DMSO-$d_6$): δ 7.12 (appt, J=0.8 Hz, 1H), 6.97 (m, 2H), 6.95 (d, J=1.2 Hz, 1H), 6.05 (s, 2H), 4.01 (s, 2H), 2.48 (s, 3H). The MA7-088 was obtained as an off white solid (31 mg, 26%) from MA6-019 (81.4 mg, 1 equiv.) and MA7-086 (970 mg, 1 equiv.) using the general method 1 (Scheme 1) (reaction was stirred at r.t., solvent DMF, reaction time 15 h). Purification was carried out using $SiO_2$ chromatography (eluent: MeOH-DCM, up to 10% MeOH). HPLC: 100% [$t_R$=4.53 min, 5-20:80 MeOH-water with 0.1% TFA, 20 min]. $^1$H NMR (400 MHz, DMSO-$d_6$): δ 10.636 (brs, 1H), 6.89 (d, J=1.2 Hz, 1H), 6.82 (d, J=8.0 Hz, 1H), 6.76 (dd, J=8.0, 1.6 Hz, 1H), 5.97 (appt, J=0.8 Hz 2H), 3.65 (d, J=5.2 Hz, 2H), 3.57 (dd, J=12, 4.8 Hz, 1H), 2.63-2.55 (m, 1H), 2.52-2.47 (m, 1H), 2.22 (s, 3H), 2.11-2.00 (m, 1H), 1.93-1.88 (m, 1H): HPLC-MS (ESI): m/z 277 $(M+H)^+$.

MA6-116

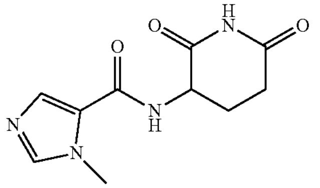

N-(2,6-Dioxopiperidin-3-yl)-1-methyl-1H-imidazole-5-carboxamide (MA6-116). First 1-Methyl-1H-imidazole-5-carboxylic acid (128.1 mg, 1 mmol) in THF (1.0 mL) was treated with $CO_2Cl_2$ (86.86 μL, 1 mmol) at ° C., 1 drop of DMF was added to the mixture and stirred for 2 h. The mixture was evaporated and the formation of acid chloride was confirmed by $^1$H NMR and the product was used in the next step. The 3-aminopiperidine-2,6-dione (128.1 mg, 1 mmol) in THF (1.0 mL) was added at 0° C. to the acid chloride mixture. The reaction was stirred at r.t. for 2 h at r.t., diluted with EtOAc (5 mL), washed with brine. The aqueous layer was extracted with EtOAc (2×5 mL), and the combined organic layers was dried ($Na_2SO_4$), and concentrated. The crude product was purified using $SiO_2$ chromatography with MeOH:DCM (gradient elution, product eluted with 10% MeOH) to obtain pure MA6-116 (25 mg, 11%). HPLC: 98.9% [$t_R$=6.02 min, gradient MeOH:water, 5-95% with 0.1% TFA, 20 min].]. $^1$H NMR (400 MHz, DMSO-$d_6$): δ 10.86 (s, 1H), 8.54 (d, J=8.4 Hz, 1H), 7.77 (s, 1H), 7.61 (s, 1H), 4.73-4.66 (m, 1H), 3.81 (s, 3H), 2.81-2.73 (m, 1H), 2.55 (m, 1H), 2.10-2.04 (m, 1H), 1.95 (m, 1H); HPLC-MS (ESI): m/z 237 $(M+H)^+$.

MA7-020

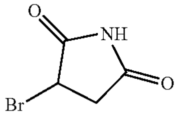

3-Bromopyrrolidine-2,5-dione (MA7-020). To a solution of succinimide (5.0 g, 50.46 mmol) in dry chloroform (10.0 mL) added bromine (8.06 g, 50.46 mmol) and heated at 110° C. (sealed tube). After 1.5 h, the mixture was cooled and evaporated (added more $CHCl_3$). The crude NMR and TLC showed a mixture of 3 compounds (starting material, mono-brominated and bis-brominated products) and the mixture was purified using $SiO_2$ chromatography (EtOAc: hexane gradient elution) to obtain the mono-brominated product (1.79 g) as a colorless oil. $^1$H NMR (400 MHz, DMSO-$d_6$): δ 11.66 (s, 1H), 4.93 (dd, J=8.4, 3.6 Hz, 1H), 3.40 (dd, J=18.8, 8.4 Hz, 1H), 2.90 (dd, J=18.8, 3.6 Hz, 1H). HPLC-MS (ESI): m/z 176 $(M+H)^+$.

MA7-026

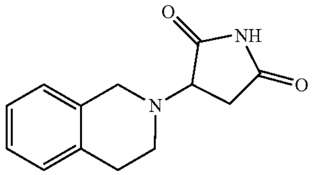

3-(3,4-Dihydroisoquinolin-2(1H)-yl)pyrrolidine-2,5-dione (MA7-026). The MA7-020 (112 mg, 0.62 mmol) and 1,2,3,4-tetrahydroisoquinoline (83.8 mg, 0.62 mmol) were dissolved in dry DMF (0.5 mL), and stirred for 3 h. The solvent was evaporated and water (5 mL) was added. The water was decanted, and the yellow precipitate (94 mg, 65%) was freeze dried. HPLC: 98% [$t_R$=9.4 min, 10:90 MeOH-water, 0.1% TFA, 20 min]. $^1$H NMR (400 MHz, DMSO-$d_6$): δ 11.27 (brs, 1H), 7.15-7.02 (m, 4H), 4.06 (dd, J=8.8, 6.0 Hz, 1H), 3.96 (d, J=14.8 Hz, 1H), 3.60 (d, J=14.8 Hz, 1H), 2.99-2.93 (m, 1H), 2.82-2.66 (m, 5H); HPLC-MS (ESI): m/z 176 $(M+H)^+$; HPLC-MS (ESI): m/z 231 $(M+H)^+$.

MA7-044

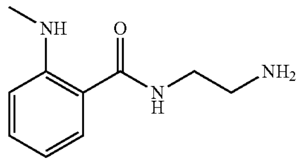

N-(2-aminoethyl)-2-(methylamino)benzamide (MA7-044). This compound was prepared as reported in the literature (WO2013/21363 A1, page 55) and de-protected using TFA and MA7-044 was obtained as a brown oil (90%). $^1$H NMR (400 MHz, DMSO-$d_6$): δ 8.23 (t, J=5.6 Hz, 1H), 7.59 (appq, J=5.2, 1H), 7.50 (dd, J=8.0, 1.6 Hz, 1H), 7.27 (t, J=8.4 Hz, 1H), 6.61 (d, J=8.4 Hz, 1H), 6.54 (t, J=8.0 Hz, 1H), 3.30-3.26 (m, 1H), 2.87-2.80 (m, 2H), 2.75 (d, J=5.2 Hz, 3H), 2.69-2.67 (m, 2H)

MA7-046

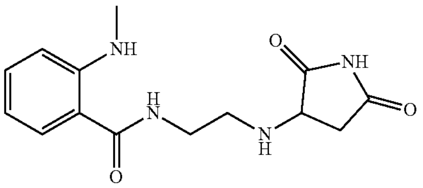

N-(2-((2,5-dioxopyrrolidin-3-yl)amino)ethyl)-2-(methylamino)benzamide (MA7-046). In a 2 mL microwave vial MA7-044 (108 mg, 0.56 mmol) was dissolved in DMF (0.5 mL), added DIPEA (97.9 μL) and the mixture was stirred to dissolve the gummy amine MA7-044. After stirring 5 min. at r.t., MA7-020 (100 mg, 0.56 mmol) was added, and the mixture was stirred at r.t. for 3-4 h. The mixture was evaporated using V-10, and partitioned between EtOAc (15 mL) and aqueous $NaHCO_3$ (10 mL). The organic layer was dried ($Na_2SO_4$) to obtain the crude product. The product was purified using preparative HPLC (MeOH: water, 20:80, 0.1% TFA). $^1$H NMR (400 MHz, DMSO-$d_6$): δ 11.123 (brs, 1H), 8.23 (t, J=5.2 Hz, 1H), 7.59 (q, J=4.8 Hz, 1H), 7.51 (dd, J=7.6, 1.6 Hz, 1H), 7.27 (t, J=8.4 Hz, 1H), 6.6.1 (dd, J=8.4, 0.8 Hz, 1H), 6.54 (t, J=7.2 Hz, 1H), 3.71-3.68 (m, 1H), 3.31-3.24 (m, 2H), 2.86-2.80 (m, 2H), 2.75 (d, J=4.8 Hz, 3H), 2.71-2.65 (m, 1H), 2.34 (dd, J=18.0, 5.2 Hz, 1H); HPLC-MS (ESI): m/z 291 $(M+H)^+$.

MA7-032

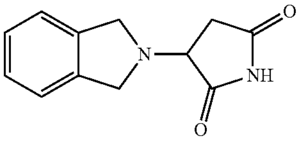

3-(Isoindolin-2-yl)pyrrolidine-2,5-dione (MA7-032). In a microwave vial isoindoline (66.95 mg, 0.56 mmol) was dissolved in DMF (0.5 mL), added DIPEA (195.7 μL) and stirred at r.t. for 5 min. The MA7-020 (100 mg, 0.56 mmol) was added, vial was capped and stirred for 4 h and the reaction was monitored by tlc. Added $NaHCO_3$ (3 mL), extracted with EtOAc (2×5 mL). The organic layer was dried ($Na_2SO_4$) to obtain the crude product, which was purified using $SiO_2$ chromatography using DCM/MeOH (gradient elution), and product was eluted around 12% MeOH as a light yellow solid (77 mg, 63%). HPLC: 84% [$t_R$=4.54 min, gradient MeOH-water 5-95%, 0.1% TFA, 20 min]. $^1$H NMR (400 MHz, DMSO-$d_6$): δ 11.28 (br s, 1H), 7.25-7.18 (m, 4H), 4.19 (d, J=12.8 Hz, 2H), 4.01 (dd, J=8.4, 5.2 Hz, 1H), 3.95 (d, J=12.8 Hz, 2H), 2.84 (dd, J=18.0, 8.8 Hz, 1H), 2.71 (dd, J=, 17.6, 1.6 Hz, 1H), HPLC-MS (ESI): m/z 217 $(M+H)^+$.

MA7-038

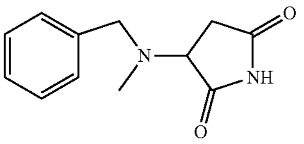

3-(Benzyl(methyl)amino)pyrrolidine-2,5-dione (MA7-038): This compound was synthesized using the procedure described for MA7-032 except using methylbenzyl amine (51 mg, 0.42 mmol). The crude compound was purified using DCM:MeOH gradient elution, and the product was eluted with 15% MeOH as an off white solid (71 mg, 77%). HPLC: 100% [$t_R$=8.48 min, MeOH:water, 10:90, 0.1% TFA, 20 min]. $^1$H NMR (400 MHz, DMSO-$d_6$): δ 11.28 (br s, 1H), 7.33-7.23 (m, 5H), 3.94 (dd, J=8.8, 5.2 Hz, 1H), 3.66 (s, 2H), 2.72 (dd, J=18, 8.8 Hz, 1H), 2.61 (dd, J=18, 5.2 Hz, 1H), 2.14 (s, 3H); HPLC-MS (ESI): m/z 219 $(M+H)^+$.

MA6-148-4

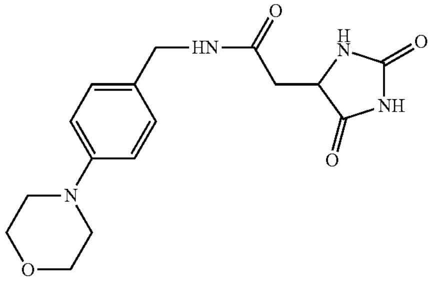

2-(2,5-Dioxoimidazolidin-4-yl)-N-(4-morpholinobenzyl) acetamide (MA6-148-4). The hydantoinacetic acid (100 mg, mg, 0.63 mmol) in dry DMF (1.00-2.00 mL), was added EDC (122.7 mg, 0.79 mmol), DIPEA (1 equiv.) HOBT (85.4 mg, 0.63 mmol) at 0° C. and the reaction was stirred for 15 min. The (4-morpholinophenyl)methanamine (121.60 mg, 0.63 mmol) was added under argon, reaction was stirred for 30 min. at 0° C. and 16 h, at r.t. The mixture was diluted with EtOAc (30 mL), washed with water (20 mL). The organic layer was dried ($Na_2SO_4$), evaporated and the product obtained was purified by $SiO_2$ chromatography using MeOH:DCM gradient elution (product was eluted with 12% MeOH) to give an off white solid (28 mg, 13% yield). HPLC: 96% [$t_R$=3.06 min, MeOH:water, 20:80, 0.1% TFA, 20 min]. $^1$H NMR (400 MHz, DMSO-$d_6$): δ 8.45 (t, J=5.6 Hz, 1H), 7.27 (brs, 1H), 7.13 (d, J=8.4 Hz, 1H), 6.88 (d, J=8.4 Hz, 1H), 4.16 (d, J=5.6 Hz, 2H), 4.05 (t, J=5.6 Hz, 1H), 3.72 (t, J=4.4 Hz, 4H), 3.05 (t, J=4.8 Hz, 4H), 2.56-2.52 (dd, overlapped with DMSO peak, 2H), 2.32 (dd, J=15.2, 7.6 Hz, 2H); HPLC-MS (ESI): m/z 333 $(M+H)^+$.

MA6-130

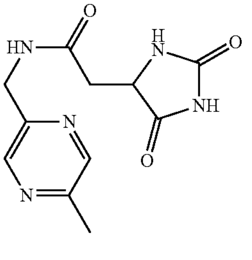

2-(2,5-Dioxoimidazolidin-4-yl)-N-((5-methylpyrazin-2-yl)methyl)acetamide (MA6-130). This compound was synthesized using the procedure described for MA6-148-4 except using (5-methylpyrazin-2-yl)methanamine (123.2 mg, 1 mmol) and hydantoinacetic acid (158.1 mg, 1 mmol), DIPEA (348.4 μmL) and DMF (2 mL). The first crop of product was precipitated by addition of water (5.0 mL), and filtered to obtain 41 mg. The filtrate further was evaporated and triturated with water (5 mL). The MA6-130 (120 mg, 46%) was obtained as a white solid. HPLC: 98% [$t_R$=7.16 min, gradient MeOH:water, 5-95%, 0.1% TFA, 20 min]. $^1$H NMR (400 MHz, DMSO-$d_6$): δ 10.56 (s, 1H), 8.60 (t, J=6.0 Hz, 1H), 8.45 and 8.46 (2×s, 2H), 7.86 (s, 1H), 4.36 (d, J=5.2 Hz, 2H), 4.23 (t, J=5.2 Hz, 1H), 2.64 (dd, J=15.6, 4.4 Hz, 1H), 2.47 (dd, partially overlapped with the residual DMSO peak, 1H), 2.46 (s, 3H); HPLC-MS (ESI): m/z 264 $(M+H)^+$.

4.52 (q, J=8.5 Hz, 1H, becomes a triplet on $D_2O$ shake), 3.13 (q, J=7.0 Hz, 1H, becomes a triplet on $D_2O$ shake), 2.78-2.65 (m, 1H), 2.50-2.45 (m, 1H, overlapped with the residual DMSO signal), 2.29 (t, J=7.2 Hz, 2H), 1.95-1.87 (m, 2H), 1.37 (s, 9H).

MA6-164

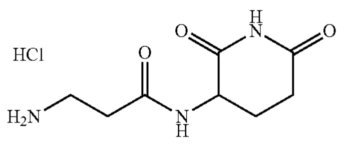

Scheme 7

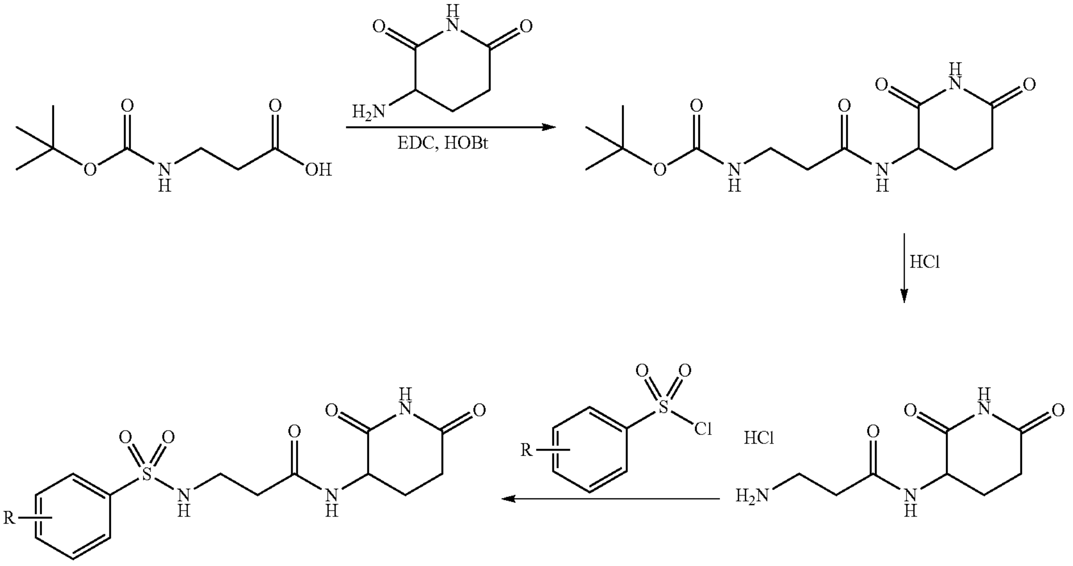

MA6-164

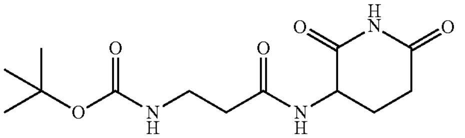

tert-Butyl (3-((2,6-dioxopiperidin-3-yl)amino)-3-oxopropyl)carbamate (MA6-164): 3-[(tert-Butoxycarbonyl)amino] propanoic acid (2.31 g, 12.23 mmol), EDC (1.90 g, 12.23 mmol), and HOBt (247.8 mg, 1.83 mmol) were added to dry DMF (60 mL) and stirred at room temperature for 10 mins. To this mixture was added 3-aminopiperidine-2,6-dione hydrochloride (2.00 g, 12.23 mmol) and DIPEA (6.39 mL, 36.68 mmol). The mixture was then stirred at room temperature for 8 h, having become clear and blue. Ethyl acetate (400 mL) and $NaHCO_3$ (200 mL, sat. aq.) were added and the layers separated. The aqueous layer was extracted with ethyl acetate (200 mL). The combined organic layers were dried ($Na_2SO_4$) and concentrated under vacuum. Trituration of the resulting solid with ethyl acetate/hexanes gave the product as a slightly-blue white solid (1.78 g, 49%). $^1$H NMR (400 MHz, DMSO-$d_6$) δ 10.80 (s, 1H, disappeared on $D_2O$ shake), 8.23 (d, J=10.4 Hz, 1H, disappeared on $D_2O$ shake), 6.74 (t, J=7.0 Hz, 1H, disappeared on $D_2O$ shake), 3-Amino-N-(2,6-dioxopiperidin-3-yl)propanamide hydrochloride (MA6-166): To MA6-164 (1.76 g, 5.88 mmol) in dry DCM (4 mL), at room temperature, was added HCl (4.41 ml, 4 N in dioxane). The mixture was stirred at room temperature for 2 h. Intermittently the mixture was sonicated in a cleaning bath to redissolve the gummy material. The solvent was removed under vacuum. Trituration of the resulting solid with ethanol and hexanes gave the product as a white highly hydroscopic solid (1.178 g, 100%). $^1$H NMR (400 MHz, DMSO-$d_6$) δ 10.84 (s, 1H, disappeared on $D_2O$ shake), 8.54 (d, J=8.3 Hz, 1H, disappeared on $D_2O$ shake), 8.05-9.95 (broad s, J=7.0 Hz, 3H, disappeared on $D_2O$ shake), 3.13 (q, J=7.0 Hz, 1H, becomes a triplet on $D_2O$ shake), 2.98 (sextet, 3H, J 6.7 Hz, 2H, becomes a triplet on $D_2O$ shake), 2.78-2.69 (m, 1H), 2.61-2.54 (m, 2H), 1.98-1.88 (m, 2H). HPLC-MS (ESI+): m/z 399.2 [20%, $(2M+H)^+$], 200.2 [100%, $(M+H)^+$].

MA6-168

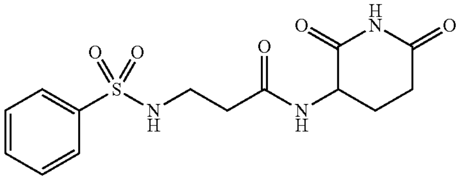

N-(2,6-Dioxopiperidin-3-yl)-3-(phenylsulfonamido)propanamide (MA6-168): Triethylamine (104.9 μL, 0.75 mmol) was added to MA6-166 (50 mg, 0.25 mmol) in DCM (0.5 mL) and DMF (0.2 mL) and the solution cooled to 0° C. Benzenesulfonyl chloride (32 μL, 0.25 mmol) was added to the mixture, which was then stirred at 0° C. for 1 h an room temperature for 1 h. The mixture was concentrated followed by addition of ethyl acetate (10 mL) and washed with $NaHCO_3$ (5 mL, sat. aq.) and water (5 mL). The organic layer was dried ($Na_2SO_4$) and evaporated. The residue was purified by chromatography to provide the product as a yellow solid (47 mg, 56%). $^1$H NMR (400 MHz, DMSO-$d_6$) δ 9.80-8.80 (broad s, 1H), 8.31 (d, J=8.0 Hz, 1H), 7.79 (d, J=8.0 Hz, 2H), 7.65-7.55 (m, 3H), 4.61-4.41 (m, 1H), 2.93 (t, J=7.4 Hz, 2H), 2.74-2.65 (m, 1H), 2.50-2.45 (m, 1H, overlapped with the residual DMSO signal), 2.31 (t, J=7.4 Hz, 2H), 1.95-1.80 (m, 2H). HPLC-MS (ESI+): m/z 701.2 [40%, $(2M+Na)^+$], 340.1 [100%, $(M+H)^+$].

MA6-174-1

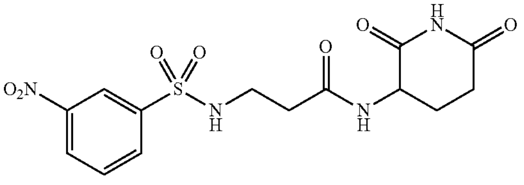

N-(2,6-Dioxopiperidin-3-yl)-3-[(3-nitrophenyl)sulfonamido]propanamide (MA6-174-1): This was prepared in the same way as MA6-168, using 3-nitrophenylsulfonyl chloride (47.22 mg). Purification by trituration from acetone/hexanes gave MA6-174-1 as a white solid (36 mg, 44%). HPLC: 96% [$t_R$=11.8 min, gradient 5-95% MeOH:water (with 0.1% TFA), 20 min]. $^1$H NMR (400 MHz, DMSO-$d_6$) δ 10.82 (s, 1H), 8.53 (t, J=1.9 Hz, 1H), 8.49 (ddd, J=8.2, 2.3, 1.0 Hz, 1H), 8.28 (d, J=8.3 Hz, 1H, disappeared on $D_2O$ shake), 8.22 (ddd, J=7.8, 1.8, 1.0 Hz, 1H), 8.07 (s, 1H, disappeared on $D_2O$ shake), 7.91 (t, J=8.1 Hz, 1H), 4.54-4.47 (m, 1H), 3.01 (t, J=7.3 Hz, 2H), 2.75-2.64 (m, 1H), 2.50-2.45 (m, 1H, overlapped with the residual DMSO signal), 2.32 (t, J=7.3 Hz, 2H), 1.91-1.83 (m, 1H). HPLC-MS (ESI−): m/z 767.3 [10%, $(2M-H)^-$], 383.1 [20%, $(M-H)^-$]. HRMS (ESI+): m/z calcd for $C_{14}H_{16}N_4O_7S$ $(M+Na)^+$407.0632, found 407.0625.

MA6-174-2

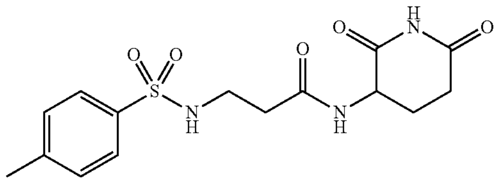

N-(2,6-Dioxopiperidin-3-yl)-3-[(4-methylphenyl)sulfonamido]propanamide (MA6-174-2): This was prepared in the same way as MA6-168, using 4-methylphenylsulfonyl chloride (40.62 mg) to give MA6-174-2 as a white solid (39 mg, 51%). HPLC: >99% [$t_R$=4.4 min, 40% MeOH, 60% water (with 0.1% TFA), 20 min]. $^1$H NMR (400 MHz, DMSO-$d_6$) δ 10.82 (s, 1H), 8.28 (d, J=8.2 Hz, 1H), 7.68 (d, J=8.3 Hz, 2H), 7.56 (t, J=7.2 Hz, 1H), 7.40 (d, J=8.3 Hz, 2H), 4.52 (q, J=8.5 Hz, 1H), 2.96-2.87 (m, 2H), 2.76-2.64 (m, 1H), 2.50-2.45 (m, 1H, overlapped with the residual DMSO signal), 2.39 (s, 3H), 2.30 (t, J=7.3 Hz, 2H), 1.91-1.83 (m, 1H). HPLC-MS (ESI+): m/z 729.3 [40%, $(2M+Na)^+$], 354.1 [100%, $(M+H)^+$]. HRMS (ESI+): m/z calcd for $C_{15}H_{19}N_3O_5S$ $(M+Na)^+$376.0938, found 407.0941.

MA6-174-4

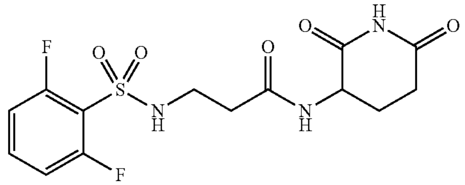

N-(2,6-Dioxopiperidin-3-yl)-3-[(2,6-difluorophenyl)sulfonamido]propanamide (MA6-174-4): This was prepared in the same way as MA6-168, using 2,6-difluorophenylsulfonyl chloride (45.3 mg). Purification by silica gel chromatography gave MA6-174-4 as a white solid (39 mg, 49%). HPLC: >99% [$t_R$=4.2 min, 30% MeOH, 70% water (with 0.1% TFA), 20 min]. $^1$H NMR (400 MHz, DMSO-$d_6$) δ 10.81 (s, 1H, disappeared on $D_2O$ shake), 8.30 (d, J=8.2 Hz, 1H, disappeared on $D_2O$ shake), 8.24 (s, 1H, disappeared on $D_2O$ shake), 7.77-7.67 (m, 1H), 7.30 (t, J=9.3 Hz, 2H), 4.50 (q, J=8.3 Hz, 1H), 3.14 (t, J=7.6 Hz, 2H), 2.76-2.63 (m, 2H), 2.50-2.45 (m, 1H, overlapped with the residual DMSO signal), 2.37 (t, J=7.5 Hz, 2H), 1.95-1.82 (m, 2H). LC-MS (ESI+): 773.1 [40%, (2M+Na)], 398.0 [100%, $(M+Na)^+$]. HPLC-MS (ESI+): m/z 773.2 [40%, $(2M+Na)^+$], 376.1 [100%, $(M+H)^+$]. HRMS (ESI+): m/z calcd for $C_{14}H_{15}F_2N_3O_5S$ $(M+Na)^+$376.0593, found 398.0580.

MA6-174-5

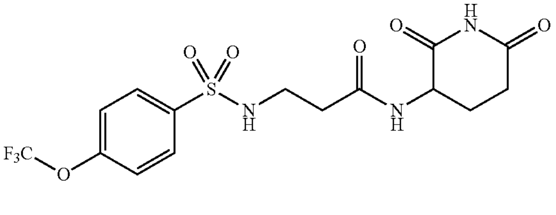

N-(2,6-Dioxopiperidin-3-yl)-3-((4-(trifluoromethoxy)phenyl)sulfonamido)propanamide (MA6-174-5): This was prepared in the same way as MA6-168, using 4-(trifluoromethoxy)phenylsulfonyl chloride (55.5 mg). Purification by silica gel chromatography gave MA6-174-5 as a white solid (42 mg, 47%). HPLC: >99% [$t_R$=5.4 min, 50% MeOH, 50% water (with 0.1% TFA), 20 min]. $^1$H NMR (400 MHz, DMSO-$d_6$) δ 10.82 (s, 1H, disappeared on $D_2O$ shake), 8.29 (d, J=8.2 Hz, 1H, disappeared on $D_2O$ shake), 8.24 (s, 1H, disappeared on $D_2O$ shake), 7.92 (d, J=8.8 Hz, 2H), 7.83 (s, 1H), 7.61 (d, J=8.8 Hz, 2H), 4.52 (q, J=8.5 Hz, 1H), 2.97 (t, J=7.3 Hz, 2H), 2.74-2.63 (m, 2H), 2.50-2.45 (m, 1H, overlapped with the residual DMSO signal), 2.33 (t, J=7.3 Hz, 2H), 1.93-1.84 (m, 2H). LC-MS (ESI+): 869.2 [60%, (2M+Na)], 446.1 [100%, $(M+Na)^+$], 424.1 [90%, $(M+H)^+$]. HPLC-MS (ESI+): m/z 869.2 [40%, $(2M+Na)^+$], 424.1 [100%, $(M+H)^+$]. m/z calcd for $C_{15}H_{16}F_3N_306S$ $(M+H)^+$ 424.0785, found 424.0775.

MA6-174-7

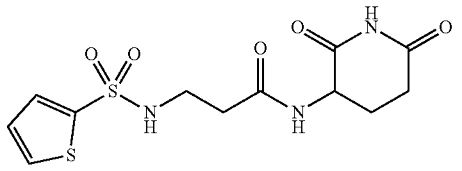

N-(2,6-Dioxopiperidin-3-yl)-3-(thiophene-2-sulfonamido)propanamide (MA6-174-7): This was prepared in the same way as MA6-168, using thiophene-2-sulfonyl chloride (38.9 mg). Purification by silica gel chromatography gave MA6-174-7 as a white solid (27 mg, 37%). HPLC: 96% [$t_R$=10.2 min, gradient MeOH (5-95%) and water (with 0.1% TFA), 20 min]. $^1$H NMR (400 MHz, DMSO-$d_6$) δ 10.82 (s, 1H), 8.31 (d, J=8.3 Hz), 7.94 (dd, J=4.9, 1.3 Hz, 1H), 7.85 (s, 1H), 7.59 (dd, J=3.9, 1.3 Hz, 1H), 7.23-7.17 (m, 1H), 4.53 (q, J=8.5 Hz, 1H), 3.03 (t, J=7.5 Hz, 2H), 2.78-2.64 (m, 2H), 2.50-2.45 (m, 1H, overlapped with the residual DMSO signal), 2.35 (t, J=7.5 Hz, 2H), 1.92-1.85 (m, 2H). LC-MS (ESI+): m/z 713.2 [30%, $(2M+Na)^+$], 368.0 [100%, $(M+Na)^+$], 346.1 [40%, $(M+H)^+$]. HPLC-MS (ESI+): m/z 713.2 [40%, $(2M+Na)^+$], 346.1 [40%, $(M+H)^+$]. m/z calcd for $C_{12}H_{15}N_3O_5S$ $(M+Na)^+$368.0345, found 368.0342.

MA6-174-7

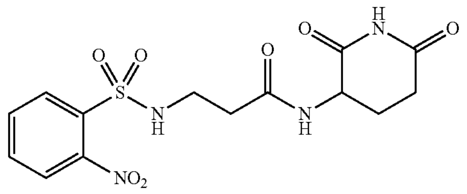

N-(2,6-Dioxopiperidin-3-yl)-3-[(2-nitrophenyl)sulfonamido]propanamide (MA6-174-7): This was prepared in the same way as MA6-168, using 2-nitrophenylsulfonyl chloride (47.22 mg). Purification by chromatography and trituration from acetone/hexanes gave MA6-174-7 as a white solid (36 mg, 44%). HPLC: 96% [$t_R$=10.6 min, gradient 5-95% MeOH:water (with 0.1% TFA), 20 min]. $^1$H NMR (400 MHz, DMSO-$d_6$) δ 10.82 (s, 1H), 8.31 (d, J=8.3 Hz, 1H), 8.09 (s, 1H), 8.04-7.95 (m, 2H), 7.92-7.84 (m, 2H), 7.91 (t, J=8.1 Hz, 1H), 4.56-4.47 (m, 1H), 3.11 (t, J=7.3 Hz, 2H), 2.78-2.65 (m, 1H), 2.50-2.45 (m, 1H, overlapped with the residual DMSO signal), 2.37 (t, J=7.3 Hz, 2H), 1.91-1.83 (m, 1H). HPLC-MS (ESI+): m/z 791.1 [30%, $(2M+Na)^+$], 385.1 [100%, $(M+H)^+$]. LC-MS (ESI+): m/z 385.1 [100%, $(M+H)^+$]. HRMS (ESI+): m/z calcd for $C_{14}H_{16}N_4O_7S$ $(M+Na)^+$407.0632, found 407.0630.

Scheme 8

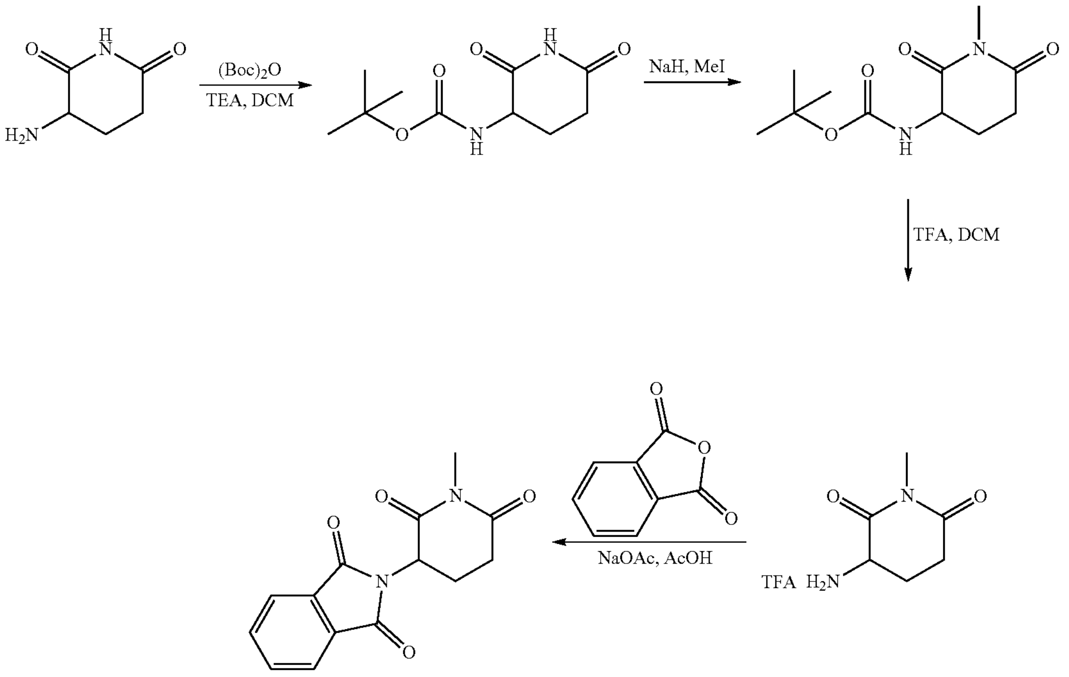

-continued

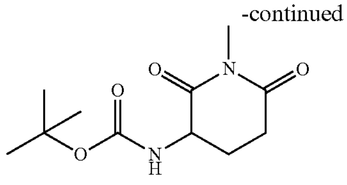

tert-butyl (2,6-dioxopiperidin-3-yl)carbamate: A mixture of 3-aminopiperidine-2,6-dione hydrochloride (500 mg, 3.04 mmol) and triethylamine (931 μL, 6.68 mmol) in DCM (3 mL) was heated in a sealed 20 mL microwave vial at 50° C. for 30 min. The mixture was cooled to 0° C. and di-tert-butyl dicarbonate (663 mg, 3.04 mmol) in DCM (1 mL) was added via syringe, and stirring at 0° C. was continued for a further 30 min. The mixture was concentrated under vacuum and ethyl acetate (200 mL) added. The resulting mixture was washed with $NaHCO_3$ (100 mL, sat. aq.), brine (50 mL), dried ($Na_2SO_4$) and concentrated under vacuum. Trituration of the residue with ethyl acetate/hexanes gave pure product (601 mg, 87%) as a yellow solid. $^1$H NMR (400 MHz, DMSO-$d_6$) δ 10.73 (s, 1H), 7.12 (d, J=8.7 Hz, 1H), 4.20 (ddd, J=11.5, 8.7, 6.2 Hz, 1H), 2.69 (ddd, J=17.2, 12.3, 6.5 Hz, 1H), 2.49-2.40 (m, 1H, overlapped with the residual DMSO signal), 1.99-1.81 (m, 2H), 1.38 (s, 9H).

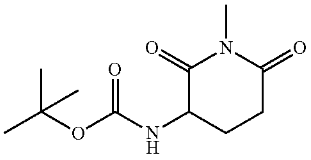 [SMILES: CN1C(=O)CCC(NC(=O)OC(C)(C)C)C1=O]

tert-Butyl (1-methyl-2,6-dioxopiperidin-3-yl)carbamate: MA7-126 (580 mg, 2.54 mmol) was added to sodium hydride (111.8 mg of a 60% suspension in oil, 2.80 mmol) in dry DMF (5 mL) at 0° C. Methyl iodide (189.9 μL, 3.05 mmol) was added via syringe. The mixture was stirred at 0° C. for 30 min and room temperature for 1 h. After cooling the mixture to 0° C., water (0.5 mL) was carefully added followed by $NaHCO_3$ (50 mL, sat. aq.) and ethyl acetate (50 mL). The organic layer was separated and the aqueous layer extracted with further ethyl acetate (2×50 mL). The combined organic layers were washed with brine (25 mL) and dried ($Na_2SO_4$) and evaporated under vacuum. Purification by column chromatography gave the product (436 mg, 71%) as a yellow solid. $^1$H NMR (400 MHz, DMSO-$d_6$) δ 7.19 (d, J=8.8 Hz, 1H), 4.28 (ddd, J=11.8, 8.7, 6.1 Hz, 1H), 2.95 (s, 3H), 2.78 (ddd, J=15.8, 12.1, 6.5 Hz, 1H), 2.67-2.56 (m, 1H), 2.00-1.82 (m, 2H), 1.38 (s, 9H).

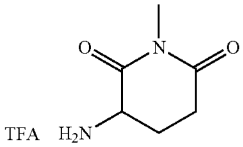

3-Amino-1-methylpiperidine-2,6-dione (TFA salt) (MA7-130): MA7-129 (410 mg, 1.69 mmol) was added to a mixture of trifluoroacetic acid (4 mL) and DCM (4 mL) and stirred at room temperature for 2 h. The mixture was concentrated under vacuum and the residual TFA azeotroped with ethyl acetate (2×5 mL) and DCM (2×5 mL). The residue was freeze dried to give MA7-130 as an off-white gummy solid (404 mg, 93%). $^1$H NMR (400 MHz, DMSO-$d_6$) δ 8.50 (s, 3H), 4.24 (broad d, J=12.7 Hz, 1H), 2.96 (s, 3H), 2.84-2.67 (m, 2H), 2.16-2.08 (m, 1H), 2.05-1.92 (m, 1H).

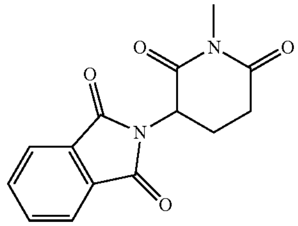 [SMILES: CN1C(=O)CCC(N2C(=O)c3ccccc3C2=O)C1=O]

2-(1-methyl-2,6-dioxopiperidin-3-yl)isoindoline-1,3-dione (MA7-166): (Goosen L., Plessis F. Pharm. Res., 2002, 19, 13-19.) MA7-130 (195 mg, 0.81 mmol), phthalic anhydride (120.8 mg, 0.81 mmol) and sodium acetate (100.3 mg, 1.22 mmol) in acetic acid (1 ml) were heated at 122° C. (external oil temperature) in a sealed 5 mL microwave vial using an oil bath for 16 h. The mixture was cooled and the solid isolated by filtration. The solid was washed with acetic acid (0.5 mL) and ether (2×5 mL). Trituration of the residue with DCM/hexanes gave pure MA7-166 (183 mg, 82%) as a white solid. HPLC: >99% [$t_R$=6.4 min, 30% MeCN, 70% water (with 0.1% TFA), 20 min]. $^1$H NMR (400 MHz, DMSO-$d_6$) δ 7.98-7.87 (m, 4H), 5.24 (dd, J=13.1, 5.4 Hz, 1H), 3.03 (s, 3H), 3.01-2.88 (m, 1H), 2.78 (ddd, J=17.2, 4.6, 2.5 Hz, 1H), 2.57 (dq, J=10.4, 3.6 Hz, 1H), 2.09 (dtd, J=13.2, 5.5, 2.5 Hz, 1H). $^{13}$C NMR (100 MHz, DMSO-$d_6$) δ 171.7, 169.6, 167.1, 134.9, 131.2, 123.4, 49.6, 31.1, 26.6, 21.2. HPLC-MS (ESI+): m/z 567.2 [100%, $(2M+Na)^+$], 295.1 [80%, $(M+Na)^+$], 273.1 [80%, $(M+H)^+$].

Scheme 9

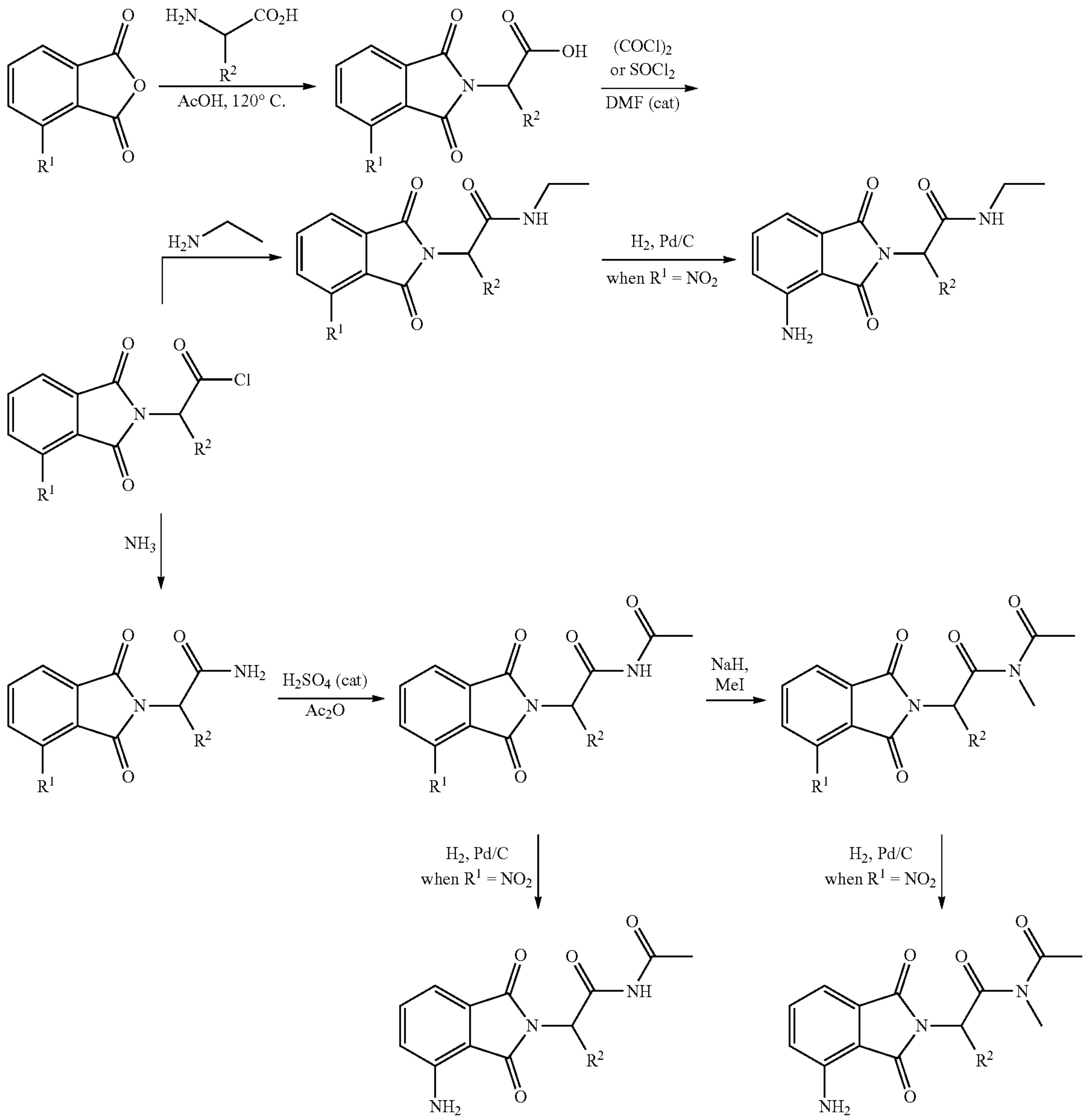

SY1-182

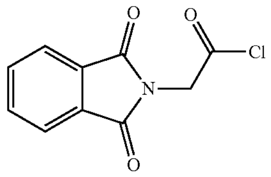

2-(1,3-dioxoisoindolin-2-yl)acetyl chloride (SY1-182): To a solution of phthaloylglycin (0.300 g, 1.46 mmol) in $CH_2Cl_2$ was added oxalyl chloride (1.480 g, 11.66 mmol) and DMF (0.010 g, 0.137 mmol) at 0° C. The mixture was stirred at 0° C. for 30 min., then warmed to room temperature and stirred for 3 h. The solvent was removed under reduced pressure. The solid residue was dissolved in $CH_2Cl_2$ and evaporated under reduced pressure (this procedure was repeated three times). The crude product was dried under vacuum to afford a yellow sold (0.310 g, 95%). This compound was used for next reaction without further purification. $^1H$ NMR (500 MHz, $CDCl_3$). δ 7.91 (dd, J=5.5, 3.2 Hz, 2H), 7.79 (dd, J=5.5, 3.1 Hz, 2H), 4.82 (s, 2H).

SY1-184

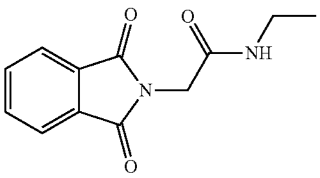

2-(1,3-dioxoisoindolin-2-yl)-N-ethylacetamide (SY1-184): To a solution of SY1-182 (0.090 g, 0.40 mmol) in 3 mL $CH_3CN$ was added ethylamine (2 M in THF, 2 mL, 0.80 mmol). The mixture was stirred at room temperature for 16 h. Solvent was removed under reduced pressure and the solid residue was triturated with $CH_2Cl_2$ and hexanes. The product was washed with $H_2O$ followed by hexanes and dried under vacuum to afford the product as a white solid (0.068 g, 74%). $^{1}$H NMR (500 MHz, DMSO-$d_6$) δ 8.20 (app t, J=5.5 Hz, 1H), 7.92-7.89 (m, 2H), 7.88-7.86 (m, 2H), 4.15 (s, 2H). 3.08 (qd, J=7.2, 5.5 Hz, 2H), 1.01 (t, J=7.2 Hz, 3H). $^{13}$C NMR (125 MHz, DMSO-$d_6$) δ 167.55, 165.58, 134.53, 131.78, 123.17, 40.14, 33.61, 14.60. HPLC-MS (ESI+): m/z 487.2 [100%, $(2M+Na)^+$], 255.2 [90%, $(M+Na)^+$], 233.2 [50%, $(M+H)^+$].

SY2-009

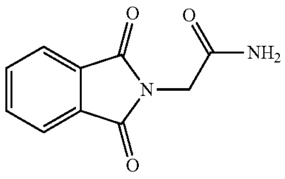

2-(1,3-dioxoisoindolin-2-yl)acetamide (SY2-009): To a solution of SY1-182 (0.300 g, 1.34 mmol) in $CH_2Cl_2$ (5 mL) was added ammonia solution (7 N in MeOH, 0.57 mL, 4.02 mmol) at 0° C. The mixture was allowed to warm to room temperature and stirred for 2 h. The mixture was diluted with hexanes and filtered. The solid product collected on frit was washed with water (20 mL) followed by hexanes (30 mL) and dried under vacuum to give the product as a white solid (0.200 g, 74%). $^{1}$H NMR (500 MHz, DMSO-$d_6$) δ 7.91-7.90 (m, 2H), 7.87-7.85 (m, 2H) 7.69 (s, 1H), 7.25 (s, 1H), 4.15 (s, 2H). $^{13}$C NMR (125 MHz, DMSO-$d_6$) δ 167.92, 167.56, 134.53, 131.75, 123.17, 39.95. HPLC-MS (ESI+): m/z 431.1 [100%, $(2M+Na)^+$], 227.2 [60%, $(M+Na)^+$], 205.2 [80%, $(M+H)^+$].

SY2-013

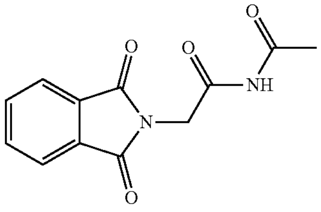

N-acetyl-2-(1,3-dioxoisoindolin-2-yl)acetamide (SY2-013): To a suspension of SY2-009 (0.200 g, 0.937 mmol) in acetic anhydride (3 mL) was added $H_2SO_4$ (5 μL, 0.094 mmol). The mixture was stirred at 90° C. for 3 h. The mixture was cooled to room temperature and quenched with saturated $NaHCO_3$ (30 mL). The mixture was extracted with EtOAc three times. The combined organic layer was dried over $Na_2SO_4$ and filtered. The filtrate was concentrated under reduced pressure and the crude product was purified by $SiO_2$ chromatography (0-50 gradient elution, EtOAc/hexanes) to afford the product as a white solid (0.160 g, 67%). $^{1}$H NMR (500 MHz, DMSO-$d_6$) δ 11.16 (s, 1H), 7.94-7.93 (m, 2H), 7.90-7.88 (m, 2H), 4.60 (s, 2H), 2.15 (s, 3H). $^{13}$C NMR (125 MHz, DMSO-$d_6$) δ 171.24, 168.12, 167.36, 134.79, 131.51, 123.37, 41.96, 24.47. HPLC-MS (ESI+): m/z 515.2 $(2M+Na)^+$, 269.1 $(M+Na)^+$, 247.2 $(M+H)^+$.

SY2-028

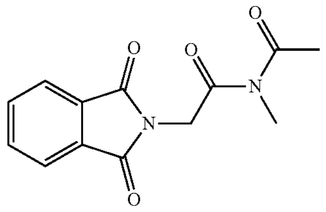

N-acetyl-2-(1,3-dioxoisoindolin-2-yl)-N-methylacetamide (SY2-028): To a solution of SY2-013 (0.060 g, 0.244 mmol) in anhydrous DMF (1 mL) was added NaH (60% dispersion in mineral oil, 0.012 g, 0.316 mmol) at 0° C. The mixture was stirred at 0° C. for 15 min then Mel (20 μL, 0.317 mmol) was added. The mixture was allowed to room temperature and stirred for 2 h, and quenched with water and extracted with EtOAc three times. The combined organic layer was dried over $Na_2SO_4$ and filtered. The filtrate was concentrated under reduced pressure and the crude product was purified by $SiO_2$ chromatography (0-50 gradient elution, EtOAc/hexanes) to afford the product as a white solid (0.052 g, 83%). HPLC: 99% [$t_R$=7.01 min, 45% MeOH, 55% water (with 0.1% TFA), 20 min, 254 nm] $^{1}$H NMR (500 MHz, DMSO-$d_6$) δ 7.94-7.90 (m, 2H), 7.90-7.88 (m, 2H), 4.80 (s, 2H), 3.19 (s, 3H), 2.36 (s, 3H). $^{13}$C NMR (125 MHz, DMSO-$d_6$) δ 171.93, 169.36, 167.42, 134.78, 131.52, 123.35, 43.61, 31.51, 25.60. HPLC-MS (ESI+): m/z 543.2 $(2M+Na)^+$, 283.1 $(M+Na)^+$, 261.1 $(M+H)^+$.

SY2-005

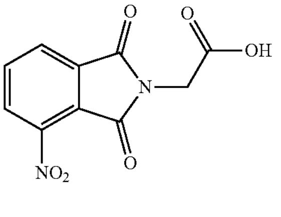

2-(4-Nitro-1,3-dioxoisoindolin-2-yl)acetic acid (SY2-005): The 3-nitrophthalic anhydride (0.500 g, 2.589 mmol) and glycine (0.194 g, 2.589 mmol) in AcOH (20 mL) were refluxed overnight.

The solution was concentrated under reduced pressure and hot 1,4-dioxane (5 mL) was added to the solid residue. Undissolved material was filtered and washed twice with 1 ml, hot 1,4-dioxane. The filtrate was diluted with water (10 mL). White solid product formed was filtered and washed with water (5 nL) three times followed by hexanes (20 mL). The product was dried under vacuum to afford SY2-005 as a white solid (0.520 g, 80%). $^{1}$H NMR (500 MHz, DMSO-$d_6$) δ 13.39 (br s, 1H), 8.35 (d, J=8.1 Hz, 1H), 8.25 (d, J=7.5 Hz, 1H), 8.12 (t, J=7.8 Hz, 1H), 4.34 (s, 2H). HPLC-MS (ESI+): m/z 523.1 $(2M+Na)^+$, 273.1 $(M+Na)^+$, 251.1 $(M+H)^+$.

SY2-007

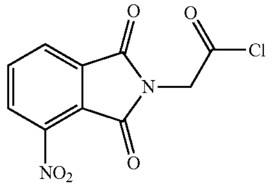

2-(4-Nitro-1,3-dioxoisoindolin-2-yl)acetyl chloride (SY2-007): To a suspension of SY2-005 (0.400 g, 1.599 mmol) in $SOCl_2$ (5 ml) was added DMF (0.012 g, 0.164 mmol) and the mixture was stirred at 75° C. for 3 h. $SOCl_2$ was removed under reduced pressure and the residue was co-evaporated with $CH_2Cl_2$ (5 mL) three times. The solid residue was dried under vacuum to afford the product as a yellow solid (0.430 g, 100.2%). $^1$H NMR (500 MHz, $CDCl_3$) δ 8.23 (dd, J=8.0, 1.0 Hz, 1H), 8.21 (dd, J=7.0, 1.0 Hz, 1H), 8.00 (dd, J=8.0, 7.5 Hz, 1H), 4.86 (s 3H).

SY2-008

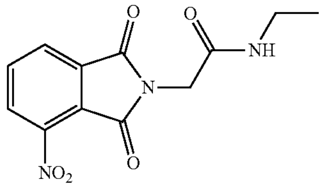

N-Ethyl-2-(4-nitro-1,3-dioxoisoindolin-2-yl)acetamide (SY2-008): This compound was synthesized using the same procedure described for SY1-184 except using SY2-007 (0.100 g, 0.372 mmol) and ethylamine (2 M in THF, 0.372 mL, 0.744 mmol) to afford an off-white solid (0.065 g, 63%). $^1$H NMR (500 MHz, DMSO-$d_6$) δ 8.34 (dd, J=8.1, 0.9 Hz, 1H), 8.23 (dd, J=7.5, 0.9 Hz, 1H), 8.22 (partially overlap with aromatic signals, 1H), 8.10 (t, J=8.1 Hz, 1H), 4.17 (s, 2H), 3.09 (qd, J=7.2, 5.5 Hz, 2H), 1.01 (t, J=7.2 Hz, 3H). HPLC-MS (ESI+): m/z 577.1 $(2M+Na)^+$, 300 $(M+Na)^+$, 278.1 $(M+H)^+$.

SY2-021

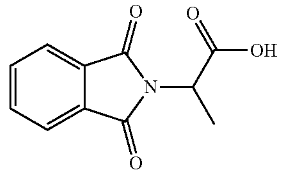

2-(1,3-Dioxoisoindolin-2-yl)propanoic acid (SY2-021): This compound was synthesized using the same procedure described for SY2-005 except using phthalicanhydride (1.00 g, 6.752 mmol) and DL-alanine (0.602, 6.752 mmol) to afford title compound as an off-white solid (1.301 g, 88%). $^1$H NMR (500 MHz, DMSO-$d_6$) δ 13.11 (br s, 1H), 7.92-7.89 (m, 2H), 7.88-7.86 (m, 2H), 4.88 (q, J=7.3 Hz, 1H), 1.55 (d, J=7.3 Hz, 3H). $^{13}$C NMR (125 MHz, DMSO-$d_6$) δ 171.03, 167.15, 134.76, 131.30, 123.30, 46.95, 14.83. HPLC-MS (ESI+): m/z 461.1 $(2M+Na)^+$, 242.1 $(M+Na)^+$, 220.1 $(M+H)^+$.

SY2-041

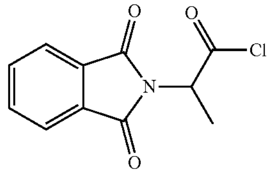

2-(1,3-Dioxoisoindolin-2-yl)propanoyl chloride (SY2-041): This compound was synthesized using the same procedure described for SY2-007 except using SY2-021 (1.300 g, 5.93 mmol) and DMF (0.043 g, 0.593 mmol) to afford title compound as a yellow solid (1.340 g, 95%). $^1$H NMR (500 MHz, $CDCl_3$) δ 7.91 (dd, J=5.5, 3.1 Hz, 2H), 7.79 (dd, J=5.5, 3.0 Hz, 2H), 5.17 (q, J=7.2 Hz, 1H), 1.79 (d, J=7.2 Hz, 3H).

SY2-047

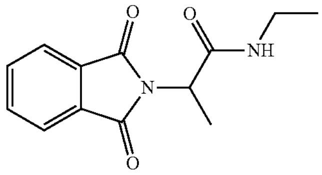

2-(1,3-Dioxoisoindolin-2-yl)-N-ethylpropanamide (SY2-047): To a solution of SY2-041 (0.200 g, 0.842 mmol) in $CH_2Cl_2$ (3 mL) was added ethylamine (2 M in THF, 0.85 mL, 1.700 mmol) at 0° C. The mixture was stirred at 0° C. for 2 h. Solvent was removed under reduced pressure and the solid residue was purified by $SiO_2$ chromatography (0-40 gradient elution, EtOAc/hexanes) to afford the product as a white solid (0.176 g, 85%). HPLC: 99% [$t_R$=5.78 min, 45% MeOH, 55% water (with 0.1% TFA), 20 min, 254 nm] $^1$H NMR (500 MHz, $CDCl_3$) δ 8.02 (app t, J=5.6 Hz, 1H), 7.89-7.84 (m, 4H), 4.68 (q, J=7.3 Hz, 1H), 3.06 (qd, J=7.2, 5.6 Hz, 2H), 1.53 (d, J=7.3 Hz, 3H), 0.97 (t, J=7.2 Hz, 3H). $^{13}$C NMR (125 MHz, DMSO-$d_6$) δ 168.17, 167.43, 134.34, 131.88, 123.01, 48.11, 33.81, 14.95, 14.66. HPLC-MS (ESI+): m/z 515.2 $(2M+Na)^+$, 247.2 $(M+H)^+$.

SY2-043

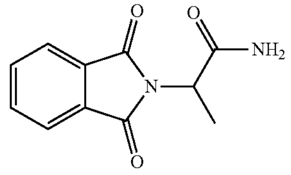

2-(1,3-Dioxoisoindolin-2-yl)propanamide (SY2-043): This compound was synthesized using the same procedure described for SY2-009 except using SY2-041 (0.600 g, 2.525 mmol) and $NH_3$ (7 N in MeOH, 0.800 mL, 5.600 mmol) to afford title compound as an off-white solid (0.473 g, 86%). $^1$H NMR (500 MHz, DMSO-$d_6$) δ 7.88-7.84 (m, 4H), 7.55 (s, 1H), 7.17 (s, 1H), 4.68 (q, J=7.3 Hz, 1H), 1.54 (d, J=7.3 Hz, 3H). $^{13}$C NMR (125 MHz, DMSO-$d_6$) δ 170.63, 167.46, 134.34, 131.82, 123.00, 48.05, 14.91. HPLC-MS (ESI+): m/z 459.2 $(2M+Na)^+$, 219.1 $(M+H)^+$.

SY2-048

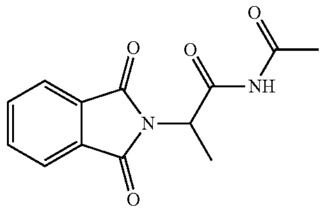

N-acetyl-2-(1,3-dioxoisoindolin-2-yl)propanamide (SY2-048): This compound was synthesized using the same procedure described for SY2-013 except using SY2-043 (0.400 g, 1.833 mmol) and $H_2SO_4$ (0.018 g, 0.184 mmol). The crude product was purified by $SiO_2$ chromatography (0-40 gradient elution, EtOAc/hexanes) to afford the title compound as a white solid (0.378 g, 78%). HPLC: 99% [$t_R$=5.99 min, 45% MeOH, 55% water (with 0.1% TFA), 20 min, 254 nm]. $^1$H NMR (500 MHz, DMSO-$d_6$) δ 10.88 (s, 1H), 7.90-7.85 (m, 4H), 4.97 (q, J=7.2 Hz, 1H), 2.21 (s, 3H), 1.52 (d, J=7.2 Hz, 3H). $^{13}$C NMR (125 MHz, DMSO-$d_6$) δ 171.62, 169.70, 167.19, 134.51, 131.70, 123.13, 49.13, 25.21, 14.70. HPLC-MS (ESI+): m/z 543.2 $(2M+Na)^+$, 283.1 $(M+Na)^+$, 261.2 $(M+H)^+$.

SY2-052

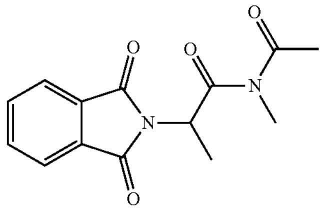

N-acetyl-2-(1,3-dioxoisoindolin-2-yl)-N-methylpropanamide (SY2-052): This compound was synthesized using the same procedure described for SY2-028 except using SY2-048 (0.201 g, 0.772 mmol), NaH (60% dispersion in mineral oil, 0.040 g, 1.00 mmol) and MeI (0.143 g, 1.01 mmol) to afford title compound as colorless oil (0.082 g, 54%). $^1$H NMR (500 MHz, $CDCl_3$) δ 7.85 (dd, J=5.4, 3.0 Hz, 2H), 7.74 (dd, J=5.5, 3.0 Hz). 5.55 (q, J=7.1 Hz, 1H), 3.15 (s, 3H), 2.35 (s, 3H), 1.67 (d, J=7.0, 3H). $^{13}$C NMR (125 MHz, $CDCl_3$) δ 173.61, 173.07, 167.58, 134.42, 131.82, 123.73, 50.75, 32.31, 25.68, 15.61. HPLC-MS (ESI+): m/z 571.3 $(2M+Na)^+$, 297.1 $(M+Na)^+$, 275.1 $(M+H)^+$.

SY2-023

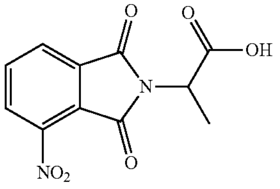

2-(4-Nitro-1,3-dioxoisoindolin-2-yl)propanoic acid (SY2-023): This compound was synthesized using the same procedure described for SY2-005 except using 3-nitrophthalic anhydride (1.500 g, 7.768 mmol) and DL-alanine (0.692, 7.767 mmol) to afford the title compound as an off-white solid (1.723 g, 84%). $^1$H NMR (500 MHz, DMSO-$d_6$) δ 13.22 (br s, 1H), 8.34 (dd, J=8.1, 0.9 Hz, 1H), 8.22 (dd, J=7.5, 0.9 Hz, 1H), 8.10 (t, J=7.8 Hz, 1H), 4.94 (q, J=7.3 Hz, 1H), 1.55 (d, J=7.3 Hz, 3H). $^{13}$C NMR (125 MHz, DMSO-$d_6$) δ 170.65, 165.16, 162.54, 144.41, 136.64, 133.09, 128.71, 127.15, 122.59, 47.48, 14.54. HPLC-MS (ESI+): m/z 551 $(2M+Na)^+$, 265.1 $(M+H)^+$.

SY2-042

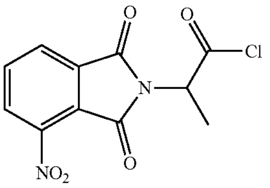

2-(4-Nitro-1,3-dioxoisoindolin-2-yl)propanoyl chloride (SY2-042): This compound was synthesized using the same procedure described for SY2-007 except using SY2-023 (1.500 g, 5.678 mmol) and DMF (0.042 g, 0.568 mmol) to afford the title compound as a brown oil (1.864 g, 110%). $^1$H NMR (500 MHz, $CDCl_3$) δ 8.21-8.18 (m, 2H), 8.00 (t, J=7.8 Hz, 1H), 5.19 (q, J=7.2 Hz, 1H), 1.82 (d, J=7.2 Hz, 3H).

SY2-046

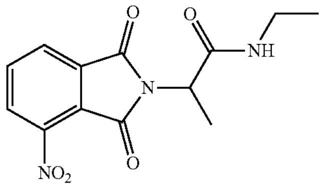

N-ethyl-2-(4-nitro-1,3-dioxoisoindolin-2-yl)propanamide (SY2-046): This compound was synthesized using the same procedure described for SY2-047 except using SY2-042 (0.300 g, 1.061 mmol) and ethylamine (2 M in THF, 1.1 mL, 2.2 mmol) to afford the title compound as a pale yellow solid (0.223 g, 72%). $^1$H NMR (500 MHz, DMSO-$d_6$) δ 8.31 (dd, J=8.1, 0.9 Hz, 1H), 8.19 (dd, J=7.5, 0.9 Hz, 1H), 8.07 (dd, J=8.1, 7.5 Hz, 1H), 8.04 (app t, J=5.6 Hz, 1H), 4.69 (q, J=7.2 Hz, 1H), 3.07 (qd, d, J=7.2, 5.6 Hz, 2H), 1.52 (d, J=7.2 Hz, 3H), 0.97 (t, J=7.2 Hz, 3H). $^{13}$C NMR (125 MHz, DMSO-$d_6$) δ 167.77, 165.44, 162.87, 144.26, 136.17, 133.69, 128.14, 126.72, 123.08, 48.05, 33.81, 14.65, 14.64. HPLC-MS (ESI+): m/z 605.2 $(2M+Na)^+$, 314.2 $(M+Na)^+$, 292.2 $(M+H)^+$.

SY2-045

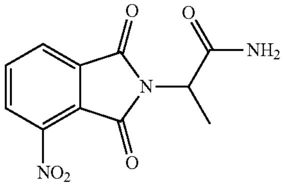

2-(4-Nitro-1,3-dioxoisoindolin-2-yl)propanamide (SY2-045): This compound was synthesized using the same procedure described for SY2-009 except using SY2-042 (1.00 g, 3.538 mmol) and $NH_3$ (7 N in MeOH, 1.1 mL 7.700 mmol) to afford the title compound as an off-white solid (0.602 g, 65%). $^1$H NMR (500 MHz, DMSO-$d_6$) δ 8.30 (d, J=8.0 Hz, 1H), 8.18 (d, J=7.4 Hz, 1H), 8.07 (t, J=7.8 Hz, 1H), 7.59 (s, 1H), 7.21 (s, 1H), 4.68 (q, J=7.3 Hz, 1H), 1.52 (d, J=7.3 Hz, 1H). HPLC-MS (ESI+): m/z 549.1 $(2M+Na)^+$, 264.1 $(M+H)^+$.

SY2-049

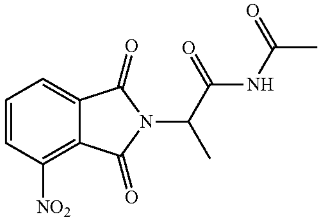

N-acetyl-2-(4-nitro-1,3-dioxoisoindolin-2-yl)propanamide (SY2-049): This compound was synthesized using the same procedure described for SY2-013 except using SY2-045 (0.600 g, 2.280 mmol) and $H_2SO_4$ (0.022 g, 0.022 mmol). The crude product was purified by $SiO_2$ chromatography (0-60 gradient elution, EtOAc/hexanes) to afford the title compound as a pale yellow solid (0.453 g, 65%). $^1H$ NMR (500 MHz, DMSO-$d_6$) δ 10.87 (s, 1H), 8.31 (dd, J=8.1, 0.9 Hz, 1H), 8.19 (dd, J=7.5, 0.9 Hz, 1H), 8.08 (t, J=7.8 Hz, 1H), 4.98 (q, J=7.1 Hz, 1H), 2.22 (s, 3H), 1.50 (d, J=7.1 Hz, 3H). $^{13}C$ NMR (125 MHz, DMSO-$d_6$) δ 171.78, 169.22, 165.21, 162.61, 144.28, 136.31, 133.53, 128.33, 126.87, 123.04, 49.37, 25.32, 14.40. HPLC-MS (ESI+): m/z 633.1 $(2M+Na)^+$, 328.2 $(M+Na)^+$, 306.2 $(M+H)^+$.

SY2-053

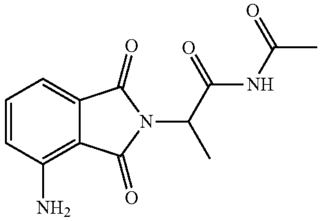

N-acetyl-2-(4-amino-1,3-dioxoisoindolin-2-yl)propanamide (SY2-053): A round bottom flask was charged with Pd/C (10% on activated carbon, 0.030 mg) and EtOAc (3 mL) was added. A solution of SY2-049 (0.150 g, 0.419 mmol) in MeOH (3 mL) was slowly added to the flask and hydrogen balloon was attached. The mixture was stirred for 6 h at room temperature. The mixture was filtered through a pad of celite and the filtrate was concentrated under reduced pressure. The residue was triturated with MeOH and hexanes to afford title compound as a yellow solid (0.112 g, 83%). $^1H$ NMR (500 MHz, DMSO-$d_6$) δ 10.87 (s, 1H), 7.44 (dd, J=8.4, 7.0 Hz, 1H), 6.99-6.96 (m, 2H), 6.47 (br s, 2H), 4.87 (q, J=7.1 Hz, 1H), 2.20 (s, 3H), 1.49 (d, J=7.1 Hz, 3H). $^{13}C$ NMR (125 MHz, DMSO-$d_6$) δ 171.56, 170.02, 168.69, 167.39, 146.52, 135.17, 132.46, 121.34, 110.68, 109.14, 48.74, 25.20, 14.82. HPLC-MS (ESI+): m/z 573.3 $(2M+Na)^+$, 298.2 $(M+Na)^+$, 276.2 $(M+H)^+$.

SY2-054

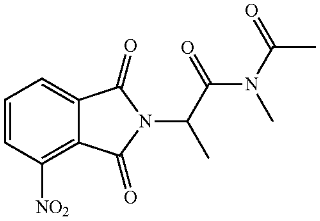

N-acetyl-N-methyl-2-(4-nitro-1,3-dioxoisoindolin-2-yl)propanamide (SY2-054): This compound was synthesized using the same procedure described for SY2-028 except using SY2-053 (0.150 g, 0.491 mmol), NaH (60% dispersion in mineral oil, 0.026 g, 0.639 mmol) and MeI (0.091 g, 0.641 mmol) to afford title compound as yellow oil (0.081 g, 54%). $^1H$ NMR (500 MHz, DMSO-$d_6$) δ 8.32 (dd, J=8.1, 0.9 Hz, H), 8.20 (dd, J=7.5, 0.9 Hz, 1H), 8.09 (t, J=8.0 Hz, 1H), 5.63 (q, J=7.0 Hz, 1H), 3.08 (s, 3H), 2.28 (s, 3H), 1.54 (d, J=7.0 Hz, 3H). $^{13}C$ NMR (125 MHz, DMSO-$d_6$) δ 173.06, 172.82, 165.27, 162.60, 144.40, 136.52, 133.07, 128.68, 127.14, 122.61, 50.84, 31.94, 25.30, 14.63. HPLC-MS (ESI+): m/z 661.2 $(2M+Na)^+$, 342.1 $(M+Na)^+$, 320.2 $(M+H)^+$.

SY2-056

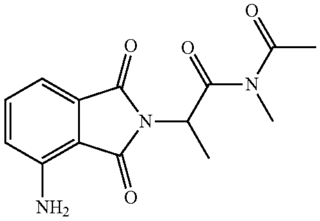

N-acetyl-2-(4-amino-1,3-dioxoisoindolin-2-yl)-N-methylpropanamide (SY2-056): This compound was synthesized using the same procedure described for SY2-053 except using SY2-054 (0.060 g, 0.188 mmol) and Pd/C (10% on activated carbon, 0.012 mg) to afford title compound as a yellow solid (0.049 g, 91%). $^1H$ NMR (500 MHz, DMSO-$d_6$) δ 7.44 (dd, J=8.4, 6.9 Hz, 1H), 6.99-6.65 (m, 2H), 6.50 (br s, 2H), 5.48 (q, J=7.0 Hz, 1H), 3.02 (s, 3H), 2.28 (s, 3H), 1.47 (d, J=7.0 Hz, 3H), $^{13}C$ NMR (125 MHz, DMSO-$d_6$) δ 173.70, 171.84, 168.55, 167.28, 146.69, 135.40, 131.87, 121.67, 110.94, 108.39, 49.44, 31.67, 25.23, 15.12. HPLC-MS (ESI+): m/z 601.3 $(2M+Na)^+$, 312.1 $(M+Na)^+$, 290.2 $(M+H)^+$.

SY2-055

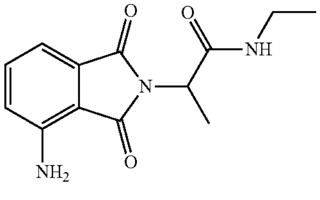

2-(4-amino-1,3-dioxoisoindolin-2-yl)-N-ethylpropanamide (SY2-055): This compound was synthesized using the same procedure described for SY2-053 except using SY2-046 (0.100 g, 0.343 mmol) and Pd/C (10% on activated carbon, 0.020 mg) to afford title compound as a yellow solid (0.082 g, 91%). $^1$H NMR (500 MHz, DMSO-$d_6$) δ 7.97 (app t, J=5.7 Hz, 1H), 7.43 (dd, J=8.4, 7.0 Hz, 1H), 7.04-6.80 (m, 2H), 6.44 (br s, 2H), 4.59 (q, J=7.3 Hz, 1H), 3.09-3.03 (m, 2H), 1.49 (d, J=7.3 Hz, 3H), 0.98 (t, J=7.2 Hz, 3H). $^{13}$C NMR (125 MHz, DMSO-$d_6$) δ 168.99, 168.47, 167.62, 146.42, 135.00, 132.63, 121.17, 110.58, 109.46, 47.65, 33.81, 15.07, 14.67. HPLC-MS (ESI+): m/z 545.2 (2M+Na)$^+$, 261.2 (M+H)$^+$.

SY2-019

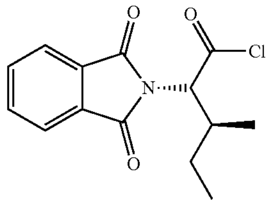

(2S,3S)-2-(1,3-Dioxoisoindolin-2-yl)-3-methylpentanoyl chloride (SY2-019): This compound was synthesized using the same procedure described for SY2-007 except using phthaloyl-L-isoleucine (1.00 g, 3.827 mmol) and DMF (0.028 g, 0.380 mmol) to afford the title compound as a brown oil (1.864 g, 110%). $^1$H NMR (500 MHz, $CDCl_3$) δ 7.93 (dd, J=5.4, 3.1, 2H), 7.80 (dd, J=5.5, 3.1, 2H), 4.82 (d, J=8.6 Hz, 1H), 2.52-2.50 (m, 1H), 1.49-1.43 (m, 1H), 1.14 (d, J=6.6 Hz, 3H), 1.12-1.04 (m, 1H), 0.87 (t, J=7.4 Hz, 3H).

SY2-031

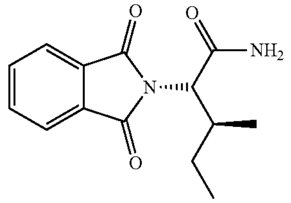

(2S,3S)-2-(1,3-Dioxoisoindolin-2-yl)-3-methylpentanamide (SY2-031): This compound was synthesized using the same procedure described for SY2-009 except using SY2-019 (0.600 g, 2.145 mmol) and $NH_3$ (7 N in MeOH, 0.9 mL, 6.300 mmol) to afford the title compound as an off-white solid (0.460 g. 82%) $^1$H NMR (500 MHz, DMSO-$d_6$) δ 7.90-7.85 (m, 4H), 7.50 (s, 1H), 7.13 (s, 1H), 4.35 (d, J=9.0 Hz, 1H), 2.54-2.48 (m, 1H), 1.40-1.35 (m, 1H), 0.99 (d, J=6.7 Hz, 3H), 0.96-0.84 (m, 1H), 0.78 (t, J=7.4 Hz, 3H). HPLC-MS (ESI+): m/z 543.3 (2M+Na)$^+$, 283.2 (M+Na)$^+$, 261.2 (M+H)$^+$.

SY2-033

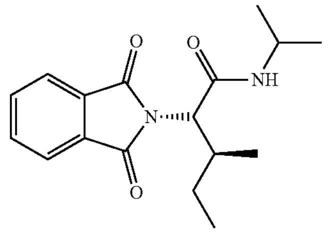

(2S,3S)—N-acetyl-2-(1,3-dioxoisoindolin-2-yl)-3-methylpentanamide (SY2-033): This compound was synthesized using the same procedure described for SY2-013 except using SY2-031 (0.46 g, 1.767 mmol) and $H_2SO_4$ (0.017 g, 0.177 mmol). The crude product was purified by $SiO_2$ chromatography (0-40% gradient elution, EtOAc/hexanes) to afford the title compound as a white solid (0.402 g, 75%). $^1$H NMR (500 MHz, DMSO-$d_6$) δ 10.84 (s, 1H), 7.91-7.86 (m, 4H), 4.67 (d, J=7.4 Hz, 1H), 2.46-2.40 (m, 1H), 2.20 (s, 3H), 1.48-1.42 (m, 1H), 0.99-0.93 (m, 1H), 0.95 (d, J=6.8 Hz, 3H), 0.81 (t, J=7.3 Hz, 3H). $^{13}$C NMR (125 MHz, DMSO-$d_6$) δ 171.69, 168.48, 167.57, 134.66, 131.34, 123.17, 58.09, 34.09, 25.36, 24.97, 16.29, 11.17. HPLC-MS (ESI+): m/z 627.4 (2M+Na)$^+$, 303.2 (M+H)$^+$.

SY2-016

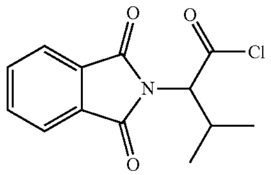

2-(1,3-Dioxoisoindolin-2-yl)-3-methylbutanoyl chloride (SY2-016): This compound was synthesized using the same procedure described for SY2-007 except using phthaloyl-DL-valine (0.50 g, 2.022 mmol) and DMF (0.015 g, 0.0205 mmol) to afford the title compound as a yellow oil (0.548 g, 102%). $^1$H NMR (500 MHz, $CDCl_3$) δ 7.93 (dd, J=5.5, 3.1 Hz, 2H), 7.81 (J=5.5, 3.1 Hz, 2H), 4.74 (d, J=8.4 Hz, 1H), 2.75 (m, 1H), 1.16 (d, J=6.6 Hz, 3H), 0.92 (d, J=6.9 Hz, 3H).

SY2-029

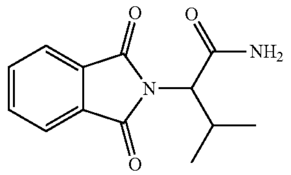

2-(1,3-dioxoisoindolin-2-yl)-3-methylbutanamide (SY2-029): This compound was synthesized using the same procedure described for SY2-009 except using SY2-016 (0.400 g, 1.506 mmol) and $NH_3$ (7 N in MeOH, 0.65 mL, 4.550 mmol) to afford the title compound as an off-white solid (0.261 g. 70%). $^1$H NMR (500 MHz, DMSO-$d_6$) δ 7.91-7.85 (m, 4H), 7.49 (s, 1H), 7.11 (s, 1H), 4.27 (d, J=8.6 Hz, 1H), 2.70-2.63 (m, 1H), 1.02 (d, J=6.7 Hz, 1H), 0.77 (d, J=6.7 Hz, 1H). $^{13}$C NMR (125 MHz, DMSO-$d_6$) δ 169.49, 167.69, 134.53, 131.37, 123.16, 58.43, 21.17, 20.98, 19.31. HPLC-MS (ESI+): m/z 515.3 (2M+Na)$^+$, 269.1 (M+Na)$^+$, 247.1 (M+H)$^+$.

SY2-017

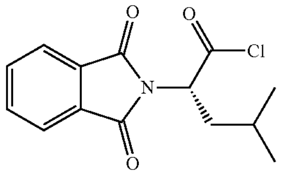

(S)-2-(1,3-Dioxoisoindolin-2-yl)-4-methylpentanoyl chloride (SY2-017): This compound was synthesized using the same procedure described for SY2-007 except using phthaloyl-L-leucine (1.00 g, 3.827 mmol) and DMF (0.028 g, 0.380 mmol) to afford the title compound as a yellow oil (1.20 g, 108%). $^1$H NMR (500 MHz, $CDCl_3$) δ 7.92 (dd, J=5.5, 3.1 Hz, 2H), 7.79 (dd, J=5.5, 3.0 Hz, 2H), 5.13 (dd, J=11.1, 4.4 Hz, 1H), 2.37 (ddd, J=14.2, 11.1, 4.2 Hz, 1H). 2.04 (ddd, J=14.3, 10.1, 4.3 Hz, 1H), 11.54-1.50 (m, 1H), 0.97, J 6.6 Hz, 3H), 0.94 (d, J 6.6 Hz, 3H)

SY2-030

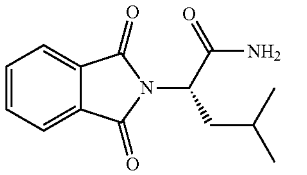

(S)-2-(1,3-Dioxoisoindolin-2-yl)-4-methylpentanamide (SY2-030): This compound was synthesized using the same procedure described for SY2-009 except using SY2-017 (0.500 g, 1.788 mmol) and $NH_3$ (7 N in MeOH, 0.760 mL, 5.250 mmol) to afford the title compound as an off-white solid (0.363 g. 78%) $^1$H NMR (500 MHz, DMSO-$d_6$) δ 7.90-7.85 (m, 4H), 7.57 (s, 1H), 7.19 (s, 1H), 4.64 (dd, J=11.9, 4.2 Hz, 1H), 2.17 (ddd, J=13.9, 11.9, 3.9 Hz, 1H), 1.86 (ddd, J=14.2, 10.4, 4.2 Hz, 1H), 1.35-1.31 (m, 1H), 0.85 (d, J=6.6 Hz, 3H), 0.83 (d, J=6.6 Hz, 1H). HPLC-MS (ESI+): m/z 543.2 $(2M+Na)^+$, 283.2 $(M+Na)^+$, 261.2 $(M+H)^+$.

SY2-036

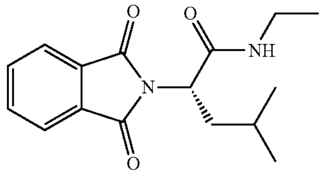

S)-2-(1,3-Dioxoisoindolin-2-yl)-N-ethyl-4-methylpentanamide (SY2-036): This compound was synthesized using the same procedure described for SY2-047 except using SY2-030 (0.130 g, 0.465 mmol) and ethylamine (2M in THF, 0.470 mL, 0.940 mmol) to afford the title compound as a white solid (0.099 g, 74%). $^1$H NMR (500 MHz, DMSO-$d_6$) δ 8.05 (app t, J=5.6 Hz, 1H), 7.91-7.85 (m, 4H), 4.65 (dd, J=11.8, 4.3 Hz, 1H), 3.06 (quintet, J=7.0 Hz, 2H), 2.15 (ddd, J=13.9, 11.8, 3.8 Hz, 1H), 1.87 (ddd, J=14.3, 10.3, 4.3 Hz, 1H)), 1.37-1.29 (m, 1H), 0.97 (t, J=7.2 Hz, 3H), 0.85 (d, J=6.5 Hz, 3H), 0.84 (d, J=6.5 Hz, 3H). $^{13}$C NMR (125 MHz, DMSO-$d_6$) δ 167.93, 167.75, 134.52, 131.56, 123.15, 51.41, 36.6, 33.82, 24.72, 23.23, 20.75, 14.63. HPLC-MS (ESI+): m/z 599.3 $(2M+Na)^+$, 311.2 $(M+Na)^+$, 289.2 $(M+H)^+$.

Scheme 10

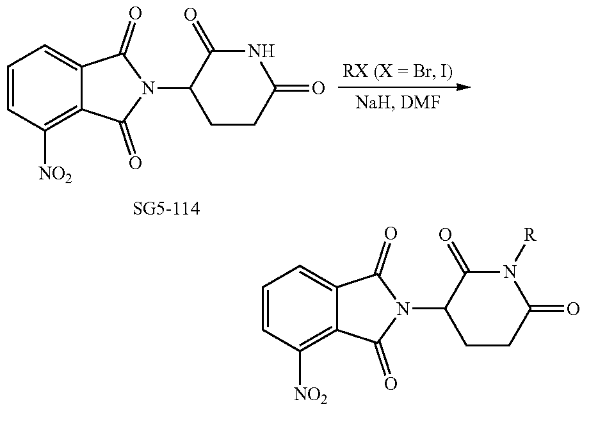

SG5-114

General procedure: The SG5-114 (0.200 g, 0.660 mmol) was dissolved in dry DMF (2 mL) and NaH (0.237 mg, 0.99 mmol, 1.5 equiv) was added at room temperature. The reaction mixture was stirred for 30 min and alkyl halide RX (1.2 equiv) was added. The mixture was stirred for 18 h at room temperature. The reaction mixture was quenched with water (1 mL) and the solvent was removed using Biotage V-10 evaporator. The residue was purified using $SiO_2$ using EtOAc and hexanes.

MA7-148-1

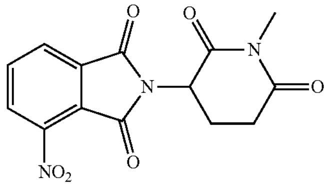

2-(1-Methyl-2,6-dioxopiperidin-3-yl)-4-nitroisoindoline-1,3-dione (MA7-148-1): This compound was prepared using the general procedure described for Scheme 10 employing MeI (0.112 g, 0.790 mmo) to afford title compound as an off-white solid (0.098 g, 47%). HPLC: 99.8% [$t_R$=5.2 min, 35% $CH_3CN$, 65% water (with 0.1% TFA), 20 min, 254 nm]. $^1$H NMR (400 MHz, DMSO-$d_6$) δ 8.36 (dd, J=8.1, 0.7 Hz, 1H), 8.25 (dd, J=7.5, 0.7 Hz, 1H), 8.13 (t, J=7.5 Hz, 1H), 5.27 (dd, J=13.1, 5.4 Hz, 1H), 3.04 (s, 3H), 2.95 (ddd, J=17.4, 13.9, 5.4 Hz, 1H), 2.78 (ddd, J=17.4, 4.3, 3.5 Hz, 1H), 2.57-2.48 (m, 1H), 2.11-2.06 (m, 1H). HPLC-MS (ESI+): m/z 657.1 $(2M+Na)^+$, 340.1 $(M+Na)^+$, 318.1 $(M+H)^+$.

MA7-148-2

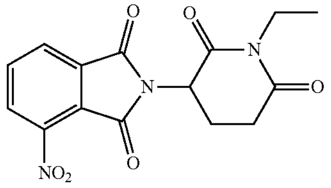

2-(1-Ethyl-2,6-dioxopiperidin-3-yl)-4-nitroisoindoline-1,3-dione (MA7-148-2): This compound was prepared using the general procedure described for Scheme 10 employing EtI (0.123 g, 0.790 mmo) to afford title compound as an off-white solid (0.096 g, 44%). HPLC: 99.8% [$t_R$=5.97 min, 35% $CH_3CN$, 65% water (with 0.1% TFA), 20 min, 254 nm]. $^1$H NMR (400 MHz, DMSO-$d_6$) δ 8.36 (d, J=8.0 Hz, 1H), 8.25 (d, J=7.4 Hz, 1H), 8.13 (t, J=7.8 Hz, 1H), 5.28 (dd, J=13.0 5.4 Hz, 1H), 3.69 (q, J=7.1 Hz, 2H), 2.97 (ddd, J=17.1, 13.9, 5.4 Hz, 1H), 2.80-2.67 (m, 1H), 2.55-2.44 (m, 1H), 2.11-2.06 (m, 1H), 1.02 (t, J=7.0 Hz, 3H). HPLC-MS (ESI+): m/z 685.2 $(2M+Na)^+$, 354.1 $(M+Na)^+$, 332.1 $(M+H)^+$.

MA7-148-3

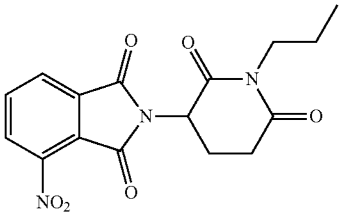

2-(2,6-Dioxo-1-propylpiperidin-3-yl)-4-nitroisoindoline-1,3-dione (MA7-148-3): This compound was prepared using the general procedure described for Scheme 10 employing n-PrI (0.135 g, 0.790 mmol) to afford title compound as a beige solid (0.117 g, 51%). HPLC: 99.8% [$t_R$=5.97 min, 35% $CH_3CN$, 65% water (with 0.1% TFA), 20 min, 254 nm]. $^1$H NMR (400 MHz, DMSO-$d_6$) δ 8.36 (d, J=8.0 Hz, 1H), 8.24 (d, J=7.5 Hz, 1H), 8.12 (t, J=7.8 Hz, 1H), 5.29 (dd, J=13.0, 5.4 Hz, 1H), 3.62 (m, 2H), 2.98 (ddd, J=17.1, 14.4, 5.4 Hz, 1H), 2.75-2.73 (m, 1H), 2.54-2.44 (m, 1H), 2.11-2.06 (m, 1H), 1.45 (sextet, J=7.4 Hz, 2H), 0.82 (t, J=7.4 Hz, 3H). HPLC-MS (ESI+): m/z 713.2 $(2M+Na)^+$, 368.1 $(M+Na)^+$, 346.2 $(M+H)^+$. HRMS (ESI+): m/z calcd for $C_{16}H_{15}N_3O_6$ $(M+Na)^+$368.0856, found 368.0849.

MA7-184-4

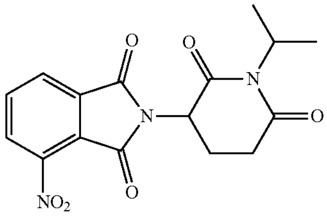

2-(1-Isopropyl-2,6-dioxopiperidin-3-yl)-4-nitroisoindoline-1,3-dione (MA7-184-4): This compound was prepared using the general procedure described for Scheme 10 employing n-PrI (0.135 g, 0.790 mmo) to afford title compound as an yellow solid (0.082 g, 36%). HPLC: 98% [$t_R$=20.6 min, 5-95 gradient elution, $CN_3CN/H_2O$ (with 0.1% TFA), 30 min, 254 nm]. $^1$H NMR (400 MHz, DMSO-$d_6$) δ 8.36 (d, J=8.1 Hz, 1H), 8.24 (d, J=7.5 Hz, 1H), 8.13 (t, J=7.8 Hz, 1H), 5.22 (dd, J=13.0, 5.4 Hz, 1H), 4.81 (septet, J=6.8 Hz, 1H), 2.94 (ddd, J=17.1, 13.9, 5.4 Hz, 1H), 2.73 (dt, J=14.6 2.8 Hz, 1H), 2.57-2.43 (m, 1H), 2.08-2.03 (m, 1H), 2.29 (d, J=6.8 Hz, δH). HPLC-MS. (ESI+): m/z 713.2 $(2M+Na)^+$, 346.2 $(M+H)^+$.

MA7-148-5

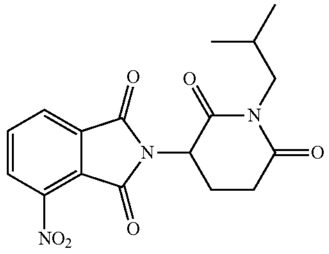

2-(1-Isobutyl-2,6-dioxopiperidin-3-yl)-4-nitroisoindoline-1,3-dione (MA7-148-5): This compound was prepared using the general procedure described for Scheme 10 employing 1-bromo-2-methylpropane (0.108 g, 0.790 mmo) to afford title compound as a white solid (0.123 g, 54%). HPLC: 99.4% [$t_R$=12.7 min, 50% $CH_3CN$, 50% water (with 0.1% TFA), 20 min, 254 nm]. $^1$H NMR (400 MHz, DMSO-$d_6$) δ 8.36 (d, J=8.0 Hz, 1H), 8.25 (d, J=7.4 Hz, 1H), 8.13 (t, J=7.8 Hz, 1H), 5.29 (dd, J=13.0, 5.4 Hz, 1H), 3.60-3.40 (m, 2H), 3.00 (ddd, J=18.6, 14.2, 5.4 Hz, 1H), 2.84-2.74 (m, 1H), 2.60-2.43 (m, 1H), 2.15-2.05 (m, 1H), 1.92-1.81 (m, 1H), 0.83 (d, J=6.6 Hz, δH). HPLC-MS (ESI+): m/z 741.2 $(2M+Na)^+$, 382.2 $(M+Na)^+$, 360.2 $(M+H)^+$.

Scheme 11

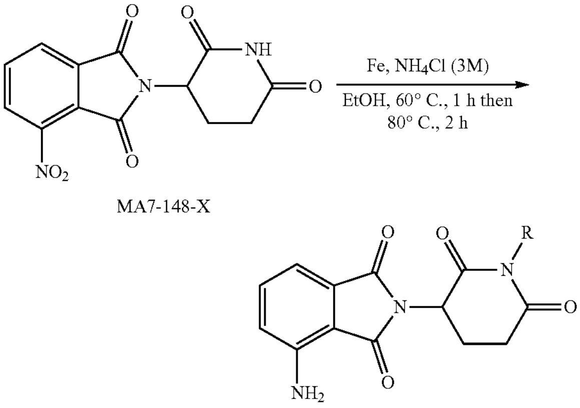

MA7-148-X

MA7-152, MA7-164-X

General procedure: The MA7-148-X was dissolved in absolute ethanol and then freshly prepared 3 M $NH_4Cl$ solution was added at room temperature followed by the addition of Fe powder (2 equiv). The mixture was heated at 60° C. for 1 h. An additional Fe powder (2 equiv) was added and the mixture was heated at 80° C. for 2h. The mixture was allowed to cool to room temperature and water (5 mL) was added. The mixture was extracted with EtOAc (10 mL×4). The combined EtOAc layer was dried over $Na_2SO_4$ and filtered. The solvent was removed under reduced pressure to give the desired product.

MA7-152

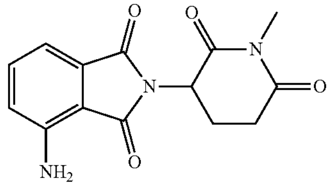

4-Amino-2-(1-methyl-2,6-dioxopiperidin-3-yl)isoindoline-1,3-dione (MA7-152): This compound was prepared using the general procedure described for Scheme 11 employing MA7-148-1 (0.040 g, 0.126 mmol), Fe (0.028 g, 0.500 mmol), and 3 M $NH_4Cl$ (336 μL) to afford the title compound as a yellow solid (0.026 g, 72%). HPLC: 98.5% [$t_R$=13.8 min, 20% $CH_3CN$, 80% $H_2O$ (with 0.1% TFA), 20 min, 254 nm]. $^1H$ NMR (400 MHz, DMSO-$d_6$) δ 7.47 (dd, J=8.4, 7.0 Hz, 1H), 7.04-6.96 (m, 2H), 6.53 (br s, 2H), 5.11 (dd, J=13.0, 5.4 Hz, 1H), 3.01 (s, 3H), 2.94 (ddd, J=17.2, 13.9, 5.4, 1H), 2.75 (ddd, J=17.1, 4.5, 2.6, Hz, 1H), 2.58-2.52 (m, 1H), 2.06-2.02 (m, 1H), HPLC-MS (ESI+): m/z 597.2 $(2M+Na)^+$, 310.1 $(M+Na)^+$, 288.2 $(M+H)^+$.

MA7-164-1

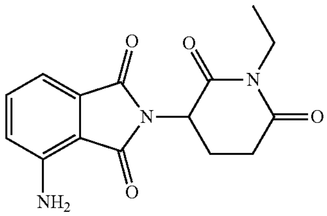

4-Amino-2-(1-ethyl-2,6-dioxopiperidin-3-yl)isoindoline-1,3-dione (MA7-164-1): This compound was prepared using the general procedure described for Scheme 11 employing MA7-148-2 (0.050 g, 0.15 mmol), Fe (0.0337 g, 0.60 mmol), and 3 M $NH_4Cl$ (402.5 μL) to afford the title compound as a green solid (0.041 g, 90%). HPLC: 98% [$t_R$=14.1 min, 5-95 gradient elution, $CN_3CN/H_2O$ (with 0.1% TFA), 20 min, 254 nm]. $^1H$ NMR (400 MHz, DMSO-$d_6$) δ 7.47 (dd, J=7.6, 6.4 Hz, 1H), 7.02 (d, J=7.6 Hz, 1H), 7.01 (d, J=6.4, 1H), 6.53 (br s, 2H), 5.12 (dd, J=12.9, 5.4 Hz, 1H), 3.75 (q, J=7.0 Hz, 2H), 2.96 (ddd, J=17.0, 14.0, 5.4 Hz, 1H), 2.73 (ddd, J=17.2, 4.4, 2.6 Hz, 1H), 2.57-2.49 (m, 1H), 2.08-1.95 (m, 1H), 1.02 (t, J=7.0 Hz, 3H). HPLC-MS (ESI+): m/z 625.2 $(2M+Na)^+$, 324.1 $(M+Na)^+$, 302.1 $(M+H)^+$.

MA7-164-2

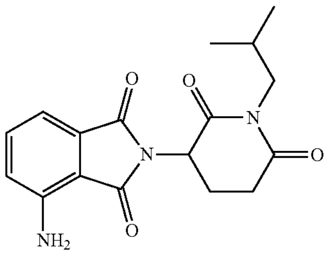

4-Amino-2-(1-isobutyl-2,6-dioxopiperidin-3-yl)isoindoline-1,3-dione (MA7-164-2): This compound was prepared using the general procedure described for Scheme 11 employing MA7-148-5 (0.050 g, 0.14 mmol), Fe (0.0311 g, 0.56 mmol), and 3 M $NH_4Cl$ (371 μL) to afford the title compound as a green solid (0.044 g, 96%). HPLC: 97.7% [$t_R$=6.7 min, 40% $CH_3CN$, 60% $H_2O$ (with 0.1% TFA), 20 min, 254 nm]. $^1H$ NMR (400 MHz, DMSO-$d_6$) δ 7.47 (dd, J=8.4, 6.8 Hz, 1H), 7.03 (d, J=8.4 Hz, 1H), 7.00 (d, J=6.8 Hz, 1H), 6.52 (br s, 2H), 5.15 (dd, J=13.0, 5.4 Hz, 1H), 3.53-3.46 (m, 2H), 2.99 (ddd, J=17.1, 14.1, 5.3 Hz, 1H), 2.82-2.67 (m, 1H), 2.58-2.45 (m, 1H), 2.11-1.94 (m, 1H), 1.91-1.81 (m, 1H), 0.82 (d, J=6.7 Hz, 6H). HPLC-MS (ESI+): m/z 681.3 $(2M+Na)^+$, 352.1 $(M+Na)^+$, 330.2 $(M+H)^+$. HRMS (ESI+): m/z calcd for $C_{17}H_{120}N_3O_4$ $(M+H)^+$330.1454, found 330.1453.

MA7-164-3

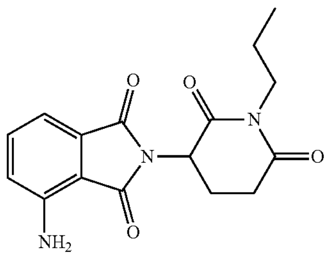

4-Amino-2-(2,6-dioxo-1-propylpiperidin-3-yl)isoindoline-1,3-dione (MA7-164-3): This compound was prepared using the general procedure described for Scheme 11 employing MA7-148-3 (0.050 g, 0.14 mmol), Fe (0.0323 g, 0.58 mmol), and 3 M $NH_4Cl$ (386 μL) to afford the title compound as a green solid (0.032 g, 70%). HPLC: 95.6% [$t_R$=6.3 min, 40% $CH_3CN$, 60% $H_2O$ (with 0.1% TFA), 20 min, 254 nm]. $^1H$ NMR (400 MHz, DMSO-$d_6$) δ 7.47 (t, J=7.6 Hz, 1H), 7.02 (d, J=7.6 Hz, 1H), 7.01 (d, J=7.6 Hz, 1H), 6.52 (br s, 2H), 5.13 (dd, J=13.0, 5.4, 1H), 3.64-3.59 (m, 2H), 2.97 (ddd, J=16.9, 14.0, 5.3 Hz, 1H), 2.74 (dt, J=16.7, 3.5 Hz, 1H), 2.56-2.45 (m, 1H), 2.05-1.98 (m, 1H), 1.45 (sextet, J=7.4 Hz, 2H), 0.83 (t, J=7.4 Hz, 3H). HPLC-MS (ESI+): m/z 653.3 $(2M+Na)^+$, 338.1 $(M+Na)^+$, 316.2 $(M+H)^+$.

MA7-164-4

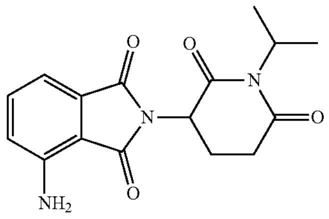

4-Amino-2-(1-isopropyl-2,6-dioxopiperidin-3-yl)isoindoline-1,3-dione (MA7-164-4) This compound was prepared using the general procedure described for Scheme 11 employing MA7-148-5 (0.050 g, 0.14 mmol), Fe (0.0323 g, 0.57 mmol), and 3 M $NH_4Cl$ (386 μL) to afford the title compound as a green solid (0.042 g, 92%). HPLC: 99.4% [$t_R$=6.3 min, 40% $CH_3CN$, 60% $H_2O$ (with 0.1% TFA), 20 min, 254 nm]. HPLC-MS (ESI+): m/z 653.2 $(2M+Na)^+$, 338.1 $(M+Na)^+$, 316.2 $(M+H)^+$. HRMS (ESI+): m/z calcd for $C_{16}H_{17}N_3O_4$ $(M+H)^+$316.1297, found 316.1294.

MA7-156

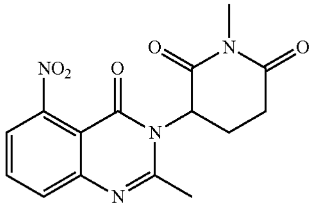

1-Methyl-3-(2-methyl-5-nitro-4-oxoquinazolin-3(4H)-yl) piperidine-2,6-dione (MA7-156): This compound was prepared using the general procedure described for Scheme 10 except using 3-(2-methyl-5-nitro-4-oxoquinazolin-3(4H)-yl)piperidine-2,6-dione MA7-164 (0.050 g, 0.158 mmol), MeI (0.0269 g, 0.189 mmol), and NaH (5.69 mg, 0.23 mmol) to afford title compound as a white solid (0.098 g, 47%). HPLC: 91.4% [$t_R$=5.4 min, 30% $CH_3CN$, 70% $H_2O$ (with 0.1% TFA), 20 min, 254 nm]. $^1$H NMR (400 MHz, DMSO-$d_6$) δ 7.98 (t, J=8.0 Hz, 1H), 7.87 (d, J=8.2 Hz, 1H), 7.82 (d, J=7.65 Hz, 1H), 5.42 (dd, J=12.0, 5.7 Hz, 1H), 3.03 (s, 3H), 2.92-3.86 (m, 1H), 2.80-2.73 (m, 1H), 2.69 (s, 3H), 2.61-2.55 (m, 1H), 2.22-2.16 (m, 1H). HPLC-MS (ESI+): m/z 683.3 $(2M+Na)^+$, 353.1 $(M+Na)^+$, 331.1 $(M+H)^+$.

MA7-157

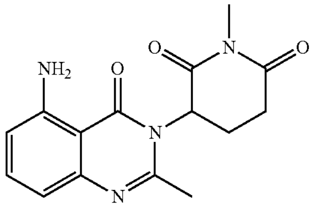

3-(5-Amino-2-methyl-4-oxoquinazolin-3(4H)-yl)-1-methylpiperidine-2,6-dione (MA7-157): This compound was prepared using the general procedure described for Scheme 11 employing MA7-156 (0.010 g, 0.03 mmol), Fe (6.76 mg, 0.12 mmol), and 3 M $NH_4Cl$ (80.7 μL). The mixture was stirred at room temperature for 24 h. The product was purified by using the general procedure described for Scheme 9 to afford the title compound as a yellow solid (6.4 mg, 70%). HPLC: 93.3% [$t_R$=9.5 min, 5-95 gradient elution, $CN_3CN/H_2O$ (with 0.1% TFA), 20 min, 254 nm]. $^1$H NMR (400 MHz, DMSO-$d_6$) δ 7.36 (t, J=8.0 Hz, 1H), 6.99 (br s, 2H), 6.60 (d, J=7.6 Hz, 1H), 6.57 (d, J=8.0 Hz, 1H), 5.23 (dd, J=11.8, 5.7 Hz, 1H), 3.04 (s, 3H), 2.95-2.86 (m, 1H), 2.76-2.96 (m, 2H), 2.54 (s, 3H), 2.17-2.13 (m, 1H). HPLC-MS (ESI+): m/z 301.2 $(M+H)^+$.

SR1-066

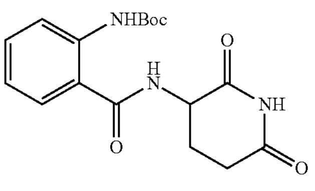

tert-Butyl (2-((2,6-dioxopiperidin-3-yl)carbamoyl)phenyl)carbamate (SR1-066): Into a mixture of Boc-2-aminobenzoic acid (0.500 g, 2.107 mmol) in acetonitrile (20 mL) was added DIPEA (1.10 mL, 6.321 mmol) and HATU (0.961 g, 2.528 mmol). After stirring for 5 min, 3-aminopiperidine-2,6-dione was added and the mixture stirred at room temperature for 20 h. The solvent was evaporated under reduced pressure and EtOAc (30 mL) added to the residue. The organic layer was washed with HCl (1N, 2×20 mL) followed by sat. aq. $NaHCO_3$ (2×20 mL), dried ($Na_2SO_4$) and concentrated. The resulting residue was purified by flash column chromatography using EtOAc/hexanes (35-70%) as eluent to afford SR1-066 as a white foam (0.654 g, 89%). HPLC: >99% [$t_R$=5.5 min, 60% MeOH, 40% water (with 0.1% TFA), 20 min]. $^1$H NMR (400 MHz, $CDCl_3$) δ 10.04 (s, 1H), 8.39 (dd, J=8.6, 1.2 Hz, 1H), 8.07 (s, 1H), 7.61-7.45 (m, 2H), 7.10-6.86 (m, 2H), 4.73 (dt, J=12.5, 5.0 Hz, 1H), 2.93-2.76 (m, 2H), 2.76-2.65 (m, 1H), 1.99-1.85 (m, 1H), 1.51 (s, 9H). HRMS (ESI+): m/z calcd for $C_{17}H_{21}N_3O_5Na$ $(M+Na)^+$ 370.1373, found 370.1378. HPLC-MS: HPLC-MS (ESI+): m/z 370.2 [80%, $(M+Na)^+$], 348.2 [90%, $(M+H)^+$] 717.3 [100%, $(2M+Na)^+$].

SR1-067-1

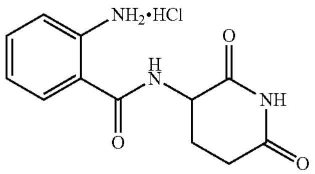

2-Amino-N-(2,6-dioxopiperidin-3-yl)benzamide hydrochloride (SR1-067-1): SR1-066 (0.594 g, 1.710 mmol) in HCl (4 N in dioxane, 5 mL) was stirred for 4 h at room temperature and then concentrated under reduced pressure. The reaction residue was triturated with EtOAc (35 mL) and the resulting white solid suspension was centrifuged. The supernatant was removed and the solid was mixed with EtOAc (35 mL). The mixture was centrifuged, and the liquid decanted. This washing process was repeated two more times and SR1-067-1 (485 mg, quantitative) was isolated as a white solid. $^1$H NMR (400 MHz, DMSO-$d_6$) δ 10.89 (s, 1H), 8.74 (d, J=8.3 Hz, 1H), 7.64 (dd, J=8.1, 1.6 Hz, 1H), 7.36-7.28 (m, 1H), 6.97 (d, J=8.2 Hz, 1H), 6.91-6.80 (m, 1H), 5.75 (bs, 2H), 4.76 (ddd, J=12.9, 8.2, 5.3 Hz, 1H), 2.80 (ddd, J=17.2, 13.3, 5.5 Hz, 1H), 2.56 (m, 1H), 2.13 (ddd, J=13.0, 4.5 Hz, 4.0 Hz, 1H), 2.01-1.91 (m, 1H). HPLC-MS (ESI+): m/z 248.2 [100%, $(M+H)^+$] 517.2 [10%, (2M+Na]+.

SR1-067-2

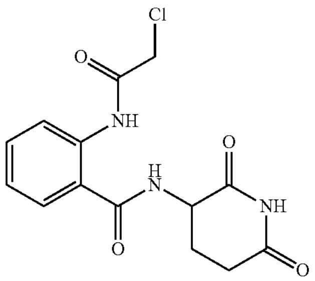

2-(2-Chloroacetamido)-N-(2,6-dioxopiperidin-3-yl)benzamide (SR1-067-2): The aniline HCl salt derivative SR1-067-1 (0.403 g, 1.427 mmol) was dissolved in THF:water (6 mL of 1:1 mixture) and the mixture was cooled to 0° C. To this mixture was added $NaHCO_3$ (0.296 g, 3.518 mmol) and chloroacetyl chloride (0.280 mL, 1.466 mmol) at 0° C. The mixture was stirred at 0° C. for 5 h (the pH was adjusted to 7-8 by addition a few drops of sat. aq. $NaHCO_3$ as reaction proceeded). The solvent was removed under reduced pressure then ethyl acetate (40 mL) and HCl (30 mL, 1N aq.) was added to the mixture and the layers separated. The aqueous layer was extracted with EtOAc (25 mL). The organic layers were combined, and dried ($Na_2SO_4$). Concentration of the organic layer under reduced pressure afforded pure SR1-067-2 as a white solid (0.463 g, 97%). HPLC: >99% [$t_R$=6.0 min, 10% MeOH, 90% water (with 0.1% TFA), 20 min]. $^1H$ NMR (400 MHz, DMSO-$d_6$) δ 11.73 (s, 1H), 10.92 (s, 1H), 9.02 (d, J=8.5 Hz, 1H), 8.41 (dd, J=8.5, 1.2 Hz, 1H), 7.78 (dd, J=8.0, 1.6 Hz, 1H), 7.59-7.50 (m, 1H), 7.23 (td, J=7.6, 1.2 Hz, 1H), 4.85 (ddd, J=12.5, 8.4, 5.4 Hz, 1H), 4.39 (s, 2H), 2.81 (ddd, J=17.3, 13.3, 5.6 Hz, 1H), 2.58-2.50 (m, 1H), 2.18-2.03 (m, 1H), 2.02-1.93 (m, 1H). HRMS (ESI+): m/z calcd for $C_{14}H_{14}ClN_3O_4Na$ $(M+Na)^+$346.0565, found 346.0564. HPLC-MS (ESI+): m/z 346.1 [100%, $(M+Na)^+$], 324.1 [50%, $(M+H)^+$]. HPLC-MS (ESI−): m/z 322.1 [100%, $M-H^-$].

SR1-059

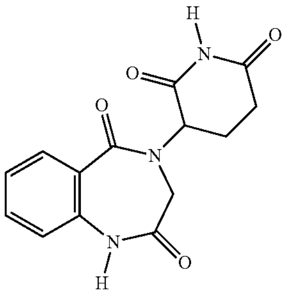

4-(2,6-Dioxopiperidin-3-yl)-3,4-dihydro-1H-benzo[e][1,4]diazepine-2,5-dione (SR1-059): To the chloroacetamide SR1-067-2 (0.039 g, 0.120 mmol), in anhydrous DMF (5 mL), in a pressure flask was added NaH (0.024 g, 0.602 mmol). The reaction was heated at 80° C. (CAUTION) for 16 h and cooled to room temperature followed by quenched with water (1 mL). The solvent was removed under reduced pressure. Purification by flash column chromatography, using MeOH/DCM (3-10%) as eluent, afforded SR1-059 as a white foam (18.0 mg, 52%). HPLC: >95% [$t_R$=11.7 min, 20% MeOH, 80% water (with 0.1% TFA), 20 min]. $^1H$ NMR (400 MHz, DMSO-$d_6$) δ 10.94 (s, 1H), 10.50 (s, 1H), 7.77 (dd, J=7.9, 1.7 Hz, 1H), 7.54 (ddd, J=8.1, 7.3, 1.6 Hz, 1H), 7.35-7.17 (m, 1H), 7.12 (dd, J=8.2, 1.1 Hz, 1H), 5.26 (bs, 1H), 3.91 (d, J=15.3 Hz, 1H), 3.74 (d, J=15.6 Hz, 1H), 2.91-2.76 (m, 1H), 2.63-2.52 (m, 1H), 2.42 (m, 1H, overlapped with DMSO-d6 peak), 1.96-1.80 (m, 1H). HRMS (ESI+): m/z calcd for $C_{14}H_{14}N_3O_4$ $(M+H)^+$288.0978, found 288.0977; m/z calcd for $C_{14}H_{13}N_3O_4Na$ $(M+Na)^+$310.0796, found 310.0793. HPLC-MS (ESI+): m/z 597.3 [60%, $(2M+Na)^+$], 288.1 [100%, $(M+H)^+$]. HPLC-MS (ESI−): m/z 286.0 [30%, $M-H^-$].

General Procedure for the Synthesis of Pyroglutamic Acid Derivatives:

A mixture of pyroglutamic acid (0.250 g, 1.936 mmol, 1.0 eq.), DIPEA (1.012 mL, 5.808 mmol, 2 eq.), EDC (0.445 g, 2.324 mmol, 1.2 eq.), and corresponding amine derivative (2.324 mmol, 1.2 eq.) in acetonitrile (5 mL) was stirred for 18-20 h at room temperature and concentrated under reduced pressure. The resulting residue was partitioned between DCM and 10% brine and the organic layer was then separated, dried ($Na_2SO_4$) and concentrated under reduced pressure. Purification of crude product by flash column chromatography using MeOH/DCM (2-10%) as eluent afforded corresponding products.

SR1-043

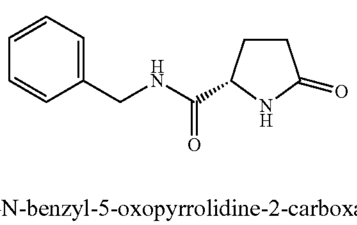

(S)—N-benzyl-5-oxopyrrolidine-2-carboxamide (SR1-043): General procedure was followed by using benzylamine (0.254 mL, 2.324 mmol). SR1-043 was obtained as a white fluffy solid (0.319 g, 76%). HPLC: >99% [$t_R$=11.7 min, 20% MeOH, 80% water (with 0.1% TFA), 20 min]. $^1H$ NMR (400 MHz, $CDCl_3$) δ 8.52 (s, 1H), 7.59 (dd, J=8.7, 1.3 Hz, 2H), 7.47 (s, 1H), 7.31 (dd, J=8.5, 7.4 Hz, 2H), 7.13 (t, J=7.4 Hz, 1H), 4.37 (dd, J=8.6, 4.7 Hz, 1H), 2.59-2.44 (m, 2H), 2.44-2.27 (m, 2H). HRMS (ESI+): m/z calcd for $C_{12}H_{15}N_2O_2$ $(M+H)^+$219.1128, found 219.1135; m/z calcd for $Cl_2H_{14}N_2O_2Na$ $(M+Na)^+$241.0947, found 241.0953. HPLC-MS (ESI+): m/z 241.2 [40%, $(M+Na)^+$], 219.2 [80%, $(M+H)^+$], 459.3 [100%, $(2M+Na)^+$]. HPLC-MS (ESI−): m/z 217.2 [40%, $M-H^-$].

SR1-045

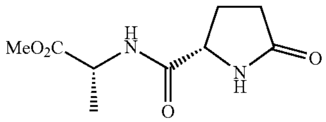

Methyl[(S)-5-oxopyrrolidine-2-carbonyl]-L-alaninate (SR1-045): General procedure was followed using (L)-Ala-OMe.HCl (0.324 g, 2.324 mmol). SR1-045 was obtained as a white foam (0.208 g, 50%). HPLC: >99% [$t_R$=5.3 min, 10% MeOH, 90% water (with 0.1% TFA), 20 min]. $^1H$ NMR (400 MHz, $CDCl_3$) δ 7.64 (dd, J=26.2, 5.0 Hz, 2H), 4.55 (t, J=7.3 Hz, 1H), 4.24 (dd, J=8.7, 4.9 Hz, 1H), 3.70 (s, 3H), 2.54-2.39 (m, 2H), 2.38-2.25 (m, 1H), 2.25-2.11 (m, 1H), 1.64 (d, J=7.3 Hz, 0.25H), 1.40 (d, J=7.3 Hz, 2.75H). HRMS (ESI+): m/z calcd for $C_9H_{15}N_2O_4$ $(M+H)^+$215.1026, found 215.1027; m/z calcd for $C_9H_{14}N_2O_4Na$ $(M+Na)^+$ 237.0845, found 237.0853. HPLC-MS (ESI+): m/z 429.2 [95%, $(2M+1)^+$1, 215.2 [80%, $(M+H)^+$451.2 [20%, $(2M+Na)^+$].

SR1-046

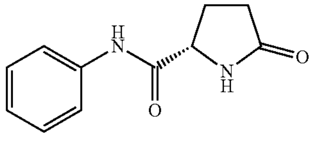

(S)-5-Oxo-N-phenylpyrrolidine-2-carboxamide (SR1-046): General procedure was followed using aniline (0.212 mL, 2.324 mmol). SR1-046 was obtained as white foam (0.078 g, 20%). HPLC: >99% [$t_R$=12.0 min, 20% MeOH, 80% water (with 0.1% TFA), 20 min]. $^1H$ NMR (400 MHz, $CDCl_3$) δ 8.52 (s, 1H), 7.59 (dd, J=8.7, 1.3 Hz, 2H), 7.47 (s, 1H), 7.31 (dd, J=8.5, 7.4 Hz, 2H), 7.13 (t, J=7.4 Hz, 1H), 4.37 (dd, J=8.6, 4.7 Hz, 1H), 2.59-2.44 (m, 2H), 2.44-2.27 (m, 2H). HRMS (ESI+): m/z calcd for $C_{11}H_{13}N_2O_2$ $(M+H)^+$ 205.0971, found 205.0979, m/z calcd for $C_{11}H_{12}N_2O_2Na$ $(M+Na)^+$227.0791, found 227.0796. HPLC-MS (ESI+): m/z 227.1 [70%, $(M+Na)^+$], 205.2 [95%, $(M+H)^+$], 431.2 [100%, $(2M+Na)^+$]. HPLC-MS (ESI−): m/z 203.1 [100%, $M-H^-$].

SR1-047

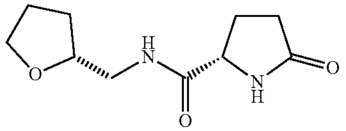

(S)-5-oxo-N—(((R)-tetrahydrofuran-2-yl)methyl)pyrrolidine-2-carboxamide (SR1-047): General procedure was followed using (R)-(−)-tetrahydrofurfuryl amine (0.237 mL, 2.324 mmol) along with a catalytic amount of HOBt.$H_2O$ (0.074 g, 0.490 mmol, 0.25 eq.). SR1-047 was obtained as white foam (isolated 0.081 g, 20%, Note: product is water soluble and poor yield reflects significant losses into aqueous phase during the work up). HPLC: >95% [$t_R$=7.6 min, 10% MeOH, 90% water (with 0.1% TFA), 20 min]. $^1H$ NMR (400 MHz, $CDCl_3$) δ 7.36 (s, 1H), 7.05 (s, 1H), 4.17 (dd, J=8.9, 5.0 Hz, 1H), 3.97 (qd, J=7.2, 3.2 Hz, 1H), 3.81 (dt, J=8.3, 6.7 Hz, 1H), 3.71 (dt, J=8.3, 6.7 Hz, 1H), 3.59 (ddd, J=13.8, 6.6, 3.2 Hz, 1H), 3.08 (ddd, J=13.7, 8.1, 4.6 Hz, 1H), 2.55-2.43 (m, 1H), 2.40 (dd, J=9.6, 6.8 Hz, 1H), 2.36-2.25 (m, 1H), 2.24-2.12 (m, 1H), 2.05-1.92 (m, 1H), 1.92-1.83 (m, 2H), 1.58-1.44 (m, 1H). HRMS (ESI+): m/z calcd for $C_{10}H_{17}N_2O_3$ $(M+H)^+$213.1233, found 213.1240; m/z calcd for $C_{10}H_{17}N_2O_3Na$ $(M+Na)^+$235.1053, found 235.1059. HPLC-MS (ESI+): m/z 213.2 [50%, $(M+H)^+$], 425.3 [100%, $(2M+H)^+$].

General protocol for the solid phase synthesis of dipeptide derivatives SR1-060, SR1-061, and SR1-062: Solid phase synthesis was carried out on Rink amide resin (0.46 mmol/g loaded, 100-200 mesh). The Kaiser test was used to confirm Fmoc-deprotection and corresponding amino acid coupling in the sequence. HATU (5.0 eq., 2.3 mL, 0.5 M in DMF) was used along with DIPEA (10.0 eq., 2.3 mL, 1 M in DMF) for coupling of amino acids. 20% solution of piperidine in DMF was utilized to remove Fmoc-protecting group. Resin washing step was consist of sequential washing with DMF, DCM, and DMF (twice, 5 mL of each solvent). Prior to cleavage, resin was washed additional 3 times with DCM followed by 3 times with MeOH and dried on high vacuum. Cleavage cocktail consist of 95:5 TFA:$H_2O$ solution. Resin was stirred in the cocktail for 2h at room temperature, filtered through cotton pad. The filtrate was concentrated under reduced pressure and the resulting residue was triturated with diethyl ether to afford corresponding products.

SR1-060

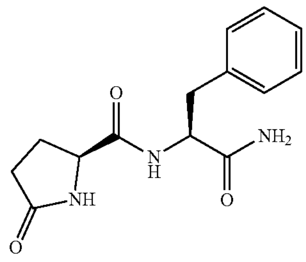

(S)—N—((S)-1-amino-1-oxo-3-phenylpropan-2-yl)-5-oxopyrrolidine-2-carboxamide (SR1-060): The general protocol was followed using Rink amide resin (597 mg, 0.275 mmol) to give SR1-060 (57 mg, 76%) as a white fluffy solid. HPLC: >99% [$t_R$=10.5 min, 20% MeOH, 80% water (with 0.1% TFA), 20 min]. $^1H$ NMR (400 MHz, DMSO-$d_6$) δ 8.04 (d, J=8.5 Hz, 1H), 7.70 (s, 1H), 7.46 (d, J=2.0 Hz, 1H), 7.29-7.07 (m, 5H), 4.42 (dt, J=9.2, 4.7 Hz, 1H), 3.93 (dd, J=9.0, 4.1 Hz, 1H), 3.01 (dd, J=13.7, 4.7 Hz, 1H), 2.79 (dd, J=13.6, 9.8 Hz, 1H), 2.23-2.09 (m, 1H), 2.06-1.94 (m, 2H), 1.69-1.55 (m, 1H). HRMS (ESI+): m/z calcd for $C_{14}H_{18}N_3O_3$ $(M+H)^+$276.1342, found 276.1341; m/z calcd for $C_{14}H_{17}N_3O_3Na$ $(M+Na)^+$298.1162, found 298.1157. HPLC-MS (ESI+): m/z 276.2 [85%, $(M+H)^+$], 551.2 [30%, $(2M+H)^+$], 573.2 [45%, $(M+Na)^+$].

SR1-061

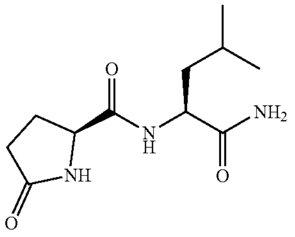

(S)—N—((S)-1-amino-4-methyl-1-oxopentan-2-yl)-5-oxopyrrolidine-2-carboxamide (SR1-061)

The general protocol was followed using Rink amide resin (500 mg, 0.23 mmol) to give SR1-061 (51 mg, 92%) as a white fluffy solid. HPLC: >99% [$t_R$=5.5 min, 20% MeOH, 80% water (with 0.1% TFA), 20 min]. $^1H$ NMR (400 MHz, DMSO-$d_6$) δ 7.99 (d, J=8.4 Hz, 1H), 7.77 (s, 1H), 7.36 (s, 1H), 6.98 (s, 1H), 4.21 (td, J=8.9, 5.7 Hz, 1H), 4.06-3.97 (m, 1H), 2.28-2.18 (m, 1H), 2.18-1.99 (m, 2H), 1.91-1.78 (m, 1H), 1.63-1.50 (m, 1H), 1.50-1.35 (m, 2H), 0.86 (d, J=6.6 Hz, 3H), 0.82 (d, J=6.5 Hz, 3H). HRMS (ESI+): m/z calcd for $C_{11}H_{20}N_3O_3$ $(M+H)^+$242.1499, found 242.1499; m/z calcd for $C_{11}H_{19}N_3O_3Na$ $(M+Na)^+$264.1318, found 264.1319. HPLC-MS (ESI+): m/z 242.2 [40%, $(M+H)^+$], 483.4 [100%, $(2M+H)^+$], 505.3 [40%, $2M+Na)^+$].

SR1-062

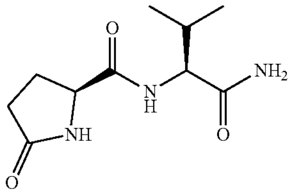

(S)—N—((S)-1-amino-3-methyl-1-oxobutan-2-yl)-5-oxopyrrolidine-2-carboxamide (SR1-062)

The general protocol was followed using Rink amide resin (500 mg, 0.23 mmol) to give SR1-062 (49 mg, 94%) as white fluffy solid. HPLC: >98% [$t_R$=4.8 min, 10% MeOH, 90% water (with 0.1% TFA), 20 min]. $^1$H NMR (400 MHz, DMSO-$d_6$) δ 7.88-7.75 (m, 1H), 7.43 (s, 1H), 7.04 (s, 1H), 4.10 (m, 2H), 2.28-2.18 (m, 1H), 2.17-1.98 (m, 2H), 1.98-1.90 (m, 1H), 1.89-1.79 (m, 1H), 0.84 (d, J=6.8 Hz, 3H), 0.81 (d, J=6.7 Hz, 3H). HRMS (ESI+): m/z calcd for $C_{10}H_{18}N_3O_3$ $(M+H)^+$2278.1342, found 227.1337; m/z calcd for $C_{10}H_{17}N_3O_3Na$ $(M+Na)^+$250.1162, found 250.1159. HPLC-MS (ESI+): m/z 228.22 [60%, $(M+H)^+$], 455.3 [100%, $(2M+H)^+$], 477.3 [40%, $2M+Na)^+$].

SR1-068

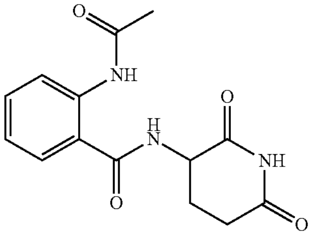

2-Acetamido-N-(2,6-dioxopiperidin-3-yl)benzamide (SR1-068): Pyridine (0.018 mL, 0.211 mmol) and acetic anhydride (0.020 mL, 0.211 mmol) were added in to a mixture of aniline HCl salt SR1-067-1 (0.030 g, 0.105 mmol) in dry DCM (2 mL). After stirring 1.5 h at room temperature, the mixture was concentrated under vacuum. The resulting residue was diluted with chloroform (25 mL) and washed with HCl (1 N, 15 mL). The organic layer was separated, dried ($Na_2SO_4$) and then concentrated under vacuum to afford SR1-068 as a white semi-solid (27 mg, 88%). HPLC: >99% [$t_R$=9.4 min, 20% MeOH, 80% water (with 0.1% TFA), 20 min]. $^1$H NMR (400 MHz, DMSO-$d_6$) δ 10.95 (s, 1H), 10.86 (s, 1H), 8.98 (d, J=8.3 Hz, 1H), 8.34 (d, J=8.4 Hz, 1H), 7.71 (dd, J=8.0, 1.6 Hz, 1H), 7.50 (ddd, J=8.7, 7.3, 1.6 Hz, 1H), 7.17 (td, J=7.6, 1.2 Hz, 1H), 4.81 (ddd, J=12.5, 8.3, 5.4 Hz, 1H), 2.81 (ddd, J=17.3, 13.3, 5.6 Hz, 1H), 2.61-2.52 (m, 1H), 2.20-2.10 (m, 1H), 2.08 (s, 2H), 2.05-1.96 (m, 1H). HRMS (ESI+): m/z calcd for $C_{14}H_{15}N_3O_4Na$ $(M+Na)^+$312.0954, found 312.0963. HPLC-MS (ESI+): m/z 290.2 [50%, $(M+H)^+$], 312.2 [100%, $(M+Na)^+$], 601.2 [60%, $(2M+Na)^+$].

SR1-074

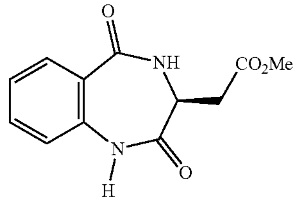

Methyl (S)-2-(2,5-dioxo-2,3,4,5-tetrahydro-1H-benzo[e][1,4]diazepin-3-yl)acetate (SR1-074): A mixture of isatoic anhydride (0.600 g, 3.678 mmol) and H-Asp(OMe)-(OMe).HCl (0.727 g, 3.678 mmol) in pyridine (7.5 mL) were heated at 120-125° C. for 20 h. The mixture was cooled and then concentrated under vacuum and diluted with EtOAc (50 mL). The organic layer was washed with HCl (1N, 35 mL) and evaporated. The resulting brown solid was washed with water (40 mL) and diethyl ether (3×50 mL) to afford SR1-074 as a brown solid (0.420 g, 46%). $^1$H NMR (400 MHz, DMSO-$d_6$) δ 10.49 (s, 1H), 8.58 (d, J=5.5 Hz, 1H), 7.73 (dd, J=7.8, 1.7 Hz, 1H), 7.52 (ddd, J=8.1, 7.3, 1.7 Hz, 1H), 7.28-7.19 (m, 1H), 7.10 (dd, J=8.2, 1.1 Hz, 1H), 4.02 (dt, J=8.5, 5.7 Hz, 1H), 3.56 (s, 3H), 2.86 (dd, J=17.0, 8.5 Hz, 1H), 2.72 (dd, J=17.0, 5.9 Hz, 1H). HPLC-MS (ESI+): m/z 249.2 [60%, $(M+H)^+$], 281.2 [50%, $(M+Na)^+$], 519.2 [55%, $(2M+Na)^+$].

SR1-076

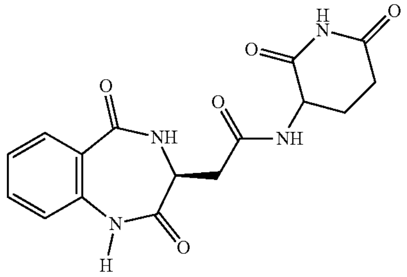

2-((S)-2,5-Dioxo-2,3,4,5-tetrahydro-1H-benzo[e][1,4]diazepin-3-yl)-N-(2,6-dioxopiperidin-3-yl)acetamide (SR1-076): Diazepine methyl ester SR1-074 (0.100 g, 0.403 mmol) was dissolved in THF:water (3:2 ratio, 5 mL). To the mixture, LiOH·$H_2O$ (0.034 g, 0.806 mmol) was added and stirred for 1 h at room temperature. The reaction mixture was concentrated under vacuum and acidified with HCl (1N, few drops until pH-3-4) washed with diethyl ether (20 mL) to afford the carboxylic acid intermediate SR2-075. (Note: product is dissolved in water thus cannot be extracted with organic solvents effectively). HPLC-MS (ESI−): m/z 233.2 [80%, $(M-H)^-$], 467.1 [10%, $(2M-H)^-$], (ESI+): m/z 235.1 [60%, $(M+H)^+$], 469.2 [40%, $(2M+H)^+$], 491.2 [80%, $(2M+Na)^+$]. HATU (0.168 g, 0.442 mmol) and DIPEA (0.210 mL, 1.206 mmol), 3-aminoglutarimide HCl salt (0.073 g, 0.442 mmol) were added into a solution of carboxylic acid derivative SR2-075 in $CH_3CN$:DMF (2:1 ratio, 6 mL). After stirring 23 h at room temperature, the reaction mixture was concentrated under vacuum. The reaction residue was diluted with EtOAc (30 mL) and washed with HCl (1 N, 20 mL) and sat. aq. $NaHCO_3$ (20 mL). Note: the product appeared in the aqueous washings. The HCl and $NaHCO_3$ were therefore combined, concentrated and the residue purified by Prep-HPLC by using 5-95% MeOH gradient in water (with 0.1% TFA), 20 min. During HPLC purification, the glutarimide moiety partly reacted with methanol to afford a mixture of product and a methyl ester side product. A fraction of SR1-076 was isolated as a white solid. HPLC: >99% [$t_R$=5.1 min, 20% MeOH, 80% water (with 0.1% TFA), 20 min]. $^1$H NMR (400 MHz, DMSO-$d_6$) δ 10.78 (d, J=5.4 Hz, 1H), 10.39 (d, J=2.1 Hz, 1H), 8.59 (dd, J=25.9, 5.6 Hz, 1H), 8.39 (dd, J=8.0, 3.5 Hz, 1H), 7.72 (ddd, J=7.9, 4.3, 1.6 Hz, 1H), 7.58-7.44 (m, 1H), 7.22 (dddd, J=8.7, 7.5, 2.3, 1.3 Hz, 1H), 7.09 (d, J=8.1 Hz, 1H), 4.65-4.32 (m, 1H), 4.16-3.93 (m, 1H), 2.95-2.75 (m, 1H), 2.69-2.59 (m, 2H), 2.31 (dd, J=3.8, 2.0 Hz, 1H), 1.97-1.78 (m, 2H). ). HRMS (ESI+): m/z calcd for $C_{16}H_{17}N_4O_5$ 345.1193, found 345.1180, m/z calcd for $C_{16}H_{16}N_4O_5Na$ $(M+Na)^+$367.1012, found 367.1008. HPLC-MS (ESI+): 345.1 [60%, $(M+H)^+$], 367.2 [30%, $(M+Na)^+$], (ESI−): m/z 344.1 [60%, $(M-H)^-$], 687.1 [20%, $(2M-H)^-$].

SR1-078

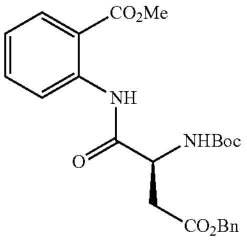

Methyl (S)-2-(4-(benzyloxy)-2-((tert-butoxycarbonyl)amino)-4-oxobutanamido)benzoate (SR1-078): A mixture of Boc-Asp(OBzl)OH (0.200 g, 0.619 mmol), HATU (0.282 g, 0.742 mmol), and DIPEA (0.323 mL, 1.857 mmol) in DMF (5 mL) was stirred for 3 min at room temperature. To the mixture, methyl anthranilate (0.096 mL, 0.742 mmol) was added and the mixture stirred for 15 h. The solvent was evaporated under vacuum and EtOAc (40 mL) added. The organic layer was washed with HCl (1 N, 25 mL) and sat. aq. $NaHCO_3$ (20 mL), dried ($Na_2SO_4$) and concentrated to give SR1-078 as a white foam, which was used in the subsequent debenzylation reaction. HPLC-MS (ESI+): m/z 478.4 [80%, $(M+Na)^+$], 935.3 [100%, $2M+Na)^+$].

SR1-079

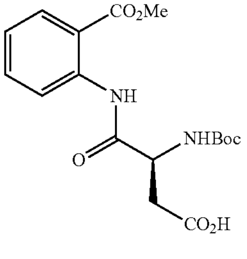

(S)-3-((tert-Butoxycarbonyl)amino)-4-((2-(methoxycarbonyl)phenyl)amino)-4-oxobutanoic acid (SR1-079): Palladium on activated carbon (10% (wet), 0.062 g, 0.100 g per mmol) was added slowly to a solution of benzyl ester SR2-078 (0.282 g, 0.619 mmol) in MeOH (3 mL) at room temperature. The mixture was purged with $H_2$ (balloon) and stirred for 3 h. The solids were filtered through celite and rinsed with MeOH. The filtrate was evaporated under vacuum and purified by flash column chromatography using EtOAc:hexanes (10-100%) as eluent to afford SR1-079 as a white solid (0.156 g, 69%). $^1$H NMR (400 MHz, $CDCl_3$) δ 11.84 (s, 1H), 8.67 (d, J=8.4 Hz, 1H), 8.00 (dd, J=8.0, 1.7 Hz, 1H), 7.51 (t, J=7.9 Hz, 1H), 7.08 (t, J=7.6 Hz, 1H), 5.80 (d, J=9.6 Hz, 1H), 4.73 (s, 2H), 3.28 (d, J=18.2 Hz, 1H), 2.80 (d, J=18.2 Hz, 1H), 1.51 (s, 9H). HPLC-MS (ESI+): m/z 755.3 [100%, $2M+Na)^+$], HPLC-MS (ESI−): m/z 365.2 [100%, $(M-1)^-$].

SR1-080

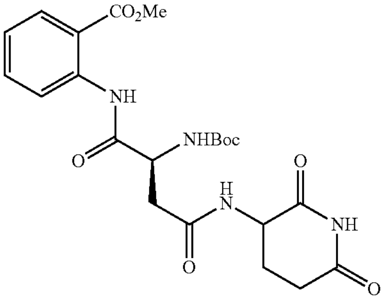

Methyl 2-((2S)-2-((tert-butoxycarbonyl)amino)-4-((2,6-dioxopiperidin-3-yl)amino)-4-oxobutanamido)-benzoate (SR1-080): 3-Aminoglutarimide (0.080 g, 0.485 mmol) was added to a mixture of carboxylic acid derivative SR1-079 (0.148 g, 0.403 mmol), DIPEA (0.154 mL, 0.887 mmol), and HATU (0.184 g, 0.485 mmol) in DMF (4 mL). The reaction was stirred for 4 h and concentrated under vacuum. Purification of the reaction residue by flash chromatography using MeOH:DCM (3-15%) as eluent afforded SR1-080 as a white solid (0.123 g, 64%). HPLC: ~98% [$t_R$=6.0 min, 20% MeOH, 80% water (with 0.1% TFA), 20 min]. $^1$H NMR (400 MHz, $CDCl_3$) δ 11.90 (s, 1H), 8.66 (d, J=8.4 Hz, 1H), 8.38 (bs, 1H), 8.01 (dt, J=8.8, 2.4 Hz, 1H), 7.51 (t, J=7.4 Hz, 1H), 7.09 (t, J=7.7 Hz, 1H), 6.92 (bs, 0.5H), 6.75 (bs, 0.5H), 6.21 (s, 1H), 4.72 (m, 1H), 4.65-4.42 (m, 1H), 3.97-3.78 (s, 3H), 3.21 (m, 1H), 2.88-2.54 (m, 3H), 2.42 (m, 1H), 1.97-1.73 (m, 1H), 1.51 (s, 9H). HRMS (ESI+): m/z calcd for $C_{22}H_{29}N_4O_8$ $(M+H)^+$477.1979, found 477.1984, m/z calcd for $C_{22}H_{28}N_4O_8Na$ $(M+Na)^+$499.1799, found 499.1801. HPLC-MS (ESI+): m/z 477.2 [100%, $(M+H)^+$], 499.2 [20%, $(M+Na)^+$], 975.4 [100%, $(2M+Na)^+$].

Method A1: A mixture of carboxylic acid (1.2-1.5 equiv.), HATU (2.0 equiv.), DIPEA (4.0 equiv.) in DMF (0.3-1 M) was stirred at room temperature for 30 min. The amine (1.0 equiv.) was added to the acid mixture and the entire solution was stirred overnight at room temperature. The mixture was concentrated under reduced pressure. Water (10 mL) was added and extracted with DCM (2×10 mL). The combined organic layers were dried ($Na_2SO_4$) and concentrated under reduced pressure. The resulting residue was purified by flash chromatography ($SiO_2$) eluting with DCM in MeOH (0-8%) to provide the title compound.

Method B1: A mixture of amine (SG5-046) (1 equiv.) and $Et_3N$ (3.0 equiv.) in THF (0.5 mL) was cooled to 0° C. The corresponding chloride (1.5 equiv.) was added. The mixture was brought to room temperature and stirred until the reaction was completed. Water (10 mL) was added and extracted with EtOAc (2×10 mL). The combined organic layers were concentrated under reduced pressure. The resulting residue was purified by flash chromatography ($SiO_2$) eluting with DCM in MeOH (0-10%) to provide the title compound.

Method C1: To a mixture of SG5-078 or SM2-002 (1 equiv.) and $K_2CO_3$ or $Cs_2CO_3$ (1.1-2.0 equiv.) in DMF was added alkyl halide (2.0 equiv.) dropwise at room temperature under Argon. The mixture was stirred overnight at room temperature. Water (5 mL) was added and extracted with EtOAc (2×10 mL). The combined organic layers were dried ($Na_2SO_4$), filtered, and concentrated under reduced pressure. The resulting residue was purified by flash chromatography ($SiO_2$) eluting with hexanes in EtOAc (0-50%) to provide the title compound.

Scheme 12

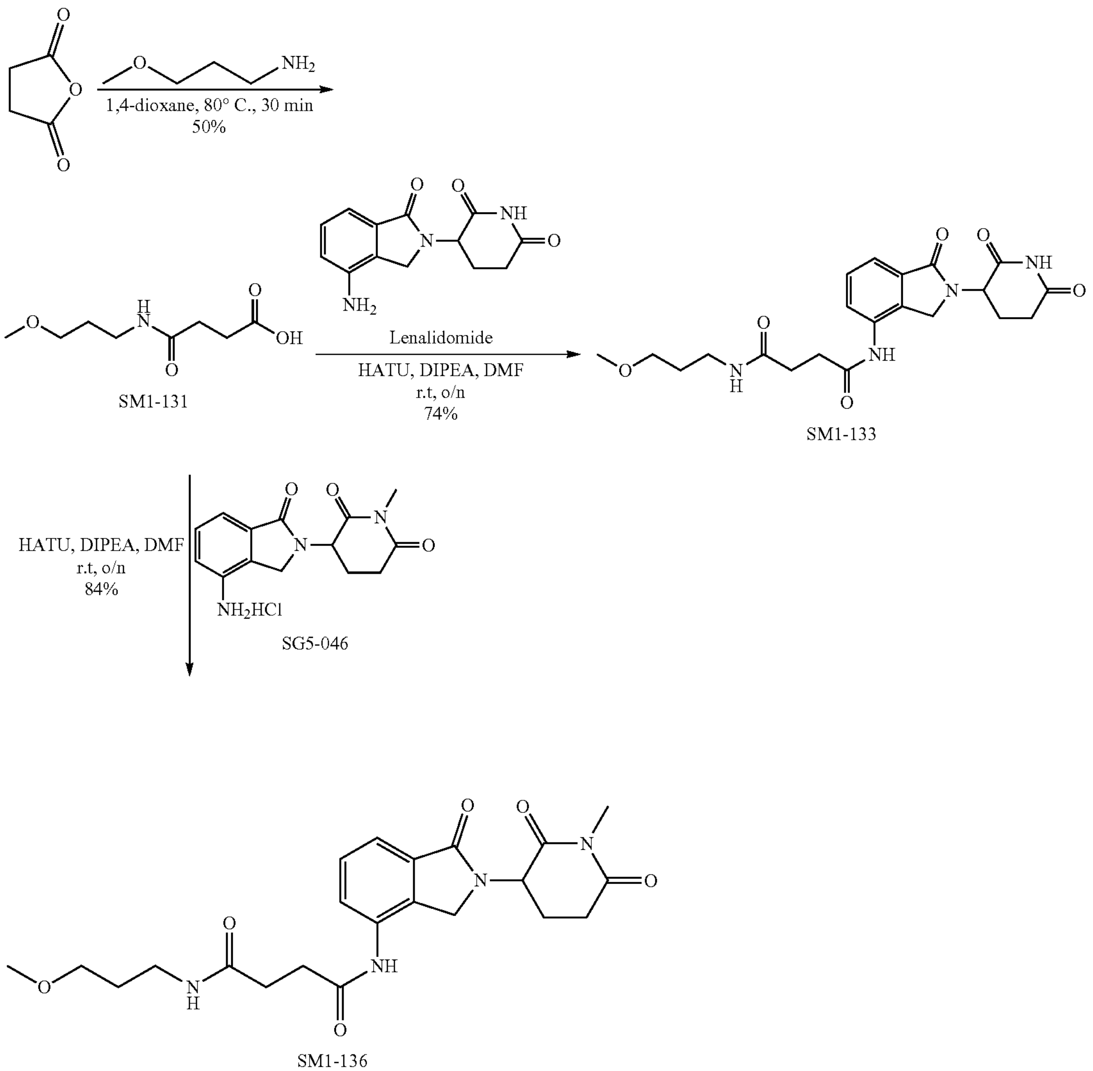

SM1-131

SM1-133

SG5-046

SM1-136

SM1-131

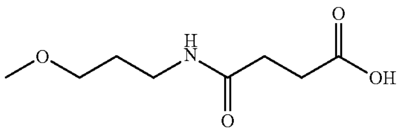

4-[(3-Methoxypropyl)amino]-4-oxobutanoic acid (SM1-131): (Scheme 12) To succinic anhydride (2.47 g, 24.68 mmol) in dioxane (10 mL) was slowly added 3-methoxy-propan-1-amine (2.29 mL, 22.44 mmol) in dioxane (10 mL). The solution was warmed to 80° C. and stirred for 30 min, and then cooled to room temperature. The white crystals were filtered off, dried, and recrystallized from dioxane to give the title compound as an white solid (2.13 g, 50%). $^1$H NMR (500 MHz, DMSO-$d_6$) δ 12.05 (s, 1H), 7.82 (t, J=5.7 Hz, 1H), 3.31 (t, J=6.4 Hz, 2H), 3.21 (s, 3H), 3.04-3.08 (m, 2H), 2.41 (t, J=7.1 Hz, 2H), 2.29 (t, J=6.9 Hz, 2H), 1.58-1.63 (m, 2H).

SM1-133

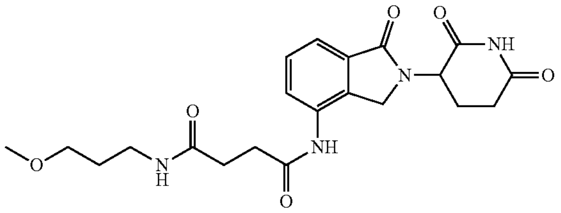

$N^1$-(2-(2,6-Dioxopiperidin-3-yl)-1-oxoisoindolin-4-yl)-$N^4$-(3-methoxypropyl)succinamide (SM1-133): This compound was prepared from Lenalidomide (100 mg, 0.385 mmol), SM1-131 (87.6 mg, 0.463 mmol), HATU (293.3 mg, 0.771 mmol), DIPEA (0.269 mL, 1.54 mmol) and DMF (1 mL) using Method A1 to give the title compound as a white solid (123 mg, 74%). HPLC: 99% [$t_R$=6.9 min, Grad MeOH 5-95% water (with 0.1% TFA), flow: 1.0 mL/min, 20 min]. $^1$H NMR (500 MHz, DMSO-$d_6$) δ 11.03 (s, 1H), 9.86 (s, 1H), 8.03-7.75 (m, 2H), 7.61-7.31 (m, 2H), 5.15 (dd, J=13.3, 5.1 Hz, 1H), 4.35 (q, J=17.5 Hz, 2H), 3.30 (t, J=6.4 Hz, 2H), 3.23-3.16 (m, 3H), 3.07 (q, J=6.7 Hz, 2H), 2.92 (ddd, J=17.2, 13.6, 5.4 Hz, 1H), 2.66-2.54 (m, 3H), 2.46-2.23 (m, 3H), 2.10-1.98 (m, 1H), 1.60 (p, J=6.7 Hz, 2H). HPLC-MS (ESI+): m/z 861.4 [20%, $(2M+H)^+$], 431.2 [40%, $(M+H)^+$]. HRMS (ESI+): m/z calcd for $C_{13}H_{14}N_2O_3$ $(M+Na)^+$ 453.1745, found 453.1762.

SM1-136

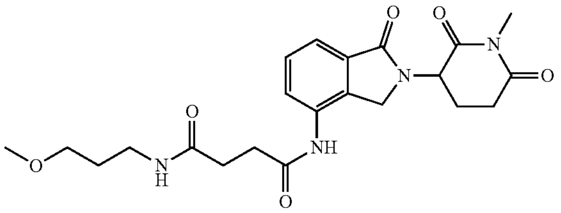

$N^1$-(3-Methoxypropyl)-$N^4$-(2-(1-methyl-2,6-dioxopiperidin-3-yl)-1-oxoisoindolin-4-yl)succinamide (SM1-136): This compound was prepared from SG5-046 (50 mg, 0.161 mmol), SM1-131 (45.8 mg, 0.242 mmol), HATU (122.8 mg, 0.323 mmol), DIPEA (0.112 mL, 0.646 mmol) and DMF (0.5 mL) using Method A1 to give the title compound as a white solid (60 mg, 84%). HPLC: 98% [$t_R$=6.9 min, gradient MeOH 5-95% water (with 0.1% TFA), flow: 1.0 mL/min, 20 min]. $^1$H NMR (500 MHz, DMSO-$d_6$) δ 9.86 (s, 1H), 7.87 (t, J=5.4 Hz, 1H), 7.81 (d, J=7.2 Hz, 1H), 7.49 (q, J=7.5 Hz, 2H), 5.22 (dd, J=13.4, 5.0 Hz, 1H), 4.42-4.27 (m, 2H), 3.30 (t, J=6.4 Hz, 2H), 3.18 (d, J=11.1 Hz, 3H), 3.06 (dt, J=12.7, 6.2 Hz, 2H), 3.03-2.95 (m, 3H), 2.77 (d, J=18.7 Hz, 1H), 2.65-2.56 (m, 2H), 2.46-2.23 (m, 4H), 2.08-2.00 (m, 1H), 1.60 (p, J=6.6 Hz, 2H). HPLC-MS (ESI+): m/z 911.4 [35%, $(2M+Na)^+$], 467.1 [50%, $(M+Na)^+$], 445.2 [100%, $(M+H)^+$]. HRMS (ESI+): m/z calcd for $C_{13}H_{14}N_2O_3$ $(M+Na)^+$ 467.1901, found 467.1919.

Scheme 13

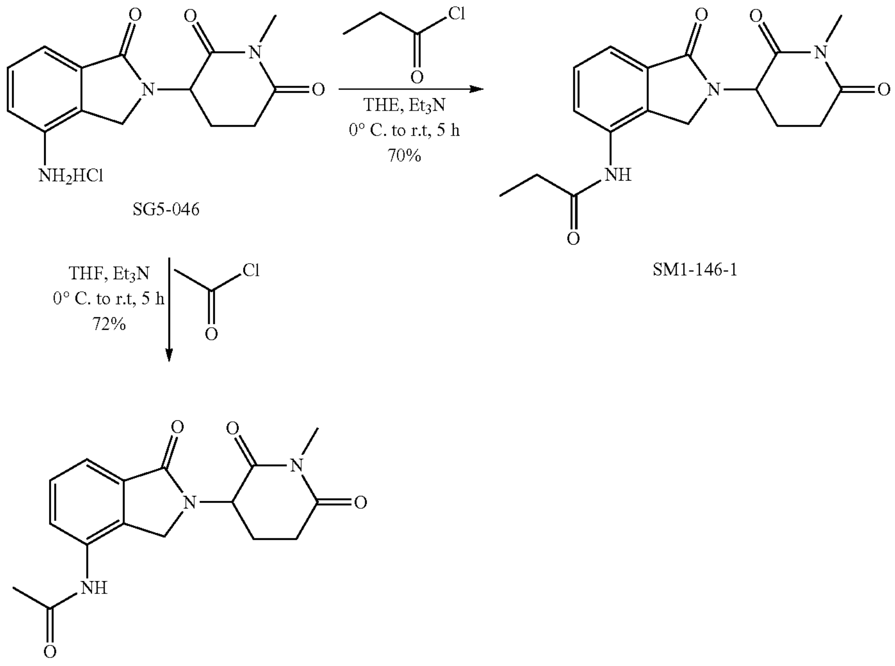

SG5-046

SM1-146-1

SM1-146-2

-continued

SM1-146-1

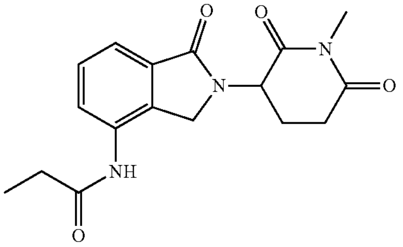

N-(2-(1-Methyl-2,6-dioxopiperidin-3-yl)-1-oxoisoindolin-4-yl)propionamide (SM1-146-1): (Scheme 13) This compound was prepared from SG5-046 (40 mg, 0.129 mmol), propionyl chloride (0.017 mL, 0.194 mmol), $Et_3N$ (0.054 mL, 0.387 mmol) and DMF (0.5 mL) using Method B1 to give the title compound as a white solid (29 mg, 70%). HPLC: 99% [$t_R$=11.5 min, Grad MeOH 5-95% water (with 0.1% formic acid), flow: 1.0 m/min, 20 min]. $^1$H NMR (500 MHz, DMSO-$d_6$) δ 9.76 (s, 1H), 7.81 (dd, J=7.3, 1.6 Hz, 1H), 7.55-7.46 (m, 2H), 5.22 (dd, J=13.5, 5.1 Hz, 1H), 4.44-4.29 (m, 2H), 3.02 (s, 4H), 2.77 (m, 1H), 2.42-2.32 (m, 3H), 2.04 (m, 1H), 1.10 (t, J=7.5 Hz, 3H). HPLC-MS (ESI+): m/z 681.3 [100%, $(2M+Na)^+$], 330.2 [70%, $(M+H)^+$].

SM1-146-2

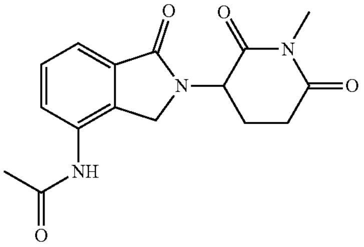

N-(2-(1-Methyl-2,6-dioxopiperidin-3-yl)-1-oxoisoindolin-4-yl)acetamide (SM1-146-2): This compound was prepared from SG5-046 (40 mg, 0.129 mmol), acetyl chloride (0.014 mL, 0.194 mmol), $Et_3N$ (0.054 mL, 0.387 mmol) and DMF (0.5 mL) using Method B1 to give the title compound as a white solid (30 mg, 72%). HPLC: 98% [$t_R$=10.5 min, gradient MeOH 5-95% water (with 0.1% formic acid), flow: 1.0 mL/min, 20 min]. $^1$H NMR (500 MHz, DMSO-$d_6$) δ 9.84 (s, 1H), 7.84-7.76 (m, 1H), 7.56-7.43 (m, 2H), 5.22 (dd, J=13.5, 5.1 Hz, 1H), 4.43-4.28 (m, 2H), 3.07-2.89 (m, 4H), 2.76 (m, 1H), 2.36 (qd, J=13.4, 4.5 Hz, 1H), 2.13-1.94 (m, 4H). HPLC-MS (ESI+): m/z 653.3 [100%, $(2M+Na)^+$], 316.2 [70%, $(M+H)^+$].

Scheme 14

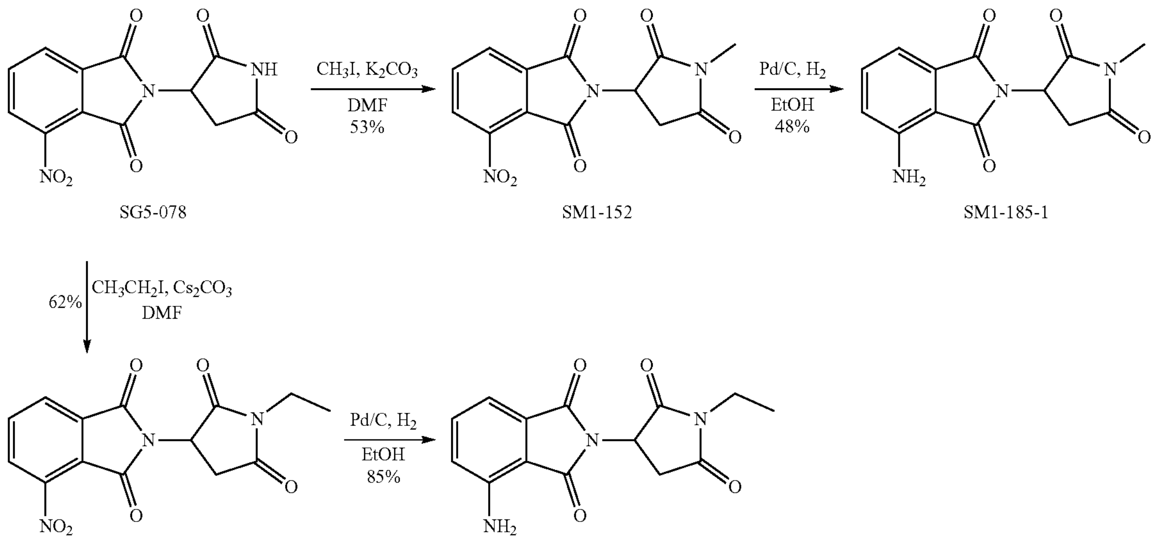

SG5-078 SM1-152 SM1-185-1 SM1-153 SM1-185-2

SM1-152

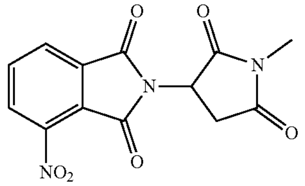

2-(1-Methyl-2,5-dioxopyrrolidin-3-yl)-4-nitroisoindoline-1,3-dione (SM1-152) (Scheme 14) This compound was prepared from SG5-078 (50 mg, 0.173 mmol), $K_2CO_3$ (47.8 mg, 0.346 mmol), iodomethane (0.022 mL, 0.346 mmol), and DMF (0.4 mL) using Method C1 to give the title compound as a white solid (28 mg, 53%). $^1$H NMR (500 MHz, DMSO-$d_6$) δ 8.35 (dd, J=8.1, 0.9 Hz, 1H), 8.25-8.20 (m, 1H), 8.11 (t, J=7.8 Hz, 1H), 5.32 (dd, J=9.5, 4.9 Hz, 1H), 3.09 (dd, J=18.1, 9.6 Hz, 1H), 2.98-2.89 (m, 4H). HPLC-MS (ESI+): m/z 629.3 [50%, $(2M+Na)^+$], 326.1 [100%, $(M+Na)^+$], 304.1 [40%, $(M+H)^+$].

SM1-153

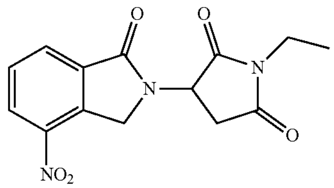

2-(1-Ethyl-2,5-dioxopyrrolidin-3-yl)-4-nitroisoindoline-1,3-dione (SM1-153): This compound was prepared from SG5-078 (50 mg, 0.173 mmol), $Cs_2CO_3$ (62.0 mg, 0.190 mmol), iodoethane (0.028 mL, 0.346 mmol), and DMF (0.4 mL) using Method C1 to give the title compound as a white solid (39 mg, 62%). $^1$H NMR (500 MHz, DMSO-$d_6$) δ 8.36 (dd, J=8.1, 0.8 Hz, 1H), 8.23 (d, J=7.5 Hz, 1H), 8.12 (t, J=7.8 Hz, 1H), 5.33 (dd, J=9.5, 4.9 Hz, 1H), 3.51 (q, J=7.2 Hz, 2H), 3.08 (dd, J=18.2, 9.6 Hz, 1H), 2.93 (dd, J=18.1, 4.9 Hz, 1H), 1.99 (s, 1H), 1.12 (t, J=7.2 Hz, 3H). HPLC-MS (ESI+): m/z 657.2 [100%, $(2M+Na)^+$], 340.1 [100%, $(M+Na)^+$], 318.2 [40%, $(M+H)^+$].

SM1-185-1

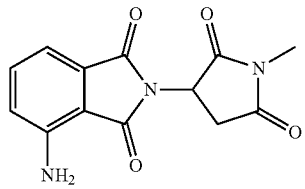

4-Amino-2-(1-methyl-2,5-dioxopyrrolidin-3-yl)isoindoline-1,3-dione (SM1-185-1): To a mixture of Pd/C (10% w/w, 5 mg) in EtOH (1.5 mL deoxygenated with Argon gas) was added SM1-152 (20 mg, 0.066 mmol) under Argon. The flask was evacuated and back filled with Argon (three times). Argon gas was evacuated and a balloon of hydrogen was attached to the system. The reaction mixture was stirred at room temperature for 12 h, filtered using a short plug of Celite, washed with DCM and MeOH, and concentrated under reduced pressure. The resulting residue was purified by preparative HPLC ($t_R$=9.0 min, gradient MeOH 30-95% water (with 0.1% formic acid), flow: 20.0 mL/min, 20 min) to provide the title compound as an yellow solid (12 mg, 43%). HPLC: 100% [$t_R$=9.0 min, Grad MeOH 30-95% water (with 0.1% formic acid), flow: 1.0 mL/min, 20 min]. $^1$H NMR (500 MHz, DMSO-$d_6$) δ 7.47 (dd, J=8.4, 7.0 Hz, 1H), 7.01 (t, J=8.1 Hz, 2H), 6.56 (s, 2H), 5.21 (dd, J=9.5, 5.0 Hz, 1H), 3.07 (dd, J=17.9, 9.6 Hz, 1H), 2.96-2.86 (m, 4H).

HPLC-MS (ESI+): m/z 569.2 [100%, $(2M+Na)^+$], 296.2 [55%, $(M+Na)^+$], 274.1 [55%, $(M+H)^+$].

SM1-185-2

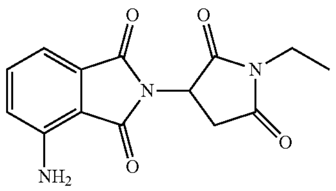

4-Amino-2-(1-ethyl-2,5-dioxopyrrolidin-3-yl)isoindoline-1,3-dione (SM1-185-2): To a mixture of Pd/C (10% w/w, 5 mg) in EtOH (1.5 mL deoxygenated with Argon gas) was added SM1-153 (30 mg, 0.095 mmol) under Argon. The flask was evacuated and back filled with Argon (three times). Argon gas was evacuated and a balloon of hydrogen was attached to the system. The reaction mixture was stirred at room temperature for 12 h, filtered using a short plug of Celite, washed with DCM and MeOH, and concentrated under reduced pressure to provide the title compound as a yellow solid (23 mg, 85%). HPLC: 96% [$t_R$=7.1 min, gradient 85% MeOH, 15% water (with 0.1% TFA), flow: 1.0 m/min, 20 min]. $^1H$ NMR (500 MHz, DMSO-$d_6$) δ 7.47 (dd, J=8.5, 7.0 Hz, 1H), 7.01 (t, J=7.9 Hz, 2H), 6.56 (s, 2H), 5.21 (dd, J=9.5, 5.0 Hz, 1H), 3.49 (q, J=7.2 Hz, 2H), 3.06 (dd, J=18.0, 9.6 Hz, 1H), 2.88 (dd, J=18.0, 5.0 Hz, 1H), 1.11 (t, J=7.2 Hz, 3H). HPLC-MS (ESI+): m/z 597.2 [100%, $(2M+Na)^+$], 310.1 [80%, $(M+Na)^+$], 288.1 [50%, $(M+H)^+$].

Scheme 15

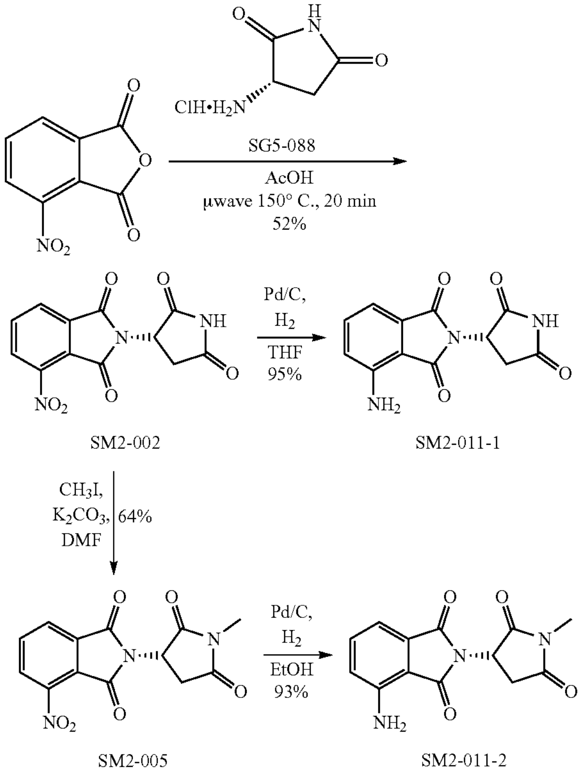

-continued

SM2-002

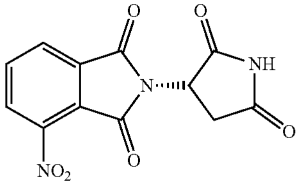

(S)-2-(2,5-Dioxopyrrolidin-3-yl)-4-nitroisoindoline-1,3-dione (SM2-002): (Scheme 15) A mixture of 3-nitrophthalic anhydride (160 mg, 0.829 mmol), SG5-088 (125 mg, 0.829 mmol), and acetic acid (0.8 mL) in a 5 mL microwave vial was heated at 150° C. for 20 min. After cooling, the mixture was added to water (10 mL) and the precipitates filtered, washed with water (2×20 mL), and dried under vacuum. The product was triturated using EtOH/hexanes to give the title compound as an off-white solid (116 mg, 52%). $^1H$ NMR (500 MHz, DMSO-$d_6$) δ 11.72 (s, 1H), 8.36 (dd, J=8.1, 0.8 Hz, 1H), 8.26-8.21 (m, 1H), 8.12 (t, J=7.8 Hz, 1H), 5.32 (dd, J=9.6, 5.5 Hz, 1H), 3.01 (dd, J=18.1, 9.6 Hz, 1H), 2.89 (dd, J=18.1, 5.5 Hz, 1H). HPLC-MS (ESI+): m/z 601.1 [76%, $(2M+Na)^+$], 312.0 [100%, $(M+Na)^+$], 290.1 [46%, $(M+H)^+$].

SM2-005

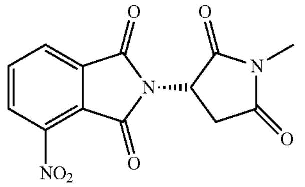

(S)-2-(1-Methyl-2,5-dioxopyrrolidin-3-yl)-4-nitroisoindoline-1,3-dione (SM2-005): This compound was prepared from SM2-002 (70 mg, 0.242 mmol), $K_2CO_3$ (67 mg, 0.484 mmol), iodomethane (0.030 mL, 0.484 mmol), and DMF (0.5 mL) using Method C1 to give the title compound as a white solid (46 mg, 64%). $^1H$ NMR (500 MHz, DMSO-$d_6$) δ 8.42 (dd, J=8.1, 0.8 Hz, 1H), 8.29 (d, J=7.6 Hz, 1H), 8.18 (t, J=7.8 Hz, 1H), 5.38 (dd, J=9.5, 4.9 Hz, 1H), 3.15 (dd, J=18.1, 9.6 Hz, 1H), 3.05-2.95 (m, 4H). HPLC-MS (ESI+): m/z 629.2 [50%, $(2M+Na)^+$], 326.0 [60%, $(M+Na)^+$], 304.1 [64%, $(M+H)^+$].

SM2-011-1

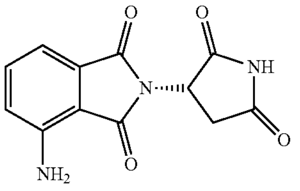

(S)-4-Amino-2-(2,5-dioxopyrrolidin-3-yl)isoindoline-1,3-dione (SM2-011-1): To a mixture of Pd/C (10% w/w, 10 mg) in THF (1.5 mL deoxygenated with Argon gas) was added SM2-002B2 (80 mg, 0.277 mmol) under Argon. The flask was evacuated and back filled with Argon (three times). Argon gas was evacuated and a balloon of hydrogen was attached to the system. The reaction mixture was stirred at room temperature for 12 h, filtered using a short plug of Celite, washed with THF, and concentrated under reduced pressure to provide the title compound as a yellow solid (68 mg, 95%). $^1$H NMR (500 MHz, DMSO-$d_6$) δ 11.58 (s, 1H), 7.46 (dd, J=8.5, 7.0 Hz, 1H), 7.00 (t, J=7.7 Hz, 2H), 6.54 (s, 2H), 5.19 (dd, J=9.7, 5.5 Hz, 1H), 2.98 (dd, J=17.9, 9.7 Hz, 1H), 2.84 (dd, J=17.9, 5.5 Hz, 1H). HPLC-MS (ESI+): m/z 541.1 [60%, $(2M+Na)^+$], 282.2 [100%, $(M+Na)^+$], 260.1 [70%, $(M+H)^+$].

SM2-011-2

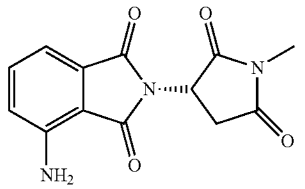

(S)-4-Amino-2-(1-methyl-2,5-dioxopyrrolidin-3-yl) isoindoline-1,3-dione (SM2-011-2): To a mixture of Pd/C (10% w/w, 5 mg) in EtOH (2.0 mL deoxygenated with Argon gas) was added SM2-005 (30 mg, 0.099 mmol) under Argon. The flask was evacuated and back filled with Argon (three times). Argon gas was evacuated and a balloon of hydrogen was attached to the system. The reaction mixture was stirred at room temperature for 14 h, filtered using a short plug of Celite, washed with DCM and EtOH, and concentrated under reduced pressure to provide the title compound as a yellow solid (25 mg, 93%). $^1$H NMR (500 MHz, DMSO-$d_6$) δ 7.47 (dd, J=8.5, 7.0 Hz, 1H), 7.00 (t, J=8.3 Hz, 2H), 6.55 (s, 2H), 5.21 (dd, J=9.6, 5.0 Hz, 1H), 3.06 (dd, J=18.0, 9.6 Hz, 1H), 2.92 (s, 3H), 2.91-2.85 (m, 1H). HPLC-MS (ESI+): m/z 569.2 [90%, $(2M+Na)^+$], 296.1 [80%, $(M+Na)^+$], 274.1 [100%, $(M+H)^+$].

Method A: A mixture of amine (3-aminopiperidine-2,6-dione hydrochloride, SG4-178, or SG5-085) (1 equiv.) and DIPEA (2.5-4 equiv.) in DMF or DCM (1 M) was stirred at room temperature for 30 min, then the corresponding acyl/sulfonyl chloride (1-1.5 equiv.) was added at 0° C. The resulting mixture was stirred and warmed to room temperature. Water (10 mL) was added and extracted with EtOAc (2×10 mL). The combined organic layers were dried ($Na_2SO_4$) and concentrated under reduced pressure. Unless otherwise mentioned, all products were collected via trituration using EtOAc/hexanes or DCM/hexanes and final $Et_2O$ wash, when necessary.

Method B: A mixture of amine (SG4-178 or SG5-085) (1 equiv.) and $Et_3N$ (1.2 equiv.) in 1,4-dioxane (~0.5-1 M) was stirred at room temperature for 30 min, then the corresponding isatoic anhydride (1 equiv.) was added at room temperature. Water (20 mL) was added and extracted with EtOAc (2×20 mL) and DCM (1×20 mL). The combined organic layers were concentrated under reduced pressure. Unless otherwise mentioned, all products were collected via trituration using EtOAc/hexanes, EtOH/hexanes, or DCM/hexanes.

Method C: A mixture of phthalic anhydride (1 equiv.), amine (1 equiv.), and acetic acid (~1 M) in a 5 mL microwave vial was irradiated at 150° C. for 20 min. Water (10 mL) was added and the precipitates were filtered, washed with water (2×20 mL), and dried. Unless otherwise mentioned, all products were collected via trituration using EtOH/hexanes.

Method D: Into a mixture of uracil (2-3 equiv.), $K_2CO_3$ (2-3 equiv.), and NaI (1 equiv.) in DMSO (0.5-1 M) was added alkyl bromide (1 equiv.). The mixture was stirred and heated at 90° C., then cooled to room temperature. Water (20 mL) was added and the mixture was acidified to pH 2 using 4 M HCl. Unless otherwise mentioned, all products were collected via trituration using EtOAc/hexanes and/or EtOH/hexanes upon filtration.

Method E: A mixture of amino acid (1 equiv.) and HBTU (1.1 equiv.) in DMF (1.5 mL) was stirred at room temperature for 30 min. In a separate reaction vessel, amine (1.05 equiv.) and DIPEA (3 equiv.) in DMF (0.5 mL) was stirred at room temperature for 30 min. The amine mixture was added to the amino acid mixture and the entire solution was stirred at room temperature. Water (10 mL) was added and extracted with EtOAc (2×10 mL). The combined organic layers were dried ($Na_2SO_4$) and concentrated under reduced pressure. The resulting residue was mixed with water and sonicated. The precipitates were filtered, dried, and triturated using EtOH/hexanes to provide the desired product.

Method F: A mixture of amino acid (1 equiv.), EDCI (1.1 equiv.), N-hydroxysuccinimide (1.1 equiv.) in DMF (~2.5 M) in a sealed tube was stirred at 60° C. (oil bath) for 20 h. The solution was cooled to room temperature then added water (50 mL) and extracted with EtOAc (2×50 mL). The combined organic layers were washed with water and brine (25 mL each), dried ($Na_2SO_4$), and concentrated under reduced pressure. The resulting residue was triturated using EtOH/hexanes (2×) to provide the desired product.

Method G: Boc-protected material was stirred in 4 M HCl in dioxane for 2 h at room temperature. Unless otherwise mentioned, all products were collected after the resulting suspension was concentrated under reduced pressure.

Method H: To a mixture of SG5-040 (1 equiv.) and $K_2CO_3$ or $Cs_2CO_3$ (1-1.1 equiv.) in DMF or NMP was added alkyl halide (1-3 equiv.) dropwise at room temperature under Argon. The mixture was stirred at 80° C. Water (5 mL) was added and extracted with EtOAc (2×5 mL). The combined organic layers were dried ($Na_2SO_4$), filtered, and concentrated under reduced pressure. The resulting residue oil was purified by flash chromatography ($SiO_2$) eluting with hexanes in EtOAc (20-100%) to provide the title compound.

SG4-125

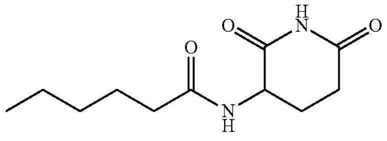

N-(2,6-dioxopiperidin-3-yl)hexanamide (SG4-125): This compound was prepared from 3-aminopiperidine-2,6-dione hydrochloride (164 mg, 1 mmol), hexanoyl chloride (0.201 mL, 1.5 mmol), DIPEA (0.522 mL, 3 mmol), and DMF (1 mL) using Method A (reaction time, 16 h) to give the title compound as an off-white solid (91.18 mg, 40%). Mp: 142-147° C. HPLC: 98% [$t_R$=7.2 min, 35% MeOH, 65% water (with 0.1% TFA), 20 min, 220 nm]. $^1$H NMR (400 MHz, DMSO-$d_6$) δ 10.78 (s, 1H, disappeared on $D_2O$ shake), 8.13 (d, J=8.2 Hz, 1H, disappeared on $D_2O$ shake), 4.51 (dt, J=10.3, 8.2 Hz, 1H), 2.77-2.62 (m, 1H), 2.50-2.43 (m, 1H, overlapped with the residual DMSO signal), 2.09 (t, J=7.2 Hz, 2H), 1.95-1.83 (m, 2H), 1.49 (p, J=7.2 Hz, 2H), 1.30-1.17 (m, 4H), 0.84 (t, J=7.2 Hz, 3H). HPLC-MS (ESI+): m/z 475.3 [90%, $(2M+Na)^+$], 249.2 [60%, $(M+Na)^+$], 227.2 [100%, $(M+H)^+$]. LC-MS (ESI+): 249.2

[100%, $(M+Na)^+$]. HRMS (ESI+): m/z calcd for $C_{11}H_8N_2O_3$ $(M+H)^+$249.1209, found 249.1225.

SG4-131

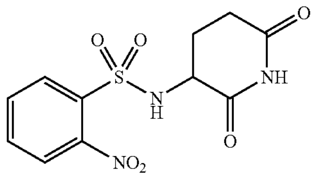

N-(2,6-dioxopiperidin-3-yl)-2-nitrobenzenesulfonamide (SG4-131): This compound was prepared from 3-aminopiperidine-2,6-dione hydrochloride (164 mg, 1 mmol), 2-nitrobenzenesulfonyl chloride (221 mg, 1 mmol), DIPEA (0.435 mL, 2.5 mmol), and DMF (1 mL) using Method A (reaction time, overnight) to give the title compound as a gray gum (283 mg, 90%). $^1$H NMR (400 MHz, DMSO-$d_6$) δ 10.81 (s, 1H), 8.40 (d, J=8.7 Hz, 1H), 8.11-8.06 (m, 1H), 8.01-7.95 (m, 1H), 7.87-7.80 (m, 2H), 4.38-4.28 (m, 1H), 2.74-2.61 (m, 1H), 2.50-2.40 (m, 1H, overlapped with the residual DMSO signal), 2.03-1.85 (m, 2H).

SG4-135-01

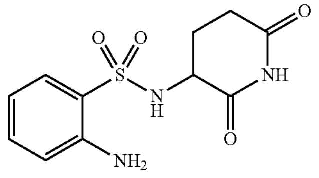

2-Amino-N-(2,6-dioxopiperidin-3-yl)benzenesulfonamide (SG4-135-01): Into a mixture of SG4-131 (50 mg, 0.160 mmol) in MeOH (1.5 mL deoxygenated with Argon gas) was added $PtO_2$ (1 mg) under Argon. The flask was evacuated and back filled with Argon (twice). Argon gas was evacuated and a balloon of hydrogen was attached to the system. The reaction mixture was stirred at room temperature for 4 h, filtered using a short plug of Celite and concentrated under reduced pressure. The crude mixture was purified via preparative TLC using DCM/MeOH 5% and afforded the title product as a white foam (19.96 mg, 44%). Mp: 146° C. (dec). HPLC: 97% [$t_R$=10.3 min, 20% MeOH, 80% water (with 0.1% TFA), 20 min]. $^1$H NMR (400 MHz, DMSO-$d_6$) δ 10.78 (s, 1H, disappeared on $D_2O$ shake), 7.95 (s, 1H, disappeared on $D_2O$ shake), 7.51 (dd, J=8.2, 1.6 Hz, 1H), 7.23 (ddd, J=8.2, 7.1, 1.6 Hz, 1H), 6.77 (dd, J=8.2, 1.0 Hz, 1H), 6.57 (ddd, J=8.2, 7.1, 1.0 Hz, 1H), 5.92 (s, 2H, disappeared on $D_2O$ shake), 4.10 (dd, J=10.8, 6.4 Hz, 1H), 2.57 (ddd, J=17.5, 10.8, 6.4 Hz, 1H), 2.41 (dt, J=17.5, 4.2 Hz, 1H), 1.82-1.68 (m, 2H). HPLC-MS (ESI+): m/z 589.1 [20%, $(2M+Na)^+$], 284.1 [40%, $(M+H)^+$]. LC-MS (ESI+): 306.0 [100%, $(M+Na)^+$]. HRMS (ESI+): m/z calcd for $C_{11}H_{13}N_3O_4S$ $(M+H)^+$306.0519, found 306.0512.

SG4-136

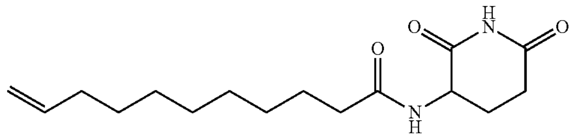

N-(2,6-Dioxopiperidin-3-yl)undec-10-enamide (SG4-136): This compound was prepared from 3-aminopiperidine-2,6-dione hydrochloride (164 mg, 1 mmol), 10-undecenoyl chloride (0.322 mL, 1.5 mmol), DIPEA (0.522 mL, 3 mmol), and DMF (1 mL) using Method A (reaction time, overnight) to give the title compound as a white solid (180.65 mg, 61%). Mp: 138-139° C. HPLC: >99% [$t_R$=9.0 min, 65% MeOH, 35% water (with 0.1% TFA), 20 min]. $^1$H NMR (400 MHz, DMSO-$d_6$) δ 10.77 (s, 1H, disappeared on $D_2O$ shake), 8.12 (d, J=8.0 Hz, 1H, disappeared on $D_2O$ shake), 5.77 (dd, J=17.2, 10.3 Hz, 1H), 4.97 (d, J=17.2 Hz, 1H), 4.91 (d, J=10.3 Hz, 1H), 4.51 (q, J=8.3 Hz, 1H), 2.77-2.63 (m, 1H), 2.50-2.43 (m, 1H, overlapped with the residual DMSO signal), 2.14-2.05 (m, 2H), 2.03-1.94 (m, 2H), 1.87 (brs, 2H), 1.48 (brs, 2H), 1.38-1.16 (m, 10H). HPLC-MS (ESI+): m/z 611.4 [40%, $(2M+Na)^+$], 317.3 [100%, $(M+Na)^+$], 295.2 [60%, $(M+H)^+$]. LC-MS (ESI+): 317.2 [100%, $(M+Na)^+$]. HRMS (ESI+): m/z calcd for $C_{16}H_{26}N_2O_3$ $(M+Na)^+$317.1835, found 317.1852.

SG4-139

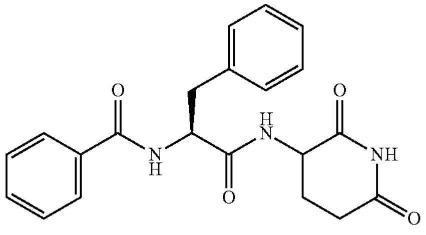

N-((2S)-1-((2,6-dioxopiperidin-3-yl)amino)-1-oxo-3-phenylpropan-2-yl)benzamide (SG4-139): This compound was prepared from benzoyl-L-phenylalanine (200 mg, 0.742 mmol), HBTU (310 mg, 0.817 mmol), 3-aminopiperidine-2,6-dione hydrochloride (128 mg, 0.780 mmol), DIPEA (0.388 mL, 2.230 mmol), and DMF (1.5 mL) using Method E (reaction time, 14 h) to give the title compound as a mixture of diastereomers, an off-white solid (188.82 mg, 67%). Mp: 209-210° C. HPLC: 63% [$t_R$=17.8 min, 40% MeOH, 60% water (with 0.1% TFA), 20 min] and 37% [$t_R$=18.8 min, 40% MeOH, 60% water (with 0.1% TFA), 20 min]. $^1$H NMR (400 MHz, DMSO-$d_6$) (reported as a mixture of diastereomers) δ 10.84 (s, 1H, 40:60, disappeared on $D_2O$ shake), 8.60 (t, J=9.2 Hz, 1H, disappeared on $D_2O$ shake), 8.47 (d, J=8.3 Hz, 1H, 40:60, reduced by 65% on $D_2O$ shake), 7.82-7.74 (m, 2H), 7.52-7.46 (m, 1H), 7.42 (td, J=7.4, 1.7 Hz, 2H), 7.34 (t, J=6.9 Hz, 2H), 7.23 (td, J=7.5, 2.3 Hz, 2H), 7.13 (t, J=7.3 Hz, 1H), 4.81-4.68 (m, 1H), 4.66-4.49 (m, 1H), 3.14 (dd, J=13.6, 4.0 Hz, 1H, 40:60), 3.06-2.94 (m, 1H), 2.81-2.63 (m, 1H), 2.56-2.47 (m, 1H, overlapped with the residual DMSO signal), 2.04-1.82 (m, 2H). HPLC-MS (ESI+): m/z 781.3 [50%, $(2M+Na)^+$], 402.2 [40%, $(M+Na)^+$], 380.2 [40%, $(M+H)^+$]. LC-MS (ESI+): 781.3 [50%, $(2M+Na)^+$], 402.2 [100%, $(M+Na)^+$]. HRMS (ESI+): m/z calcd for $C_{21}H_{21}N_3O_4$ $(M+Na)^+$402.1424, found 402.1407.

SG4-140

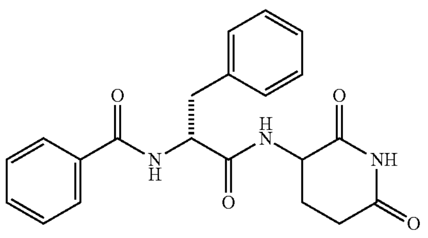

N-((2R)-1-((2,6-dioxopiperidin-3-yl)amino)-1-oxo-3-phenylpropan-2-yl)benzamide (SG4-140): This compound was prepared from benzoyl-D-phenylalanine (200 mg, 0.742 mmol), HBTU (310 mg, 0.817 mmol), 3-aminopiperidine-2,6-dione hydrochloride (128 mg, 0.780 mmol), DIPEA (0.388 mL, 2.230 mmol), and DMF (1.5 mL) using Method E (reaction time, 1 h) to give the title compound as a mixture of diastereomers, an off-white solid (192.37 mg, 68%). Mp: 206-210° C. HPLC: 60% [$t_R$=10.5 min, 45% MeOH, 55% water (with 0.1% TFA), 20 min] and 40% [$t_R$=11.0 min, 45% MeOH, 55% water (with 0.1% TFA), 20 min]. $^1$H NMR (400 MHz, DMSO-$d_6$) (reported as a mixture of diastereomers) δ 10.84 (s, 1H, 40:60, disappeared on $D_2O$ shake), 8.61 (t, J=9.2 Hz, 1H, disappeared on $D_2O$ shake), 8.47 (d, J=8.3 Hz, 1H, 40:60, disappeared on $D_2O$ shake), 7.78 (t, J=8.1 Hz, 2H), 7.49 (t, J=7.2 Hz, 1H), 7.45-7.39 (m, 2H), 7.34 (t, J=7.2 Hz, 2H), 7.27-7.19 (m, 2H), 7.13 (t, J=7.2 Hz, 1H), 4.81-4.68 (m, 1H), 4.67-4.49 (m, 1H), 3.14 (dd, J=13.6, 4.0 Hz, 1H, 40:60), 3.05-2.94 (m, 1H), 2.81-2.62 (m, 1H), 2.56-2.47 (m, 1H, overlapped with the residual DMSO signal), 2.05-1.81 (m, 2H). HPLC-MS (ESI+): m/z 781.3 [100%, $(2M+Na)^+$], 402.2 [40%, $(M+Na)^+$], 380.2 [70%, $(M+H)^+$]. LC-MS (ESI+): 781.3 [50%, $(2M+Na)^+$], 402.1 [100%, $(M+Na)^+$]. HRMS (ESI+): m/z calcd for $C_{21}H_{21}N_3O_4$ $(M+Na)^+$402.1424, found 402.1414.

SG4-141

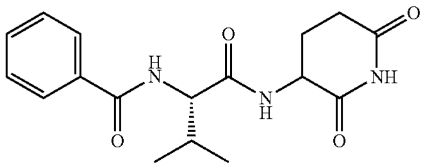

N-((2S)-1-((2,6-dioxopiperidin-3-yl)amino)-3-methyl-1-oxobutan-2-yl)benzamide (SG4-141): This compound was prepared from benzoyl-L-valine (221 mg, 1 mmol), HBTU (417 mg, 1.1 mmol), 3-aminopiperidine-2,6-dione hydrochloride (173 mg, 1.05 mmol), DIPEA (0.522 mL, 3 mmol), and DMF (2 mL) using Method E (reaction time, 1 h) to give the title compound as a mixture of diastereomers, an off-white solid (258.47 mg, 78%). Mp: 206-210° C. Mp: 221-226° C. HPLC: 62% [$t_R$=10.8 min, 35% MeOH, 65% water (with 0.1% TFA), 20 min] and 38% [$t_R$=11.2 min, 35% MeOH, 65% water (with 0.1% TFA), 20 min]. H NMR (400 MHz, DMSO-$d_6$) (reported as a mixture of diastereomers) δ 10.81 (s, 1H, 40:60, disappeared on $D_2O$ shake), 8.47 (d, J=8.2 Hz, 1H, 40%, reduced on $D_2O$ shake), 8.36 (d, J=8.2 Hz, 1H, 60%, reduced on $D_2O$ shake), 8.26 (dd, J=8.8, 2.7 Hz, 1H, disappeared on $D_2O$ shake), 7.90-7.84 (m, 2H), 7.55-7.49 (m, 1H), 7.48-7.41 (m, 2H), 4.64-4.49 (m, 1H), 4.39-4.29 (m, 1H), 2.77-2.63 (m, 1H), 2.20-2.05 (m, 1H), 2.01-1.85 (m, 2H), 1.00-0.90 (m, 6H). HPLC-MS (ESI+): m/z 685.3 [60%, $(2M+Na)^+$], 332.2 [100%, $(M+H)^+$]. LC-MS (ESI+): 685.3 [80%, $(2M+Na)^+$], 354.1 [100%, $(M+Na)^+$]. HRMS (ESI+): m/z calcd for $C_{17}H_{21}N_3O_4$ $(M+Na)^+$354.1424, found 354.1424.

SG4-142

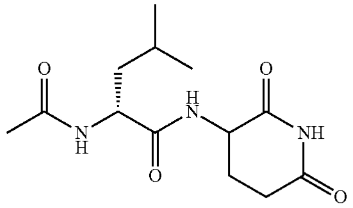

(2R)-2-acetamido-N-(2,6-dioxopiperidin-3-yl)-4-methylpentanamide (SG4-142): This compound was prepared from acetyl-D-leucine (173 mg, 1 mmol), HBTU (417 mg, 1.1 mmol), 3-aminopiperidine-2,6-dione hydrochloride (173 mg, 1.05 mmol), DIPEA (0.522 mL, 3 mmol), and DMF (2 mL) using Method E (reaction time, 1 h) to give the title compound as a mixture of diastereomers, an off-white solid (142.03 mg, 50%). Mp: 251° C. (dec). HPLC: 89% [$t_R$=5.9 min, 35% MeOH, 65% water (with 0.1% TFA), 20 min] and 11% [$t_R$=6.9 min, 35% MeOH, 65% water (with 0.1% TFA), 20 min]. $^1$H NMR (400 MHz, DMSO-$d_6$) (reported as a mixture of diastereomers) δ 10.78 (s, 1H, disappeared on $D_2O$ shake), 8.22 (d, J=8.3 Hz, 1H, disappeared on $D_2O$ shake), 8.00 (d, J=8.4 Hz, 1H, disappeared on $D_2O$ shake), 4.58-4.44 (m, 1H), 4.35-4.26 (m, 1H), 2.76-2.61 (m, 1H), 2.56-2.47 (m, 1H, overlapped with the residual DMSO signal), 2.00-1.76 (m, 2H), 1.82 (s, 3H), 1.67-1.54 (m, 1H), 1.51-1.37 (m, 1H), 0.86 (d, J=5.7 Hz, δH, 50%), 0.82 (d, J=5.7 Hz, δH, 50%). HPLC-MS (ESI−): m/z 565.4 [30%, $(2M-H)^-$], 282.1 [40%, $(M-H)^-$]. LC-MS (ESI+): 589.3 [30%, $(2M+Na)^+$], 306.1 [100%, $(M+Na)^+$]. HRMS (ESI+): m/z calcd for $C_{13}H_{21}N_3O_4$ $(M+Na)^+$306.1424, found 306.1411.

SG4-143

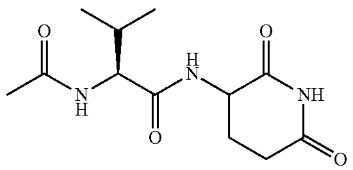

(2R)-2-acetamido-N-(2,6-dioxopiperidin-3-yl)-4-methylpentanamide (SG4-143): This compound was prepared from acetyl-D-leucine (159 mg, 1 mmol), HBTU (417 mg, 1.1 mmol), 3-aminopiperidine-2,6-dione hydrochloride (173 mg, 1.05 mmol), DIPEA (0.522 mL, 3 mmol), and DMF (2 mL) using Method E (reaction time, 1 h) to give the title compound as a mixture of diastereomers, an off-white solid (55.41 mg, 20%). Mp: 267° C. (dec). HPLC: 94% [$t_R$=8.4 min, 35% MeOH, 65% water (with 0.1% TFA), 20 min] and 6% [$t_R$=10.9 min, 35% MeOH, 65% water (with 0.1% TFA), 20 min]. $^1$H NMR (400 MHz, DMSO-$d_6$) (reported as a mixture of diastereomers) δ 10.77 (s, 1H, disappeared on $D_2O$ shake), 8.27 (d, J=8.2 Hz, 1H, reduced by 15% on $D_2O$ shake), 7.90 (d, J=8.9 Hz, 1H, reduced by 55% on $D_2O$ shake), 4.59-4.48 (m, 1H), 4.21-4.11 (m, 1H), 2.77-2.63 (m, 1H), 2.56-2.47 (m, 1H, overlapped with the residual DMSO signal), 2.01-1.76 (m, 3H), 1.84 (s, 3H), 0.88 (d, J=6.8 Hz, δH, 50%), 0.84 (d, J=6.8 Hz, δH, 50%). HPLC-MS (ESI+): m/z 561.3 [20%, $(2M+Na)^+$], 270.2 [20%, $(M+H)^+$]. LC-MS (ESI+): 292.1 [100%, $(M+Na)^+$]. HRMS (ESI+): m/z calcd for $C_{12}H_{19}N_3O_4$ $(M+Na)^+$292.1268, found 292.1263.

SG4-144

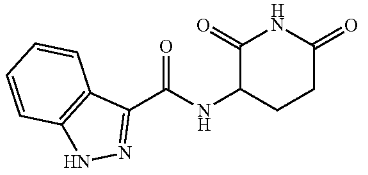

N-(2,6-dioxopiperidin-3-yl)-1H-indazole-3-carboxamide (SG4-144): This compound was prepared from 1H-indazole-3-carboxylic acid (162 mg, 1 mmol), HBTU (417 mg, 1.1 mmol), 3-aminopiperidine-2,6-dione hydrochloride (173 mg, 1.05 mmol), DIPEA (0.522 mL, 3 mmol), and DMF (2 mL) using Method E (reaction time, overnight) to give the title compound as an off-white solid (158.82 mg, 58%). Mp: 275° C. (dec). HPLC: 98% [$t_R$=4.5 min, 40% MeOH, 60% water (with 0.1% TFA), 20 min]. $^1$H NMR (400 MHz, DMSO-$d_6$) δ 13.65 (s, 1H, disappeared on $D_2O$ shake), 10.85 (s, 1H, disappeared on $D_2O$ shake), 8.65 (d, J=8.5 Hz, 1H, disappeared on $D_2O$ shake), 8.15 (d, J=8.3 Hz, 1H), 7.61 (d, J=8.3 Hz, 1H), 7.41 (ddd, J=8.3, 7.2, 1.0 Hz, 1H), 7.24 (t, J=7.2 Hz, 1H), 4.80 (ddd, J=12.9, 8.5, 5.4 Hz, 1H), 2.79 (ddd, J=19.0, 13.8, 5.4 Hz, 1H), 2.56-2.47 (m, 1H, overlapped with the residual DMSO signal), 2.21 (qd, J=12.9, 4.2 Hz, 1H), 2.04-1.93 (m, 1H). HPLC-MS (ESI+): 567.2 [100%, $(2M+Na)^+$], 273.2 [60%, $(M+H)^+$]. LC-MS (ESI+): 295.1 [100%, $(M+Na)^+$]. HRMS (ESI+): m/z calcd for $C_{13}H_{12}N_4O_3$ $(M+Na)^+$295.0802, found 295.0807.

SG4-146

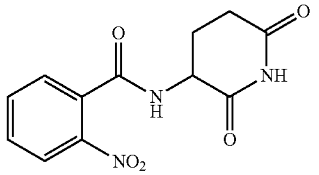

N-(2,6-Dioxopiperidin-3-yl)-2-nitrobenzamide (SG4-146): This compound was prepared from 3-aminopiperidine-2,6-dione hydrochloride (164 mg, 1 mmol), 2-nitrobenzoyl chloride (0.198 mL, 1.5 mmol), DIPEA (0.522 mL, 3 mmol), and DCM (1 mL) using Method A (reaction time, 17 h) to give the title compound as a light yellow solid (134 mg, 48%). Mp: 211-213° C. $^1$H NMR (400 MHz, DMSO-$d_6$) δ 10.89 (s, 1H, disappeared on $D_2O$ shake), 9.04 (d, J=8.3 Hz, 1H, disappeared on $D_2O$ shake), 8.04 (dd, J=8.1, 1.3 Hz, 1H), 7.81 (td, J=7.6, 1.3 Hz, 1H), 7.70 (ddd, J=8.1, 7.6, 1.3 Hz, 1H), 7.63 (dd, J=7.6, 1.3 Hz, 1H), 4.78-4.67 (m, 1H), 2.77 (ddd, J=18.2, 11.9, 6.6 Hz, 1H), 2.58-2.49 (m, 1H), 2.06-1.91 (m, 2H). HPLC-MS (ESI+): m/z 577.2 [60%, $(2M+Na)^+$], 300.1 [40%, $(M+Na)^+$], 278.1 [100%, $(M+H)^+$].

SG4-147

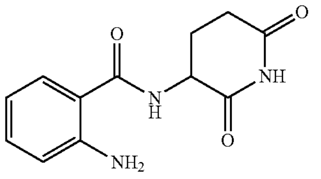

2-Amino-N-(2,6-dioxopiperidin-3-yl)benzamide (SG4-147): Into a mixture of SG4-146 (50 mg, 0.180 mmol) in MeCN (1 mL deoxygenated with Argon gas) was added $PtO_2$ (1 mg) under Argon. The flask was evacuated and back filled with Argon (twice). Argon gas was evacuated and a balloon of hydrogen was attached to the system. The reaction mixture was stirred at room temperature for 18 h, filtered using a short plug of Celite and concentrated under reduced pressure. The resulting residue was purified by chromatography ($SiO_2$) eluting with DCM (with 0-10% MeOH) to provide the title compound as a white solid (10.58 mg, 24%). Mp: 224-229° C. HPLC: 98% [$t_R$=6.0 min, 10% MeOH, 90% water (with 0.1% TFA), 20 min]. $^1$H NMR (400 MHz, DMSO-$d_6$) δ 10.84 (s, 1H, disappeared on $D_2O$ shake), 8.46 (d, J=8.4 Hz, 1H, disappeared on $D_2O$ shake), 7.49 (dd, J=8.2, 1.3 Hz, 1H), 7.14 (ddd, J=8.2, 7.1, 1.3 Hz, 1H), 6.68 (dd, J=8.2, 1.3 Hz, 1H), 6.50 (ddd, J=8.2, 7.1, 1.3 Hz, 1H), 6.42 (s, 2H, disappeared on $D_2O$ shake), 4.76-4.66 (m, 1H), 2.82-2.71 (m, 1H), 2.56-2.47 (m, 1H, overlapped with the residual DMSO signal), 2.09 (qd, J=13.0, 4.5 Hz, 1H), 1.96-1.87 (m, 1H). HPLC-MS (ESI+): m/z 517.2 [10%, $(2M+Na)^+$], 248.2 [100%, $(M+H)^+$]. LC-MS (ESI+): 270.1 [100%, $(M+Na)^+$]. HRMS (ESI+): m/z calcd for $C_{12}H_{13}N_3O_3$ $(M+Na)^+$270.0849, found 270.0841.

SG4-149

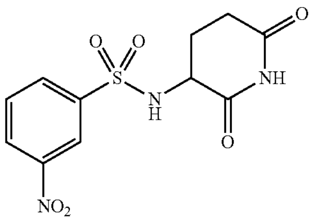

N-(2,6-Dioxopiperidin-3-yl)-3-nitrobenzenesulfonamide (SG4-159): This compound was prepared from 3-aminopiperidine-2,6-dione hydrochloride (164 mg, 1 mmol), 3-nitrobenzenesulfonyl chloride (221 mg, 1 mmol), DIPEA (0.435 mL, 2.5 mmol), and DMF (1 mL) using Method A (reaction time, overnight) to give the title compound as a dark gray solid (234.21 g, 75%). Mp: 224° C. (dec). $^1$H NMR (400 MHz, DMSO-$d_6$) δ 10.77 (s, 1H), 8.59 (brs, 1H), 8.57 (t, J=2.0 Hz, 1H), 8.44 (ddd, J=8.0, 2.0, 1.0 Hz, 1H), 8.22 (ddd, J=8.0, 2.0, 1.0 Hz, 1H), 7.86 (t, J=8.0 Hz, 1H), 4.34 (s, 1H), 2.70-2.60 (m, 1H), 2.46-2.39 (m, 1H), 1.93-1.80 (m, 2H). HPLC-MS (ESI+): m/z 649.1 [50%, $(2M+Na)^+$], 336.1 [100%, $(M+Na)^+$], 314.0 [30%, $(M+H)^+$].

SG4-154B2

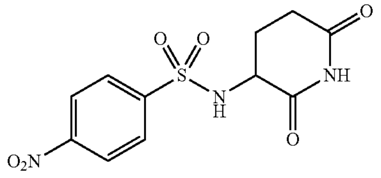

N-(2,6-dioxopiperidin-3-yl)-4-nitrobenzenesulfonamide (SG4-154B2): This compound was prepared from 3-aminopiperidine-2,6-dione hydrochloride (822.95 mg, 5 mmol), 4-nitrobenzenesulfonyl chloride (1.11 g, 5 mmol), DIPEA (2.15 mL, 12.5 mmol), and DMF (5 mL) using Method A (reaction time, overnight) to give the title compound as a dark green solid (1.021 g, 65%). Mp: 235° C. (dec). $^1H$ NMR (400 MHz, DMSO-$d_6$) δ 10.77 (s, 1H), 8.59 (brs, 1H), 8.57 (t, J=2.0 Hz, 1H), 8.44 (ddd, J=8.0, 2.0, 1.0 Hz, 1H), 8.22 (ddd, J=8.0, 2.0, 1.0 Hz, 1H), 7.86 (t, J=8.0 Hz, 1H), 4.34 (s, 1H), 2.70-2.60 (m, 1H), 2.46-2.39 (m, 1H), 1.93-1.80 (m, 2H). HPLC-MS (ESI+): m/z 649.1 [50%, $(2M+Na)^+$], 336.1 [100%, $(M+Na)^+$], 314.0 [30%, $(M+H)^+$]. $^1H$ NMR (400 MHz, DMSO-$d_6$) δ 10.79 (s, 1H), 8.60 (d, J=8.7 Hz, 1H), 8.38 (d, J=9.0 Hz, 2H), 8.05 (d, J=9.0 Hz, 2H), 4.38-4.29 (m, 1H), 2.72-2.60 (m, 1H), 2.46-2.39 (m, 1H), 1.92-1.77 (m, 2H).

SG4-163-01

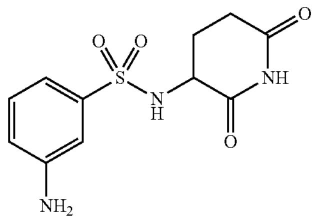

3-Amino-N-(2,6-dioxopiperidin-3-yl)benzenesulfonamide (SG4-163-01): Into a mixture of SG4-159 (100 mg, 0.319 mmol) in MeCN (2 mL deoxygenated with Argon gas) was added Pd/C (10% w/w, 34 mg) under Argon. The flask was evacuated and back filled with Argon (twice). Argon gas was evacuated and a balloon of hydrogen was attached to the system. The reaction mixture was stirred at room temperature for 2 d, filtered using a short plug of Celite and concentrated under reduced pressure. The resulting residue was purified by chromatography ($SiO_2$) eluting with DCM (with 0-10% MeOH) to provide the title compound as an off-white solid (32.73 mg, 36%). Mp: 191° C. (dec). HPLC: 98% [$t_R$=6.0 min, 10% MeOH, 90% water (with 0.1% TFA), 20 min]. $^1H$ NMR (400 MHz, DMSO-$d_6$) δ 10.76 (s, 1H, disappeared on $D_2O$ shake), 7.85 (d, J=8.3 Hz, 1H, disappeared on $D_2O$ shake), 7.14 (t, J=7.9 Hz, 1H), 6.99 (t, J=1.9 Hz, 1H), 6.92 (ddd, J=7.9, 1.9, 0.8 Hz, 1H), 6.71 (ddd, J=7.9, 1.9, 0.8 Hz, 1H), 5.50 (s, 2H, disappeared on $D_2O$ shake), 4.15-4.05 (m, 1H), 2.66-2.55 (m, 1H), 2.41 (dt, J=17.4, 4.2 Hz, 1H), 1.81-1.70 (m, 2H). HPLC-MS (ESI+): m/z 567.2 [60%, $(2M+H)^+$], 284.1 [100%, $(M+H)^+$]. LC-MS (ESI+): 589.1 [20%, $(2M+Na)^+$], 306.0 [100%, $(M+H)^+$]. HRMS (ESI+): m/z calcd for $C_{11}H_{13}N_3O_4S$ $(M+Na)^+$306.0519, found 306.0510.

SG4-167

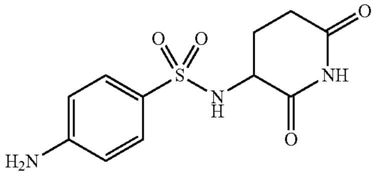

4-Amino-N-(2,6-dioxopiperidin-3-yl)benzenesulfonamide (SG4-167): Into a mixture of SG4-154B2 (100 mg, 0.319 mmol) in MeCN (1 mL deoxygenated with Argon gas) was added Pd/C (10% w/w, 90 mg) under Argon. The flask was evacuated and back filled with Argon (twice). Argon gas was evacuated and a balloon of hydrogen was attached to the system. The reaction mixture was stirred at room temperature for 2 d, filtered using a short plug of Celite and concentrated under reduced pressure. The resulting residue was purified by chromatography ($SiO_2$) eluting with DCM (with 0-10% MeOH) to provide the title compound as a light blue solid (32.83 mg, 36%). Mp: 195° C. (dec). HPLC: 99% [$t_R$=5.6 min, 10% MeOH, 90% water (with 0.1% TFA), 20 min]. $^1H$ NMR (400 MHz, DMSO-$d_6$) δ 10.76 (s, 1H, disappeared on $D_2O$ shake), 7.53 (d, J=8.1 Hz, 1H, disappeared on $D_2O$ shake), 7.43 (d, J=8.7 Hz, 2H), 6.55 (d, J=8.7 Hz, 2H), 5.91 (s, 2H, disappeared on $D_2O$ shake), 4.06-3.97 (m, 1H), 2.64-2.52 (m, 1H), 2.39 (dt, J=17.4, 4.1 Hz, 1H), 1.77-1.64 (m, 2H). HPLC-MS (ESI+): m/z 589.2 [20%, $(2M+Na)^+$], 284.2 [30%, $(M+H)^+$]. LC-MS (ESI+): 588.6 [20%, $(2M+Na)^+$], 305.8 [100%, $(M+H)^+$]. HRMS (ESI+): m/z calcd for $C_{11}H_{13}N_3O_4S$ $(M+Na)^+$306.0519, found 306.0511.

SG4-168

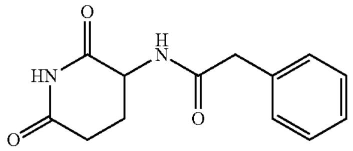

N-(2,6-dioxopiperidin-3-yl)-2-phenylacetamide (SG4-168): This compound was prepared from 3-aminopiperidine-2,6-dione hydrochloride (164 mg, 1 mmol), 2-phenylacetyl chloride (0.198 mL, 1.5 mmol), DIPEA (0.522 mL, 3 mmol), and DMF (1 mL) using Method A (reaction time, 15 h) to give the title compound as an off-white solid (122.44 mg, 50%). Mp: 199-200° C. HPLC: 99% [$t_R$=5.6 min, 10% MeOH, 90% water (with 0.1% TFA), 20 min]. $^1H$ NMR (400 MHz, DMSO-$d_6$) δ 10.81 (s, 1H), 8.44 (d, J=8.2 Hz, 1H), 7.34-7.15 (m, 5H), 4.58-4.48 (m, 1H), 3.46 (s, 2H), 2.76-2.63 (m, 1H), 2.49-2.41 (m, 1H, overlapped with the residual DMSO signal), 2.44 (d, J=3.4 Hz, 1H), 1.98-1.83 (m, 2H). HPLC-MS (ESI+): m/z 515.3 [100%, $(2M+Na)^+$], 269.1 [90%, $(M+Na)^+$], 247.2 [100%, $(M+H)^+$]. LC-MS (ESI+): 268.8 [100%, $(M+Na)^+$]. HRMS (ESI+): m/z calcd for $C_{13}H_{14}N_2O_3$ $(M+Na)^+$269.0897, found 269.0892.

SG4-170

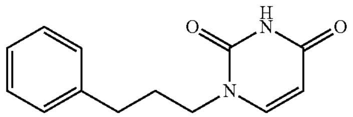

1-(3-Phenylpropyl)pyrimidine-2,4(1H,3H)-dione (SG4-170): [*J Med Chem* 1968, 682] This compound was prepared from uracil (398 mg, 6 mmol), $K_2CO_3$ (829 mg, 6 mmol), and NaI (299 mg, 2 mmol), 1-bromo-3-phenylpropane (0.303 mL, 2 mmol), and DMSO (2 mL) using Method D (reaction time, 3.5 h) to give the title compound as a white solid (240.57 mg, 52%). Mp: 114-116° C. HPLC: >99% [$t_R$=15.8 min, 40% MeOH, 60% water (with 0.1% TFA), 20 min]. $^1$H NMR (400 MHz, DMSO-$d_6$) δ 11.17 (s, 1H), 7.61 (d, J=7.8 Hz, 1H), 7.30-7.12 (m, 5H), 5.51 (dd, J=7.8, 1.9 Hz, 1H), 3.67 (t, J=7.5 Hz, 2H), 2.60-2.52 (m, 2H), 1.86 (p, J=7.5 Hz, 2H). HPLC-MS (ESI+): m/z 483.3 [10%, $(2M+Na)^+$], 253.1 [20%, $(M+Na)^+$], 231.2 [30%, $(M+H)^+$]. LC-MS (ESI+): 230.9 [100%, $(M+H)^+$]. HRMS (ESI+): m/z calcd for $C_{13}H_{14}N_2O_2$ $(M+H)^+$231.1128, found 231.1118.

SG4-172

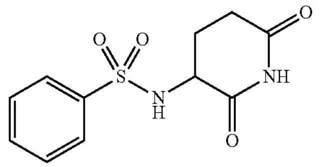

N-(2,6-Dioxopiperidin-3-yl)benzenesulfonamide (SG4-172): This compound was prepared from 3-aminopiperidine-2,6-dione hydrochloride (164 mg, 1 mmol), benzenesulfonyl chloride (0.127 mL, 1 mmol), DIPEA (0.435 mL, 2.5 mmol), and DMF (1 mL) using Method A (reaction time, overnight) to give the title compound as a light brown solid (140.42 mg, 52%). Mp: 224° C. (dec). HPLC: >99% [$t_R$=10.7 min, 20% MeOH, 80% water (with 0.1% TFA), 20 min]. $^1$H NMR (400 MHz, DMSO-$d_6$) δ 10.81 (s, 1H, disappeared on $D_2O$ shake), 8.19 (d, J=8.4 Hz, 1H, disappeared on $D_2O$ shake), 7.90-7.81 (m, 2H), 7.67-7.55 (m, 3H), 4.26 (q, J=8.5 Hz, 1H), 2.74-2.61 (m, 1H), 2.49-2.39 (m, 1H), 1.85-1.76 (m, 2H). HPLC-MS (ESI+): m/z 559.2 [50%, $(2M+Na)^+$], 286.1 [40%, $(M+NH_4)^+$], 269.1 [100%, $(M+H)^+$]. HRMS (ESI+): m/z calcd for $C_{11}H_{12}N_2O_4S$: 268.0519, found 291.0412 $(M+Na)^+$.

SG4-173

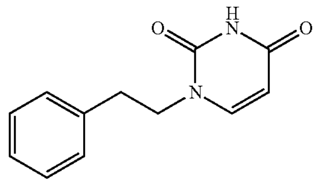

1-Phenethylpyrimidine-2,4(1H,3H)-dione (SG4-173): This compound was prepared from uracil (672 mg, 6 mmol), $K_2CO_3$ (829 mg, 6 mmol), NaI (299 mg, 2 mmol), 2-phenylethyl bromide (0.273 mL, 2 mmol), and DMSO (3 mL) using Method D (reaction time, 3.5 h). Upon acidification, water (20 mL) was added and the mixture was extracted with EtOAc (2×25 mL) and DCM (1×25 mL). The combined organic layers were washed with water (20 mL), dried ($Na_2SO_4$), and concentrated under reduced pressure to give the title compound as an off-white solid (109.72 mg, 25%). Mp: 247° C. (dec). HPLC: >99% [$t_R$=8.8 min, 40% MeOH, 60% water (with 0.1% TFA), 20 min]. $^1$H NMR (400 MHz, DMSO-$d_6$) δ 11.20 (s, 1H), 7.45 (d, J=7.8 Hz, 1H), 7.33-7.15 (m, 6H), 5.44 (dd, J=7.8, 2.2 Hz, 1H), 3.87 (t, J=7.3 Hz, 2H), 2.87 (t, J=7.3 Hz, 2H). HPLC-MS (ESI+): m/z 455.2 [80%, $(2M+Na)^+$], 433.2 [40%, $(2M+H)^+$], 239.2 [60%, $(M+Na)^+$], 217.1 [100%, $(M+H)^+$]. HRMS (ESI+): m/z calcd for $C_{12}H_{12}N_2O_2$: 216.0909, found 239.0803 $(M+Na)^+$.

SG4-174

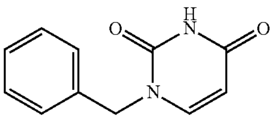

1-Benzylpyrimidine-2,4(1H,3H)-dione (SG4-174): This compound was prepared from uracil (672 mg, 6 mmol), $K_2CO_3$ (829 mg, 6 mmol), NaI (299 mg, 2 mmol), benzyl bromide (0.237 mL, 2 mmol), and DMSO (3 mL) using Method D (reaction time, 3.5 h). Upon acidification, the resulting solid was filtered, washed with water (3×10 mL), dried, triturated using EtOH/hexanes, and finally washed with hexanes (2×10 mL) and water (3×10 mL) to give the title compound as an off-white solid (178.50 mg, 44%). Mp: 170-172° C. HPLC: >99% [$t_R$=8.1 min, 35% MeOH, 65% water (with 0.1% TFA), 20 min]. $^1$H NMR (400 MHz, DMSO-$d_6$) δ 11.30 (s, 1H), 7.74 (d, J=7.8 Hz, 1H), 7.41-7.22 (m, 6H), 5.58 (dd, J=7.8, 2.1 Hz, 1H), 4.86 (s, 2H). HPLC-MS (ESI+): m/z 427.2 [90%, $(2M+Na)^+$], 405.2 [40%, $(2M+H)^+$], 225.1 [50%, $(M+Na)^+$], 203.1 [100%, $(M+H)^+$]. HRMS (ESI+): m/z calcd for $C_{11}H_{10}N_2O_2$: 202.0748, found 203.0820 $(M+H)^+$.

SG4-181

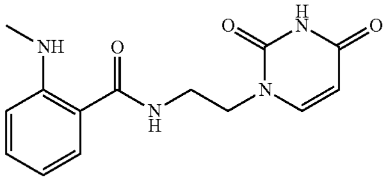

N-(2-(2,4-dioxo-3,4-dihydropyrimidin-1(2H)-yl)ethyl)-2-(methylamino)benzamide (MANT-uracil) (SG4-181): [*J Med Chem* 1968, 11 (4), 777-787] mixture of SG4-178 (100 mg, 0.522 mmol) and $Et_3N$ (0.087 mL, 0.626 mmol) in 1,4-dioxane (0.5 mL) was stirred at room temperature for 15 min. Then, N-methyl isatoic anhydride (92 mg, 0.522 mmol) was added and the mixture was stirred at room temperature overnight and heated at 100° C. for 6 h. $Et_3N$ (0.044 mL, 0.313 mmol) was added and the mixture was further stirred at 100° C. for 1 h. Water (10 mL) was added and extracted with EtOAc (2×20 mL) and DCM (1×20 mL). The combined organic layers were dried ($Na_2SO_4$), filtered, and concentrated under reduced pressure. The resulting residue was triturated using EtOAc/hexanes to give the title compound as a white solid (83.46 mg, 55%). Mp: 261-262° C. HPLC: 99% [$t_R$=5.5 min, 20% MeOH, 80% water (with 0.1% TFA), 20 min]. $^1$H NMR (400 MHz, DMSO-$d_6$) δ 11.19 (s, 1H, disappeared on $D_2O$ shake), 8.37 (t, J=5.8 Hz, 1H, reduced by 50% on $D_2O$ shake), 7.45 (brs, 1H, disappeared on $D_2O$ shake), 7.44 (d, J=7.8 Hz, 1H), 7.40 (dd, J=7.8, 1.4 Hz, 1H), 7.26 (ddd, J=8.6, 7.2, 1.6 Hz, 1H), 6.59 (d, J=7.9 Hz, 1H), 6.56-6.47 (m, 1H), 5.44 (dd, J=7.8, 2.1 Hz, 1H), 3.80-3.75 (m, 2H), 3.44 (dd, J=11.0, 5.8 Hz, 2H), 2.73 (d, J=5.5 Hz, 3H). HPLC-MS (ESI+): m/z 599.3 [10%, $(2M+Na)^+$], 289.2 [100%, $(M+H)^+$]. LC-MS (ESI+): 311.1

[40%, $(M+H)^+$]. HRMS (ESI+): m/z calcd for $C_{14}H_{16}N_4O_3$ $(M+Na)^+$311.1115, found 311.1108.

SG5-001

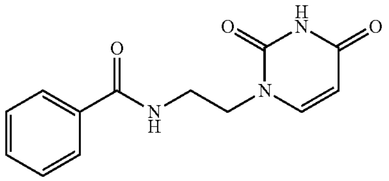

N-(2-(2,4-dioxo-3,4-dihydropyrimidin-1(2H)-yl)ethyl) benzamide (SG5-001): This compound was prepared from SG4-178 (100 mg, 0.522 mmol), benzoyl chloride (0.091 mL, 0.783 mmol), DIPEA (0.363 mL, 2.09 mmol), and DMF (1 mL) using Method A (reaction time, 17 h) to give the title compound as an off-white solid (81.12 mg, 60%). Mp: 255-256° C. HPLC: >99% [$t_R$=5.5 min, 30% MeOH, 70% water (with 0.1% TFA), 20 min]. $^1$H NMR (400 MHz, DMSO-$d_6$) δ 11.20 (s, 1H, disappeared on $D_2O$ shake), 8.57 (t, J=5.8 Hz, 1H, reduced by 50% on $D_2O$ shake), 7.78-7.73 (m, 2H), 7.54-7.48 (m, 1H), 7.48-7.41 (m, 3H), 5.43 (dd, J=7.8, 2.2 Hz, 1H), 3.84-3.75 (m, 2H), 3.48 (dd, J=11.1, 5.8 Hz, 2H). HPLC-MS (ESI+): m/z 541.3 [70%, $(2M+Na)^+$], 282.1 [30%, $(M+Na)^+$], 260.1 [100%, $(M+H)^+$]. LC-MS (ESI+): 282.1 [100%, $(M+H)^+$]. HRMS (ESI+): m/z calcd for $C_{13}H_{13}N_3O_3$ $(M+Na)^+$282.0849, found 282.0844.

SG5-002

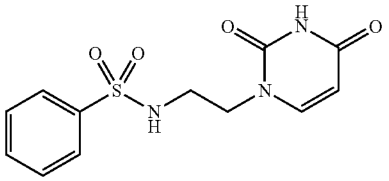

N-(2-(2,4-dioxo-3,4-dihydropyrimidin-1(2H)-yl)ethyl) benzenesulfonamide (SG5-002): This compound was prepared from SG4-178 (100 mg, 0.522 mmol), benzenesulfonyl chloride (0.100 mL, 0.783 mmol), DIPEA (0.363 mL, 2.09 mmol), and DMF (1 mL) using Method A (reaction time, 17 h) to give the title compound as an off-white solid (89.99 mg, 58%). Mp: 196° C. (dec). HPLC: 98% [$t_R$=5.3 min, 30% MeOH, 70% water (with 0.1% TFA), 20 min]. $^1$H NMR (400 MHz, DMSO-$d_6$) δ 11.17 (s, 1H, disappeared on $D_2O$ shake), 7.81 (t, J=6.2 Hz, 1H, disappeared on $D_2O$ shake), 7.76-7.72 (m, 2H), 7.65-7.60 (m, 1H), 7.60-7.54 (m, 2H), 7.45 (d, J=7.8 Hz, 1H), 5.49 (dd, J=7.8, 2.3 Hz, 1H), 3.67 (t, J=6.0 Hz, 2H), 2.98 (q, J=6.0 Hz, 2H). HPLC-MS (ESI+): m/z 613.2 [30%, $(2M+Na)^+$], 296.2 [30%, $(M+H)^+$]. HPLC-MS (ESI−): m/z 589.2 [30%, $(2M-H)^-$], 294.1 [100%, $(M-H)^-$]. LC-MS (ESI+): 318.0 [65%, $(M+Na)^+$], 296.1 [100%, $(M+H)^+$]. HRMS (ESI+): m/z calcd for $C_{12}H_{13}N_3O_4S$ $(M+H)^+$296.0699, found 296.0694.

SG5-003

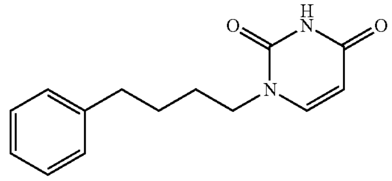

1-(4-phenylbutyl)pyrimidine-2,4(1H,3H)-dione (SG5-003): This compound was prepared from uracil (448 mg, 4 mmol), $K_2CO_3$ (552 mg, 4 mmol), NaI (299 mg, 2 mmol), 1-bromo-4-phenylbutane (0.351 mL, 2 mmol), and DMSO (4 mL) using Method D (reaction time, 17 h at 90° C. and 30 min at 120° C.). Upon acidification, water (20 mL) was added and the mixture was extracted with EtOAc (2×20 mL) and DCM (1×20 mL). The combined organic layers were dried ($Na_2SO_4$), concentrated under reduced pressure, and the resulting oil was triturated using EtOH/hexanes to give the title compound as a light yellow solid (370.62 mg, 76%). Mp: 116-117° C. HPLC: >99% [$t_R$=12.6 min, 50% MeOH, 50% water (with 0.1% TFA), 20 min]. $^1$H NMR (400 MHz, DMSO-$d_6$) δ 11.19 (s, 1H, disappeared on $D_2O$ shake), 7.62 (d, J=7.8 Hz, 1H), 7.30-7.21 (m, 2H), 7.21-7.11 (m, 3H), 5.51 (dd, J=7.8, 2.2 Hz, 1H), 3.65 (t, J=7.0 Hz, 2H), 2.57 (t, J=7.0 Hz, 2H), 1.62-1.45 (m, 4H). HPLC-MS (ESI+): m/z 511.3 [30%, $(2M+Na)^+$], 489.3 [30%, $(2M+H)^+$], 267.2 [100%, $(M+Na)^+$], 245.2 [90%, $(M+H)^+$]. HRMS (ESI+): m/z calcd for $C_{14}H_{16}N_2O_2$: 244.1220, found 245.1295 $(M+H)^+$.

SG5-004

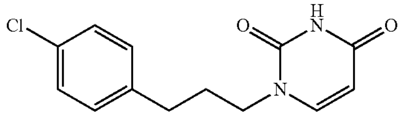

1-(3-(4-Chlorophenyl)propyl)pyrimidine-2,4(1H,3H)-dione (SG5-004): This compound was prepared from uracil (224 mg, 2 mmol), $K_2CO_3$ (276 mg, 2 mmol), NaI (150 mg, 1 mmol), 1-(3-bromopropyl)-4-chlorobenzene (233 mg, 1 mmol), and DMSO (2 mL) using Method D (reaction time, 17 h at 90° C. and 4 h at 120° C.) to give the title compound as a yellow solid (110.42 mg, 42%). Mp: 139-142° C. HPLC: 99% [$t_R$=9.7 min, 55% MeOH, 45% water (with 0.1% TFA), 20 min]. $^1$H NMR (400 MHz, DMSO-$d_6$) δ 11.19 (s, 1H, disappeared on $D_2O$ shake), 7.61 (d, J=7.8 Hz, 1H), 7.31 (d, J=8.4 Hz, 2H), 7.23 (d, J=8.4 Hz, 2H), 5.51 (dd, J=7.8, 2.1 Hz, 1H), 3.65 (t, J=7.5 Hz, 2H), 2.56 (t, J=7.5 Hz, 2H), 1.85 (p, J=7.5 Hz, 2H). HPLC-MS (ESI+): m/z 553.2 [40%, $(2M^{37}Cl+Na)^+$], 551.1 [100%, $(2M^{35}Cl+Na)^+$], 289.1 [30%, $(M^{37}Cl+Na)^+$], 287.2 [70%, $(M^{35}Cl+Na)^+$], 267.2 [30%, $(M^{37}Cl+H)^+$], 265.1 [90%, $(M^{35}Cl+H)^+$]. HRMS (ESI+): m/z calcd for $C_{13}H_{13}ClN_2O_2$: 264.0671, found 265.0746 $(M+H)^+$.

SG5-005

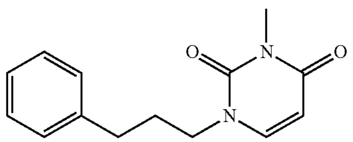

3-Methyl-1-(3-phenylpropyl)pyrimidine-2,4(1H,3H)-dione (SG5-005): Into a mixture of SG4-170 (50 mg, 0.217 mmol) and $K_2CO_3$ (60 mg, 0.434 mmol) in DMF (0.6 mL) was added methyl iodide (0.027 mL, 0.434 mmol) at room temperature. The mixture was stirred at room temperature for 16 h. Water (20 mL) was added and the mixture was extracted with DCM (1×20 mL) and EtOAc (2×20 mL). The combined organic layers were dried ($Na_2SO_4$) and concentrated under reduced pressure to give the title compound as yellow oil (49.72 mg, 94%). HPLC: >99% [$t_R$=12.7 min, 50% MeOH, 50% water (with 0.1% TFA), 20 min]. $^1H$ NMR (400 MHz, DMSO-$d_6$) δ 7.66 (d, J=7.8 Hz, 1H), 7.29-7.11 (m, 5H), 5.65 (d, J=7.8 Hz, 1H), 3.74 (t, J=7.5 Hz, 2H), 3.11 (s, 3H), 2.56 (t, J=7.5 Hz, 2H), 1.89 (p, J=7.5 Hz, 2H). HPLC-MS (ESI+): m/z 511.3 [30%, $(2M+Na)^+$], 267.2 [100%, $(M+Na)^+$], 245.2 [80%, $(M+H)^+$]. LC-MS (ESI+): 267.1 [40%, $(M+Na)^+$], 245.1 [100%, $(M+H)^+$]. HRMS (ESI+): m/z calcd for $C_{14}H_{16}N_2O_2$ $(M+H)^+$245.1284, found 245.1292.

SG5-006

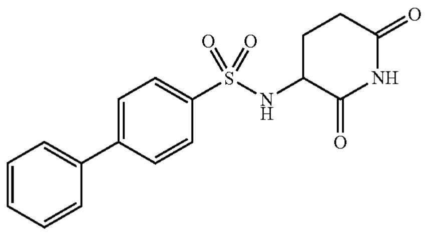

N-(2,6-Dioxopiperidin-3-yl)-[1,1'-biphenyl]-4-sulfonamide (SG5-006): This compound was prepared from 3-aminopiperidine-2,6-dione hydrochloride (164 mg, 1 mmol), [1,1'-biphenyl]-4-sulfonyl chloride (252 mg, 1 mmol), DIPEA (0.435 mL, 2.5 mmol), and DMF (1 mL) using Method A (reaction time, overnight) to give the title compound as an off-white solid (290.15 mg, 84%). Mp: 215° C. (dec). HPLC: 99% [$t_R$=8.6 min, 55% MeOH, 45% water (with 0.1% TFA), 20 min]. $^1H$ NMR (400 MHz, DMSO-$d_6$) δ 10.78 (s, 1H, disappeared on $D_2O$ shake), 8.20 (d, J=8.4 Hz, 1H, disappeared on $D_2O$ shake), 7.90 (d, J=8.5 Hz, 2H), 7.85 (d, J=8.5 Hz, 2H), 7.73 (d, J=7.3 Hz, 2H), 7.49 (t, J=7.3 Hz, 2H), 7.42 (t, J=7.3 Hz, 1H), 4.31-4.22 (m, 1H), 2.72-2.60 (m, 1H), 2.47-2.38 (m, 1H), 1.88-1.74 (m, 2H). HPLC-MS (ESI+): m/z 711.2 [100%, $(2M+Na)^+$], 367.2 [40%, $(M+Na)^+$], 345.2 [40%, $(M+H)^+$]. LC-MS (ESI+): 367.0 [100%, $(M+Na)^+$]. HRMS (ESI+): m/z calcd for $C_{17}H_{16}N_2O_4S$ $(M+2H)^{2+}$ 173.0488, found 173.0419.

SG5-007

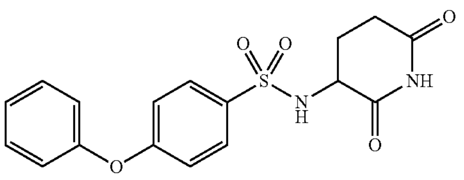

N-(2,6-Dioxopiperidin-3-yl)-4-phenoxybenzenesulfonamide (SG5-007): This compound was prepared from 3-aminopiperidine-2,6-dione hydrochloride (164 mg, 1 mmol), 4-phenoxybenzenesulfonyl chloride (268 mg, 1 mmol), DIPEA (0.435 mL, 2.5 mmol), and DMF (1 mL) using Method A (reaction time, overnight) to give the title compound as a light purple solid (220.29 mg, 61%). Mp: 229° C. (dec). HPLC: >99% [$t_R$=9.4 min, 55% MeOH, 45% water (with 0.1% TFA), 20 min]. $^1H$ NMR (400 MHz, DMSO-$d_6$) δ 10.77 (s, 1H, disappeared on $D_2O$ shake), 8.09 (d, J=8.4 Hz, 1H, disappeared on $D_2O$ shake), 7.81 (d, J=8.9 Hz, 2H), 7.45 (tt, J=7.5, 2.2 Hz, 2H), 7.23 (tt, J=7.5, 1.1 Hz, 1H), 7.11 (dq, J=7.5, 1.1 Hz, 2H), 7.07 (d, J=8.9 Hz, 2H), 4.19 (ddd, J=11.3, 8.4, 6.2 Hz, 1H), 2.64 (ddd, J=17.5, 11.3, 6.2 Hz, 1H), 2.43 (dt, J=17.5, 4.1 Hz, 1H), 1.88-1.71 (m, 2H). HPLC-MS (ESI+): m/z 743.2 [100%, $(2M+Na)^+$], 383.1 [70%, $(M+Na)^+$], 361.1 [40%, $(M+H)^+$]. LC-MS (ESI+): 383.0 [85%, $(M+Na)^+$]. HRMS (ESI+): m/z calcd for $C_{17}H_{16}N_2O_5S$ $(M+Na)^+$383.0672, found 383.0677.

SG5-012

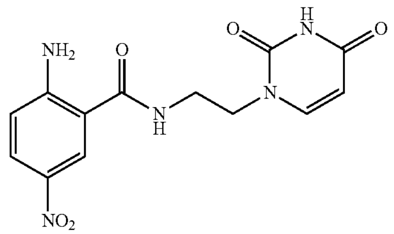

2-Amino-N-(2-(2,4-dioxo-3,4-dihydropyrimidin-1(2H)-yl)ethyl)-5-nitrobenzamide (SG5-012): This compound was prepared from SG4-178 (100 mg, 0.522 mmol), 5-nitroisatoic anhydride (108 mg, 0.522 mmol), $Et_3N$ (0.124 mL, 0.887 mmol), and 1,4-dioxane (0.5 mL) using Method B (reaction time, 17 h) to give the title compound as a yellow solid (80.04 mg, 48%). Mp: 291° C. (dec). HPLC: 97% [$t_R$=5.4 min, 30% MeOH, 70% water (with 0.1% TFA), 20 min]. $^1H$ NMR (400 MHz, DMSO-$d_6$) δ 11.20 (s, 1H, disappeared on $D_2O$ shake), 8.79 (t, J=5.7 Hz, 1H, disappeared on $D_2O$ shake), 8.42 (d, J=2.6 Hz, 1H), 8.00 (dd, J=9.2, 2.6 Hz, 1H), 7.70 (s, 2H, disappeared on $D_2O$ shake), 7.49 (d, J=7.8 Hz, 1H), 6.77 (d, J=9.2 Hz, 1H), 5.45 (d, J=7.8 Hz, 1H), 3.80 (t, J=5.7 Hz, 2H), 3.46 (q, J=5.7 Hz, 2H). HPLC-MS (ESI+): m/z 661.2 [100%, $(2M+Na)^+$], 639.3 [40%, $(2M+H)^+$], 342.3 [30%, $(M+Na)^+$], 320.1 [60%, $(M+H)^+$]. LC-MS (ESI+): 342.1 [100%, $(M+Na)^+$]. HRMS (ESI+): m/z calcd for $C_{13}H_{13}N_5O_5$ $(M+Na)^+$342.0809, found 342.0810.

SG5-016

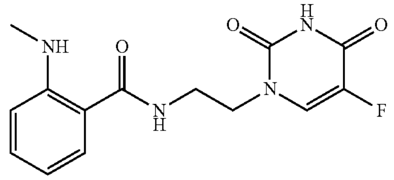

N-(2-(5-Fluoro-2,4-dioxo-3,4-dihydropyrimidin-1(2H)-yl)ethyl)-2-(methylamino)benzamide (SG5-016): A mixture of SG5-014 (100 mg, 0.477 mmol) and $Et_3N$ (0.113 mL, 0.811 mmol) in 1,4-dioxane (0.5 mL) was stirred at room temperature for 30 min. Then, N-methyl isatoic anhydride (84 mg, 0.477 mmol) was added and the mixture was stirred at room temperature overnight and heated at 100° C. for 1 h. Water (10 mL) was added and extracted with EtOAc (2×20 mL) and DCM (1×20 mL). The combined organic layers were dried ($Na_2SO_4$), filtered, and concentrated under reduced pressure. The resulting residue was triturated using EtOH/hexanes to give the title compound as a white solid (24.81 mg, 17%). Mp: 248-252° C. HPLC: >99% [$t_R$=8.8 min, 20% MeOH, 80% water (with 0.1% TFA), 20 min]. $^1$H NMR (400 MHz, DMSO-$d_6$) δ 11.71 (s, 1H, disappeared on $D_2O$ shake), 8.35 (t, J=5.8 Hz, 1H, disappeared on $D_2O$ shake), 7.94 (d, J=6.7 Hz, 1H), 7.41 (dd, J=7.8, 1H), 7.39 (q, J=5.1 Hz, 1H, disappeared on $D_2O$ shake), 7.26 (t, J=7.8 Hz, 1H), 6.59 (d, J=7.8 Hz, 1H), 6.52 (t, J=7.8 Hz, 1H), 3.74 (t, J=5.8 Hz, 2H), 3.45 (q, J=5.8 Hz, 2H), 2.72 (d, J=5.1 Hz, 3H). $^{19}$F NMR (376 MHz, DMSO-$d_6$) δ −170.81 (d, J=6.7 Hz). HPLC-MS (ESI+): m/z 307.2 [100%, $(M+H)^+$]. LC-MS (ESI+): 329.1 [70%, $(M+Na)^+$]. HRMS (ESI+): m/z calcd for $C_{14}H_{15}FN_4O_3(M+Na)^+$329.1020, found 329.1026.

SG5-017

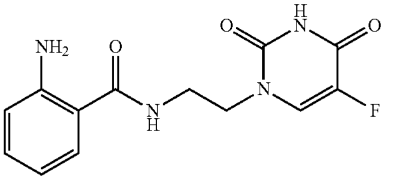

2-Amino-N-(2-(5-fluoro-2,4-dioxo-3,4-dihydropyrimidin-1(2H)-yl)ethyl)benzamide (SG5-017): A mixture of SG5-014 (100 mg, 0.477 mmol) and $Et_3N$ (0.113 mL, 0.811 mmol) in 1,4-dioxane (0.5 mL) was stirred at room temperature for 30 min. Then, isatoic anhydride (78 mg, 0.477 mmol) was added and the mixture was stirred at room temperature overnight and heated at 100° C. for 1 h. Water (10 mL) was added and extracted with EtOAc (2×20 mL) and DCM (1×20 mL). The combined organic layers were dried ($Na_2SO_4$), filtered, and concentrated under reduced pressure. The resulting residue was purified by chromatography ($SiO_2$) eluting with DCM (with 0-10% MeOH) to provide the title compound as an off-white solid (21.88 mg, 16%). Mp: 192-194° C. HPLC: >99% [$t_R$=6.3 min, 15% MeOH, 85% water (with 0.1% TFA), 20 min]. $^1$H NMR (400 MHz, DMSO-$d_6$) δ 11.71 (s, 1H, disappeared on $D_2O$ shake), 8.27 (t, J=5.8 Hz, 1H, disappeared on $D_2O$ shake), 7.94 (d, J=6.7 Hz, 1H), 7.36 (dd, J=7.9, 1.2 Hz, 1H), 7.10 (t, J=7.9, 1H), 6.65 (dd, J=7.9, 1.2 Hz, 1H), 6.48 (t, J=7.9, 1H), 6.29 (s, 2H, disappeared on $D_2O$ shake), 3.74 (t, J=5.8 Hz, 2H), 3.45 (q, J=5.8 Hz, 2H). $^{19}$F NMR (376 MHz, DMSO-$d_6$) δ −170.79 (d, J=6.7 Hz). HPLC-MS (ESI+): m/z 293.2 [100%, $(M+H)^+$]. LC-MS (ESI+): 315.1 [50%, $(M+Na)^+$]. HRMS (ESI+): m/z calcd for $C_{13}H_{13}FN_4O_3(M+Na)^+$ 315.0864, found 315.0872.

SG5-020

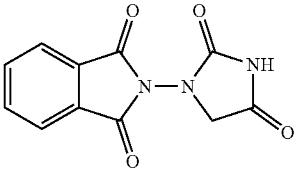

2-(2,4-Dioxoimidazolidin-1-yl)isoindoline-1,3-dione (SG5-020): This compound was prepared from phthalic anhydride (296 mg, 2 mmol), 1-aminohydantoin hydrochloride (303 mg, 2 mmol), and AcOH (2 mL) using Method C to give the title compound as a white solid (313.98 mg, 64%). Mp: 279-281° C. HPLC: 99% [$t_R$=6.1 min, 25% MeOH, 75% water (with 0.1% TFA), 20 min]. $^1$H NMR (400 MHz, DMSO-$d_6$) δ 11.76 (s, 1H, disappeared on $D_2O$ shake), 8.03-7.90 (m, 4H), 4.29 (d, J=1.7 Hz, 2H). HPLC-MS (ESI+): m/z 513.1 [50%, $(2M+Na)^+$], 268.1 [70%, $(M+Na)^+$], 246.1 [100%, $(M+H)^+$]. LC-MS (ESI+): 268.0 [100%, $(M+Na)^+$]. HRMS (ESI+): m/z calcd for $C_{11}H_7N_3O_4$ $(M+Na)^+$268.0329, found 268.0333.

SG5-029

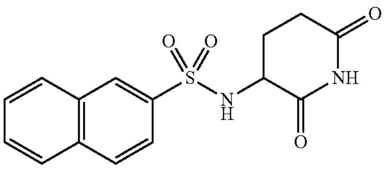

N-(2,6-dioxopiperidin-3-yl)naphthalene-2-sulfonamide (SG5-029): This compound was prepared from 3-aminopiperidine-2,6-dione hydrochloride (164 mg, 1 mmol), naphthalene-2-sulfonyl chloride (227 mg, 1 mmol), DIPEA (0.435 mL, 2.5 mmol), and DMF (1 mL) using Method A (reaction time, overnight) to give the title compound as an off-white solid (241.28 mg, 76%). Mp: 227° C. (dec). HPLC: 98% [$t_R$=6.1 min, 45% MeOH, 55% water (with 0.1% TFA), 20 min]. $^1$H NMR (400 MHz, DMSO-$d_6$) δ 10.74 (s, 1H, disappeared on $D_2O$ shake), 8.44 (s, 1H), 8.25 (d, J=8.1 Hz, 1H, disappeared on $D_2O$ shake), 8.10 (t, J=8.4 Hz, 2H), 8.02 (d, J=7.8 Hz, 1H), 7.85 (dd, J=8.6, 1.6 Hz, 1H), 7.71-7.60 (m, 2H), 4.27 (q, J=8.2 Hz, 1H), 2.68-2.57 (m, 1H), 2.40 (dt, J=17.6, 3.5 Hz, 1H), 1.85-1.74 (m, 2H). HPLC-MS (ESI+): m/z 659.2 [100%, $(2M+Na)^+$], 341.1 [60%, $(M+Na)^+$], 336.1 [50%, $(M+NH_4)^+$], 319.1 [80%, $(M+H)^+$]. LC-MS (ESI+): 659.1 [30%, $(2M+Na)^+$], 341.0 [100%, $(M+Na)^+$]. HRMS (ESI+): m/z calcd for $C_{15}H_{14}N_2O_4S$ $(M+Na)^+$341.0566, found 341.0555.

SG5-030

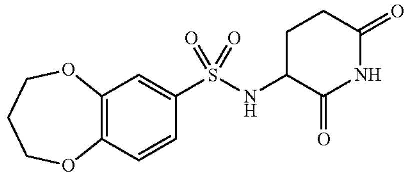

N-(2,6-Dioxopiperidin-3-yl)-3,4-dihydro-2H-benzo[b][1,4]dioxepine-7-sulfonamide (SG5-030): This compound was prepared from 3-aminopiperidine-2,6-dione hydrochloride (82 mg, 0.5 mmol), 3,4-dihydro-2H-benzo[b][1,4]dioxepine-7-sulfonyl chloride (124 mg, 0.5 mmol), DIPEA (0.218 mL, 1.25 mmol), and DMF (0.5 mL) using Method A (reaction time, overnight) to give the title compound as a white solid (98.20 mg, 57%). Mp: 158-159° C. HPLC: 99% [$t_R$=6.4 min, 35% MeOH, 65% water (with 0.1% TFA), 20 min]. $^1$H NMR (400 MHz, DMSO-$d_6$) δ 10.77 (s, 1H, disappeared on $D_2O$ shake), 8.05 (d, J=7.6 Hz, 1H, disappeared on $D_2O$ shake), 7.41-7.35 (m, 2H), 7.10-7.05 (m, 1H), 4.24-4.14 (m, 5H), 2.64 (ddd, J=17.7, 11.5, 6.6 Hz, 1H), 2.42 (dt, J=17.7, 4.0 Hz, 1H), 2.13 (p, J=5.6 Hz, 2H), 1.86-1.71 (m, 2H). HPLC-MS (ESI+): m/z 703.2 [100%, $(2M+Na)^+$], 363.1 [20%, $(M+Na)^+$], 358.2 [100%, $(M+NH_4)^+$], 341.1 [90%, $(M+H)^+$]. LC-MS (ESI+): 703.1 [70%, $(2M+Na)^+$], 363.1 [100%, $(M+Na)^+$]. HRMS (ESI+): m/z calcd for $C_{14}H_{16}N_2O_6S$ $(M+Na)^+$363.0621, found 363.0612.

SG5-031

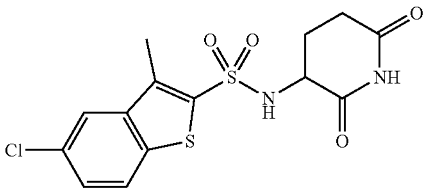

5-Chloro-N-(2,6-dioxopiperidin-3-yl)-3-methylbenzo[b]thiophene-2-sulfonamide (SG5-031): This compound was prepared from 3-aminopiperidine-2,6-dione hydrochloride (164 mg, 1 mmol), 5-chloro-3-methylbenzo[b]thiophene-2-sulfonyl chloride (281 mg, 1 mmol), DIPEA (0.435 mL, 2.5 mmol), and DMF (1 mL) using Method A (reaction time, overnight) to give the title compound as an off-white solid (269.75 mg, 72%). Mp: 240° C. (dec). HPLC: 99% [$t_R$=16.4 min, 50% MeOH, 50% water (with 0.1% TFA), 20 min]. $^1H$ NMR (400 MHz, DMSO-$d_6$) δ 10.75 (s, 1H, disappeared on $D_2O$ shake), 8.70 (d, J=8.7 Hz, 1H, disappeared on $D_2O$ shake), 8.06 (d, J=8.7 Hz, 1H), 8.03 (s, 1H), 7.54 (d, J=8.7 Hz, 1H), 4.26 (q, J=9.0 Hz, 1H), 2.73-2.61 (m, 1H), 2.60 (s, 3H), 2.45-2.37 (m, 1H), 1.91-1.77 (m, 2H). HPLC-MS (ESI+): m/z 769.1 [10%, $(2M^{37}Cl+Na)^+$], 767.2 [25%, $(2M^{35}Cl+Na)^+$], 397.1 [50%, $(M^{37}Cl+Na)^+$], 395.1 [100%, $(M^{35}Cl+Na)^+$], 373.1 [40%, $(M^{35}Cl+H)^+$]. LC-MS (ESI+): 395.0 [100%, $(M^{35}Cl+Na)^+$]. HRMS (ESI+): m/z calcd for $C_{14}H_{13}ClN_2O_4S_2$ $(M+Na)^+$394.9897, found 394.9890.

SG5-034

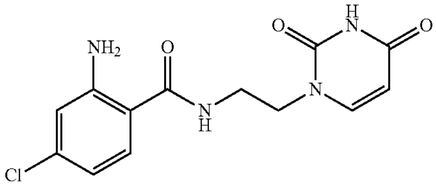

2-Amino-4-chloro-N-(2-(2,4-dioxo-3,4-dihydropyrimidin-1(2H)-yl)ethyl)benzamide (SG5-034): This compound was prepared from SG4-178 (50 mg, 0.261 mmol), 4-chloroisatoic anhydride (52 mg, 0.261 mmol), $Et_3N$ (0.062 mL, 0.443 mmol), and 1,4-dioxane (0.26 mL) using Method B (reaction time, 17 h) to give the title compound as an off-white solid (37.26 mg, 46%). Mp: 229° C. (dec). HPLC: 99% [$t_R$=8.2 min, 45% MeOH, 55% water (with 0.1% TFA), 20 min]. $^1H$ NMR (400 MHz, DMSO-$d_6$) δ 11.19 (s, 1H, disappeared on $D_2O$ shake), 8.37 (t, J=5.8 Hz, 1H, disappeared on $D_2O$ shake), 7.45 (d, J=7.8 Hz), 7.38 (d, J=8.5 Hz, 1H), 6.71 (d, J=2.2 Hz, 1H), 6.59 (s, 2H, disappeared on $D_2O$ shake), 6.50 (dd, J=8.5, 2.2 Hz, 1H), 5.44 (dd, J=7.8, 2.3 Hz, 1H), 3.86 (t, J=5.8 Hz, 2H), 3.43 (q, J=5.8 Hz, 2H). HPLC-MS (ESI+): m/z 639.1 [10%, $(2M^{35}Cl+Na)^+$], 311.2 [40%, $(M^{37}Cl+H)^+$], 309.1 [100%, $(M^{35}Cl+H)^+$]. LC-MS (ESI+): 331.0 [100%, $(M^{35}Cl+Na)^+$]. HRMS (ESI+): m/z calcd for $C_{13}H_{13}ClN_4O_3$$(M+Na)^+$331.0568, found 331.0564.

SG5-035

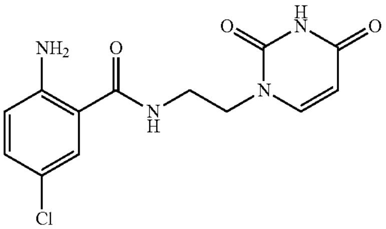

2-Amino-5-chloro-N-(2-(2,4-dioxo-3,4-dihydropyrimidin-1(2H)-yl)ethyl)benzamide (SG5-035): This compound was prepared from SG4-178 (50 mg, 0.261 mmol), 5-chloroisatoic anhydride (52 mg, 0.261 mmol), $Et_3N$ (0.062 mL, 0.443 mmol), and 1,4-dioxane (0.26 mL) using Method B (reaction time, 17 h) to give the title compound as an off-white solid (31.56 mg, 39%). Mp: 216° C. (dec). HPLC: 99% [$t_R$=6.4 min, 30% MeOH, 70% water (with 0.1% TFA), 20 min]. $^1H$ NMR (400 MHz, DMSO-$d_6$) δ 11.20 (s, 1H, disappeared on $D_2O$ shake), 8.42 (t, J=5.8 Hz, 1H, disappeared on $D_2O$ shake), 7.47 (d, J=7.8 Hz, 1H), 7.43 (d, J=2.5 Hz, 1H), 7.13 (dd, J=8.8, 2.5 Hz, 1H), 6.68 (d, J=8.8 Hz, 1H), 6.46 (s, 2H, disappeared on $D_2O$ shake), 5.45 (dd, J=7.8, 2.3 Hz, 1H), 3.77 (t, J=5.8 Hz, 2H), 3.43 (q, J=5.8 Hz, 2H). HPLC-MS (ESI+): m/z 639.0 [10%, $(2M^{35}Cl+Na)^+$], 311.2 [40%, $(M^{37}Cl+H)^+$], 309.1 [90%, $(M^{35}Cl+H)^+$]. LC-MS (ESI+): 331.0 [100%, $(M^{35}Cl+Na)^+$]. HRMS (ESI+): m/z calcd for $C_{13}H_{13}ClN_4O_3$$(M+Na)^+$331.0568, found 331.0561.

SG5-036

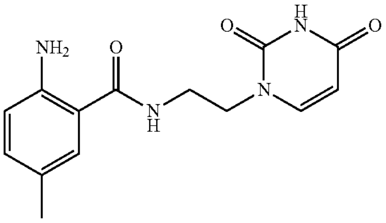

2-Amino-N-(2-(2,4-dioxo-3,4-dihydropyrimidin-1(2H)-yl)ethyl)-5-methylbenzamide (SG5-036): This compound was prepared from SG4-178 (50 mg, 0.261 mmol), 5-methylisatoic anhydride (46 mg, 0.261 mmol), $Et_3N$ (0.062 mL, 0.443 mmol), and 1,4-dioxane (0.26 mL) using Method B (reaction time, 17 h) to give the title compound as an off-white solid (32.48 mg, 43%). Mp: 242° C. (dec). HPLC: 99% [$t_R$=13.4 min, 10% MeOH, 90% water (with 0.1% TFA), 20 min]. $^1H$ NMR (400 MHz, DMSO-$d_6$) δ 11.19 (s, 1H, disappeared on $D_2O$ shake), 8.25 (t, J=5.8 Hz, 1H, disappeared on $D_2O$ shake), 7.44 (d, J=7.8 Hz, 1H), 7.19 (d, J=1.5 Hz, 1H), 6.94 (dd, J=8.3, 1.5 Hz, 1H), 6.57 (d, J=8.3 Hz, 1H), 6.08 (s, 2H, disappeared on $D_2O$ shake), 5.44 (dd, J=7.8, 2.1 Hz, 1H), 3.77 (t, J=5.8 Hz, 2H), 3.42 (q, J=5.8 Hz, 2H), 2.13 (s, 3H). HPLC-MS (ESI+): m/z 599.2 [10%, $(2M+Na)^+$], 289.2 [100%, $(M+H)^+$]. LC-MS (ESI+): 311.1 [100%, $(M+Na)^+$]. HRMS (ESI+): m/z calcd for $C_{14}H_{16}N_4O_3$ $(M+Na)^+$311.1115, found 311.1106.

SG5-037

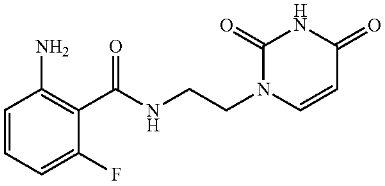

2-Amino-N-(2-(2,4-dioxo-3,4-dihydropyrimidin-1(2H)-yl)ethyl)-6-fluorobenzamide (SG5-037): This compound was prepared from SG4-178 (50 mg, 0.261 mmol), 6-fluoroisatoic anhydride (47 mg, 0.261 mmol), $Et_3N$ (0.062 mL, 0.443 mmol), and 1,4-dioxane (0.26 mL) using Method B (reaction time, 17 h) to give the title compound as an off-white solid (32.27 mg, 42%). Mp: 161-165° C. HPLC: 99% [$t_R$=9.2 min, 10% MeOH, 90% water (with 0.1% TFA), 20 min]. $^1H$ NMR (400 MHz, DMSO-$d_6$) δ 11.20 (s, 1H, disappeared on $D_2O$ shake), 8.36 (t, J=5.8 Hz, 1H, disappeared on $D_2O$ shake), 7.47 (d, J=7.8 Hz, 1H), 7.22 (dd, J=10.1, 3.0 Hz, 1H), 7.02 (ddd, J=9.0, 8.4, 3.0 Hz, 1H), 6.67 (dd, J=9.0, 5.0 Hz, 1H), 6.20 (s, 2H, disappeared on $D_2O$ shake), 5.45 (dd, J=7.8, 2.3 Hz, 1H), 3.77 (t, J=5.8 Hz, 2H), 3.43 (q, J=5.8 Hz, 2H). $^{19}F$ NMR (376 MHz, DMSO-$d_6$) δ −130.09 (ddd, J=10.1, 8.4, 5.0 Hz). HPLC-MS (ESI+): m/z 607.3 [10%, $(2M+Na)^{2+}$ ], 293.2 [100%, $(M+H)^+$]. LC-MS (ESI+): 315.1 [100%, $(M+Na)^+$]. HRMS (ESI+): m/z calcd for $C_{13}H_{13}FN_4O_3(M+Na)^+$315.0864, found 315.0859.

SG5-038

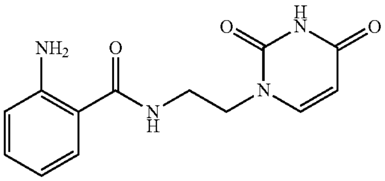

2-Amino-N-(2-(2,4-dioxo-3,4-dihydropyrimidin-1(2H)-yl)ethyl)benzamide (SG5-038): This compound was prepared from SG4-178 (50 mg, 0.261 mmol), isatoic anhydride (42 mg, 0.261 mmol), $Et_3N$ (0.062 mL, 0.443 mmol), and 1,4-dioxane (0.26 mL) using Method B (reaction time, 17 h) to give the title compound as an off-white solid (32.00 mg, 45%). Mp: 200-203° C. HPLC: 99% [$t_R$=6.6 min, 10% MeOH, 90% water (with 0.1% TFA), 20 min]. $^1H$ NMR (400 MHz, DMSO-$d_6$) δ 11.19 (s, 1H, disappeared on $D_2O$ shake), 8.29 (t, J=5.8 Hz, 1H, disappeared on $D_2O$ shake), 7.45 (d, J=7.8 Hz, 1H), 7.37 (dd, J=8.2, 1.3 Hz, 1H), 7.10 (ddd, J=8.2, 7.2, 1.3 Hz, 1H), 7.96-7.90 (m, 2H), 6.47 (ddd, J=8.2, 7.2, 1.3 Hz, 1H), 6.31 (s, 2H, disappeared on $D_2O$ shake), 5.44 (dd, J=7.8, 2.2 Hz, 1H), 3.77 (t, J=5.8 Hz, 2H), 3.43 (q, J=5.8 Hz, 2H). HPLC-MS (ESI+): m/z 571.3 [10%, $(2M+Na)^+$], 275.2 [100%, $(M+H)^+$]. LC-MS (ESI+): 297.1 [100%, $(M+Na)^+$]. HRMS (ESI+): m/z calcd for $C_{13}H_{14}N_4O_3$ $(M+Na)^+$297.0958, found 297.0955.

SG5-039

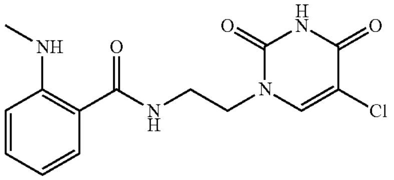

N-(2-(5-Chloro-2,4-dioxo-3,4-dihydropyrimidin-1(2H)-yl)ethyl)-2-(methylamino)benzamide (SG5-039): SG5-033 (65 mg, 0.224 mmol) was stirred in TFA/DCM (1:1, 1 mL) at room temperature for 2 h. The mixture was concentrated under reduced pressure and the resulting oil was solidified after dilution and evaporation with hexanes/EtOAc to provide a mono TFA salt (64.90 mg, 95%). The resulting salt and $Et_3N$ (0.093 mL, 0.673 mmol) were mixed in 1,4-dioxane (2 mL) and stirred at room temperature for 30 min. Then, N-methyl isatoic anhydride (40 mg, 0.224 mmol) was added and the mixture was stirred at room temperature for 18 h. Water (10 mL) was added and the resulting solid was filtered and washed with water (2×5 mL). Upon drying, the solid was triturated using EtOH/hexanes to give the title compound as a white solid (18.82 mg, 26%). Mp: 242° C. (dec). HPLC: >99% [$t_R$=6.2 min, 25% MeOH, 75% water (with 0.1% TFA), 20 min]. $^1H$ NMR (400 MHz, DMSO-$d_6$) δ 10.67 (s, 1H, disappeared on $D_2O$ shake), 8.35 (t, J=5.8 Hz, 1H, disappeared on $D_2O$ shake), 7.97 (s, 1H), 7.39 (dd, J=7.8, 1.5 Hz, 1H), 7.33 (q, J=5.0 Hz, 1H), 7.28-7.23 (m, 1H), 6.59 (d, J=7.8 Hz, 1H), 6.52 (t, J=7.8 Hz, 1H), 3.80 (t, J=5.8 Hz, 2H), 3.45 (q, J=5.8 Hz, 2H), 2.72 (d, J=5.0 Hz, 3H). HPLC-MS (ESI+): m/z 325.1 [40%, $(M^{37}Cl+H)^+$], 323.2 [100%, $(M^{35}Cl+H)^+$]. LC-MS (ESI+): 345.1 [35%, $(M^{35}Cl+Na)^+$], 323.1 [100%, $(M^{35}Cl+H)^+$]. HRMS (ESI+): m/z calcd for $C_{14}H_{15}ClN_4O_3$ $(M+H)^+$323.0905, found 323.0911.

SG5-042

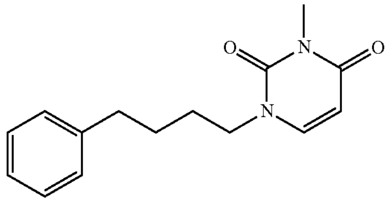

3-Methyl-1-(4-phenylbutyl)pyrimidine-2,4(1H,3H)-dione (SG5-042): Into a mixture of SG5-003 (50 mg, 0.204 mmol) and $K_2CO_3$ (58 mg, 0.490 mmol) in DMF (0.5 mL) was added methyl iodide (0.025 mL, 0.409 mmol) at room temperature. The mixture was stirred at room temperature for 16 h. Water (20 mL) was added and the mixture was extracted with DCM (1×20 mL) and EtOAc (2×20 mL). The combined organic layers were dried ($Na_2SO_4$) and concentrated under reduced pressure to give the title compound as yellow oil (50.04 mg, 95%). HPLC: 95% [$t_R$=12.3 min, 50% MeOH, 50% water (with 0.1% TFA), 20 min]. $^1H$ NMR (400 MHz, DMSO-$d_6$) δ 7.67 (d, J=7.8 Hz, 1H), 7.28-7.21 (m, 2H), 7.19-7.12 (m, 3H), 5.65 (d, J=7.8 Hz, 1H), 3.71 (t, J=7.0 Hz, 2H), 3.12 (s, 3H), 2.57 (t, J=7.0 Hz, 2H), 1.64-1.47 (m, 4H). HPLC-MS (ESI+): m/z 517.3 [20%, $(2M+Na)^+$], 281.2 [80%, $(M+Na)^+$], 259.2 [100%, $(M+H)^+$]. LC-MS (ESI+): 281.2 [45%, $(M+Na)^+$], 259.2 [100%, $(M+H)^+$]. HRMS (ESI+): m/z calcd for $C_{15}H_{18}N_2O_2$ $(M+H)^+$259.1441, found 259.1441.

SG5-045

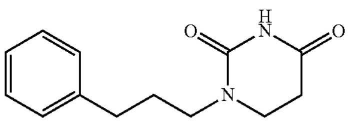

1-(3-Phenylpropyl)dihydropyrimidine-2,4(1H,3H)-dione (SG5-045): [*Pharm Chem J* 1983, 17, 727-730] A mixture of 3-phenylpropan-1-amine (0.525 mL, 3.7 mmol), ethyl acrylate (0.403 mL, 3.7 mmol), and MeOH (2.5 mL) was stirred at room temperature overnight. MeOH was removed and the resulting oil was purified by chromatography ($SiO_2$) eluting with hexanes (with 0-100% EtOAc) to provide a mixture of methyl/ethyl esters, which were used in the subsequent step. A mixture of methyl/ethyl esters (350 mg, 1.49 mmol), urea (447 mg, 7.44 mmol), and glacial acetic acid (0.8 mL) was heated at reflux for 3 h. Sulfuric acid (0.5 mL) was added and the mixture was further heated at reflux for 3 h. Water (10 mL) was added and the precipitates were filtered and triturated using EtOH/hexanes to give the title compound as a white solid (173.68 mg, 20%, two steps). Mp: 99-101° C. HPLC: 99% [$t_R$=7.5 min, 45% MeOH, 55% water (with 0.1% TFA), 20 min]. $^1$H NMR (400 MHz, MeOD) δ 7.30-7.12 (m, 5H), 3.42 (dt, J=10.5, 7.1 Hz, 4H), 2.65 (t, J=7.3 Hz, 2H), 2.54 (t, J=7.3 Hz, 2H), 1.91 (p, J=7.3 Hz, 2H). HPLC-MS (ESI+): m/z 465.3 [20%, $(2M+H)^+$], 255.2 [100%, $(M+Na)^+$], 233.2 [80%, $(M+H)^+$]. LC-MS (ESI+): 255.1 [50%, $(M+Na)^+$], 233.1 [100%, $(M+H)^+$]. HRMS (ESI+): m/z calcd for $C_{13}H_{16}N_2O_2$ $(M+H)^+$233.1284, found 233.1288.

SG5-058

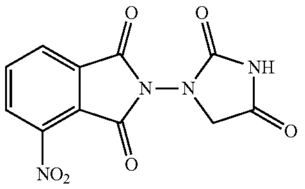

2-(2,4-Dioxoimidazolidin-1-yl)-4-nitroisoindoline-1,3-dione (SG5-058): This compound was prepared from 3-nitrophthalic anhydride (386 mg, 2 mmol), 1-aminohydantoin hydrochloride (303 mg, 2 mmol), and AcOH (2 mL) using Method C to give the title compound as a white solid (339.77 mg, 59%). Mp: 288° C. (dec). HPLC: 99% [$t_R$=6.4 min, 20% MeOH, 80% water (with 0.1% TFA), 20 min]. $^1$H NMR (400 MHz, DMSO-$d_6$) δ 11.81 (s, 1H, disappeared on $D_2O$ shake), 8.41 (dd, J=8.1, 0.9 Hz, 1H), 8.30 (dd, J=7.6, 0.9 Hz, 1H), 8.16 (dd, J=8.1, 7.6 Hz, 1H), 4.26 (s, 2H). HPLC-MS (ESI+): m/z 603.1 [60%, $(2M+Na)^+$], 313.1 [60%, $(M+Na)^+$], 291.1 [50%, $(M+H)^+$]. LC-MS (ESI+): 313.0 [50%, $(M+Na)^+$]. HRMS (ESI+): m/z calcd for $C_{11}H_6N_4O_6$ $(M+Na)^+$313.0179, found 313.0161.

SG5-058

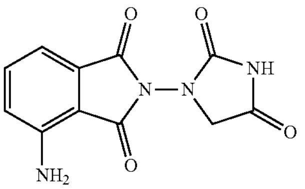

4-Amino-2-(2,4-dioxoimidazolidin-1-yl)isoindoline-1,3-dione (SG5-059): Into a mixture of SG5-058 (100 mg, 0.319 mmol) in EtOH (5 mL deoxygenated with Argon gas) was added Pd/C (10% w/w, 50 mg) under Argon. The flask was evacuated and back filled with Argon (twice). Argon gas was evacuated and a balloon of hydrogen was attached to the system. The reaction mixture was stirred at room temperature for 20 h, filtered using a short plug of Celite, washed with copious amount of DCM, EtOH, EtOAc, acetone, and THF, and concentrated under reduced pressure. The resulting residue was triturated using EtOH/hexanes to provide the title compound as a yellow solid (213.08 mg, 79%). Mp: 285° C. (dec). HPLC: 97% [$t_R$=8.4 min, 20% MeOH, 80% water (with 0.1% TFA), 20 min]. $^1$H NMR (400 MHz, DMSO-$d_6$) δ 11.68 (s, 1H, disappeared on $D_2O$ shake), 7.51 (dd, J=8.5, 7.0 Hz, 1H), 7.06 (d, J=8.5 Hz, 1H), 7.04 (d, J=7.0 Hz, 1H), 6.65 (s, 2H, disappeared on $D_2O$ shake), 4.25 (s, 2H). HPLC-MS (ESI+): m/z 543.1 [40%, $(2M+Na)^+$], 283.1 [60%, $(M+Na)^+$], 261.2 [50%, $(M+H)^+$]. HPLC-MS (ESI−): m/z 259.0 [100%, $(M-H)^-$]. HRMS (ESI+): m/z calcd for $C_{11}H_8N_4O_4$$(M+H)^+$261.0618, found 261.0615.

SG5-068

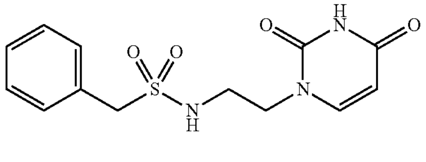

N-(2-(2,4-Dioxo-3,4-dihydropyrimidin-1(2H)-yl)ethyl)-1-phenylmethanesulfonamide (SG5-068): This compound was prepared from SG4-178 (50 mg, 0.258 mmol), phenylmethanesulfonyl chloride (75 mg, 0.391 mmol), DIPEA (0.182 mL, 1.040 mmol), and DMF (1 mL) using Method A (reaction time, overnight) to give the title compound as an off-white solid (25.92 mg, 32%). Mp: 220-226° C. HPLC: 98% [$t_R$=5.3 min, 30% MeOH, 70% water (with 0.1% TFA), 20 min]. $^1$H NMR (400 MHz, DMSO-$d_6$) δ 11.21 (s, 1H, disappeared on $D_2O$ shake), 7.44 (d, J=7.9 Hz, 1H), 7.38-7.31 (m, 5H), 7.26 (t, J=5.9 Hz, 1H, disappeared on $D_2O$ shake), 5.51 (d, J=7.9 Hz, 1H), 4.31 (s, 2H), 3.65 (t, J=5.9 Hz, 2H), 3.10 (q, J=5.9 Hz, 2H). HPLC-MS (ESI+): m/z 641.2 [100%, $(2M+Na)^+$], 619.2 [40%, $(2M+H)^+$], 332.2 [50%, $(M+Na)^+$], 310.1 [80%, $(M+H)^+$]. LC-MS (ESI+): 332.1 [100%, $(M+Na)^+$]. HRMS (ESI+): m/z calcd for $C_{13}H_{15}N_3O_4S$ $(M+Na)^+$332.0675, found 332.0674.

SG5-069

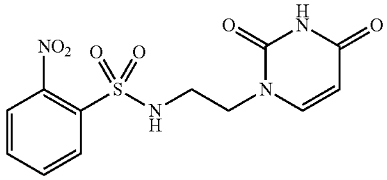

N-(2-(2,4-Dioxo-3,4-dihydropyrimidin-1(2H)-yl)ethyl)-2-nitrobenzenesulfonamide (SG5-069): This compound was prepared from SG4-178 (100 mg, 0.522 mmol), 2-nitrobenzenesulfonyl chloride (173 mg, 0.783 mmol), DIPEA (0.363 mL, 2.090 mmol), and DMF (1 mL) using Method A (reaction time, overnight) to give the title compound as a light yellow solid (36.73 mg, 21%).Mp: 296° C. (dec). HPLC: >99% [$t_R$=4.0 min, 30% MeOH, 70% water (with 0.1% TFA), 20 min]. $^1$H NMR (400 MHz, DMSO-$d_6$) δ 11.17 (s, 1H, disappeared on $D_2O$ shake), 8.21 (brt, J=5.9 Hz, 1H, disappeared on $D_2O$ shake), 7.96-7.90 (m, 2H), 7.85-7.80 (m, 2H), 7.42 (d, J=7.8 Hz, 1H), 5.44 (dd, J=7.8, 2.3 Hz, 1H), 3.71 (t, J=5.9 Hz, 2H), 3.18 (br q, J=5.9 Hz, 2H). HPLC-MS (ESI+): m/z 703.2 [100%, $(2M+Na)^+$], 681.1 [80%, $(2M+H)^+$], 363.1 [30%, $(M+Na)^+$], 341.1 [80%, $(M+H)^+$]. LC-MS (ESI+): 363.0 [75%, $(M+Na)^+$], 341.0 [100%, $(M+H)^+$]. HRMS (ESI+): m/z calcd for $C_{12}H_{12}N_4O_6S$ $(M+H)^+$341.0550, found 341.0540.

SG5-075

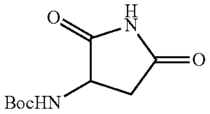

tert-Butyl (2,5-dioxopyrrolidin-3-yl)carbamate (SG5-075): This was prepared from Boc-asparagine (2.32 g, 10 mmol), EDCI (2.11 g, 11 mmol), N-hydroxysuccinimide (1.27 g, 11 mmol), DMF (4 mL) using Method F to give the title compound as a white solid (475 mg, 22%).

$^1$H NMR (400 MHz, DMSO-$d_6$) δ 11.17 (s, 1H), 7.42 (d, J=8.2 Hz, 1H), 4.32-4.22 (m, 1H), 2.83 (dd, J=17.5, 9.3 Hz, 1H), 2.42 (dd, J=17.5, 5.7 Hz, 1H), 1.36 (s, 9H).

SG5-075

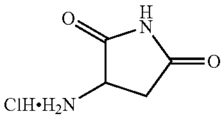

3-Aminopyrrolidine-2,5-dione hydrochloride (SG5-076): [Heterocycles, 2015, 91, 764-781] This compound was prepared from SG5-075 (475 mg, 2.22 mmol) and 4 M HCl in dioxane (2 mL) using Method G. EtOAc (10 mL) was added to the suspension and sonicated, filtered, washed with EtOAc (2×10 mL), and dried to give the title compound as a white solid (318 mg, 95%). $^1$H NMR (400 MHz, $CD_3OD$) δ 4.38 (dd, J=9.3, 6.0 Hz, 1H), 3.13 (dd, J=17.9, 9.3 Hz, 1H), 2.69 (dd, J=17.9, 6.0 Hz, 1H).

SG5-078

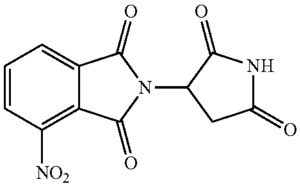

2-(2,5-Dioxopyrrolidin-3-yl)-4-nitroisoindoline-1,3-dione (SG5-078): This was prepared from 3-nitrophthalic anhydride (100 mg, 0.517 mmol), SG5-076 (78 mg, 0.517 mmol), and AcOH (0.5 mL) using Method C to give the title compound as a white solid (106.61 mg, 71%). Mp: 272° C. (dec). HPLC: 99% [$t_R$=7.5 min, 25% MeOH, 75% water (with 0.1% TFA), 20 min]. $^1$H NMR (400 MHz, DMSO-$d_6$) δ 11.71 (s, 1H, disappeared on $D_2O$ shake), 8.34 (d, J=7.6 Hz, 1H), 8.21 (d, J=7.6 Hz, 1H), 8.09 (t, J=7.6 Hz, 1H), 5.29 (dd, J=9.5, 5.4 Hz, 1H), 2.99 (dd, J=18.0, 9.5 Hz, 1H), 2.86 (dd, J=18.0, 5.4 Hz, 1H). HPLC-MS (ESI−): m/z 288.1 [100%, $(M-H)^-$]. LC-MS (ESI−): 288.0 [100%, $(M-H)^-$]. HRMS (ESI−): m/z calcd for $C_{12}H_7N_3O_6(M-H)^-$ 288.0262, found 288.0247.

SG5-081

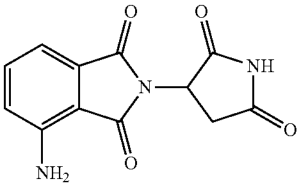

4-Amino-2-(2,5-dioxopyrrolidin-3-yl)isoindoline-1,3-dione (SG5-081): Into a mixture of SG5-078 (20 mg, 0.069 mmol) in THF (2 mL deoxygenated with Argon gas) was added Pd/C (10% w/w, 5 mg) under Argon. The flask was evacuated and back filled with Argon (twice). Argon gas was evacuated and a balloon of hydrogen was attached to the system. The reaction mixture was stirred at room temperature for 5.5 h, filtered using a short plug of Celite, washed with THF (5 mL), and concentrated under reduced pressure to provide the title compound as a bright yellow solid (15.30 mg, 85%).Mp: 286° C. (dec). HPLC: 99% [$t_R$=4.9 min, 25% MeOH, 75% water (with 0.1% TFA), 20 min]. $^1$H NMR (400 MHz, DMSO-$d_6$) δ 11.60 (s, 1H, disappeared on $D_2O$ shake), 7.45 (dd, J=8.4, 7.0 Hz, 1H), 6.99 (d, J=8.4 Hz, 1H), 6.98 (d, J=7.0 Hz, 1H), 6.53 (s, 2H, disappeared on $D_2O$ shake), 5.18 (dd, J=9.6, 5.6 Hz, 1H), 2.96 (dd, J=18.0, 9.6 Hz, 1H), 2.82 (dd, J=18.0, 5.6 Hz, 1H). HPLC-MS (ESI+): m/z 541.2 [100%, $(2M+Na)^+$], 282.1 [75%, $(M+Na)^+$], 260.1 [80%, $(M+H)^+$]. LC-MS (ESI−): 258.0 [100%, $(M-H)^-$]. HRMS (ESI−): m/z calcd for $C_{12}H_9N_3O_4(M-H)^-$ 258.0520, found 258.0501.

SG5-091

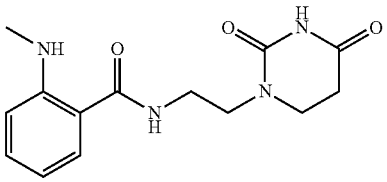

N-(2-(2,4-dioxotetrahydropyrimidin-1(2H)-yl)ethyl)-2-(methylamino)benzamide (SG5-091): A mixture of SG5-085 (50 mg, 0.258 mmol), N-methyl isatoic anhydride (46 mg, 0.258 mmol), and $Et_3N$ (0.043 mL, 0.310 mmol) in 1,4-dioxane (0.5 mL) was stirred at room temperature for 18 h and further heated at 80° C. for 2 h. Water (5 mL) was added and the precipitates were filtered, washed with water (5 mL), and dried. The resulting solid was triturated using EtOH/hexanes to give the title compound as a white solid (41.98 mg, 56%). Mp: 221-224° C. HPLC: >99% [$t_R$=4.6 min, 20% MeOH, 80% water (with 0.1% TFA), 20 min]. $^1$H NMR (400 MHz, DMSO-$d_6$) δ 10.07 (s, 1H, disappeared on $D_2O$ shake), 8.35 (t, J=5.6 Hz, 1H, reduced by 60% on $D_2O$ shake), 7.52 (q, J=5.0 Hz, 1H, disappeared on $D_2O$ shake), 7.44 (dd, J=7.8, 1.5 Hz, 1H), 7.25 (t, J=7.8 Hz, 1H), 6.59 (d, J=7.8 Hz, 1H), 6.52 (t, J=7.8 Hz, 1H), 3.46-3.32 (m, 6H), 2.73 (d, J=5.0 Hz, 3H), 2.50 (t, J=6.8 Hz, 1H). HPLC-MS (ESI+): m/z 603.3 [10%, $(2M+Na)^+$], 291.2 [100%, $(M+H)^+$]. LC-MS (ESI+): 313.1 [100%, $(M+Na)^+$]. HRMS (ESI+): m/z calcd for $C_{14}H_{18}N_4O_3$ $(M+Na)^+$313.1271, found 313.1269.

SG5-084

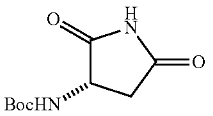

tert-Butyl (S)-(2,5-dioxopyrrolidin-3-yl)carbamate (SG5-084): This compound was prepared from Boc-L-asparagine (2.32 g, 10 mmol), EDCI (2.11 g, 11 mmol), N-hydroxysuccinimide (1.27 g, 11 mmol), DMF (4 mL) using Method F to give the title compound as a white solid (543.58 mg, 25%). Mp: 161-163° C. $^1$H NMR (400 MHz, DMSO-$d_6$) δ 11.16 (s, 1H, disappeared on $D_2O$ shake), 7.42 (d, J=8.2 Hz, 1H, reduced by 50% on $D_2O$ shake), 4.31-4.22 (m, 1H), 2.83 (dd, J=17.5, 9.4 Hz, 1H), 2.42 (dd, J=17.5, 5.8 Hz, 1H), 1.35 (s, 9H).

SG5-088

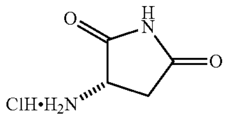

(S)-3-aminopyrrolidine-2,5-dione hydrochloride (SG5-088): This was prepared from SG5-084 (474.44 mg, 2.22 mmol) and 4 M HCl in dioxane (10 mL) using Method G to give the title compound as an off-white solid (341.38 mg, quantitative yield). Mp: 210° C. (dec). $^1$H NMR (400 MHz, DMSO-$d_6$) δ 11.69 (s, 1H, disappeared on $D_2O$ shake), 8.69 (s, 3H, disappeared on $D_2O$ shake), 4.28 (dd, J=9.2, 5.6 Hz, 1H), 2.91 (dd, J=17.7, 9.2 Hz, 1H), 2.65 (dd, J=17.7, 5.6 Hz, 1H).

SG5-083

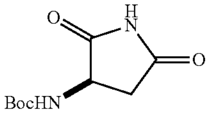

tert-Butyl (R)-(2,5-dioxopyrrolidin-3-yl)carbamate (SG5-083): This compound was prepared from Boc-D-asparagine (2.32 g, 10 mmol), EDCI (2.11 g, 11 mmol), N-hydroxysuccinimide (1.27 g, 11 mmol), DMF (4 mL) using Method F to give the title compound as an off-white solid (555.17 mg, 26%). Mp: 151-154° C. $^1$H NMR (400 MHz, DMSO-$d_6$) δ 11.19 (s, 1H, disappeared on $D_2O$ shake), 7.42 (d, J=8.2 Hz, 1H, reduced by 50% on $D_2O$ shake), 4.31-4.22 (m, 1H), 2.83 (dd, J=17.5, 9.4 Hz, 1H), 2.42 (dd, J=17.5, 5.8 Hz, 1H), 1.35 (s, 9H).

SG5-089

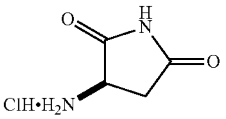

(R)-3-aminopyrrolidine-2,5-dione hydrochloride (SG5-089): This compound was prepared from SG5-083 (540 mg, 2.52 mmol) and 4 M HCl in dioxane (10 mL) using Method G to give the title compound as an off-white solid (384.12 mg, quantitative yield). Mp: 207° C. (dec). $^1$H NMR (400 MHz, DMSO-$d_6$) δ 11.67 (s, 1H, disappeared on $D_2O$ shake), 8.69 (s, 3H, disappeared on $D_2O$ shake), 4.27 (dd, J=9.2, 5.6 Hz, 1H), 2.91 (dd, J=17.7, 9.2 Hz, 1H), 2.67 (dd, J=17.7, 5.6 Hz, 1H).

SG5-092

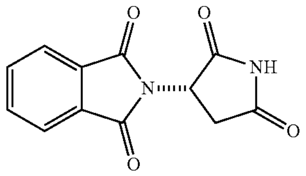

(S)-2-(2,5-Dioxopyrrolidin-3-yl)isoindoline-1,3-dione (SG5-092): This was prepared from phthalic anhydride (50 mg, 0.337 mmol), SG5-088 (51 mg, 0.337 mmol), and AcOH (0.5 mL) using Method C to give the title compound as an off-white solid (40.41 mg, 49%). Mp: 214-216° C. HPLC: 99% [$t_R$=6.6 min, 25% MeOH, 75% water (with 0.1% TFA), 20 min]. $^1$H NMR (400 MHz, DMSO-$d_6$) δ 11.66 (s, 1H, disappeared on $D_2O$ shake), 7.95-7.83 (m, 4H), 5.27 (dd, J=9.6, 5.7 Hz, 1H), 2.98 (dd, J=18.0, 9.6 Hz, 1H), 2.87 (dd, J=18.0, 5.7 Hz, 1H). HPLC-MS (ESI−): m/z 510.2 [10%, $(2M-Na)^-$], 243.1 [30%, $(M-H)^-$].

SG5-086

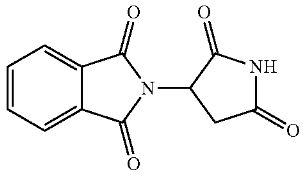

2-(2,5-Dioxopyrrolidin-3-yl)isoindoline-1,3-dione (SG5-086): This compound was prepared from phthalic anhydride (50 mg, 0.337 mmol), SG5-076 (51 mg, 0.337 mmol), and AcOH (0.5 mL) using Method C to give the title compound as a white solid (42.07 mg, 51%). HPLC: 99% [$t_R$=6.0 min, 25% MeOH, 75% water (with 0.1% TFA), 20 min]. $^1$H NMR (400 MHz, DMSO-$d_6$) δ 11.66 (s, 1H, disappeared on $D_2O$ shake), 7.95-7.84 (m, 4H), 5.26 (dd, J=9.5, 5.7 Hz, 1H), 2.98 (dd, J=18.0, 9.5 Hz, 1H), 2.87 (dd, J=18.0, 5.7 Hz, 1H). HPLC-MS (ESI+): m/z 267.0 [30%, $(M+Na)^+$]. HPLC-MS (ESI−): m/z 242.9 [50%, $(M-H)^-$]. HRMS (ESI+): m/z calcd for $C_{12}H_8N_2O_4(M+Na)^+$267.0376, found 267.0338.

SG5-096

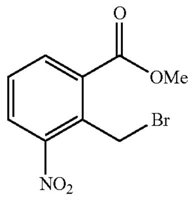

Methyl 2-(bromomethyl)-3-nitrobenzoate (SG5-096): [Pharm. Chem. J. 2013, 46, 676-678]

A mixture of methyl 2-methyl-3-nitrobenzoate (1.95 g, 10 mmol), N-bromosuccinimide (2.14 g, 12 mmol), and AIBN (164.21 mg, 1 mmol) in $CCl_4$ (25 mL) was heated at reflux for 14 h. N-bromosuccinimide (0.877 g, 5 mmol) and AIBN (164.21 mg, 1 mmol) were added and the mixture was heated at reflux for additional 4 h. The mixture was filtered, washed with $CCl_4$ (10 mL), and concentrated under reduced pressure. The resulting oil, which solidified upon standing at room temperature, was triturated using EtOAc/hexanes and washed with hexanes to give the title compound as a yellow solid (2.09 mg, 76%). Mp: 63-63° C. $^1H$ NMR (400 MHz, $CDCl_3$) δ 8.10 (dd, J=8.0, 1.4 Hz, 1H), 7.95 (dd, J=8.0, 1.4 Hz, 1H), 7.54 (t, J=8.0 Hz, 1H), 5.15 (s, 2H), 3.99 (s, 3H).

SG5-097

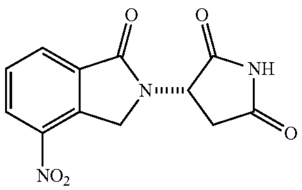

(S)-3-(4-Nitro-1-oxoisoindolin-2-yl)pyrrolidine-2,5-dione (SG5-097): [Pharm. Chem. J. 2013, 46, 676-678] A mixture of SG5-096 (100 mg, 0.365 mmol), SG5-088 (54.94 mg, 0.365 mmol), and triethylamine (0.061 mL, 0.438 mmol) in DMF (0.5 mL) was stirred at 80° C. for 15 h. Water (5 mL) was added and extracted with EtOAc (2×8 mL). The combined organic layers were washed with water (5 mL), dried ($Na_2SO_4$), and concentrated under reduced pressure to give the title compound as an off-white solid (49.87 mg, 49%). $^1H$ NMR (400 MHz, DMSO-$d_6$) δ 11.56 (s, 1H), 8.46 (dd, J=7.6, 0.8 Hz, 1H), 8.15 (d, J=7.6 Hz, 1H), 7.82 (t, J=7.6 Hz, 1H), 5.29 (dd, J=8.6, 6.9 Hz, 1H), 5.07 (d, J=19.3 Hz, 1H), 4.80 (d, J=19.3 Hz, 1H), 2.97 (d, J=8.6 Hz, 1H), 2.96 (d, J=6.9 Hz, 1H). HPLC-MS (ESI−): m/z 274.1 [100%, $(M-H)^-$].

SG5-093

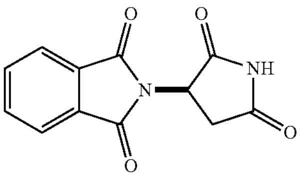

(R)-2-(2,5-Dioxopyrrolidin-3-yl)isoindoline-1,3-dione (SG5-093): This compound was prepared from phthalic anhydride (50 mg, 0.337 mmol), SG5-089 (51 mg, 0.337 mmol), and AcOH (0.5 mL) using Method C to give the title compound as an off-white solid (40.83 mg, 50%). Mp: 209-214° C. HPLC: 98% [$t_R$=5.2 min, 25% MeOH, 75% water (with 0.1% TFA), 20 min]. $^1H$ NMR (400 MHz, DMSO-$d_6$) δ 11.66 (s, 1H, disappeared on $D_2O$ shake), 7.96-7.81 (m, 4H), 5.27 (dd, J=9.6, 5.7 Hz, 1H), 2.98 (dd, J=18.0, 9.6 Hz, 1H), 2.87 (dd, J=18.0, 5.7 Hz, 1H). HPLC-MS (ESI−): m/z 243.1 [30%, $(M-H)^-$]. HRMS (ESI+): m/z calcd for $C_{12}H_8N_2O_4$: 244.0491, found 245.0564 $(M+H)^+$.

SG5-102

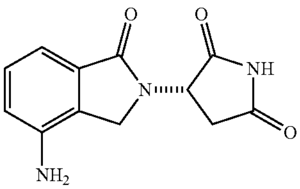

(S)-3-(4-Amino-1-oxoisoindolin-2-yl)pyrrolidine-2,5-dione (SG5-102): Into a mixture of SG5-097 (45 mg, 0.162 mmol) in THF (4 mL deoxygenated with Argon gas) was added Pd/C (10% w/w, 10 mg) under Argon. The flask was evacuated and back filled with Argon (twice). Argon gas was evacuated and a balloon of hydrogen was attached to the system. The reaction mixture was stirred at room temperature for 20 h, filtered using a short plug of Celite, washed with THF, and concentrated under reduced pressure. The resulting residue was purified by chromatography ($SiO_2$) eluting with DCM (with 0-10% MeOH) to provide the title compound as an off-white solid (17.26 mg, 43%). Mp: 196-200° C. HPLC: >99% [$t_R$=4.8 min, 10% MeOH, 90% water (with 0.1% TFA), 20 min]. $^1H$ NMR (400 MHz, DMSO-$d_6$) δ 11.54 (s, 1H, disappeared on $D_2O$ shake), 7.16 (t, J=7.7 Hz, 1H), 6.86 (d, J=7.4 Hz, 1H), 6.77 (d, J=7.9 Hz, 1H), 5.44 (s, 2H, disappeared on $D_2O$ shake), 5.20 (dd, J=9.3, 5.9 Hz, 1H), 4.32 (d, J=17.0 Hz, 1H), 4.10 (d, J=17.0 Hz, 1H), 2.97 (dd, J=18.0, 9.3 Hz, 1H), 2.87 (dd, J=18.0, 5.9 Hz, 1H). HPLC-MS (ESI+): m/z 513.2 [30%, $(2M+Na)^+$], 246.2 [100%, $(M+H)^+$]. HRMS (ESI+): m/z calcd for $C_{12}H_{11}N_3O_3$: 245.0806, found 246.0880 $(M+H)^+$.

SG5-125

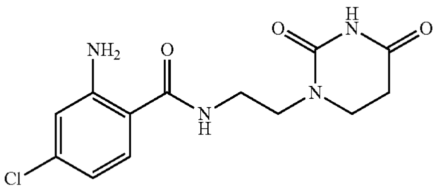

2-Amino-4-chloro-N-(2-(2,4-dioxotetrahydropyrimidin-1(2H)-yl)ethyl)benzamide (SG5-125): Mp: 258° C. (dec). This was prepared from SG5-085 (50 mg, 0.258 mmol), 4-chloroisatoic anhydride (51 mg, 0.258 mmol), $Et_3N$ (0.043 mL, 0.310 mmol), and 1,4-dioxane (0.5 mL) using Method B (reaction time: 17 h at room temperature, 6 h at 80° C., and overnight at 60° C.) to give the title compound as an off-white solid (41.70 mg, 52%). HPLC: 99% [$t_R$=8.6 min, 30% MeOH, 70% water (with 0.1% TFA), 20 min]. $^1$H NMR (400 MHz, DMSO-$d_6$) δ 10.07 (s, 1H, disappeared on $D_2O$ shake), 8.35 (t, J=5.3 Hz, 1H, disappeared on $D_2O$ shake), 7.40 (d, J=8.5 Hz, 1H), 6.72 (d, J=2.1 Hz, 1H), 6.61 (s, 2H, disappeared on $D_2O$ shake), 6.49 (dd, J=8.5, 2.1 Hz, 1H), 3.46-3.33 (m, 6H), 2.50 (d, J=7.0 Hz, 2H). HPLC-MS (ESI+): m/z 643.2 [20%, $(M^{35}Cl+Na)^+$], 313.1 [40%, $(M^{37}Cl+H)^+$], 311.1 [100%, $(M^{35}Cl+H)^+$]. LC-MS (ESI+): 333.1 [100%, $(M^{35}Cl+Na)^+$]. HRMS (ESI+): m/z calcd for $C_{13}H_{15}ClN_4O_3(M+Na)^+$333.0725, found 333.0729.

SG5-127

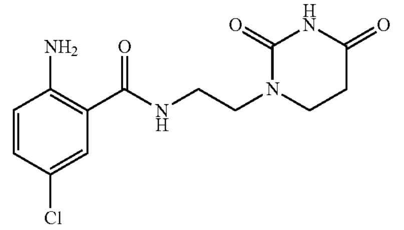

2-Amino-5-chloro-N-(2-(2,4-dioxotetrahydropyrimidin-1(2H)-yl)ethyl)benzamide (SG5-127): Mp: 259° C. (dec). This compound was prepared from SG5-085 (50 mg, 0.258 mmol), 5-chloroisatoic anhydride (51 mg, 0.258 mmol), $Et_3N$ (0.043 mL, 0.310 mmol), and 1,4-dioxane (0.5 mL) using Method B (reaction time, 17 h) to give the title compound as an off-white solid (24.10 mg, 30%). HPLC: 99% [$t_R$=5.4 min, 30% MeOH, 70% water (with 0.1% TFA), 20 min]. $^1$H NMR (400 MHz, DMSO-$d_6$) δ 10.08 (s, 1H, disappeared on $D_2O$ shake), 8.41 (t, J=5.6 Hz, 1H, disappeared on $D_2O$ shake), 7.45 (d, J=2.5 Hz, 1H), 7.13 (dd, J=8.8, 2.5 Hz, 1H), 6.68 (d, J=8.8 Hz, 1H), 6.48 (s, 2H, disappeared on $D_2O$ shake), 3.46-3.33 (m, 6H), 2.51 (d, J=6.8 Hz, 2H). HPLC-MS (ESI+): m/z 643.1 [15%, $(M^{35}Cl+Na)^+$], 313.2 [40%, $(M^{37}Cl+H)^+$], 311.2 [100%, $(M^{35}Cl+H)^+$]. LC-MS (ESI+): 333.1 [100%, $(M^{35}Cl+Na)^+$]. HRMS (ESI+): m/z calcd for $C_{13}H_{15}ClN_4O_3(M+Na)^+$ 333.0725, found 333.0730.

SG5-129

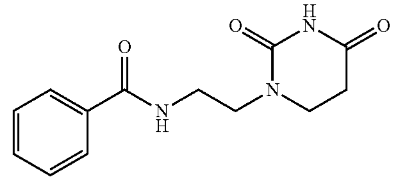

N-(2-(2,4-Dioxotetrahydropyrimidin-1(2H)-yl)ethyl)benzamide (SG5-129): This compound was prepared from SG5-085 (50 mg, 0.258 mmol), benzoyl chloride (0.045 mL, 0.387 mmol), DIPEA (0.180 mL, 1.030 mmol), and DMF (0.5 mL) using Method A (reaction time, overnight) to give the title compound as an off-white solid (25.05 mg, 37%). Mp: 183-185° C. (dec). HPLC: 97% [$t_R$=6.9 min, 20% MeOH, 80% water (with 0.1% TFA), 20 min]. $^1$H NMR (400 MHz, DMSO-$d_6$) δ 10.07 (s, 1H, disappeared on $D_2O$ shake), 8.55 (t, J=5.3 Hz, 1H, disappeared on $D_2O$ shake), 7.81-7.75 (m, 2H), 7.54-7.47 (m, 1H), 7.47-7.41 (m, 2H), 3.50-3.36 (m, 6H), 2.51 (d, J=6.8 Hz, 2H). HPLC-MS (ESI+): m/z 545.3 [100%, $(2M+Na)^+$], 284.1 [80%, $(M+Na)^+$], 262.2 [100%, $(M+H)^+$]. LC-MS (ESI+): 284.1 [100%, $(M+Na)^+$]. HRMS (ESI+): m/z calcd for $C_{13}H_{15}N_3O_3$ $(M+Na)^+$284.1005, found 284.0992.

SG5-130

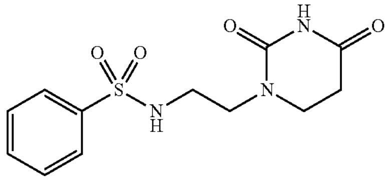

N-(2-(2,4-Dioxotetrahydropyrimidin-1(2H)-yl)ethyl)benzenesulfonamide (SG5-130): This compound was prepared from SG5-085 (50 mg, 0.258 mmol), benzenesulfonyl chloride (0.050 mL, 0.387 mmol), DIPEA (0.180 mL, 1.030 mmol), and DMF (0.5 mL) using Method A (reaction time, overnight) to give the title compound as an off-white solid (42.77 mg, 56%). Mp: 287° C. (dec). HPLC: 99% [$t_R$=6.1 min, 25% MeOH, 75% water (with 0.1% TFA), 20 min]. $^1$H NMR (400 MHz, DMSO-$d_6$) δ 10.08 (s, 1H, disappeared on $D_2O$ shake), 7.81-7.73 (m, 3H; 1H disappeared on $D_2O$ shake), 7.66-7.55 (m, 3H), 3.34-3.28 (m, 4H, overlapped with residual water signals), 2.88 (q, J=6.3 Hz, 2H), 2.49-2.44 (m, 2H, overlapped with the residual DMSO signal). HPLC-MS (ESI+): m/z 617.2 [100%, $(2M+Na)^+$], 320.2 [70%, $(M+Na)^+$], 298.1 [60%, $(M+H)^+$]. LC-MS (ESI+): 320.1 [95%, $(M+Na)^+$], 298.1 [100%, $(M+H)^+$]. HRMS (ESI+): m/z calcd for $C_{12}H_{15}N_3O_4S$ $(M+H)^+$298.0856, found 298.0835.

SG5-150-1

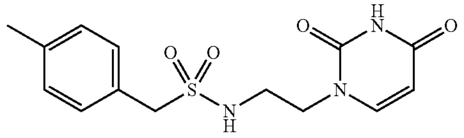

N-(2-(2,4-Dioxo-3,4-dihydropyrimidin-1(2H)-yl)ethyl)-1-(p-tolyl)methanesulfonamide (SG5-150-1): This compound was prepared from SG4-178B2 (50 mg, 0.261 mmol), p-tolylmethanesulfonyl chloride (80 mg, 0.391 mmol), DIPEA (0.182 mL, 1.040 mmol), and DMF (1 mL) using Method A (reaction time, overnight) to give the title compound as an off-white solid (47.28 mg, 56%). Mp: 217-218° C. HPLC: 99% [$t_R$=9.3 min, 30% MeOH, 70% water (with 0.1% TFA), 20 min]. $^1$H NMR (400 MHz, DMSO-$d_6$) δ 11.21 (s, 1H, disappeared on $D_2O$ shake), 7.44 (d, J=7.8 Hz, 1H), 7.24-7.18 (m, 3H; 1H disappeared on $D_2O$ shake), 7.16 (d, J=8.0 Hz, 2H), 5.51 (dd, J=7.8, 2.3 Hz, 1H), 4.26 (s, 2H), 3.65 (t, J=5.9 Hz, 2H), 3.09 (q, J=5.9 Hz, 2H), 2.28 (s, 3H). HPLC-MS (ESI+): m/z 346.1 [30%, $(M+Na)^+$]. HRMS (ESI+): m/z calcd for $C_{14}H_{17}N_3O_4S$: 323.0946, found 324.1020 $(M+H)^+$.

SG5-150-2

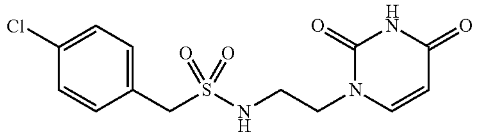

1-(4-Chlorophenyl)-N-(2-(2,4-dioxo-3,4-dihydropyrimidin-1(2H)-yl)ethyl)methanesulfonamide (SG5-150-2): This compound was prepared from SG4-178B2 (50 mg, 0.261 mmol), (4-chlorophenyl)methanesulfonyl chloride (88 mg, 0.391 mmol), DIPEA (0.182 mL, 1.040 mmol), and DMF (1 mL) using Method A (reaction time, overnight) to give the title compound as an off-white solid (46.35 mg, 52%). Mp: 233-234° C. HPLC: 99% [$t_R$=10.1 min, 30% MeOH, 70% water (with 0.1% TFA), 20 min]. $^1$H NMR (400 MHz, DMSO-$d_6$) δ 11.22 (s, 1H, disappeared on $D_2O$ shake), 7.45 (d, J=7.8 Hz, 1H), 7.43 (d, J=8.5 Hz, 1H), 7.36 (d, J=8.5 Hz, 1H), 7.29 (t, J=5.9 Hz, 1H, disappeared on $D_2O$ shake), 5.51 (dd, J=7.8, 2.3 Hz, 1H), 4.35 (s, 2H), 3.66 (t, J=5.9 Hz, 2H), 3.12 (q, J=5.9 Hz, 2H). HPLC-MS (ESI+): m/z 709.2 [25%, $(2M^{35}Cl+Na)^+$], 366.1 [35%, $(M^{35}Cl+Na)^+$], 346.1 [5%, $(M^{37}Cl+H)^+$], 344.0 [30%, $(M^{35}Cl+H)^+$]. HRMS (ESI+): m/z calcd for $C_{13}H_{14}ClN_3O_4S$: 343.0399, found 344.0470 $(M+H)^+$.

SG5-150-3

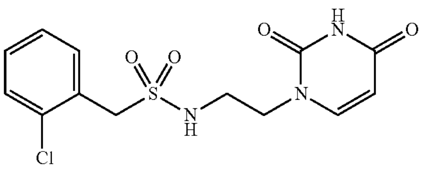

1-(2-Chlorophenyl)-N-(2-(2,4-dioxo-3,4-dihydropyrimidin-1(2H)-yl)ethyl)methanesulfonamide (SG5-150-3): This compound was prepared from SG4-178B2 (50 mg, 0.261 mmol), (2-chlorophenyl)methanesulfonyl chloride (88 mg, 0.391 mmol), DIPEA (0.182 mL, 1.040 mmol), and DMF (1 mL) using Method A (reaction time, overnight) to give the title compound as an off-white solid (34.98 mg, 39%). Mp: 193-195° C. HPLC: 99% [$t_R$=7.5 min, 30% MeOH, 70% water (with 0.1% TFA), 20 min]. $^1$H NMR (400 MHz, DMSO-$d_6$) δ 11.22 (s, 1H, disappeared on $D_2O$ shake), 7.53-7.43 (m, 4H; 1H disappeared on $D_2O$ shake), 7.40-7.32 (m, 2H), 5.51 (dd, J=7.8, 2.3 Hz, 1H), 4.47 (s, 2H), 3.68 (t, J=5.8 Hz, 2H), 3.17 (q, J=5.8 Hz, 2H). HPLC-MS (ESI−): m/z 685.2 [15%, $(M^{35}Cl—H)^-$], 344.1 [40%, $(M^{37}Cl—H)^-$], 342.1 [100%, $(M^{35}Cl—H)^-$]. HRMS (ESI+): m/z calcd for $C_{13}H_{14}ClN_3O_4S$: 343.0399, found 344.0471 $(M+H)^+$.

SG5-150-4

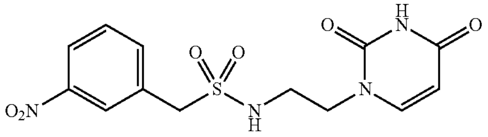

N-(2-(2,4-Dioxo-3,4-dihydropyrimidin-1(2H)-yl)ethyl)-1-(3-nitrophenyl)methanesulfonamide (SG5-150-4): This compound was prepared from SG4-178B2 (50 mg, 0.261 mmol), (3-nitrophenyl)methanesulfonyl chloride (92 mg, 0.391 mmol), DIPEA (0.182 mL, 1.040 mmol), and DMF (1 mL) using Method A (reaction time, overnight) to give the title compound as a light yellow solid (28.77 mg, 31%). Mp: 212-214° C. HPLC: 99% [$t_R$=4.2 min, 30% MeOH, 70% water (with 0.1% TFA), 20 min]. $^1$H NMR (400 MHz, DMSO-$d_6$) δ 11.22 (s, 1H, disappeared on $D_2O$ shake), 8.25 (t, J=2.1 Hz, 1H), 8.22 (ddd, J=7.9, 2.1, 1.2 Hz, 1H), 7.80 (dt, J=7.9, 1.2 Hz, 1H), 7.68 (t, J=7.9 Hz, 1H), 7.46 (d, J=7.8 Hz, 1H), 7.38 (t, J=6.0 Hz, 1H, disappeared on $D_2O$ shake), 5.51 (dd, J=7.8, 2.3 Hz, 1H), 4.57 (s, 2H), 3.68 (t, J=6.0 Hz, 2H), 3.17 (q, J=6.0 Hz, 2H). HPLC-MS (ESI−): m/z 353.1 [80%, $(M-H)^-$]. HRMS (ESI+): m/z calcd for $C_{13}H_{14}N_4O_6S$: 354.0635, found 355.0714 $(M+H)^+$.

SG5-150-5

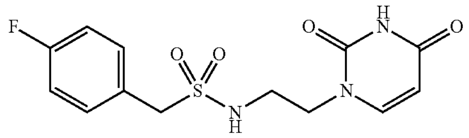

N-(2-(2,4-Dioxo-3,4-dihydropyrimidin-1(2H)-yl)ethyl)-1-(4-fluorophenyl)methanesulfonamide (SG5-150-5): This compound was prepared from SG4-178B2 (50 mg, 0.261 mmol), (4-fluorophenyl)methanesulfonyl chloride (82 mg, 0.391 mmol), DIPEA (0.182 mL, 1.040 mmol), and DMF (1 mL) using Method A (reaction time, overnight) to give the title compound as an off-white solid (30.92 mg, 36%). Mp: 211-213° C. HPLC: 95% [$t_R$=6.1 min, 30% MeOH, 70% water (with 0.1% TFA), 20 min]. $^1$H NMR (400 MHz, DMSO-$d_6$) δ 11.22 (s, 1H, disappeared on $D_2O$ shake), 7.45 (d, J=7.8 Hz, 1H), 7.37 (ddd, J=8.8, 5.4, 2.6 Hz, 2H), 7.26 (t, J=6.0 Hz, 1H, disappeared on $D_2O$ shake), 7.19 (td, J=8.8, 2.6 Hz, 2H), 5.51 (dd, J=7.8, 2.2 Hz, 1H), 4.33 (s, 2H), 3.66 (t, J=6.0 Hz, 2H), 3.11 (q, J=6.0 Hz, 2H). $^{19}$F NMR (376 MHz, DMSO-$d_6$) δ −114.26 (tt, J=8.8, 5.4 Hz). HPLC-MS (ESI+): m/z 677.2 [100%, $(2M+Na)^+$], 655.2 [100%, $(2M+H)^+$], 350.1 [60%, $(M+Na)^+$], 328.2 [60%, $(M+H)^+$]. HRMS (ESI+): m/z calcd for $C_{13}H_{14}FN_3O_4S$: 327.0700, found 328.0773 $(M+H)^+$.

SG5-163-1

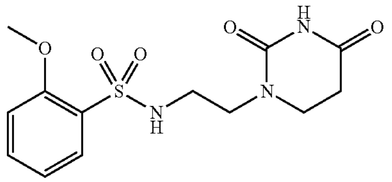

N-(2-(2,4-dioxotetrahydropyrimidin-1(2H)-yl)ethyl)-2-methoxybenzenesulfonamide (SG5-163-1): Mp: 168-170° C. This compound was prepared from SG5-085 (25 mg, 0.129 mmol), 2-methoxybenzenesulfonyl chloride (40 mg, 0.194 mmol), DIPEA (0.092 mL, 0.516 mmol), and DMF (1 mL) using Method A (reaction time, overnight) to give the title compound as an off-white solid (12.49 mg, 30%). HPLC: >99% [$t_R$=5.2 min, 30% MeOH, 70% water (with 0.1% TFA), 20 min]. $^1$H NMR (400 MHz, DMSO-$d_6$) δ 10.08 (s, 1H, disappeared on $D_2O$ shake), 7.70 (dd, J=7.6, 1.8 Hz, 1H), 7.59 (ddd, J=8.4, 7.6, 1.8 Hz, 1H), 7.35 (t, J=6.0 Hz, 1H, disappeared on $D_2O$ shake), 7.20 (dd, J=8.4, 0.9 Hz, 1H), 7.05 (td, J=7.6, 0.9 Hz, 1H), 3.88 (s, 3H), 3.34-3.28 (m, 4H, overlapped with residual water signals), 2.90 (q, J=6.0 Hz, 2H), 2.49-2.45 (m, 2H, overlapped with the residual DMSO signal). HPLC-MS (ESI+): m/z 677.2 [100%, $(2M+Na)^+$], 350.1 [60%, $(M+Na)^+$], 328.1 [70%, $(M+H)^+$]. HRMS (ESI+): m/z calcd for $C_{13}H_{17}N_3O_5S$: 327.0898, found 328.0975 $(M+H)^+$.

SG5-163-2

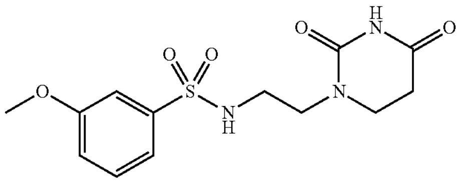

N-(2-(2,4-dioxotetrahydropyrimidin-1(2H)-yl)ethyl)-3-methoxybenzenesulfonamide (SG5-163-2): This compound was prepared from SG5-085 (25 mg, 0.129 mmol), 3-methoxybenzenesulfonyl chloride (0.027 mL, 0.194 mmol), DIPEA (0.092 mL, 0.516 mmol), and DMF (1 mL) using Method A (reaction time, overnight) to give the title compound as an off-white solid (26.98 mg, 64%). Mp: 171-172° C. HPLC: >99% [$t_R$=7.3 min, 30% MeOH, 70% water (with 0.1% TFA), 20 min]. $^1H$ NMR (400 MHz, DMSO-$d_6$) δ 10.08 (s, 1H, disappeared on $D_2O$ shake), 7.75 (t, J=6.1 Hz, 1H, disappeared on $D_2O$ shake), 7.50 (t, J=8.0 Hz, 1H), 7.34 (dd, J=8.0, 0.9 Hz, 1H), 7.28 (t, J=2.3 Hz, 1H), 7.19 (ddd, J=8.0, 2.3, 0.9 Hz, 1H), 3.81 (s, 3H), 3.34-3.28 (m, 4H, overlapped with residual water signals), 2.88 (q, J=6.1 Hz, 2H), 2.49-2.45 (m, 2H, overlapped with the residual DMSO signal). HPLC-MS (ESI+): m/z 677.2 [100%, $(2M+Na)^+$], 655.2 [60%, $(2M+H)^+$], 328.2 [100%, $(M+H)^+$]. HRMS (ESI+): m/z calcd for $C_{13}H_{17}N_3O_5S$: 327.0898, found 328.0969 $(M+H)^+$.

SG5-163-3

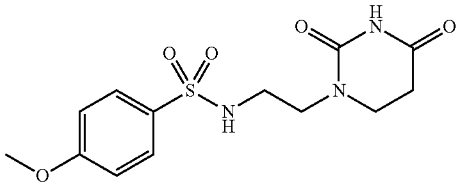

N-(2-(2,4-dioxotetrahydropyrimidin-1(2H)-yl)ethyl)-4-methoxybenzenesulfonamide (SG5-163-3): This compound was prepared from SG5-085 (25 mg, 0.129 mmol), 4-methoxybenzenesulfonyl chloride (40 mg, 0.194 mmol), DIPEA (0.092 mL, 0.516 mmol), and DMF (1 mL) using Method A (reaction time, overnight) to give the title compound as an off-white solid (22.90 mg, 54%). Mp: 147-149° C. HPLC: 99% [$t_R$=6.4 min, 30% MeOH, 70% water (with 0.1% TFA), 20 min]. $^1H$ NMR (400 MHz, DMSO-$d_6$) δ 10.08 (s, 1H, disappeared on $D_2O$ shake), 7.70 (d, J=8.9 Hz, 2H), 7.58 (t, J=6.3 Hz, 1H, disappeared on $D_2O$ shake), 7.09 (d, J=8.9 Hz, 2H), 3.81 (s, 3H), 3.33-3.27 (m, 4H, overlapped with residual water signals), 2.84 (q, J=6.3 Hz, 2H), 2.49-2.45 (m, 2H, overlapped with the residual DMSO signal). HPLC-MS (ESI+): m/z 677.2 [100%, $(2M+Na)^+$], 350.1 [90%, $(M+Na)^+$], 328.1 [80%, $(M+H)^+$]. HRMS (ESI+): m/z calcd for $C_{13}H_{17}N_3O_5S$: 327.0898, found 328.0972 $(M+H)^+$.

SG5-163-4

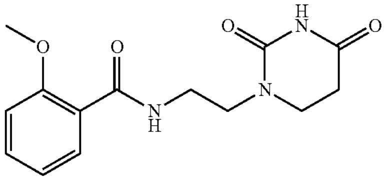

N-(2-(2,4-dioxotetrahydropyrimidin-1(2H)-yl)ethyl)-2-methoxybenzamide (SG5-163-4): This compound was prepared from SG5-085 (25 mg, 0.129 mmol), 2-methoxybenzoyl chloride (0.029 mL, 0.194 mmol), DIPEA (0.092 mL, 0.516 mmol), and DMF (1 mL) using Method A (reaction time, overnight) to give the title compound as an off-white solid (9.22 mg, 25%). Mp: 156-157° C. HPLC: 99% [$t_R$=6.4 min, 30% MeOH, 70% water (with 0.1% TFA), 20 min]. $^1H$ NMR (400 MHz, DMSO-$d_6$) δ 10.10 (s, 1H, disappeared on $D_2O$ shake), 8.28 (t, J=5.2 Hz, 1H, disappeared on $D_2O$ shake), 7.67 (dd, J=7.5, 1.8 Hz, 1H), 7.43 (ddd, J=8.4, 7.5, 1.8 Hz, 1H), 7.09 (dd, J=8.4, 1.0 Hz, 1H), 6.99 (td, J=7.5, 1.0 Hz, 1H), 3.83 (s, 3H), 3.49-3.44 (m, 2H), 3.44-3.37 (m, 4H), 2.52 (t, J=6.8 Hz, 2H). HPLC-MS (ESI+): m/z 605.3 [100%, $(2M+Na)^+$], 314.2 [100%, $(M+Na)^+$], 292.1 [80%, $(M+H)^+$]. HRMS (ESI+): m/z calcd for $C_{14}H_{17}N_3O_4$: 291.1229, found 292.1302 $(M+H)^+$.

SG5-163-5

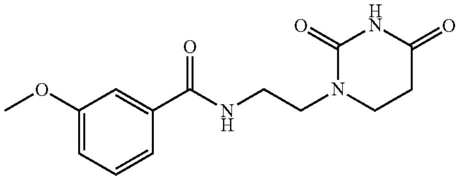

N-(2-(2,4-dioxotetrahydropyrimidin-1(2H)-yl)ethyl)-3-methoxybenzamide (SG5-163-5): This compound was prepared from SG5-085 (25 mg, 0.129 mmol), 3-methoxybenzoyl chloride (0.027 mL, 0.194 mmol), DIPEA (0.092 mL, 0.516 mmol), and DMF (1 mL) using Method A (reaction time, overnight) to give the title compound as an off-white solid (13.94 mg, 37%). Mp: 161-162° C. HPLC: >99% [$t_R$=7.3 min, 30% MeOH, 70% water (with 0.1% TFA), 20 min]. $^1H$ NMR (400 MHz, DMSO-$d_6$) δ 10.08 (s, 1H, disappeared on $D_2O$ shake), 8.54 (t, J=5.5 Hz, 1H), 7.38-7.31 (m, 3H), 7.08-7.04 (m, 1H), 3.77 (s, 3H), 3.47-3.36 (m, 6H), 2.51 (t, J=6.8 Hz, 2H, overlapped with the residual DMSO signal). HPLC-MS (ESI+): m/z 605.3 [100%, $(2M+Na)^+$], 314.1 [80%, $(M+Na)^+$], 292.1 [60%, $(M+H)^+$]. HRMS (ESI+): m/z calcd for $C_{14}H_{17}N_3O_4$: 291.1231, found 292.1302 $(M+H)^+$.

SG5-163-6

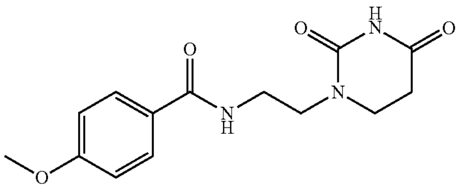

N-(2-(2,4-dioxotetrahydropyrimidin-1(2H)-yl)ethyl)-4-methoxybenzamide (SG5-163-6): This compound was prepared from SG5-085 (25 mg, 0.129 mmol), 4-methoxybenzoyl chloride (0.026 mL, 0.194 mmol), DIPEA (0.092 mL, 0.516 mmol), and DMF (1 mL) using Method A (reaction time, overnight) to give the title compound as an off-white solid (9.15 mg, 24%). Mp: 169-178° C. HPLC: 99% [$t_R$=5.7 min, 30% MeOH, 70% water (with 0.1% TFA), 20 min]. $^1$H NMR (400 MHz, DMSO-$d_6$) δ 10.07 (s, 1H, disappeared on $D_2O$ shake), 8.41 (t, J=5.5 Hz, 1H, disappeared on $D_2O$ shake), 7.77 (d, J=8.9 Hz, 2H), 6.97 (d, J=8.9 Hz, 2H), 3.78 (s, 3H), 3.47-3.35 (m, 6H), 2.52-2.48 (m, 2H, overlapped with the residual DMSO signal). HPLC-MS (ESI+): m/z 605.2 [100%, $(2M+Na)^+$], 314.2 [60%, $(M+Na)^+$], 292.2 [80%, $(M+H)^+$]. HRMS (ESI+): m/z calcd for $C_{14}H_{17}N_3O_4$: 291.1228, found 292.1301 $(M+H)^+$.

SG5-175

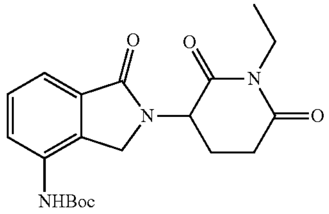

tert-butyl (2-(1-ethyl-2,6-dioxopiperidin-3-yl)-1-oxoisoindolin-4-yl)carbamate (SG5-175): This compound was prepared from SG5-040 (50 mg, 0.139 mmol), $K_2CO_3$ (19 mg, 0.139 mmol), ethyl iodide (0.033 mL, 0.417 mmol), and DMF (0.3 mL) using Method H (reaction time, overnight) to give the title compound as a white foam (26.85 mg, 50%). $^1$H NMR (400 MHz, DMSO-$d_6$) δ 9.16 (s, 1H, disappeared on $D_2O$ shake), 7.74 (dd, J=6.9, 2.2 Hz, 1H), 7.47-7.35 (m, 2H), 5.14 (dd, J=13.4, 5.3 Hz, 1H), 4.40 (d, J=17.6 Hz, 1H), 4.29 (d, J=17.6 Hz, 1H), 3.73-3.54 (m, 2H), 2.96 (ddd, J=18.4, 13.4, 5.3 Hz, 1H), 2.75-2.68 (m, 1H), 2.29 (qd, J=13.4, 4.4 Hz, 1H), 2.04-1.96 (m, 1H), 1.44 (s, 9H), 0.99 (t, J=7.0 Hz, 3H). HPLC-MS (ESI+): m/z 797.4 [100%, $(2M+Na)^+$], 410.2 [90%, $(M+Na)^+$], 388.2 [40%, $(M+H)^+$].

SG5-183

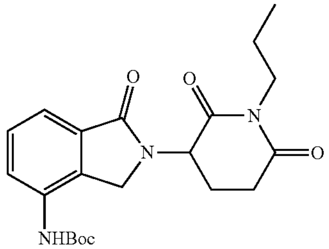

tert-butyl (2-(1-propyl-2,6-dioxopiperidin-3-yl)-1-oxoisoindolin-4-yl)carbamate (SG5-183): This compound was prepared from SG5-040 (100 mg, 0.278 mmol), $Cs_2CO_3$ (100 mg, 0.306 mmol), propyl iodide (0.054 mL, 0.556 mmol), and NMP (0.5 mL) using Method H (reaction time, overnight) to give the title compound as a white foam (60.99 mg, 55%). $^1$H NMR (400 MHz, DMSO-$d_6$) δ 9.19 (s, 1H, disappeared on $D_2O$ shake), 7.74 (dd, J=6.9, 2.1 Hz, 1H), 7.47-7.38 (m, 2H), 5.16 (dd, J=13.4, 5.1 Hz, 1H), 4.41 (d, J=17.6 Hz, 1H), 4.29 (d, J=17.6 Hz, 1H), 3.65-3.48 (m, 2H), 2.99 (ddd, J=18.1, 13.4, 5.3 Hz, 1H), 2.74 (brd, J=18.1 Hz, 1H), 2.30 (qd, J=13.4, 4.4 Hz, 1H), 2.06-1.96 (m, 1H), 1.45 (s, 9H), 1.43-1.38 (m, 2H), 0.80 (t, J=7.4 Hz, 3H). HPLC-MS (ESI+): m/z 825.4 [100%, $(2M+Na)^+$], 402.2 [40%, $(M+H)^+$].

SG6-003-1

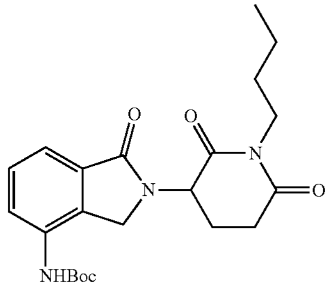

tert-butyl (2-(1-butyl-2,6-dioxopiperidin-3-yl)-1-oxoisoindolin-4-yl)carbamate (SG6-003-1): This compound was prepared from SG5-040 (100 mg, 0.278 mmol), $Cs_2CO_3$ (100 mg, 0.306 mmol), butyl iodide (0.095 mL, 0.835 mmol), and NMP (0.5 mL) using Method H (reaction time, 16 h) to give the title compound as an off-white solid (44.35 mg, 38%). Mp=188° C. (dec). $^1$H NMR (400 MHz, DMSO-$d_6$) δ 9.19 (s, 1H, disappeared on $D_2O$ shake), 7.74 (d, J=6.7 Hz, 1H), 7.48-7.38 (m, 2H), 5.16 (dd, J=13.4, 5.2 Hz, 1H), 4.41 (d, J=17.5 Hz, 1H), 4.29 (d, J=17.5 Hz, 1H), 3.60 (hept, J=7.2, 2H), 2.98 (ddd, J=18.1, 13.4, 5.2 Hz, 1H), 2.78-2.69 (m, 1H), 2.29 (qd, J=13.4, 4.6 Hz, 1H), 2.05-1.95 (m, 1H), 1.45 (s, 9H), 1.39 (q, J=7.2 Hz, 2H), 1.22 (h, J=7.2 Hz, 2H), 0.85 (t, J=7.2 Hz, 3H). HPLC-MS (ESI+): m/z 853.4 [100%, $(2M+Na)^+$], 831.4 [40%, $(2M+Na)^+$], 438.2 [30%, $(M+Na)^+$], 416.2 [60%, $(M+H)^+$].

SG6-003-2

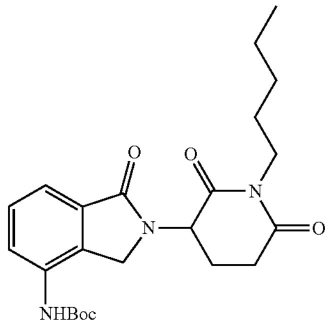

tert-butyl (2-(1-pentyl-2,6-dioxopiperidin-3-yl)-1-oxoisoindolin-4-yl)carbamate (SG6-003-2): This compound was prepared from SG5-040 (100 mg, 0.278 mmol), $Cs_2CO_3$ (100 mg, 0.306 mmol), pentyl iodide (0.102 mL, 0.835 mmol), and NMP (0.5 mL) using Method H (reaction time, 16 h) to give the title compound as an off-white solid (90.21 mg, 75%). Mp=144-148° C. $^1$H NMR (400 MHz, DMSO-$d_6$) δ 9.18 (s, 1H, disappeared on $D_2O$ shake), 7.73 (dd, J=6.7, 2.3 Hz, 1H), 7.47-7.38 (m, 2H), 5.16 (dd, J=13.4, 5.3 Hz, 1H), 4.41 (d, J=17.5 Hz, 1H), 4.28 (d, J=17.5 Hz, 1H), 3.67-3.50 (m, 2H), 2.98 (ddd, J=18.3, 13.4, 5.3 Hz, 1H), 2.78-2.67 (m, 1H), 2.29 (qd, J=13.4, 4.5 Hz, 1H), 2.06-1.94 (m, 1H), 1.45 (s, 9H), 1.41 (dd, J=9.2, 5.4 Hz, 2H), 1.31-1.15 (m, 4H), 0.83 (t, J=7.1 Hz, 3H). HPLC-MS (ESI+): m/z 881.5 [100%, $(2M+Na)^+$], 436.2 [40%, $(M+Na)^+$].

SG6-003-2

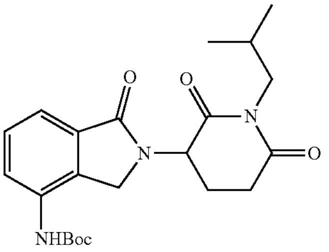

tert-butyl (2-(1-isobutyl-2,6-dioxopiperidin-3-yl)-1-oxoisoindolin-4-yl)carbamate (SG6-003-3): This compound was prepared from SG5-040 (100 mg, 0.278 mmol), $Cs_2CO_3$ (100 mg, 0.306 mmol), butyl iodide (0.095 mL, 0.835 mmol), and NMP (0.5 mL) using Method H (reaction time, 16 h) to give the title compound as an off-white solid (44.35 mg, 38%). Mp=175-178° C. $^1$H NMR (400 MHz, DMSO-$d_6$) δ 9.20 (s, 1H, disappeared on $D_2O$ shake), 7.73 (dd, J=6.7, 2.3 Hz, 1H), 7.47-7.37 (m, 2H), 5.18 (dd, J=13.4, 5.2 Hz, 1H), 4.41 (d, J=17.5 Hz, 1H), 4.29 (d, J=17.5 Hz, 1H), 3.53-3.41 (m, 2H), 3.01 (ddd, J=18.3, 13.4, 5.2 Hz, 1H), 2.82-2.69 (m, 1H), 2.30 (tt, J=13.4, 6.6 Hz, 1H), 2.06-1.97 (m, 1H), 1.85 (hept, J=6.8 Hz, 1H), 1.45 (s, 9H), 0.80 (d, J=6.8 Hz, 6H). HPLC-MS (ESI+): m/z 853.4 [100%, $(2M+Na)^+$], 438.2 [100%, $(M+Na)^+$], 416.2 [20%, $(M+H)^+$].

SG6-003-4

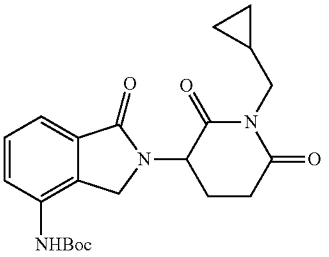

tert-butyl (2-(1-cyclopropylmethyl-2,6-dioxopiperidin-3-yl)-1-oxoisoindolin-4-yl)carbamate (SG6-003-4): This compound was prepared from SG5-040 (100 mg, 0.278 mmol), $Cs_2CO_3$ (100 mg, 0.306 mmol), methylcyclopropyl bromide (0.081 mL, 0.835 mmol), and NMP (0.5 mL) using Method H (reaction time, 16 h) to give the title compound as an off-white solid (71.07 mg, 62%). Mp=173-176° C. $^1$H NMR (400 MHz, DMSO-$d_6$) δ 9.19 (s, 1H, disappeared on $D_2O$ shake), 7.74 (dd, J=6.7, 2.3 Hz, 1H), 7.48-7.38 (m, 2H), 5.18 (dd, J=13.4, 5.3 Hz, 1H), 4.42 (d, J=17.5 Hz, 1H), 4.29 (d, J=17.5 Hz, 1H), 3.51 (d, J=7.0 Hz, 2H), 3.02 (ddd, J=18.3, 13.4, 5.3 Hz, 1H), 2.81-2.71 (m, 1H), 2.30 (qd, J=13.4, 4.5 Hz, 1H), 2.07-1.99 (m, 1H), 1.45 (s, 9H), 1.06-0.94 (m, 1H), 0.42-0.34 (m, 2H), 0.26-0.17 (m, 2H). HPLC-MS (ESI+): m/z 849.4 [100%, $(2M+Na)^+$], 452.2 [20%, $(M+Na)^+$], 430.2 [20%, $(M+H)^+$].

SG6-003-6

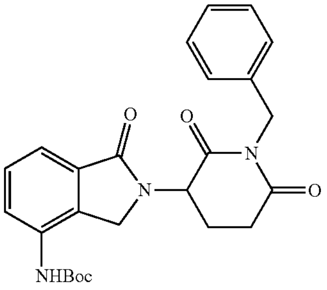

tert-butyl (2-(1-benzyl-2,6-dioxopiperidin-3-yl)-1-oxoisoindolin-4-yl)carbamate (SG6-003-6): This compound was prepared from SG5-040 (100 mg, 0.278 mmol), $Cs_2CO_3$ (100 mg, 0.306 mmol), benzyl bromide (0.099 mL, 0.835 mmol), and NMP (0.5 mL) using Method H (reaction time, 16 h) to give the title compound as an off-white solid (47.87 mg, 38%). Mp=185-187° C. $^1$H NMR (400 MHz, DMSO-$d_6$) δ 9.20 (s, 1H, disappeared on $D_2O$ shake), 7.73 (dd, J=6.6, 2.4 Hz, 1H), 7.47-7.39 (m, 2H), 7.32-7.17 (m, 5H), 5.27 (dd, J=13.4, 5.2 Hz, 1H), 4.85 (d, J=14.8 Hz, 1H), 4.78 (d, J=14.8 Hz, 1H), 4.43 (d, J=17.5 Hz, 1H), 4.30 (d, J=17.5 Hz, 1H), 3.09 (ddd, J=18.1, 13.4, 5.2 Hz, 1H), 2.85-2.74 (m, 1H), 2.37 (td, J=13.4, 4.4 Hz, 1H), 2.11-1.99 (m, 1H), 1.45 (s, 9H). HPLC-MS (ESI+): m/z 921.4 [100%, $(2M+Na)^+$], 472.2 [20%, $(M+Na)^+$], 450.2 [25%, $(M+H)^+$].

SG6-009

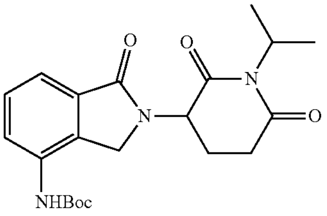

tert-butyl (2-(1-isopropyl-2,6-dioxopiperidin-3-yl)-1-oxoisoindolin-4-yl)carbamate (SG6-009): This compound was prepared from SG5-040 (100 mg, 0.278 mmol), $Cs_2CO_3$ (100 mg, 0.306 mmol), isopropyl bromide (0.078 mL, 0.835 mmol), and NMP (0.5 mL) using Method H (reaction time, 16 h) to give the title compound as a white solid (59.89 mg, 54%). Mp=198-199° C. $^1$H NMR (400 MHz, DMSO-$d_6$) δ 9.18 (s, 1H, disappeared on $D_2O$ shake), 7.76 (d, J=6.2 Hz, 1H), 7.47-7.38 (m, 2H), 5.09 (dd, J=13.4, 5.3 Hz, 1H), 4.77 (hept, J=6.5 Hz, 1H), 4.40 (d, J=17.5 Hz, 1H), 4.28 (d, J=17.5 Hz, 1H), 2.94 (ddd, J=18.2, 13.4, 5.3 Hz, 1H), 2.76-2.66 (m, 1H), 2.27 (qd, J=13.4, 4.6 Hz, 1H), 2.02-1.95 (m, 1H), 1.45 (s, 9H), 1.27 (t, J=6.5 Hz, δH). HPLC-MS (ESI+): m/z 825.4 [100%, $(2M+Na)^+$], 424.2 [100%, $(M+Na)^+$], 402.3 [30%, $(M+H)^+$].

SG5-182

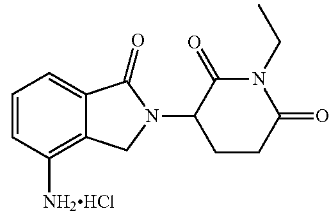

3-(4-Amino-1-oxoisoindolin-2-yl)-1-ethylpiperidine-2,6-dione hydrochloride (SG5-182): This compound was prepared from SG5-175 (19.50 mg, 0.053 mmol) and 4 M HCl in dioxane (0.4 mL) using Method G to give the title compound as a white solid (13.77 mg, 85%). Mp: 189° C. (dec). HPLC: 99% [$t_R$=12.2 min, 15% MeOH, 85% water (with 0.1% TFA), 20 min]. $^1$H NMR (400 MHz, DMSO-$d_6$) δ 7.23 (t, J=7.6 Hz, 1H), 7.01 (d, J=7.6 Hz, 1H), 6.90 (d, J=7.6 Hz, 1H), 5.13 (dd, J=13.4, 5.3 Hz, 1H), 4.23 (d, J=17.0 Hz, 1H), 4.11 (d, J=17.0 Hz, 1H), 3.64 (hept, J=6.8 Hz, 2H), 2.97 (ddd, J=17.2, 13.4, 5.3 Hz, 1H), 2.77-2.68 (m, 1H), 2.26 (qd, J=13.4, 4.6 Hz, 1H), 2.03-1.96 (m, 1H), 0.99 (t, J=6.8 Hz, 3H). HPLC-MS (ESI+): m/z 597.2 [50%, $(2M+Na)^+$], 288.2 [100%, $(M+H)^+$]. HRMS (ESI+): m/z calcd for $C_{15}H_{17}N_3O_3$: 287.1274, found 288.1348 $(M+H)^+$.

SG6-001

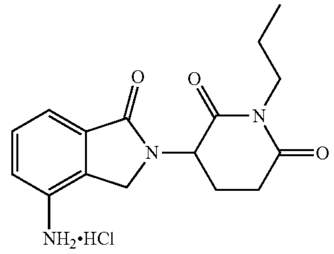

3-(4-Amino-1-oxoisoindolin-2-yl)-1-propylpiperidine-2,6-dione hydrochloride (SG6-001): This compound was prepared from SG5-183 (45 mg, 0.112 mmol) and 4 M HCl in dioxane (0.5 mL) using Method G. The resulting residue was triturated using EtOAc/hexanes to give the title compound as an off-white solid (38.57 mg, 100%). Mp: 167° C. (dec). HPLC: 99% [$t_R$=10.7 min, 25% MeOH, 75% water (with 0.1% TFA), 20 min]. $^1$H NMR (400 MHz, DMSO-$d_6$) δ 7.29 (t, J=7.7 Hz, 1H), 7.11 (d, J=7.7 Hz, 1H), 6.99 (d, J=7.7 Hz, 1H), 5.17 (dd, J=13.4, 5.3 Hz, 1H), 4.29 (d, J=17.1 Hz, 1H), 4.16 (d, J=17.1 Hz, 1H), 3.66-3.52 (m, 2H), 3.00 (ddd, J=17.2, 13.4, 5.3 Hz, 1H), 2.75 (ddd, J=17.2, 4.4, 2.5 Hz, 1H), 2.29 (qd, J=13.4, 4.4 Hz, 1H), 2.04 (ddq, J=10.4, 5.3, 2.5 Hz, 1H), 1.44 (q, J=7.4 Hz, 2H), 0.81 (t, J=7.4 Hz, 3H). HPLC-MS (ESI+): m/z 625.3 [40%, $(2M+Na)^+$], 302.2 [100%, $(M+H)^+$]. HRMS (ESI+): m/z calcd for $C_{16}H_{19}N_3O_3$: 301.1429, found 324.1322 $(M+Na)^+$.

SG6-007-1

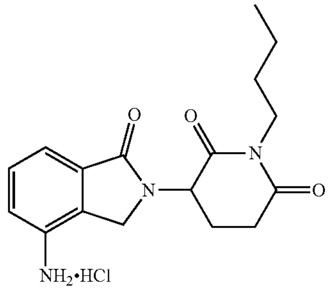

3-(4-Amino-1-oxoisoindolin-2-yl)-1-butylpiperidine-2,6-dione hydrochloride (SG6-007-1): This compound was prepared from SG5-003-1 (29.44 mg, 0.071 mmol) and 4 M HCl in dioxane (0.5 mL) using Method G. The resulting residue was triturated using EtOAc/hexanes to give the title compound as an off-white solid (24.20 mg, 97%). Mp: 132-134° C. HPLC: 99% [$t_R$=16.9 min, 30% MeOH, 70% water (with 0.1% TFA), 20 min]. $^1$H NMR (400 MHz, DMSO-$d_6$) δ 7.28 (t, J=7.7 Hz, 1H), 7.11 (d, J=7.7 Hz, 1H), 7.00 (d, J=7.7 Hz, 1H), 5.15 (dd, J=13.4, 5.3 Hz, 1H), 4.28 (d, J=17.1 Hz, 1H), 4.15 (d, J=17.1 Hz, 1H), 3.68-3.54 (m, 2H), 2.99 (ddd, J=18.5, 13.4, 5.3 Hz, 1H), 2.79-2.68 (m, 1H), 2.27 (qd, J=13.4, 4.4 Hz, 1H), 2.07-1.98 (m, 1H), 1.39 (p, J=7.3 Hz, 2H), 1.22 (h, J=7.3 Hz, 2H), 0.84 (t, J=7.3 Hz, 3H). HPLC-MS (ESI+): m/z 653.3 [60%, $(2M+Na)^+$], 338.3 [40%, $(M+Na)^+$], 316.2 [100%, $(M+H)^+$]. HRMS (ESI+): m/z calcd for $C_{17}H_{21}N_3O_3$: 315.1594, found 316.1669 $(M+H)^+$.

SG6-007-2

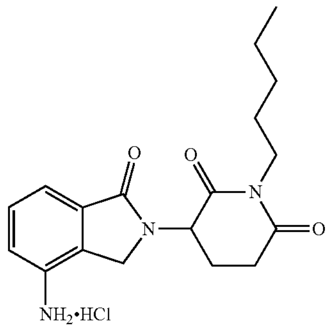

3-(4-Amino-1-oxoisoindolin-2-yl)-1-pentylpiperidine-2,6-dione hydrochloride (SG6-007-2): This compound was prepared from SG5-003-2 (73 mg, 0.170 mmol) and 4 M HCl in dioxane (0.5 mL) using Method G. The resulting residue was triturated using EtOAc/hexanes to give the title compound as an off-white solid (61.87 mg, 99%). Mp: 133-135° C. HPLC: 99% [$t_R$=6.5 min, 50% MeOH, 50% water (with 0.1% TFA), 20 min]. $^1$H NMR (400 MHz, DMSO-$d_6$) δ 7.29 (t, J=7.7 Hz, 1H), 7.12 (d, J=7.7 Hz, 1H), 7.01 (d, J=7.7 Hz, 1H), 5.16 (dd, J=13.4, 5.3 Hz, 1H), 4.29 (d, J=17.1 Hz, 1H), 4.16 (d, J=17.1 Hz, 1H), 3.66-3.55 (m, 2H), 2.99 (ddd, J=18.6, 13.4, 5.3 Hz, 1H), 2.74 (ddd, J=17.1, 4.4, 2.3 Hz, 1H), 2.28 (qd, J=13.4, 4.4 Hz, 1H), 2.07-1.96 (m, 1H), 1.41 (p, J=7.3 Hz, 2H), 1.30-1.13 (m, 4H), 0.83 (t, J=7.3 Hz, 3H). HPLC-MS (ESI+): m/z 681.3 [80%, $(2M+Na)^+$], 352.2 [40%, $(2M+Na)^+$], 330.2 [100%, $(M+H)^+$]. HRMS (ESI+): m/z calcd for $C_{18}H_{23}N_3O_3$: 329.1747, found 330.1822 $(M+H)^+$.

SG6-007-3

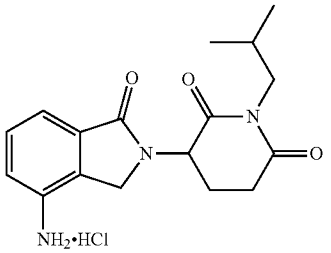

3-(4-Amino-1-oxoisoindolin-2-yl)-1-isobutylpiperidine-2,6-dione hydrochloride (SG6-007-3): This compound was prepared from SG5-003-3 (51 mg, 0.122 mmol) and 4 M HCl in dioxane (0.5 mL) using Method G. The resulting residue was triturated using EtOAc/hexanes to give the title compound as an off-white solid (42.68 mg, 99%). Mp: 142-145° C. HPLC: 99% [$t_R$=3.7 min, 50% MeOH, 50% water (with 0.1% TFA), 20 min]. $^1$H NMR (400 MHz, DMSO-$d_6$) δ 7.32 (t, J=7.6 Hz, 1H), 7.18 (d, J=7.6 Hz, 1H), 7.07 (d, J=7.6 Hz, 1H), 5.18 (dd, J=13.5, 5.3 Hz, 1H), 4.33 (d, J=17.1 Hz, 1H), 4.18 (d, J=17.1 Hz, 1H), 3.54-3.40 (m, 2H), 3.01 (ddd, J=18.3, 13.5, 5.3 Hz, 1H), 2.76 (ddd, J=17.4, 4.4, 2.4 Hz, 1H), 2.30 (qd, J=13.5, 4.5 Hz, 1H), 2.09-1.98 (m, 1H), 1.84 (hept, J=6.8 Hz, 1H), 0.80 (d, J=6.8 Hz, 6H). HPLC-MS (ESI+): m/z 653.4 [50%, $(2M+Na)^+$], 316.2 [100%, $(M+H)^+$]. HRMS (ESI+): m/z calcd for $C_{17}H_{21}N_3O_3$: 315.1592, found 316.1666 $(M+H)^+$.

SG6-007-4

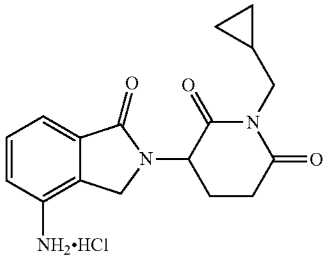

3-(4-Amino-1-oxoisoindolin-2-yl)-1-(cyclopropylmethyl)piperidine-2,6-dione hydrochloride (SG6-007-4): This compound was prepared from SG5-003-4 (55 mg, 0.133 mmol) and 4 M HCl in dioxane (0.5 mL) using Method G. The resulting residue was triturated using EtOAc/hexanes to give the title compound as an off-white solid (46.37 mg, 99%). Mp: 142-149° C. HPLC: 94% [$t_R$=3.1 min, 50% MeOH, 50% water (with 0.1% TFA), 20 min]. $^1$H NMR (400 MHz, DMSO-$d_6$) δ 7.28 (t, J=7.6 Hz, 1H), 7.11 (d, J=7.6 Hz, 1H), 6.99 (d, J=7.6 Hz, 1H), 5.18 (dd, J=13.5, 5.3 Hz, 1H), 4.30 (d, J=17.0 Hz, 1H), 4.15 (d, J=17.0 Hz, 1H), 3.53-3.49 (m, 2H), 3.03 (ddd, J=18.4, 13.5, 5.3 Hz, 1H), 2.77 (ddd, J=17.4, 4.5, 2.3 Hz, 1H), 2.28 (qd, J=13.5, 4.5 Hz, 1H), 2.09-2.00 (m, 1H), 1.05-0.95 (m, 1H), 0.43-0.32 (m, 2H), 0.25-0.16 (m, 2H). HPLC-MS (ESI+): m/z 649.3 [50%, $(2M+Na)^+$], 314.2 [100%, $(M+H)^+$]. HRMS (ESI+): m/z calcd for $C_{17}H_{19}N_3O_3$: 313.1434, found 314.1510 $(M+H)^+$.

SG6-007-6

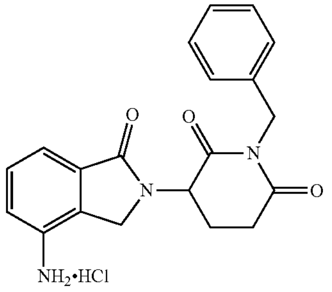

3-(4-Amino-1-oxoisoindolin-2-yl)-1-benzylpiperidine-2,6-dione hydrochloride (SG6-007-6): This compound was prepared from SG5-003-6 (38 mg, 0.084 mmol) and 4 M HCl in dioxane (0.5 mL) using Method G. The resulting residue was triturated using EtOAc/hexanes to give the title compound as an off-white solid (32.09 mg, 98%). Mp: 150-155° C. HPLC: 99% [$t_R$=4.3 min, 50% MeOH, 50% water (with 0.1% TFA), 20 min]. $^1$H NMR (400 MHz, DMSO-$d_6$) δ 7.32-7.18 (m, 6H), 7.10 (d, J=7.6 Hz, 1H), 6.99 (d, J=7.6 Hz, 1H), 5.27 (dd, J=13.4, 5.0 Hz, 1H), 4.85 (d, J=14.8 Hz, 1H), 4.79 (d, J=14.8 Hz, 1H), 4.30 (d, J=17.0 Hz, 1H), 4.16 (d, J=17.0 Hz, 1H), 3.10 (ddd, J=18.3, 13.4, 5.3 Hz, 1H), 2.81 (ddd, J=17.4, 4.6, 2.4 Hz, 1H), 2.34 (td, J=13.4, 4.6 Hz, 1H), 2.12-2.02 (m, 1H). HPLC-MS (ESI+): m/z 721.4 [60%, $(2M+Na)^+$], 350.2 [100%, $(M+H)^+$]. HRMS (ESI+): m/z calcd for $C_{20}H_{19}N_3O_3$: 349.1436, found 350.1512 $(M+H)^+$.

SG6-010

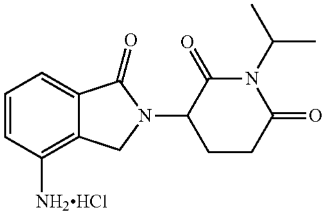

3-(4-Amino-1-oxoisoindolin-2-yl)-1-isopropylpiperidine-2,6-dione hydrochloride (SG6-010): This compound was prepared from SG5-009 (48 mg, 0.119 mmol) and 4 M HCl in dioxane (0.5 mL) using Method G. The resulting residue was triturated using EtOAc/hexanes to give the title compound as an off-white solid (40.01 mg, 99%). Mp: 186° C. (dec). HPLC: 99% [$t_R$=7.4 min, 30% MeOH, 70% water (with 0.1% TFA), 20 min]. $^1$H NMR (400 MHz, DMSO-$d_6$) δ 7.29 (t, J=7.6 Hz, 1H), 7.13 (d, J=7.6 Hz, 1H), 7.02 (d, J=7.6 Hz, 1H), 5.09 (dd, J=13.4, 5.0 Hz, 1H), 4.77 (hept, J=6.6 Hz, 1H), 4.29 (d, J=16.6 Hz, 1H), 4.16 (d, J=16.6 Hz, 1H), 2.94 (ddd, J=18.4, 13.4, 5.4 Hz, 1H), 2.70 (ddd, J=17.3, 4.4, 2.3 Hz, 1H), 2.24 (qd, J=13.4, 4.4 Hz, 1H), 2.01-1.94 (m, 1H), 1.25 (d, J=6.6 Hz, 3H), 1.23 (d, J=6.6 Hz, 3H). HPLC-MS (ESI+): m/z 625.3 [30%, $(2M+Na)^+$], 302.2 [100%, $(M+H)^+$]. HRMS (ESI+): m/z calcd for $C_{16}H_{19}N_3O_3$: 301.1437, found 302.1510 $(M+H)^+$.

SG6-003-5

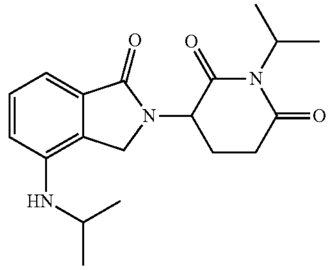

1-isopropyl-3-(4-(isopropylamino)-1-oxoisoindolin-2-yl) piperidine-2,6-dione (SG6-003-5): This compound was prepared from SG5-040 (100 mg, 0.278 mmol), $Cs_2CO_3$ (100 mg, 0.306 mmol), isopropyl iodide (0.166 mL, 1.670 mmol), and NMP (0.5 mL) using Method H (reaction time, 16 h) to give the title compound as a yellow solid (28.14 mg, 29%). Mp: 101-105° C. HPLC: 95% [$t_R$=7.5 min, 50% MeOH, 50% water (with 0.1% TFA), 20 min]. $^1$H NMR (400 MHz, DMSO-$d_6$) δ 7.26 (t, J=7.7 Hz, 1H), 6.89 (d, J=7.7 Hz, 1H), 6.75 (d, J=7.7 Hz, 1H), 5.26 (brs, 1H), 5.10 (dd, J=13.5, 5.3 Hz, 1H), 4.78 (hept, J=6.9 Hz, 1H), 4.19 (d, J=17.0 Hz, 1H), 4.06 (d, J=17.0 Hz, 1H), 3.72-3.59 (m, 1H), 2.97 (ddd, J=18.7, 13.5, 5.3 Hz, 1H), 2.72 (ddd, J=17.4, 4.6, 2.4 Hz, 1H), 2.27-2.14 (m, 1H), 2.03-1.93 (m, 1H), 1.27 (dd, J=6.9, 3H), 1.26 (dd, J=6.9, 3H), 1.16 (dd, J=6.3, 3H), 1.15 (dd, J=6.3, 3H). HPLC-MS (ESI+): m/z 709.4 [60%, $(2M+Na)^+$], 344.2 [100%, $(M+H)^+$]. HRMS (ESI+): m/z calcd for $C_{19}H_{25}N_3O_3$: 343.1906, found 344.1981 $(M+H)^+$.

Scheme 16

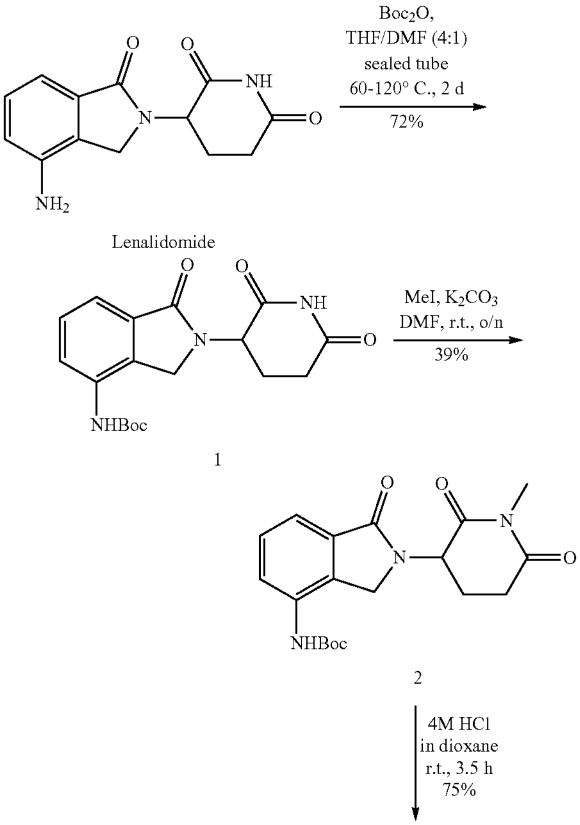

-continued

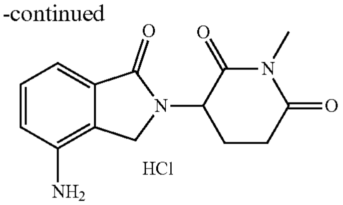

3, SG5-046

1

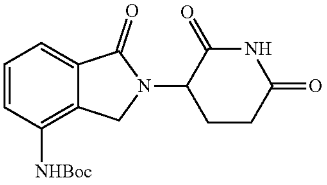

tert-Butyl (2-(2,6-dioxopiperidin-3-yl)-1-oxoisoindolin-4-yl)carbamate (1): Lenalidomide (259 mg, 1 mmol) and $Boc_2O$ (218 mg, 1.1 mmol) were mixed in THF (1 mL) in a sealed tube and stirred at 60° C. overnight. The next day, $Boc_2O$ (110 mg, 0.5 equiv.), THF (1 mL), and DMF (0.5 mL) were added and the solution was further stirred at 120° C. overnight. Water (20 mL) was added and the mixture was sonicated. The precipitate was filtered, washed with water (10 mL), and dried. The resulting solid was triturated using EtOH/EtOAc/hexanes and filtered to give the desired product as an off-white solid (258 mg, 72%). Mp: 196-198° C. HPLC-MS (ESI+): m/z 741.3 [(100%, $2M+Na)^+$], 719.4 [(40%, $2M+H)^+$], 360.2 [(90%, $M+H)^+$]. $^1$H NMR (400 MHz, DMSO-$d_6$): δ 11.00 (s, 1H), 9.21 (s, 1H), 7.74 (dd, J=6.8, 1.7 Hz, 1H), 7.49-7.39 (m, 2H), 5.10 (dd, J=13.3, 4.7 Hz, 1H), 4.41 (d, J=17.6 Hz, 1H), 4.32 (d, J=17.6 Hz, 1H), 2.95-2.83 (m, 1H), 2.64-2.54 (m, 1H), 2.40-2.26 (m, 1H), 2.05-1.95 (m, 1H), 1.46 (s, 9H). Compound 1 was reported [4].

2

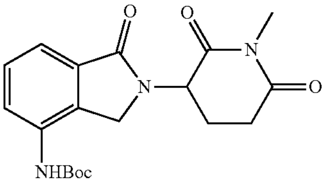

tert-Butyl (2-(1-methyl-2,6-dioxopiperidin-3-yl)-1-oxoisoindolin-4-yl)carbamate (2): To a mixture of 1 (100 mg, 0.278 mmol) and $K_2CO_3$ (38 mg, 0.278 mmol) in DMF (0.8 mL) was added methyl iodide (0.017 mL, 0.278 mmol) dropwise at room temperature under Argon. The mixture was stirred overnight. Water (10 mL) was added and extracted with EtOAc (2×20 mL). The combined organic layers were dried ($Na_2SO_4$), filtered, and concentrated under reduced pressure. The resulting yellow oil was purified by flash chromatography ($SiO_2$) eluting with hexanes in EtOAc (80% to 100%) to provide the title compound as a white solid (40.37 mg, 39%). Mp: 192° C. (dec). HPLC-MS (ESI+): m/z 741.3 [(100%, $2M+Na)^+$], 719.4 [(40%, $2M+H)^+$], 360.2 [(90%, $M+H)^+$]. $^1$H NMR (400 MHz, DMSO-$d_6$): δ 9.20 (s, 1H), 7.73 (dd, J=6.5, 2.3 Hz, 1H), 7.49-7.41 (m, 2H), 5.16 (dd, J=13.4, 5.1 Hz, 1H), 4.42 (d, J=17.6 Hz, 1H), 4.30 (d, J=17.6 Hz, 1H), 3.02-2.90 (m, 1H), 2.99 (s, 3H), 2.80-2.71 (m, 1H), 2.40-2.27 (m, 1H), 2.07-1.97 (m, 1H), 1.46 (s, 9H).

3

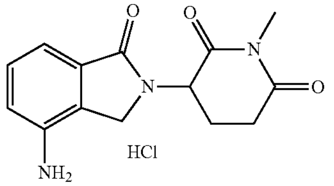

3-(4-Amino-1-oxoisoindolin-2-yl)-1-methylpiperidine-2,6-dione (3, SG5-046): 2 (35 mg, 0.093 mmol) was stirred in 4 M HCl in dioxane (0.5 mL) for 3.5 h at room temperature. The white suspension was concentrated under reduced pressure and the resulting solid was triturated in DCM/hexanes, washed with EtOAc and hexanes (10 mL each), and dried to provide the title compound as light yellow flakes (21.81 mg, 75%). Mp: 207° C. (dec). HPLC: 99% [$t_R$=11.6 min, 10% MeOH, 90% water (with 0.1% TFA), 20 min]. $^1$H NMR (400 MHz, DMSO-$d_6$): δ 7.29 (t, J=7.5 Hz, 1H), 7.11 (d, J=7.5 Hz, 1H), 6.99 (d, J=7.5 Hz, 1H), 5.17 (dd, J=13.4, 4.7 Hz, 1H), 5.20-4.80 (br s, 2H, disappeared on $D_2O$ shake), 4.28 (d, J=17.0 Hz, 1H), 4.17 (d, J=17.0 Hz, 1H), 3.05-2.91 (m, 1H), 2.99 (s, 3H), 2.80-2.70 (m, 1H), 2.39-2.25 (m, 1H), 2.08-1.97 (m, 1H). HPLC-MS (ESI+): m/z 569.2 [(30%, 2M+Na)$^+$], 274.2 [(100%, M+H)$^+$]. LC-MS (ESI+): 569.2 [40%, (2M+Na)$^+$], 296.1 [100%, (M+Na)$^+$]. HRMS (ESI+): m/z calcd for $C_{14}H_{15}N_3O_3$ (M+H)$^+$274.1186, found 274.1176.

Scheme 17

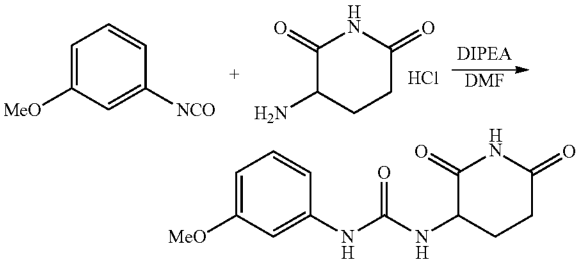

MA5-170

MA5-170

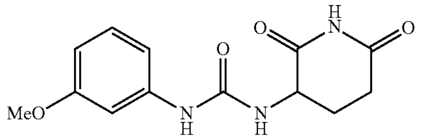

1-(2,6-Dioxopiperidin-3-yl)-3-(3-methoxyphenyl)urea (MA5-170): To a solution of α-aminoglutarimide hydrochloride (0.081 g, 0.492 mmol) in DMF (0.5 mL) was added DIPEA (164 μL, 0.949 mmol) at room temperature under argon. The mixture was stirred for 5 min and 3-methoxyphenyl isocyanate (0.07 g, 0.469 mmol) was added at 0° C. The mixture was stirred for 5 min at 0° C. and allowed to warm to room temperature. The mixture was stirred for an additional 18 h. The solvent was removed using Biotage V-10 evaporator and the residue was purified by $SiO_2$ column using 10% MeOH in $CH_2Cl_2$ to afford the title compound as a white solid (0.133 g, 87%). HPLC: 96.9% [$t_R$=12.6 min, 5-95 gradient elution, MeOH/$H_2O$ (with 0.1% TFA), 20 min, 254 nm]. $^1$H NMR (400 MHz, DMSO-$d_6$) δ 10.87 (s, 1H), 8.80 (s, 1H), 7.17-7.06 (m, 2H), 6.87 (d, J=8.0 Hz, 1H), 6.55-6.42 (m, 2H), 4.45 (dt, J=12.3, 6.1 Hz, 1H), 2.74 (m, 1H), 2.55-2.45 (m, 1H), 2.13-2.04 (m, 1H), 1.96 (qd, J=12.9, 4.8, 1H). HPLC-MS (ESI+): m/z 577.3 (2M+Na)$^+$, 278.2 (M+H)$^+$.

Scheme 18

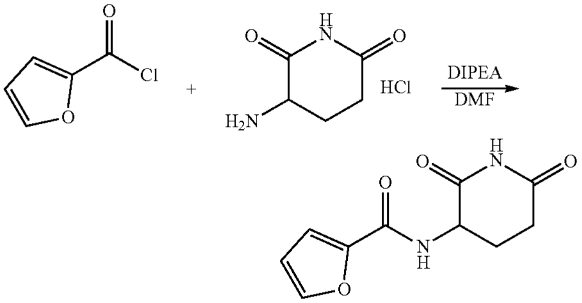

MA5-178

MA5-178

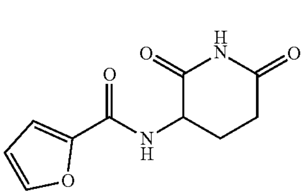

N-(2,6-dioxopiperidin-3-yl)furan-2-carboxamide (MA5-178): To a solution of α-aminoglutarimide hydrochloride (0.082 g, 0.50 mmol) in DMF (1 mL) was added DIPEA (174 μL, 1.0 mmol) at room temperature under argon. The mixture was cooled to 0° C. and 2-furancarbonyl chloride (74.2 μL, 0.75 mmol) was added. The mixture was stirred for 30 min at 0° C. and allowed to warm to room temperature. The mixture was stirred overnight and quenched with $H_2O$ (2 mL). The solvent was removed using Biotage V-10 evaporator. The residue was purified by $SiO_2$ chromatography (0-20 gradient elution, MeOH/DCM) to afford the product as a white solid (0.058 g, 52%). HPLC: 98.2% [$t_R$=5.6 min, 15% MeOH, 85% water (with 0.1% TFA), 20 min, 254 nm]. $^1$H NMR (400 MHz, DMSO-$d_6$) δ 10.87 (s, 1H), 8.64 (d, J=8.5 Hz, 1H), 7.88 (dd, J=1.7, 0.8 Hz, 1H), 7.14 (dd, J=3.5, 0.7 Hz, 1H), 6.55 (dd, J=3.5, 1.7 Hz, 1H), 4.74 (m, 1H), 2.79 (ddd, J=18.9, 13.5, 5.5, 1H), 2.56-2.48 (m, 1H), 2.12 (qd, J=12.9, 4.3 Hz, 1H), 1.99-1.86 (m, 1H). HPLC-MS (ESI+): m/z 467.2 (2M+Na)$^+$, 223.1 (M+H)$^+$.

REFERENCES

1. Sakamoto K M, Kim K B, Kumagai A, Mercurio F, Crews C M, Deshaies R J. Protacs: chimeric molecules that target proteins to the Skp1-Cullin-F box complex for ubiquitination and degradation. Proc Natl Acad Sci USA. 2001; 98:8554-9.
2. Sakamoto K M, Kim K B, Verma R, Ransick A, Stein B, Crews C M, et al. Development of Protacs to target cancer-promoting proteins for ubiquitination and degradation. Mol Cell Proteomics. 2003; 2:1350-8.
3. Sakamoto K M. Protacs for treatment of cancer. Pediatr Res. 2010; 67:505-8.
4. Zengerle M, Chan K H, Ciulli A. Selective Small Molecule Induced Degradation of the BET Bromodomain Protein BRD4. ACS Chem Biol. 2015; 10:1770-7.
5. Winter G E, Buckley D L, Paulk J, Roberts J M, Souza A, Dhe-Paganon S, et al. DRUG DEVELOPMENT. Phthalimide conjugation as a strategy for in vivo target protein degradation. Science. 2015; 348:1376-81.
6. Lu J, Qian Y, Altieri M, Dong H, Wang J, Raina K, et al. Hijacking the E3 Ubiquitin Ligase Cereblon to Efficiently Target BRD4. Chem Biol. 2015; 22:755-63.
7. Kronke J, Udeshi N D, Narla A, Grauman P, Hurst S N, McConkey M, et al. Lenalidomide causes selective degradation of IKZF1 and IKZF3 in multiple myeloma cells. Science. 2014; 343:301-5.
8. Bjorklund C C, Lu L, Kang J, Hagner P R, Havens C G, Amatangelo M, et al. Rate of CRL4(CRBN) substrate Ikaros and Aiolos degradation underlies differential activity of lenalidomide and pomalidomide in multiple myeloma cells by regulation of c-Myc and IRF4. Blood Cancer J. 2015; 5:e354.
9. Zeldis J B, Williams B A, Thomas S D, Elsayed M E. S. T. E. P. S.: a comprehensive program for controlling and monitoring access to thalidomide. Clin Ther. 1999; 21:319-30.
10. Petzold G, Fischer E S, Thoma N H. Structural basis of lenalidomide-induced CK1alpha degradation by the CRL4 ubiquitin ligase. Nature. 2016.
11. Kronke J, Fink E C, Hollenbach P W, MacBeth K J, Hurst S N, Udeshi N D, et al. Lenalidomide induces ubiquitination and degradation of CK1alpha in del(5q) MDS. Nature. 2015; 523:183-8.
12. Rajadhyaksha A M, Ra S, Kishinevsky S, Lee A S, Romanienko P, DuBoff M, et al. Behavioral characterization of cereblon forebrain-specific conditional null mice: a model for human non-syndromic intellectual disability. Behavioural brain research. 2012; 226:428-34.
13. Sabel C E, Neureuther J M, Siemann S. A spectrophotometric method for the determination of zinc, copper, and cobalt ions in metalloproteins using Zincon. Anal Biochem. 2010; 397:218-26.
14. Hartmann M D, Boichenko I, Coles M, Zanini F, Lupas A N, Hernandez Alvarez B. Thalidomide mimics uridine binding to an aromatic cage in cereblon. J Struct Biol. 2014; 188:225-32.
15. Chamberlain P P, Lopez-Girona A, Miller K, Carmel G, Pagarigan B, Chie-Leon B, et al. Structure of the human Cereblon-DDB1-lenalidomide complex reveals basis for responsiveness to thalidomide analogs. Nat Struct Mol Biol. 2014; 21:803-9.
16. Fischer E S, Bohm K, Lydeard J R, Yang H, Stadler M B, Cavadini S, et al. Structure of the DDB1-CRBN E3 ubiquitin ligase in complex with thalidomide. Nature. 2014; 512:49-53.
17. Martin M P, Alam R, Betzi S, Ingles D J, Zhu J Y, Schonbrunn E. A novel approach to the discovery of small-molecule ligands of CDK2. Chembiochem. 2012; 13:2128-36.
18. Shannon E J, Sandoval F. Thalidomide increases the synthesis of IL-2 in cultures of human mononuclear cells stimulated with Concanavalin-A, Staphylococcal enterotoxin A, and purified protein derivative. Immunopharmacology. 1995; 31:109-16.
19. Nunes J, Klasen S, Franco M D, Lipcey C, Mawas C, Bagnasco M, et al. Signalling through CD28 T-cell activation pathway involves an inositol phospholipid-specific phospholipase C activity. Biochem J. 1993; 293 (Pt 3):835-42.
20. Gandhi A K, Kang J, Havens C G, Conklin T, Ning Y, Wu L, et al. Immunomodulatory agents lenalidomide and pomalidomide co-stimulate T cells by inducing degradation of T cell repressors Ikaros and Aiolos via modulation of the E3 ubiquitin ligase complex CRL4(CRBN.). Br J Haematol. 2014; 164:811-21.
21. Hagner P R, Man H W, Fontanillo C, Wang M, Couto S, Breider M, et al. CC-122, a pleiotropic pathway modifier, mimics an interferon response and has antitumor activity in DLBCL. Blood. 2015; 126:779-89.
22. Otahal P, Prukova D, Kral V, Fabry M, Vockova P, Lateckova L, et al. Lenalidomide enhances antitumor functions of chimeric antigen receptor modified T cells. Oncoimmunology. 2016; 5:e1115940.
23. McDaniel J M, Pinilla-Ibarz J, Epling-Burnette P K. Molecular action of lenalidomide in lymphocytes and hematologic malignancies. Adv Hematol. 2012; 2012: 513702.
24. McDaniel J M, Zou J X, Fulp W, Chen D T, List A F, Epling-Burnette P K. Reversal of T-cell tolerance in myelodysplastic syndrome through lenalidomide immune modulation. Leukemia. 2012; 26:1425-9.
25. Haslett P A, Corral L G, Albert M, Kaplan G. Thalidomide costimulates primary human T lymphocytes, preferentially inducing proliferation, cytokine production, and cytotoxic responses in the CD8+ subset. The Journal of experimental medicine. 1998; 187:1885-92.
26. Gandhi A K, Mendy D, Waldman M, Chen G, Rychak E, Miller K, et al. Measuring cereblon as a biomarker of response or resistance to lenalidomide and pomalidomide requires use of standardized reagents and understanding of gene complexity. Br J Haematol. 2014; 164:233-44.
27. Jonasova A, Bokorova R, Polak J, Vostry M, Kostecka A, Hajkova H, et al. High level of full-length cereblon mRNA in lower risk myelodysplastic syndrome with isolated 5q deletion is implicated in the efficacy of lenalidomide. Eur J Haematol. 2015; 95:27-34.
28. Zhu Y X, Braggio E, Shi C X, Bruins L A, Schmidt J E, Van Wier S, et al. Cereblon expression is required for the antimyeloma activity of lenalidomide and pomalidomide. Blood. 2011; 118:4771-9.
29. Sherman W, Beard H S, Farid R. Use of an induced fit receptor structure in virtual screening. Chem Biol Drug Des. 2006; 67:83-4.
30. Lu J, Palmer B D, Kestell P, Browett P, Baguley B C, Muller G, et al. Thalidomide metabolites in mice and patients with multiple myeloma. Clin Cancer Res. 2003; 9:1680-8.
31. Diggle G E. Thalidomide: 40 years on. Int J Clin Pract. 2001; 55:627-31.
32. Singhal S, Mehta J, Desikan R, Ayers D, Roberson P, Eddlemon P, et al. Antitumor activity of thalidomide in refractory multiple myeloma. N Engl J Med. 1999; 341: 1565-71.
33. List A, Kurtin S, Roe D J, Buresh A, Mahadevan D, Fuchs D, et al. Efficacy of lenalidomide in myelodysplastic syndromes. N Engl J Med. 2005; 352:549-57.
34. Robak T, Blonski J Z, Robak P. Antibody therapy alone and in combination with targeted drugs in chronic lymphocytic leukemia. Semin Oncol. 2016; 43:280-90.
35. Arora M, Gowda S, Tuscano J. A comprehensive review of lenalidomide in B-cell non-Hodgkin lymphoma. Ther Adv Hematol. 2016; 7:209-21.
36. Zhang L H, Kosek J, Wang M, Heise C, Schafer P H, Chopra R. Lenalidomide efficacy in activated B-cell-like subtype diffuse large B-cell lymphoma is dependent upon IRF4 and cereblon expression. Br J Haematol. 2013; 160:487-502.
37. Lindner S, Kronke J. The molecular mechanism of thalidomide analogs in hematologic malignancies. J Mol Med (Berl). 2016.

38. LeBlanc R, Hideshima T, Catley L P, Shringarpure R, Burger R, Mitsiades N, et al. Immunomodulatory drug costimulates T cells via the B7-CD28 pathway. Blood. 2004; 103:1787-90.
39. Gopalakrishnan R, Matta H, Tolani B, Triche T, Jr., Chaudhary P M. Immunomodulatory drugs target IKZF1-IRF4-MYC axis in primary effusion lymphoma in a cereblon-dependent manner and display synergistic cytotoxicity with BRD4 inhibitors. Oncogene. 2016; 35:1797-810.
40. Fionda C, Abruzzese M P, Zingoni A, Cecere F, *Vulpis* E, Peruzzi G, et al. The IMiDs targets IKZF-1/3 and IRF4 as novel negative regulators of N K cell-activating ligands expression in multiple myeloma. Oncotarget. 2015; 6:23609-30.
41. Fang J, Liu X, Bolanos L, Barker B, Rigolino C, Cortelezzi A, et al. A calcium- and calpain-dependent pathway determines the response to lenalidomide in myelodysplastic syndromes. Nat Med. 2016; 22:727-34.
42. O'Brien S, Thomas R M, Wertheim G B, Zhang F, Shen H, Wells A D. Ikaros imposes a barrier to CD8+ T cell differentiation by restricting autocrine IL-2 production. J Immunol. 2014; 192:5118-29.
43. Ito T, Ando H, Suzuki T, Ogura T, Hotta K, Imamura Y, et al. Identification of a primary target of thalidomide teratogenicity. Science. 2010; 327:1345-50.
44. Mahon C, Krogan N J, Craik C S, Pick E. Cullin E3 ligases and their rewiring by viral factors. Biomolecules. 2014; 4:897-930.
45. Kim W, Lee S, Son Y, Ko C, Ryu W S. DDB1 Stimulates Viral Transcription of Hepatitis B Virus via HBx-Independent Mechanisms. J Virol. 2016; 90:9644-53.
46. Belzile J P, Duisit G, Rougeau N, Mercier J, Finzi A, Cohen E A. HIV-1 Vpr-mediated G2 arrest involves the DDB1-CUL4AVPRBP E3 ubiquitin ligase. PLoS Pathog. 2007; 3:e85.
47. Paul I, Cui J, Maynard E L. Zinc binding to the HCCH motif of HIV-1 virion infectivity factor induces a conformational change that mediates protein-protein interactions. Proc Natl Acad Sci USA. 2006; 103:18475-80.
48. Lebraud H, Wright D J, Johnson C N, Heightman T D. Protein Degradation by In-Cell Self-Assembly of Proteolysis Targeting Chimeras. ACS Cent Sci. 2016; 2:927-34.
49. Raina K, Lu J, Qian Y, Altieri M, Gordon D, Rossi A M, et al. PROTAC-induced BET protein degradation as a therapy for castration-resistant prostate cancer. Proc Natl Acad Sci USA. 2016; 113:7124-9.
50. Saenz D T, Fiskus W, Qian Y, Manshouri T, Rajapakshe K, Raina K, et al. Novel BET protein proteolysis targeting chimera (BET-PROTAC) exerts superior lethal activity than bromodomain inhibitor (BETi) against post-myeloproliferative neoplasm (MPN) secondary (s) AML cells. Leukemia. 2017.
51. Denonne F., Celanire S., Valade A., Defays S., Durieux V., WO2009/92764A1A1, page-74-75.
52. Hashem, M. M.; Berlin, K. D.; Chesnut, R. W.; Durham, N. N. *J. Med. Chem.,* 1976, 19, 229-239.
53. Kagayama, K.; Morimoto, T.; Nagata, S'; Katoh, F.; Zhang, X.; Inoue, N.; Hashino, A.; Kageyama, K.; Shikaura, J.; Niwa, T. *Bioorg. Med. Chem.,* 2009, 17, 6959-6970.
54. Yong X, Lie L, Diliang G, Yang L, Xuwen Z, Zhongwen Y, Lei W, Hua T. Method for preparing lenalidomide, CN103497175 (A). 2014.

What is claimed is:

1. A composition comprising a compound having a structure represented by Formula I:

Formula I

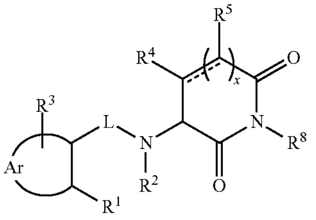

wherein,

Ar is aryl, heteroaryl, cycloalkyl, or heterocyclyl;

L is —$SO_2$;

$R^1$, $R^2$, and $R^3$ are individually selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, amine, amide, nitro, ester, morpholino, dioxolane, alkyl, alkylhalide, aralkyl, alkenyl, alkynyl, cycloalkyl, heterocyclyl; cycloalkenyl, aryl, heteroaryl, arylalkyl, heteroalkyl, and combinations thereof $R^4$ and $R^5$ are individually selected from the group consisting of hydrogen, halogen, hydroxyl, azide, alkoxyl, sulfhydryl, alkylthio, sulfonamido, alkyl, alkylhalide, aralkyl, alkenyl, alkynyl, cycloalkyl, heterocyclyl, and combinations thereof;

$R^8$ is selected from the group consisting of hydrogen, alkyl, alkylhalide, aralkyl, alkenyl, alkynyl, cycloalkyl, heterocyclyl, aryl, alkylaryl, and combinations thereof;

the bond --- is present or absent; and x is 1.

2. The composition of claim 1, wherein

Ar is selected from phenyl, pyrrolyl, furanyl, thiophenyl, imidazolyl, aoxazolyl, thiazolyl, triazolyl, pyrazolyl, pyridinyl, pyrazinyl, pyridazinyl, pyrazolyl, oxazoyl, isoxazoyl, pyrimidinyl, furyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl, indolyl, isoquinolyl, quinolyl, isoquinolinyl, quinolinyl, piperidine, piperazine, pyrimidine, thiane, thiopyran, morpholine, oxazine, tetrahydropyran, pyrolidine, pyroline, imidazoline, pyrazoline, indoline, benzofuran, indoline, indole.

3. The composition claim 1, wherein $R^2$ and $R^3$ are hydrogen.

4. The composition of claim 1, wherein $R^2$ is selected from the group consisting of hydrogen, halogen, and substituted or unsubstituted $C_1$-$C_6$ alkyl.

5. The composition of claim 1, wherein $R^3$ is hydrogen.

6. The composition of claim 1, wherein $R^4$ and $R^5$ are individually selected from the group consisting of hydrogen and $C_1$-$C_6$ alkyl.

7. The composition of claim 1, wherein the compound has a structure as represented below:

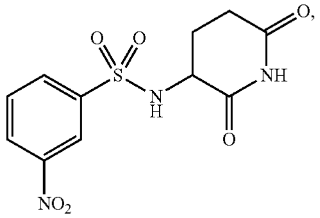

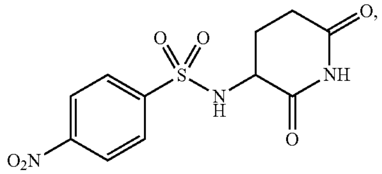

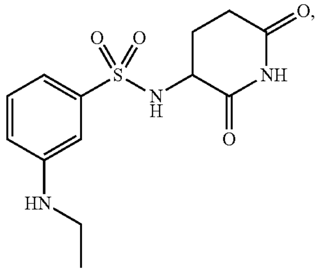

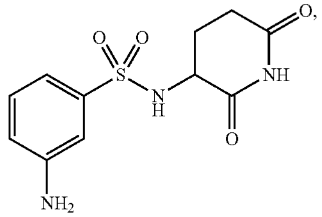

or

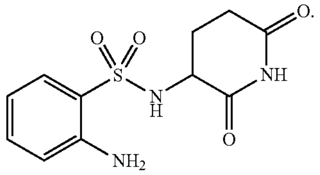

* * * * *